US007927793B2

(12) United States Patent
Hodge et al.

(10) Patent No.: US 7,927,793 B2
(45) Date of Patent: Apr. 19, 2011

(54) CELL LINES AND HOST NUCLEIC ACID SEQUENCES RELATED TO INFECTIOUS DISEASE

(75) Inventors: Thomas W. Hodge, Roswell, GA (US); Natalie J. McDonald, Atlanta, GA (US); Michael W. Shaw, Decatur, GA (US); Donald H. Rubin, Nashville, TN (US); Anthony Sanchez, Lilburn, GA (US)

(73) Assignees: The United States of America as represented by the Department of Health and Human Services, Washington, DC (US); Vanderbilt University, Nashville, TN (US)

( * ) Notice: Subject to any disclaimer, the term of this patent is extended or adjusted under 35 U.S.C. 154(b) by 1276 days.

(21) Appl. No.: 10/535,523

(22) PCT Filed: Nov. 18, 2003

(86) PCT No.: PCT/US03/37143

§ 371 (c)(1),
(2), (4) Date: Mar. 24, 2006

(87) PCT Pub. No.: WO2004/070002

PCT Pub. Date: Aug. 19, 2004

(65) Prior Publication Data

US 2006/0257872 A1 Nov. 16, 2006

Related U.S. Application Data

(60) Provisional application No. 60/427,464, filed on Nov. 18, 2002, provisional application No. 60/482,604, filed on Jun. 25, 2003.

(51) Int. Cl.
*C12Q 1/68* (2006.01)
*C12P 21/06* (2006.01)

(52) U.S. Cl. ................................ 435/6; 435/69.1; 435/5

(58) Field of Classification Search ........................ None
See application file for complete search history.

(56) References Cited

U.S. PATENT DOCUMENTS

| | | | |
|---|---|---|---|
| 5,616,472 A | 4/1997 | Choi et al. | |
| 5,928,881 A | 7/1999 | Barnette et al. | |
| 6,080,576 A | 6/2000 | Zambrowicz et al. | |
| 6,136,566 A | 10/2000 | Sands et al. | |
| 6,139,833 A | 10/2000 | Burgess et al. | |
| 6,207,371 B1 | 3/2001 | Zambrowicz et al. | |
| 6,218,123 B1 | 4/2001 | Nehls et al. | |
| 6,436,707 B1 | 8/2002 | Zambrowicz et al. | |
| 6,448,000 B1 | 9/2002 | Rubin et al. | |
| 2003/0166870 A1* | 9/2003 | Wu et al. | 530/388.2 |

FOREIGN PATENT DOCUMENTS

| | | |
|---|---|---|
| WO | WO 97/45543 A2 | 4/1997 |
| WO | WO 98/30716 | 7/1998 |
| WO | WO 01/83754 A2 | 8/2001 |
| WO | WO 02/44321 A2 | 6/2002 |
| WO | WO2005/092924 A2 | 10/2005 |

OTHER PUBLICATIONS

Hanna et al. (PNAS, May 2002, vol. 99, p. 7450-7454).*
Blot et al. (Journal of Virology, Jun. 2003, vol. 77, p. 6931-6945).*
Fridell, PNAS, 1996, vol. 93, p. 4421-4424.*
Muzny et al. Accession No. AC 079383, 2000, p. 1-64.*
Murray et al. Journal of Virology 2005, vol. 79. p. 11742-11751.*
Froeyen et al., "RNA as a Target for Drug Design, the Example of Tat-TAR Interaction," *Curr. Top. Med. Chem.* 2:1123-1145 (2002).
Gitlin et al., "Short Interfering RNA Confers Intracellular Antiviral Immunity in Human Cells," *Nature* 418:430-434 (2002).
Gulakowski et al., "A Semiautomated Multiparameter Approach for Anti-HIV Drug Screening," *J. Virol. Methods* 33:87-100 (1991).
Hata et al., "A Simple Purification and Fluorescent Assay Method of the Poliovirus 3C Protease Searching for Specific Inhibitors," *J. Virol. Methods.* 84:117-126 (2000).
Kashani-Sabet, "Ribozyme Therapeutics," *JID Symposium Proceedings* 7:76-78 (2002).
Manetta et al., "Design and Implementation of a Particle Concentration Fluorescence Method for the Detection of HIV-1 Protease Inhibitors," *Anal. Biochem.* 202(1):10-15 (1992).
Marschall et al., "Inhibition of Gene Expression with Ribozymes," *Cell Mol. Neurobiol.* 14:523-538 (1994).
Scherr et al., "Gene Silencing Mediated by Small Interfering RNAs in Mammalian Cells," *Curr. Med. Chem.* 10:245-256 (2003).
Singh et al., "The Complestatins as HIV-1 Integrase Inhibitors. Efficient Isolation, Structure Elucidation, and Inhibitory Activities of Isocomplestatin, Chloropeptin I, New Completatins A and B, and Acid-Hydrolysis Products of Chloropeptin I," *J. Natl. Prod.* 64:874-882 (2001).
Ueda et al., "An In Vitro System for Screening Anti-Hepatitis B. Virus Drugs," *Virology* 169:213-216 (1989).
DesJarlais et al., "A Shape- and Chemistry-Based Docking Method and Its Use in the Design of HIV-1 Protease Inhibitors," *J. Comput. Aided Mol. Des.* 8:231-242 (1994).
Argaet et al., "Dominant Selection of an Invariant T Cell Antigen Receptor in Response to Persistent Infection by Epstein-Barr Virus," *J. Exp. Med.* 180:2335-2340, 1994.
Gavrilovskaya et al., "$\beta_3$ Integrins Mediate the Cellular Entry of Hantaviruses that Cause Respiratory Failure," *Proc. Natl. Acad. Sci. USA* 95:7074-7079, 1998.
Groh et al., "Costimulation of CD8 αβ T Cells by NKG2D via Engagement by MIC Induced on Virus-Infected Cells," *Nature Immunol.* 2:255-260, 2001.
Blot et al., "Targeting of the human immunodeficiency virus type 1 envelope to the trans-Golgi network through binding to TIP47 is required for Env incorporation into virions and infectivity," *Journal of Virology*, vol. 77, No. 12, pp. 6391-6945, 2003.

(Continued)

*Primary Examiner* — Zachariah Lucas
*Assistant Examiner* — Agnieszka Boesen
(74) *Attorney, Agent, or Firm* — Klarquist Sparkman, LLP

(57) ABSTRACT

Host nucleic acids and host proteins that participate in viral infection, such as human immunodeficiency virus (HIV), influenza A, and Ebola virus, have been identified. Interfering with or disrupting the interaction between a host nucleic acid or host protein and a virus or viral protein confers an inhibition of or resistance to infection. Thus, interfering with such an interaction in a host subject can confer a therapeutic or prophylactic effect against a virus. The sequences identified can be used to identify agents that reduce or inhibit viral infection.

3 Claims, 5 Drawing Sheets

OTHER PUBLICATIONS

Lombardi et al., "Rab9 functions in transport between late endosomes and the trans Golgi network," *European Molecular Biology Organization Journal*, vol. 12, No. 2, pp. 677-682, 1993.

Murray et al., "Rab9 GTPase is required for replication of human immunodeficiency virus type 1, filoviruses, and measles virus ," *American Society for Microbiology*, vol. 79, No. 18, pp. 11742-11751, 2005.

Rodman et al., "Rab GTPases coordinate endocytosis," *Journal of Cell Science*, vol. 113, No. 2, pp. 183-192, 2000.

Sieczkarski et al., "Dissecting virus entry via endocytosis," *Journal of General Virology*, vol. 83, No. 7, pp. 1535-1545, 2002.

Van Der Sluijs et al., "Rab GTPases as regulators of transport through endosomes," *Protoplasma*, vol. 210, Nos. 1-2, pp. 1-10, 1999.

* cited by examiner

CELL LINES AND HOST NUCLEIC ACID SEQUENCES RELATED TO INFECTIOUS DISEASE

CROSS REFERENCE TO RELATED APPLICATIONS

This is the U.S. National Stage of International Application No. PCT/US2003/037143, filed Nov. 18, 2003 (published in English under PCT Article 21(2)), which in turn claims the benefit of U.S. Provisional Application Nos. 60/427,464 filed Nov. 18, 2002 and 60/482,604 filed Jun. 25, 2003, both herein incorporated by reference.

STATEMENT OF GOVERNMENT SUPPORT

This invention was made by the National Center for Infectious Diseases, Centers for Disease Control and Prevention, an agency of the United States Government. Therefore, the U.S. Government has certain rights in this invention.

REFERENCE TO A SEQUENCE LISTING SUBMITTED ON A COMPACT DISC

This application contains a sequence listing submitted on a compact disc, identified as "seq listing.app," created May 13, 2005 (452 KB/462,908 bytes), which is incorporated herein by reference in its entirety.

FIELD

The present disclosure relates to host nucleic acid sequences, and proteins encoded by these sequences, that are involved in viral infection or are otherwise associated with the life cycle of a virus. Decreasing or inhibiting the interaction of these host sequences with a viral sequence can be used to decrease or inhibit infection by the virus.

BACKGROUND

Infectious diseases affect the health of people and animals around the world, causing serious illness and death. Public health efforts have focused on behavioral modification and other public health efforts to reduce the incidences of infection, while treatment regimens for these diseases have focused on pharmaceuticals, such as antibiotics and anti-viral medications. However, educating people about modifying behavior can be difficult, and that approach alone rarely can significantly diminish the incidence of infection. Furthermore, modifying the behavior of domestic or wild animals would not result in diminished infections. Stopping the spread of infections in an animal population typically involves wholesale slaughter. Few vaccines are available or wholly effective, and they tend to be specific for particular conditions.

The rate of HIV (human immunodeficiency virus) infection is increasing. HIV and its associated acquired immune deficiency syndrome (AIDS) accounted for approximately 5% of all deaths in the United States in the year 2000, while over 313,000 persons were reported to be living with AIDS in that same year. Centers for Disease Control and Prevention, *HIV/AIDS Surveillance Supplemental Report,* 8(1):1-22 (2002). These increasing infection rates have occurred, even though the mode of HIV infection has been known for almost 20 years, and educational programs around the world have promoted behavioral modifications meant to reduce HIV infection. Incidence and death rates due to HIV disease have been decreasing since the mid-90's, in part due to aggressive antiviral therapies, which frequently have toxic side effects and strict dosage schedules. However, even with treatment, the patient is not cured of the disease, and to date, no effective vaccine therapy has been found.

In other diseases, such as infection by the Ebola virus, not only are treatments limited, but containment or prevention of infections is difficult because the life cycle of the virus is not well known. The natural reservoir for the Ebola virus, that is the place or population in nature where the virus resides between human outbreaks, has not yet been identified.

Additionally, different viral strains can rapidly evolve in response to drug usage, producing drug-resistant strains. For example, strains of the influenza virus resistant to amantadine and rimantadine have recently arisen. A recent study of 80 newly-infected people conducted by the AIDS Research Center at Rockefeller University in New York, found that as many as 16.3% of these individuals had strains of HIV associated with resistance to some treatments, and 3.8% appeared to be resistant to several currently available anti-HIV drugs. Thus, a need exists for alternative treatments for infectious disease and methods of designing new drugs to combat infectious disease.

SUMMARY

Several host nucleic acid sequences involved in viral infection have been identified using gene trap methods. The identification of these host sequences and their encoded products permits the identification of sequences that can be targeted for therapeutic intervention.

The disclosed host sequences (including the target sequences associated with SEQ ID NOS: 1-227, 229, and 231, and the proteins encoded thereby (such as SEQ ID NOS: 228, 230, and 232), as well as variants, fusions, and fragments thereof that retain the appropriate biological activity) can mediate infection, and in some examples these host nucleic acids are required for infection. For example, the host nucleic acid can encode a cellular receptor or ligand or a fragment thereof that is recognized by a virus, such as the T-cell V-D-J beta 2.1 chain. In another example, the host nucleic acid encodes an enzyme that mediates viral infection, such as the β-chimerin rho-GTPase (referred to herein as β-chimerin). In another example, the host nucleic acid encodes a Ras oncogene family member such as Rab9. It is demonstrated herein that Rab9 is a host protein involved in infection by pathogens (such as viruses and bacteria) that use similar pathways for morphogenesis of infectious particles. In particular examples, Rab9 is involved in infection by pathogens (such as viruses and bacteria) that utilize lipid rafts. Thus, for example, interfering with the interaction between the disclosed host proteins and a viral or pathogen protein, for example by disrupting the expression of the host nucleic acid within a host cell, or by administering an agent that decreases binding between a host protein and a viral protein, can inhibit, or even prevent, infection of that host cell by the associated virus. Moreover, the identification of particular host enzymes or other host proteins involved in infection provides a method for developing new therapies targeted at inhibiting infection, at the protein or nucleic acid level.

In some examples, the nucleic acid itself mediates viral infection. For example, the nucleotide sequence of a host nucleic acid in the host genome can be recognized by the virus during integration of the viral genome into the host genome. The identification of nucleic acid sequences that are involved in the pathogenesis of infection therefore provides an important tool for interfering with infection.

This genomics-based discovery of nucleic acids and proteins involved in, or even required for, infection provides a new paradigm for identifying and validating various aspects of infectious disease, including assessing individual or population resistance to infection and finding novel diagnostic and drug targets for infectious disease and altering the nucleotide sequence of the host nucleic acid.

Based on the identification of several host nucleic acid and protein sequences involved in viral infection, provided herein are methods for decreasing infection of a host cell by a virus, such as HIV, Ebola, or influenza A, or treating such a viral infection, by interfering with the activity or expression of one or more host proteins shown in Table 1 (including the target sequences associated with any of SEQ ID NOS: SEQ ID NOS: 1-232, as well as variants, fragments, and fusions thereof), such as at least two host proteins, or at least three host proteins. Also provided are methods for identifying agents that can decrease viral infection of a host cell, such as infection by HIV, Ebola, or influenza A. In addition, cells and non-human mammals are provided that have decreased susceptibility to viral infection, such as HIV, Ebola, or influenza A infection.

SEQUENCE LISTING

Figure 1:
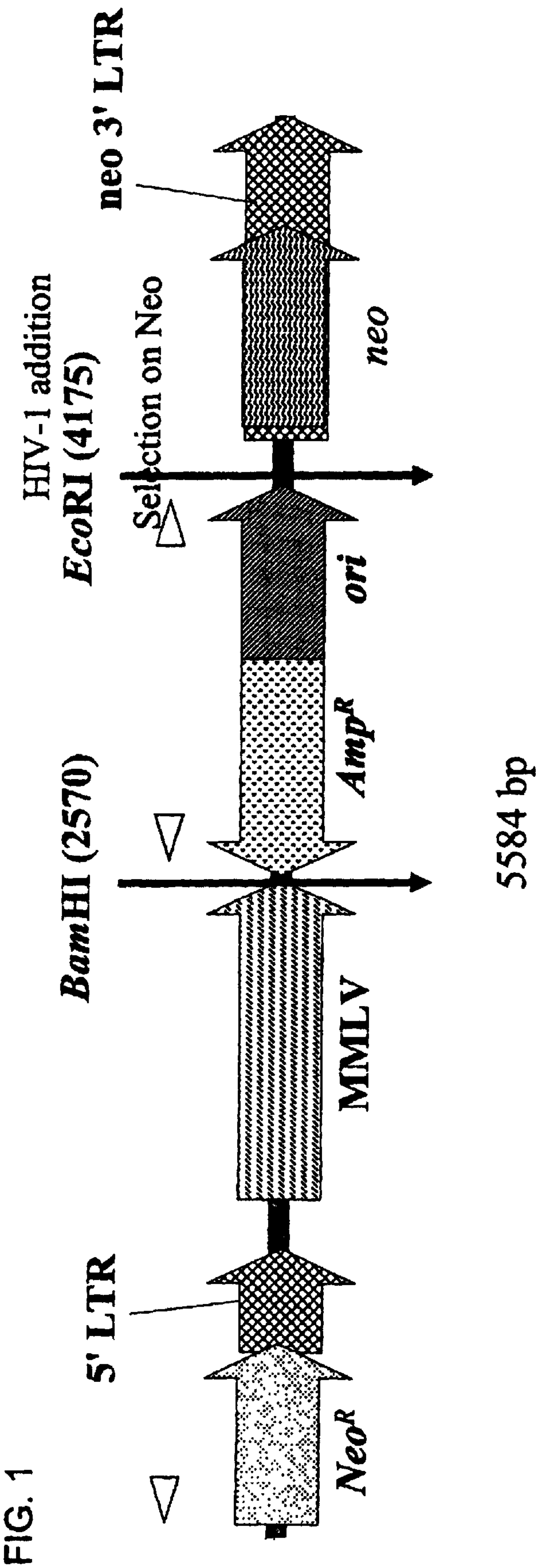
FIG. 1 is a schematic illustration of the U3neoSV1 retroviral vector, which is capable of isolating the nucleic acids described herein using the gene-trap method.

The nucleotide sequences of the nucleic acids described herein are shown using standard letter abbreviations for nucleotide bases, and three letter code for amino acids. Only one strand of each nucleic acid sequence is shown, but the complementary strand is understood as included by any reference to the displayed strand. Additionally, the nucleic acid sequences shown in SEQ ID NOS: 1-226 inherently disclose the corresponding polypeptide sequences of coding sequences (resulting translations of the nucleotide sequences), even when those polypeptide sequences are not explicitly provided herein.

SEQ ID NO: 1 is a nucleic acid sequence associated with viral, such as HIV, infection, and is the clone identified as Nucleotide Sequence 18E8, entire insert. The human homolog is the (−) strand of GenBank Accession No. NG_001333.1, T-ell receptor V beta chain (T-cell receptor beta). Further information on the T-cell receptor V beta chain can be found in WO 01/23409, WO 01/55302, WO 01/57182, and WO 01/94629.

SEQ ID NO: 2 is a nucleic acid sequence associated with viral, such as HIV, infection, and is the clone identified as Nucleotide Sequence 18BA, distal end. The human homolog is the (−) strand of GenBank Accession No. AC 104597.3, T-cell receptor V beta chain.

SEQ ID NO: 3 is a nucleic acid sequence associated with viral, such as HIV, infection, and is the clone identified as Nucleotide Sequence 18BA, proximal end. The human homolog is the (+) strand of GenBank Accession No. NG_001333.1, T-cell receptor beta.

SEQ ID NO: 4 is a nucleic acid sequence associated with viral, such as HIV, infection, and is the clone identified as Nucleotide Sequence 18BE, distal end. The human homolog is the (+) strand of GenBank Accession No. AC00616.7, T-cell receptor beta.

SEQ ID NO: 5 is a nucleic acid sequence associated with viral, such as HIV, infection, and is the clone identified as Nucleotide Sequence 18BE, middle of insert. The human homolog is the (−) strand of GenBank Accession No. AC104597.3, T-cell receptor beta.

SEQ ID NO: 6 is a nucleic acid sequence associated with viral, such as HIV, infection, and is the clone identified as Nucleotide Sequence 18BE, proximal end. The human homolog is the (+) strand of GenBank Accession No. NG_001333.1, T-ell receptor beta.

SEQ ID NO: 7 is a nucleic acid sequence associated with viral, such as HIV, infection which corresponds to the sequence identified as Nucleotide Sequence 18E6, proximal end. The human homolog is the (−) strand of GenBank Accession No. NG_001333.1, T-cell receptor beta.

SEQ ID NO: 8 is a nucleic acid sequence associated with viral, such as HIV, infection, and is the clone identified as Nucleotide Sequence 2E21, proximal end The human homolog is the (+) strand of GenBank Accession No. NG_001333.1, T-cell receptor beta.

SEQ ID NO: 9 is a nucleic acid sequence associated with viral, such as HIV, infection which corresponds to the sequence identified as Nucleotide Sequence 2E22, proximal end. The human homolog is the (−) strand of GenBank Accession No. AC099395.2, T-cell receptor beta.

SEQ ID NO: 10 is a nucleic acid sequence associated with viral, such as HIV, infection, and is the clone identified as Nucleotide Sequence 2B13, proximal end. The human homolog is the (−) strand of GenBank Accession No. NG_001333.1, T-cell receptor beta.

SEQ ID NO: 11 is a nucleic acid sequence associated with viral, such as HIV, infection, and is the clone identified as Nucleotide Sequence 2B14, proximal end. The human homolog is the (−) strand of GenBank Accession No. NG_001333.1, T-ell receptor beta.

SEQ ID NO: 12 is a nucleic acid sequence associated with viral, such as HIV, infection, and is the clone identified as Nucleotide Sequence 2B15, distal end. The human homolog is the (+) strand of GenBank Accession No. NG_001333.1, T-cell receptor beta.

SEQ ID NO: 13 is a nucleic acid sequence associated with viral, such as HIV, infection, and is the clone identified as Nucleotide Sequence 2B15, proximal end. The human homolog is the (−) strand of GenBank Accession No. NG_001333.1, T-cell receptor beta.

SEQ ID NO: 14 is a nucleic acid sequence associated with viral, such as HIV, infection, and is the clone identified as Nucleotide Sequence 2B16, proximal end. The human homolog is the (−) strand of GenBank Accession No. NG_001333.1, T-cell receptor beta.

SEQ ID NO: 15 is a nucleic acid sequence associated with viral, such as HIV, infection, and is the clone identified as Nucleotide Sequence 2E23, distal end. The human homolog is the (−) strand of GenBank Accession No. NG_001333.1, T-ell receptor beta.

SEQ ID NO: 16 is a nucleic acid sequence associated with viral, such as HIV, infection, and is the clone identified as Nucleotide Sequence 2E23, proximal end. The human homolog is the (+) strand of GenBank Accession No. NG_001333.1, T-cell receptor beta.

SEQ ID NO: 17 is a nucleic acid sequence associated with viral such as HIV, infection, and is the clone identified as Nucleotide Sequence 2E24, proximal end. The human homolog is the (+) strand of GenBank Accession No. NG_001333.1, T-cell receptor beta.

SEQ ID NO: 18 is a nucleic acid sequence associated with viral such as HIV, infection, and is the clone identified as Nucleotide Sequence 2E25, proximal end. The human homolog is the (+) strand of GenBank Accession No. NG_001333.1, T-cell receptor beta.

SEQ ID NO: 19 is a nucleic acid sequence associated with viral, such as HIV, infection, and is the clone identified as Nucleotide Sequence 2E26, proximal end. The human homolog is the (+) strand of GenBank Accession No. NG_001333.1, T-cell receptor beta.

SEQ ID NO: 20 is a nucleic acid sequence associated with viral, such as HIV, infection, and is the clone identified as Nucleotide Sequence 18BD, proximal end. The human homolog is the (+) strand of GenBank Accession No. M16834.1, T-ell receptor V-D-J-beta 2.1 chain (described in WO 02/057414 and Reynolds et al., *Cell* 50(1):107-17, 1987).

SEQ ID NO: 21 is a nucleic acid sequence associated with viral, such as HIV, infection, and is the clone identified as Nucleotide Sequence 18E7, distal end. The human homolog is the (−) strand of GenBank Accession No. AC004593.1 including beta-chimerin rho GTPase (CHN2) (for example see WO 01/12659).

SEQ ID NO: 22 is a nucleic acid sequence associated with viral, such as HIV, infection, and is the clone identified as Nucleotide Sequence 18E7, proximal end. The human homologs are the (−) strand of GenBank Accession No. NG_001333.1, T-cell receptor beta; and the (+) strand of GenBank Accession No. AC004593.1 including beta-chimaerin (CHN2).

SEQ ID NO: 23 is a nucleic acid sequence associated with viral, such as HIV and influenza A, infection, and is the clone identified as Nucleotide Sequence 18E6, distal end. The human homolog is the (+) strand of GenBank Accession No. AL049699.8, including malic enzyme 1 (ME1) NADP(+)-dependent cytosolic. Further information on this gene can be found in WO 01/55301 and WO 01/53312.

SEQ ID NO: 24 is a nucleic acid sequence associated with viral, such as HIV and influenza A, infection, and is the clone identified as Nucleotide Sequence 18BD, distal end. The human homolog is the (+) strand of GenBank Accession No. AC123903.1, including hypothetical protein XP_174419.

SEQ ID NO: 25 is a nucleic acid sequence associated with viral, such as HIV and influenza A, infection, and is the clone identified as Nucleotide Sequence 18E9, distal end. The human homolog is the (+) strand of GenBank Accession No. AC096736.3, a region of chromosome 4q31.3-32.

SEQ ID NO: 26 is a nucleic acid sequence associated with viral, such as HIV and influenza A, infection, and is the clone identified as Nucleotide Sequence 18E9, middle of insert. The human homolog is the (+) strand of GenBank Accession No. AC096736.3, a region of chromosome 4q31.3-32.

SEQ ID NO: 27 is a nucleic acid sequence associated with viral, such as HIV and influenza A, infection, and is the clone identified as Nucleotide Sequence 18E9, proximal end. The human homologs are the (−) strand of GenBank Accession No. NG_001333.1, T-cell receptor beta; and (−) strand of GenBank Accession No. AC096736.3, a region of chromosome 4q31.3-32.

SEQ ID NO: 28 is a nucleic acid sequence associated with viral, such as HIV, infection, and is the clone identified as Nucleotide Sequence 2E21, distal end. The human homolog is the (−) strand of GenBank Accession No. M26920.1, alpha satellite DNA.

SEQ ID NO: 29 is a nucleic acid sequence associated with viral, such as HIV, infection, and is the clone identified as Nucleotide Sequence 2E22, distal end. The human homologs are the (+) strand of GenBank Accession No. AP004369.3, including LOC253788 (and neighboring similar to RIKEN cDNA 1700001L23 (LOC219938)); and the (+) strand of GenBank Accession No. AC093117.2, between coagulation factor III, thromboplastin, tissue factor (F3) and LOC91759.

SEQ ID NO: 30 is a nucleic acid sequence associated with viral, such as HIV, infection, and is the clone identified as Nucleotide Sequence 2B13, distal end. The human homolog is the (−) strand of GenBank Accession No. AC092043.2, between similar to zinc finger protein 7 KOX4 (LOC131880) and LOC166140.

SEQ ID NO: 31 is a nucleic acid sequence associated with viral, such as HIV, infection, and is the clone identified as Nucleotide Sequence 2B 14, distal end. The human homologs are the (−) strand of GenBank Accession No. AL136963.17, between LOC222474 and similar to Rho guanine nucleotide exchange factor 4, isoform a, APC-stimulated guanine nucleotide exchange factor (LOC221178); and the (+) strand of GenBank Accession No. NG_001333.1, T-ell receptor beta.

SEQ ID NO: 32 is a nucleic acid sequence associated with viral, such as HIV, infection, and is the clone identified as Nucleotide Sequence 2B16, distal end. The human homolog is the (−) strand of GenBank Accession No. AL133293.28, between ribosomal protein L7A-like 4 (RPL7AL4) and v-src sarcoma (Schmidt-Ruppin A-2) viral oncogene homolog (avian) (SRC).

SEQ ID NO: 33 is a nucleic acid sequence associated with viral, such as HIV, infection, and is the clone identified as Nucleotide Sequence 2E24, distal end. The human homolog is the (−) strand of GenBank Accession No. AL161417.17, KIAA0564.

SEQ ID NO: 34 is a nucleic acid sequence associated with viral, such as HIV, infection, and is the clone identified as Nucleotide Sequence 2E25, distal end. The human homologs are the (−) strand of GenBank Accession No. Z12006.1, alpha satellite DNA; and the (+) and (−) strands of GenBank Accession No. AC093577.2, M96 protein.

SEQ ID NO: 35 is a nucleic acid sequence associated with viral, such as HIV, infection, and is the clone identified as Nucleotide Sequence 2E26, distal end. The human homologs are the (−) strand of GenBank Accession No. Z78022.1, hypothetical protein similar to G proteins, especially RAP-2A (LOC57826); and the (+) strand of GenBank Accession No. AL136220.14, between LOC161005 and osteoblast specific factor 2 (fasciclin I-like; OSF-2).

SEQ ID NO: 36 is a nucleic acid sequence associated with viral, such as influenza A, infection, and is the clone identified as Nucleotide Sequence B3B1, distal end. The canine homolog is the (+) and (−) strand portions of GenBank Accession No. AJ012166.1, *Canis familiaris* TCTA gene, AMT gene, DAG1 gene, and BSN gene.

SEQ ID NO: 37 is a nucleic acid sequence associated with viral, such as influenza A, infection, and is the clone identified as Nucleotide Sequence B5B5, distal end. The canine homolog is the (+) and (−) strand portions of GenBank Accession No. AJ012166.1, *Canis familiaris* TCTA gene, AMT gene, DAG1 gene, and BSN gene.

SEQ ID NO: 38 is a nucleic acid sequence associated with vial, such as influenza A, infection, and is the clone identified as Nucleotide Sequence B1B1, distal end The human homolog is the (+) strand of GenBank Accession No. AC117507.5, including LIM domain containing preferred translocation partner in lipoma (LPP).

SEQ ID NO: 39 is a nucleic acid sequence associated with viral such as influenza A, infection, and is the clone identified as Nucleotide Sequence B1B2, distal end. The human homolog is the (−) strand of GenBank Accession No. AC117507.5, including LIM domain containing preferred translocation partner in lipoma (LPP).

SEQ ID NO: 40 is a nucleic acid sequence associated with viral, such as influenza A, infection, and is the clone identified as Nucleotide Sequence B1B4, distal end. The human homolog is the (−) strand of GenBank Accession No. AC117507.5, including LIM domain containing preferred translocation partner in lipoma (LPP).

SEQ ID NO: 41 is a nucleic acid sequence associated with viral, such as influenza A, infection, and is the clone identified as Nucleotide Sequence B1B5, distal end. The human homolog is the (−) strand of GenBank Accession No. AC117507.5, including LIM domain containing preferred translocation partner in lipoma (LPP).

SEQ ID NO: 42 is a nucleic acid sequence associated with viral, such as influenza A, infection, and is the clone identified as Nucleotide Sequence B1B6, distal end. The human homolog is the (−) strand of GenBank Accession No. AC117507.5, including LIM domain containing preferred translocation partner in lipoma (LPP).

SEQ ID NO: 43 is a nucleic acid sequence associated with viral, such as influenza A, infection, and is the clone identified as Nucleotide Sequence B1E3, entire insert. The human homolog is the (+) strand of GenBank Accession No. AC117507.5, including LIM domain containing preferred translocation partner in lipoma (LPP).

SEQ ID NO: 44 is a nucleic acid sequence associated with viral, such as influenza A, infection, and is the clone identified as Nucleotide Sequence B1E5, proximal end. The human homolog is the (−) strand of GenBank Accession No. AC117507.5, including LIM domain containing preferred translocation partner in lipoma (LPP).

SEQ ID NO: 45 is a nucleic acid sequence associated with viral such as influenza A, infection, and is the clone identified as Nucleotide Sequence B6B1, entire insert. The human homolog is the (−) strand of GenBank Accession No. AC117507.5, including LIM domain containing preferred translocation partner in lipoma (LPP).

SEQ ID NO: 46 is a nucleic acid sequence associated with viral, such as influenza A, infection, and is the clone identified as Nucleotide Sequence B6E1, distal end. The human homolog is the (+) strand of GenBank Accession No. AC117507.5, including LIM domain containing preferred translocation partner in lipoma (LPP).

SEQ ID NO: 47 is a nucleic acid sequence associated with viral, such as influenza A, infection, and is the clone identified as Nucleotide Sequence B6E1, proximal end. The human homolog is the (−) stand of GenBank Accession No. AC117507.5, including LIM domain containing preferred translocation partner in lipoma (LPP).

SEQ ID NO: 48 is a nucleic acid sequence associated with viral, such as influenza A, infection, and is the clone identified as Nucleotide Sequence B6E3, proximal end. The human homolog is the (−) stand of GenBank Accession No. AC117507.5, including LIM domain containing preferred translocation partner in lipoma (LPP).

SEQ ID NO: 49 is a nucleic acid sequence associated with viral, such as influenza A, infection, and is the clone identified as Nucleotide Sequence B1E1, distal end. The human homolog is the (+) strand of GenBank Accession No. AC104036.8, between LOC253121 and hyaluronan synthase 2 (HAS2).

SEQ ID NO: 50 is a nucleic acid sequence associated with viral, such as influenza A, infection, and is the clone identified as Nucleotide Sequence B1E1, proximal end. The human homolog is the (−) strand of GenBank Accession No. AF260225.1, Testin 2 and Testin 3 (see WO 01/57270, WO 01/57271, WO 01/57273, WO 01/57274, WO 01/57275, WO 01/57276, WO 01/57277, WO 01/57278, or Tatarelli et al., *Genomics* 68(1):1-12, 2000).

SEQ ID NO: 51 is a nucleic acid sequence associated with viral, such as influenza A, infection, and is the clone identified as Nucleotide Sequence B1E4, distal end. The human homolog is the (+) strand of GenBank Accession No. AF260225.1, Testin 2 and Testin 3.

SEQ ID NO: 52 is a nucleic acid sequence associated with viral, such as influenza A, infection, and is the clone identified as Nucleotide Sequence B1E4, proximal end. The human homolog is the (−) strand of GenBank Accession No. AF260225.1, Testin 2 and Testin 3.

SEQ ID NO: 53 is a nucleic acid sequence associated with viral, such as influenza A, infection, and is the clone identified as Nucleotide Sequence B6E2, distal end. The human homolog is the (+) strand of GenBank Accession No. AF260225.1, Testin 2 and Testin 3.

SEQ ID NO: 54 is a nucleic acid sequence associated with viral, such as influenza A, infection, and is the clone identified as Nucleotide Sequence B6E2, proximal end. The human homolog is the (−) strand of GenBank Accession No. AF260225.1, Testin 2 and Testin 3.

SEQ ID NO: 55 is a nucleic acid sequence associated with viral, such as influenza A, infection, and is the clone identified as Nucleotide Sequence B6E4, proximal end. The human homolog is the (−) strand of GenBank Accession No. AF260225.1, Testin 2 and Testin 3.

SEQ ID NO: 56 is a nucleic acid sequence associated with viral, such as influenza A, infection, and is the clone identified as Nucleotide Sequence B7E1, distal end. The human homolog is the (+) strand of GenBank Accession No. AF260225.1, Testin 2 and Testin 3.

SEQ ID NO: 57 is a nucleic acid sequence associated with viral, such as influenza A, infection, and is the clone identified as Nucleotide Sequence B7E1, proximal end. The human homolog is the (−) strand of GenBank Accession No. AF260225.1, Testin 2 and Testin 3.

SEQ ID NO: 58 is a nucleic acid sequence associated with viral, such as influenza A, infection, and is the clone identified as Nucleotide Sequence B5E2, distal end. The human homolog is the (−) strand of GenBank Accession No. AL133230.25, PTPN1 gene for protein tyrosine phosphatase, non-receptor type 1 (see Watanabe et al., *Jpn. J. Cancer Res.* 93:1114-22, 2002).

SEQ ID NO: 59 is a nucleic acid sequence associated with viral, such as influenza A, infection, and is the clone identified as Nucleotide Sequence B5E2, middle of insert. The human homolog is the (−) strand of GenBank Accession No. AL133230.25, PTPN1 gene for protein tyrosine phosphatase, non-receptor type 1.

SEQ ID NO: 60 is a nucleic acid sequence associated with viral, such as influenza A, infection, and is the clone identified as Nucleotide Sequence B3E11, distal end. The human homolog is the (+) strand of GenBank Accession No. AL445675.9, between LOC149360 and LOC253961.

SEQ ID NO: 61 is a nucleic acid sequence associated with viral, such as influenza A, infection, and is the clone identified as Nucleotide Sequence B3E11, proximal end. The human homolog is the (−) strand of GenBank Accession No. AL391986.12, between KIKAA1560 and Tectorin beta (TECTB).

SEQ ID NO: 62 is a nucleic acid sequence associated with viral, such as influenza A, infection, and is the clone identified as Nucleotide Sequence B6E3, distal end. The human homolog is the (−) strand of GenBank Accession No. AC016826.9, including Cadherin related 23 (CDH23).

SEQ ID NO: 63 is a nucleic acid sequence associated with viral, such as influenza A, infection, and is the clone identified as Nucleotide Sequence B6B4, distal end. The human homolog is the (+) strand of GenBank Accession No. AL357372.12, Myeloid/lymphoma or mixed lineage leukemia, translocated to 10 (MNMLT10).

SEQ ID NO: 64 is a nucleic acid sequence associated with viral, such as Ebola, infection, and is the clone identified as Nucleotide Sequence ZV1-1B5, distal end. The human homolog is the (−) strand of GenBank Accession No. AL355802.13, between exportin 5 (XPO5) and DNA polymerase eta (POLH).

SEQ ID NO: 65 is a nucleic acid sequence associated with viral, such as Ebola, infection, and is the clone identified as Nucleotide Sequence ZV1-1B5, proximal end. The human homolog is the (+) strand of GenBank Accession No. AL355802.13, between XPO5 and POLH.

SEQ ID NO: 66 is a nucleic acid sequence associated with viral, such as Ebola, infection, and is the clone identified as Nucleotide Sequence ZV1-1E, proximal end. The human homolog is the (−) stand of GenBank Accession No. AL355802.13, between XPO5 and POLH.

SEQ ID NO: 67 is a nucleic acid sequence associated with viral, such as Ebola, infection, and is the clone identified as Nucleotide Sequence MV1-2E1, proximal end. The human homolog is the (+) strand of GenBank Accession No. AL135744.4, including heterogenous nuclear riboprotein C (C1/C2) (HNRPC).

SEQ ID NO: 68 is a nucleic acid sequence associated with viral, such as Ebola, infection, and is the clone identified as Nucleotide Sequence MV1-2E5, proximal end. The human homolog is the (+) strand of GenBank Accession No. AL135744.4, including HNRPC.

SEQ ID NO: 69 is a nucleic acid sequence associated with viral such as Ebola, infection, and is the clone identified as Nucleotide Sequence MV1-2E6, proximal end. The human homolog is the (+) strand of GenBank Accession No. AL135744.4, including HNRPC.

SEQ ID NO: 70 is a nucleic acid sequence associated with viral, such as Ebola, infection, and is the clone identified as Nucleotide Sequence MV1-2B2, proximal end. The human homolog is the (−) strand of GenBank Accession No. ALI35744.4, including HNRPC.

SEQ ID NO: 71 is a nucleic acid sequence associated with viral, such as Ebola, infection, and is the clone identified as Nucleotide Sequence MV1-2B13, proximal end. The human homolog is the (−) strand of GenBank Accession No. ALI35744.4, including HNRPC.

SEQ ID NO: 72 is a nucleic acid sequence associated with viral, such as Ebola, infection, and is the clone identified as Nucleotide Sequence MV1-2B14, proximal end. The human homolog is the (−) strand of GenBank Accession No. AL135744.4, including HNRPC.

SEQ ID NO: 73 is a nucleic acid sequence associated with viral, such as Ebola, infection, and is the clone identified as Nucleotide Sequence MV1-2B21, proximal end. The human homolog is the (−) strand of GenBank Accession No. AL135744.4, including HNRPC.

SEQ ID NO: 74 is a nucleic acid sequence associated with viral, such as Ebola, infection, and is the clone identified as Nucleotide Sequence MV1-2B25, proximal end. The human homolog is the (−) strand of GenBank Accession No. AL135744.4, including HNRPC.

SEQ ID NO: 75 is a nucleic acid sequence associated with viral, such as Ebola, infection, and is the clone identified as Nucleotide Sequence MV1-2B35, proximal end. The human homolog is the (−) strand of GenBank Accession No. ALI 35744.4, including HNRPC.

SEQ ID NO: 76 is a nucleic acid sequence associated with viral, such as Ebola, infection, and is the clone identified as Nucleotide Sequence MV1-2E5, distal end. The human homolog is the (+) and (−) strands of GenBank Accession No. AL050324.5, including alpha-endosulfine pseudogene (ENSAP) and LOC128741.

SEQ ID NO: 77 is a nucleic acid sequence associated with viral, such as Ebola, infection, and is the clone identified as Nucleotide Sequence MV1-2E6, distal end. The human homolog is the (+) strand of GenBank Accession No. AC017060.7, including LOC222888.

SEQ ID NO: 78 is a nucleic acid sequence associated with viral, such as Ebola, infection, and is the clone identified as Nucleotide Sequence MV1-2B13, distal end. The human homolog is the (+) strand of GenBank Accession No. AL161731.20, between LOC138421 and zinc finger protein 297B (ZNF297B).

SEQ ID NO: 79 is a nucleic acid sequence associated with viral, such as Ebola, infection, and is the clone identified as Nucleotide Sequence MV1-2B14, distal end. The human homolog is the (−) strand of GenBank Accession No. AC012366.10, including sideroflexin 5 (SFXN5).

SEQ ID NO: 80 is a nucleic acid sequence associated with viral, such as Ebola, infection, and is the clone identified as Nucleotide Sequence MV1-2B35, distal end. The human homolog is the (+) strand of GenBank Accession No. AL645504.10, including importin 9 (FLJ10402).

SEQ ID NO: 81 is a nucleic acid sequence associated with viral, such as Ebola, infection, and is the clone identified as Nucleotide Sequence GV1-1B1, distal end. The human homolog is the (+) strand of GenBank Accession No. NG_001333.1, T-cell receptor beta.

SEQ ID NO: 82 is a nucleic acid sequence associated with viral, such as Ebola, infection, and is the clone identified as Nucleotide Sequence GV1-1B1, proximal end. The human homolog is the (+) strand of GenBank Accession No. NG_001333.1, T-cell receptor beta.

SEQ ID NO: 83 is a nucleic acid sequence associated with viral, such as Ebola, infection, and is the clone identified as Nucleotide Sequence MV2-B1, distal end. The human homolog is the (−) strand of GenBank Accession No. AC058791.4, adjacent to LOC135952.

SEQ ID NO: 84 is a nucleic acid sequence associated with viral, such as Ebola, infection, and is the clone identified as Nucleotide Sequence MV2-E2, distal end. The human homolog is the (+) strand of GenBank Accession No. AC058791.4, adjacent to LOC135952.

SEQ ID NO: 85 is a nucleic acid sequence associated with viral, such as Ebola, infection, and is the clone identified as Nucleotide Sequence MV2-E2, proximal end. The human homolog is the (−) strand of GenBank Accession No. AC058791.4, adjacent to LOC135952.

SEQ ID NO: 86 is a nucleic acid sequence associated with viral, such as Ebola, infection, and is the clone identified as Nucleotide Sequence MV2-E3, proximal end. The human homolog is the (−) strand of GenBank Accession No. AC058791.4, adjacent to LOC135952.

SEQ ID NO: 87 is a nucleic acid sequence associated with viral, such as Ebola, infection, and is the clone identified as Nucleotide Sequence MV2-E4, proximal end. The human homolog is the (−) strand of GenBank Accession No. AC058791.4, adjacent to LOC135952.

SEQ ID NO: 88 is a nucleic acid sequence associated with viral, such as Ebola, infection, and is the clone identified as Nucleotide Sequence MV2-E5, distal end. The human homolog is the (+) strand of GenBank Accession No. AC058791.4, adjacent to LOC135952.

SEQ ID NO: 89 is a nucleic acid sequence associated with viral, such as Ebola, infection, and is the clone identified as Nucleotide Sequence MV2-E5, proximal en The human homolog is the (−) strand of GenBank Accession No. AC058791.4, adjacent to LOC135952.

SEQ ID NO: 90 is a nucleic acid sequence associated with viral, such as Ebola, infection, and is the clone identified as Nucleotide Sequence MV3-B1, distal ends The human homolog is the (−) strand of GenBank Accession No. AC058791.4, adjacent to LOC135952.

SEQ ID NO: 91 is a nucleic acid sequence associated with viral, such as Ebola, infection, and is the clone identified as Nucleotide Sequence MV3-E2, distal end. The human homolog is the (+) strand of GenBank Accession No. AC058791.4, adjacent to LOC135952.

SEQ ID NO: 92 is a nucleic acid sequence associated with viral, such as Ebola, infection, and is the clone identified as Nucleotide Sequence MV3-E2, proximal end. The human homolog is the (−) strand of GenBank Accession No. AC058791.4, adjacent to LOC135952.

SEQ ID NO: 93 is a nucleic acid sequence associated with viral such as Ebola, infection, and is the clone identified as Nucleotide Sequence MV3-E4, proximal end. The human homolog is the (−) strand of GenBank Accession No. AC058791.4, adjacent to LOC135952.

SEQ ID NO: 94 is a nucleic acid sequence associated with viral, such as Ebola, infection, and is the clone identified as Nucleotide Sequence MV6-B1, distal end. The human homolog is the (+) and (−) strand of GenBank Accession No. AC058791.4, adjacent to LOC135952.

SEQ ID NO: 95 is a nucleic acid sequence associated with viral, such as Ebola, infection, and is the clone identified as Nucleotide Sequence MV6-E1, distal end The human homolog is the (+) strand of GenBank Accession No. AC058791.4, adjacent to LOC135952.

SEQ ID NO: 96 is a nucleic acid sequence associated with viral, such as Ebola, infection, and is the clone identified as Nucleotide Sequence MV6-E1, proximal end. The human homolog is the (−) stand of GenBank Accession No. AC058791.4, adjacent to LOC135952.

SEQ ID NO: 97 is a nucleic acid sequence associated with viral, such as Ebola, infection, and is the clone identified as Nucleotide Sequence MV6-E4, proximal end. The human homolog is the (−) strand of GenBank Accession No. AC058791.4, adjacent to LOC135952.

SEQ ID NO: 98 is a nucleic acid sequence associated with viral, such as Ebola, infection, and is the clone identified as Nucleotide Sequence MV6-E5, distal end. The human homolog is the (+) strand of GenBank Accession No. AC058791.4, adjacent to LOC135952.

SEQ ID NO: 99 is a nucleic acid sequence associated with viral, such as Ebola, infection, and is the clone identified as Nucleotide Sequence MV6-E5, proximal end. The human homolog is the (−) strand of GenBank Accession No. AC058791.4, adjacent to LOC135952.

SEQ ID NO: 100 is a nucleic acid sequence associated with viral, such as Ebola, infection, and is the clone identified as Nucleotide Sequence MV2-E1, distal end. The human homolog is the (+) stand of GenBank Accession No. AC021753.7, hypothetical protein KIAA1259.

SEQ ID NO: 101 is a nucleic acid sequence associated with viral, such as Ebola, infection, and is the clone identified as Nucleotide Sequence MV2-E1, proximal end. The human homolog is the (−) strand of GenBank Accession No. AC021753.7, hypothetical protein KIAA1259.

SEQ ID NO: 102 is a nucleic acid sequence associated with viral, such as Ebola, infection, and is the clone identified as Nucleotide Sequence MV2-E3, distal end. The human homolog is the (+) and (−) strands of GenBank Accession No. AC107081.5, copper metabolism gene (MURR1) and chaperonin containing TCP1, subunit 4 (CCT4).

SEQ ID NO: 103 is a nucleic acid sequence associated with viral, such as Ebola, infection, and is the clone identified as Nucleotide Sequence MV2-E4, distal end. The human homolog is the (−) strand of GenBank Accession No. AC099785.2, hypothetical protein FLJ40773 and similar to ribosomal protein L24-like (LOC149360).

SEQ ID NO: 104 is a nucleic acid sequence associated with viral, such as Ebola, infection, and is the clone identified as Nucleotide Sequence MV2-E4, distal end. The human homolog is the (+) strand of GenBank Accession No. AF260225.1, Testin 2 and 3 (TES).

SEQ ID NO: 105 is a nucleic acid sequence associated with viral, such as Ebola, infection, and is the clone identified as Nucleotide Sequence MV2-E4, proximal end. The human homolog is the (−) strand of GenBank Accession No. AF260225.1, Testin 2 and 3 (TES).

SEQ ID NO: 106 is a nucleic acid sequence associated with viral, such as Ebola, infection, and is the clone identified as Nucleotide Sequence MV3-E7, distal end. The human homolog is the (+) strand of GenBank Accession No. AF260225.1, Testin 2 and 3 (TES).

SEQ ID NO: 107 is a nucleic acid sequence associated with viral, such as Ebola, infection, and is the clone identified as Nucleotide Sequence MV3-E7, proximal end. The human homolog is the (−) strand of GenBank Accession No. AF260225.1, Testin 2 and 3 (TES).

SEQ ID NO: 108 is a nucleic acid sequence associated with viral, such as Ebola, infection, and is the clone identified as Nucleotide Sequence MV3-B2, distal end. The human homolog is the (+) and (−) strands of GenBank Accession No. AC105934.2, polybromo 1 (PB1).

SEQ ID NO: 109 is a nucleic acid sequence associated with viral, such as Ebola, infection, and is the clone identified as Nucleotide Sequence MV3-B4, distal end. The human homolog is the (+) strand of GenBank Accession No. AC022506.38, between DNA damage inducible transcript 3 (DDIT3) and KIAA1887.

SEQ ID NO: 110 is a nucleic acid sequence associated with viral, such as Ebola, infection, and is the clone identified as Nucleotide Sequence MV3-B5, distal end. The human homolog is the (−) strand of GenBank Accession No. AL157834.12, PDZ and LIM domain 1 (elfin) (PDLIM1).

SEQ ID NO: 111 is a nucleic acid sequence associated with viral, such as Ebola, infection, and is the clone identified as Nucleotide Sequence MV3-E1, distal end. The human homolog is the (+) strand of GenBank Accession No. AL110115.38, LOC284803.

SEQ ID NO: 112 is a nucleic acid sequence associated with viral, such as Ebola, infection, and is the clone identified as Nucleotide Sequence MV3-E1, proximal end. The human homolog is the (−) strand of GenBank Accession No. AL110115.38, signal peptide peptidase (HM13) and LOC284803.

SEQ ID NO: 113 is a nucleic acid sequence associated with viral, such as Ebola, infection, and is the clone identified as Nucleotide Sequence MV3-E3, distal end. The human homolog is the (−) strand of GenBank Accession No. AL117341.26, containing PRO0097 and adjacent to FL31958.

SEQ ID NO: 114 is a nucleic acid sequence associated with viral, such as Ebola, infection, and is the clone identified as Nucleotide Sequence MV3-E3, proximal end. The human homolog is the (−) strand of GenBank Accession No. AP002076.3, small inducible cytokine E, member 1 (endothelial monocyte-activating) (SCYE1).

SEQ ID NO: 115 is a nucleic acid sequence associated with viral, such as Ebola, infection, and is the clone identified as Nucleotide Sequence MV3-E6, distal end. The human homolog is the (+) strand of GenBank Accession No. AP002076.3, containing SCYE1.

SEQ ID NO: 116 is a nucleic acid sequence associated with viral, such as Ebola, infection, and is the clone identified as Nucleotide Sequence MV3-E6, proximal end. The human homolog is the (−) strand of GenBank Accession No. AP002076.3, containing SCYE1.

SEQ ID NO: 117 is a nucleic acid sequence associated with viral, such as Ebola, infection, and is the clone identified as Nucleotide Sequence MV3-E4, distal end. The human homolog is the (+) and (−) strands of GenBank Accession No. AC132812.9, between E3 ubiquitin ligase (SMURF2) and hypothetical protein MGC40489.

SEQ ID NO: 118 is a nucleic acid sequence associated with viral, such as Ebola, infection, and is the clone identified as Nucleotide Sequence MV3-E5, distal end. The human homolog is the (+) strand of GenBank Accession No. AC079383.17, Ras oncogene family member Rab9.

SEQ ID NO: 119 is a nucleic acid sequence associated with viral, such as Ebola, infection, and is the clone identified as Nucleotide Sequence MV3-E5, proximal end. The human homolog is the (−) strand of GenBank Accession No. AC079383.17, Ras oncogene family member Rab9.

SEQ ID NO: 120 is a nucleic acid sequence associated with viral such as Ebola, infection, and is the clone identified as Nucleotide Sequence MV6-E2, distal end. The human homolog is the (−) strand of GenBank Accession No. AL132989.5, between PRO1617 and retinoblastoma binding protein 1 (RBBP1).

SEQ ID NO: 121 is a nucleic acid sequence associated with viral, such as Ebola, infection, and is the clone identified as Nucleotide Sequence MV6-E2, proximal end. The human homolog is the (+) strand of GenBank Accession No. AL132989.5, RBBP1.

SEQ ID NO: 122 is a nucleic acid sequence associated with viral, such as Ebola, infection, and is the clone identified as Nucleotide Sequence MV6-E3, proximal end. The human homolog is the (+) strand of GenBank Accession No. AL132989.5, retinoblastoma binding protein 1 (RBBP1).

SEQ ID NO: 123 is a nucleic acid sequence associated with viral, such as Ebola, infection, and is the clone identified as Nucleotide Sequence MV6-E3, distal end. The human homolog is the (+) and (−) strands of GenBank Accession No. AC096669.1, a region of chromosome 2q12.

SEQ ID NO: 124 is a nucleic acid sequence associated with viral, such as Ebola, infection, and is the clone identified as Nucleotide Sequence MV6-E4, distal end. The human homolog is the (−) strands of GenBank Accession No. AF196968.4, elongation factor for selenoprotein translation (SELB).

SEQ ID NO: 125 is a nucleic acid sequence associated with viral, such as Ebola, infection, and is the clone identified as Nucleotide Sequence MV13-B1, distal end. The human homolog is the (−) strand of GenBank Accession No. AC112218.2, transcription factor SMIF (HSA275986).

SEQ ID NO: 126 is a nucleic acid sequence associated with viral, such as Ebola, infection, and is the clone identified as Nucleotide Sequence MV13-B1, proximal end. The human homolog is the (+) strand of GenBank Accession No. AC112218.2, transcription factor SMIF (HSA275986).

SEQ ID NO: 127 is a nucleic acid sequence associated with viral, such as Ebola, infection, and is the clone identified as Nucleotide Sequence MV13-E1, proximal end. The human homolog is the (−) strand of GenBank Accession No. AC112218.2, transcription factor SMIF (HSA275986).

SEQ ID NO: 128 is a nucleic acid sequence associated with viral, such as Ebola, infection, and is the clone identified as Nucleotide Sequence MV13-E1, distal end. The human homolog is the (+) strand of GenBank Accession No. AC112218.2, transcription factor SMIF (HSA275986).

SEQ ID NO: 129 is a nucleic acid sequence associated with viral, such as Ebola, infection, and is the clone identified as Nucleotide Sequence MV13-E2, proximal end. The human homolog is the (−) strand of GenBank Accession No. AC112218.2, transcription factor SMIF (HSA275986).

SEQ ID NO: 130 is a nucleic acid sequence associated with viral, such as Ebola, infection, and is the clone identified as Nucleotide Sequence MV13-E3, proximal end. The human homolog is the (−) strand of GenBank Accession No. AC112218.2, transcription factor SMIF (HSA275986).

SEQ ID NO: 131 is a nucleic acid sequence associated with viral, such as Ebola, infection, and is the clone identified as Nucleotide Sequence MV13-E4, proximal end. The human homolog is the (−) strand of GenBank Accession No. AC1112218.2, transcription factor SMIF (HSA275986).

SEQ ID NO: 132 is a nucleic acid sequence associated with viral, such as Ebola, infection, and is the clone identified as Nucleotide Sequence MV13-E5, proximal end. The human homolog is the (−) strand of GenBank Accession No. AC112218.2, transcription factor SMIF (HSA275986).

SEQ ID NO: 133 is a nucleic acid sequence associated with viral, such as Ebola, infection, and is the clone identified as Nucleotide Sequence MV13-E6, proximal end. The human homolog is the (−) strand of GenBank Accession No. AC112218.2, transcription factor SMIF (HSA275986).

SEQ ID NO: 134 is a nucleic acid sequence associated with viral, such as Ebola, infection, and is the clone identified as Nucleotide Sequence MV13-E7, proximal end. The human homolog is the (−) strand of GenBank Accession No. AC112218.2, transcription factor SMIF (HSA275986).

SEQ ID NO: 135 is a nucleic acid sequence associated with viral, such as Ebola, infection, and is the clone identified as Nucleotide Sequence MV13-E8, proximal end. The human homolog is the (−) strand of GenBank Accession No. AC112218.2, transcription factor SMIF (HSA275986).

SEQ ID NO: 136 is a nucleic acid sequence associated with viral, such as Ebola, infection, and is the clone identified as Nucleotide Sequence MV13-E9, proximal end. The human homolog is the (−) strand of GenBank Accession No. AC112218.2, transcription factor SMIF (HSA275986).

SEQ ID NO: 137 is a nucleic acid sequence associated with viral, such as Ebola, infection, and is the clone identified as Nucleotide Sequence MV13-E10, proximal end. The human homolog is the (−) strand of GenBank Accession Neo. AC112218.2, transcription factor SMIF (HSA75986).

SEQ ID NO: 138 is a nucleic acid sequence associated with viral, such as Ebola, infection, and is the clone identified as Nucleotide Sequence MV13-E2, distal end. The human homolog is the (+) strand of GenBank Accession No. AL031293.1, KIAA1026.

SEQ ID NO: 139 is a nucleic acid sequence associated with viral, such as Ebola, infection, and is the clone identified as Nucleotide Sequence MV13-E3, distal end. The human homolog is the (+) strand of GenBank Accession No. AL035587.5, trinucleotide repeat containing 5 (TNRC5).

SEQ ID NO: 140 is a nucleic acid sequence associated with viral, such as Ebola, infection, and is the clone identified as Nucleotide Sequence MV13-E4, distal end. The human homolog is the (−) strand of GenBank Accession No. AC126182.2, homogentisate 1,2-dioxygenase (HGD).

SEQ ID NO: 141 is a nucleic acid sequence associated with viral, such as Ebola, infection, and is the clone identified as Nucleotide Sequence MV13-E5, distal end. The human homolog is the (+) strand of GenBank Accession No. AL591643.4, a region of chromosome Xq23-24.

SEQ ID NO: 142 is a nucleic acid sequence associated with viral, such as Ebola, infection, and is the clone identified as Nucleotide Sequence MV13-E6, distal end. The human homolog is the (−) strand of GenBank Accession No. AC113603.3, a region of chromosome 4p15.3.

SEQ ID NO: 143 is a nucleic acid sequence associated with viral, such as Ebola, infection, and is the clone identified as Nucleotide Sequence MV13-E7, distal end. The human homolog is the (+) strand of GenBank Accession No. AC011995.8, similar to LWamide neuropeptide precursor protein [*Hydractinia echinata*] (LOC129883).

SEQ ID NO: 144 is a nucleic acid sequence associated with viral, such as Ebola, infection, and is the clone identified as Nucleotide Sequence MV13-E8, distal end. The human homolog is the (−) stand of GenBank Accession No. AC084208.5, a region of chromosome 2q21.

SEQ ID NO: 145 is a nucleic acid sequence associated with viral, such as Ebola, infection, and is the clone identified as Nucleotide Sequence MV13-E9, distal end. The human homolog is the (−) strand of GenBank Accession No. AL391259.15, a region of chromosome Xp11.4, including ubiquitin specific protease 9 (USP9X).

SEQ ID NO: 146 is a nucleic acid sequence associated with viral, such as Ebola, infection, and is the clone identified as Nucleotide Sequence MV13-E10, distal end. The human homolog is the (+) strand of GenBank Accession No. AC006397.1, LOC221829.

SEQ ID NO: 147 is a nucleic acid sequence associated with viral, such as Ebola, infection, and is the clone identified as Nucleotide Sequence MV7-B2, distal end. The human homolog is the (+) strand of GenBank Accession No. X14945.1, U3 small nuclear RNA gene.

SEQ ID NO: 148 is a nucleic acid sequence associated with viral, such as Ebola, infection, and is the clone identified as Nucleotide Sequence MV7-B2, proximal end. The human homolog is the (+) stand of GenBank Accession No. X14945.1, U3 small nuclear RNA gene.

SEQ ID NO: 149 is a nucleic acid sequence associated with viral, such as Ebola, infection, and is the clone identified as Nucleotide Sequence MV7-E1, proximal end. The human homolog is the (−) strand of GenBank Accession No. X14945.1, U3 small nuclear RNA gene.

SEQ ID NO: 150 is a nucleic acid sequence associated with viral, such as Ebola, infection, and is the clone identified as Nucleotide Sequence MV7-E2, proximal end. The human homolog is the (−) strand of GenBank Accession No. X14945.1, U3 small nuclear RNA gene.

SEQ ID NO: 151 is a nucleic acid sequence associated with viral, such as Ebola, infection, and is the clone identified as Nucleotide Sequence MV7-E2, distal end. The human homolog is the (−) stand of GenBank Accession No. X14945.1, U3 small nuclear RNA gene.

SEQ ID NO: 152 is a nucleic acid sequence associated with viral, such as Ebola, infection, and is the clone identified as Nucleotide Sequence MV7-E5, proximal end. The human homolog is the (−) strand of GenBank Accession No. X14945.1, U3 small nuclear RNA gene.

SEQ ID NO: 153 is a nucleic acid sequence associated with viral, such as Ebola, infection, and is the clone identified as Nucleotide Sequence MV8-E1, proximal end. The human homolog is the (−) strand of GenBank Accession No. X14945.1, U3 small nuclear RNA gene.

SEQ ID NO: 154 is a nucleic acid sequence associated with viral, such as Ebola, infection, and is the clone identified as Nucleotide Sequence MV8-E1, distal end. The human homolog is the (+) strand of GenBank Accession No. X14945.1, U3 small nuclear RNA gene.

SEQ ID NO: 155 is a nucleic acid sequence associated with viral, such as Ebola, infection, and is the clone identified as Nucleotide Sequence MV7-B3, distal end. The human homolog is the (+) strand of GenBank Accession No. AL365203.19, integrin, beta 1 (ITGB1).

SEQ ID NO: 156 is a nucleic acid sequence associated with viral, such as Ebola, infection, and is the clone identified as Nucleotide Sequence MV7-B3, proximal end. The human homolog is the (−) strand of GenBank Accession No. AL365203.19, ITGB1.

SEQ ID NO: 157 is a nucleic acid sequence associated with viral, such as Ebola, infection, and is the clone identified as Nucleotide Sequence MV7-E3, proximal end. The human homolog is the (+) strand of GenBank Accession No. AL365203.19, ITGB1.

SEQ ID NO: 158 is a nucleic acid sequence associated with viral, such as Ebola, infection, and is the clone identified as Nucleotide Sequence MV7-E3, distal end. The human homolog is the (−) strand of GenanB Accession No. AL365203.19, ITGB1.

SEQ ID NO: 159 is a nucleic acid sequence associated with viral, such as Ebola, infection, and is the clone identified as Nucleotide Sequence MV7-E1, distal end. The human homolog is the (+) strand of GenBank Accession No. AP001132.4, acrosomal vesicle protein 1 (ACRV1) and CHK1 checkpoint homolog (CHEK1).

SEQ ID NO: 160 is a nucleic acid sequence associated with viral, such as Ebola, infection, and is the clone identified as Nucleotide Sequence MV7-E5, distal end. The human homolog is the (−) strand of GenBank Accession No. AK025453.1, prospero-related homeobox 1 (PROX1).

SEQ ID NO: 161 is a nucleic acid sequence associated with viral, such as Ebola, infection, and is the clone identified as Nucleotide Sequence MV14-E1, proximal end. The human homolog is the (+) strand of GenBank Accession No. AL590543.8, hypothetical protein FLJ20627.

SEQ ID NO: 162 is a nucleic acid sequence associated with viral, such as Ebola, infection, and is the clone identified as Nucleotide Sequence MV14-E2, proximal end. The human homolog is the (+) strand of GenBank Accession No. AL590543.8, hypothetical protein FLJ20627.

SEQ ID NO: 163 is a nucleic acid sequence associated with viral, such as Ebola, infection, and is the clone identified as Nucleotide Sequence MV14-E3, proximal end. The human homolog is the (+) strand of GenBank Accession No. AL590543.8, hypothetical protein FLJ20627.

SEQ ID NO: 164 is a nucleic acid sequence associated with viral, such as Ebola, infection, and is the clone identified as Nucleotide Sequence MV14-E4, proximal end. The human homolog is the (+) strand of GenBank Accession No. AL590543.8, hypothetical protein FLJ20627.

SEQ ID NO: 165 is a nucleic acid sequence associated with viral, such as Ebola, infection, and is the clone identified as Nucleotide Sequence MV14-E4, distal end. The human homolog is the (−) strand of GenBank Accession No. AL590543.8, between hypothetical proteins FLJ20627 and FLJ12910.

SEQ ID NO: 166 is a nucleic acid sequence associated with viral, such as Ebola, infection, and is the clone identified as Nucleotide Sequence MV14-E5, proximal end. The human homolog is the (+) strand of GenBank Accession No. AL590543.8, hypothetical protein FLJ20627.

SEQ ID NO: 167 is a nucleic acid sequence associated with viral, such as Ebola, infection, and is the clone identified as Nucleotide Sequence MV14-E8, proximal end. The human homolog is the (+) strand of GenBank Accession No. AL590543.8, hypothetical protein FLJ20627.

SEQ ID NO: 168 is a nucleic acid sequence associated with viral, such as Ebola, infection, and is the clone identified as Nucleotide Sequence MV14-E9, proximal end. The human homolog is the (+) strand of GenBank Accession No. AL590543.8, hypothetical protein FLJ20627.

SEQ ID NO: 169 is a nucleic acid sequence associated with viral such as Ebola, infection, and is the clone identified as Nucleotide Sequence MV14-E9, distal end. The human homolog is the (−) strand of GenBank Accession No. AL590543.8, between hypothetical proteins FLJ20627 and FLJ12910.

SEQ ID NO: 170 is a nucleic acid sequence associated with viral, such as Ebola, infection, and is the clone identified as Nucleotide Sequence MV14-E10, proximal end. The human homolog is the (+) strand of GenBank Accession No. AL590543.8, hypothetical protein FLJ20627.

SEQ ID NO: 171 is a nucleic acid sequence associated with viral, such as Ebola, infection, and is the clone identified as Nucleotide Sequence MV14-E10, distal end. The human homolog is the (−) strand of GenBank Accession No. AL590543.8, hypothetical protein FLJ20627.

SEQ ID NO: 172 is a nucleic acid sequence associated with viral such as Ebola, infection, and is the clone identified as Nucleotide Sequence MV19-E2, proximal end. The human homolog is the (+) strand of GenBank Accession No. AL590543.8, hypothetical protein FLJ20627.

SEQ ID NO: 173 is a nucleic acid sequence associated with viral, such as Ebola, infection, and is the clone identified as Nucleotide Sequence MV19-E2, distal end. The human homolog is the (−) strand of GenBank Accession No. AL590543.8, between hypothetical proteins FLJ20627 and FLJ12910.

SEQ ID NO: 174 is a nucleic acid sequence associated with viral, such as Ebola, infection, and is the clone identified as Nucleotide Sequence MV14-E1, distal end. The human homolog is the (+) strand of GenBank Accession No. AC105001.3, between PIN2-interacting protein 1 (PINX1) and SRY (sex-determining region Y)-box7 (SOX7).

SEQ ID NO: 175 is a nucleic acid sequence associated with viral, such as Ebola, infection, and is the clone identified as Nucleotide Sequence MV14-E2, distal end. The human homolog is the (−) strand of GenBank Accession No. AC009520.16, LOC131920.

SEQ ID NO: 176 is a nucleic acid sequence associated with viral, such as Ebola, infection, and is the clone identified as Nucleotide Sequence MV14-E3, distal end. The human homolog is the (−) strand of GenBank Accession No. AL596329.5, a region of chromosome 13q14.

SEQ ID NO: 177 is a nucleic acid sequence associated with viral, such as Ebola, infection, and is the clone identified as Nucleotide Sequence MV14-E5, distal end. The human homolog is the (+) strand of GenBank Accession No. AC023844.6, neurotrophic tyrosine kinase, receptor, type 3 (NTRK3).

SEQ ID NO: 178 is a nucleic acid sequence associated with viral, such as Ebola, infection, and is the clone identified as Nucleotide Sequence MV14-E7, promimal end. The human homolog is the (−) strand of GenBank Accession No. AC024940.39, between TERA protein (TERA) and hypothetical protein FLJ13224.

SEQ ID NO: 179 is a nucleic acid sequence associated with viral, such as Ebola, infection, and is the clone identified as Nucleotide Sequence MV14-E7, distal end. The human homolog is the (+) strand of GenBank Accession No. AC024940.39, flanking TERA protein (TERA) and hypothetical protein FLJ13224.

SEQ ID NO: 180 is a nucleic acid sequence associated with viral, such as Ebola, infection, and is the clone identified as Nucleotide Sequence MV14-E8, distal end. The human homolog is the (−) stand of GenBank Accession No. AC084335.6, hypothetical gene LOC284260.

SEQ ID NO: 181 is a nucleic acid sequence associated with viral, such as Ebola, infection, and is the clone identified as Nucleotide Sequence MV14-E11, proximal end. The human homolog is the (+) strand of GenBank Accession No. AC073108.9, POM (POM121 homolog) and ZP3 fusion (POMZP3).

SEQ ID NO: 182 is a nucleic acid sequence associated with viral, such as Ebola, infection, and is the clone identified as Nucleotide Sequence MV14-E11, distal end. The human homolog is the (−) strand of GenBank Accession No. AC073108.9, POM (POM121 homolog) and ZP3 fusion (POMZP3).

SEQ ID NO: 183 is a nucleic acid sequence associated with viral, such as Ebola, infection, and is the clone identified as Nucleotide Sequence MV19-E4, distal end. The human homolog is the (+) strand of GenBank Accession No. AC087650.12, between DEAD/H box polypeptide 8 (DDX8) and similar to ribosomal protein L29 (cell surface heparin binding protein HIP) (LOC284064).

SEQ ID NO: 184 is a nucleic acid sequence associated with viral, such as Ebola, infection, and is the clone identified as Nucleotide Sequence MV20-E2, distal end. The human homolog is the (−) stand of GenBank Accession No. AC105285.3, LOC345307 and UDP-N-acetyl-D-galactosamine:polypeptide N-acetylgalactosaminyltransferase 7 (GALNT7).

SEQ ID NO: 185 is a nucleic acid sequence associated with viral such as Ebola, infection, and is the clone identified as Nucleotide Sequence MV20-E2, proximal end. The human homolog is the (+) strand of GenBank Accession No. AC105285.3, LOC345307 and UDP-N-acetyl-D-galactosmine:polypeptide N-acetylgalactosaminyltransferase 7 (GALNT7).

SEQ ID NO: 186 is a nucleic acid sequence associated with viral, such as Ebola, infection, and is the clone identified as Nucleotide Sequence MV20-B1, distal end. The human homolog is the (+) strand of GenBank Accession No.

AC105285.3, LOC345307 and UDP-N-acetyl-D-galactosamine:polypeptide N-acetylgalactosaminyltransferase 7 (GALNT7).

SEQ ID NO: 187 is a nucleic acid sequence associated with viral, such as Ebola, infection, and is the clone identified as Nucleotide Sequence MV20-E3, distal end. The murine homolog is the (+) strand of GenBank Accession No. NG_001440.1, *Mus musculus* 55 rRNA pseudogene ($Rn5_s$-ps1).

SEQ ID NO: 188 is a nucleic acid sequence associated with viral, such as Ebola, infection, and is the clone identified as Nucleotide Sequence MV20-E5, proximal end. The human homolog is the (+) strand of GenBank Accession No. AL121886.22, between ribosomal protein L27a pseudogene (RPL27AP) and v-myb myeloblastosis viral oncogene homolog-like 2 (MYBL2).

SEQ ID NO: 189 is a nucleic acid sequence associated with viral, such as Ebola, infection, and is the clone identified as Nucleotide Sequence MV28-E2, proximal end. The human homolog is the (+) strand of GenBank Accession No. AL121886.22, between RPL27AP and MYBL2.

SEQ ID NO: 190 is a nucleic acid sequence associated with viral, such as Ebola, infection, and is the clone identified as Nucleotide Sequence MV28-E6, proximal end. The human homolog is the (+) strand of GenBank Accession No. AL121886.22, between RPL27AP and MYBL2.

SEQ ID NO: 191 is a nucleic acid sequence associated with viral, such as Ebola, infection, and is the clone identified as Nucleotide Sequence MV28-E9, proximal end. The human homolog is the (+) stand of GenBank Accession No. AL121886.22, between RPL27AP and MYBL2.

SEQ ID NO: 192 is a nucleic acid sequence associated with viral, such as Ebola, infection, and is the clone identified as Nucleotide Sequence MV28-E9, distal end. The human homolog is the (−) strand of GenBank Accession No. AL121886.22, between RPL27AP and MYBL2.

SEQ ID NO: 193 is a nucleic acid sequence associated with viral, such as Ebola, infection, and is the clone identified as Nucleotide Sequence MV20-E6, distal end. The human homolog is the (+) strand of GenBank Accession No. AP000711.4, Down's syndrome cell adhesion molecule like 1 (DSCAML1).

SEQ ID NO: 194 is a nucleic acid sequence associated with viral, such as Ebola, infection, and is the clone identified as Nucleotide Sequence MV20-E7, distal end. The human homolog is the (+) strand of GenBank Accession No. AL391555.19, LOC148529.

SEQ ID NO: 195 is a nucleic acid sequence associated with viral, such as Ebola, infection, and is the clone identified as Nucleotide Sequence MV20-B4, distal end. The human homolog is the (−) strand of GenBank Accession No. AC112129.4, Huntingtin-associated protein interacting protein (HAPIP).

SEQ ID NO: 196 is a nucleic acid sequence associated with viral, such as Ebola, infection, and is the clone identified as Nucleotide Sequence MV22-E1, proximal end. The human homolog is the (−) stand of GenBank Accession No. Z69732.1, between LOC158525 and similar to RIKEN cDNA 1210001E11 (LOC347366).

SEQ ID NO: 197 is a nucleic acid sequence associated with viral, such as Ebola, infection, and is the clone identified as Nucleotide Sequence MV22-E3, proximal end. The human homolog is the (−) strand of GenBank Accession No. Z69732.1, between LOC158525 and similar to RIKEN cDNA 1210001E11 (LOC347366).

SEQ ID NO: 198 is a nucleic acid sequence associated with viral, such as Ebola, infection, and is the clone identified as Nucleotide Sequence MV22-E5, proximal end. The human homolog is the (−) strand of GenBank Accession No. Z69732.1, between LOC158525 and similar to RIKEN cDNA 1210001E11 (LOC347366).

SEQ ID NO: 199 is a nucleic acid sequence associated with viral, such as Ebola, infection, and is the clone identified as Nucleotide Sequence MV22-E5, proximal end. The human homolog is the (−) strand of GenBank Accession No. Z69732.1, between LOC158525 and similar to RIKEN cDNA 1210001E11 (LOC347366).

SEQ ID NO: 200 is a nucleic acid sequence associated with viral, such as Ebola, infection, and is the clone identified as Nucleotide Sequence MV22-E8, proximal end. The human homolog is the (−) strand of GenBank Accession No. Z69732.1, between LOC158525 and similar to RIKEN cDNA 1210001E11 (LOC347366).

SEQ ID NO: 201 is a nucleic acid sequence associated with viral, such as Ebola, infection, and is the clone identified as Nucleotide Sequence MV22-E2, distal end. The human homolog is the (−) strand of GenBank Accession No. AL590543.8, hypothetical protein FLJ12910.

SEQ ID NO: 202 is a nucleic acid sequence associated with viral, such as Ebola, infection, and is the clone identified as Nucleotide Sequence MV22-E2, proximal end. The human homolog is the (+) strand of GenBank Accession No. AL590543.8, hypothetical protein FLJ12910.

SEQ ID NO: 203 is a nucleic acid sequence associated with viral, such as Ebola, infection, and is the clone identified as Nucleotide Sequence MV22-E6, distal end. The human homolog is the (−) strand of GenBank Accession No. AL590543.8, hypothetical protein FLJ12910.

SEQ ID NO: 204 is a nucleic acid sequence associated with viral, such as Ebola, infection, and is the clone identified as Nucleotide Sequence MV22-E6, proximal end. The human homolog is the (+) strand of GenBank Accession No. AL590543.8, hypothetical protein FLJ12910.

SEQ ID NO: 205 is a nucleic acid sequence associated with viral, such as Ebola, infection, and is the clone identified as Nucleotide Sequence MV22-E7, distal end. The human homolog is the (+) strand of GenBank Accession No. AC005284.1, LOC350411.

SEQ ID NO: 206 is a nucleic acid sequence associated with viral, such as Ebola, infection, and is the clone identified as Nucleotide Sequence MV22-E9, proximal end. The human homolog is the (+) strand of GenBank Accession No. AP000505.1, between allograft inflammatory factor 1 (AIF1) and HLA-B associated transcript 2 (BAT2).

SEQ ID NO: 207 is a nucleic acid sequence associated with viral, such as Ebola, infection, and is the clone identified as Nucleotide Sequence MV27-E1, distal end. The human homolog is the (−) strand of GenBank Accession No. AC008755.8, C19orf7.

SEQ ID NO: 208 is a nucleic acid sequence associated with viral, such as Ebola, infection, and is the clone identified as Nucleotide Sequence MV27-E2, distal end. The human homolog is the (+) strand of GenBank Accession No. AC058791.4, between LOC346658 and LOC340349.

SEQ ID NO: 209 is a nucleic acid sequence associated with viral, such as Ebola, infection, and is the clone identified as Nucleotide Sequence MV27-E2, proximal end. The human homolog is the (−) strand of GenBank Accession No. AC058791.4, between LOC346658 and LOC340349.

SEQ ID NO: 210 is a nucleic acid sequence associated with viral, such as Ebola, infection, and is the clone identified as Nucleotide Sequence MV27-E3, distal end. The human homolog is the (+) strand of GenBank Accession No. AC079030.13, a region of chromosome 12q21.

SEQ ID NO: 211 is a nucleic acid sequence associated with viral, such as Ebola, infection, and is the clone identified as Nucleotide Sequence MV27-E3, proximal end. The human homolog is the (−) strand of GenBank Accession No. AC139138.2, between LOC339248 and hypothetical protein FLJ22659.

SEQ ID NO: 212 is a nucleic acid sequence associated with viral, such as Ebola, infection, and is the clone identified as Nucleotide Sequence MV27-E4, distal end. The human homolog is the (−) strand of GenBank Accession No. AL513550.9, between SR rich protein DKFZp564B0769 and hypothetical protein MGC14793.

SEQ ID NO: 213 is a nucleic acid sequence associated with viral, such as Ebola, infection, and is the clone identified as Nucleotide Sequence MV28-B1, distal end. The human homolog is the (−) stand of GenBank Accession No. AP001160.4, hypothetical protein FLJ10439.

SEQ ID NO: 214 is a nucleic acid sequence associated with vial, such as Ebola, infection, and is the clone identified as Nucleotide Sequence MV28-B1, proximal end. The human homolog is the (+) strand of GenBank Accession No. AP001160.4, hypothetical protein FLJ10439.

SEQ ID NO: 215 is a nucleic acid sequence associated with viral, such as Ebola, infection, and is the clone identified as Nucleotide Sequence MV28-B3, distal end. The human homolog is the (+) strand of GenBank Accession No. AC090826.15, between cytochrome P450, family 11, subfamily A, polypeptide 1 (CYP11A1) and sema domain, immunoglobulin domain (Ig) and GPI membrane anchor, (semaphoring) 7A.

SEQ ID NO: 216 is a nucleic acid sequence associated with viral, such as Ebola, infection, and is the clone identified as Nucleotide Sequence MV28-B3, proximal end. The human homolog is the (−) strand of GenBank Accession No. AC090826.15, between cytochrome P450, family 11, subfamily A, polypeptide 1 (CYP11A1) and sema domain, immunoglobulin domain (Ig) and GPI membrane anchor, (semaphoring) 7A.

SEQ ID NO: 217 is a nucleic acid sequence associated with viral, such as Ebola, infection, and is the clone identified as Nucleotide Sequence MV28-E11, proximal end. The human homolog is the (+) strand of GenBank Accession No. AC090826.15, between cytochrome P450, family 11, subfamily A, polypeptide 1 (CYP11A1) and sema domain, immunoglobulin domain (Ig) and GPI membrane anchor, (semaphoring) 7A.

SEQ ID NO: 218 is a nucleic acid sequence associated with vial, such as Ebola, infection, and is the clone identified as Nucleotide Sequence MV28-EB11, distal end. The human homolog is the (−) strand of GenBank Accession No. AC090826.15, between cytochrome P450, family 11, subfamily A, polypeptide 1 (CYP11A1) and sema domain, immunoglobulin domain (Ig) and GPI membrane anchor, (semaphoring) 7A.

SEQ ID NO: 219 is a nucleic acid sequence associated with viral, such as Ebola, infection, and is the clone identified as Nucleotide Sequence MV28-E1, proximal end. The human homolog is the (−) strand of GenBank Accession No. AC011500.7, ribosomal protein S16 (RPS16).

SEQ ID NO: 220 is a nucleic acid sequence associated with viral, such as Ebola, infection, and is the clone identified as Nucleotide Sequence MV28-E1, distal end. The human homolog is the (+) stand of GenBank Accession No. AC011500.7, ribosomal protein S16 (RPS16).

SEQ ID NO: 221 is a nucleic acid sequence associated with viral, such as Ebola, infection, and is the clone identified as Nucleotide Sequence MV28-E4, distal end. The human homolog is the (−) strand of GenBank Accession No. AC091172.11, between hypothetical protein DKFZp434H0115 and ATP citrate lyase (ACLY).

SEQ ID NO: 222 is a nucleic acid sequence associated with viral, such as Ebola, infection, and is the clone identified as Nucleotide Sequence MV28-E4, proximal end. The human homolog is the (+) strand of GenBank Accession No. AC091172.11, between hypothetical protein DKFZp434H0115 and ACLY.

SEQ ID NO: 223 is a nucleic acid sequence associated with viral, such as Ebola, infection, and is the clone identified as Nucleotide Sequence MV28-E7, distal end. The human homolog is the (+) strand of GenBank Accession No. AL035594.7, protein tyrosine phosphatase, receptor type, K (PTPRK).

SEQ ID NO: 224 is a nucleic acid sequence associated with viral, such as Ebola, infection, and is the clone identified as Nucleotide Sequence MV28-E7, proximal end. The human homolog is the (+) strand of GenBank Accession No. AC124857.2, calnexin (CANX) and (−) strand of GenBank Accession No. AL035594.7, protein tyrosine phosphatase, receptor type, K (PTPRK).

SEQ ID NO: 225 is a nucleic acid sequence associated with viral, such as Ebola, infection, and is the clone identified as Nucleotide Sequence MV28-E8, distal end. The human homolog is the (+) strand of GenBank Accession No. AC009144.5, cyclin M2 (CNNM2).

SEQ ID NO: 226 is a nucleic acid sequence associated with viral, such as Ebola, infection, and is the clone identified as Nucleotide Sequence MV28-E8, proximal end. The human homolog is the (+) strand of GenBank Accession No. AC011510.7, AXL receptor tyrosine kinase (AXL).

SEQ ID NO: 227 is a nucleic acid sequence showing GenBank Accession No. BC008947, *Homo sapiens* chromosome 10 open reading frame 3, mRNA (cDNA clone MGC:3422 IMAGE:3028566). This sequence is associated with viral infection, such as Ebola infection.

SEQ ID NO: 228 is an amino acid sequence encoded by SEQ ID NO: 227.

SEQ ID NO: 229 is a nucleic acid sequence showing GenBank Accession No. NM_018131, *Homo sapiens* chromosome 10 open reading frame 3 (C10orf3). This sequence is associated with viral infection, such as Ebola infection.

SEQ ID NO: 230 is an amino acid sequence encoded by SEQ ID NO: 229.

SEQ ID NO: 231 is a nucleic acid sequence showing GenBank Accession No. NM_013451, *Homo sapiens* fer-1-like 3, myoferlin (*C. elegans*) (FER1L3), transcript variant 1, mRNA. This sequence is associated with viral infection, such as Ebola infection.

SEQ ID NO: 232 is an amino acid sequence encoded by SEQ ID NO: 231.

SEQ ID NOS: 233 and 234 are exemplary complementary primers.

SEQ ID NOS: 235-237 are primer sequences used to sequence the shuttle clones as described in Example 2.

SEQ ID NOS: 238-241 are Rab9 siRNA sequences.

SEQ ID NOS: 242-245 are AXL receptor tyrosine kinase siRNA sequences.

SEQ ID NOS: 246-295 are beta-chimerin receptor tyrosine kinase RNAi sequences.

SEQ ID NOS: 296-345 are retinoblastoma binding protein 1 RNAi sequences.

SEQ ID NOS: 346-395 are *Homo sapiens* chromosome 10 open reading frame 3 RNAi sequences.

SEQ ID NOS: 396-445 are *Homo sapiens* fer-1-like 3, myoferlin (*C. elegans*), transcript variant 1 RNAi sequences.

SEQ ID NOS: 446-495 are *Homo sapiens* chromosome 10 open reading frame 3 (C10orf3) RNAi sequences.

SEQ ID NOS: 496-545 are malic enzyme RNAi sequences.

SEQ ID NOS: 546-595 are cadherin related 23 RNAi sequences.

SEQ ID NOS: 596-645 are sideroflexin 5 RNAi sequences.

SEQ ID NOS: 646-695 are polybromo 1 (PB1) RNAi sequences.

SEQ ID NOS: 696-720 are elongation factor for selenoprotein translation RNAi sequences.

SEQ ID NOS: 721-745 are integrin, beta 1 RNAi sequences.

SEQ ID NOS: 746-795 are huntingtin interacting protein 1 RNAi sequences.

SEQ ID NOS: 796-845 are cyclin M2 RNAi sequences.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid" includes single or plural nucleic acids and is considered equivalent to the phrase "comprising at least one nucleic acid." The term "or" refers to a single element of stated alternative elements or a combination of two or more elements, unless the context clearly indicates otherwise. For example, the phrase "a first nucleic acid or a second nucleic acid" refers to the first nucleic acid, the second nucleic acid, or a combination of both the first and second nucleic acids. As used herein, "comprises" means "includes." Thus, "comprising a promoter and an open reading frame," means "including a promoter and an open reading frame," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

A=adenine
C=cytosine
DNA=deoxyribonucleic acid
ds=double-stranded (for example, dsDNA)
G=guanine
mg=milligram
ng=nanogram
PCR=polymerase chain reaction
Pu=purine
Py=pyrimidine
RNA=ribonucleic acid
mRNA=messenger RNA
MOI=multiplicity of infection
siRNA=short interfering or interrupting RNA
ss=single-stranded (for example, ssDNA)
T=thymine
$T_m$=melting temperature
U=uracil
μg=microgram
μl=microliter Amplification of a nucleic acid. To increase the number of copies of a nucleic acid. Several methods can be used to amplify a nucleic acid, such as polymerase chain reaction (PCR). Other examples of amplification include, but are not limited to, strand displacement amplification (U.S. Pat. No. 5,744,311); transcription-free isothermal amplification (U.S. Pat. No. 6,033,881); repair chain reaction amplification (WO 90/01069); ligase chain reaction amplification (European Patent Appl. 320 308); gap filling ligase chain reaction amplification (U.S. Pat. No. 5,427,930); and NASBA™ RNA transcription-free amplification (U.S. Pat. No. 6,025,134).

The amplification products ("amplicons") can be further processed, manipulated, or characterized by electrophoresis, restriction endonuclease digestion, hybridization, nucleic acid sequencing, ligation, or other molecular biology techniques. Standard protocols can be modified. For example, PCR can be modified by using reverse transcriptase PCR (RT-PCR) to amplify RNA molecules.

Antisense, Sense, and Antigene. Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a particular dsDNA target. These molecule can be used to interfere with gene expression.

Double-stranded DNA (dsDNA) has two strands, a 5' to 3' strand, referred to as the plus (+) strand, and a 3' to 5' strand (the reverse complement), referred to as the minus (−) strand. Because RNA polymerase adds nucleic acids in a 5' to 3' direction, the minus strand of the DNA serves as the template for the RNA during transcription. Thus, the RNA formed will have a sequence complementary to the minus strand and virtually identical to the plus strand, except that U is substituted for T in RNA molecules.

Array. An arrangement of biological samples or molecules, such as an arrangement of tissues, cells, or biological macromolecules (including, but not limited to, peptides or nucleic acids) in addressable locations on or in a substrate. The arrangement of molecules within the array can be regular, such as being arranged in uniform rows and columns, or irregular. The number of addressable locations within the array can vary, for example from a few (such as two or three) to more than 50, 100, 200, 500, 1000, 10,000, or more. In certain examples, the array includes one or more molecules or samples occurring on the array a plurality of times (twice or more) to provide an added feature to the array, such as redundant activity or to provide internal controls. A "microarray" is an array that is miniaturized and evaluated or analyzed using microscopy.

Within an array, each arrayed sample or molecule is addressable, such that its location can be reliably and consistently determined within the at least two dimensions of the array. The location or address of each sample or molecule can be assigned when it is applied to the array, and a key or guide can be provided in order to correlate each location with the appropriate target sample or molecule position. Ordered arrays can be arranged in a symmetrical grid pattern or other patterns, for example, in radially distributed lines, spiral lines, or ordered clusters. Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

The sample or molecule addresses on an array can assume many different shapes. For example, substantially square regions can be used as addresses within arrays, but addresses can be differently shaped, for example, substantially rectangular, triangular, oval, irregular, or another shape. The term "spot" refers generally to a localized placement of molecules, tissue or cells, and is not limited to a round or substantially round region or address.

Examples of macroarrays include the Histo™-array and INSTA-blot™ lines of products available from Imgenix, Inc. (San Diego, Calif.) and the Max Array™ line of products available from Zymed Laboratories, Inc. (South San Francisco, Calif.), while exemplary microarrays include the various GeneChip® technologies and products available from Affymetrix, Inc. (Santa Clara, Calif.) and the Hilight™, Label Star™, and Array-Ready Oligo Set lines of products available from Qiagen, Inc. (Valencia, Calif.).

β-chimerin. The term β-chimerin includes any β-chimerin gene, cDNA, RNA, or protein from any organism and is a β-chimerin that can function as a type of rho-GTPase. In some examples, β-chimerin is involved in viral infection.

Rho-GTPases are a family of small GTPases implicated as components of cellular signal transduction cascades. Signals that pass through rho-GTPase cascades can be initiated by the activation of cell surface proteins, such as growth factors. Functions of signaling cascades mediated by rho-GTPases, include, but are not limited to, alterations in cellular morphology which are linked to processes such as immune cell function, oncogenesis, metastasis and certain diseases (Peck, *FEBS Lett.* 528:27, 2002).

Examples of native β-chimerin nucleic acid sequences include, but are not limited to those shown in SEQ ID NOS: 21-22 (such as a target sequence associated with SEQ ID NOS: 21-22), as well as the protein sequence encoded thereby. This cell line remains $CD4^+$ after exposure to HIV 1 and HIV 2 and is resistant to HIV infection. β-chimerin also includes variants, fusions, and fragments of the disclosed nucleic acid and amino acid sequences that retain β-chimerin biological activity.

Examples of β-chimerin amino acid sequences include, but are not limited to: Genbank Accession Nos: NM__004067 (mRNA) and NP__004058.1 (protein). In one example, a β-chimerin sequence includes a full-length wild-type (or native) sequence, as well as β-chimerin allelic variants, variants, fragments, homologs or fusion sequences that retain the ability to function as a type of rho-GTPase. In certain examples, β-chimerin has at least 80% sequence identity, for example at least 85%, 90%, 95%, or 98% sequence identity to a native β-chimerin.

cDNA (complementary DNA). A piece of DNA lacking internal, non-coding segments (introns) and transcriptional regulatory sequences. A cDNA also can contain untranslated regions (UTRs) that are responsible for translational control in the corresponding RNA molecule. cDNA can be produced using various methods, such as synthesis in the laboratory by reverse transcription from messenger RNA extracted from cells.

Complementary. Complementary binding occurs when the base of one nucleic acid molecule forms a hydrogen bond the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA.

Nucleic acid molecules can be complementary to each other even without complete hydrogen-bonding of all bases of each molecule. By way of example only (and without limitation), the ssDNA: 5'-GCTTGCCAAACCTACA-3' (SEQ ID NO: 233) is considered complementary to the ssDNA 3'-CGAACGGTCTGGATOT-5' (SEQ ID NO: 234) even though there is a mismatched base pair (A-C rather than A-T or G-C) at the ninth position.

Conservative substitution: A substitution of an amino acid residue for another amino acid residue having similar biochemical properties. Typically, conservative substitutions have little to no impact on the biological activity of a resulting polypeptide. In a particular example, a conservative substitution is an amino acid substitution in a peptide that does not substantially affect the biological function of the peptide. A peptide can include one or more amino acid substitutions, for example 2-10 conservative substitutions, 2-5 conservative substitutions, 4-9 conservative substitutions, such as 2, 5 or 10 conservative substitutions.

For example, a conservative substitution in a β-chimerin peptide (such as a peptide encoded by a target sequence associated with SEQ ID NO: 21 or 22) does not substantially affect the ability of β-chimerin to confer resistance to HIV infection. In another example, a conservative substitution in a Rab9 peptide (such as a peptide encoded by a target sequence associated with SEQ ID NOS: 118 or 119) is one that does not substantially affect the ability of Rab9 to confer resistance to infection by a pathogen that can hijack a lipid raft, such as HIV or Ebola.

A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids.

Examples of amino acids which can be substituted for an original amino acid in a protein and which are regarded as conservative substitutions include, but are not limited to: Ser for Ala; Lys for Arg; Gln or His for Asn; Glu for Asp; Ser for Cys; Asn for Gin; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Tbr; Tyr for Trp; Trp or Phe for Tyr; and Ile or Leu for Val.

Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988) and in standard textbooks of genetics and molecular biology.

Ebola virus. A highly contagious hemorrhagic virus named after a river in the Democratic Republic of the Congo (formerly Zaire) in Africa, where it was first recognized. Ebola is one of two members of a family of RNA viruses called the Filoviridae. There are four identified subtypes of Ebola virus. Three of the four have caused disease in humans: Ebola-Zaire, Ebola-Sudan, and Ebola-Ivory Coast. The fourth, Ebola-Reston, has caused disease in nonhuman primates, but not in humans.

Ebola hemorrhagic fever (Ebola BF) is a severe, often fatal disease in humans and nonhuman primates (for example, monkeys, gorillas, and chimpanzees) that is caused by Ebola virus infection. Diagnosing Ebola HF in a recently infected individual can be difficult because early symptoms, such as red eyes and a skin rash, are nonspecific to the virus and are seen in other subjects with diseases that occur much more frequently. Antigen-capture enzyme-linked immunosorbent assay (ELISA) testing, IgM ELISA, PCR, and virus isolation can be used to diagnose a case of Ebola HF within a few days after the onset of symptoms. Subjects tested later in the course of the disease, or after recovery, can be tested for IgM and IgG antibodies. The disease also can be diagnosed retrospectively in deceased patients by using immunohistochemistry testing, virus isolation, or PCR.

Encodes: Unless evident from its context, includes DNA sequences that encode a polypeptide, as the term is typically used, as well as DNA sequences that are transcribed into inhibitory antisense molecules.

Expression: With respect to a gene sequence, refers to transcription of the gene and, as appropriate, translation of the resulting mRNA script to a protein. Thus, expression of a protein coding sequence results from transcription and translation of the coding sequence.

Functional deletion: A mutation, partial or complete deletion, insertion, or other variation made to a gene sequence that inhibits production of the gene product or renders the gene product non-functional. For example, a functional deletion of a Rab9 gene in a cell results in a cells having non-functional Rab9 protein, which results in the cell having an increase resistance to infection by a pathogen that uses a lipid raft.

Gene. A nucleic acid sequence that encodes a polypeptide under the control of a regulatory sequence, such as a promoter or operator. A gene includes an open reading frame encoding a polypeptide of the present disclosure, as well as exon and (optionally) intron sequences. An intron is a DNA sequence present in a given gene that is not translated into protein and is generally found between exons. The coding sequence of the gene is the portion transcribed and translated into a polypeptide (in vivo, in vitro or in situ) when placed under the control of an appropriate regulatory sequence. The boundaries of the coding sequence can be determined by a start codon at the 5' (amino) terminus and a stop codon at the 3' (carboxyl) terminus. If the coding sequence is intended to be expressed in a eukaryotic cell, a polyadenylation signal and transcription termination sequence can be included 3' to the coding sequence.

Transcriptional and translational control sequences include, but are not limited to, DNA regulatory sequences such as promoters, enhancers, and terminators that provide for the expression of the coding sequence, such as expression in a host cell. A polyadenylation signal is an exemplary eukaryotic control sequence. A promoter is a regulatory region capable of binding RNA polymerase and initiating transcription of a downstream (3' direction) coding sequence. Additionally, a gene can include a signal sequence at the beginning of the coding sequence of a protein to be secreted or expressed on the surface of a cell. This sequence can encode a signal peptide, N-terminal to the mature polypeptide, which directs the host cell to translocate the polypeptide.

Host Cell. Any cell that can be infected with a virus or other pathogen, such as a bacterium. A host cell can be prokaryotic or eukaryotic, such as a cell from an insect, crustacean, mammal, bird, reptile, yeast, or a bacteria such as *E. coli*. Exemplary host cells include, but are not limited to, mammalian B-lymphocyte cells. Examples of viruses include, but are not limited to HIV, influenza A, and Ebola.

The host cell can be part of an organism, or part of a cell culture, such as a culture of mammalian cells or a bacterial culture. A host nucleic acid is a nucleic acid present in a host cell that expresses a host protein. Decreasing or inhibiting the interaction between a host polypeptide or host nucleic acid and a virus or viral protein can occur in vitro, in vivo, and in situ environments.

Human Immunodeficiency Virus (HIV). A retrovirus that causes immunosuppression in humans and leads to a disease complex known as acquired immunodeficiency syndrome (AIDS). This immunosuppression results from a progressive depletion and functional impairment of T lymphocytes expressing the CD4 cell surface glycoprotein. The loss of CD4 helper/inducer T cell function may underlie the loss of cellular and humoral immunity leading to the opportunistic infections and malignancies seen in AIDS.

Depletion of CD4 T cells results from the ability of HIV to selectively infect, replicate in, and ultimately destroy these T cells (for example see Klatzmann et al., *Science* 225:59, 1984). CD4 itself is an important component, and in some examples an essential component, of the cellular receptor for HIV.

HIV subtypes can be identified by particular number, such as HIV-1 and HIV-2. In the HIV life cycle, the virus enters a host cell in at least three stages: receptor docking, viral-cell membrane fusion, and particle uptake (D'Souza et al., *JAMA* 284:215, 2000). Receptor docking begins with a gp120 component of a virion spike binding to the CD4 receptor on the host cell. Conformational changes in gp120 induced by gp120-CD4 interaction promote an interaction between gp120 and either CCR5 or CXCR4 cellular co-receptors. The gp41 protein then mediates fusion of the viral and target cell membranes. More detailed information about HIV can be found in Coffin et al., *Retroviruses* (Cold Spring Harbor Laboratory Press, 1997).

Hybridization. Hybridization of a nucleic acid occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acids used. For example, temperature and ionic strength (such as $Na^+$ concentration) can affect the stringency of hybridization. Calculations regarding hybridization conditions required for attaining particular degrees of stringency are discussed in Sambrook et al., *Molecular Cloning: A Laboratory Manual* (Cold Spring Harbor Laboratory Press, Cold Spring Harbor, N.Y., 2001); and Tijssen, *Laboratory Techniques in Biochemistry and Molecular Biology—Hybridization with Nucleic Acid Probes* Part I, Chapter 2 (Elsevier, N.Y., 1993).

The $T_m$ is the temperature at which 50% of a given strand of nucleic acid is hybridized to its complementary strand. The $T_m$ of a particular nucleic acid can be determined by various methods, such as observing the transition state between a single-stranded and double-stranded state during a temperature change, such as heating a dsDNA from about 30° C. to about 110° C., and detecting when the dsDNA denatures to ssDNA. This can be accomplished by determining a melting profile for the nucleic acid. For longer nucleic acid fragments, such as PCR products, the nearest-neighbor method can be used to determine $T_m$ (Breslauer et al., *Proc. Natl. Acad. Sci. USA* 83:3746-50, 1986). Additionally, MeltCalc software can be used to determine $T_m$ (Schütz and von Ahsen, *Biotechniques* 30:8018-24, 1999).

For purposes of this disclosure, "stringent conditions" encompass conditions under which hybridization only will occur if there is less than 25% mismatch between the hybridization molecule and the target sequence. "Moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 5% mismatch will not hybridize.

Moderately stringent hybridization conditions are when the hybridization is performed at about 42° C. in a hybridization solution containing 25 mM $KPO_4$ (pH 7.4), 5×SSC, 5× Denhart's solution, 50 μg/mL denatured, sonicated salmon sperm DNA, 50% formamide, 100% Dextran sulfate, and 1-15 ng/mL probe (about $5\times10^7$ cpm/μg), while the washes are performed at about 50° C. with a wash solution containing 2×SSC and 0.1% sodium dodecyl sulfate.

Highly stringent hybridization conditions are when the hybridization is performed at about 42° C. in a hybridization solution containing 25 mM $KPO_4$ (pH 7.4), 5×SSC, 5× Denhart's solution, 50 μg/mL denatured, sonicated salmon sperm DNA, 50% formamide, 10% Dextran sulfate, and 1-15 ng/mL probe (about $5\times10^7$ cpm/μg), while the washes are performed at about 65° C. with a wash solution containing 0.2×SSC and 0.1% sodium dodecyl sulfate.

Infection. The entry, replication, insertion, lysis or other event or process involved with the pathogensis of a virus or other infectious agent into a host cell. Thus, decreasing infection includes decreasing entry, replication, insertion, lysis, or other pathogensis of a virus or other pathogen into a cell or subject, or combinations thereof. Infection includes the introduction of an infectious agent, such as a non-recombinant virus, recombinant virus, plasmid, bacteria, prion, eukaryotic microbe, or other agent capable of infecting a host, such as the cell of a subject.

In another example, infection is the introduction of a recombinant vector into a host cell via transduction, transformation, transfection, or other method. Vectors include, but are not limited to, viral, plasmid, cosmid, and artificial chromosome vectors. For example, a recombinant vector can include an antisense molecule, RNAi molecule, or siRNA that recognizes any target sequences associated with SEQ ID NOS: 1-227, 229, and 231, or variants, fusions, or fragments thereof, as well as SEQ ID NOS: 1-227, 229, and 231 themselves.

Influenza virus. A virus that causes respiratory disease or influenza ("the flu") and can lead to a secondary infection in the host, such as a bacterial infection of the lungs. Three types of influenza are currently known: influenza A, influenza B, and influenza C. Influenza A is the most common form of the virus and is capable of infection humans and non-human animals, such as pigs, horses, chickens, ducks and other birds.

The viral genome includes eight RNA molecules. HA, which encodes hemagglutinin (three hemagglutinin subtypes: H1, H2, and H3); M, which encodes two matrix proteins based on two different open reading frames within the nucleic acid sequence; NA encodes for neuraminidase; NP encodes the nucleoprotein; NS encodes two non-structural proteins based on different open reading frames within the nucleic acid sequence; and three genes that encode RNA polymerases (PA, PB1, PB2). The influenza virus can be categorized into subtypes on the bases of the surface glycoproteins.

The replication cycle of the influenza virus begins with binding of the viral hemagglutinin molecules to the surface carbohydrate of epithelial cell of a host cell, which draws the virus into the cell by receptor-mediated endocytosis. The viral membrane fuses with the endocytotic vesicle membrane, allowing the RNA molecules of the viral genome to enter the interior of the cell where these molecules later enter the cell nucleus and are replicated into viral-complementary RNA and new viral RNA and transcribed into viral mRNA, which are transported into the cytosol where they are translated into the proteins of new viral particles. After viral particles are assembled into new viruses, the neuraminidase glycoproteins proteins aid in the budding of the viruses from the cellular membrane of the host cell, thus releasing new viruses capable of infecting other host cells.

Isolated: An "isolated" biological component (such as a nucleic acid or protein) has been substantially separated, produced apart from, or purified away from other biological components in the cell of the organism in which the component naturally occurs, such as other chromosomal and extra-chromosomal DNA and RNA, and proteins. Nucleic acids and proteins which have been "isolated" include nucleic acids and proteins purified by standard purification methods. The term also embraces nucleic acids and proteins prepared by recombinant expression in a host cell as well as chemically synthesized nucleic acids, proteins and peptides.

Nucleic acid. A deoxyribonucleotide or ribonucleotide polymer in either single (ss) or double stranded (ds) form, and can include analogues of natural nucleotides that hybridize to nucleic acids in a manner similar to naturally occurring nucleotides. In some examples, a nucleic acid is a nucleotide analog.

Unless otherwise specified, any reference to a nucleic acid molecule includes the reverse complement of nucleic acid. Except where single-strandedness is required by the text herein (for example, a ssRNA molecule), any nucleic acid written to depict only a single strand encompasses both strands of a corresponding double-stranded nucleic acid. For example, depiction of a plus-strand of a dsDNA also encompasses the complementary minus-strand of that dsDNA. Additionally, reference to the nucleic acid molecule that encodes a specific protein, or a fragment thereof, encompasses both the sense strand and its reverse complement.

In particular examples, a nucleic acid includes a nucleotide sequence shown in any of SEQ ID NOS: 1-227, 229, and 231, or a variant, fragment, or fusion thereof. In other examples, a nucleic acid has a nucleotide sequence including a target sequence associated with SEQ ID NOS: 1-227, 229, and 231, or a variant, fragment, or fusion thereof, such as the corresponding cDNA or mRNA of SEQ ID NOS: 1-227, 229, and 231.

The fragment can be any portion of the nucleic acid corresponding to at least 5 contiguous bases from any target nucleic acid sequence associated with SEQ ID NOS: 1-227, 229, and 231, for example at least 20 contiguous bases, at least 50 contiguous bases, at least 100 contiguous bases, at least 250 contiguous bases, or even at least 500 or more contiguous bases. A fragment can be chosen from a particular portion of any of the target sequences associated with SEQ ID NOS: 1-227, 229, and 231, such as a particular half, third, fourth, fifth, sixth, seventh, eighth, ninth, tenth, or smaller portion of any of the target sequences associated with SEQ ID NOS: 1-227, 229, and 231. Fragments of the nucleic acids described herein can be used as probes and primers.

Oligonucleotide. A linear polynucleotide (such as DNA or RNA) sequence of at least 9 nucleotides, for example at least 15, 18, 24, 25, 30, 50, 100, 200 or even 500 nucleotides long. In particular examples, an oligonucleotide is about 6-50 bases, for example about 10-25 bases, such as 12-20 bases.

An oligonucleotide analog refers to moieties that function similarly to oligonucleotides, but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Open reading frame (ORF). A series of nucleotide triplets (codons) coding for amino acids without any internal termination codons. These sequences are usually translatable into a peptide.

Operably linked. A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pathogen: A disease-producing agent. Examples include, but are not limited to viruses, bacteria, and fungi.

Pharmaceutical agent or drug: A chemical compound or composition capable of inducing a desired therapeutic or prophylactic effect when administered to a subject, alone or in combination with another therapeutic agent(s) or pharmaceutically acceptable carriers. In a particular example, a pharmaceutical agent decreases or even inhibits infection of a cell, such as the cell of a subject, by a pathogen, such as a virus.

Polymorphism. A polymorphism exists when two or more versions of a nucleic acid sequence exist within a population of subjects. For example, a polymorphic nucleic acid can be one where the most common allele has a frequency of 99% or less. Different alleles can be identified according to differences in nucleic acid sequences, and genetic variations occurring in more than 1% of a population (which is the commonly accepted frequency for defining polymorphism) are useful polymorphisms for certain applications.

The allelic frequency (the proportion of all allele nucleic acids within a population that are of a specified type) can be determined by directly counting or estimating the number and type of alleles within a population. Polymorphisms and methods of determining allelic frequencies are discussed in Hartl, D. L. and Clark, A. G., Principles of Population Genetics, Third Edition (Sinauer Associates, Inc., Sunderland Mass., 1997), particularly in chapters 1 and 2.

Preventing or treating a disease: "Preventing" a disease refers to inhibiting the full development of a disease, for example preventing development of a viral infection. "Treatment" refers to a therapeutic intervention that ameliorates a sign or symptom of a disease or pathological condition related to a viral infection, such as inhibiting or decreasing viral infection.

Probes and primers. A probe includes an isolated nucleic acid attached to a detectable label or other reporter molecule. Typical labels include, but are not limited to radioactive isotopes, enzyme substrates, co-factors, ligands, chemiluminescent or fluorescent agents, haptens, and enzymes. Methods for labeling and guidance in the choice of labels appropriate for various purpose are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Primers are short nucleic acid molecules, such as DNA oligonucleotides ten nucleotides or more in length. Longer DNA oligonucleotides can be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example by the polymerase chain reaction (PCR) or other nucleic-acid amplification methods.

Nucleic acid probes and primers can be prepared based on the nucleic acid molecules of the target sequences associated with SEQ ID NOS: 1-227, 229, and 231, as indicators of resistance to infection. Probes and primers can be based on fragments or portions of these nucleic acid molecules, or on the reverse complement of these sequences, as well as probes and primers to 5' or 3' regions of the nucleic acids.

The specificity of a probe or primer increases with its length. Thus, for example, a primer that includes 30 consecutive nucleotides of a β-chimerin or Rab9 gene will anneal to a target sequence, such as another homolog of a β-chimerin or Rab9 gene, respectively, with a higher specificity than a corresponding primer of only 15 nucleotides. Thus, to obtain greater specificity, probes and primers can be selected that include at least 20, 25, 30, 35, 40, 45, 50 or more consecutive nucleotides of a nucleic acid disclosed herein.

Protein coding sequence or a sequence that encodes a peptide: A nucleic acid sequence that is transcribed (in the case of DNA) and is translated (in the case of mRNA) into a peptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence is usually be located 3' to the coding sequence.

Purified. The term purified does not require absolute purity; rather, it is a relative term. Thus, for example, a purified peptide preparation is one in which the peptide or protein is more enriched than the peptide or protein is in its environment within a cell, such that the peptide is substantially separated from cellular components (nucleic acids, lipids, carbohydrates, and other polypeptides) that may accompany it. In another example, a purified peptide preparation is one in which the peptide is substantially-free from contaminants, such as those that might be present following chemical synthesis of the peptide.

In one example, an peptide is purified when at least 60% by weight of a sample is composed of the peptide, for example when 75%, 95%, or 99% or more of a sample is composed of the peptide, such as a β-chimerin or Rab9 peptide. Examples of methods that can be used to purify proteins, include, but are not limited to the methods disclosed in Sambrook et al. (Molecular Cloning: A Laboratory Manual, Cold Spring Harbor, N.Y., 1989, Ch. 17). Protein purity can be determined by, for example, polyacrylamide gel electrophoresis of a protein sample, followed by visualization of a single polypeptide band upon staining the polyacrylamide gel; high-pressure liquid chromatography; sequencing; or other conventional methods.

Rab9: The term Rab9 includes any Rab9 gene, cDNA, RNA, or protein from any organism and that is a Rab9 that can transport late endosomes to trans-golgi and function as a ras-like GTPase. In some examples, Rab9 is involved in lipid raft formation.

Examples of native Rab9 nucleic acid sequences include, but are not limited to, target sequences associated with SEQ ID NOS: 118 and 119. Examples of Rab9 amino acid sequences include, but arm not limited to: Genbank Accession Nos: BC017265.2 and NM_004251.3 (cDNA) as well as P51151 and AAH17265 (proteins). In one example, a Rab9 sequence includes a full-length wild-type (or native) sequence, as well as Rab9 allelic variants, variants, fragments, homologs or fusion sequences that retain the ability to transport late endosomes to trans-golgi. In certain examples, Rab9 has at least 80% sequence identity, for example at least 85%, 90%, 95%, or 98% sequence identity to a native Rab9.

In other examples, Rab9 has a sequence that hybridizes to a sequence set forth in GenBank Accession No. BC017265.2 or NM_004251.3, and retains Rab9 activity.

Recombinant. A recombinant nucleic acid or protein is one that has a sequence that is not naturally occurring or has a sequence that is made by an artificial combination of two otherwise separated segments of sequence. This artificial combination can be accomplished, for example, by chemical synthesis or by the artificial manipulation of isolated segments of nucleic acids or proteins, for example, by genetic engineering techniques.

RNA interference (RNAi): A post-transcriptional gene silencing mechanism mediated by double-stranded RNA (dsRNA). Introduction of dsRNA into cells, such as RNAi compounds or siRNA compounds, induces targeted degradation of RNA molecules with homologous sequences. RNAi compounds are typically longer than an siRNA molecule. For example, an RNAi molecule can be at least about 25 nucleic acids, at least about 27 nucleic acids, or even at least about 400 nucleotides in length.

RNAi compounds can be used to modulate transcription, for example, by silencing genes, such as Rab9, β-chimerin, or combinations thereof. In certain examples, an RNAi molecule is directed against a certain target gene, such as Rab9, β-chimerin, or combinations thereof, and is used to decrease viral infection.

Sequence identity: The similarity between nucleic acid or amino acid sequences is expressed in terms of the similarity between the sequences. Sequence identity is frequently measured in terms of percentage identity (or similarity or homology); the higher the percentage, the more similar the two sequences are. Homologs or variants of a protein or nucleic acid disclosed herein, such as target sequences associated with SEQ ID NOS: 1-232, and their corresponding cDNA and protein sequences, will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-44, 1988; Higgins and Sharp, *CABIOS* 5:151-3, 1989; Corpet et al., *Nucl. Acids Res.* 16:10881-90, 1988; Pearson and Lipman, *Proc. Natl. Acad. Sci. U.S.A.* 85:2444, 1988; and Altschul et al., *Nature Genet.* 6:119-29, 1994.

The NCBI Basic Local Alignment Search Tool (BLAST™) (Altschul et al., *J. Mol. Biol.* 215:403-10, 1990) is available from several sources, including the National Center for Biotechnology Information (NCBI, Bethesda, Md.) and on the Internet, for use in connection with the sequence analysis programs blastp, blastn, blastx, tblastn and tblastx.

Variants of a peptide, such as a peptide encoded by any target sequence associated with SEQ ID NOS: 1-227, 229, and 231, as well as any target sequence associated with SEQ ID NOS: 228, 230, and 232, are typically characterized by possession of at least 70% sequence identity counted over the full length alignment with the amino acid sequence encoded by any target sequence associated with SEQ ID NOS: 1-227, 229, or 231, using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existance cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 90%, at least 95%, at least 98%, or even at least 99% sequence identity. When less than the entire sequence is being compared for sequence identity, homologs and variants will typically posses at least 80% sequence identity over short windows of 10-20 amino acids, and may possess sequence identities of at least 85%, at least 90%, at least 95%, or at least 98% depending on their similarity to the reference sequence. Methods for determining sequence identity over such short windows are described at the website that is maintained by the National Center for Biotechnology Information in Bethesda, Md. One of skill in the art will appreciate that these sequence identity ranges are provided for guidance only; it is entirely possible that strongly significant homologs could be obtained that fall outside of the ranges provided.

Similar methods can be used to determine the sequence identity between two or more nucleic acids. To compare two nucleic acid sequences, the BLASTN options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to −1; -r is set to 2; and all other options are left at their default setting. For example, the following command can be used to generate an output file containing a comparison between two sequences: C:\B12seq -i c:\seq1.txt-j c:\seq2.txt-p blastn-o c:\output.txt-q −1-r2.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (for example, 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (for example, 1166+1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (for example, 15+20*100=75).

```
                                 1                  20
Target Sequence:           AGGTCGTGTACTGTCAGTCA
                                 | || ||| |||| |||| |
Identified Sequence:       ACGTGGTGAACTGCCAGTGA
```

The nucleic acids disclosed herein include nucleic acids have nucleotide sequences that are at least 70%, at least 75%, at least 80%, at least 85%, at least 90%, at least 95%, at least 98%, or at least 99% identical to the nucleotide sequence of any target sequence associated with SEQ ID NOS: 1-227, 229, and 231. In particular examples, a nucleic acid is substantially similar to the nucleotide sequence of any target sequence associated with SEQ ID NOS: 1-227, 229, and 231. A first nucleic acid is "substantially similar" to a second nucleic acid if, when the first nucleic acid is optimally aligned (with appropriate nucleotide deletions or gap insertions) with the second nucleic acid (or its complementary strand) and there is nucleotide sequence identity of at least about 90%, for example at least about 95%, at least 98% or at least 99% identity. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Short interfering or interrupting RNA (siRNA). Double-stranded RNAs that can induce sequence-specific post-transcriptional gene silencing, thereby decreasing or even inhibiting gene expression. In some examples, siRNA molecules are about 19-23 nucleotides in length, such as at least 21 nucleotides, for example at least 23 nucleotides.

In one example, siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends. The direction of dsRNA processing determines whether a sense or an antisense target RNA can be cleaved by the produced siRNA endonuclease complex. Thus, siRNAs can be used to modulate transcription, for example, by silencing genes, such as Rab9, β-chimerin, or combinations thereof. The effects of siRNAs have been demonstrated in cells from a variety of organisms, including *Drosophila, C. elegans*, insects, frogs, plants, fungi, mice and humans (for example, WO 02/44321; Gitlin et al., *Nature* 418:430-4, 2002; Caplen et al., *Proc. Natl. Acad. Sci.* 98:9742-9747, 2001; and Elbashir et al., *Nature* 411:494-8, 2001).

In certain examples, siRNAs are directed against certain target genes, such as Rab9, β-chimerin, or combinations thereof, to confirm results of the gene-trap method used against the same nucleic acid sequence.

Specific binding agent. An agent that binds substantially only to a defined target. For example, a protein-specific binding agent binds substantially only the specified protein and a nucleic acid specific binding agent binds substantially only the specified nucleic acid.

As used herein, the term "protein [X] specific binding agent" includes anti-[X] protein antibodies (including polyclonal or monoclonal antibodies and functional fragments thereof) and other agents (such as soluble receptors) that bind substantially only to the [X] protein. In this context, [X] refers to any specific or designated protein, for instance β-chimerin, Rab9, or any protein listed in Table 1 or encoded by a target sequence associated with SEQ ID NOS: 1-227, 229, and 231 (including variants, fragments, and fusions thereof).

Anti-[X] protein antibodies can be produced using standard procedures such as those described in Harlow and Lane (*Using Antibodies: A Laboratory Manual*, Cold Spring Harbor Laboratory Press: Cold Spring Harbor, 1998). Antibodies can be polyclonal or monoclonal antibodies, humanized antibodies, Fab fragments, F(ab')2 fragments, single chain antibodies, or chimeric antibodies. For example, polyclonal antibodies can be produced by immunizing a host animal by injection with polypeptides described herein, including the target sequences associated with SEQ ID NOS: 1-227, 229, 231 (or variants, fragments, or fusions thereof). The production of monoclonal antibodies can be accomplished by a variety of methods, such as the hybridoma technique (Kohler and Milstein, *Nature* 256:495-7, 1975), the human B-cell technique (Kosbor et al., *Immunology Today* 4:72, 1983), or the EBV-hybridoma technique (Cole et al., in *Monoclonal Antibodies and Cancer Therapy*, Alan R. Liss, Inc., pp. 77-96, 1983). Additionally, chimeric antibodies can be produced (for example, see Morrison et al., *J. Bacteriol.* 159:870, 1984; Neuberger et al., *Nature* 312:604-8, 1984; and Takeda et al., *Nature* 314:452-4, 1985), as well as single-chain antibodies (for example, see U.S. Pat. Nos. 5,476,786; 5,132,405; and 4,946,778).

The determination that a particular agent binds substantially only to the specified protein readily can be made by using or adapting routine procedures. For example, Western blotting can be used to determine that a given protein binding agent, such as an anti-[X] protein monoclonal antibody, binds substantially only to the [X] protein. Other assays include, but are not limited to, competitive and non-competitive homogenous and heterogeneous enzyme-linked immunosorbent assays (ELISA) as symmetrical or asymmetrical direct or indirect detection formats; "sandwich" immunoassays; immunodiffusion assays; in situ immunoassays (for example, using colloidal gold, enzyme or radioisotope labels); agglutination assays; complement fixing assays; immunoelectrophorectic assays; enzyme-linked immunospot assays (ELISPOT); radioallergosorbent tests (RAST); fluorescent tests, such as used in fluorescent microscopy and flow cytometry; Western, grid, dot or tissue blots; dip-stick assays; halogen assays; or antibody arrays (for example, see O'Meara and Tovey, *Clin. Rev. Allergy Immunol.,* 18:341-95, 2000; Sambrook et al., 2001, Appendix 9; Simonnet and Guilloteau, in: *Methods of Immunological Analysis*, Masseyeff et al. (Eds.), VCH, New York, 1993, pp. 270-388).

A specific binding agent also can be labeled for direct detection (see Chapter 9, Harlow and Lane, *Antibodies: A Laboratory Manual.* 1988). Suitable labels include (but are not limited to) enzymes (such as alkaline phosphatase (AP) or horseradish peroxidase (HRP)), fluorescent labels, colorimetric labels, radioisotopes, chelating agents, dyes, colloidal gold, ligands (such as biotin), and chemiluminescent agents.

Shorter fragments of antibodies can also serve as specific binding agents. For instance, Fabs, Fvs, and single-chain Fvs (SCFvs) that bind to a specified protein would be specific binding agents. These antibody fragments include: (1) Fab, the fragment containing a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab)2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of malting these fragments are routine. For example, construction of Fab expression libraries permits the rapid and easy identification of monoclonal Fab fragments with the desired specificity for a protein described herein.

Subject: Living multi-cellular vertebrate organisms, including human and veterinary subjects, such as cows, pigs, horses, dogs, cats, birds, reptiles, and fish.

Target sequences associated with SEQ ID NO: When used herein, this phrase refers to any nucleic acid sequence, amino acid sequence, or combination of nucleic acid and amino acid sequences, that are involved in viral infection, and therefore serve as targets for inhibiting viral infection, and which are or include a specified SEQ ID NO, are involved in the expression of the SEQ ID NO, or are peptide (including protein) sequences that are expressed by such specified SEQ ID NO. Although a target sequence may refer to a SEQ ID NO of a sequence obtained from a particular species, the target sequences also include homologues of the sequence from other related species, such as other mammals. For example, the phrase "target sequences associated with SEQ ID NO. X" can refer to the entire gene sequence of which the particular SEQ ID NO X is a part, the appropriate coding sequence, a promoter sequence associated with the gene, or the corresponding protein sequence, as well as variants, fragments, homologues, and fusions thereof that retain the activity of the native sequence.

For example, when using the phrase "sequences associated with SEQ ID NOS: 21-22," this term encompases β-chimerin genomic sequences, endogenous promoter sequences that promote the expression of β-chimerin, coding sequences, and β-chimerin proteins, as well as variants, fragments homologues and fusions thereof that retain the activity of the native sequence. A particular cDNA sequence associated with SEQ ID NOS: 21-22 is provided in GenBank Accession No. NM_004067, and a particular protein sequence associated with SEQ ID NOS: 21-22 is provided in NP_004058.1.

The term "a GenBank Accession No. associated with SEQ ID NO. X" refers to a GenBank Accession No. that includes SEQ ID NO. X, or is a homolog of SEQ ID NO: X from another mammal, for example a human homolog. The GenBank Accession No. may, in some examples, also identify a coding sequence of an open reading frame, and the sequence of the protein encoded by SEQ ID NO. X.

Although sequences are provided herein that encode (or are included within sequences that encode) host proteins that are involved in viral infection, it should be understood that the ultimate goal is to interfere with the activity of the protein that has been identified to be involved in viral pathogenesis. Such interference can be at either the level of the nucleic acid that encodes the protein (for example by reducing or otherwise disrupting expression of the protein), or at the level of the protein itself (for example by interfering with the activity of the protein, or its interaction with the virus). The disclosure of specific techniques for achieving these goals in particular species should not be interpreted to limit the method to these particular techniques, or to particular species in which the viral interaction is first identified. The identification of the viral interaction in one species indicates the importance of the interaction between the virus and the protein in that species, as well as the interaction of the virus with homologues of that protein in other species.

Target sequence of a nucleic acid: A portion of a nucleic acid that, upon hybridization to a therapeutically effective oligonucleotide or oligonucleotide analog, results in reduction or even inhibition of infection by an infectious agent. An antisense or a sense molecule can be used to target a portion of dsDNA, since either can interfere with the expression of that portion of the dsDNA. The antisense molecule can bind to the plus strand, and the sense molecule can bind to the minus strand. Thus, target sequences can be ssDNA, dsDNA, and RNA.

Therapeutically active molecule: An agent, such as a protein, antibody or nucleic acid, that can decrease expression of a host protein involved in viral infection (such as those listed in Table 1 or target sequences associated with any of SEQ ID NOS: 1-232, or can decrease an interaction between a host protein involved in viral infection and a viral protein, such as HIV, Ebola, or influenza A, as measured by clinical response (for example, a decrease in infection by a virus, such as an inhibition of infection). Therapeutically active agents also include organic or other chemical compounds that mimic the effects of the therapeutically effective peptide or nucleic acids.

Therapeutically Effective Amount: An amount of a pharmaceutical preparation that alone, or together with an additional therapeutic agent(s), induces the desired response. The preparations disclosed herein arm administered in therapeutically effective amounts.

In one example, a desired response is to decrease or inhibit viral infection of a cell, such as a cell of a subject. Viral infection does not need to be completely inhibited for the pharmaceutical preparation to be effective. For example, a pharmaceutical preparation can decrease viral infection by a desired amount, for example by at least 20%, at least 50%, at least 60%, at least 70%, at least 80%, at least 90%, at least 95%, at least 98%, or even at least 100%, as compared to an amount of viral infection in the absence of the pharmaceutical preparation. This decrease or inhibition can result in halting or slowing the progression of, or inducing a regression of a pathological condition caused by the viral infection, or which is capable of relieving signs or symptoms caused by the condition.

In another or additional example, it is an amount sufficient to partially or completely alleviate symptoms of viral infection within a host subject. Treatment can involve only slowing the progression of the infection temporarily, but can also include halting or reversing the progression of the infection permanently.

Effective amounts of the therapeutic agents described herein can be determined in many different ways, such as assaying for a reduction in the rate of infection of cells or subjects, a reduction in the viral load within a host, improvement of physiological condition of an infected subject, or increased resistance to infection following exposure to the virus. Effective amounts also can be determined through various in vitro, in vivo or in situ assays, including the assays described herein.

The disclosed therapeutic agents can be administered in a single dose, or in several doses, for example daily, during a course of treatment. However, the effective amount of can be dependent on the source applied (for example a nucleic acid isolated from a cellular extract versus a chemically synthesized and purified nucleic acid), the subject being treated, the severity and type of the condition being treated, and the manner of administration. In addition, the disclosed therapeutic agents can be administered alone, or in the presence of a pharmaceutically acceptable carrier, or in the presence of other therapeutic agents, for example other anti-viral agents.

Transduced and Transformed: A virus or vector "transduces" or "transfects" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transfected: A transfected cell is a cell into which has been introduced a nucleic acid molecule by molecular biology techniques. The term transfection encompasses all techniques by which a nucleic acid molecule can be introduced into such a cell, including transfection with viral vectors, transformation with plasmid vectors, and introduction of naked DNA by electroporation, lipofection, and particle gun acceleration.

Transgene: An exogenous nucleic acid sequence supplied by a vector. In one example, a transgene includes any target sequence associated with SEQ ID NOS: 1-227, 229, 231 (or variants, fragments, or fusions thereof), for example a nucleic acid that encodes a beta-chimerin or Rab9.

Variants, fragments or fusions: The disclosed nucleic acid sequences, such as target sequences associated with SEQ ID NOS: 1-227, 229, and 231, and the proteins encoded thereby, include variants, fragments, and fusions thereof that retain the native biological activity (such as playing a role in viral infection). DNA sequences which encode for a protein or fusion thereof, or a fragment or variant of thereof can be engineered to allow the protein to be expressed in eukaryotic cells or organisms, bacteria, insects, and/or plants. To obtain expression, the DNA sequence can be altered and operably linked to other regulatory sequences. The final product, which contains the regulatory sequences and the therapeutic protein, is referred to as a vector. This vector can be introduced into eukaryotic, bacteria, insect, and/or plant cells. Once inside the cell the vector allows the protein to be produced.

One of ordinary skill in the art will appreciate that the DNA can be altered in numerous ways without affecting the biological activity of the encoded protein. For example, PCR can be used to produce variations in the DNA sequence which encodes a protein. Such variants can be variants optimized for codon preference in a host cell used to express the protein, or other sequence changes that facilitate expression.

Vector: A nucleic acid molecule as introduced into a host cell, thereby producing a transformed host cell. A vector can include nucleic acid sequences that permit it to replicate in a host cell, such as an origin of replication, and can also include one or more selectable marker genes and other genetic elements. An insertional vector is capable of inserting itself into a host nucleic acid. For example, recombinant lambda-phage vectors of host genomes (Coffin et al., *Retroviruses*, Chapter 5).

Wild-type. A naturally occurring, non-mutated version of a nucleic acid sequence. Among multiple alleles, the allele with the greatest frequency within the population is usually (but not necessarily) the wild-type. The term "native" can be used as a synonym for "wild-type."

Nucleic Acids and Proteins Involved in Viral Infection

Examples of host nucleic acids and proteins that play a role in viral infection have been identified and are summarized in Table 1. These nucleic acids and proteins offer new targets for therapies that reduce or even inhibit or prevent viral infection, and offer new strategies for assessing the risk of infection among certain populations. While the target genes were identified in an assay using the recited virus, it is appreciated that infections agents such as viruses will share common pathways. Thus, the host sequences set forth below can be interfered with to decrease infection in a host cell.

Examples of viruses that can be inhibited are described in Virology, Volumes 1 and 2 by Bernard Fields, Second Edition, 1990, Raven Press. Exemplary viruses include, but are not limited to members of the family: Picornaviridae (such as Poliovirus, Coxsackievirus, Echovirus, Rhinovirus, and Hepatitis A and E); Calciviridae (such as Norwalk and related viruses); Togaviridae and Flavivirdae (such as hepatitis C, Alphavirus, and Rubella); Coronaviridae (such as SARS); Rhabdoviridae (such as Rabies); Filoviridae (such as Marburg and Ebola); Paramyxoviridae (such as Parainfluenza, Mumps, Measles, Hydra and Respiratory Synctial virus); Orthomyxoviridae; Bunyaviridae (including all subtypes and strains); Arenaviridae (such as lymphocytic choreomeningitis virus and lassa fever and related viruses); Reoviridae (such as Reovirus and Rotavirus); Retroviridae (such as HTLV, HIV, and Lentivirus); Papoviridae (such as Polyoma and Papilloma); Adenoviridae (such as Adenovirus); Parvoviridae (such as Parvovirus); Herpesviridae (such as Herpes 1 and 2, Cytomegalovirus, Varicella-Zoster, Kaposi sarcoma related virus (HHV9), Epstein Barr Virus, and HHV6.7 (roseolavirus)); Poxviridae (such as Pox); Hepadnaviridae (such as Hepatitis B); as well as Hepatitis D virus, Hanta virus, and newly identified infectious agents.

TABLE 1

Examples of Host Genes and Protlens Implicated in Pathogenesis

| Nucleic Acid or Protein | Associated Virus | SEQ ID NO: | GenBank Accession Nos for cDNA and Protein |
|---|---|---|---|
| T-cell receptor V beta chain | HIV | 1-19 | |
| T-cell receptor V-D-J beta 2.1 chain | HIV | 20 | |
| β-chimerin (CHN2) | HIV | 21-22 | NM_004067; NP_004058.1 |
| Malic enzyme 1 (ME1) | HIV and Influenza A | 23 | BC025246; AAH25246.1 |

TABLE 1-continued

| Examples of Host Genes and Protlens Implicated in Pathogenesis | | | |
|---|---|---|---|
| Nucleic Acid or Protein | Associated Virus | SEQ ID NO: | GenBank Accession Nos for cDNA and Protein |
| Hypothetical protein XP_174419 | HIV and Influenza A | 24 | |
| sequence from Chromosome 4q31.3-32 | HIV and Influenza A | 25-27 | |
| alpha satellite DNA | HIV | 28 | |
| LOC2537888 and LOC219938; coagulation factor III (F3) and LOC91759 | HIV | 29 | |
| similar to KOX4 (LOC131880) and LOC166140 | HIV | 30 | |
| LOC222474 and similar to Rho guanine nucleotide exchange factor 4, isoform a, APC-stimulated guanine nucleotide exchange factor (LOC221178); T-cell receptor beta | HIV | 31 | |
| ribosomal protein L7A-like 4 (RPL7ALA) and v-src sarcoma (Schmidt-Ruppin A-2) viral oncogene homolog (avian) (SRC) | HIV | 32 | |
| KIAA0564 | HIV | 33 | |
| alpha satellite DNA; M96 protein | HIV | 34 | |
| hypothetical protein similar to G proteins, especially RAP-2A (LOC57826); LOC161005 and osteoblast specific factor 2 (fasciclin I-like; OSF-2) | HIV | 35 | |
| Canis familiaris T-cell leukemia translocation-associated (TCTA) gene, aminomethyltransferase (AMT) gene, dystroglycan (DAG1) gene, and bassoon (BSN) gene | Influenza A | 36-37 | |
| LIM domain containing preferred translocation partner in lipoma (LPP) | Influenza A | 38-48 | |
| sequence between LOC253121 and hyaluronan synthase 2 (HAS2) | Influenza A | 49 | |
| Testin 2 and Testin 3 (TES) | Influenza A | 50-57 | |
| PTPN1 gene for protein tyrosine phosphatase, non-receptor type 1 | Influenza A | 58-59 | |
| sequence between LOC149360 and LOC253961 | Influenza A | 60 | |
| sequence between KIAA 1560 and Tectorin beta (TECTB) | Influenza A | 61 | |
| Cadherin related 23 (CDH23) | Influenza A | 62 | BC032581; AAH32581.1 |
| Mycloid/lyniphoma or mixed lineage leukemia, translocated to 10 (MMLT10) | Influenza A | 63 | |
| exportin 5 (XPO5) and DNA polymerase eta (POLH) | Ebola | | |
| heterogenous nuclear riboprotein C (C1/C2) (HNRPC) | Ebola | 67-75 | |
| alpha-endosulfine pseudogene (ENSAP) and LOC128741 | Ebola | 76 | |
| LOC222888 | Ebola | 77 | |
| LOC138421 and zinc finger protein 297B (ZNF297B) | Ebola | 78 | |
| sideroflexin 5 (SFXN5) | Ebola | 79 | AY044437; AAK95826 |
| importin 9 (FLJ10402) | Ebola | 80 | |
| T-cell receptor beta | Ebola | 81-82 | |
| similar to murine putative transcription factor ZNFI3l (LOC 135952) | Ebola | 83-99 | |
| KIAA1259 | Ebola | 100-101 | AB033085; NP_115572 |
| MURRI and CCT4 | Ebola | 102 | |
| FLJ40773 and similar to ribosonial protein L24-like (LOC149360) | Ebola | 103 | |
| Testin 2 slid 3 (TES) | Ebola | 104-107 | See above |
| polybromol(PB1) | Ebola | 108 | NM_018165.2; NP_060635 |
| DNA damage inducible transcript 3 | Ebola | 109 | |
| PDZ and LIM domain 1 (elfin) (PDLIM1) | Ebola | 110 | |
| LOC284803 | Ebola | 111-112 | |
| PRO0097 and FLJ31958 | Ebola | 113 | |
| small inducible cytokine E, member 1 (endothelial monocyte-activating) (SCYE1) | Ebola | 114-116 | |

TABLE 1-continued

Examples of Host Genes and Protlens Implicated in Pathogenesis

| Nucleic Acid or Protein | Associated Virus | SEQ ID NO: | GenBank Accession Nos for cDNA and Protein |
|---|---|---|---|
| E3 ubiquitin ligase (SMURF2) and MGC40489 | Ebola | 117-119 | |
| Ras oncogene family member Rab9 | Ebola | 118-119 | |
| PRO1617 and retinoblastonia binding protein 1 (RBBP1) | Ebola | 120-122 | NM_000321; NP_000312.1 |
| region of chromosome 2q12 | Ebola | 123 | |
| elongation factor for selenoprotein translation | Ebola | 124 | NM_021937.1 NP_068756.1 |
| Transcription factor SMIF (HSA275986) | Ebola | 125-137 | |
| KIAA1026 | Ebola | 138 | |
| trinucleotide repeat containing 5 (TNRC5) | Ebola | 139 | |
| homogentisate 1,2-dioxygenase (HGD) | Ebola | 140 | |
| region of chromosome Xq23-24 | Ebola | 141 | |
| region of chromosome 4p15.3 | Ebola | 142 | |
| similar to LWamide neuropeptide precursor protein [Hydractinia echinata] LOC129883 | Ebola | 143 | |
| region of chromosome 2q21 | Ebola | 144 | |
| region of chromosome Xp11.4, including UPS9X | Ebola | 145 | |
| LOC221829 | Ebola | 146 | |
| U3 small nuclear RNA | Ebola | 147-154 | |
| integrin, beta 1 (ITGB1) | Ebola | 155-158 | BC020057; AAH20057.1 |
| acrosornal vesicle protein 1 (ACRV1) and CHK1 checkpoint homolog (CHEK1) | Ebola | 159 | |
| prospero-related homeobox 1 (PROX1) | Ebola | 160 | |
| FLJ20627 and FLJ12910 | Ebola | 161-173 | |
| PIN2-interacting protein (PINX1) and SRY (sex-determining region Y)-box 7 (SOX7) | Ebola | 174 | |
| LOC131920 | Ebola | 175 | |
| region of chromosome 13q14 | Ebola | 176 | |
| neurotropliic tyrosine kinase, receptor, type 3 (NTRK3) | Ebola | 177 | |
| TERA protein and FLJ13224 | Ebola | 178-179 | |
| LOC284260 | Ebola | 180 | |
| POM (POM121 homolog) and ZP3 fusion (POMZP3) | Ebola | 181-182 | |
| DEAD/H box polypeptide 8 (DDX8) and similar to ribosomal protein L29 (cell) surface heparin binding protein HIP) (LOC284064) | Ebola | 183 | |
| LOC345307 and UDP-N-acctyl-D-galactosamine:polypeptide N-acetylgalactosaminyltransferase 7 (GALNT7) | Ebola | 184-186 | |
| Mus musculus 5S rRNA pseudogene (Rn5s-ps1) | Ebola | 187 | |
| ribosomal protein L27a pseudogene (RPL27AP) and v-myb myeloblastosis viral oncogene homolog-like 2 (MYBL2) | Ebola | 188-192 | |
| Down's syndrome cell adhesion molecule | Ebola | 193 | |
| LOC148529 | Ebola | 194 | |
| Huntingtin-associated protein interacting protein (HAPIP) | Ebola | 195 | NM_005338.4; NP_005329.3 |
| LOC158525 and similar to RIKEN cDNA 1210001E11 (LOC347366) | Ebola | 196-200 | |
| hypothetical protein FLJ12910 | Ebola | 201-204 | |
| LOC350411 | Ebola | 205 | |
| allograft inflammatory factor 1 (AIF1) and HLA-B associated transcript 2 (BAT2) | Ebola | 206 | |
| C10orf7 | Ebola | 207 | |
| LOC346658 and LOC340349 | Ebola | 208-209 | |
| region of chromosome 12q21 | Ebola | 210 | |
| LOC339248 and FLJ22659 | Ebola | 211 | |
| SR rich protein DKFZp564B0769 and hypothetical protein MGC14793 | Ebola | 212 | |
| FLJ10439 | Ebola | 213-214 | NM_018093.1, NP_060563.1 |
| cytochrome P450, family 11, subfamily A, polypeptide 1 (CYP11A1) and sema domain, immunoglobulin domain (Ig) and GPI membrane anchor, (semaphoring) 7A | Ebola | 215-218 | |

TABLE 1-continued

Examples of Host Genes and Protlens Implicated in Pathogenesis

| Nucleic Acid or Protein | Associated Virus | SEQ ID NO: | GenBank Accession Nos for cDNA and Protein |
|---|---|---|---|
| ribosomal protein S16 (RPS 16) | Ebola | 219-220 | BC004324.2; AAH04324.1 |
| hypothetical protein DKFZp434H0115 and ATP citrate lyase (ACLY) | Ebola | 221-222 | |
| calnexin (CANX); protein tyrosine phosphatase, receptor type, K (PTPRK) | Ebola | 223-224 | |
| cyclin M2 (CNNM2) | Ebola | 225 | NM_017649.2; NP_060119.2 |
| AXL receptor tyrosine kinase (AXL) | Ebola | 226 | BC032229; AAH32229.1 |
| *Homo sapiens* chromosome 10 open reading frame 3 | Ebola | 227-228 | |
| *Homo sapiens* chromosome 10 open reading frame 3 (C10orf3) | Ebola | 229-230 | |
| *Homo sapiens* fer-1-like 3, myoferlin (*C. elegans*) | Ebola | 231-232 | NM_013451.; NP_038479.1 |

Some of the host nucleic acids described in Table 1 and target sequences associated with SEQ ID NOS: 1-227, 229, and 231 encode polypeptides that are receptors or ligands recognized by a particular virus, such as HIV, influenza A, or the Ebola virus. For example, the T-cell receptor V beta and V-D-J beta 2.1 chain polypeptides are part of the T-cell receptor complex that are recognized by certain glycoproteins in the HIV envelope. Other host nucleic acids encode polypeptides that provide an enzymatic function related to a viral life cycle, such as the signaling pathways controlling viral packaging or enzymes involved in viral replications. For example, the β-chimerin rho-GTPase may mediate a cellular signal that initiates or triggers a process leading to passage of an HIV viral particle into the host cell. The data presented herein indicate that Rab9 is involved in pathogen infectivity, for example by interfering with trafficking of proteins and lipids within cells. In particular examples, it is demonstrated that Rab9 is involved in lipid raft formation, and that decreasing functional Rab9 and lipid rafts decreases the ability of pathogens, such as viruses and bacteria, that hijack lipid rafts to bud or be infectious.

Still other host nucleic acids participate in the life cycle of a virus. For example, a certain nucleotide sequence of a host nucleic acid, such as a gene within the host genome can be recognized during insertion and integration of a viral genome (reverse transcribed into DNA from the viral RNA genomic template) into the host genome. Viral integration is described in, for example, Coffin et al., *Retroviruses*, Chapter 5.

The nucleic acids and proteins disclosed herein can be identified, isolated, and characterized using any number of techniques of molecular biology, including the specific methods and protocols described herein, such as in the examples below. In some examples, the nucleic acids were identified and isolated using the Lexicon Genetics, Inc. (The Woodlands, Tex.) "gene trap" technology disclosed in U.S. Pat. Nos. 6,080,576; 6,136,566; 6,207,371; 6,139,833; 6,218,123 and 6,448,000.

Gene trap technology is a powerful method for cloning and identifying functional genes, as it marks a gene with a tag and simultaneously generates a corresponding genetic variation for that particular locus. The method involves introducing into a cell a DNA construct that can monitor and potentially disrupt the transcriptional activity of the region of the cell's genome into which it is inserted. The gene-trap method used to identify the host sequences is disclosed in U.S. Pat. No. 6,448,000 (herein incorporated by reference).

Figure 2:
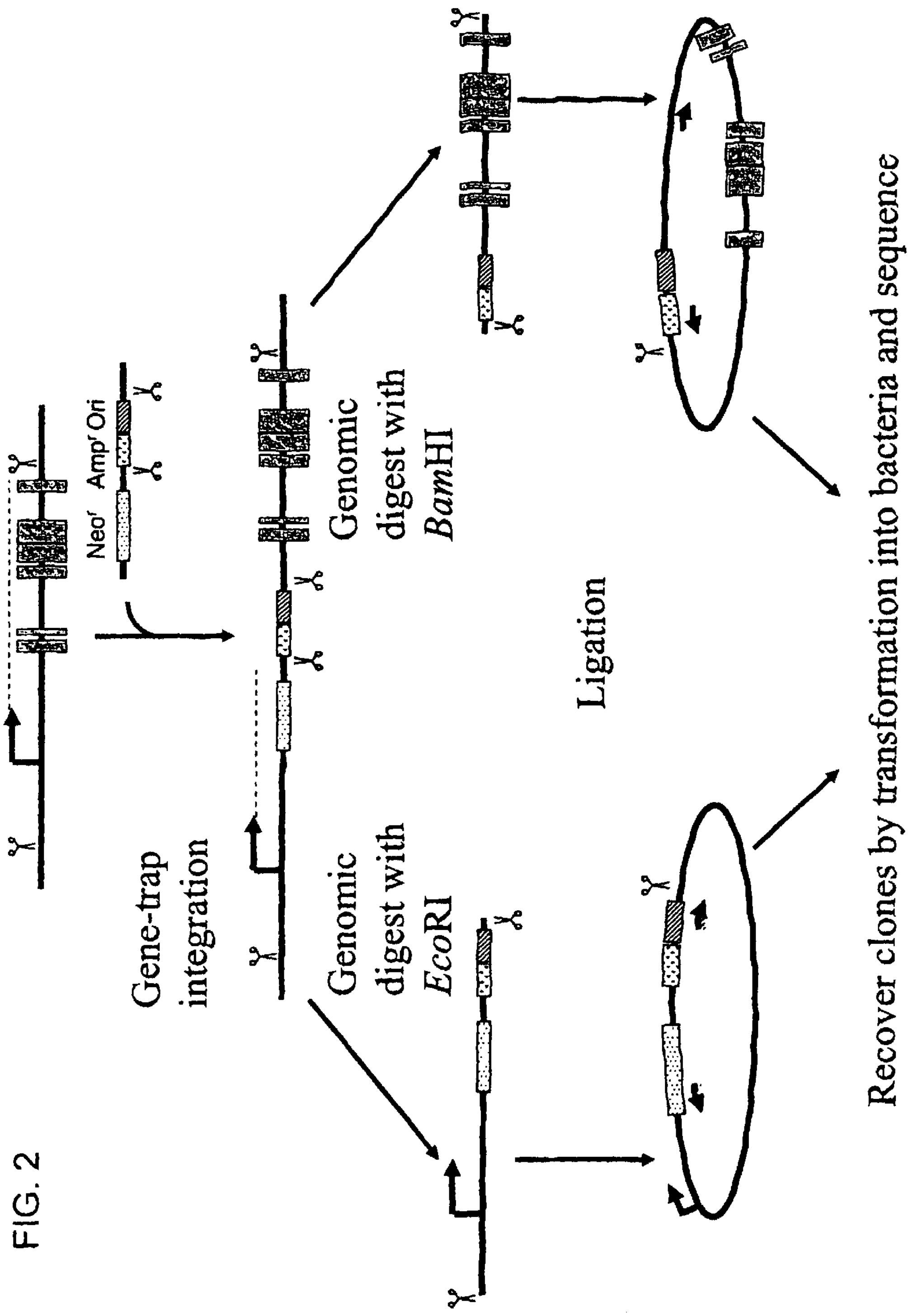
FIG. 2 is a schematic illustration of the gene-trap method.

Briefly, the gene trap protocol involves infecting a host cell (for example, a cell of a Sup T-1 cell line (human), MDCK cells (canine), or Vero cells (monkey)) with a recombinant vector (for example, U3neoSV1, FIG. 1). The recombinant vector includes a selectable maker or other sequence capable of being used to select infected host cells. However, the selectable marker or other sequence does not have a promoter at its 5' end. An exemplary selectable marker is a nucleic acid encoding resistance to an antibiotic (such as neomycin). A summary of the gene trap method is provided in FIGS. 2 and 3. Infection of the host cell is performed in culture under conditions that yield about one copy of the vector per cell. The vector incorporates into the host cell genome adjacent to an active promoter and interrupts or disrupts the transcription of a nucleic acid in the host cell (FIG. 2). The host promoter drives expression of the selectable marker or other sequence on the vector, and infected cells can then be selected. For example, if the vector carries a nucleic acid encoding neomycin resistance, cells can be selected on a medium that contains neomycin or G418, the neomycin analog for mammalian cells, depending on the type of host cell used.

Figure 3:
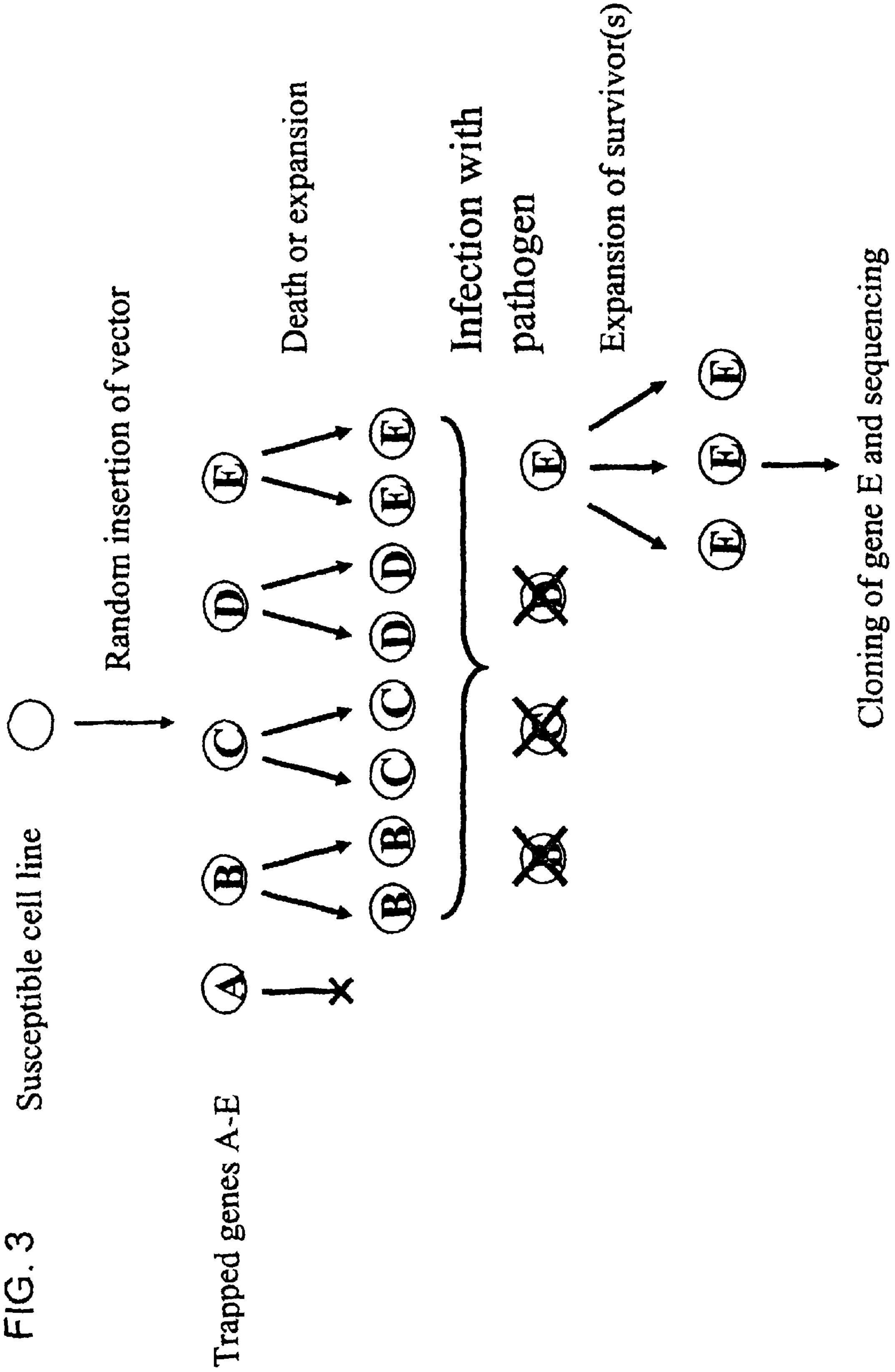
FIG. 3 is a schematic illustration of one method of identifying host genes described herein.

The selected host cells are expanded in culture to form a library of cells that contain randomly disrupted host genes (FIG. 3). An aliquot of the library of cells is exposed to the appropriate virus, such as HIV, influenza A, or Ebola, to determine the effect of the disrupted host sequence on viral infection of the host cells. Host cells that survive the viral infection, or are relatively resistant to such infection (such as those cells that survive for a longer period of time than about at least 50% of the infected cells), can include one or more disrupted genes involved in viral infection. Thus, by using the vector one can decrease viral or pathogenic infection of a host cell or in a subject. Therefore, by identifying these disrupted genes that decreased or otherwise interfered with viral infection of the host cell, candidate sequences are identified that can be used as targets to decrease or inhibit viral infection.

Those host cells that survive viral infection, or are relatively resistant to such infection, are cloned, for example, by limit dilution using a chambered plate or by growth on methylcellulose. The interrupted host nucleic acid is identified using standard molecular biology methods. For example, host DNA can be isolated from the cell and digested using an appropriate restriction enzyme to free the 5' and 3' sequences adjacent the incorporated vector. The isolated DNA fragment can then be amplified, for example using PCR or by introducing the DNA fragment into a bacterial host cell then growing the bacteria. Once isolated, the host nucleic acid can be further characterized and analyzed. For example, the nucleic acid can be sequenced and compared to other similar nucleic acids. Methods of using these nucleic acids, and the proteins encoded thereby, are discussed below.

Using these gene trap methods, several host molecules were identified that were previously not known to be involved in viral pathogenesis (SEQ ID NOS: 1-232, Table 1, and target sequences associated with SEQ ID NOS: 1-232). For example, the AMT gene (target sequences associated with SEQ ID NOS: 36 and 37) participates in influenza A infection of host cells. Fragments of host sequences involved in viral infection and pathogenesis can now be identified, even including fragments or sequences that were previously known to be important in the pathogenesis of intracellular pathogens. For example, although the T-cell receptor was previously implicated in HIV infection, the results disclosed herein demonstrate that the T-cell receptor V-D-J beta 2.1 chain (target sequences associated with SEQ ID NO: 20) is involved and in some examples required for HIV infection, and host cells lacking the T-cell receptor V-D-J beta 2.1 chain are unexpectedly highly resistant to HIV infection. Hence the V-D-J beta 2.1 chain is a target for anti-viral therapy at the DNA or polypeptide level, and other pathogenically active subcomponents of other known pathogenic sequences can also be identified with this method.

Examples of these host nucleic acid molecules are target sequences associated with SEQ ID NOS: 1-227, 229, and 231 (including variants, fragments, and fusions thereof) and summarized in Table 1. In addition to these specifically disclosed nucleotide sequences, a host nucleic acid can include nucleotide sequences that are similar to any of the target sequences associated with SEQ ID NOS: 1-227, 229, and 231, such as having at least 70% identity, at least 80% identity, at least 85% identity, at least 90% identity, at least 95% identity, at least 98% identity, or even at least 99% identity to any of the target sequences associated with SEQ ID NOS: 1-227, 229, and 231. The disclosed host nucleic acid sequences, and methods of using them, may comprise, consist, or consist essentially of any of the disclosed nucleic acid sequences shown in SEQ ID NOS: 1-227, 229, and 231, as well as target sequences associated with SEQ ID NOS: 1-227, 229, and 231, or variants or fragments thereof, or sequences that hybridize to the identified sequences under stringent or moderately stringent conditions.

The host nucleic acid molecules also include a fragment of any target sequence associated with SEQ ID NOS: 1-227, 229, and 231, such as a probe or primer as described below.

Host polypeptides corresponding to these nucleic acids also can be used to practice the disclosed methods. In some examples, the polypeptide includes an amino acid sequence that corresponds to a coding sequence of any target sequence associated with SEQ ID NOS: 1-227, 229, and 231, or a target protein sequence associated with SEQ ID NOS: 228, 230, and 232. However, host polypeptides can also include those having similar amino acid sequences, such as polypeptides that are at least 70% identical, at least 80% identical, at least 90% identical, at least 95% identical, at least 98% identical, or at least 99% identical to the amino acid sequences corresponding to translations of the coding sequence of any target sequence associated with SEQ ID NOS: 1-227, 229, and 231, or a target protein sequence associated with SEQ ID NOS: 228, 230, and 232. For example, the disclosed host polypeptides and methods of using them, may comprise, consist, or consist essentially of an amino acid sequence corresponding to a translation of the nucleotide sequence in any target sequence associated with SEQ ID NOS: 1-227, 229, and 231, a target protein sequence associated with SEQ ID NOS: 228, 230, and 232, or any of the protein sequences listed in Table 1. Alternatively, the polypeptides include homologous polypeptides from other mammals (for example human, monkeys, and dogs).

The host polypeptide can have an amino acid sequence that varies by one or more conservative substitutions from the amino acid sequences of the proteins encoded by target sequences associated with SEQ ID NOS: 1-227, 229, and 231, or from the target amino acid sequences associated with SEQ ID NOS: 228, 230, and 232. In one example, there is no more than 1, 2, 3, 4, 5, or 10 conservative amino acid substitutions. In another example, there are 1, 2, 3, 4, 5 or 10 conservative amino acid substitutions. The effects of these amino acid substitutions, deletions, or additions on host polypeptides can be assayed, for example, by analyzing the ability of cells transformed with the derivative proteins to resist infection by the corresponding virus.

Also included are fragments of any host polypeptide encoded by any of the target sequences associated with SEQ ID NOS: 1-227, 229, and 231, as well as fragments of the target amino acid sequences associated with SEQ ID NOS: 228, 230, and 232. For example, a protein can include at least 5-500 contiguous amino acids of the protein, such as at least 6-200, at least 6100, at least 10-100, at least 10-50, or at least 20-50 contiguous amino acids of the protein. A host polypeptide fragment can be at least 5, at least 10, at least 15, at least 25, at least 50, at least 100, at least 200, at least 500, or more amino acids of a polypeptide having an amino acid sequence corresponding to a coding region of the nucleotide sequence in any of the target sequences associated with SEQ ID NOS: 1-227, 229, and 231, or a conservative variant thereof, as well as target amino acid sequences associated with SEQ ID NOS: 228, 230, and 232.

Fragments of a nucleic acid target sequences associated with SEQ ID NOS: 1-227, 229, and 231 can include 10-5000 contiguous nucleic acids, such as 12-1000, 12-500, 15-100, or 18-50 contiguous nucleic acids. A host nucleic acid fragment can be at least at least 5, at least 10, at least 15, at least 20, at least 25, at least 50, at least 100, at least 200, at least 500, at least 1000, at least 2000, at least 5000 or more contiguous nucleic acids in any target sequence associated with SEQ ID NOS: 1-227, 229, and 231, or a variant or fusion thereof.

Also included are host nucleic acids that encode the same polypeptide encoded by any target sequence associated with SEQ ID NOS: 1-227, 229, and 231, or a conservative variant of the polypeptide, or a fragment thereof. For example, a host nucleic acid provided by target sequences associated with SEQ ID NOS: 36-37 encodes AMT. A second host nucleic acid also can encode an AMT having the same amino acid sequence as the AMT encoded by target sequences associated with SEQ ID NOS: 36-37, a conservative variant of this AMT, or a fragment thereof, yet this second host nucleic acid can have a different nucleotide sequence than a target sequence associated with SEQ ID NOS: 36-37 due to the degeneracy of the genetic code.

Methods of Using Host Sequences to Decrease Viral Infection

The interaction between a host nucleic acid or polypeptide (such as target sequences associated with SEQ ID NOS:

1-232 and those shown in Table 1) and a virus or viral protein can be decreased or inhibited using the methods provided. Decreasing or inhibiting this interaction can be used to decrease viral infection of a host cell, and/or to decrease symptoms associated with a viral infection in a subject. For example, decreasing or even inhibiting the interaction of a host nucleic acid or polypeptide and a virus can decrease, inhibit, or even prevent infection of a host cell by that virus, or otherwise inhibit the progression or clinical manifestation of the viral infection. In addition, decreasing the interaction of a host nucleic acid or polypeptide and a virus can reduce or alleviate one or more symptoms associated with viral infection, such as a fever.

Several methods can be used to decrease or inhibit the interaction between a viral protein and a host protein or nucleic acid. The viral and host proteins or nucleic acids can be part of an in vitro solution, an in vivo expression system, or in situ with a host tissue or subject. The viral protein can be part of a larger molecule or complex, such as an envelope protein on the envelope of a mature virus or a fragment of a viral envelope. The host protein also can be part of a larger molecule or complex, such as a host polypeptide expressed as part of a fusion protein or contained as one subunit of a larger protein, such as a transport protein, cell receptor, structural protein, or an enzyme. A host nucleic acid can be part of a larger molecule, complex, organism or microorganism such as a host nucleic acid contained within its host genome, a recombinant vector, or a transgenic organism or microorganism (including both extrachromosomal molecules or genomic insertions).

In accordance with the disclosed methods, interaction is decreased or inhibited between a virus or viral protein and more than one (such as 2 or more, such as 3 or more) host nucleic acids or polypeptides. Decreasing or inhibiting the interactions of one or more host nucleic acids or polypeptides with one or more viral proteins can have additive or exponentially increasing effects. For example, it is believed that decreasing the interaction between a host T-ell receptor V-D-J beta 2.1 chain and HIV, or decreasing the activity of a host β-chimerin, within a host cell can enhance the inhibitory effect on HIV infection of that host cell compared to inhibiting the interaction of only one of the host polypeptides. Hence, the methods include interfering with an interaction between the virus or viral protein and more than one of the proteins associated with infection by the same virus.

For example, for infection with HIV, the method could interfere with one, or two or more (such as three or more) of the following: T-cell receptor V beta chain; T-ell receptor V-D-J beta 2.1 chain; β-chimerin (CHN2); malic enzyme 1; Hypothetical protein XP_174419; sequence from Chromosome 4q31.3-32; alpha satellite DNA; LOC253788; LOC219938; coagulation factor III (F3); LOC91759; similar to KOX4 (LOC131880); LOC166140; LOC222474; similar to Rho guanine nucleotide exchange factor 4, isoform a; APC-stimulated nucleotide exchange factor (LOC221178); T-cell receptor beta; ribosomal protein L7A-like 4 (RPL7AL4); v-src sarcoma (Schmidt-Ruppin A-2) viral oncogene homolog (avian) (SRC); KIAA0564; alpha satellite DNA; M96 protein; hypothetical protein similar to G proteins (such as RAP-2A; LOC57826); LOC161005 and osteoblast specific factor 2 (fasciclin I-like).

For Ebola virus, examples of targets include one, or two or more (such as three or more) of the following: exportin 5; DNA polymerase eta (POLH); heterogenous nuclear riboprotein C (C1/C2); alpha-endosulfine pseudogene; LOC128741; LOC222888; LOC138421; zinc finger protein 297B; sideroflexin 5; importin 9; T-cell receptor beta; similar to murine putative transcription factor ZNF131 (LOC135952); KIAA1259; MURR1; CCT4; FLJ40773 and similar to ribosomal protein L24-like (LOC149360); testin 2; testin 3; polybromo 1; DNA damage inducible transcript 3 (DDIT3); KIAA1887; PDZ and LIM domain 1 (elfin) (PDLIM1); LOC284803; PRO0097 and FLJ31958; small inducible cytokine E, member 1 (endothelial monocyte-activating); E3 ubiquitin ligase (SMURF2) and MGC40489; Rab9; PRO1617 and retinoblastoma binding protein 1 (RBBP1); region of chromosome 2q12; elongation factor for selenoprotein translation; transcription factor SMIF (HSA275986); KIAA1026; trinucleotide repeat containing 5; homogentisate 1,2 dioxygenase; region of chromosome Xq23-24; region of chromosome 4p15.3; similar to LWamide neuropeptide precursor protein [*Hydractinia echinata*] (LOC129883); region of chromosome 2q21; region of chromosome Xp11.4, including UPS9X; LOC221829; U3 small nuclear RNA; integrin, beta 1; acrosomal vesicle protein 1 (ACRV1) and CHK1 checkpoint homolog (CHEK1); prospero-related homeobox 1 (PROX1); FLJ20627 and FLJ12910; PIN2-interacting protein (PINX1) and SRY (sex-determining region Y)-box 7 (SOX7); LOC131920; region of chromosome 13q14; neurotrophic tyrosine kinase, receptor, type 3 (NTRK3); TERA protein; FLJ13224; LOC284260; POM (POM121 homolog) and ZP3 fusion (POMZP3); DEAD/H box polypeptide 8 (DDX8) and similar to ribosomal protein L29 (cell surface heparin binding protein HIP) (LOC284064); LOC345307 and UDP-N-acetyl-D-galactosamine:polypeptide N-acetyl-galactosaminyltransferase 7 (GALNT7); 5S rRNA pseudogene; ribosomal protein L27a pseudogene (RPL27AP) and v-myb myeloblastosis viral oncogene homolog-like 2 (MYBL2); Down's syndrome cell adhesion molecule like 1; LOC148529; Huntingtin-associated protein interacting protein; LOC158525 and similar to RIKEN cDNA 1210001E11 (LOC347366); hypothetical protein FLJ12910; LOC350411; allograft inflammatory factor 1 (AIF1); HLA-B associated transcript 2 (BAT2); C10orf7; LOC346658; LOC340349; region of chromosome 12q21; LOC339248; FLJ22659; SR rich protein DKFZp564B0769; hypothetical protein MGC14793; FLJ10439; cytochrome P450, family 11, subfamily A, polypeptide 1; sema domain, immunoglobulin domain (Ig) and GPI membrane anchor, (semaphoring) 7A; ribosomal protein S16; hypothetical protein DKFZp434H0115; ATP citrate lyase; calnexin; protein tyrosine phosphatase, receptor type, K (PTPRK); cyclin M2; AXL receptor tyrosine kinase; *Homo sapiens* chromosome 10 open reading frame 3, mRNA (cDNA clone MGC:3422 IMAGE:3028566); *Homo sapiens* chromosome 10 open reading frame 3 (C10orf3); and *Homo sapiens* fer-1-like 3, myoferlin (*C. elegans*) (FER1L3), transcript variant 1.

For influenza, examples of targets include one, or two or more (such as three or more) of the following: T-cell leukemia translocation-associated (TCTA) gene, aminomethyltransferase; dystroglycan; BSN; LIM domain containing preferred translocation partner in lipoma (LPP); sequence between LOC253121 and hyaluronan synthase 2 (HAS2); testin 2; testin 3; PTPN1 gene for protein tyrosine phosphatase, non-receptor type 1; sequence between LOC149360 and LOC253961; sequence between KIAA1560 and tectorin beta; cadherin related 23; myeloid/lymphoma or mixed lineage leukemia, translocated to 10; malic enzyme 1; hypothetical protein XP-174419; and sequence from chromosome 4q31.3-32.

In examples where a host polypeptide is a cell receptor or part of a cell receptor, decreasing or preventing expression of the polypeptide, or altering the three-dimensional structure of the polypeptide, can reduce or inhibit the interaction between the host cell receptor and a viral protein. Similarly, decreasing, inhibiting or preventing expression of a host ligand polypeptide (or altering the structure of such a ligand) can decrease or inhibit an interaction between the viral protein and the ligand. For example, decreasing or inhibiting expression of one or more enzymes involved in viral pathogenesis, such as those listed in Table 1 and those target sequences associated with SEQ ID NOS: 1-232, can block a component of the viral life cycle, such as blocking a signal pathway leading to transcription or translation of the viral genome, or assembly of viral sub-parts. Decreasing or inhibiting the enzymatic activity of an enzyme (rather than its expression) can have a similar effect Altering the nucleotide sequence of a host nucleic acid, for example by targeting disruption of the nucleotide sequence using complementary nucleic acid sequences, can decrease, inhibit or prevent integration of a viral nucleic acid into the host nucleic acid. Methods that can be used to interrupt or alter translation of a host nucleic acid include, but are not limited to, using an antisense RNA, RNAi molecule, or an siRNA that binds to a messenger RNA transcribed by the nucleic acid encoding a host polypeptide as described herein Decreasing or inhibiting the expression of the host nucleic acid can also alter the course of the disease. In one example, altering the nucleotide sequence of a host gene that is targeted by a virus for viral integration can decrease, inhibit, or even prevent, integration of that virus into the host genome.

A host nucleic acid involved in viral infection, including variants, fusions and fragments thereof, can be used to design agents that bind to a target sequence of that nucleic acid, such as antisense nucleic acids or siRNAs. Such nucleic acid binding agents can be used to decrease or inhibit expression of the nucleic acid, to reduce the incidence of viral infection. For example, an expression vector that transcribes antisense RNA or siRNA that recognizes human β-chimerin mRNA is used to transform cell lines obtained from simians. These transformed cell lines are analyzed for infection by simian immunodeficiency virus (SIV), which is related to HIV. If those cells are resistant to SIV infection, the disrupted gene is identified, sequenced, and compared to the human β-chimerin gene. Sequence similarities between the two genes will offer insight into common molecular mechanisms for infection by HIV and SIV, for example, common structural regions within their respective translated proteins.

A binding agent that recognizes a host nucleic acid involved in viral infection can be used for prophylactic or therapeutic purposes. For example, expression vectors having antisense RNA, RNAi molecules, or siRNA molecules that target a host nucleic acid involved in viral infection, such as β-chimerin, are introduced into the bone marrow of a subject. Uptake of the vector and expression of the antisense RNA, RNAi, or siRNA within cells infected by HIV offers a prophylactic or therapeutic effect by disrupting the β-chimerin genes within those cells, thus decreasing or inhibiting HIV infection. Similarly, expression vectors including Rab9 antisense RNA, RNAi, or siRNA molecules can be introduced into the bone marrow of a subject. Uptake of the vector and expression of Rab9 antisense RNA, RNAi, or siRNA within cells infected by a pathogen that can hijack a lipid raft, such as HIV or Ebola, offers a prophylactic or therapeutic effect by disrupting the Rab9 genes within those cells, thus decreasing or even inhibiting infection by a pathogen that can hijack a lipid raft. The vector, or other nucleic acid carrying the nucleic acid specific binding agent, is introduced into a subject by any standard molecular biology method and can be included in a composition containing a pharmaceutically acceptable carrier.

Decreasing or inhibiting the interaction between a viral protein and a host protein can decrease or inhibit viral infection. Methods that can be used to decrease an interaction between a viral protein and one or more host proteins (such as at least 2 host proteins, or at least 3 host proteins), include but are not limited to, disrupting expression of a host nucleic acid sequence encoding the host protein, (for example by functionally deleting the coding sequence, such as by a mutation, insertion, or deletion), altering the amino acid sequence or overall shape of the host protein, degrading the host protein, employing an agent that interferes with the viral protein or host protein (such as a specific binding agent, for example an antibody or small molecule), or a combination thereof.

For example, expression of a host protein can occur during transcription or translation of a nucleic acid encoding the host protein, or as a result of post-translational modification of a host protein. Methods that can be used to interrupt or alter transcription of a nucleic acid include, but are not limited to, site-directed mutagenesis, including mutations caused by a transposon or an insertional vector; and providing a DNA-binding protein that binds to the coding region of the host protein, thus blocking or interfering with RNA polymerase or another protein involved in transcription. Various inactive and recombinant DNA-binding proteins, and their effects on transcription, are discussed in Lewin, *Genes VII*. Methods that can be used to interrupt or alter translation of a nucleic acid include, but are not limited to, using an antisense RNA or an siRNA that binds to a messenger RNA transcribed by the nucleic acid encoding the host polypeptide as described herein.

For example, exemplary host T-cell receptor polypeptides are encoded by target sequences associated with SEQ ID NOS: 1-20. Disrupting the expression of a nucleic acid including any target sequence associated with SEQ ID NOS: 1-20 can reduce or prevent production of the corresponding T-cell receptor polypeptide, and without access to the T-cell receptor polypeptide, an HIV virus cannot infect the host cell. Even if expression of the host nucleic acid is not completely blocked or disrupted, virus infection can still be inhibited. For example, interference with a host protein encoded by any target sequence associated with SEQ ID NOS: 1-20 reduces the number of T-cell receptors within that host cell available for recognition by an HIV virus, thus inhibiting HIV infection.

It is shown herein that inhibiting the interaction or activity between host Rab9 and HIV and Ebola using Rab9 siRNA molecules decreases infection of a host cell by the virus compared to the amount of infection in the absence of the siRNA molecules.

Host proteins involved in viral infection, such as those encoded by target cDNA sequences associated with SEQ ID NOS: 1-227, 229, and 231, as well as target sequences associated with SEQ ID NOS: 228, 230, and 232, can be used to generate specific binding agents to those proteins. The specific binding agent can be an anti-protein binding agent, such as a monoclonal or polyclonal antibody. Anti-protein binding agents can provide a prophylactic or therapeutic effect, for example by interfering with viral infection. Assays to determine whether an antibody interferes with viral infection are described herein. Antibodies that recognize a host protein involved in viral infection can prevent a virus or portion thereof (such as a viral protein) from binding to a host protein involved in viral infection. For example, a monoclonal or polyclonal antibody that binds to a V beta T-cell receptor on a cell can block the binding of HIV to that T-cell receptor, thus blocking infection of that cell. Effective amounts of such specific binding agents can be administered alone to a subject, or as part of a pharmaceutical composition, for the treatment of viral infection or as a prophylactic measure prior to the time the subject is exposed to the virus. In another example, specific binding agents that recognize a host protein involved in viral infection, such as β-chimerin or Rab9, can be used can be used to screen for the presence of the host protein, in other cells, tissues or lysates, including a biological sample obtained from a subject.

Host nucleic acids and polypeptides described herein, such as target sequences associated with SEQ ID NOS: 1-232, can be used for prophylactic or therapeutic uses. For example, polypeptides with structures mimicking a protein recognized by a virus can be administered to a subject as a pharmaceutical composition. These polypeptides interact with a virus already infecting that subject, or provide a prophylactic defense mechanism against infection if the subject is at risk of exposure to a virus. For example, polypeptides structurally similar to the T-cell receptor V beta 2.1 chain are recognized by HIV. If such polypeptides are administered to an HIV-positive subject, the viruses already present in the subject interact with those polypeptides in addition to that subject's T-cell receptors, thus inhibiting the rate at which my infects T-cells. The administered polypeptides act as "decoys" to block HIV from interacting with T-cell receptors. As another example, an agent that otherwise interferes with the interaction between a virus and a host protein can provide a similar prophylactic effect. For example, a chemical compound or anti-AMT binding agent (such as an antibody) that interferes with the interaction between AMT and an influenza virus (including an enzymatic inhibitor of AMT) provides a prophylactic or therapeutic effect against influenza A infection when provided to a host cell or administered to a host subject.

Additionally, the proteins described herein can be used to screen samples for the presence or absence of a particular antibody. For example, a β-chimerin or Rab9 protein can be used in an ELISA to screen a sample obtained from an individual for the presence of anti-β-chimerin or anti-Rab9 antibodies generated by that individual, such as a blood sample.

Using a method similar to that described for nucleic acid binding agents above, protein binding agents (such as agents that specifically bind β-chimerin, Rab9, or V beta T-cell receptor proteins) can be used to screen cells, individuals or populations for the presence or absence of polypeptides related to infection (such as HIV, Ebola, or influenza infection), thus providing information about the susceptibility or resistance of that individual or population to viral infection.

The host nucleic acids, proteins, and related specific binding agents described herein can be used as models for the design of anti-viral drugs. For example, the three-dimensional structure of a protein described herein, such as β-chimerin, can be used in computer modeling of chemotherapeutic agents that block the activity of that moiety, for example by binding the protein. As another example, a monoclonal antibody can be used in a competitive binding assay to screen for other compounds that bind the same antigen.

Screening for Resistance to Infection

Also provided herein are methods of screening host subjects for resistance to infection by characterizing a nucleotide sequence of a host nucleic acid or the amino acid sequence of a host polypeptide (such as those shown in Table 1, or any target sequence associated with SEQ ID NOS: 1-232).

For example, the T-cell receptor V beta 2.1 chain nucleic acid of a subject can be isolated, sequenced, and compared to SEQ ID NO: 20 (or a target sequence associated with SEQ ID NO: 20). The greater the similarity between that subject's V beta 2.1 chain nucleic acid and the sequence shown in SEQ ID NO: 20 (or a target sequence associated with SEQ ID NO: 20), the more susceptible that person is to HIV infection, while a decrease in similarity between that subject's V beta 2.1 chain nucleic acid and SEQ ID NO: 20 (or a target sequence associated with SEQ ID NO: 20), the more resistant that subject can be to HIV infection.

In another example, the aminomethyltransferase (AMT) nucleic acid of a subject can be isolated, sequenced, and compared to SEQ ID NOS: 36-37 (or a target sequence associated with SEQ ID NOS: 36-37). The greater the similarity between that subject's AMT nucleic acid and the sequence shown in SEQ ID NOS: 36-37 (or a target sequence associated with SEQ ID NOS: 36-37), the more susceptible that person is to influenza A infection, while a decrease in similarity between that subject's AMT nucleic acid and SEQ ID NOS: 36-37 (or a target sequence associated with SEQ ID NOS: 36-37), the more resistant that subject can be to influenza A infection.

In yet another example, the Ras oncogene family member Rab9 nucleic acid of a subject can be isolated, sequenced, and compared to SEQ ID NOS: 118-119 (or a target sequence associated with SEQ ID NOS: 118-119). The greater the similarity between that subject's Rab9 nucleic acid and the sequence shown in SEQ ID NOS: 118-119 (or a target sequence associated with SEQ ID NOS: 118-119), the more susceptible that person is to infection by a pathogen that uses lipid rafts, such as those listed in Table 2, while a decrease in similarity between that subject's Rab9 nucleic acid and SEQ ID NOS: 118-119 (or a target sequence associated with SEQ ID NOS: 118-119), the more resistant that subject nay be to infection by a pathogen that uses lipid rafts.

Assessing the genetic characteristics of a population can provide information about the susceptibility or resistance of that population to viral infection. For example, polymorphic analysis of AMT alleles in a particular human population, such as the population of a particular city or geographic area, can indicate how susceptible that population is to influenza A infection. A higher percentage of AMT alleles substantially similar to SEQ ID NOS: 36-37 (or a target sequence associated with SEQ ID NOS: 36-37) indicates that the population is more susceptible to influenza A infection, while a large number of polymorphic alleles that are substantially different than SEQ ID NOS: 36-37 (or a target sequence associated with SEQ ID NOS: 36-37) indicates that a population is more resistant to influenza A infection. Such information can be used, for example, in making public health decisions about vaccinating susceptible populations.

Transgenic Cells and Non-Human Mammals

Transgenic animal models, including recombinant and knock-out animals, can be generated from the host nucleic acids described herein. Exemplary transgenic non-human mammals include, but are not limited to, mice, rats, chickens, cows, and pigs. In certain examples, a transgenic non-human mammal has a knock-out of one or more of the target sequences associated with SEQ ID NOS: 1-35, and has a decreased viral susceptibility, for example infection by HIV. In certain embodiments, a transgenic non-human mammal has a knock-out of any of the target sequences associated with SEQ ID NOS: 36-63, and has a decreased viral susceptibility, for example infection by influenza A. In certain examples, a transgenic non-human mammal has a knock-out of any of the target sequences associated with SEQ ID NOS: 64-232, and has a decreased viral susceptibility, for example infection by Ebola. In certain examples, a transgenic non-human mammal has a knock-out of any target sequence associated with SEQ ID NOS: 118-119, and has a decreased susceptibility to infection by a pathogen that uses a lipid raft, such as those listed in Table 2. Such knock-out animals are useful for reducing the transmission of viruses from animals to humans. In addition, animal viruses that utilize the same targets provided herein can be decreased in the animals.

Expression of the sequence used to knock-out or functionally delete the desired gene can be regulated by choosing the appropriate promoter sequence. For example, constitutive promoters can be used to ensure that the functionally deleted gene is never expressed by the animal. In contrast, an inducible promoter can be used to control when the transgenic animal does or does not express the gene of interest. Exemplary inducible promoters include tissue-specific promoters and promoters responsive or unresponsive to a particular stimulus (such as light, oxygen, chemical concentration, such as a tetracycline inducible promoter).

For example, a transgenic mouse including an AMT gene (such as a target sequence associated with SEQ ID NOS: 36-37), or a mouse having a disrupted AMT gene, can be examined during exposure to various mammalian viruses related to influenza A. Comparison data can provide insight into the life cycles of influenza and related viruses. Moreover, knock-out animals (such as pigs) that are otherwise susceptible to an infection (for example influenza) can be made to determine the resistance to infection conferred by disruption of the gene.

Transgenic pigs having a disrupted human protein tyrosine phosphatase gene can be produced and used as an animal model to determine other types of infections, including viral infections in mammals related to influenza A. A transgenic pig resistant to infection by viruses other than influenza A is used to demonstrate the relatedness of influenza and those other viruses. Transgenic animals, including methods of making and using transgenic animals, are described in various patents and publication, such as WO 01/43540; WO 02/19811; U.S. Pub. Nos: 2001-0044937 and 2002-0066117; and U.S. Pat. Nos. 5,859,308; 6,281,408; and 6,376,743; and the references cited therein.

Cells including an altered or disrupted host nucleic acid or polypeptide having a role in viral infection (such as a target sequence associated with SEQ ID NOS: 1-232), are resistant to infection by a virus (see Example 2). Such cells may therefore include cells having decreased susceptibility to HIV infection (such as cells having altered or disrupted target sequence associated with SEQ ID NOS: 1-35), Ebola infection (such as cells having altered or disrupted target sequence associated with SEQ ID NOS: 64-232), or influenza A (such as cells having altered or disrupted target sequence associated with SEQ ID NOS: 36-63). For example, cells in which a β-chimerin gene was died using the gene-trap method remain $CD4^+$ after HIV infection and do not produce further detectable HIV virus particles. Thus, disrupting the expression of β-chimerin can confer resistance on the cell to infection by HIV. Additionally, interfering with the activity of β-chimerin, such as contacting a β-chimerin with an enzymatic inhibitor or an anti-β-chimerin binding agent, can confer a similar resistance to HIV infection.

Screening for Agents that Decrease Viral Infection

A host nucleic acid or polypeptide involved in viral infection, such as a target sequence associated with SEQ ID NOS: 1-232, and peptides listed in Table 1, can be used to identify agents that inhibit the binding of a virus or viral protein to a host nucleic acid, a host protein, or another target protein capable of binding to the virus or viral protein. In some examples, a host molecule, such as a host protein or nucleic acid is contacted with a viral molecule, such as a virus or portion thereof, for example as a viral protein. One or more test agents are contacted with the host molecule, the viral molecule, both molecules, before, during or after contacting the host and viral molecules. Subsequently, it is determined whether binding of the viral molecule to the host molecule is decreased in the presence of the test agent, wherein a decrease in binding is an indication that the test agent decreases the binding of viral protein to the target protein.

In other examples, a cell-based assay is used to identify proteins that decrease viral infection, for example using the yeast two-hybrid system.

For example, the binding of the T-cell receptor V-D-J beta 2.1 chain polypeptide to HIV (or an HIV envelope glycoprotein) can be determined in the presence of a test agent. A decrease in binding activity between the T-cell receptor V-D-J beta 2.1 chain polypeptide and HIV indicates that the test agent decreases the binding of HIV to the T-cell receptor V-D-J beta 2.1 chain, and the agent is a candidate for use as an anti-HIV agent. A decrease in binding activity can be determined by a comparison to a reference standard, such as a binding activity reported in the scientific literature, or to a control. Any suitable compound or composition can be used as a test agent, such as organic or inorganic chemicals, including aromatics, fatty acids, and carbohydrates; peptides, including monoclonal antibodies, polyclonal antibodies, and other specific binding agents; or nucleic acids. The virus or viral molecule can be obtained from any suitable virus, such as HIV, influenza A, Ebola, and related viruses.

Therapeutic agents identified with the disclosed approaches can be used as lead compounds to identify other agents having even greater antiviral activity. For example, chemical analogs of identified chemical entities, or variant, fragments of fusions of peptide agents, are tested for their ability to decrease viral infection using the disclosed assays. Candidate agents are also tested for safety in animals and then used for clinical trials in animals or humans.

Microarrays

The host nucleic acids or proteins disclosed herein having a role in viral infection, such as a target sequence associated with SEQ ID NOS: 1-232, can be used in an array. The array can be a microarray, such as a nucleic acid array that includes probes to different polymorphic alleles of a human AMT gene (for example target sequence associated with SEQ ID NOS: 36-37) or a human Rab9 gene (for example target sequence associated with SEQ ID NOS: 118-119). Kits can be generated, such as diagnostic kits or kits for screening for the presence or absence of a host nucleic acid within a biological sample obtained from a subject or kits for administering an effective amount of a specific binding agent to a subject for a therapeutic or prophylactic purpose.

The following examples are provided to illustrate particular features of certain embodiments, but the scope of the claims should not be limited to those features exemplified.

EXAMPLE 1

Generation of Cells with Increased Resistance to Viral Infection

The gene-trap method was used to identify cellular genes needed for viral propagation but whose inactivation is not lethal to the host cell. This was accomplished by using a Moloney murine leukemia virus-derived shuttle vector that encodes for a promoterless neomycin-resistance gene (FIG. 1). This vector integrates into the host genome at transcriptionally active genes, thereby disrupting the host gene but utilizing the host promoter to drive neomycin resistance carried by the vector. The cells are then infected with the desired virus. Cells surviving the viral infection carry an interrupted host gene that is needed during the viral life cycle. Since the construct is a shuttle vector, it can function as a plasmid and can be moved from mammalian to bacterial systems, facilitating subcloning and DNA sequencing. Using this approach, loci involved in, and in some cases required for viral infection, for example by HIV-1 and HIV-2, influenza A and Ebola virus were identified.

Tissue Culture

Sup-T1 human lymphoblastic leukemia cells were cultured in RPMI-1640 medium supplemented with 10% heat-inactivated fetal calf serum (FCS), penicillin, streptomycin and Fungisome. MDCK normal canine kidney cells were cultured in DMEM supplemented with 10% fetal bovine serum (FBS), penicillin, streptomycin. Vero African green monkey kidney cells were cultured in DMEM supplemented with 10% FBS, amphotericin B, streptomycin, and Glutamine. All cultures were grown under 5% $CO_2$. Selection by all media was done in the presence of either 1 mg/ml (Sup-T1 and MDCK cells) or 400 mg/ml G418 (Geneticin; Vero cells).

Generation of Gene-Trapped Library of Cells

Parental, virus sensitive cells were plated and infected with U3neoSV1 as follows. Retrovirus vectors were obtained from H. Earl Ruley (Department of Microbiology and Immunology, Vanderbilt University School of Medicine, Nashville, Tenn.). Stocks of the U3neoSV1 virus were prepared as described (Chen et al., Gene trap retroviruses in *Methods in Molecular Genetics* (1994), page 123, herein incorporated by reference).

FIG. 1 illustrates the U3neoSV1 retroviral vector, which contains a promoterless neomycin phosphotransferase gene ($Neo^R$) within the U3 unique sequence of the 5' long terminal repeat (LTR) of MMLV. Additionally, a second mutationally inactivated copy of neo is present in the 3' LTR. Portions of the MMLV genome were removed to impair replication, and were replaced with the β-lactamase gene which confers ampicillin resistance ($Amp^R$) to *E. coli* as well as an *E. coli* origin of replication (ori), flanked by two unique restriction sites for BamHI (position 2570) and EcoRI (position 4175). Sites and orientations of primers used for sequence analysis of cloned genomic fragments are indicated by the triangular arrowheads.

Parental, virus sensitive cells (106 Sup-T1 for HIV, Madin-Darby canine kidney, (MDCK) for influenza A, or Vero cells for Ebola) were plated for 12 hours before infection, after which U3neoSV1 was added at a multiplicity of infection (MOI) of 0.1, as titered by adding 1 ml of diluted stocks to cultured cells in the presence of 4 μg/ml polybrene. The cells were incubated at 37° C. for one hour, 10 ml of fresh medium added, and the cells were incubated overnight at 37° C. The next day, the medium was replaced with the appropriate media containing 1 mg/ml G418 and maintained until surviving cells approached confluence, which was usually about two weeks.

Upon random integration of the U3neoSV1 vector into the host genome, endogenous promoters result in expression of $Neo^R$, while expression of the exons 3' to the site of integration is disrupted. Therefore, only those events occurring at transcriptionally active promoters of non-essential genes are selected.

A pool of the surviving cells, termed a library, including many cells bearing different disrupted genes was then exposed to the pathogen of interest. The resulting Sup-T1 library cells, MDCK library cells, and Vero library cells were infected HIV-1 and HIV-2; the A/PR/8/34 virus reassortant having A/Johannesburg/82/96 glycoproteins (H1N1); and Ebola, respectively, as follows.

Figure 4:
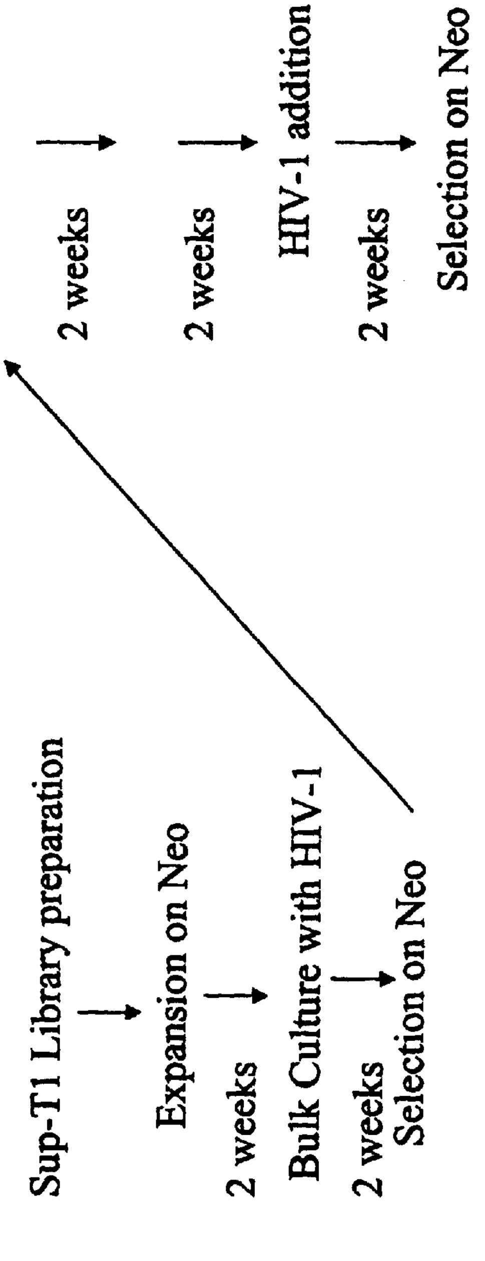
FIG. 4 is a flow chart illustrating a method for isolating cells resistant to HIV infection, including HIV-1 and HIV-2 infection.

An aliquot of the cell library was infected with three rounds of HIV-1 and three rounds of HIV-2 (3Bx in BC7 cells), normally a lethal event for Sup T-1 cells (FIG. 4). Approximately $3\times10^8$ actively growing Sup-T1 library cells were infected with the CXCR4 cytopathic HIV-1 strain LAI at an MOI of 10, approximately 100 fold greater that that normally used for spreading infection in culture. The cells were incubated with the virus for four hours in 2 ml of medium, then grown in bulk at $10^6$ cells/ml for two weeks, at which time G418 was added to a final concentration of 1 mg/ml and the cultures continued for an additional two weeks. The surviving cells were exposed to two further rounds of HIV-1 infection as described above and shown in FIG. 4.

Following HIV-1 infection, surviving cells were incubated 1:100 with BC7 T cells constitutively expressing the HIV-2 strain 3BX, which was modified to infect regardless of CD4 status, solely using the CXCR4 receptor. Cells were coincubated for two weeks followed by selection with 1 mg/ml G418 (same as FIG. 4, but with HIV-2 instead of HIV-1). The surviving cells were exposed to two further rounds of HIV-2 infection.

The final cell culture was selected using anti-CD4 magnetic microbeads (Miltyni) and divided into 2.0 ml cultures containing 1000 cells each These were then infected with LAI at an MOI of 10. Surviving cells from each culture were subjected to limit dilution, or growth on methylcellulose, and expanded in selection medium. The isolated clones were identified as being CD4 and CXCR4 positive following flow cytometry analysis using standard protocols. Several cell isolates were resistant to further HIV infection with unique expression of CD4 cell surface antigen.

For influenza infection, approximately $10^7$ actively growing MDCK library cells were washed with phosphate buffered saline (Gibco) and infected with the A/PR/8/34 virus reassortant having A/Johannesburg/82/96 glycoproteins (H1N1) at an MOI of 20-30 in 250 μl DMEM in a T-25 flask. The cells were incubated with the virus for two hours, and the inoculum was subsequently replaced with DMEM, supplemented with 2% FBS and 1 μg/ml TPCK trypsin (to cleavage-activate HA of new progeny virus). The cells were incubated for 18 hours to provide 2-3 rounds of infection. The maintenance medium was removed and replaced with selection medium (DMEM with 10% FBS and 1 mg/ml neomycin) and survivors allowed to expand. The surviving cells were exposed to one additional round of infection as described.

For filovirus infection, vero library cells were infected with either the Gulu 2000 or Zaire 1976 Ebola (EBO) strains, or the Voege 1967 strain of Marburg (MBG) at an MOI of greater than one in T-75 flasks in medium supplemented with 400 mg/ml G418. After a cytopathic effect (CPE) of 4+ was attained (greater than one week), survivors were harvested and reseeded undiluted and at 1:16 and 1:256 dilutions in selection medium Wells with growth after 10 or more days were reinoculated into T12.5 flasks in selection medium and allowed to expand.

Cells surviving Ebola or influenza infection were cloned by either limiting dilution or growth on methylcellulose. The isolates were characterized phenotypically by flow cytometry and the interrupted gene determined by inverse PCR, cloning into BAC, or by the use of the shuttle feature of the vector followed by DNA sequence analysis.

EXAMPLE 2

Cloning and Sequencing of Trapped Genes

This example describes the methods used to clone the sequences conferring resistance to the library of cells surviving viral infection. The identified sequences (SEQ ID NOS: 1-227, 229, 231) encode host proteins that are involved in pathogen infection, and in some cases are required for the infectivity by the pathogen.

Isolation of Trapped Genes

The genomic DNA from actively growing virus-resistant isolates was extracted, prepared, and electroporated into cells as follows. Cellular DNA from actively growing virus-resistant isolates was extracted from one million cells using the QIAamp DNA Blood Mini Kit (Qiagen, Inc.) according to the manufacturer's instructions. Genomic DNA was digested at a final concentration of 150 μg/ml with either EcoRI or BamHI (New England Biolabs) at 1.5 or 2 units/μl, respectively (see FIG. 1). Digested DNA was ethanol precipitated using oyster glycogen (Sigma) as a carrier, resuspended to a final concentration of 60 ng/μl and ligated using T4 DNA ligase (New England Biolabs). Genomic digestion resulted in the fragmentation of the retrovirus and the genomic DNA. Ligations were subsequently ethanol precipitated in the presence of glycogen, resuspended in 3 μl water and used directly to transform *E. coli.*

A 1.5 μl aliquot of each precipitated ligation was added to thawed Genehog cells (Invitrogen) or SURE cells (Stratagene), electroporated using a GenePulser (BioRad) according to the manufacturer's instructions, and plated onto Luria broth (LB) agar (1% tryptone, 0.5% yeast extract, 0.5% NaCl, 2% agar) containing 100 μg/μl carbenicillin (Sigma). Clones were isolated after 24 hours and used to inoculate 3 ml LB containing 100 μg/μl carbenicillin. Plasmid DNA was prepared after overnight growth using the QIAprep Spin Miniprep Kit (QIAGEN, Inc.) according to the manufacturer's instructions and eluted in water.

Sequencing of Shuttle Clones

Due to the position of the unique sites in U3neoSV1, BamHI digestion facilitates cloning of DNA 3' to the site of integration, while EcoRI digestion results in the cloning of genomic DNA 5' to the site of integration. Using oligonucleotides homologous to the U3neoSV1 fragment, the sequence of the disrupted genomic DNA flanking the gene-trap insertion site was determined as follows.

Sequencing reactions were performed using the ABI Big-Dye terminator cycle sequencing kit with reaction products resolved on either an ABI 3100 Genetic Analyzer or an ABI 377 DNA Sequencer (Applied Biosystems, Foster City, Calif.). Sequences were obtained by using oligonucleotides 5'-ATCTTGTTCAATCATGCG (SEQ ID NO: 235) and 5'-GGGTCTGACGCTCATG (SEQ ID NO: 236) for EcoRI-generated shuttle clones, or 5'-GATAGGTGCCTCACTG (SEQ ID NO: 237) for BamHI-generated shuttle clones.

Sequence Analysis

Sequences obtained from shuttle clones were analyzed by the Repeatmasker Web Server, available on the Internet at the website for the Department of Molecular Biotechnology, University of Washington, followed by standard nucleotide-nucleotide BLAST (blastn) against the National Center for Biotechnology Information database, including nr (non-redundant GenBank+EMBL+DDBJ+PDB sequences), est (expressed sequence tags) and htgs (unfinished High Throughput Genomic Sequences: phases 0, 1 and 2). Additionally, a nucleotide-protein database (blastx) analysis was performed against the nr database.

Candidate Host Genes Required for Pathogenesis

Candidate host genes required for the indicated pathogen, which were cloned via the gene-trap method and sequenced, are presented in Table 1 and in SEQ ID NOS: 1-226. The $CD4^+$, latently infected, noninfectious HIV-resistant isolates 18B, 18E, 2B, and 2E were used to recover the genes involved in HIV-1 and HIV-2 pathogenesis, influenza A-resistant isolates B1, B3, B5, B6, and B7 were use to recover the host genes involved in influenza A pathogenesis, and Ebola-resistant isolates ZV and MV were used to recover the host genes involved in Ebola pathogenesis. Candidate genes can be validated by siRNA and cDNA complementation, as described in Example 3.

In summary, using the U3neoSV1 gene-trap, sixteen HIV-1 and -2 resistant Sup-T1 cell lines, and fifteen influenza A resistant MDCK cell lines were isolated and characterized. Twenty-three EBO-Zaire resistant Vero cell line pools, twenty-four EBO-Gulu resistant pools, and thirty MBG resistant pools were screened. The shuttle-vector design of the U3neoSV1 gene-trap allowed identification of multiple host genes involved in the pathogenesis of HIV-1, HIV-2, influenza A, and Ebola, which are described herein and summarized in Table 1 and sequences provided in SEQ ID NOS: 1-232. Cross-resistance of resistant isolates to multiple pathogens can be quickly examined to reveal common pathways in the viral life cycles.

EXAMPLE 3 siRNA Molecules Decrease Viral Infection

This example describes methods used to express siRNAs that recognize Rab9 (such as a target sequence associated with SEQ ID NOS: 118-119), AXL (AXL receptor tyrosine kinase; such as a target sequence associated with SEQ ID NO: 226), CHN (beta-chimerin; such as a target sequence associated with SEQ ID NOS: 21-22), KOX (such as a target sequence associated with SEQ ID NO: 30), RBB (retinoblastoma binding protein 1; such as a target sequence associated with SEQ ID NOS: 120-122), KIAA1259; F3 (such as a target sequence associated with SEQ ID NO: 29), and Mselb (mammalian selenium binding protein; such as a target sequence associated with SEQ ID NO: 124).

The following Rab9 siRNA sequences were generated by Dharmacon, RNA Technologies (Lafayette, Colo.) using chemical synthesis: GGGAAGAGTTCACTTATGA (SEQ ID NO: 238); TCACAAAGCTTCCAGAACT (SEQ ID NO: 239); GTAACAAGATTGACATAAG (SEQ ID NO: 240); and GGAAGTGGATGGACATTTT (SEQ ID NO: 241).

The following AXL (AXL receptor tyrosine kinase) siRNA sequences were generated by Dharmacon, RNA Technologies using chemical synthesis: GGUCAGAGCUGGAGGAUUU (SEQ ID NO: 242); GAAAGAAGGAGACCCGUUA (SEQ ID NO: 243); CCAAGAAGAUCUACAAUGG (SEQ ID NO: 244); and GGAACUGCAUGCUGAAUGA (SEQ ID NO: 245).

siRNA sequences were also used that recognized CHN (beta-chimerin); KOX (similar to KOX4 (LOC131880) and LOC166140); RBB (retinoblastoma binding protein 1); KIAA1259; F3 and mammalian selenium binding protein. One skilled in the art will understand that siRNA sequences that recognize other sequences involved in viral infection (such as a target sequence associated with any of SEQ ID NOS: 1-232) can be designed and prepared by commercial entities, such as Dharmacon, RNA Technologies.

The four siRNA sequences for each gene (CHN, KOX, RBB, RAB, KIAA1259, F3, ASL and Mselb) were separately pooled. Each of the eight pools of siRNAs, hybridized to its appropriate complement sequence, were used to transfect JC53 (HeLa cells modified to accept HIV), Vero (monkey kidney cells), MDCK (dog kidney cells), or HEK (human kidney cells). All cells were obtained from American Type Culture Collection (ATCC, Mannassas, Va.). GFP siRNA sequences were used as a negative control.

Cells (20,000 to 250,000) were incubated in serum free media for 24 hours. Cocktails were made by mixing the appropriate duplex siRNAs (50-100 pmoles) with lipofectamine 2000 (4-16 μl) and RNAse Inhibitor (1-4 μl) in a solution of Optimem (serum free medium) in a total volume of 200-2000 μl. The lipofectamine was allowed to incubate at room temperature for 5 minutes before the addition of siRNA. Aliquots (50-500 μl) of the cocktail were added to the cells which were incubated at 37° C. for 48 hours. The cells were then infected with HIV, Ebola, or influenza and the incubation continued for 3-7 days. Following transfection, several assays were conducted to confirm transfection efficiency, and to determine the resistance of the cells to infection by various agents.

Figure 5:
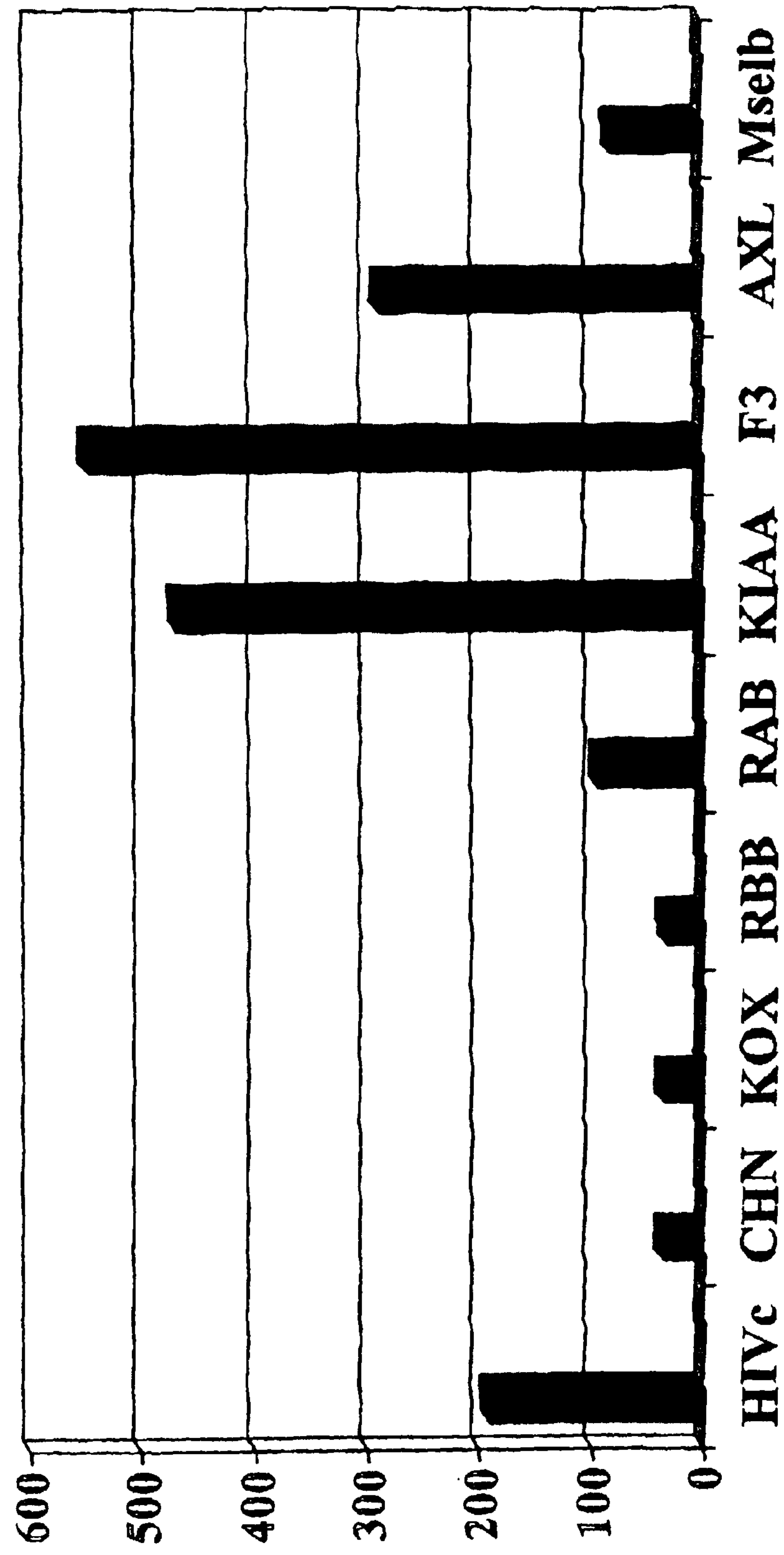
FIG. 5 is a bar graph showing the relative amount of p24 in HIV-infected cells in the presence of various siRNAs. CHN (β-chimerin); KOX (similar to KOX4 (LOC131880) and LOC166140); RBB (retinoblastoma binding protein 1); RAB (Rab9); KIAA1259; F3 (tissue factor 3; thromboplastin); AXL (AXL receptor tyrosine kinase); Msleb (mammalian selenium binding protein).

Quantitation of p24 levels in HIV infected JC53 cells was determined using the Coulter HIV-1 p24 Antigen Neutralization Kit according to the manufacturers recommendation. As shown in FIG. 5, Rab9 siRNAs and mammalian selenium binding protein siRNAs each decreased HIV infection by about 50% on day 4 post infection (day 7 post addition of siRNA). In addition, HIV infection decreased by about 80-90% in the presence of beta-chimerin siRNAs, KOX (similar to KOX4 (LOC131880) and LOC166140) siRNAs, or retinoblastoma binding protein 1 siRNAs. However, HIV infection did not decrease in the presence of siRNAs that recognize KIAA1259, tissue factor 3, or AXL receptor tyrosine kinase. It is possible that apoptosis is interrupted by the siRNAs, so the cell lives through the infection but still makes virus. It is also possible that the p24 levels are elevated but is not associated with infectious particles.

To determine the level of Ebola infection in HEK293 cells transfected with Rab9 or AXL siRNA, the presence of gp1 antigen was determined by using a fluorescent antibody to gp1 envelope protein. Infection by Ebola decreased by at least about 90-95% in the presence of Rab9 siRNA, as compared to the amount of infection in the absence of Rab9 siRNA. Infection by Ebola decreased by at least about 80% in the presence of AXL siRNA, as compared to the amount of infection in the absence of AXL siRNA.

EXAMPLE 4

Expression of Rab9 siRNA Decreases Lipid Raft Formation

Figure 6:
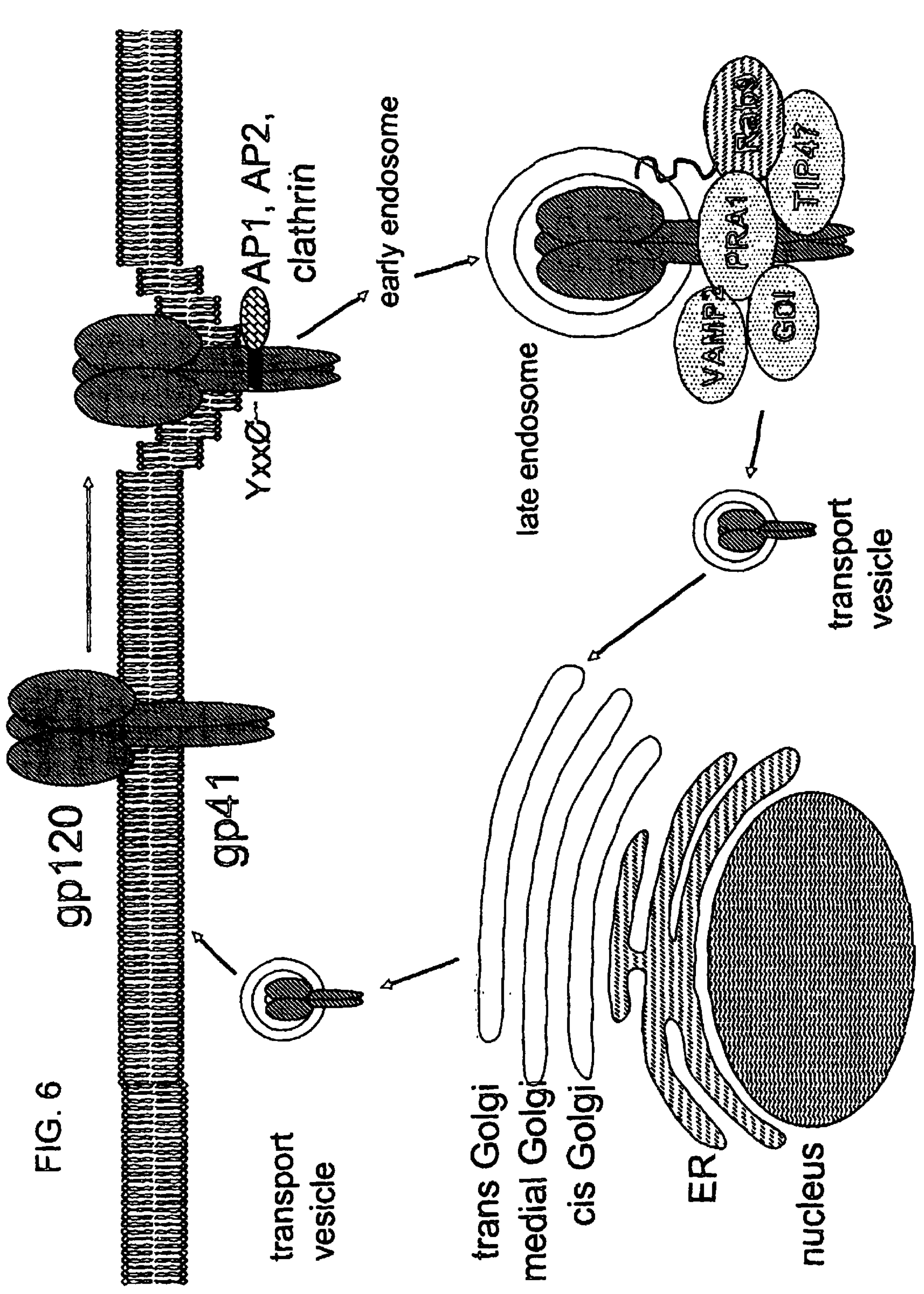
FIG. 6 is a schematic drawing showing a model of Rab9 involvement in lipid raft formation.

As described in Example 3, siRNA molecules that recognize Rab9 decrease viral infection Rab9 transports late endosomes to trans-golgi. Based on these results, a model is proposed whereby Rab9 plays a role in lipid raft formation (FIG. 6). Lipid rafts are liquid-ordered microdomains enriched in sphingolipids and cholesterol and are involved in biosynthetic traffic, signal transduction, and endocytosis. Viruses take advantage of ("hijack") rafts for completion of some steps of their replication cycle, such as entry into their cell host, assembly, and budding. Without wishing to be bound to a particular theory, it is proposed that Rab9 trafficks cholesterol, the dynamic glue that holds lipid rafts together. Further evidence for this hypothesis is based on observations of Neimann-Pick type C disease cells. Neimann-Pick type C is a genetic disease that results in accumulation of abnormally high levels of intracellular cholesterol. However, over expression of Rab9 in Neimann-Pick type C disease cells, decreases the level of cholesterol.

Examples of pathogens that hijack lipid rafts include, but are not limited to those shown in Table 2. In the absence of functional Rab9 and lipid rafts (or a decrease in the number of rafts), viruses may not be able to bud or be infectious. Therefore, the use of agents that decrease or inhibit Rab9 expression or activity can be used to decrease infection by other pathogens, as well as toxins such as anthrax, that hijack lipid rafts, such as those shown in Table 2.

TABLE 2

Pathogens that hijack lipid rafts.

| Bacteria Intracellular survival | Toxin binding/oligomerization | Viruses | Protozoa |
|---|---|---|---|
| *Campylobaceer jujuni* | *Vibrio cholerae* | SV40 | *Toxoplasma gondii* |
| *Legionella pneumophila* | *Aeromonas hydrophilia* | Echovirus I and II | *Plasmodium falciparum* |
| *Brucella spp* | *Clostridium spp.* | Avian sarcoma and leukosis virus | |
| FimH and Dr *Escherichia coli* | *Streptcoccus pyogenes* | Semiliki forest virus | |
| *Salmonella typhimurium* | *Bacillus anthracis* | Ecotropic mouse leukaemia virus | |
| *Shigella flexneri* | *Bacillus thuringiensis* | HTLV-I | |
| *Chlamydia spp.* | *Heliobacter pylori* | HIV-1 | |
| *Mycobacterium spp.* | *Lysteria monocytogenes* | Ebola and Marburg viruses | |
| | | Measles virus | |
| | | Herpes Simplex virus | |
| | | Influenza virus | |
| | | Epstein-Barr virus | |

This example therefore illustrates that identification of an agent (such as a small molecule or siRNA) that inhibits a particular pathogen can be used to inhibit other pathogens that have a similar mechanism of action.

EXAMPLE 5

RNAi Molecules

This example describes methods that can be used to decease or inhibit expression of any of the genes listed in Table 1, or target sequences associated with SEQ ID NOS: 1-232, to decrease viral infection, such as infection by HIV, Ebola, or influenza. Exemplary RNAi compounds are provided for several different genes, such as beta-chimerin receptor tyrosine kinase, retinoblastoma binding protein 1, *Homo sapiens* chromosome 10 open reading frame 3, *Homo sapiens* fer-1-like 3, myoferlin (*C. elegans*), transcript variant 1, *Homo sapiens* chromosome 10 open reading frame 3 (C10orf3), malic enzyme, cadherin related 23, sideroflexin 5, polybromo 1, elongation factor for selenoprotein translation, integrin, beta 1, huntingtin interacting protein 1 and cyclin M2.

One skilled in the art will understand that RNAi molecules can be generated to any of the genes listed in Table 1. Although only 27mers are shown in SEQ ID NOS: 246-845, this disclosure is not limited to RNAi compounds of a particular length. An RNAi molecule can be any length, such as at least about 25 nucleotides, or even as many as 400 nucleotides. One skilled in the art will also understand that RNAi sequences that recognize other sequences involved in viral infection (such as a target sequence associated with any of SEQ ID NOS: 1-232) can be designed and prepared by commercial entities, such as Sequitur, Inc. (Natick, Mass.).

Using the methods described in Example 3, the disclosed RNAi compounds are used to decrease viral infection. For example, a 27mer RNAi compound shown in any of SEQ ID NOS: 246-845 is incubated with its reverse complement, allowing hybridization of the two molecules. In particular examples, two or more, such as three or more, 27mer RNAi compounds are transfected into a cell. This duplex molecule is contacted with a cell, such as a cell of a subject in whom decreased viral infection is desired, under conditions that allow the duplex to enter the cell.

EXAMPLE 6

Disruption of Gene Expression

This example describes methods that can be used to disrupt expression of a host gene, such as those shown in Table 1 and target sequences associated with SEQ ID NOS: 1-232, and thereby decrease activity of the proteins encoded by these sequences. Such methods are useful when it is desired to decrease or inhibit viral infection. In a particular example, disrupted expression of at least one target sequence associated with SEQ ID NOS: 1-232 in a host cell is used to treat a subject having a viral infection, or susceptible to a viral infection. Methods useful for disrupting gene function or expression are the use of antisense oligonucleotides, siRNA molecules (see Example 3), RNAi molecules (see Example 5), ribozymes, and triple helix molecules. Techniques for the production and use of such molecules are well known to those of skill in the art.

Antisense Methods

To design antisense oligonucleotides, a host mRNA sequence is examined. Regions of the sequence containing multiple repeats, such as TTTTTTTT, are not as desirable because they will lack specificity. Several different regions can be chosen. Of those, oligos are selected by the following characteristics: those having the best conformation in solution; those optimized for hybridization characteristics; and those having less potential to form secondary structures. Antisense molecules having a propensity to generate secondary structures are less desirable.

Plasmids including antisense sequences that recognize one or more of the target sequences associated with SEQ ID NOS: 1-232 (such as a sequence that encodes a protein listed in Table 1) can be generated using standard methods. For example, cDNA fragments or variants coding for a host protein involved in viral infection are PCR amplified. The nucleotides are amplified using Pfu DNA polymerase (Stratagene) and cloned in antisense orientation a vector, such as pcDNA vectors (InVitrogen, Carlsbad, Calif.). The nucleotide sequence and orientation of the insert can be confirmed by sequencing using a Sequenase kit (Amersham Pharmacia Biotech).

Generally, the term "antisense" refers to a nucleic acid capable of hybridizing to a portion of a host RNA sequence (such as mRNA) by virtue of some sequence complementarity. The antisense nucleic acids disclosed herein can be oligonucleotides that are double-stranded or single-stranded, RNA or DNA or a modification or derivative thereof, which can be directly administered to a cell, or which can be produced intracellularly by transcription of exogenous, introduced sequences.

Antisense nucleic acids are polynucleotides, and can be oligonucleotides (ranging from about 6 to about 100 oligonucleotides). In one example, an antisense polynucleotide recognizes one or more of the target nucleic acid sequences associated with SEQ ID NOS: 1-227, 229, or 231. In specific examples, the oligonucleotide is at least 10, 15, or 100 nucleotides, or a polynucleotide of at least 200 nucleotides. However, antisense nucleic acids can be much longer. The nucleotide can be modified at the base moiety, sugar moiety, or phosphate backbone, and can include other appending groups such as peptides, or agents facilitating transport across the cell membrane (Letsinger et al., *Proc. Natl. Acad. Sci. USA* 1989, 86:6553-6; Lemaitre et al., *Proc. Natl. Acad. Sci. USA* 1987, 84:648-52; WO 88/09810) or blood-brain barrier (WO 89/10134), hybridization triggered cleavage agents (Krol et al., *BioTechniques* 1988, 6:958-76) or intercalating agents (Zon, *Pharm. Res.* 3:539-49, 1988).

An antisense polynucleotide (including oligonucleotides) that recognizes one or more of the target sequences associated with SEQ ID NOS: 1-227, 229, or 231, can be modified at any position on its structure with substituents generally known in the art. For example, a modified base moiety can be 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylesters uracil-5-oxyacetic acid, 5-methyl-2-thiouracil, 3-(3-amino-3-N-2-carboxypropyl) uracil, and 2,6-diaminopurine.

An antisense polynucleotide that recognizes one or more of the target sequences associated with SEQ ID NOS: 1-227, 229, or 231, can include at least one modified sugar moiety such as arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

In a particular example, an antisense polynucleotide that recognizes one or more of the target sequences associated with SEQ ID NOS: 1-227, 229, or 231 is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625-41, 1987). The oligonucleotide can be conjugated to another molecule, such as a peptide, hybridization triggered cross-linking agent, transport agent, or hybridization-triggered cleavage agent. Oligonucleotides can include a targeting moiety that enhances uptake of the molecule by host cells. The targeting moiety can be a specific binding molecule, such as an antibody or fragment thereof that recognizes a molecule present on the surface of the host cell.

Polynucleotides disclosed herein can be synthesized by standard methods, for example by use of an automated DNA synthesizer. As examples, phosphorothioate oligos can be synthesized by the method of Stein et al. (*Nucl. Acids Res.* 1998, 16:3209), methylphosphonate oligos can be prepared by use of controlled pore glass polymer supports (Sarin et al., *Proc. Natl. Acad. Sci. USA* 85:7448-51, 1988). In a specific example, antisense oligonucleotide that recognizes one or more of the target sequences associated with SEQ ID NOS: 1-227, 229, or 231 includes catalytic RNA, or a ribozyme (see WO 90/11364, Sarver et al., *Science* 247:1222-5, 1990). In another example, the oligonucleotide is a 2'-0-methylribonucleotide (Inoue et al., *Nucl. Acids Res.* 15:6131-48, 1987), or a chimeric RNA-DNA analogue (Inoue et al., *FEBS Lett.* 215:327-30, 1987).

The antisense polynucleic acids disclosed herein include a sequence complementary to at least a portion of an RNA transcript of a gene, such as a target sequence associated with SEQ ID NOS: 1-227, 229, or 231. However, absolute complementarity, although advantageous, is not required. A sequence can be complementary to at least a portion of an RNA, meaning a sequence having sufficient complementarily to be able to hybridize with the RNA, forming a stable duplex; in the case of double-stranded antisense nucleic acids, a single strand of the duplex DNA may thus be tested, or triplex formation can be assayed. The ability to hybridize depends on the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The relative ability of polynucleotides (such as oligonucleotides) to bind to complementary strands is compared by determining the $T_m$, of a hybridization complex of the poly/oligonucleotide and its complementary strand. The higher the $T_m$ the greater the strength of the binding of the hybridized strands. As close to optimal fidelity of base pang as possible achieves optimal hybridization of a poly/oligonucleotide to its target RNA.

The amount of antisense nucleic acid that is effective in the treatment of a particular disease or condition (the therapeutically effective amount) depends on the nature of the disease or condition, and can be determined by standard clinical techniques. For example, it can be useful to use compositions to achieve sustained release of an antisense nucleic acid, for example an antisense molecule that recognizes one or more target sequences associated with SEQ ID NOS: 1-227, 229, or 231. In another example, it may be desirable to utilize liposomes targeted via antibodies to specific cells.

As an alternative to antisense inhibitors, catalytic nucleic acid compounds, such as ribozymes or anti-sense conjugates, can be used to inhibit gene expression. Ribozymes can be synthesized and administered to the subject, or can be encoded on an expression vector, from which the ribozyme is synthesized in the targeted cell (as in WO 9523225, and Beigelman et al. *Nucl. Acids Res.* 1995, 23:4434-42). Examples of oligonucleotides with catalytic activity are described in WO 9506764. Conjugates of antisense with a metal complex, such as terpyridylCu (II), capable of mediating mRNA hydrolysis, are described in Basklin et al. (*Appl. Biochem Biotechnol.* 54:43-56, 1995).

Ribozymes

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Methods of using ribozymes to decrease or inhibit RNA expression are known in the art. An overview of ribozymes and methods of their use is provided in Kashani-Sabet (*J. Imvestig. Dermatol. Symp. Proc.,* 7:76-78, 2002).

Ribozyme molecules include one or more sequences complementary to the target host mRNA and include the well-known catalytic sequence responsible for mRNA cleavage (see U.S. Pat. No. 5,093,246, herein incorporated by reference).

A ribozyme gene directed against any of the target sequences associated with SEQ ID NOS: 1-227, 229, or 231 can be delivered to a subject endogenously (where the ribozyme coding gene is transcribed intracellularly) or exogenously (where the ribozymes are introduced into a cell, for example by transfection). Methods describing endogenous and exogenous delivery are provided in Marschall et al. (*Cell Mol. Neurobiol.* 14:523-38, 1994).

Specific ribozyme cleavage sites within any potential RNA target are initially identified by scanning the target molecule for ribozyme cleavage sites that include the following sequence: GUA, GUU and GUC. Once identified, short RNA sequences of between 15 and ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays.

For example, a plasmid that contains a ribozyme gene directed against a β-chimerin rho-GTPase, placed behind a promoter, can be transfected into the cells of a subject, for example a subject susceptible to HIV infection. Expression of this plasmid in a cell will decrease or inhibit β-chimerin rho-GTPase RNA expression in the cell. In another example, a plasmid that contains a ribozyme gene directed against Rab9 placed behind a promoter, can be transfected into the cells of a subject, for example a subject susceptible to infection by a pathogen that utilizes lipid rafts, such as Ebola. Expression of this plasmid in a cell will decrease or inhibit Rab9 RNA expression in the cell. Other examples of using ribozymes to decrease or inhibit RNA expression can be found in WO 01/83754 (herein incorporated by reference).

Triple Helix Molecules

Nucleic acid molecules used in triplex helix formation should be single stranded and composed of deoxynucleotides. The base composition of these oligonucleotides is ideally designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of guanidine residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with one strand of a duplex first and then the other, eliminating the necessity for a sizeable stretch of either purines or pyrimidines to be present on one strand of a duplex.

EXAMPLE 7

Methods of Treatment

When the activity of a host cell protein or nucleic acid involved in viral infection is decreased by prematurely down-regulating their levels of expressing using antisense molecules, a reduction in viral infection can be achieved. Antisense oligonucleotides, RNAi molecules, ribozymes, and siRNA molecules that recognize a host nucleic acid involved in viral infection (Example 6) can therefore be used to disrupt cellular expression of a host protein involved in viral infection. The disclosed antisense, ribozyme, RNAi molecules and siRNA molecules can be administered to a subject alone, or in combination with other therapeutic agents such as anti-viral compounds.

A subject susceptible to or suffering from a viral infection, wherein decreased amounts of infection by the virus is desired, can be treated with a therapeutically effective amount of antisense, ribozyme, RNAi molecule or siRNA molecule (or combinations thereof) that recognizes a host sequence involved in viral infection, such as those shown in Table 1 or target sequences associated with SEQ ID NOS: 1-232. After the antisense, ribozyme, RNAi molecule or siRNA molecule has produced an effect (a decreased level of viral infection is observed, or symptoms associated with viral infection decrease), for example after 24-48 hours, the subject can be monitored for diseases associated with viral infection.

Similarly, other agents, such as an antibody that recognizes a host protein involved in viral infection and prevents the protein from interacting with a viral protein, can also be used to decrease or inhibit viral infection. Other exemplary agents are those identified using the methods described in the Examples below. These agents, such as antibodies, peptides, nucleic acids, organic or inorganic compounds, can be can be administered to a subject in a therapeutically effective amount. After the agent has produced an effect (a decreased level of viral infection is observed, or symptoms associated with viral infection decrease), for example after 24-48 hours, the subject can be monitored for diseases associated with viral infection.

The treatments disclosed herein can also be used prophylactically, for example to inhibit or prevent a viral infection. Such administration is indicated where the treatment is shown to have utility for treatment or prevention of the disorder. The prophylactic use is indicated in conditions known or suspected of progressing to disorders associated with a viral infection.

EXAMPLE 8

Recombinant Expression

With the disclosed host sequences involved in viral infection, native and variant sequences can be generated. Expression and purification by standard laboratory techniques of any variant, such as a polymorphism, mutant, fragment or fusion of a sequence involved in viral infection, such as a target sequence associated with SEQ ID NOS: 1-232, is enabled. One skilled in the art will understand that the sequences involved in viral infection, as well as variants thereof, can be produced recombinantly in any cell or organism of interest, and purified prior to use.

Methods for producing recombinant proteins are well known in the art. Therefore, the scope of this disclosure includes recombinant expression of any host protein or variant or fragment thereof involved in viral infection. For example, see U.S. Pat. No. 5,342,764 to Johnson et al.; U.S. Pat. No. 5,846,819 to Pausch et al.; U.S. Pat. No. 5,876,969 to Fleer et al. and Sambrook et al. (*Molecular Cloning: A Laboratory Manual*, Cold Spring Harbor, N.Y., 1989, Ch. 17, herein incorporated by reference).

Briefly, partial, full-length, or variant cDNA sequences that encode for a protein involved in viral infection, such as a target sequence associated with SEQ ID NOS: 1-232, can be ligated into an expression vector, such as a bacterial expression vector. Proteins or peptides can be produced by placing a promoter upstream of the cDNA sequence. Examples of promoters include, but are not limited to lac, trp, tac, trc, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

Vectors suitable for the production of intact proteins include pKC30 (Shimatake and Rosenberg, 1981, *Nature* 292:128), pKK177-3 (Amann ad Brosius, 1985, *Gene* 40:183) and pET-3 (Studiar and Moffatt, 1986, *J. Mol. Biol.* 189:113). A DNA sequence can be transferred to other cloning vehicles, such as other plasmids, bacteriophages, cosmids, animal viruses and yeast artificial chromosomes (YACs) (Burke et al., 1987, *Science* 236:806-12). These vectors can be introduced into a variety of hosts including somatic cells, and simple or complex organisms, such as bacteria, fungi (Timberlake and Marshall, 1989, *Science* 244:1313-7), invertebrates, plants (Gasser and Fraley, 1989, *Science* 244:1293), and mammals (Pursel et al., 1989, *Science* 244:1281-8), that are rendered transgenic by the introduction of the heterologous cDNA.

For expression in mammalian cells, a cDNA sequence, such as a coding sequence of any target sequence associated with SEQ ID NOS: 1-227, 229, or 231, can be ligated to heterologous promoters, such as the simian virus SV40, promoter in the pSV2 vector (Mulligan and Berg, 1981, *Proc. Natl. Acad. Sci. USA* 78:2072-6), and introduced into cells, such as monkey COS-1 cells (Gluzman, 1981, *Cell* 23:175-82), to achieve transient or long-term expression. The stable integration of the chimeric gene construct may be maintained in mammalian cells by biochemical selection, such as neomycin (Southern and Berg, 1982, *J. Mol. Appl. Genet.* 1:327-41) and mycophenolic acid (Mulligan and Berg, 1981, *Proc. Natl. Acad. Sci. USA* 78:2072-6).

The transfer of DNA into eukaryotic, such as human or other mammalian cells is a conventional technique. The vectors are introduced into the recipient cells as pure DNA (transfection) by, for example, precipitation with calcium phosphate (Graham and vander Eb, 1973, *Virology* 52:466) strontium phosphate (Brash et al., 1987, *Mol. Cell Biol.* 7:2013), electroporation (Neumann et al., 1982, *EMBO J.* 1:841), lipofection (Felgner et al., 1987, *Proc. Natl. Acad. Sci USA* 84:7413), DEAE dextran (McCuthan et al., 1968, *J. Natl. Cancer Inst.* 41:351), microinjection (Mueller et al., 1978, *Cell* 15:579), protoplast fusion (Schafner, 1980, *Proc. Natl. Acad. Sci. USA* 77:2163-7), or pellet guns (Klein et al., 1987, *Nature* 327:70). Alternatively, the cDNA can be introduced by infection with virus vectors, for example retroviruses (Bernstein et al., 1985, *Gen. Engrg.* 7:235) such as adenoviruses (Ahmad et al., *J. Virol.* 57:267, 1986) or Herpes (Spaete et al., *Cell* 30:295, 1982).

EXAMPLE 9

Pharmaceutical Compositions and Modes of Administration

Various delivery systems for administering the therapies disclosed herein are known, and include encapsulation in liposomes, microparticles, microcapsules, expression by recombinant cells, receptor-mediated endocytosis (Wu and Wu, *J. Biol. Chem.* 1987, 262:4429-32), and construction of therapeutic nucleic acids as part of a retroviral or other vector. Methods of introduction include, but are not limited to, topical, intradermal, intramuscular, intraperitoneal, intravenous, subcutaneous, intranasal, and oral routes. The compounds can be administered by any convenient route, for example by infusion or bolus injection, by absorption through epithelial or mucocutaneous linings (for example, oral mucosa, rectal, vaginal and intestinal mucosa, etc.) and can be administered together with other biologically active agents. Administration can be systemic or local. Pharmaceutical compositions can be delivered locally to the area in need of treatment, for example by topical application.

Pharmaceutical compositions are disclosed that include a therapeutically effective amount of an RNA, DNA, antisense molecule, ribozyme, RNAi molecule, siRNA molecule, specific-binding agent, or other therapeutic agent, alone or with a pharmaceutically acceptable carrier. Furthermore, the pharmaceutical compositions or methods of treatment can be administered in combination with (such as before, during, or following) other therapeutic treatments, such as other antiviral agents.

Delivery Systems

The pharmaceutically acceptable carriers useful herein are conventional: *Remington's Pharmaceutical Sciences*, by Martin, Mack Publishing Co., Easton, Pa., 15th Edition (1975), describes compositions and formulations suitable for pharmaceutical delivery of the therapeutic agents herein disclosed. In general, the nature of the carrier will depend on the mode of administration being employed. For instance, parenteral formulations usually include injectable fluids that include pharmaceutically and physiologically acceptable fluids such as water, physiological saline, balanced salt solutions, aqueous dextrose, sesame oil, glycerol, ethanol, combinations thereof, or the like, as a vehicle. The carrier and composition can be sterile, and the formulation suits the mode of administration. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The composition can be a liquid solution, suspension, emulsion, tablet, pill, capsule, sustained release formulation, or powder. For solid compositions (for example powder, pill, tablet, or capsule forms), conventional non-toxic solid carriers can include, for example, pharmaceutical grades of mannitol, lactose, starch, sodium saccharine, cellulose, magnesium carbonate, or magnesium stearate. The composition can be formulated as a suppository, with traditional binders and carriers such as triglycerides.

Embodiments of the disclosure including medicaments can be prepared with conventional pharmaceutically acceptable carriers, adjuvants and counterions as would be known to those of skill in the art.

The amount of therapeutic agent effective in decreasing or inhibiting viral infection can depend on the nature of the virus and its associated disorder or condition, and can be determined by standard clinical techniques. In addition, in vitro assays can be employed to identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

Administration of Nucleic Acids

In an example in which a nucleic acid is employed to reduce viral infection, such as an antisense, RNAi molecule, or siRNA molecule, the nucleic acid can be delivered intracellularly (for example by expression from a nucleic acid vector or by receptor-mediated mechanisms), or by an appropriate nucleic acid expression vector which is administered so that it becomes intracellular, for example by use of a retroviral vector (see U.S. Pat. No. 4,980,286), or by direct injection, or by use of microparticle bombardment (such as a gene gun; Biolistic, Dupont), or coating with lipids or cell-surface receptors or transfecting agents, or by administering it in linkage to a homeobox-like peptide which is known to enter the nucleus (for example Joliot et al., *Proc. Natl. Acad. Sci. USA* 1991, 88:1864-8). The present disclosure includes all forms of nucleic acid delivery, including synthetic oligos, naked DNA, plasmid and viol, integrated into the genome or not.

EXAMPLE 10

In Vitro Screening Assay for Agents that Decrease Viral Infection

This example describes in vitro methods that can be used to screen test agents for their ability to interfere with or even inhibit viral infection of a host cell. As disclosed in the Examples above, the disclosed host proteins (such as those listed in Table 1 and the target protein sequences associated with SEQ ID NOS: 1-232, as well as variants, fragments, and fusions thereof) are involved in viral infection (such as infection by HIV, Ebola, and influenza A), and the host protein/viral protein interaction is a component in the ability of a virus to infect a cell. Therefore, screening assays can be used to identify and analyze agents that decrease or interfere with this interaction. For example, the following assays can be used to identify agents that interfere with the interaction of the disclosed host proteins (such as those listed in Table 1 and the target protein sequences associated with SEQ ID NOS: 1-232) with a viral protein sequence. However, the present disclosure is not limited to the particular methods disclosed herein.

Agents identified via the disclosed assays can be useful, for example, in decreasing or even inhibiting viral infection by more than an amount of infection in the absence of the agent, such as a decrease of at least about 10%, at least about 20%, at least about 50%, or even at least about 90%. This decrease in viral infection can serve to ameliorate symptoms associated with viral infection, such as fever. Assays for testing the effectiveness of the identified agents, are discussed below.

Exemplary test agents include, but are not limited to, any peptide or non-peptide composition in a purified or non-purified form, such as peptides made of D- and/or L-configuration amino acids (in, for example, the form of random peptide libraries; see Lam et al., *Nature* 354:824, 1991), phosphopeptides (such as in the form of random or partially degenerate, directed phosphopeptide libraries; see, for example, Songyang et al., *Cell* 72:767-78, 1993), antibodies, and small or large organic or inorganic molecules. A test agent can also include a complex mixture or "cocktail" of molecules.

The basic principle of the assay systems used to identify agents that interfere with the interaction between a host protein, such as those listed in Table 1 and the target protein sequences associated with SEQ ID NOS: 1-232, and its viral protein binding partner or partners, involves preparing a reaction mixture containing the host protein and a viral protein under conditions and for a time sufficient to allow the two proteins to interact and bind, thus forming a complex. In order to test an agent for inhibitory activity, the reaction is conducted in the presence and absence of the test agent. The test agent can be initially included in the reaction mixture, or added at a time subsequent to the addition of a host protein and a viral protein. Controls are incubated without the test agent or with a placebo. Exemplary controls include agents known not to bind to viral or host proteins. The formation of any complexes between the host protein and the viral protein is then detected. The formation of a complex in the control reaction, but not in the reaction mixture containing the test agent, indicates that the agent interferes with the interaction of the host protein and the viral protein, and is therefore possibly an agent that can be used to decrease viral infection.

The assay for agents that interfere with the interaction of host and viral proteins can be conducted in a heterogeneous or homogeneous format. Heterogeneous assays involve anchoring the host protein or the viral protein onto a solid phase and detecting complexes anchored on the solid phase at the end of the reaction. In some examples, the method further involves quantitating the amount of complex formation or inhibition. Exemplary methods that can be used to detect the presence of complexes, when one of the proteins is labeled, include ELISA, spectrophotometry, flow cytometry, and microscopy. In homogeneous assays, the entire reaction is performed in a liquid phase. In either method, the order of addition of reactants can be varied to obtain different information about the agents being tested. For example, test agents that interfere with the interaction between the proteins, such as by competition, can be identified by conducting the reaction in the presence of the test agent, for example by adding the test agent to the reaction mixture prior to or simultaneously with the host protein and viral protein. On the other hand, test agents that disrupt preformed complexes, such as agents with higher binding constants that displace one of the proteins from the complex, can be tested by adding the test agent to the reaction mixture after complexes have been formed. The various formats are described briefly below.

Once identified, test agents found to inhibit or decrease the interaction between a host protein and a viral protein can be formulated in therapeutic products (or even prophylactic products) in pharmaceutically acceptable formulations, and used for specific treatment or prevention of a viral disease, such as HIV, Ebola, or influenza A.

Heterogeneous Assay System

In a heterogeneous assay system, one binding partner, either the host protein (such as those listed in Table 1 and target protein sequences associated with SEQ ID NOS: 1-232) or the viral protein (such as an HIV, Ebola, or influenza A virus preparation) is anchored onto a solid surface (such as a microtiter plate), and its binding partner, which is not anchored, is labeled, either directly or indirectly. Exemplary labels include, but are not limited to, enzymes, fluorophores, ligands, and radioactive isotopes. The anchored protein can be immobilized by non-covalent or covalent attachments. Non-covalent attachment can be accomplished simply by coating the solid surface with a solution of the protein and drying. Alternatively, an immobilized antibody (such as a monoclonal antibody) specific for the protein can be used to anchor the protein to the solid surface. The surfaces can be prepared in advance and stored.

To conduct the assay, the binding partner of the immobilized species is added to the coated surface with or without the test agent. After the reaction is complete, unreacted components are removed (such as by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; for example by using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test agent, the reaction products separated from unreacted components, and complexes detected; for example by using an immobilized antibody specific for one binding partner to anchor any complexes formed in solution, and a labeled antibody specific for the other binding partner to detect anchored complexes.

Again, depending upon the order of addition of reactants to the liquid phase, test agents which inhibit complex or which disrupt preformed complexes can be identified.

Homogenous Assays

In an alternate example, a homogeneous assay can be used. In this method, a preformed complex of the host protein and the viral protein is prepared in which one of the proteins is labeled, but the signal generated by the label is quenched due to complex formation (for example, see U.S. Pat. No. 4,109,496 by Rubenstein which utilizes this approach for immunoassays). The addition of a test substance that competes with and displaces one of the binding partners from the preformed complex will result in the generation of a signal above background. In this way, test agents that disrupt host protein-viral protein interactions are identified.

Immobilization of Proteins

In a particular example, a host protein involved in viral infection (such as those listed in Table 1 and the target protein sequences associated with SEQ ID NOS: 1-232) can be prepared for immobilization using recombinant DNA techniques. For example, a coding region of a protein listed in Table 1, or any target sequence associated with SEQ ID NOS: 1-232, can be fused to a glutathione. S-transferase (GST) gene using the fusion vector pGEX-5X-1, in such a manner that its binding activity is maintained in the resulting fusion protein. The viral protein (such as an Ebola, HIV, or influenza A protein or viral preparation) can be purified and used to raise a monoclonal antibody, using methods routinely practiced in the art and described above. This antibody can be labeled with the radioactive isotope $^{125}I$ using methods routinely practiced in the art.

In a heterogeneous assay, for example, the GST-host fusion protein can be anchored to glutathione-agarose beads. The viral protein preparation can then be added in the presence or absence of the test agent in a manner that allows interaction and binding to occur. At the end of the reaction period, unbound material can be washed away, and the labeled monoclonal antibody can be added to the system and allowed to bind to the complexed binding partners. The interaction between the host protein and the viral protein can be detected by measuring the amount of radioactivity that remains associated with the glutathione-agarose beads. A successful inhibition of the interaction by the test compound will result in a decrease in measured radioactivity.

Alternatively, the GST-host fusion protein and the viral protein can be mixed together in liquid in the absence of the solid glutathione agarose beads. The test agent can be added either during or after the binding partners are allowed to interact. This mixture can then be added to the glutathione-agarose beads and unbound material is washed away. Again, the extent of inhibition of the binding partner interaction can be detected by adding the labeled antibody and measuring the radioactivity associated with the beads.

In another example, these same techniques can be employed using peptide fragments that correspond to the binding domains of the host protein and the viral protein, respectively, in place of one or both of the full length proteins. Any number of methods routinely practiced in the art can be used to identify and isolate the proteins binding site. These methods include, but are not limited to, mutagenesis of one of the genes encoding the proteins and screening for disruption of binding in a co-immunoprecipitation assay. Compensating mutations in a host gene can be selected. Sequence analysis of the genes encoding the respective proteins will reveal the mutations that correspond to the region of the protein involved in interactive binding. Alternatively, one protein can be anchored to a solid surface using methods described in above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the for the cellular or extracellular protein is obtained, short gene segments can be engineered to express peptide fragments of the protein, which can then be tested for binding activity and purified or synthesized.

For example, a host protein can be anchored to a solid material as described above by making a GST-host protein fusion protein and allowing it to bind to glutathione agarose beads. The viral protein can be labeled with a radioactive isotope, such as $^{35}S$, and cleaved with a proteolytic enzyme such as trypsin. Cleavage products can then be added to the anchored GST-host protein fusion protein and allowed to bind. After washing away unbound peptides, labeled bound material, representing the cellular or extracellular protein binding domain, can be elute purified, and analyzed for amino acid sequence. Peptides so identified can be produced synthetically or fused to appropriate facilitative proteins using recombinant DNA technology.

EXAMPLE 11

Cell-Based Screening Assay for Agents that Decrease Viral Infection

This example describes methods using intact cells that can be used to screen test agents for their ability to interfere with or even inhibit viral infection of a host cell. For example, a yeast two-hybrid assay or the inverse two-hybrid assay method of Schreiber and coworkers (*Proc. Natl. Acad. Sci., USA* 94:13396, 1977) is used to screen for an agent that disrupts the association between a host protein (such as those listed in Table 1, proteins encoded by any target sequence associated with SEQ ID NOS: 1-227, 229, and 231, and any target sequence associated with SEQ ID NOS: 229, 230, and 232) and a viral protein (such as HIV, Ebola, or influenza A virus). Similar to Example 10, therapeutic agents identified by these approaches are tested for their ability to decrease or inhibit infection of a host cell, such as a human cell, by HIV, Ebola, or influenza A.

In one example, the yeast two-hybrid system is used to identify anti-viral agents. One version of this system has been described (Chien et al., *Proc. Natl. Acad. Sci. USA,* 88:9578-82, 1991) and is commercially available from Clontech (Palo Alto, Calif.). Briefly, utilizing such a system, plasmids are constructed that encode two hybrid proteins: one includes the DNA-binding domain of a transcription activator protein fused to one test protein "X" and the other includes the activator proteins activation domain fused to another test protein fly. Thus, either "X" or "Y" in this system can be a host protein (such as those listed in Table 1 and any target sequences associated with SEQ ID NOS: 1-232), while the other can be a test protein or peptide. The plasmids are transformed into a strain of *Saccharomyces cerevisiae* that contains a reporter gene (such as lacZ) whose regulatory region contains the activators binding sites. Either hybrid protein alone cannot activate transcription of the reporter gene, the DNA-binding domain hybrid because it does not provide activation function and the activation domain hybrid because it cannot localize to the activator's binding sites. Interaction of the two proteins reconstitutes the functional activator protein and results in expression of the reporter gene, which is detected by an assay for the reporter gene product.

The two-hybrid system or related methodology can be used to screen activation domain libraries for proteins that interact with a host protein involved in viral infection. Total genomic or cDNA sequences are fused to the DNA encoding an activation domain. This library and a plasmid encoding a hybrid of the host protein involved in viral infection fused to the DNA-binding domain are cotransformed into a yeast reporter strain, and the resulting transformants are screened for those that express the reporter gene. These colonies are purified and the plasmids responsible for reporter gene expression are isolated. DNA sequencing is then used to identify the proteins encoded by the library plasmids.

For example, and not by way of limitation, a host gene encoding a protein involved in viral infection (such as those listed in Table 1 and target sequences associated with SEQ ID NOS: 1-232) can be cloned into a vector such that it is translationally fused to the DNA encoding the DNA-binding domain of the GAL4 protein. A cDNA library of the cell line from which proteins that interact with the host protein are to be detected can be made using methods routinely practiced in the art. In this particular system, the cDNA fragments can be inserted into a vector such that they are translationally fused to the activation domain of GAL4. This library can be co-transformed along with the host-GAL4 DNA binding domain fusion plasmid into a yeast strain which contains a lacZ gene driven by a promoter which contains GAL4 activation sequences. A cDNA encoded protein, fused to GAL4 activation domain, that interacts with the host protein will reconstitute an active GAL4 protein and thereby drive expression of the lacZ gene. Colonies which express lacZ can be detected by their blue color in the presence of X-gal. The cDNA can then be extracted from strains derived from these and used to produce and isolate the host protein-interacting protein using techniques routinely practiced in the art.

EXAMPLE 12

Rapid Screening Assays

Prior to performing any assays to detect interference with the association of a host protein involved in viral infection and a viral protein such as an HIV, Ebola, or influenza A protein, rapid screening assays can be used to screen a large number of agents to determine if they bind to the host or viral protein. Rapid screening assays for detecting binding to HIV proteins have been disclosed, for example in U.S. Pat. No. 5,230,998, which is incorporated by reference. In that assay, a host protein (such as those listed in Table 1 and target protein sequences associated with SEQ ID NOS: 1-232) or a viral protein, such as an HIV protein, is incubated with a first antibody capable of binding to the host or viral protein, and the agent to be screened. Excess unbound first antibody is washed and removed, and antibody bound to the host or viral protein is detected by adding a second labeled antibody which binds the first antibody. Excess unbound second antibody is then removed, and the amount of the label is quantitated. The effect of the binding effect is then determined in percentages by the formula: (quantity of the label in the absence of the test agent)−(quantity of the label in the presence of the test agent/quantity of the label in the absence of the test agent)×100.

Agents that are found to have a high binding affinity to the host or viral protein can then be used in other assays more specifically designed to test inhibition of the host protein/viral protein interaction, or inhibition of viral replication.

EXAMPLE 13

Assays for Measuring Inhibition of Viral Infection

Any of the test agents identified in the foregoing assay systems can be tested for their ability to decrease or inhibit infection by a pathogen or virus such as HIV, Ebola, or influenza A.

Cell-Based Assays

Exemplary methods are provided in Example 3 above. Briefly, cells (20,000 to 250,000) are infected with the desired pathogen, such as HIV, Ebola, or influenza A, and the incubation continued for 3-7 days. The test agent can be applied to the cells before, during, or after infection with the virus. The amount of virus and agent administered can be determined by skilled practitioners. In some examples, several different doses of the potential therapeutic agent can be administered, to identify optimal dose ranges. Following transfection, assays are conducted to determine the resistance of the cells to infection by various agents.

For example, the presence of a viral antigen can be determined by using antibody specific for the viral protein then detecting the antibody. In one example, the antibody that specifically binds to the viral protein is labeled, for example with a detectable marker such as a flurophore. In another example, the antibody is detected by using a secondary antibody containing a label. The presence of bound antibody is then detected, for example using microscopy, flow cytometry, and ELISA.

Alternatively or in addition, the ability of the cells to survive viral infection is determined, for example by performing a cell viability assay, such as trypan blue exclusion.

Animal Model Assays

The ability of an agent, such as those identified using the methods provide above, to prevent or decrease infection by a virus, such as HIV, Ebola, or influenza A, can be assessed in animal models. Several animal models for viral infection are known in the art. For example, mouse HIV models are disclosed in Sutton et al. (*Res. Initiat Treat. Action,* 8:22-4, 2003) and Pincus et al. (*AIDS Res. Hum. Retroviruses* 19:901-8, 2003); guinea pig models for Ebola infection are disclosed in Parren et al. (*J. Virol.* 76:6408-12, 2002) and Xu et al. (*Nat. Med.* 4:37-42, 1998); and cynomolgus monkey (*Macaca fascicularis*) models for influenza infection are disclosed in Kuiken et al. (*Vet. Pathol.* 40:304-10, 2003). Such animal models can also be used to test agents for an ability to ameliorate symptoms associated with viral infection. In addition, such animal models can be used to determine the LD50 and the ED50 in animal subjects, and such data can be used to determine the in veto efficacy of potential agents.

Animals of any species, including, but not limited to, mice, rats, rabbits, guinea pigs, pigs, micro-pigs, goats, and non-human primates, such as baboons, monkeys, and chimpanzees, can be used to generate an animal model of viral infection if needed.

The appropriate animal is inoculated with the desired virus, in the presence or absence of the test agents identified in the examples above. The amount of virus and agent administered can be determined by skilled practitioners. In some examples, several different doses of the potential therapeutic agent can be administered to different test subjects, to identify optimal dose ranges. The therapeutic agent can be administered before, during, or after infection with the virus. Subsequent to the treatment, animals are observed for the development of the appropriate viral infection and symptoms associated therewith. A decrease in the development of the appropriate viral infection, or symptoms associated therewith, in the presence of the test agent provides evidence that the test agent is a therapeutic agent that can be used to decrease or even inhibit viral infection in a subject.

Having illustrated and described the principles of the invention by several examples, it should be apparent that those embodiments can be modified in arrangement and detail without departing from the principles of the invention. Thus, the invention includes all such embodiments and variations thereof, and their equivalents.

We claim:

1. A method of identifying a compound that decreases binding of an HIV envelope protein to a full length wild-type human Rab9 protein, comprising:

contacting the full length wild-type human Rab9 protein with an HIV envelope protein and a test compound to allow interaction between the full length wild-type human Rab9 protein and the HIV envelope protein; and determining whether binding of the HIV envelope protein to the full length wild-type human Rab9 protein is decreased in the presence of the test compound, the decrease in binding being an indication that the test compound decreases the binding of the HIV envelope protein to the full length wild-type human Rab9 protein.

2. The method of claim 1, wherein the method comprises expressing the full length wild-type human Rab9 protein in a cell, and contacting the full length wild-type human Rab9 protein with the HIV envelope protein and a test compound comprises exposing the cell to the HIV envelope protein and the test compound.

3. The method of claim 1, wherein the full length wild-type human Rab9 protein or the HIV envelope protein comprises a label, and determining whether binding is decreased comprises detecting an amount of label present on full length wild-type human Rab9 protein or the HIV envelope protein.

* * * * *

SEQUENCE LISTING

```
<160> NUMBER OF SEQ ID NOS: 845

<210> SEQ ID NO 1
<211> LENGTH: 937
<212> TYPE: DNA
<213> ORGANISM: Homo sapiens
<220> FEATURE:
<221> NAME/KEY: misc_feature
<222> LOCATION: (1)..(937)
<223> OTHER INFORMATION: n is a, g, c, or t

<400> SEQUENCE: 1

gaanagcctn tccacccaag ngncggagaa ccagngngca attcnttttg ttcaatcatg      60

cgaaacgatc ctyrgstacc gcttgccaaa cctacaggtg gggtctttca agaggtctcc     120

agacctaggg gagcatctca gcgtcactcg ctgtccagtt gctgtgatca ggtgctttgg     180

ggtttgtgtg actccagaat ccactgggcc tgtgtgtcag aagacaaaag ttaaccataa     240

ggcacagaag aaagcctcct gctgaagcca tcgttggccc acatgcattt cagggacaag     300

aaatgaagat cggagacttt caagttgtgc ccaggactca cctgctccca ggagacaaaa     360

ggccacacag cagaggagcc tgaagcccat ggcaggatct cctagcttgg ggctggtgtc     420

tctgtagtaa gcattctgaa gttcctaagc tcccttcttc ctgataggag cattgacctg     480

tgatgtcacc acactgacat actttcccct gcaggccact ccagcccact gtactctttg     540

gcaggcctca ggttctgcta ctccatgtac tattcctgtc ttgcacaggc cagaagctaa     600

aggtgaggag gactgaacac agtaccaaca tacccacatc acaccttact ttcctctgcc     660

cgccctgtcc ctgccctgac actgattccc cagcccttgc caccccagcc ccttcaccct     720

ccactgcccg tgcagcagca gagacactcc ctccttgatg caaactgagg cctctggcac     780

cccaactctt tcaaggcaat gatagtctgt gcttaactct acatggccag gcccccactc     840

agggaattnc tgtgtgaaat tgttatccgc tgsacaattc cacacaacat ggnncgtcag     900

accccgaaga aaagaancaa nggatctttt ggnnacc                              937


<210> SEQ ID NO 2
<211> LENGTH: 1515
<212> TYPE: DNA
<213> ORGANISM: Homo sapiens
<220> FEATURE:
<221> NAME/KEY: misc_feature
<222> LOCATION: (1)..(1515)
<223> OTHER INFORMATION: n is a, c, g, or t

<400> SEQUENCE: 2

cccgtgttga cgccgggcaa gngcaactcg gtcgccgcat acactattct cagaatgact      60

tggttgagta ctcaccagtc acagaaaagc atcttacgga tggcatgaca gtaagagaat     120

tatgcagtgc tgccataacc atgagtgata acactgcggc caacttactt ctgacaacga     180

tcggaggacc gaaggagcta accgcttttt tgcacaacat gggggatcat gtaactcgcc     240

ttgatcgttg ggaaccggag ctgaatgaag ccataccaaa cgacgagcgt gacaccacga     300

tgcctgcagc aatggcaaca acgttgcgca aactattaac tggcgaacta cttactctag     360
```

cttcccggca acaattaata gactggatgg aggcggataa agttgcagga ccacttctgc 420
gctcggccct tccggctggc tggtttattg ctgataaatc tggagccggt gagcgtgggt 480
ctcgcggtat cattgcagca ctggggccag atggtaagcc ctcccgtatc gtagttatct 540
acacgacggg gagtcaggca actatggatg aacgaaatag acagatcgct gagataggtg 600
cctcactgat taagcattng gkaanctgtc agaccattkt ttactgcata tacsgatcca 660
ttgcccttat ctcaaactct tattatgaaa tcactnccct tgagagaraa aaagcctttt 720
tctcttnngg atkgtcccag magytyccga mcatccccac tycccaacct tatgkggccc 780
agcaatgans cctagtagta ggaaaatcty tatggatacy ggkgnctgak gggaarattc 840
ttcytctcat gaarwgatgg kgactggggc tytgggatgc tcacgggaat ccctatttcc 900
cccacaaaga agttatttta ttacacaacc atttggatga ccccctttt cttccaattn 960 nccaaataaa tctgtaaagg tcacaggtga agttcttctc tttaagagct actccatgct 1020
aagttcagcg agaacttggg gtaccctaga cattcttcca gagatgcttt tcttgtaact 1080
cttttcaata agtaagcatg ctttgctctg cactgggtgt cacctgtgtt ggatgctgtt 1140
gtccctgcct tgccctatat tctgtccaca tggtttcttc ataggatgat gcttaggtca 1200
gccctgaggt ttgaaccagt caacaagtcc aggttggtgt ggagtccctt tagtacctcc 1260
ctttgcagga ataatgctgc acccagaaac tccctcagag cctctccact gggaggggcc 1320
ttgtgaccat tcctggttta ctcctcttgt tccagcatcc catgtggcca atgggcccct 1380
ttcattttca atggtatctc anttnttaca gtaagttata ttattgccct acatngaact 1440
catctttttt cantgttacc tgnngaagaa tggnnaagga tgcccnaaan tnggcccaaa 1500
anaatccact tcgnn 1515

<210> SEQ ID NO 3
<211> LENGTH: 885
<212> TYPE: DNA
<213> ORGANISM: Homo sapiens
<220> FEATURE:
<221> NAME/KEY: misc_feature
<222> LOCATION: (1)..(885)
<223> OTHER INFORMATION: n is a, g, c, or t

<400> SEQUENCE: 3
tgtggtttnc ggtatcgccg cttccgattc gcagcgcatc gccttctatc gccttcttga 60
cgagttcttc tgagcgggac tctggggttc gaaatgagct agcccttaag taacgccatt 120
ttgcaaggca tggaaaaata cataactgag aatagaaaag ttcagatcga ggtcaggaac 180
agatggaaca gggtcgaccg gtcgaccggt cgaccctaga gaaccatcag atgtttccag 240
ggtgccccaa ggacctgaaa tgaccctgtg ccttatttga actaaccaat cagttcgctt 300
ctcgcttctg ttcgcgcgct tctgctcccc gagctcaata aaagagccca caacccctca 360
ctcggggcgc cagtcctccg attgactgag tcgcccgggt acccgtgtat ccaataaacc 420
ctcttgcagt tgcatccgac ttgtggtctc gctgttcctt gggagggtct cctctgagtg 480
attgactacc cgtcagcggg ggtctttcac tctctgtgta ctggtaccaa cagagcctgg 540
accagggcct ccagttcctc attcagtatt ataatggaga agagagagca aaaggaaaca 600
ttcttgaacg attctccgca caacagttcc ctgacttgca ctctgaacta aacctgagct 660
ctctggagct gggggactca gctttgtatt tctgtgccag cagcgtaggt ggtagcttga 720
aacagttctt cgggccaggg acacggctca ccgtgctagg taagaagggg gctccagtgg 780
gagagagggt gagcagccca ncctgnncga ccccanancc tgttnttagg ggagtggnca 840
ctgggcatcc aggccctnct cnaggaancg ggttncgccn ggncc 885

<210> SEQ ID NO 4
<211> LENGTH: 900
<212> TYPE: DNA
<213> ORGANISM: Homo sapiens
<220> FEATURE:
<221> NAME/KEY: misc_feature
<222> LOCATION: (1)..(900)
<223> OTHER INFORMATION: n is a, g, c, or t

<400> SEQUENCE: 4
ttggtaactg tcagaccaag tttactcata tcggatccag ttggagccat aagtcgtcag 60
acatagaaaa aaatctgaaa agatatctca aaagcccaga catttattca cactaacggt 120
gaaaagcata ccccacagtg tcagtggagg caacatgggg tcctggattt cctcttcacc 180
ctcagtggta gtgaggtgtt cctctcactc cttctgagta gaggaagcca agaggaaagc 240
tggaacttgt accatcatcc agtggtgata aagcctctgt ccctccacct tacccccagg 300
ttatcagtgg caaccacatg gctagtggta cccctcccgc tcctagccag aatgatatca 360
gcagaggcct agagagtagc ccaaaaactc atctgcaccc agcaggactg aggtttccta 420
cccccaccaa tggaagccaa gtgaggaacc taagccttca cctctcactc agcaggaacc 480
agacaacacc ccctaacaca cacacacaca cacacacaca cacacccttc tgttagtgtg 540
gtatcaagga ggcttgataa aatagaagat ttaaatagga tccattgccc ttatctcaaa 600
ctcttattat gaaatcactc ccttgagaga gaaaaaagcc tttttctctt ggattgtccc 660
agcagctccc gaccatcccc actccccaac cttatgtggc cccagcaatg agcctagtag 720
taggaaaatc tctatggata ctggtgctga tgggaagatt cttcctctca ngaagtgatg 780
gtgactgggg ctctgggatg ctcacgggaa tnccatttcc ccccacaagaa nttattttat 840 naccaaccat ttggatgacc cctttttntt ccatttncca annaatttgt aaggncaaag 900

<210> SEQ ID NO 5
<211> LENGTH: 869
<212> TYPE: DNA
<213> ORGANISM: Homo sapiens
<220> FEATURE:
<221> NAME/KEY: misc_feature
<222> LOCATION: (1)..(869)
<223> OTHER INFORMATION: n is a, g, c, or t

<400> SEQUENCE: 5
ttgggnancc ccccacaaag naagttattt tattacacaa ccatttggat gaccccccttt 60 ttcttccaat ttcccaaata aatctgtaaa ggtcacaggt gaagttcttc tctttaagag 120
ctactccatg ctaagttcag cgagaacttg gggtacccta gacattcttc cagagatgct 180
tttcttgtaa ctcttttcaa taagtaagca tgctttgctc tgcactgggt gtcacctgtg 240
ttggatgctg ttgtccctgc cttgccctat attctgtcca catggtttct tcataggatg 300
atgcttaggt cagccctgag gtttgaacca gtcaacaagt ccaggttggt gtggagtccc 360
tttagtacct ccctttgcag gaataatgct gcacccagaa actccctcag agcctctcca 420
ctggaggggc cttgtgacca ttcctggttt actcctcttg ttccagcatc ccatgtggcc 480
aatgggcccc tttcattttc aatggtatct caattcttac agtaagttat attattgccc 540
tacatcgaac tcatcttttc tcagtgttac ctgaggaaga atggagagga tgcccagaat 600
tggcccagaa gaatccactt cgattctaga gaaaaaggca ggtagaggca gaagagattc 660
acttcccagt gcatgcgtgc tgaatgttgg gggtgttgtt tgagagagac aaggaaatgg 720

```
ctgtaaaact tgggaagagg aacctgccct gggtcaagta gggtgttggg aggaccagat    780

ggagcttgaa gctctctcca tctttgtcaa gtcccctgga ctgagagggn aaaatnacat    840

ggcctttatc ctccagagga aantnattc                                      869
```

```
<210> SEQ ID NO 6
<211> LENGTH: 850
<212> TYPE: DNA
<213> ORGANISM: Homo sapiens
<220> FEATURE:
<221> NAME/KEY: misc_feature
<222> LOCATION: (1)..(850)
<223> OTHER INFORMATION: n is a, g, c, or t

<400> SEQUENCE: 6

tgggggttcc ggtatcgccg cttcgattcg cagcgcatcg ccttctatcg ccttcttgac     60

gagttcttct gagcgggact ctggggttcg aaatgagcta gcccttaagt aacgccattt    120

tgcaaggcat ggaaaaatac ataactgaga atagaaaagt tcagatcgag gtcaggaaca    180

gatggaacag ggtcgaccgg tcgaccggtc gaccctagag aaccatcaga tgtttccagg    240

gtgccccaag gacctgaaat gaccctgtgc cttatttgaa ctaaccaatc agttcgcttc    300

tcgcttctgt tcgcgcgctt ctgctccccg agctcaataa aagagcccac aacccctcac    360

tcggggcgcc agtcctccga ttgactgagt cgcccgggta cccgtgtatc caataaaccc    420

tcttgcagtt gcatccgact tgtggtctcg ctgttccttg ggagggtctc ctctgagtga    480

ttgactaccc gtcagcgggg gtctttcact ctctgtgtac tggtaccaac agagcctgga    540

ccagggcctc cagttcctca ttcagtatta taatggagaa gagagagcaa aaggaaacat    600

tcttgaacga ttctccgcac aacagttccc tgacttgcac tctgaactaa acctgagctc    660

tctggagctg ggggactcag ctttgtattt ctgtgccagc agcgtaggtg gtagcttgaa    720

acagttcttc gggccaggga cacggctcac cgtgctaggt aagaaggggg ctccaggtgg    780

gagagagggt gagcagccca ncctgcacga ccccanaacc ctgttcttag gggagnggac    840

actgggncat                                                           850
```

```
<210> SEQ ID NO 7
<211> LENGTH: 847
<212> TYPE: DNA
<213> ORGANISM: Homo sapiens
<220> FEATURE:
<221> NAME/KEY: misc_feature
<222> LOCATION: (1)..(847)
<223> OTHER INFORMATION: n is a, g, c, or t

<400> SEQUENCE: 7

ttgggggacc gcttgccaaa cctacaggtg gggtctttca agaggtctcc agacctaggg     60

gagcatctca gcgtcactcg ctgtccagtt gctgtgatca ggtgctttgg ggtttgtgtg    120

actccagaat ccactgggcc tgtgtgtcag aagacaaaag ttaaccataa ggcacagaag    180

aaagcctcct gctgaagcca tcgttggccc acatgcattt cagggacaag aaatgaagat    240

cggagacttt caagttgtgc ccaggactca cctgctccca ggagacaaaa ggccacacag    300

cagaggagcc tgaagcccat ggcaggatct cctagcttgg ggctggtgtc tctgtagtaa    360

gcattctgaa gttcctaagc tcccttcttc ctgataggag cattgacctg tgatgtcacc    420

acactgacat actttcccct gcaggccact ccagcccact gtactctttg gcaggcctca    480

ggttctgcta ctccatgtac tattcctgtc ttgcacaggc cagaagctaa aggtgaggag    540

gactgaacac agtaccaaca tacccacatc acaccttact ttcctctgcc cgccctgtcc    600
```

ctgccctgac actgattccc cagcccttgc caccccagcc ccttcaccct ccactgcccg 660
tgcagcagca gagacactcc ctccttgatg caaactgagg cctctggcac cccaactctt 720
tcagggcaat gatagtctgt gcttaactct acatggccag gccccactca gggaattctc 780
acctagaatt tcatatncag ccaaactaag cttcataagt gaaggggaaa taaaatgctt 840
tacagac 847

<210> SEQ ID NO 8
<211> LENGTH: 755
<212> TYPE: DNA
<213> ORGANISM: Homo sapiens
<220> FEATURE:
<221> NAME/KEY: misc_feature
<222> LOCATION: (1)..(755)
<223> OTHER INFORMATION: n is a, g, c, or t

<400> SEQUENCE: 8
ttcactncaa ggatnttaca acaggacatt ttttaaaacc tcaaacatca ccaaaatttc 60
taagtgcaag tttattttta tttttttttt tttttgaga cagagtctcg ctctgtcacc 120
caggctagag tgcagtggca tgatcttggc tcactgcaac ctccacctcc caggttcaag 180
tgattctctt gcctcagcct cccaagtagc tagtattaca gacgcctgcc accacgcccg 240
gttaattttt gtacttttag tagagacagg tttcaccata ttggccaggc tggtctcaaa 300
ctcctgacct caggtgatcc tcctgcctca gcctcccaaa gtgctgggat tacaggcatg 360
agctaccacg tctggcctaa gtgcatgtta cctatactaa caaaaccaca cttctgcctc 420
gaatgagaac agtctcctga acatcttgcc tctttgcctg actcaaagcc tcaggtctaa 480
gcctccccat aatttctagt ctcagcagaa agatcaatga caggagactc tccaggtgat 540
gaaattaacc aattaagtaa cctgggttgg catcctcccg tttgttcacc agctcacctn 600
ctgccacagg tatatccttt ctctcancca tatatgcaca aaccccctnc ccacggnaca 660
catannaana atttggaaga ctanaaaatc aggcanggtn tancncacct tgngggctgg 720
agtatggnan cctgggccgg nacatncata cattg 755

<210> SEQ ID NO 9
<211> LENGTH: 839
<212> TYPE: DNA
<213> ORGANISM: Homo sapiens
<220> FEATURE:
<221> NAME/KEY: misc_feature
<222> LOCATION: (1)..(839)
<223> OTHER INFORMATION: n is a, g, c, or t

<400> SEQUENCE: 9
cnntntttgn gnngnnnaag aaantncnga cntnngccnc caaatnaact tggggggna 60 accttcacta caaggatatt acaacaggac attttttaaa acctcaaaca tcaccaaaat 120
ttctaagtgc aagtttattt ttattttttt tttttttttt gagacagagt ctcgctctgt 180
cacccaggct agagtgcagt ggcatgatct tggctcactg caacctccac ctcccaggtt 240
caagtgattc tcttgcctca gcctcccaag tagctagtat tacagacgcc tgccaccacg 300
cccggttaat ttttgtactt ttagtagaga caggtttcac catattggcc aggctggtct 360
caaactcctg acctcaggtg atcctcctgc ctcagcctcc caaagtgctg ggattacagg 420
catgagctac cacgtctggc ctaagtgcat gttacctata ctaacaaaac cacacttctg 480
cctcgaatga gaacagtctc ctgaacatct tgcctctttg cctgactcaa agcctcaggt 540
ctaagcctcc ccataatttc tagtctcagc agaaagatca atgacaggag actctccagg 600
tgatgaaatt aaccaattaa gtaacctggg ttggcatcct cccgtttgtt caccagctca 660
cctcctgcca caggtatatc ctttctctca gccatatatg cacaaacccc ctccccacgg 720
cacacataga aanaatttgg aagactagaa aatcaggcna gggnttanca caccttngag 780
ggctggagta tggnanccng ggnccgggan atncatncnn tngaaaactt gactatggg 839

<210> SEQ ID NO 10
<211> LENGTH: 829
<212> TYPE: DNA
<213> ORGANISM: Homo sapiens
<220> FEATURE:
<221> NAME/KEY: misc_feature
<222> LOCATION: (1)..(829)
<223> OTHER INFORMATION: n is a, g, c, or t

<400> SEQUENCE: 10
tcgccttcaa tcgtcttatt nacgagttct tctgagcggg actctggggt tcgaaatgag 60
ctagccctta agtaacgcca ttttgcaagg catggaaaaa tacataactg agaatagaaa 120
agttcagatc gaggtcagga acagatggaa cagggtcgac cggtcgaccg gtcgacccta 180
gagaaccatc agatgtttcc agggtgcccc aaggacctga aatgaccctg tgccttattt 240
gaactaacca atcagttcgc ttctcgcttc tgttcgcgcg cttctgctcc ccgagctcaa 300
taaaagagcc cacaacccct cactcggggc gccagtcctc cgattgactg agtcgcccgg 360
gtacccgtgt atccaataaa ccctcttgca gttgcatccg acttgtggtc tcgctgttcc 420
ttgggagggt ctcctctgag tgattgacta cccgtcagcg ggggtctttc agtagccctt 480
cctttgtagc aaagacagac agatggtgat ccaagagata cgcaagaaga ggaccgtgtg 540
tgtcatggtt gagctctaaa aaagagaaat cacttggatg gaantgaagg agaggaaaag 600
gctgatgtgg atggcctgga agangttcga ttggttacct tggcaccgag cttccttcct 660
catcctcatn cctccctagt ccttgttctt aaaaanantt ttctttctaa ngtcccttcc 720
ccctccncaa gggggcacaa ggatntttaa aaaacncctt tccgggcnta attttaacct 780
angatccatc ccagncccgt nccnnttttc nnagattcat ttaaacnng 829

<210> SEQ ID NO 11
<211> LENGTH: 710
<212> TYPE: DNA
<213> ORGANISM: Homo sapiens
<220> FEATURE:
<221> NAME/KEY: misc_feature
<222> LOCATION: (1)..(710)
<223> OTHER INFORMATION: n is a, g, c, or t

<400> SEQUENCE: 11
ttttttgcnn taccgtatcg ccgctntcga ttcgcagcnc atcgccttct atcgccttct 60
tgacgagttc ttctgagcgg gactctgggg ttcgaaatga gctagccctt aagtaacgcc 120
attttgcaag gcatggaaaa atacataact gagaatagaa aagttcagat cgaggtcagg 180
aacagatgga acagggtcga ccggtcgacc ggtcgaccct agagaaccat cagatgtttc 240
cagggtgccc caaggacctg aaatgaccct gtgccttatt tgaactaacc aatcagttcg 300
cttctcgctt ctgttcgcgc gcttctgctc cccgagctca ataaaagagc ccacaacccc 360
tcactcgggg cgccagtcct ccgattgact gagtcgcccg ggtacccgtg tatccaataa 420
accctcttgc agttgcatcc gacttgtggt ctcgctgttc cttgggaggg tctcctctga 480
gtgattgact acccgtcagc gggggtcttt cagtagccct tcctttgtag caaagacaga 540
cagatggtga tccaagagat acgcaagaag aggaccgtgt gtgtaatggt tgagctctaa 600
aaagagaaat cacttggatg gaaatgaagg agaggaaagg ctgatgtgga tggctgggaa 660
gaggttcgat ggttaccttg gcanccganc ttcnttnctn atncccatcc 710

<210> SEQ ID NO 12
<211> LENGTH: 752
<212> TYPE: DNA
<213> ORGANISM: Homo sapiens
<220> FEATURE:
<221> NAME/KEY: misc_feature
<222> LOCATION: (1)..(752)
<223> OTHER INFORMATION: n is a, g, c, or t

<400> SEQUENCE: 12
ttgggaaccg tcagnaccaa gttttnctca tatcggctcc cttctggtcc cacatcactc 60
aggcaactct ctcttcccac ctgcccccca aactcccttc cacctccctc cacatgtatc 120
ctcccacttc cttccactca tgtaatgaga ggtgctgatg agtcacagga gaggtagccc 180
tagataacca acagactgca aaacggacag tccctggatg tctgagccag tgtttgtgca 240
ctgcattgac tggctcctcg tagttttttc ctgtagttgc taaagcctgt aaggtctgtg 300
tgatgaatat tttctaacac atcttagaag aacataatgc aagacagaat gaaaaactag 360
agaggcagaa acccccaaag taagtagtgg gaaattacca ggtatataat aggtcaagcc 420
tgctctgcag gagctcaagg gattgtagca ttcttatccc aaaccactga atcctgggca 480
aaaataagaa gtcgcctaat tttagtatta ccagcttccc aaccccgggc attcttcatc 540
ttactcaagc tgtccagagg ccccagggtg actccctata agtcccatgg gtggctgaga 600
tctatttaga ggcacaaggg tatctnctta taagtccaat ggggnggctg agatctatga 660
gaagcatctt gggggagagt gccntttggc caccagcatg tggnccctna attttncatg 720
nnncaactgg nccngggaag gaaaantttt ga 752

<210> SEQ ID NO 13
<211> LENGTH: 749
<212> TYPE: DNA
<213> ORGANISM: Homo sapiens
<220> FEATURE:
<221> NAME/KEY: misc_feature
<222> LOCATION: (1)..(749)
<223> OTHER INFORMATION: n is a, g, c, or t

<400> SEQUENCE: 13
ttccttggcg ntaccgtatc gccgctntng attcgcagcg catcgccttc tatcgccttc 60
ttgacgagtt cttctgagcg ggactctggg gttcgaaatg agctagccct taagtaacgc 120
cattttgcaa ggcatggaaa aatacataac tgagaataga aaagttcaga tcgaggtcag 180
gaacagatgg aacagggtcg accggtcgac cggtcgaccc tagagaacca tcagatgttt 240
ccagggtgcc ccaaggacct gaaatgaccc tgtgccttat ttgaactaac caatcagttc 300
gcttctcgct tctgttcgcg cgcttctgct ccccgagctc aataaaagag cccacaaccc 360
ctcactcggg gcgccagtcc tccgattgac tgagtcgccc gggtacccgt gtatccaata 420
aaccctcttg cagttgcatc cgacttgtgg tctcgctgtt ccttgggagg gtctcctctg 480
agtgattgac tacccgtcag cgggggtctt tcagtagccc ttcctttgta gcaaagacag 540
acagatggtg atccaagaga tacgcaagaa gaggaccgtg tgtgtaatgg ttgagcttta 600
aaaaangaga aatcacttgg atggaaatga agganaggaa aaggcntgat ntngatngcn 660
gggaaanagg ttccatnggt nnctttggnn anccgannct tnctttcctn atccccntnc 720
cntccctann nccntnnttn ttaaaaaag 749

<210> SEQ ID NO 14
<211> LENGTH: 794
<212> TYPE: DNA
<213> ORGANISM: Homo sapiens
<220> FEATURE:
<221> NAME/KEY: misc_feature
<222> LOCATION: (1)..(794)
<223> OTHER INFORMATION: n is a, g, c, or t

<400> SEQUENCE: 14
tttttttgcg ntaccgtatc gccgctntcg attcgcagcn catcgccttc tatcgccttc 60
ttgacgagtt cttctgagcg ggactctggg gttcgaaatg agctagccct taagtaacgc 120
cattttgcaa ggcatggaaa aatacataac tgagaataga aaagttcaga tcgaggtcag 180
gaacagatgg aacagggtcg accggtcgac cggtcgaccc tagagaacca tcagatgttt 240
ccagggtgcc ccaaggacct gaaatgaccc tgtgccttat ttgaactaac caatcagttc 300
gcttctcgct tctgttcgcg cgcttctgct ccccgagctc aataaaagag cccacaaccc 360
ctcactcggg gcgccagtcc tccgattgac tgagtcgccc gggtacccgt gtatccaata 420
aaccctcttg cagttgcatc cgacttgtgg tctcgctgtt ccttgggagg gtctcctctg 480
agtgattgac tacccgtcag cgggggtctt tcagtagccc ttcctttgta gcaaagacag 540
acagatggtg atccaagaga tacgcaagaa gaggaccgtg tgtgtaatgg ttgagctcta 600
aaaaagagaa atcacttgga tggaaatgaa ggagaggaaa aggctgatgt ggatggctgg 660
gaagaggttc gatggttacc ttggcaaccg agcttccttn ctcatnccca tccctnccta 720
gtccttgttc tttaaaaaga ttttntttnt aatgtccctt nccctccaca agggggcaca 780
agatgttttn aaac 794

<210> SEQ ID NO 15
<211> LENGTH: 784
<212> TYPE: DNA
<213> ORGANISM: Homo sapiens
<220> FEATURE:
<221> NAME/KEY: misc_feature
<222> LOCATION: (1)..(784)
<223> OTHER INFORMATION: n is a, g, c, or t

<400> SEQUENCE: 15
ccttggnggg naanacggnt aacaattttt acacaggaat tactacaaaa gactctacta 60
agttctcagg gngaacaaaa aattgtatgt gtgcagaacc tgtgatttgc ctgcacatag 120
tcaagttctc aatgtatgga tgtcccggcc caggctacca tactccagcc ctcaaggtgt 180
gctatacctt gcctgatttt ctagtcttcc aaattcttct atgtgtgccg tggggagggg 240
gtttgtgcat atatggctga gagaaaggat atacctgtgg caggaggtga gctggtgaac 300
aaacgggagg atgccaaccc aggttactta attggttaat ttcatcacct ggagagtctc 360
ctgtcattga tctttctgct gagactagaa attatgggga ggcttagacc tgaggctttg 420
agtcaggcaa agaggcaaga tgttcaggag actgttctca ttcgaggcag aagtgtggtt 480
ttgttagtat aggtaacatg cacttaggcc agacgtggta gctcatgcct gtaatcccag 540
cactttggga ggctgaggca ggaggatcac ctgaggtcag gagttttgag accagcctgg 600
ccaatatggg ggaaaacctg tctctactaa aaagtacaaa aattaacccg gncgtnggng 660
gcaggnnntc tgtaatacta nnctacttgg ggngntgnag gcaanaaaat cantttgaac 720
ctnggnaggg gggngnttgc aatnnnccna aaaanatgcc cnntggncct ttaaccntgg 780 gngn 784

<210> SEQ ID NO 16
<211> LENGTH: 757
<212> TYPE: DNA
<213> ORGANISM: Homo sapiens
<220> FEATURE:
<221> NAME/KEY: misc_feature
<222> LOCATION: (1)..(757)
<223> OTHER INFORMATION: n is a, g, c, or t

<400> SEQUENCE: 16
tcctgggccc ncttgccaaa ccttcaggtg gggtctttca ctacaagata gtacaacagg 60 acattttta aaacctcaaa catcaccaaa atttctaagt gcaagtttat ttttattttt 120
tttttttttt ttttgagaca gagtctcgct ctgtcaccca ggctagagtg cagtggcatg 180
atcttggctc actgcaacct ccacctccca ggttcaagtg attctcttgc ctcagcctcc 240
caagtagcta gtattacaga cgcctgccac cacgcccggt taatttttgt acttttagta 300
gagacaggtt tcaccatatt ggccaggctg gtctcaaact cctgacctca ggtgatcctc 360
ctgcctcagc ctcccaaagt gctgggatta caggcatgag ctaccacgtc tggcctaagt 420
gcatgttacc tatactaaca aaaccacact tctgcctcga atgagaacag tctcctgaac 480
atcttgcctc tttgcctgac tcaaagcctc aggtctaagc ctccccataa tttctagtct 540
cagcagaaag atcaatgaca ggagactctn caggtgatga aattaaccaa ttaagtaacc 600
tgggttggca tcctcccgtt tgttcaccag ctcacctnct gncacaggta tatncttttt 660
tctnagccat atatgcccaa anccccctnc ccacggnaca catngaagaa nttnggaaga 720
ctngaaaatc aggccagggt tnngcccacc ttgnggg 757

<210> SEQ ID NO 17
<211> LENGTH: 783
<212> TYPE: DNA
<213> ORGANISM: Homo sapiens
<220> FEATURE:
<221> NAME/KEY: misc_feature
<222> LOCATION: (1)..(783)
<223> OTHER INFORMATION: n is a, g, c, or t

<400> SEQUENCE: 17
annaacttga atgacccctc tngccaaatc cttagggggg ggtccttcac tacaagatag 60
tacaacagga catttttttt aacctnaaac attaccacaa atttctaagt gcaagtttat 120
ttttattttt tttttttttt ttgagacaga gtctcgctct gtcacccagg ctagagtgca 180
gtggcatgat cttggctcac tgcaacctcc acctcccagg ttcaagtgat tctcttgcct 240
cagcctccca agtagctagt attacagacg cctgccacca cgcccggtta atttttgtac 300
ttttagtaga gacaggtttc accatattgg ccaggctggt ctcaaactcc tgacctcagg 360
tgatcctcct gcctcagcct cccaaagtgc tgggattaca ggcatgagct accacgtctg 420
gcctaagtgc atgttaccta tactaacaaa accacacttc tgcctcgaat gagaacagtc 480
tcctgaacat cttgcctctt tgcctgactc aaagcctcag gtctaagcct ccccataatt 540
tctagtctca gcagaaagat caatgacagg agactctcca ggtgatgaaa ttaaccaatt 600
aagtaacctg ggttggcatc ctcccgtttg ttcaccagct cacctcctgc cacaggtata 660
tcctttctct cagccatata tgcacaaacc ccctncccac ggcacacata gaagaatttg 720
gaagactaga aaatcaggca nggtatagca caccttggag ggctggagta tggtagcctg 780
ggc 783

<210> SEQ ID NO 18
<211> LENGTH: 770
<212> TYPE: DNA
<213> ORGANISM: Homo sapiens
<220> FEATURE:
<221> NAME/KEY: misc_feature
<222> LOCATION: (1)..(770)
<223> OTHER INFORMATION: n is a, g, c, or t

<400> SEQUENCE: 18
tccgggnncc gcttgccaaa ccttcaggtg gggtctttca ctacaagata gtacaacagg 60
acatttttta aaacctcaaa catcaccaaa atttctaagt gcaagtttat ttttattttt 120
tttttttttt ttgagacaga gtctcgctct gtcacccagg ctagagtgca gtggcatgat 180
cttggctcac tgcaacctcc acctcccagg ttcaagtgat tctcttgcct cagcctccca 240
agtagctagt attacagacg cctgccacca cgcccggtta atttttgtac ttttagtaga 300
gacaggtttc accatattgg ccaggctggt ctcaaactcc tgacctcagg tgatcctcct 360
gcctcagcct cccaaagtgc tgggattaca ggcatgagct accacgtctg gcctaagtgc 420
atgttaccta tactaacaaa accacacttc tgcctcgaat gagaacagtc tcctgaacat 480
cttgcctctt tgcctgactc aaagcctcag gtctaagcct ccccataatt tctagtctca 540
gcagaaagat caatgacagg agactctcca ggtgatgaaa ttaaccaatt aagtaacctg 600
ggttggcatc ctcccgtttg ttcaccagct cacctnctgc cacaggtata tccttttttct 660 tagccatata tgcacaaacc cccttcccac ggnacacata gaaaaatttn ggaagactag 720
aaaatcaggc agggtntagc acaccttngn gggctnggag tntnggtanc 770

<210> SEQ ID NO 19
<211> LENGTH: 774
<212> TYPE: DNA
<213> ORGANISM: Homo sapiens
<220> FEATURE:
<221> NAME/KEY: misc_feature
<222> LOCATION: (1)..(774)
<223> OTHER INFORMATION: n is a, g, c, or t

<400> SEQUENCE: 19
tccgggncnc gcttgccaaa ccttcaggtg gggtctttca ctacaagata gtacaacagg 60
acatttttta aaacctcaaa catcaccaaa atttctaagt gcaagtttat ttttattttt 120
tttttttttt ttgagacaga gtctcgctct gtcacccagg ctagagtgca gtggcatgat 180
cttggctcac tgcaacctcc acctcccagg ttcaagtgat tctcttgcct cagcctccca 240
agtagctagt attacagacg cctgccacca cgcccggtta atttttgtac ttttagtaga 300
gacaggtttc accatattgg ccaggctggt ctcaaactcc tgacctcagg tgatcctcct 360
gcctcagcct cccaaagtgc tgggattaca ggcatgagct accacgtctg gcctaagtgc 420
atgttaccta tactaacaaa accacacttc tgcctcgaat gagaacagtc tcctgaacat 480
cttgcctctt tgcctgactc aaagcctcag gtctaagcct ncccataatt tctagtctca 540
gcagaaagat caatgacagg agactctnca ggtgatgaaa ttaaccaatt aagtaacctg 600
ggttggcatc ctcccgtttg ntcaccagnc tnacctnctg ncacaggnat atncttttnt 660
ttnagccata tntgcacaaa ccccctnccc acggnacaca tagaaaaant tnggnagact 720
ngaaaattca ggncagggnt tagcncnccc ttgggggnnt ggnntntngg aacc 774

<210> SEQ ID NO 20
<211> LENGTH: 914
<212> TYPE: DNA
<213> ORGANISM: Homo sapiens
<220> FEATURE:
<221> NAME/KEY: misc_feature
<222> LOCATION: (1)..(914)
<223> OTHER INFORMATION: n is a, g, c, or t

<400> SEQUENCE: 20
tggggntncc ggtatcgccg cttccgattc gcagcgcatc gccttctatc gccttcttga 60
cgagttcttc tgagcgggac tctggggttc gaaatgagct agcccttaag taacgccatt 120
ttgcaaggca tggaaaaata cataactgag aatagaaaag ttcagatcga ggtcaggaac 180
agatggaaca gggtcgaccg gtcgaccggt cgaccctaga gaaccatcag atgtttccag 240
ggtgccccaa ggacctgaaa tgaccctgtg ccttatttga actaaccaat cagttcgctt 300
ctcgcttctg ttcgcgcgct tctgctcccc gagctcaata aaagagccca caacccctca 360
ctcggggcgc cagtcctccg attgactgag tcgcccgggt acccgtgtat ccaataaacc 420
ctcttgcagt tgcatccgac ttgtggtctc gctgttcctt gggagggtct cctctgagtg 480
attgactacc cgtcagcggg ggtctttcac tctctgtgta ctggtaccaa cagagcctgg 540
accagggcct ccagttcctc attcagtatt ataatggaga agagagagca aaaggaaaca 600
ttcttgaacg attctccgca caacagttcc ctgacttgca ctctgaacta aacctgagct 660
ctctggagct gggggactca gcttttgtat ttctgtgcca gcagcgtagg tggtagcttg 720
aaacagttct tcngggccag gggacncggc tnaccgggnn aggtaagaag ggggcctcca 780
ggtgggaaan aagggtgagc agnccanccc tgcacgaccc nnnaaccntn ttcttagggg 840
gaggggnnca ctgggncatn ncagggccnt cntngnggaa nnggggtttg cgccnagggt 900
ccccagggct gngc 914

<210> SEQ ID NO 21
<211> LENGTH: 1604
<212> TYPE: DNA
<213> ORGANISM: Homo sapiens
<220> FEATURE:
<221> NAME/KEY: misc_feature
<222> LOCATION: (1)..(1604)
<223> OTHER INFORMATION: n is a, g, c, or t

<400> SEQUENCE: 21
gngtggnatt gtgagcggat aacaatttca cacagnaatt cagtaaatgt tgatgtcaca 60
ttgggggcag cagctctagc tacattcaac tctacctgaa aactggcttt tagtataagc 120
catggatcca taacacatag gctagtttac aacaagtaat ttcagcattt ttggataatt 180
acattccctc cgacaatttc taaggagcct gcatgatact gaactgtgtc agaaaatagg 240
tgctacagtg aatatgtgat tctaatcagg ctttttttact atggaattat agtaaaatgc 300
actataatca actcatataa attgctctgt gcctatactt atctctaatg aagggaagca 360
aattgcctta cctgaaatta taaaagaaaa tgattacaaa ggtatggaag tttataggca 420
tcttataaga cctgatttta ttatgcatta tatagatggc aaaaaattcc tatttatcca 480
gaatctaaat gaccaggaag ctcaaataaa atgtgtttca tgggaatttg tttttatgtg 540
ctgaattgca agatcctgaa gggtctttaa gatcatcaaa gaaacatgaa tgctcacaca 600
actttagagc tgtaagaggt gtggagttca catggcccaa cctgtccatt tgacagctgc 660
gtgctgagcc caggggagag catggcttgc ccaatgaatt tgtgacaaag cgagacctgg 720
rgnnaccttt cagtttccct yataccccac aaatgggtct ttgtgctcta ctaggkgnaa 780
tggtattaaa taccacagnc cttttgtgta ttctaantyc ttagaaattt cctaatttat 840
gcatgggycc mcccttgcta aaatttcagc atacaccatg atatcttaga gctcccttcc 900

```
cacttaatct tctctcttag cattttcacg atttaaaaaa atcatctgta ttccccatta    960

gcaggcaaga ttcctaagga caaataactt tttttctttt attcactgct gaatcaccta   1020

gaacggtacc cagcacaaag tgagaggttg agaaatagtt gttgaatgaa aaaaaaaatg   1080

aatcgtttat gataatcctc aaatcccatc actgcattat cagaataccc catttttat   1140

gtcatctatt tgacactttt ccagaacttc tgatgtgcca ggcattttac aaggctgagg   1200

tgaaccacag agtaataggc ttattttatt cattcaggga gcttaattta aggtgatcct   1260

attattgtaa cctcctaatg caatgtcatc tcttatcagc ttaattctgc agactgtagc   1320

tatgtattac tccctgaagg aattattttc accttcaacc tgaagttagg actcatgatt   1380

cagcaatctg ctttctggga tcatacaagg gaaattgcaa tctttgtgct tgcttgccaa   1440

agctgagaaa gatggagcag natcaaaata agcaggattt gccaggcaat tttgacatat   1500

tcttcctctc acatataacc atcacaaagt aatgcatttc ataatgagaa ganccttgca   1560

ctagaagcat acatagtatc acatgnctca tcttctngnt tctn                    1604
```

<210> SEQ ID NO 22
<211> LENGTH: 844
<212> TYPE: DNA
<213> ORGANISM: Homo sapiens
<220> FEATURE:
<221> NAME/KEY: misc_feature
<222> LOCATION: (1)..(844)
<223> OTHER INFORMATION: n is a, g, c, or t

<400> SEQUENCE: 22

```
ttggggancc gcttgccaaa cnttcaggtg gggtctttca agaggtctcc agacctaggg     60

gagcatctca gcgtcactcg ctgtccagtt gctgtgatca ggtgctttgg ggtttgtgtg    120

actccagaat ccactgggcc tgtgtgtcag aagacaaaag ttaaccataa ggcacagaag    180

aaagcctcct gctgaagcca tcgttggccc acatgcattt cagggacaag aaatgaagat    240

cggagacttt caagttgtgc ccaggactca cctgctccca ggagacaaaa ggccacacag    300

cagaggagcc tgaagcccat ggcaggatct cctagcttgg ggctggtgtc tctgtagtaa    360

gcattctgaa gttcctaagc tcccttcttc ctgataggag cattgacctg tgatgtcacc    420

acactgacat actttcccct gcaggccact ccagcccact gtactctttg gcaggcctca    480

ggttctgcta ctccatgtac tattcctgtc ttgcacaggc cagaagctaa aggtgaggag    540

gactgaacac agtaccaaca tacccacatc acaccttact ttcctctgcc cgccctgtcc    600

ctgccctgac actgattccc cagcccttgc accccagccc cttcaccctc cactgcccgt    660

gcagcagcag agacactccc tccttgatgc aaactgaggc ctctggcacc cnactctttc    720

agggcaatga tagtctgtgc ttaactctac atggccaggc cccactcagg gaattcttat    780

gaaattatta tttttttnta tttctgggaa acaaagcgat gtatttattt ctgtttnggg    840

gata                                                                844
```

<210> SEQ ID NO 23
<211> LENGTH: 1562
<212> TYPE: DNA
<213> ORGANISM: Homo sapiens
<220> FEATURE:
<221> NAME/KEY: misc_feature
<222> LOCATION: (1)..(1562)
<223> OTHER INFORMATION: n is a, g, c, or t

<400> SEQUENCE: 23

```
ttttacanaa ctnncccccc tnaatcaaca gaatatacat tttnttnagc cccncaatac     60
```

```
acttattcta aantgnccca cataatngga agtaaaccac tcagcaaata taaagancag    120

aaatcccanc aaactgtctc tcagaccaca gtgcaatcaa attagaactc agggttaaga    180

atcacactca aaaccacaca actacatgga aactgaacaa cctgctcctg aatgactact    240

gggtaaataa tgaaatgaag gcagaaataa acacgttctt tgaaaccaac tagaacaaag    300

acacaatgta ccagaatctc tgggacacat ttaaagcagt gtgtagaggg aaatttatag    360

cactaaatgc ccacaagaga aagcaggaga gatctaaaat cgacatccta acatcacaat    420

taaaagaact agagaagcaa gagcaaacat attcaaaagc tagcagaaga cgagaaataa    480

ctaagatcag agcagaactg aaggagatag agacacaaaa aaaaccttca aaaattaatg    540

aatgcaggag ctggtttttt gaaaagatca acaaaatagc cctctagcaa gactaataaa    600

ggataaaaga gggaagaatc aaatagatgc aataaaaatg ataaagggga tatcaccacc    660

aatcccmcmg aaatacaaac taccmtcaga gaatactata aacmcctgta tgcaaataaa    720

ctagaaaatc tagaagaagc agataaattc ctggacacat acaacctccc aagactaaac    780

caggaagaag ttgaatctct gaatagacca ataataggtt ctgaaattga ggcaataatt    840

aatagcctac caaccaaraa aagtcgagga ccagatggat tcacagccgt attctaccag    900

aggtacaaag aggagctggt accattcctt ctgaaactat tctgatcaat gagaaaaaag    960

ggaatcctcc ctaactcatt tatgaggcta gcatcatcct gataccaaag cctggcagag   1020

acacaacaaa aaaagaaaat ttcaggccaa tatccctgat gaacattgat gtgaaaatcc   1080

tcaatacaat actggcaaat caaaaagctt atccaccacg atcaagtcag cttcatcgct   1140

gggatgcaag tctggttcaa catatgcaaa tcaataaaca aaatccatca cataaacaga   1200

accaatgaca aaaaccacat gattatctca atagatgcag aaaaggcctt caacaatatt   1260

caacagcctt tcatgctaaa aactctcaat aaactagata ttgatggaac atatctcaac   1320

ataataagag ctatttatga caaacccata gccaatatca tactgaatgg gcaaaaactg   1380

gaagcattcc ctttgaaaac cagcacaaga caaggatgcc ctctttcacc acttcgattc   1440

aacctagtat tggaagttct ggccagggcc atcaagcaag agaaagcaat aaggggtatt   1500

caagtaggaa gagaggggnt ttctgtgtga aaangttanc cgctggnnan ccccaaanan   1560

aa                                                                  1562
```

<210> SEQ ID NO 24
<211> LENGTH: 1446
<212> TYPE: DNA
<213> ORGANISM: Homo sapiens
<220> FEATURE:
<221> NAME/KEY: misc_feature
<222> LOCATION: (1)..(1446)
<223> OTHER INFORMATION: n is a, g, c, or t

<400> SEQUENCE: 24

```
ttggtactgt cagaccaagt ttactcatat cggatccgag gagcaggcgg gcctgaggcc     60

gagtcagctg cgcgggcccc cggatcctgg gctgtcatgt aacatcttcc aataaatgtg    120

atcttgggag gagaccattt tgggccttgg tttccacatc tgcgaaatgt tattatagcc    180

atgaacactt actgaaagct taccccatat gccagacaca tcttccaatc aacttatgtg    240

agttatctca tttaattttc acaacaatac aaagtagcgg ggaaaacttc tggcttctct    300

tgaaaactca gaaaatctaa caatgttgag tatgagtcca aaatgtcagc aagaagccag    360

agctgaatag ggaaggctgt tttagatgag accattagcc acagacctca ccactcttct    420

tactgtgcta cttatttcct ttatagtacc tgagtggttc ctgctgcgtg tgggtttgtg    480
```

gcccctgcat tagatggncc ttnatnattc ctcttcaccc ctgagctttg atgtttttttg 540 ctccatgtca ccttcaccag agtggtcagg ccattcttca atattcwkac ctrggcaaaa 600
ggtgcatgac tttgaactcc cctagttaag ttaaggcttc takaawgaac angannangc 660
tttgggagct gaggaagggt gctcactgtg ccctataaaa tagagtttca atagacactg 720
ggtcctctgt ggcctgacct cccctgtgtc agcaacttga gtctcacttg aatggggaaa 780
gaaagtawtg arangaaakg aacwwkgaam ytcwgaaaca ngacctcttm akanswarcm 840
aggrccctms tagtctanyt wrggtaaagc caagtgtgac cctaaggcaa gttacttaac 900
ctctgcgtct cagtttcctc atctataagt taatgacaac ctctacccca taagggagct 960
tgaaagaaaa tccaaaaaag aaagaatctc tttgagttgc taatgactct taagtttctg 1020
gttctagtcc tttgaccatc atgacagtcc tatggtttta cgaaagaact atccatctct 1080
atttaaaaaa caaaaaacac aaagaccttt tttgcttaag ctaacttgtg ttgggtttca 1140
tccaccagga agttagagag agaaattact tagagataaa cttacacatt acaaatcctt 1200
ctgttctgtg tgcttttaaa aatgttcaat ttctaaatgg gcctctggtg aagataatga 1260
tcacctcatt gatttgttcc caggagaaca gggtaaaatg aagtcctgct gatcacattt 1320
tctaaatctt tttantccca ttgctttggg aaagtttcta caccagtnat ccttntacag 1380
cctccctctt tcccatggtt cnttctctgc accaccagga aaggaggaat cccanancag 1440
tcttgc 1446

<210> SEQ ID NO 25
<211> LENGTH: 840
<212> TYPE: DNA
<213> ORGANISM: Homo sapiens
<220> FEATURE:
<221> NAME/KEY: misc_feature
<222> LOCATION: (1)..(840)
<223> OTHER INFORMATION: n is a, g, c, or t

<400> SEQUENCE: 25
ggaattgnna gcggntaaca atttcacaca gnaattctta ttatggtaag ttcctgagat 60
ttgagatggt ttgttataca acagggaact gataggctta ttcttcaaga ggagcaaaac 120
agggatgatt gctattctct tcaatgggtt gaggaaagaa gaaattatgt gaacatttat 180
acactaataa tttattctgt catatttcag tcagattaaa gcaaacagcc aaaaacaagg 240
acaaagtcca aggtaagaga ctgatgataa gtggcctgtt tacaaggaaa ataagatcac 300
tagctctact tacagctgat tcagaataac ttcattttta aagcctaaaa ttttacagtc 360
aagctcttga gtgcaatttc cttaacattt tctaaaccat acagaaaatc ataaagaaac 420
aatatttctt tgtttgagtt tcctttttag gagttaggtc ttattttaaa aatattttct 480
agcctgttta ggctcttatt taaaattatc tacttttctc aaagtctttc tcatacttga 540
gatatccaaa atattgaatg agtgatgtaa actataccag ataaactatg agtctatatt 600
tttaccctga ttcagtcagt ttccaaggag aactttgaac aactaaaaat gtgtattact 660
ataatctctc tgaaatattn ctnattaatt ttttgggggn aaaatgagtc attctgagcc 720
aaaaaaaaaa anggtnacca gacantttcc actnctaact tgnntgggcg attncagcag 780
attcaanttc cagcatnggn agatncggna gatnnnggnc ctaccatgan cttaccttcc 840

<210> SEQ ID NO 26
<211> LENGTH: 861
<212> TYPE: DNA
<213> ORGANISM: Homo sapiens
<220> FEATURE:
<221> NAME/KEY: misc_feature
<222> LOCATION: (1)..(861)
<223> OTHER INFORMATION: n is a, g, c, or t

<400> SEQUENCE: 26
ttttnctcct aacttgagtt ggcgatatca gcagattcaa attaccagca atgggaagat 60
acaggaagat gtaggtacct accaatgagc ttaccttccc agtgctctat ataacctcac 120
ttctatagcc caaagtatta aaaagaagaa aaaataataa ttcaggctta ctatttaaaa 180
atacagtgat tctggccggg cacggtggct cacgactgca atcccagcac tttgggaggc 240
cgaggcgggt ggatcacgtg aggccaggag tttgagacca gcctggccaa tgtggtgaaa 300
ccctgtctcc actaaaaata caaaaattag ctgggcatgg tggcgggcgc ctgtaatccc 360
agctactcgg gaggttgaga tgggagaatt gcttggaccc aggaggcaga gcttgcagtg 420
agccaagatt gcaccactgc attccaccct gggtgacaga gtgagaccct gtctcaaaaa 480
acaaataaaa atacagtgat tctgagaggc cttccctttc cacaccacct cctacttgtt 540
tgatagctct catcccattt tcctcaactg ccacatatgg ccaggacttc cacagtgtat 600
taaacatctt ctttggacaa gagaaatttc actgaagcaa tgagtgtaga agttattagc 660
atgaattgaa gactgatgct ggcacacaaa tagggagaca catcaatata atgacctaat 720
gaatctagaa atagcttcan gaantntgga aaagtagatg tgataaaagn tgcatttnaa 780
tcanngagca aagtnttaat anaattgaga cacctatgtn gctattngga aacattaang 840
tnggntgcat antngaaact t 861

<210> SEQ ID NO 27
<211> LENGTH: 875
<212> TYPE: DNA
<213> ORGANISM: Homo sapiens
<220> FEATURE:
<221> NAME/KEY: misc_feature
<222> LOCATION: (1)..(875)
<223> OTHER INFORMATION: n is a, g, c, or t

<400> SEQUENCE: 27
ttgggnnacc gcttgccaaa cctacaggtg gggtctttca agaggtctcc agacctaggg 60
gagcatctca gcgtcactcg ctgtccagtt gctgtgatca ggtgctttgg ggtttgtgtg 120
actccagaat ccactgggcc tgtgtgtcag aagacaaaag ttaaccataa ggcacagaag 180
aaagcctcct gctgaagcca tcgttggccc acatgcattt cagggacaag aaannnagat 240
cggagacttt caagttgtgc ccaggactca cctgctccca ggagacaaaa ggccacacag 300
cagaggagcc tgaagcccat ggcaggatct cctagcttgg ggctggtgtc tctgtagtaa 360
gcattctgaa gttcctaagc tcccttcttc ctgataggag cattgacctg tgatgtcacc 420
acactgacat actttcccct gcaggccact ccagcccact gtactctttg gcaggcctca 480
ggttctgcta ctccatgtac tattcctgtc ttgcacaggc cagaagctaa aggtgaggag 540
gactgaacac agtaccaaca tacccacatc acaccttact ttcctctgcc cgccctgtcc 600
ctgccctgac actgattccc cagcccttgc caccccagcc ccttcaccct ccactgcccg 660
tgcagcagca gagacactcc ctccttgatg caaactgagg cctctggcac cccaactctt 720
tcagggcaat gatagtctgt gcttaactct acatggccag gcccccactc agggaattct 780
aatatgaatg taaactncag gtgttgncag ctagtgcttc cntggaaaan cccctgttnc 840
agctnctaca catgctctta tctntagctn ganca 875

<210> SEQ ID NO 28
<211> LENGTH: 901
<212> TYPE: DNA
<213> ORGANISM: Homo sapiens
<220> FEATURE:
<221> NAME/KEY: misc_feature
<222> LOCATION: (1)..(901)
<223> OTHER INFORMATION: n is a, g, c, or t

<400> SEQUENCE: 28
ctncttctng ggngtnnnnn nacnatntan nnnnatcgnc tcnacantnn nttncnnggg 60
aaaaacctct gtctaacctt acatgaaaaa acccgtttcc aacgaaggcc tctaagaggc 120
caagatatcc acttgcagac tttacaaaca gagtgtttcc aaactgctga atgaaaagaa 180
aagttaaact ctgtgagttg aacgcacaca tcacagagca gtttctgaga atgattctgt 240
cgggttttta tacgaagata ttccctttc tgcctttggc ctcaaagcgc ttgaagtctc 300
cacttgcaaa ttgcagaaaa agagtgtttc gaatctgctc tgtctaaaag aaggttcaac 360
tctgtcagtt gaatacacac aacacaagga agttactgag atttcttctg tctagcctta 420
catgaaaaaa acccgtttcc aacgaaggcc tcaaagaggt caaaatatcc acgtgcagac 480
tttccaaaca gagtgtttcc aaactgctga atgaaaagaa aagttaaact ctgtgagttg 540
aacgcacaca tcccagagca gtttctgaga aagattctgt ctagttttta taggaaaata 600
tttccttttc tgcttttggc ctcaaagtgc ttgaaatctc cacttgcaaa ttccacaaaa 660
agagtgtttc aaatctgctc tgtctaaagg aaggttgaac tctgtgagtt gcatacacac 720
aacacaaaga agttactgag aaatcttctg tctagcataa tatgaagaaa tcccgtttcc 780
acgaaggcct caagaggncc aatatncact ggcaggcttn caacagagtg ttnctactgc 840
tctgtgaaag aangntaact ttgnngttga ccaccatnan aagnnttttg naanatttgn 900 n 901

<210> SEQ ID NO 29
<211> LENGTH: 856
<212> TYPE: DNA
<213> ORGANISM: Homo sapiens
<220> FEATURE:
<221> NAME/KEY: misc_feature
<222> LOCATION: (1)..(856)
<223> OTHER INFORMATION: n is a, g, c, or t

<400> SEQUENCE: 29
cntttggnng tttaaaangg gcnganatat gcttnacatc nattgggggn aaacctcttg 60
cgtgagtatt caagaaccct ctcttgggat ctggatcggg accccttcc tgtaacatat 120 gcaaggaaag aaatgcagag gaatggaact gagccatgga acagacattt ggggttgggc 180
aggaggagtt agcagagaga tctgcatagc tcttatccta cttagcacta gtgctgttca 240
aggtagaact cacagcataa gaattctagc atctgcataa atttggagag caacttgcct 300
tctccttaga tacacgaata tggaaaatgc aatagaagtt gcttatcatg cactcaggtt 360
gagtgaagtt ttatcataat gaagctaaat gaaattccca aattgctctg gtggagagga 420
acgccttgat attccacttg tggaaaaatg gctctatgcc aaaaataaag ttacatcaac 480
ctcagtacag gagaaatcag agtttctgct cacagcagca gcagaggaat catctgcaac 540
acagagactt ttgggttgta tgtaaggcag ccttgctgga tggtctttaa cagggttttg 600
gtagggacat ggtagaggct ggttcctaaa ctcttcaaac gtttcttccc agccctttag 660
ctttgacctc acgtgcagag ttgagttaat tataagcctt atttatgggc acactttcac 720
cattaagttc atacacagcc ccatttttgt gccattcttc actcctatgt ccttttctcc 780
cctaagcaac catgtaaaca tgttagagng ggngagcgtg cacacnccat acacacacat 840
tcatttacac atgatt 856

<210> SEQ ID NO 30
<211> LENGTH: 890
<212> TYPE: DNA
<213> ORGANISM: Homo sapiens
<220> FEATURE:
<221> NAME/KEY: misc_feature
<222> LOCATION: (1)..(890)
<223> OTHER INFORMATION: n is a, g, c, or t

<400> SEQUENCE: 30
cnnnttctgg gggngtannn aactaannna nntnaatncc ncccaatnnn ttcggggggg 60 aaaanccccca gnactccata attcncaagn atcacatgna tcacaggaga ggagactggg 120
ggagtcaatg gatagaggat ttataagcca agaaaaaaaa atggagcccc aaactgtgaa 180
atccaagaag ggggtcatgt gaaccccaat ttatagccag tttttcagaa gaataagtga 240
caacctacta cttgtgattg gcacttgaag tgggaggcag tcgtgaggga gttaatatgt 300
gggaactaac cctactctag gtagtgttga attgaatcaa atcataggac atctagttgg 360
tgtttgctgg aaaactggtt gttggtggag tgaaacccct acatattttg gtgatcagag 420
gtgaagtgtt gtgttaagtg gtatgagact gggaaaaaca ctttggtttt tcctgtctct 480
cacagaatta aagtttccaa gagaagcatc agaagagtgg aaggttggga ccagcaaacc 540
acaagcccta ggccccaaac tagggtcaag tggaaaagca gggtataata gtgaaatggc 600
cctcctctcc acttctgcag ctccagtgac gctgttccta ctcattgtca cactggaatg 660
gttgcaggat gaacacgatc ctctggaaat ggagacatct tctgaaggta gaggaaactg 720
cagtcttcct gccccgacc gccactcgca gaggttggga atgtcagcct nctccaaccc 780
antcttttnt atgggatttt ccttactttg gggggggact gnaatgntac ctatcttttt 840
tttacaantt gggggggntc cnccccactt anngacccng nttnnccnng 890

<210> SEQ ID NO 31
<211> LENGTH: 732
<212> TYPE: DNA
<213> ORGANISM: Homo sapiens
<220> FEATURE:
<221> NAME/KEY: misc_feature
<222> LOCATION: (1)..(732)
<223> OTHER INFORMATION: n is a, g, c, or t

<400> SEQUENCE: 31
attcttttgg gnaccgtcag naccaagttt tactcatatc ggcatcctct ctcggtggct 60
gctgcagcgg ggctggtgtg ctgcaacccg gacggagctg agtgaggggc acaatggcag 120
caacctgcag gcaccaaaga gcccccaaga gctgctcagc ggtgcctgat caaagtttgt 180
ctgggccagt gcttgtgcat tgtgtacgct gtgcgacaac caggaaggag agctgggttt 240
tgccatcctc caacgcttct taaataggaa actttttggg tagcacctgg cctagttcct 300
ggaacacaga aggtgctgag tgatgttagt ttcattcgct catcttgtct cttgggcatg 360
gaaaagagtt tacaagtgct ctttcattat ccatcttgat gtgggaaggt ggggcagggg 420
aagatgagta cccgctctcg ccctttggtg tgatgtttgt gacgtacatg aggcatgtgg 480
gagagtggat cacagcattg gacagactgg atcccttctg gtcccacatc actcaggcaa 540
ctctctcttc ccacctgccc cccaaactcc cttncacctc cctccacatg tatcctccca 600
cttncttcca ctcatgtaat gagaggtgct gatgagtcac aggaagaggt agccctagat 660
aaccaacaga ctgcaaaacg ggacagtncc ntggatgtct gagccagtgt ttngngcact 720
gcattgactg gc 732

<210> SEQ ID NO 32
<211> LENGTH: 672
<212> TYPE: DNA
<213> ORGANISM: Homo sapiens
<220> FEATURE:
<221> NAME/KEY: misc_feature
<222> LOCATION: (1)..(672)
<223> OTHER INFORMATION: n is a, g, c, or t

<400> SEQUENCE: 32
tttggnaacc gtcagaccaa gtttactcat atcggatccc aggagacacg ctccaagggc 60
tgggtgggaa aagccccaga aaggggaggg ctgcggggag tgagaatcgg gatggacctc 120
acagacgaca aacagatgga caaaaagctt ctctccctgc cgctccctcc ccgccaccaa 180
ctccagcccc tctgtctcca tcccctttc ctgtctgtcc tgtctgaatc tctgaatctc 240
tgcctgtttn tttttctctc tatgaatcac agcgtttcag agcctctgag agaaaaatgg 300
gaaaagaaga cagagatgat agaaaatgca gagtgtgcgt gtgtgtgtgt gtgtgtgcat 360
gtgtatgcgc gcgtgtgtgt gtgtgtctgt gcatgcgtgc acccagcatg aagtctggtc 420
tggagaatgt aactagggag ggaggaagag aggggacgag agaagcagag gatgaacaaa 480
gagactttcg aagctcatag gaaaaagcct gggaggcaac agcagcaggg acacgcatat 540
gccgcacacc cctacacaca ccacacacca cacaccacac acaccctgca tgcaccctgg 600
agacatgccc cagactccag gcgggagggg tggagcaggg ggtgtgaaat atggttggtt 660
gggttgggtt tg 672

<210> SEQ ID NO 33
<211> LENGTH: 770
<212> TYPE: DNA
<213> ORGANISM: Homo sapiens
<220> FEATURE:
<221> NAME/KEY: misc_feature
<222> LOCATION: (1)..(770)
<223> OTHER INFORMATION: n is a, g, c, or t

<400> SEQUENCE: 33
nttttgnant gtncgcggnt aacaatttca cacagnaatt cattttaacg ttgtacatat 60
ttattataca agaaatattt tttccatcaa aaagtactca ttcaaaaaat atttaatcta 120
gaatagagat tataaatttt taacttaatt ttattttttt cttaaggaaa actctaagat 180
atcattacca ttttcaaaac tgtcaagtag tggtgaatga cacttcttat atgttaattt 240
ttaaaagaat atttctaaca cacattctta atggagaatt atatcttata cagaatgata 300
cattctaagg gtgatgttta tgaaagaaat ttaagcttgg ttaacatgct tagtaaaatt 360
ttttaataca aataaaattc agagtatatg gtgtgaagtg agttatatgg tgcaaatact 420
attttaattc ttgaacactt ccacaaaatt agcttgtaaa ataaaattaa acccacactg 480
agatgctaga tttgcagatg aatcattcat ttttttacat ttctttttat ttctctaact 540
aaattatatg acagaaggca agggtcatga ttaattcatt gttgtattct ttatatatta 600
aatataagct cctcaataaa tattatggaa aaaatgaaca aacacttcac attttattgt 660
tttctatatt tttcaaggtt tttattaatt cttcatgtgc tttgtgactt tattttctcc 720
aaagaaattc ttcttgaaat gaaaagttca caanagttag gataactgga 770

<210> SEQ ID NO 34
<211> LENGTH: 777
<212> TYPE: DNA
<213> ORGANISM: Homo sapiens
<220> FEATURE:
<221> NAME/KEY: misc_feature
<222> LOCATION: (1)..(777)
<223> OTHER INFORMATION: n is a, g, c, or t

<400> SEQUENCE: 34
nttttgnatt gtngcgcggn taacaatttt cacacagnaa ttcttttgtc aagaattata 60
agaagaaatc ccgtttccaa cgaaggcctc aaagagttcc aaatatccac ttgcacactg 120
cacaaactaa gtctttccaa actgctctat gcaaagaaat gttcaactct gtgagtttaa 180
tacacacatc acaaagcagt ttctgagaat gatactgtct agtttttata cgaagatatt 240
tccttttgta ccattggcct catactgcta gaattttcca cttgcaaatt ccacaaaaag 300
agtgtttcca atccgctctg tctaaaggaa ggttcaactc tctgatttga atacatacat 360
cccaaaagaa gttactgaga attcacaaga acaaacgaaa aaaaaaatgg taattaaggt 420
caatataaaa cgtagattgt cacttcaaga aaatacctgc cttatacaga actaagtggc 480
tgtttcaagt aaaaatggtg ttccatgaaa aagctgctag ttcagctggc aactcaaaca 540
atggcacaag tgccttatgc catttctatt ttatcacaca tattaaaaac ctggccagca 600
cggtggctca tgcctgtaat tccagcattt tggnaaggcc gaggcaggtg gatcatttga 660
ggccagnagt tcaagacang cctggccaac atagcaaaac ccccattttt actaaaatac 720
aaaattagcc aggcntgggg gcgcgtgcct gtantccnnc ttctcgggag gctgagg 777

<210> SEQ ID NO 35
<211> LENGTH: 799
<212> TYPE: DNA
<213> ORGANISM: Homo sapiens
<220> FEATURE:
<221> NAME/KEY: misc_feature
<222> LOCATION: (1)..(799)
<223> OTHER INFORMATION: n is a, g, c, or t

<400> SEQUENCE: 35
tnnttttgga gtgancgcgg ntaacaattt tacacaggaa ttctagggtt ggttcatggt 60
ttgagacttg agagtggaca ggtgcctagt tagacctgct ctggatgtgg aggtgtctgg 120
tgattagaat gactctttgt atatctgttc cctctttaat tgcttccttt taacctcaag 180
attaggcttt tattgcataa taaaatgcat atgagccatt cagttttact ccattacctc 240
tctggcttag aatgaactat cagtagaatt aacaaaaatt gcatcataga gttggagaat 300
tgccaccaag gaagtgttct agccatacta cagaaaagat tctccccatg ggattacttc 360
tcagtagaat tcagcaacca attcctggtg aatctatcca agcagagaaa tgaaaacata 420
tattcactaa aagacttgaa cacaaatgct catagcagcc ttaatcaaaa tagagaaaaa 480
ctggaaacat ttcaaatgtc tatcaactga tcaatatata agcaaaatat ataaagcatt 540
tgcagacaat aaaaaacaaa atattgatat atactaaaac atggnatgaa cctcaaagcc 600
actatactag atgagagatg tcagacacaa acctactgta tttgcaagat gccatttact 660
tgaaaaatcc agaaaagtcg catttacaga gacagtaaaa cagataagtg ggctgcctgc 720
ggctgggggg ttgnaaaagc nattttgctg caaatgaact tanggaaatt ttttttgngg 780
ggggggngat anaaaattn 799

<210> SEQ ID NO 36
<211> LENGTH: 417

<212> TYPE: DNA
<213> ORGANISM: Canis familiaris
<220> FEATURE:
<221> NAME/KEY: misc_feature
<222> LOCATION: (1)..(417)
<223> OTHER INFORMATION: n is a, g, c, or t

<400> SEQUENCE: 36
ancttggtaa ctgtcagnac caagatttac tcatatcgga tccccaggaa tactattctt 60
taaagactat caatattcta caaagggaaa ttagagttct caattgtgaa cggaaaggaa 120
catcaatggg catgacctaa gacctccttc tacacagtta aacaacaatt tcacaagata 180
tgatttaaga gaaagctttc agggacgcct gggtggctca gtggttgagc gtctgccttc 240
cgctcagggt gtgatcctgg agttccggga ctgagtcccc atggggctcc ctgcatggag 300
cctgcttctc cctctgccta tgtctctgcc tctctctgtg tctcatgaat aaataaataa 360
agnncttatt tttttaaga ttntatttat ttatncatga nagagagaga gaggcng 417

<210> SEQ ID NO 37
<211> LENGTH: 434
<212> TYPE: DNA
<213> ORGANISM: Canis familiaris
<220> FEATURE:
<221> NAME/KEY: misc_feature
<222> LOCATION: (1)..(434)
<223> OTHER INFORMATION: n is a, g, c, or t

<400> SEQUENCE: 37
tggtaactcg tcagnaccaa gatttactca tatcggcatc cccaggaata ctattcttta 60
aagactatca atattctaca aagggaaatt agagttctca attgtgaacg gaaaggaaca 120
tcaatgggca tgacctaaga cctccttcta cacagttaaa caacaatttc acaagatatg 180
atttaagaga aagctttcag ggacgcctgg gtggctcagt ggttgagcgt ctgccttccg 240
ctcagggtgt gatcctggag ttccgggact gagtcccaca tggggctccc tgcatggagc 300
ctgcttctcc ctctgcctat gtctctgcct ctctctgtgt ctcatgaata aataaataaa 360
gtccttattt tttttaagat tttatttatt tattcatgag agagagagag agncngngnc 420
ntnggcngng ggng 434

<210> SEQ ID NO 38
<211> LENGTH: 1425
<212> TYPE: DNA
<213> ORGANISM: Canis familiaris
<220> FEATURE:
<221> NAME/KEY: misc_feature
<222> LOCATION: (1)..(1425)
<223> OTHER INFORMATION: n is a, g, c, or t

<400> SEQUENCE: 38
cnggncggng angattntng tcgnnaccca tggcgaatgc ctggctngcc gaatattcat 60
ggtggaaaat ggccngcttt tctggattca tcgnactgtg nccggctggg tgtggcggac 120
ccgctatnca gnacatagcg ttgggctacc cngtgataat gctgaagagc ttggcggncg 180
aatgggctga ccgcttcctc gtgskkkanc ggtatcgccg ctcyccgatt cgcagcgcat 240
cgccttctat cgccttcttg acgagttctt ctgagcggga ctnctggggt tcgaaatgag 300
ctagccctta agtaacgcca ttttgcaagg catggaaaaa tacataactg agaatagaaa 360
agttcatctc tgctgtcttt ggccattctc tctaggcatc tgctcatgtg gaggcataag 420
aaaatattga catgcttcac attacatttt cagagtatgt tattcatgta atttatttgt 480
aaaatctacc aatacaattt ccccccaatc aagtaaaact aggtaaaaag atctctgcaa 540
agattagctg aggaagaaac atatgtgagt agaatcagaa tgttaagagc tgacaggtta 600
gcagatagca tgcccatgat ttttgtgggt ttggcccctt tgttgaagct aaatcttaca 660
gagaggccca accctagagg taaaatgatt aaaacagatg tgctgcagtt ggcggggagg 720
gtgctgcgcc aggggaagcc caagactgct gctggctgcc ttccctcctg aycttatccc 780
atgtctcatt tgaaaaccaa tagttgaaaa actctcaatt ttcagatgag aacgaaaaca 840
aaaatgcaaa gaaggcaaat gattcaytca aarwtactca gtgaatkrga sccawsatgt 900
gggaatacaa ctctggcctt ctgtttctga atctagtggt atttccaggc tcacaggaag 960
cttcctgtac cttgctccac tgtgtgtgtt tttggatggc cctggtgttt gattacctyt 1020
cgtggcaggc ccaacagccc ttgctaaggc acagactgca tatttgctga tccctgaggn 1080
ggaaagctgt gattcagact ttgaggtcta agaattgcag acttagtttc tagtctcccg 1140
atgaaactgc taatctgggt gccagtggtg tttctgctac acggacacct gcccacacag 1200
catgattaga aattataatg atgacggcga tgagtcttcc aggacaccta cgttctttgc 1260
aagatatttc tgctaatcgt ctctaccaga atcagttgga gaactttttt tagttttttt 1320
tttttttttt taatttcccc ctttctaagt caagtaaaaa tactagttta attnctggtg 1380
tagggtaatg atttgtcctc accattactg atgtgtcatt ttttg 1425

<210> SEQ ID NO 39
<211> LENGTH: 674
<212> TYPE: DNA
<213> ORGANISM: Canis familiaris
<220> FEATURE:
<221> NAME/KEY: misc_feature
<222> LOCATION: (1)..(674)
<223> OTHER INFORMATION: n is a, g, c, or t

<400> SEQUENCE: 39
caaaaaatga cacatcagta atggtgagga caaatcatta ccctacacca gnaattaaac 60
tagtattttt acttgactta gaaaggggga aattaaaaaa aaaaaaaaaa aactaaaaaa 120
agttctccaa ctgattctgg tagagacgat tagcagaaat atcttgcaaa gaacgtaggt 180
gtcctggaag actcatcgcc gtcatcatta taatttctaa tcatgctgtg tgggcaggtg 240
tccgtgtagc agaaacacca ctggcaccca gattagcagt ttcatcggga gactagaaac 300
taagtctgca attcttagac ctcaaagtct gaatcacagc tttcccctca gggatcagca 360
aatatgcagt ctgtgcctta gcaagggctg ttgggcctgc cacgagaggt aatcaaacac 420
cagggccatc caaaaacaca cacagtggag caaggtacag gaagcttcct gtgagcctgg 480
aaataccact agattcagaa acagaaggcc agagttgtat tcccacatga tggctctaat 540
tcactgagta actttgaatg aatcatttgc cttctttgca tttttgtttt cgttctcatc 600
tgaaaattga gagtttttca actattggtt ttcaaatgag acatgggata agatcaggag 660
ggaaggcagc cagc 674

<210> SEQ ID NO 40
<211> LENGTH: 666
<212> TYPE: DNA
<213> ORGANISM: Canis familiaris
<220> FEATURE:
<221> NAME/KEY: misc_feature
<222> LOCATION: (1)..(666)
<223> OTHER INFORMATION: n is a, g, c, or t

<400> SEQUENCE: 40
cccatgagca aaaaatgaca catcagtaat ggtgaggaca aatcattacc ctacaccagn 60

```
aattaaacta gtatttttac ttgacttaga aaggggaaa ttaaaaaaaa aaaaaaaaaa    120

ctaaaaaaag ttctccaact gattctggta gagacgatta gcagaaatat cttgcaaaga   180

acgtaggtgt cctggaagac tcatcgccgt catcattata atttctaatc atgctgtgtg   240

ggcaggtgtc cgtgtagcag aaacaccact ggcacccaga ttagcagttt catcgggaga   300

ctagaaacta agtctgcaat tcttagacct caaagtctga atcacagctt tcccctcagg   360

gatcagcaaa tatgcagtct gtgccttagc aagggctgtt gggcctgcca cgagaggtaa   420

tcaaacacca gggccatcca aaaacacaca cagtggagca aggtacagga agcttcctgt   480

gagcctggaa ataccactag attcagaaac agaaggccag agttgtattc ccacatgatg   540

gctctaattc actgagtaac tttgaatgaa tcatttgcct tctttgcatt tttgttttcg   600

ttctcatctg aaaattgaga gtttttcaac tattggtttt caaatgagac atgggataag   660

atcagg                                                              666
```

<210> SEQ ID NO 41
<211> LENGTH: 603
<212> TYPE: DNA
<213> ORGANISM: Canis familiaris
<220> FEATURE:
<221> NAME/KEY: misc_feature
<222> LOCATION: (1)..(603)
<223> OTHER INFORMATION: n is a, g, c, or t

<400> SEQUENCE: 41

```
cccatgagca aaaaatgaca catcagtaat ggtgaggaca aatcattacc ctacaccaga    60

attaaactag tatttttact tgacttagaa aggggaaat taaaaaaaaa aaaaaaaaac   120

taaaaaaagt tctccaactg attctggtag agacgattag cagaaatatc ttgcaaagaa   180

cgtaggtgtc ctggaagact catcgccgtc atcattataa tttctaatca tgctgtgtgg   240

gcaggtgtcc gtgtagcaga aacaccactg gcacccagat tagcagtttc atcgggagac   300

tagaaactaa gtctgcaatt cttagacctc aaagtctgaa tcacagcttt cccctcaggg   360

atcagcaaat atgcagtctg tgccttagca agggctgttg ggcctgccac gagaggtaat   420

caaacaccag ggccatccaa aaacacacac agtggagcaa ggtacaggaa gcttcctgtg   480

agcctggaaa taccactaga ttcagaaaca gaaggccaga gttgtattcc cacatgatgg   540

ctctaattca ctgagtaact ttgaatgaat catttgcctt ctttgcattt ttgttttcgt   600

tct                                                                 603
```

<210> SEQ ID NO 42
<211> LENGTH: 749
<212> TYPE: DNA
<213> ORGANISM: Canis familiaris
<220> FEATURE:
<221> NAME/KEY: misc_feature
<222> LOCATION: (1)..(749)
<223> OTHER INFORMATION: n is a, g, c, or t

<400> SEQUENCE: 42

```
ggtnactgtn cgnaccagtt tactncatat ncggntnccc atgagcaaaa aatgacacat    60

cagtaatggt gaggacaaat cattacccta caccagnaat taaactagta tttttacttg   120

acttagaaag ggggaaatta aaaaaaaaaa aaaaaaacta aaaaaagttc tccaactgat   180

tctggtagag acgattagca gaaatatctt gcaaagaacg taggtgtcct ggaagactca   240

tcgccgtcat cattataatt tctaatcatg ctgtgtgggc aggtgtccgt gtagcagaaa   300

caccactggc acccagatta gcagtttcat cgggagacta gaaactaagt ctgcaattct   360
```

-continued

```
tagacctcaa agtctgaatc acagctttcc cctcagggat cagcaaatat gcagtctgtg    420

ccttagcaag ggctgttggg cctgccacga gaggtaatca aacaccaggg ccatccaaaa    480

acacacacag tggagcaagg tacaggaagc ttcctgtgag cctggaaata ccactagatt    540

cagaaacaga aggccagagt tgtattccca catgatggct ctaattcact gagtaacttt    600

gaatgaatca tttgccttct ttgcattttt gttttcgttc tcatctgaaa attgagagtt    660

tttcaactat tggttttcaa atgagacatg ggataagatc aggagggaag gcagccagca    720

gcagtcttgg gcttcccctg gcgcagcac                                      749


<210> SEQ ID NO 43
<211> LENGTH: 1778
<212> TYPE: DNA
<213> ORGANISM: Canis familiaris
<220> FEATURE:
<221> NAME/KEY: misc_feature
<222> LOCATION: (1)..(1778)
<223> OTHER INFORMATION: n is a, g, c, or t

<400> SEQUENCE: 43

gkggtagngn rcggtaaaca atttncacac agcaattncc cctgtgnaaa ctgccttgac     60

ttggtgcctt ttttggaggg gtggagttgt ttccactttg acaaattttt atatttctcc    120

catcctaatt ggactaattt gcttttatat ctcttctgtg gttattttgt taatcgtatt    180

ttaggaaagt cacctatttc aaattgattt gcatggagct aaataatttc ttccaatttt    240

ttcatttcct ttgtgtttat ggttatttct acattattag tgaaagtttt gtggttttgt    300

gttttagttc tctatctcct cttttgatta gtttcacaga gtttagttgt tatttttttca   360

gaaaacagct cttgcactta tttatcggct ctactgttct taatttgctc ctaaaaattg    420

tcaataatat gtttcttttg ctttgcccgg gctcattttg ttgtttttct aattgtttga    480

gcttgactct taattcatct atttttgttt ctgctttttt gttaatgtaa atttaaaaaa    540

tgcgagatcc aattagaata agcctcaccg gacaagaacc tgtctgtgca cttcgagact    600

accataatgc ctatcacata gcaggtgctt aagcaaaatt tttgtatgaa taaataaacc    660

cctatgaaat aattatggga tttgtgtgac agccctcgtt cttctctgct gtctttggsc    720

aytctctcta ggcatctgct catgtggagg cataagaaaa tattgacatg cttcacatta    780

cattttcaga gtatgttatt catgtattta tttgtaaaat ctaccaatac aatttccccc    840

caatcaagta aaactaggta aaaagatctc tgcaaagatt agctgaggaa gaaacatatg    900

tgagtaraat caraatgtta agagctrmca ggttarcaga tagcatgccc atgatttttg    960

tgggkttggc ccctttgttg aagctaaatc ttacagagag gcccaaccct agaggtaaaa   1020

tgattaaaac agatgtgctg cagttggcgg ggagggtgct gcgccarggg aagncccaag   1080

actgctgctg gctgccttcc ctccntgatc ttatcccatg tctcatttga aaaccaatag   1140

ttgaaaaact ctcaattttc agatgagaac gaaaacaaaa atgcaaagaa ggcaaatgat   1200

tcattcaaag ttactcagtg aattagagcc atcatgtggg aatacaactc tggccttctg   1260

tttctgaatc tagtggtatt tccaggctca caggaagctt cctgtacctt gctccactgt   1320

gtgtgttttt ggatggccct ggtgtttgat tacctctcgt ggcaggccca acagcccttg   1380

ctaaggcaca gactgcatat ttgctgatcc ctgaggggaa agctgtgatt cagactttga   1440

ggtctaagaa ttgcagactt agtttctagt ctcccgatga aactgctaat ctgggtgcca   1500

gtggtgtttc tgctacacgg acacctgccc acacagcatg attagaaatt ataatgatga   1560

cggcgatgag tcttccagra cacctacgtt ctttgcaaga watttctgct aatcgnttnc   1620
```

tctaccagaa tcagttggag aactttttt agttttttt ttttttttt aatttccccc 1680 tttctaagtc aagtaaaaat actagtttaa ttctggtgta gggtaatgat ttgtcctcac 1740
cattacttga aagaccccac ctgtaggttg gcaagcgg 1778

<210> SEQ ID NO 44
<211> LENGTH: 868
<212> TYPE: DNA
<213> ORGANISM: Canis familiaris
<220> FEATURE:
<221> NAME/KEY: misc_feature
<222> LOCATION: (1)..(868)
<223> OTHER INFORMATION: n is a, g, c, or t

<400> SEQUENCE: 44
ttcctgagac ngcttgccaa acctacaggt ggggtctttc aagtaatggt gaggacaaat 60
cattacccta caccagaatt aaactagtat ttttacttga cttagaaagg gggaaattaa 120
aaaaaaaaaa aaaaaactaa aaaaagttct ccaactgatt ctggtagaga cgattagcag 180
aaatatcttg caaagaacgt aggtgtcctg gaagactcat cgccgtcatc attataattt 240
ctaatcatgc tgtgtgggca ggtgtccgtg tagcagaaac accactggca cccagattag 300
cagtttcatc gggagactag aaactaagtc tgcaattctt agacctcaaa gtctgaatca 360
cagctttccc ctcagggatc agcaaatatg cagtctgtgc cttagcaagg gctgttgggc 420
ctgccacgag aggtaatcaa acaccagggc catccaaaaa cacacacagt ggagcaaggt 480
acaggaagct tcctgtgagc ctggaaatac cactagattc agaaacagaa ggccagagtt 540
gtattcccac atgatggctc taattcactg agtaactttg aatgaatcat ttgccttctt 600
tgcatttttg ttttcgttct catctgaaaa ttgagagttt ttcaactatt ggttttcaaa 660
tgagacatgg gataagatca ggagggaagg cagccagcag cagtcttggg cttccctggc 720
gcagcaccnt cccgccaact gcagcacatc tgtttaatca tttaacctct aggntgggcc 780
tttctgtaag atttagcttn acaangggcc aaacccaaaa aatcatgggc atgcttctgc 840
tacctgncan tntaacattt gattntac 868

<210> SEQ ID NO 45
<211> LENGTH: 1237
<212> TYPE: DNA
<213> ORGANISM: Canis familiaris
<220> FEATURE:
<221> NAME/KEY: misc_feature
<222> LOCATION: (1)..(1237)
<223> OTHER INFORMATION: n is a, g, c, or t

<400> SEQUENCE: 45
ggtatcgccg ctcccgattc gcaccgcatc gccttctatc gccttcttga cgagttcttc 60
tgagcgggac tctggggttc gaaatgagct agcccttaag taacgccatt ttgcaaggca 120
tggaaaaata cataactgag aatagaaaag ttcatctctg ctgtctttgg ccattctctc 180
taggcatctg ctcatgtgga ggcataagaa aatattgaca tgcttcacat tacattttca 240
gagtatgtta ttcatgtatt tatttgtaaa atctaccaat acaatttccc cccaatcaag 300
taaaactagg taaaaagatc tctgcaaaga ttagctgagg aagaaacata tgtgagtaga 360
atcagaatgt taagagctga caggttagca gatagcatgc ccatgatttt tgtgggtttg 420 gccccttttgt tgaagctaaa tcttacagag aggcccaacc ctagaggtaa aatgattaaa 480
acagatgtgc tgcagttggc ggggagggtg ctgcgccagg ggaagcccaa gactgctgct 540
ggctgccttc cctcctgatc ttatccccat gtctcatttg aaaaaccaat agttgaaaaa 600

```
ctctcaattt tcagatgaga acgaaaacaa aaatgcaaag aaggcaaatg attcattcaa    660

agttactcag tgaattagag ccatcatgtg ggaatacaac tctggccttc tgtttctgaa    720

tctagtggta tttccaggct cacaggaagc ttcctgtacc ttgctccact gtgtgtgttt    780

ttggatggcc ctggtgtttg attacctctc gtggcaggcc caacagccct tgctaaggca    840

cagactgcat atttgctgat ccctgagggg aaagctgtga ttcagacttt gaggtctaag    900

aattgcagac ttagtttcta gtctcccgat gaaactgcta atctgggtgc cagtggtgtt    960

tctgctacac ggacacctgc ccacacagca tgattagaaa ttataatgat gacggcgatg   1020

agtcttccag gacacctacg ttctttgcaa gatatttctg ctaatcgtct ctaccagaat   1080

cagttggaga actttttta gttttttttt ttttttttta atttcccccct ttctaagtca   1140

agtaaaaata ctagtttaat tctggtgtag ggtaatgatt tgtcctcacc attactgatg   1200

tgtcattttt tgctcatggg atccgatatg agtaaac                             1237
```

<210> SEQ ID NO 46
<211> LENGTH: 703
<212> TYPE: DNA
<213> ORGANISM: Canis familiaris
<220> FEATURE:
<221> NAME/KEY: misc_feature
<222> LOCATION: (1)..(703)
<223> OTHER INFORMATION: n is a, g, c, or t

<400> SEQUENCE: 46

```
ccctgtgaaa ctgccttgac ttggtgcctt ttttggaggg gtggagttgt ttccactttg     60

acaaattttt atatttctcc catcctaatt ggactaattt gcttttatat ctcttctgtg    120

gttattttgt taatcgtatt ttaggaaagt cacctatttc aaattgattt gcatggagct    180

aaataatttc ttccaatttt ttcatttcct ttgtgtttat ggttatttct acattattag    240

tgaaagtttt gtggttttgt gttttagttc tctatctcct cttttgatta gtttcacaga    300

gtttagttgt tattttttca gaaaacagct cttgcactta tttatcggct ctactgttct    360

taatttgctc ctaaaaattg tcaataatat gtttcttttg ctttgcccgg gctcattttg    420

ttgtttttct aattgtttga gcttgactct taattcatct atttttgttt ctgctttttt    480

gttaatgtaa atttaaaaaa tgcgagatcc aattagaata agcctcaccg gacaagaacc    540

tgtctgtgca cttcgagact accataatgc ctatcacata gcaggtgctt aagcaaaatt    600

tttgtatgaa taaataaacc cctatgaaaa aattatggga tttgtgtgac agccctcgtt    660

cttctctgct gnctttggcc attctctcta ggcatctgct cat                      703
```

<210> SEQ ID NO 47
<211> LENGTH: 304
<212> TYPE: DNA
<213> ORGANISM: Canis familiaris
<220> FEATURE:
<221> NAME/KEY: misc_feature
<222> LOCATION: (1)..(304)
<223> OTHER INFORMATION: n is a, g, c, or t

<400> SEQUENCE: 47

```
ctagcttgcc aaacctacag gtggggtctt tcaagtaatg gtgaggacaa atcattaccc     60

tacaccagaa ttaaactagt atttttactt gacttagaaa gggggaaatt aaaaaaaaaa    120

aaaaaaaact aaaaaaagtt ctccaactga ttctggtaga gacgattagc agaaatatct    180

tgcaaagaac gtaggtgtcc tggaagactc atcgccgtca tcattataat ttctaatcat    240

gctgtgtggg caggtgtccg tgtagcagaa acaccactgg ncccccagat nagagttttc    300
```

```
ttgg                                                                304

<210> SEQ ID NO 48
<211> LENGTH: 735
<212> TYPE: DNA
<213> ORGANISM: Canis familiaris
<220> FEATURE:
<221> NAME/KEY: misc_feature
<222> LOCATION: (1)..(735)
<223> OTHER INFORMATION: n is a, g, c, or t

<400> SEQUENCE: 48

agcttgccaa acctacaggt ggggtctttc aagtaatggt gaggacaaat cattacccta    60

caccagaatt aaactagtat ttttacttga cttagaaagg gggaaattaa aaaaaaaaaa   120

aaaaaactaa aaaaagttct ccaactgatt ctggtagaga cgattagcag aaatatcttg   180

caaagaacgt aggtgtcctg gaagactcat cgccgtcatc attataattt ctaatcatgc   240

tgtgtgggca ggtgtccgtg tagcagaaac accactggca cccagattag cagtttcatc   300

gggagactag aaactaagtc tgcaattctt agacctcaaa gtctgaatca cagctttccc   360

ctcagggatc agcaaatatg cagtctgtgc cttagcaagg gctgttgggc ctgccacgag   420

aggtaatcaa acaccagggc catccaaaaa cacacacagt ggagcaaggt acaggaagct   480

tcctgtgagc ctggaaatac cactagattc agaaacagaa ggccagagtt gtattcccac   540

atgatggctc taattcactg agtaactttg aatgaatcat ttgccttctt tgcatttttg   600

ttttcgttct catctgaaaa ttgagagttt ttcaactatt ggttttcaaa tgagacatgg   660

gataagatca ggagggaagg cagccagcag cagtcttggg ctttccctgg cgcaaaaccn   720

tccccgcaac tggag                                                    735

<210> SEQ ID NO 49
<211> LENGTH: 1412
<212> TYPE: DNA
<213> ORGANISM: Canis familiaris
<220> FEATURE:
<221> NAME/KEY: misc_feature
<222> LOCATION: (1)..(1412)
<223> OTHER INFORMATION: n is a, g, c, or t

<400> SEQUENCE: 49

cttcccacct nnnacccntg gnccttaaca gncacnnncc tttggagata gctaactcct    60

acncattcaa catcagtgnn anggntctcc tccagaaggc ttcctcnacc ctttcaattc   120

ccacttacnt gtaagcctag gatgcctcct ctcagattca gactggttgn cncagtgttt   180

aagaacttna gctgtacagc canagagttt gtattggaaa ataatctctg tggtttttttg  240

tcngcatgat cttggacgag ttatttaacc ccctcagtnt agtttcttca tccatataat   300

ctggcaaatg atagtncnca gtccatacaa ttgtnagcac taaacaaaat aatgtacacg   360

agcctggcac actgaaggan cccagtgaaa ggtggttgtg attactnaca gtccttctca   420

ttctctagca tagcacttac cgtgttgcgt tccgattttc tgtctgcatg tctacctgca   480

tgtcggtttg catgcagact atgaactgga agctgaatcc ccagtgcctg gtacaatgtg   540

agaccccata ncagttcatt gaatgaattc agacacttca gtttttccat aaatttcagc   600

cttcttcaat attttgctcc tattttctag aagtttctga aagagcagct tggaatatgt   660

cagcaatttc taatttctta gcttttcagt gtgtgtgcgc gtgtgtgcgt gtgtgtttga   720

tattttctgc tgtggaaacc gctggactta gatgatcagn ctgtgagata caggcaggac   780

anagataaga agtaggagga gggctncgat gatgaagctt aggcactgaa gcaactcagc   840
```

cacccaccag gaagcctcag tnccctgaar aggtggaccc tkkcasscyg wggtgaacca 900
ttgtgggcca aagaggccca gtgcatgcat gaggcagacc tccctctaca gggaggcttt 960
gccctactgg gatttatttc cttgctgctt aaggacctgg ctttgctcct gcctttcctt 1020
gtccccttca tctgattctc tggccttatt ttggccagca gattgcattt gcctgtccag 1080
tttaccatat aaatgcattc tcctcctcat gacctcttct cagcctgctg gtctaaggga 1140
ggagctctgt ttcttgatcc tgccctctga ctaaattttc tcttgctgct cttccctttc 1200
ctgatgattc agtacagaca cctgcccaat tccacttttt ctcttcatct ccaattattt 1260
ggtggtcaag actgtttact caaatatgca tctggtttaa tcacgagcca cgactctgac 1320
taaagtagcc tgattatatg gttctttaag ggatagctga ctttcacaaa cctaagaaaa 1380
gttncttaaa gtggtgtnct aagggnccta ca 1412

<210> SEQ ID NO 50
<211> LENGTH: 866
<212> TYPE: DNA
<213> ORGANISM: Canis familiaris
<220> FEATURE:
<221> NAME/KEY: misc_feature
<222> LOCATION: (1)..(866)
<223> OTHER INFORMATION: n is a, g, c, or t

<400> SEQUENCE: 50
ttnngggacn gcttgccaaa cctacaggtg gggtctttca agatctgctg acagtgaagc 60
taaatctggc ggaagcaaag gattcacttt ctcataatgg attaactcat cctatttgcc 120
tcttaaacaa tgggtatttt aaagacagaa gttgaaggaa gtccaagtat ccaattttaa 180
ggatgcctat tagagcagtt ataagagagt gtctctcttt ctctctcttc tttctttctc 240
ttggtaggag tatgcaggag gtcatttaaa agccagatag tgatacaaat cacaatgcag 300
aaaaacatcc ccgtggactc ctccctgtcc tatgtttgac attcttaaaa tctatgtccc 360
aggtcttgaa atctttaaat aatctaccat gttctttggc ctgccctggg aaatctattt 420
cagtaccaga gctatgctgg ttacacacct tttctgactc atgttcccaa gtgattttat 480
tccagatacg atttggggac agttacgtgt actgttctga tatcttccta aaaggaaatt 540
attttggaag taaagtcact gataaaatca actcaggaaa atgcactttg taaatattaa 600
aatataaaca ttattaaagg ccatgctgta aaaatactaa ttgattttcc tgtgtagcag 660
ttacaataga acaacgatag atctctaagg ggagagtgaa aggacctcaa tttgagaaac 720
gtgaggcagg aaaagtttca aataattata ttcagagtgn tacctaagtt gttacttaaa 780
gacattctct acgtaaaana aacaataagg ccaaatgaag gaatgagagt tatgttatcg 840
cagaaacaan gtaancggnt tntttt 866

<210> SEQ ID NO 51
<211> LENGTH: 597
<212> TYPE: DNA
<213> ORGANISM: Canis familiaris
<220> FEATURE:
<221> NAME/KEY: misc_feature
<222> LOCATION: (1)..(597)
<223> OTHER INFORMATION: n is a, g, c, or t

<400> SEQUENCE: 51
acacagcaat tcattncaat gaactgttat ggggtctcac attgtaccag gcactgggga 60
ttcagcttcc agttcatagt ctgcatgcaa accgacatgc aggtagacat gcagacagaa 120
aatcggaacg caacacggta agtgctatgc tagagaatga gaaggactgt cagtaatcac 180
aaccaccttt cactgggttc cttcagtgtg ccaggctcgt gtacattatt ttgtttagtg 240
ctcacaattg tatggactgt gtactatcat ttgccagatt atatggatga agaaactaga 300
ctgagggggt taaataactc gtccaagatc atgcagacaa aaaaccacag agattatttt 360
ccaatacaaa ctctctggct gtacagctca agttcttaaa cactgggcca accagtctga 420
atctgagagg aggcattcta aggcttacag gtaagtggga attgaaaggg ttgagggaag 480
ccttctggag gagatgccat tacactgaat gttgaatgag taggagttag ctatctccag 540
aggggtagtg gctgtgaagg ggcgaggggt agagggtggg aaggggatga tggaagg 597

<210> SEQ ID NO 52
<211> LENGTH: 875
<212> TYPE: DNA
<213> ORGANISM: Canis familiaris
<220> FEATURE:
<221> NAME/KEY: misc_feature
<222> LOCATION: (1)..(875)
<223> OTHER INFORMATION: n is a, g, c, or t

<400> SEQUENCE: 52
cgcttgccaa cctacaggtg gggtctttca agatctgctg acagtgaagc taaatctggc 60
ggaagcaaag gattcacttt ctcataatgg attaactcat cctatttgcc tcttaaacaa 120
tgggtatttt aaagacagaa gttgaaggaa gtccaagtat ccaattttaa ggatgcctat 180
tagagcagtt ataagagagt gtctctcttt ctctctcttc tttctttctc ttggtaggag 240
tatgcaggag gtcatttaaa agccagatag tgatacaaat cacaatgcag aaaaacatcc 300
ccgtggactc ctccctgtcc tatgtttgac attcttaaaa tctatgtccc aggtcttgaa 360
atctttaaat aatctaccat gttctttggc ctgccctggg aaatctattt cagtaccaga 420
gctatgctgg ttacacacct tttctgactc atgttcccaa gtgattttat tccagatacg 480
atttggggac agttacgtgt actgttctga tatcttccta aaaggaaatt attttggaag 540
taaagtcact gataaaatca actcaggaaa atgcactttg taaatattaa aatataaaca 600
ttattaaagg ccatgctgta aaaatactaa ttgattttcc tgtgtagcag ttacaataga 660
acaacgatag atctctaagg ggagagtgaa aggacctcaa tttgagaaac gtgaggcagg 720
aaaagtttca aataattata ttcaagagtg ttacctaagt tgttacttaa agacattttc 780
tacgtaaaat aaacacataa ggccaaanga agggaatgag anttangtta tngcaggana 840
aaaggtaaat cggnttttt ttgtatccat tgcaa 875

<210> SEQ ID NO 53
<211> LENGTH: 612
<212> TYPE: DNA
<213> ORGANISM: Canis familiaris
<220> FEATURE:
<221> NAME/KEY: misc_feature
<222> LOCATION: (1)..(612)
<223> OTHER INFORMATION: n is a, g, c, or t

<400> SEQUENCE: 53
agcggataac aatttcacac agnaattcat tcaatgaact gttatggggt ctcacattgt 60
accaggcact ggggattcag cttccagttc atagtctgca tgcaaaccga catgcaggta 120
gacatgcaga cagaaaatcg gaacgcaaca cggtaagtgc tatgctagag aatgagaagg 180
actgtcagta atcacaacca cctttcactg ggttccttca gtgtgccagg ctcgtgtaca 240
ttattttgtt tagtgctcac aattgtatgg actgtgtact atcatttgcc agattatatg 300
gatgaagaaa ctagactgag ggggttaaat aactcgtcca agatcatgca gacaaaaaac 360
cacagagatt attttccaat acaaactctc tggctgtaca gctcaagttc ttaaacactg 420
ggccaaccag tctgaatctg agaggaggca ttctaaggct tacaggtaag tgggaattga 480
aagggttgag ggaagccttc tggaggagat gccattacac tgaatgttga atgagtagga 540
gttagctatc tccagagggg tagtggctgt gaaggggcga ggggtagagg gtggnaaggg 600
atgatngaaa gg 612

<210> SEQ ID NO 54
<211> LENGTH: 732
<212> TYPE: DNA
<213> ORGANISM: Canis familiaris
<220> FEATURE:
<221> NAME/KEY: misc_feature
<222> LOCATION: (1)..(732)
<223> OTHER INFORMATION: n is a, g, c, or t

<400> SEQUENCE: 54
agcttgccaa acctacaggt ggggtctttc aagatctgct gacagtgaag ctaaatctgg 60
cggaagcaaa ggattcactt tctcataatg gattaactca tcctatttgc ctcttaaaca 120
atgggtattt taaagacaga agttgaagga agtccaagta tccaatttta aggatgccta 180
ttagagcagt tataagagag tgtctctctt tctctctctt ctttctttct cttggtagga 240
gtatgcagga ggtcatttaa aagccagata gtgatacaaa tcacaatgca gaaaaacatc 300
cccgtggact cctccctgtc ctatgtttga cattcttaaa atctatgtcc caggtcttga 360
aatctttaaa taatctacca tgttctttgg cctgccctgg gaaatctatt tcagtaccag 420
agctatgctg gttacacacc ttttctgact catgttcnca agtgatttta ttccagatac 480
gatttgggga cagttacgtg tactgttctg atatcttcct aaaaggaaat tattttggaa 540
gtaaagtcac tgataaaatc aactcaggaa aatgcacttt gtaaatatta aaatataaac 600
attattaaag gccatgctgt aaaaaactaa ttgattttcc tgtgtagcag ttacaataga 660
acacgatgat ctctaagggg agagtgaaag gaccttattt ggtaaccgtg aggcagnaaa 720
gtttcaaata tt 732

<210> SEQ ID NO 55
<211> LENGTH: 697
<212> TYPE: DNA
<213> ORGANISM: Canis familiaris
<220> FEATURE:
<221> NAME/KEY: misc_feature
<222> LOCATION: (1)..(697)
<223> OTHER INFORMATION: n is a, g, c, or t

<400> SEQUENCE: 55
ctagcttgcc aaacctacag gtggggtctt tcaagatctg ctgacagtga agctaaatct 60
ggcggaagca aaggattcac tttctcataa tggattaact catcctattt gcctcttaaa 120
caatgggtat tttaaagaca gaagttgaag gaagtccaag tatccaattt taaggatgcc 180
tattagagca gttataagag agtgtctctc tttctctctc ttctttcttt ctcttggtag 240
gagtatgcag gaggtcattt aaaagccaga tagtgataca aatcacaatg cagaaaaaca 300
tccccgtgga ctcctccctg tcctatgttt gacattctta aaatctatgt cccaggtctt 360
gaaatcttta aataatctac catgttcttt ggcctgccct gggaaatcta tttcagtacc 420
agagctatgc tggttacaca ccttttctga ctcatgttcc caagtgattt tattccagat 480
acgatttggg gacagttacg tgtactgttc tgatatcttc ctaaaaggaa attattttgg 540
aagtaaagtc actgataaaa tcaactcagg aaaatgcact ttgtaaatat taaaatataa 600
acattattaa aggccatgct gtaaaatact aattgatttt cctgtgtagc agttacaata 660
gaacacgata gatctctang gggagagtga aaggact 697

<210> SEQ ID NO 56
<211> LENGTH: 617
<212> TYPE: DNA
<213> ORGANISM: Canis familiaris
<220> FEATURE:
<221> NAME/KEY: misc_feature
<222> LOCATION: (1)..(617)
<223> OTHER INFORMATION: n is a, g, c, or t

<400> SEQUENCE: 56
tggattgcga gcggataaca atttcacaca gaattcattc aatgaactgt tatggggtct 60
cacattgtac caggcactgg ggattcagct tccagttcat agtctgcatg caaaccgaca 120
tgcaggtaga catgcagaca gaaaatcgga acgcaacacg gtaagtgcta tgctagagaa 180
tgagaaggac tgtcagtaat cacaaccacc tttcactggg ttccttcagt gtgccaggct 240
cgtgtacatt attttgttta gtgctcacaa ttgtatggac tgtgtactat catttgccag 300
attatatgga tgaagaaact agactgaggg ggttaaataa ctcgtccaag atcatgcaga 360
caaaaaacca cagagattat tttccaatac aaactctctg gctgtacagc tcaagttctt 420
aaacactggg ccaaccagtc tgaatctgag aggaggcatt ctaaggctta caggtaagtg 480
ggaattgaaa gggttgaggg aagccttctg gaggagatgc cattacactg aatgttgaat 540
gagtaggagt tagctatctc cagaggggta gtggctgtga aggggcgagg ggtagagggt 600
ggnaagggga tgaattg 617

<210> SEQ ID NO 57
<211> LENGTH: 803
<212> TYPE: DNA
<213> ORGANISM: Canis familiaris
<220> FEATURE:
<221> NAME/KEY: misc_feature
<222> LOCATION: (1)..(803)
<223> OTHER INFORMATION: n is a, g, c, or t

<400> SEQUENCE: 57
cctgcagcta gcttgccaaa cctacaggtg gggtctttca agatctgctg acagtgaagc 60
taaatctggc ggaagcaaag gattcacttt ctcataatgg attaactcat cctatttgcc 120
tcttaaacaa tgggtatttt aaagacagaa gttgaaggaa gtccaagtat ccaattttaa 180
ggatgcctat tagagcagtt ataagagagt gtctctcttt ctctctcttc tttctttctc 240
ttggtaggag tatgcaggag gtcatttaaa agccagatag tgatacaaat cacaatgcag 300
aaaaacatcc ccgtggactc ctccctgtcc tatgtttgac attcttaaaa tctatgtccc 360
aggtcttgaa atctttaaat aatctaccat gttctttggc ctgccctggg aaatctattt 420
cagtaccaga gctatgctgg ttacacacct tttctgactc atgttcccaa gtgattttat 480
tccagatacg atttggggac agttacgtgt actgttctga tatcttccta aaaggaaatt 540
attttggaag taaagtcact gataaaatca actcaggaaa atgcactttg taaatattaa 600
aatataaaca ttattaaagg ccatgctgta aaaatactaa ttgattttcc tgtgtagcag 660
ttacaataga acaacgatag atctctaagg ggagagtgaa aggacctcaa tttgagaaac 720
gtgaggcagg aaaagtttca aatattatat tcaagagtgt acctaagttg ttacttaaag 780
acaattctnc acttaaataa acc 803

-continued

<210> SEQ ID NO 58
<211> LENGTH: 786
<212> TYPE: DNA
<213> ORGANISM: Canis familiaris
<220> FEATURE:
<221> NAME/KEY: misc_feature
<222> LOCATION: (1)..(786)
<223> OTHER INFORMATION: n is a, g, c, or t

<400> SEQUENCE: 58
gngnggnaat gtgcagncgg ntaacaattt cacacagnaa ttccatttcc ctcaacaagc 60
aggagaaatt ttctcaagag tttaccagaa gtcactctta acgtcaggct tgcaaatttt 120
aaaaagcatg aaaaagaacg tctactacat aatcctccag gcacattcca acacgctgcc 180
aacagtattc ctgaaaatcc tctgtcaaac ccctccataa atcatagcct cagagctctg 240
tgtgtgtggc tgcagcaggc tcgtagctgc agagcacttg catggaggag acatgcgctc 300
aggaactgca ccgccgcatt ccgcagaagc cacgcgactt acttccctct gctgcatgtt 360
aacctgtgct atgttctaga tcttacttta gttagtaatt caacaacagg agtcatgtgg 420
gctggcaagt agtcagctga aaactaacat gtgaacagaa ctctcagggg caggcctcca 480
gcaagctccc acccgagtca gtactgctcc cgccttccct tcagcttgtg ggtgggtact 540
gctccctggg taaccccgtt acttcaaccc cacagaacct gctaatcctt cccatagatt 600
accttctgaa gcctcacaaa acccccatct gaaagaagag gaaactgaga cacggtgaga 660
catggtgccc ctcgcccaaa gtctgacagt ttgatatggt agagccagga atccatccca 720
gggnagtggg ccagaaggta gtggctgact gccatgcccg aggacgtccc caggagctgc 780
cgtgaa 786

<210> SEQ ID NO 59
<211> LENGTH: 837
<212> TYPE: DNA
<213> ORGANISM: Canis familiaris
<220> FEATURE:
<221> NAME/KEY: misc_feature
<222> LOCATION: (1)..(837)
<223> OTHER INFORMATION: n is a, g, c, or t

<400> SEQUENCE: 59
tctggnnccc cgggacgtnn ttgggagctg ccctgagctc ccacctgctg ctgccagtac 60
tagcacaggg tcctcaagtg atggctgctg gtgaattatt tagaatctcc atgggcaggg 120
cattctgctt tttagcactg tgtcttgacc tgttccaaga ccatcttcca aggagagcca 180
gcagctggtg ttgtaagttc ttcccatgac aaataagccc aagacctcac ttaggaaaca 240
tacaatgatt atatgatctt gggagtcagc cctagaaggg cccttcttct cttgcttcaa 300
gctaaaaaga ctctggacaa caaaagaggc agtggctgct aagtaacttg caactaccac 360
ttcagtctca ctgcagctgc aaagatagga acagagaagt tttaggtgag aaactccttt 420
ttcccaagaa actgtgatga accagtgtta cagtttaggg agagagctct gtagacaagg 480
agggacctaa ggaccccccag gactcaccac cccccacacct agctcccctg gtcacctggt 540
acgtaagcag gtaggctctg cttagcatag tgctaagatc acatcttgct cagagtgtac 600
aaactcagga aagctggcat taggtagtat cacaagtgaa aaaatacctc aaccagtggc 660
cattggaagt gcggaagtac atgccatact cactgcaagg ttctccattc cagctgccgt 720
actgtgtaat acgacttaat atcttcagag natcaaggtt aatttcaaat ttgtgtcttc 780
aaagaacatt tctttttnnt tcttttgggg ncagtactgc gcacatttta actagga 837

<210> SEQ ID NO 60
<211> LENGTH: 866
<212> TYPE: DNA
<213> ORGANISM: Canis familiaris
<220> FEATURE:
<221> NAME/KEY: misc_feature
<222> LOCATION: (1)..(866)
<223> OTHER INFORMATION: n is a, g, c, or t

<400> SEQUENCE: 60
ttgtcgagcg gataacaatt tcacacagna attccagcac catgcactct ctgagacagg 60
tgaggatttt gcagcagctg ataaggacac aagtgaacag gagcataata atgaaaacac 120
aaagactagt tagctgttac tacttgcttc tagggcttct agtgttctct gttgtgatac 180
ttggtcaaat gttgtttggg agtcactgaa gaatgcttca tcatttgcaa agataggacc 240
ctaacttgta agccccttaa attaaaagaa tgctttttag tacaaaatta atgatcttag 300
tcacaaaaag caaagaagaa atcaaaatca caaagtcatc attcaaagtt gtattcttta 360
tagcaaaaat ggggcaagct acaggattgc caaaagtctt ataaaacagg aggaaggttt 420
atgaaatgat gctcagagag aatgcagaat gtgctattag cacaaatcct ttctgaaatg 480
gaacctgagc aaagtgatgg catttgatgt agaggaatag ccaccatcac atatgtgtga 540
gagaaaatag tttgctttgg ggatgaacaa taccaccgtt gtacaaagca tgaataagca 600
cttggaaaat gtatagtatg tataacagag ggacttttat ctgtttggca ttgaaaatca 660
atgccattaa aagtaggaac aattggttat tgggnctgat tttttaaaag aattcattta 720
tttnttttng gggganagaa nncccccccc cctntnaccc cnggggaaan annnaggggn 780
aaaaaanaat ntnnagccna ctnttttctt nntgggnccc cgggnggggg ctttancnca 840
aancccngna aannannntn ngnccn 866

<210> SEQ ID NO 61
<211> LENGTH: 886
<212> TYPE: DNA
<213> ORGANISM: Canis familiaris
<220> FEATURE:
<221> NAME/KEY: misc_feature
<222> LOCATION: (1)..(886)
<223> OTHER INFORMATION: n is a, g, c, or t

<400> SEQUENCE: 61
ttgngaaccc gcttgccaaa cctacaggtg gggcctttca agaacataag cccaaataag 60
cactggcaca tagtaggagc agcataaacg ctccccctcc tattcctaac ccaccaagaa 120
ttctagattg acagtttttt ctttgagtat tttaaagatg ctgcttccct gacttcttgt 180
ttgcaaattt ctgatgagaa atctgctgtc attttatctt ccttcctttg cataatgatg 240
tatctttttc tctctgcttt taagattttc attttatcac tggttctaag caatttaatt 300
atgatgttcc ttggtatagt gctcttcata tttctattag gagtttgttg agcttcttgg 360
atttgtgagt ttatagtttt tatcaaattt ggcaagtttt cagctactat ttcttcaact 420 tttttttcc tgtcctccct tgactcctcc tcattcccat atttctcctg tccttcaggg 480
actccagtta tctgtatgtt aagctcattg ataccctatt tgtgtatatt ttaaggcttt 540
ttattccctg tatttcattt tggatagttt ctactgcaat gttttcaggt tctttaacct 600
cttttttttt ttccccccag taatgtctaa tctgctcttc atcccaaaga catgtagtgg 660
tgtgtgtgct aaaaatccca gacaatgttt ttatgattcc taggtatttg ctttggggct 720
tttcaaagat tttccatatt tctacttcct tggccatata gaatgcggnt attattattt 780
tttagnggcc tatgctacta aatcctataa ttnctgggac tccnttgatt nagnntnncc 840
tttttattta ttnattaagn anggttttat tgggagttng attncc 886

<210> SEQ ID NO 62
<211> LENGTH: 728
<212> TYPE: DNA
<213> ORGANISM: Canis familiaris
<220> FEATURE:
<221> NAME/KEY: misc_feature
<222> LOCATION: (1)..(728)
<223> OTHER INFORMATION: n is a, g, c, or t

<400> SEQUENCE: 62
ggattgtcag cggataacaa tttcacacag aattcccagg acccagcatg atgcctggtg 60
tgcacatggg tgggccctcc tatgtaagcg tcaccactcg ggagcagtgg cggggatgcc 120
tggatgcgcc ggctcctgcg tgtagggtgc tatcaggaca ttgctgggtt gccacctctg 180
tctgaggctc cagagagcga ggggacaccc cacatcatga atgccctgtg ggttaccag 240 tgggggcaat tacctgcatt gctcctgggc ctcagcggcc tcatctgtga aatgggtaca 300
ttcatatcac gtatgggaga gggctgccgt ggggtttaat ggaggcaacc catttgagcg 360
ctgggcccgg caccgctcct gctcttactg tgactatggc cagcgtcact gttgcagggc 420
cttgaccggc cggggtggac gctggtgcca ccgttgctct ctcccagggt gggaggagac 480
aggcctgcgg ggcggactca ccgtggcgtt gacggtgagc tggtaggcct gcgtggtctc 540
gtagtccagc tcgcggacca ccgtgacgat gccgcgggcg ctgtcgatgg cgaacaacgg 600
ggaccggggc tggaaggagt acaggacgct gccccctgca ccaagtcggg gtccgtggcg 660
ttacgataaa atgggtgtcc ccaccggcgt gttctggggg ccaagcaaac aaccaaggtg 720
agtgggct 728

<210> SEQ ID NO 63
<211> LENGTH: 785
<212> TYPE: DNA
<213> ORGANISM: Canis familiaris
<220> FEATURE:
<221> NAME/KEY: misc_feature
<222> LOCATION: (1)..(785)
<223> OTHER INFORMATION: n is a, g, c, or t

<400> SEQUENCE: 63
attgtcgagc ggataacaat ttcacacaga attcctaaaa cccttactgt tgtttttata 60
tggcacttcc tgatgtgatt gcaggctttt agcaaagcca tttttgttaa caaaaaatga 120
tttaaattct tttaaacaag tgtttagtga caagtcagta tttagtcatc tagttattga 180
tacagcaccc ataaaattta tcactgaggg gagggatcag gaggaaatgt gggcattcta 240
acttaatgat taataatatg tgtctataac aaatgtgatg gctaagttat aaaatattta 300
aaaaattttt tcttgcaggt atttataaca gcaatgatgt agcagtatca tttccaaatg 360
tggtatctgg ctcaggatct agcactcctg tctccagttc tcatttacct cagcagtctt 420
ctgggcattt gcaacaagtg ggagcactct ccccatcagc agcatcatct gcaaccccctg 480 ctgttgctac aactcaggta atcattacag tgctatgaag taacctgtag atggctttgt 540
cgtttttgaa agtgagtttg attggagaag aaagaaacct tgtatagaaa ccttcctata 600
taaattccta taggaattta taagtatctc catttgtttt gacacgttag tggatataat 660
agacattttt atgtgatatt catgagaaag gacaaaagaa tacattggca ttaactgatt 720
cttttcagtt tctgagtttc taatttttcc tgaagatgna aacaaaaatt tgggggggaac 780 tttta 785

<210> SEQ ID NO 64
<211> LENGTH: 981
<212> TYPE: DNA
<213> ORGANISM: Cercopithecus aethiops
<220> FEATURE:
<221> NAME/KEY: misc_feature
<222> LOCATION: (1)..(981)
<223> OTHER INFORMATION: n is a, g, c, or t

<400> SEQUENCE: 64

```
ttggnaancg tcagaccaag tttactcata tcggatccaa agtgcttgag actgcatttt     60

tttcaaattt tgcaatattt gcattataat caccagttaa gcatccgtaa tccaaaaatc    120

ctaaacctac aatgctctaa taaatatttc ctttggctgt gttggtgcaa aaaatgtttt    180

ggattttgga agacttcaaa tttcacatta gggataccct gagtggaaaa aatagttttt    240

gtttttaaga ttctttcact caacaacaat caacaaggta gacttctgtg atcaaatgtg    300

tgaggatttc tccccaccaa taagcaatca attctgcagc agacaccaag tgggtatcct    360

ccaattcaag tctgacatta cctacctgga gaaagcgtca gatctcacag gttgatggct    420

cagtcccaca agactgctcc ctacttctga tgtcaatcac aagccacagt ttgttttacc    480

tgtgcttcta actgactgga tataaactgg gaatctcatg agcccctctt tgggttcggt    540

taatttgcta gagtggctca cagaactcag ggaatcacat ttattagttt attataaagg    600

atatacagtt gaagagatac acatggcaag gtatgccctc cctgggaaca ccactctcca    660

ggaacctnct tttgttcctg tccagaagct cttcgaatcc tctcctcttg ggccttttat    720

ggagacttna ttagatgggc atgactgaca cacatgtaga aatgtgactg gagaaaaaat    780

atatgatcta atattaatag actggggaaa ctcancaggg cctgtntgtt caaattnttc    840

nggncntttt gggtagcatt ncttnctcca gggttngggg gngnacnttt ttgaaagaaa    900

gtntttgacc ctanncaaaa gngggggaag annaantnct ctttnggcag nnaaaaaaaa    960

aaaaattttt tttttnggnt n                                              981
```

<210> SEQ ID NO 65
<211> LENGTH: 981
<212> TYPE: DNA
<213> ORGANISM: Cercopithecus aethiops
<220> FEATURE:
<221> NAME/KEY: misc_feature
<222> LOCATION: (1)..(981)
<223> OTHER INFORMATION: n is a, g, c, or t

<400> SEQUENCE: 65

```
ttggnaancg tcagaccaag tttactcata tcggatccaa agtgcttgag actgcatttt     60

tttcaaattt tgcaatattt gcattataat caccagttaa gcatccgtaa tccaaaaatc    120

ctaaacctac aatgctctaa taaatatttc ctttggctgt gttggtgcaa aaaatgtttt    180

ggattttgga agacttcaaa tttcacatta gggataccct gagtggaaaa aatagttttt    240

gtttttaaga ttctttcact caacaacaat caacaaggta gacttctgtg atcaaatgtg    300

tgaggatttc tccccaccaa taagcaatca attctgcagc agacaccaag tgggtatcct    360

ccaattcaag tctgacatta cctacctgga gaaagcgtca gatctcacag gttgatggct    420

cagtcccaca agactgctcc ctacttctga tgtcaatcac aagccacagt ttgttttacc    480

tgtgcttcta actgactgga tataaactgg gaatctcatg agcccctctt tgggttcggt    540

taatttgcta gagtggctca cagaactcag ggaatcacat ttattagttt attataaagg    600

atatacagtt gaagagatac acatggcaag gtatgccctc cctgggaaca ccactctcca    660
```

```
ggaacctnct tttgttcctg tccagaagct cttcgaatcc tctcctcttg ggccttttat    720

ggagacttna ttagatgggc atgactgaca cacatgtaga aatgtgactg gagaaaaaat    780

atatgatcta atattaatag actggggaaa ctcancaggg cctgtntgtt caaattnttc    840

nggncntttt gggtagcatt ncttnctcca gggttngggg gngnacnttt ttgaaagaaa    900

gtntttgacc ctanncaaaa gngggggaag annaantnct ctttnggcag nnaaaaaaaa    960

aaaaattttt tttttnggnt n                                              981
```

<210> SEQ ID NO 66
<211> LENGTH: 1005
<212> TYPE: DNA
<213> ORGANISM: Cercopithecus aethiops
<220> FEATURE:
<221> NAME/KEY: misc_feature
<222> LOCATION: (1)..(1005)
<223> OTHER INFORMATION: n is a, g, c, or t

<400> SEQUENCE: 66

```
ctnagctngc ttgccaaacc tacaggtggg gtctttcaaa aaacagacat gcagacttta     60

acagataata aggtttttga ggttttccgt ttatgtattt actcgagaaa gcaagagctt    120

tatttattta tttttgagac ggagtttcgc tctgtcgccc gggctggagt gcaatggctc    180

catctcgtct cactgaaacc tctgcctccc gggttcaagc gattctccca tctcaacctc    240

ccgagtagct gggattacag gcgcgcgacg ccacgcctgt ataaaaatac taaaaatgca    300

aaaataattt ttgtattttt agtagagatg gcgtttcatc atgttggcga aactccaggc    360

tggtctcgaa ccctgacctc ggtgatctgc ccgcctcggc ctcccaaagt gctgggatta    420

caggcgtgag ccaccgcgac cggccaagag ctttataaag atggaaaacg aagcagactt    480

tctgcccaag ccatgctttt ggataaggat tacactactt tgaaatctta catatatagc    540

acttggccaa ctatcaaaac tgcacaaacc ttcactaatt gcaattattc cctttaacat    600

ctcgagttac cccaatccgc acaaaacaag tttagtgccc accaggtaat aatacattca    660

ggaaaataat tccaagaaca gacgtttaag aactacagag aaaaacatac ttttttctac    720

aagaaaaaat cttagaggac agtaccaggg nccttatctc tgttagcatg atttatattt    780

cacgtaacgt tggcccagtc actgctncat tntaaancna tagccanggc anatagaaag    840

tctgaacana ttgacngcna ngggtttaaa ttttttacca ggnaacaaan cctggcaaac    900

tgccancang ggtgcccaaa tgctggnctn gggtccctgg aagnaaacgg agggctttga    960

atttttttcc ntttnggaac ngncnnggnt ttnggcnaan tnttc                   1005
```

<210> SEQ ID NO 67
<211> LENGTH: 863
<212> TYPE: DNA
<213> ORGANISM: Cercopithecus aethiops
<220> FEATURE:
<221> NAME/KEY: misc_feature
<222> LOCATION: (1)..(863)
<223> OTHER INFORMATION: n is a, g, c, or t

<400> SEQUENCE: 67

```
nttttgggng nntancttnt ananatnngc caattattgg ggggnacctt catcataagt     60

attaatataa taataataat aagtaatagt aactagtaac aacaataaaa aggaaatcag    120

cggaaagtca ggaaaaatgt taaaaaaaaa ttggaataac ttactgtagc tgaagatcaa    180

aaaaatctca ctgtaaaaaa acaaaaataa aaatagccca gattagaaaa acgggaggtg    240

caaaaatgtc aagtcagtaa agttcatttc ttttctcttt ccaaaagcag tttccacaaa    300
```

aaccgcaagg ataaagtttt cagtagcaga caagcaaagc cctttcgaca tcatcaatca 360
atcttaaaaa tacacgagga agtagagagg tcagtttatg agaggctaaa aggctcctcc 420
tcctctaacc caactgctgc agaaaaaata gaaatagaaa ttttaaaaat tacatcttaa 480
atccaggtcc cggttttgga aacaattaaa aaaaaaacac ctgtacattt gccgtagtgc 540
acaccaagtt gcatcattat gtttaaaatg tctttataaa atcagttttg gaatggaatg 600
tgtgtgttct ggaagggtgg ggaagggagg ttaaaaatca aagctgagct ccagtgagta 660
gggatggggt tcgccttgct gccctgtgaa agggaaagga cagatnagtc aanttnctaa 720
aaatgtntgc cctaanccen anaaaaaact ttgnntttng aantaaaaat ttggtaagct 780
ttaaattccc tgggngggaa nccncntaaa nacctttnca ngnnngntta aaattttaan 840
aaaangggnn naaaaaaaaa ncc 863

<210> SEQ ID NO 68
<211> LENGTH: 918
<212> TYPE: DNA
<213> ORGANISM: Cercopithecus aethiops
<220> FEATURE:
<221> NAME/KEY: misc_feature
<222> LOCATION: (1)..(918)
<223> OTHER INFORMATION: n is a, g, c, or t

<400> SEQUENCE: 68
cnnnttctgg nngatnaaan tnnttnnnna nttcnccaat nnattggggg gaannnttca 60
tcataagtat tnatataata ataataataa gtaatagtaa ctagtaacaa caataaaaag 120
gaaatcagcg gaaagtcagg aaaaatgtta aaaaaaaatt ggaataactt actgtagctg 180
aagatcaaaa aaatctcact gtaaaaaaac aaaaataaaa atagcccaga ttagaaaaac 240
gggaggtgca aaaatgtcaa gtcagtaaag ttcatttctt ttctctttcc aaaagcagtt 300
tccacaaaaa ccgcaaggat aaagttttca gtagcagaca agcaaagccc tttcgacatc 360
atcaatcaat cttaaaaata cacgaggaag tagagaggtc agtttatgag aggctaaaag 420
gctcctcctc ctctaaccca actgctgcag aaaaaataga aatagaaatt ttaaaaatta 480
catcttaaat ccaggtcccg gttttggaaa caattaaaaa aaaaacacct gtacatttgc 540
cgtagtgcac accaagttgc atcattatgt ttaaaatgtc tttataaaat cagttttgga 600
atggaatgtg tgtgttctgg aagggtgggg aagggaggtt aaaaatcaaa gctgagctcc 660
agtgagtagg gatggggttc gccttgctgc cctgtgaaag gagaagggac agattgagtc 720
agagttcctc aaaaatgttg tgccctaaac ccccaagaca gaaacatctt gtttattntn 780
gctaacacaa tntttntgna naatnatnaa cctccccngg ggagggnacn ccctnnnnaa 840
aannnccctt nccanggant gnnttnaaan tttttnaana tnantggggg nanaaaatna 900
acnaanccct gnnaattn 918

<210> SEQ ID NO 69
<211> LENGTH: 887
<212> TYPE: DNA
<213> ORGANISM: Cercopithecus aethiops
<220> FEATURE:
<221> NAME/KEY: misc_feature
<222> LOCATION: (1)..(887)
<223> OTHER INFORMATION: n is a, g, c, or t

<400> SEQUENCE: 69
tncantcttt nnnnggcnna nacgcgcgnc nantcgccaa tnactggggg ggnancttca 60
tcataagtat taatataata ataataataa gtaatagtaa ctagtaacaa caataaaaag 120
gaaatcagcg gaaagtcagg aaaaatgtta aaaaaaaatt ggaataactt actgtagctg 180
aagatcaaaa aaatctcact gtaaaaaaac aaaaataaaa atagcccaga ttagaaaaac 240
gggaggtgca aaaatgtcaa gtcagtaaag ttcatttctt ttctctttcc aaaagcagtt 300
tccacaaaaa ccgcaaggat aaagttttca gtagcagaca agcaaagccc tttcgacatc 360
atcaatcaat cttaaaaata cacgaggaag tagagaggtc agtttatgag aggctaaaag 420
gctcctcctc ctctaaccca actgctgcag aaaaaataga aatagaaatt ttaaaaatta 480
catcttaaat ccaggtcccg gttttggaaa caattaaaaa aaaaacacct gtacatttgc 540
cgtagtgcac accaagttgc atcattatgt ttaaaatgtc tttataaaat cagttttgga 600
atggaatgtg tgtgttctgg aagggtgggg aagggaggtt aaaaatcaaa gctgagctcc 660
agtgagtagg gatggggttc gccttgctgc cctgtgaaag gagaagggac agattgagtc 720
agagttcctc agaaatgttg tgccctaacc cccaagacag aaacatctgt ctttgcagct 780
aacacatttt ggnaagcatn acatncactg ggatggacag ccncntaaaa aaccttnncn 840
ngncnnnttt naanttttaa nnnaaagggg nnnaaataan naacccn 887

<210> SEQ ID NO 70
<211> LENGTH: 897
<212> TYPE: DNA
<213> ORGANISM: Cercopithecus aethiops
<220> FEATURE:
<221> NAME/KEY: misc_feature
<222> LOCATION: (1)..(897)
<223> OTHER INFORMATION: n is a, g, c, or t

<400> SEQUENCE: 70
ctttggggng tnnttcanac nttttancac nntnntcgcc antccncttg aggggnaaac 60
ccatcgcctt ctatcgnctt cttgacgagt tcttctgagc gggactctgg ggttcgaaat 120
gagctagccc ttaagtaacg ccattttgca aggcatggaa aaatacataa ctgagaatag 180
aaaagttcag atcgaggtca ggaacagatg gaacagggtc gaccggtcga ccggtcgacc 240
ctagagaacc atcagatgtt tccagggtgc cccaaggacc tgaaatgacc ctgtgcctta 300
tttgaactaa ccaatcagtt cgcttctcgc ttctgttcgc gcgcttctgc tccccgagct 360
caataaaaga gcccacaacc cctcactcgg ggcgccagtc ctccgattga ctgagtcgcc 420
cgggtacccg tgtatccaat aaaccctctt gcagttgcat ccgacttgtg gtctcgctgt 480
tccttgggag ggtctcctct gagtgattga ctacccgtca gcgggggtct ttcaatgatg 540
gtgatgatga tgatgataat gacactgatg atttttaacc ggattaaaat cgagtttttc 600
tgaatgtttc taagaatttc tccggcctcc tgattgactt tggagttttg catcttggga 660
gagaaagcga aggcattagt atttttaagt ggattgatca cataaacctt ttctctccca 720
accccaccct tgcccttatc cccttcccca cactgaacag aattttactg gctgntaagt 780
ctatgacctt attttttcct gatctttaac ttaactgntt tagagcatct ntggacgncn 840
ggattttnaa attttttnat tttnggnttt ttnntttnaa annttnnatt gggaaan 897

<210> SEQ ID NO 71
<211> LENGTH: 878
<212> TYPE: DNA
<213> ORGANISM: Cercopithecus aethiops
<220> FEATURE:
<221> NAME/KEY: misc_feature
<222> LOCATION: (1)..(878)
<223> OTHER INFORMATION: n is a, g, c, or t

<400> SEQUENCE: 71

```
tcggggngnn ctccactnnt gntgcnnntc nncgccantc cncttgnggg gnaaaccatc     60
gccttctatc gncttcttga cgagttcttc tgagcgggac tctggggttc gaaatgagct    120
agcccttaag taacgccatt ttgcaaggca tggaaaaata cataactgag aatagaaaag    180
ttcagatcga ggtcaggaac agatggaaca gggtcgaccg gtcgaccggt cgaccctaga    240
gaaccatcag atgtttccag ggtgccccaa ggacctgaaa tgaccctgtg ccttatttga    300
actaaccaat cagttcgctt ctcgcttctg ttcgcgcgct tctgctcccc gagctcaata    360
aaagagccca caacccctca ctcggggcgc cagtcctccg attgactgag tcgcccgggt    420
acccgtgtat ccaataaacc ctcttgcagt tgcatccgac ttgtggtctc gctgttcctt    480
gggagggtct cctctgagtg attgactacc cgtcagcggg ggtctttcaa tgatggtgat    540
gatgatgatg ataatgacac tgatgatttt taaccggatt aaaatcgagt tttctgaat     600
gtttctaaga atttctccgg cctcctgatt gactttggag ttttgcatct tgggagagaa    660
agcgaaggca ttagtatttt taagtggatt gatcacataa accttttctt tnccaacccc    720
acccttgccc ttatcccctt ccccacactg aacagaattt tactggctgn taagtctatg    780
accttatttt tcctgatctt taactnactg ntttagannt ctctggacgn cggnntttna    840
aatttnttat tttgggtttt tantttaaan cttnattn                           878
```

<210> SEQ ID NO 72
<211> LENGTH: 964
<212> TYPE: DNA
<213> ORGANISM: Cercopithecus aethiops
<220> FEATURE:
<221> NAME/KEY: misc_feature
<222> LOCATION: (1)..(964)
<223> OTHER INFORMATION: n is a, g, c, or t

<400> SEQUENCE: 72

```
cttctgggnn gannnaanca nttcgnncan nnctccncca atctacttgn ggggcaaacc     60
catcgccttc tatcgttctt cttgacgagt tcttctgagc gggactctgg ggttcgaaat    120
gagctagccc ttaagtaacg ccattttgca aggcatggaa aaatacataa ctgagaatag    180
aaaagttcag atcgaggtca ggaacagatg gaacagggtc gaccggtcga ccggtcgacc    240
ctagagaacc atcagatgtt tccagggtgc cccaaggacc tgaaatgacc ctgtgcctta    300
tttgaactaa ccaatcagtt cgcttctcgc ttctgttcgc gcgcttctgc tccccgagct    360
caataaaaga gcccacaacc cctcactcgg ggcgccagtc ctccgattga ctgagtcgcc    420
cgggtacccg tgtatccaat aaaccctctt gcagttgcat ccgacttgtg gtctcgctgt    480
tccttgggag ggtctcctct gagtgattga ctacccgtca gcgggggtct ttcaatgatg    540
gtgatgatga tgatgataat gacactgatg atttttaacc ggattaaaat cgagtttttc    600
tgaatgtttc taagaatttc tccggcctcc tgattgactt tggagttttg catcttggga    660
gagaaagcga aggcattagt atttttaagt ggattgatca cataaacctt ttttttncca    720
accccaccct tgnccttatn cccttnccca cactgaacag aaanttactg gctggnannn    780
natganccta nttttncngn ncttnaanta acnggnnnna anaaancnng gcnnccggnn    840
nnnaaaaaan ttnnnnnnng nngntttttt naaaaancnt nnttnnaaaa ntaaaancgg    900
nnnnnaaaaa ngggggggggn cnncnnancn tnannnnggg ngggttttcc nnnaancntt    960
ttcc                                                                 964
```

<210> SEQ ID NO 73
<211> LENGTH: 986

<212> TYPE: DNA
<213> ORGANISM: Cercopithecus aethiops
<220> FEATURE:
<221> NAME/KEY: misc_feature
<222> LOCATION: (1)..(986)
<223> OTHER INFORMATION: n is a, g, c, or t

<400> SEQUENCE: 73
catcnttctg nnnngnaana aacgtncnnn nnncnnctcc cnaatttaac ttgggggggn 60
aaaancatcg ccttctattt ttcttcttga cgagttcttc tgagcgggac tctggggttc 120
gaaatgagct agcccttaag taacgccatt ttgcaaggca tggaaaaata cataactgag 180
aatagaaaag ttcagatcga ggtcaggaac agatggaaca gggtcgaccg gtcgaccggt 240
cgaccctaga gaaccatcag atgtttccag ggtgccccaa ggacctgaaa tgaccctgtg 300
ccttatttga actaaccaat cagttcgctt ctcgcttctg ttcgcgcgct tctgctcccc 360
gagctcaata aaagagccca caacccctca ctcggggcgc cagtcctccg attgactgag 420
tcgcccgggt acccgtgtat ccaataaacc ctcttgcagt tgcatccgac ttgtggtctc 480
gctgttcctt gggagggtct cctctgagtg attgactacc cgtcagcggg ggtctttcaa 540
tgatggtgat gatgatgatg ataatgacac tgatgatttt taaccggatt aaaatcgagt 600
ttttctgaat gtttctaaga atttctccgg cctcctgatt gactttggag ttttgcatct 660
tgggagagaa agcgaaggca ttagtatttt taagtggatt gatcacataa accttttctc 720
tcccaacccc acccttgccc ttatcccctt ccccacactg aacagaattt tactggctgt 780
taagtctatg accttatttt tcctgatctt taacttaact gntttanagc atctntggac 840
gnnngnattt naaannttt tatttnggnt tttnatttta aannttnatt ngnaaanntt 900
naactgggct gnanaaaagg gnggggncta ctnaaantnn nnacgggagg gntttncctg 960
nanncanttn ctccnnttcc ntgaan 986

<210> SEQ ID NO 74
<211> LENGTH: 748
<212> TYPE: DNA
<213> ORGANISM: Cercopithecus aethiops
<220> FEATURE:
<221> NAME/KEY: misc_feature
<222> LOCATION: (1)..(748)
<223> OTHER INFORMATION: n is a, g, c, or t

<400> SEQUENCE: 74 tttttgcnt taccgtatcg ccgctnncga ttcgcagcgc atcgccttct atcgccttct 60
tgacgagttc ttctgagcgg gactctgggg ttcgaaatga gctagccctt aagtaacgcc 120
attttgcaag gcatggaaaa atacataact gagaatagaa aagttcagat cgaggtcagg 180
aacagatgga acagggtcga ccggtcgacc ggtcgaccct agagaaccat cagatgtttc 240
cagggtgccc caaggacctg aaatgaccct gtgccttatt tgaactaacc aatcagttcg 300
cttctcgctt ctgttcgcgc gcttctgctc cccgagctca ataaaagagc ccacaacccc 360
tcactcgggg cgccagtcct ccgattgact gagtcgcccg ggtacccgtg tatccaataa 420
accctcttgc agttgcatcc gacttgtggt ctcgctgttc cttgggaggg tctcctctga 480
gtgattgact acccgtcagc gggggtcttt caatgatggt gatgatgatg atgataatga 540
cactgatgat ttttaaccgg attaaaatcg agtttttctg aatgtttcta agaatttctc 600
cggcctcctg attgactttg gagttttgca tcttgggaga gaaagcgaag gcattagtat 660
ttttaagtgg attgatcaca taaaccnttt tntcttccaa ccccaccctt gcccttatnc 720
ccttncccac actgaacaga attttact 748

<210> SEQ ID NO 75
<211> LENGTH: 881
<212> TYPE: DNA
<213> ORGANISM: Cercopithecus aethiops
<220> FEATURE:
<221> NAME/KEY: misc_feature
<222> LOCATION: (1)..(881)
<223> OTHER INFORMATION: n is a, g, c, or t

<400> SEQUENCE: 75
tnctttgcgg acccgtatcg ccgcttccga ttcgcagcgc atcgccttct atcgccttct 60
tgacgagttc ttctgagcgg gactctgggg ttcgaaatga gctagccctt aagtaacgcc 120
attttgcaag gcatggaaaa atacataact gagaatagaa aagttcagat cgaggtcagg 180
aacagatgga acagggtcga ccggtcgacc ggtcgaccct agagaaccat cagatgtttc 240
cagggtgccc caaggacctg aaatgaccct gtgccttatt tgaactaacc aatcagttcg 300
cttctcgctt ctgttcgcgc gcttctgctc cccgagctca ataaaagagc ccacaacccc 360
tcactcgggg cgccagtcct ccgattgact gagtcgcccg ggtacccgtg tatccaataa 420
accctcttgc agttgcatcc gacttgtggt ctcgctgttc cttgggaggg tctcctctga 480
gtgattgact acccgtcagc gggggtcttt caatgatggt gatgatgatg atgataatga 540
cactgatgat ttttaaccgg attaaaatcg agtttttctg aatgtttcta agaatttctc 600
cggcctcctg attgactttg gagttttgca tcttgggaga gaaagcgaan gccttantat 660
tttttagngg gtnggnnaca tataaccttt ttttttccaa ncccccccctt nccctttttnc 720 cctttccccc actgaaaaaa attttacngg ctgnnaannn tnnnaccntn ttttnccnnn 780
ncttnannna annggttnaa gaccnnnnng ggccnnnggn tttnaaantt ttttntttng 840
ggnttttnnt tnnaancnnn cnttggnaaa ntttnaanng g 881

<210> SEQ ID NO 76
<211> LENGTH: 906
<212> TYPE: DNA
<213> ORGANISM: Cercopithecus aethiops
<220> FEATURE:
<221> NAME/KEY: misc_feature
<222> LOCATION: (1)..(906)
<223> OTHER INFORMATION: n is a, g, c, or t

<400> SEQUENCE: 76
cannnttctg gggngtnnnn aactnannnn nnnnatcgcn nccacantnn nnttgggggg 60
aaaaacctga atacatttgt ngttatttcc cttagatctt tttttttttt tttttttttt 120
ttgagacatc tcactctgtc acccaggcta gagtgaagtg gcacaatctc tggctcactg 180 caaccccccac ctgcctggtt caagcgattc tcctgcctca gcttcccgag tagctggtac 240
tataggtgtg caccaccaca cctggctaat ttttttaaaa aatattttta gtggagatgg 300
ggtttcacca tgttgaccag gctggtctca aactcctgac ctcaaaggat ccacctgcct 360
tggcctccca aagtgctggg attataagca tgagccacca tgccagcctg tttcttttag 420
atcttgattt gatattctgg atatgaatga aagaaaatta atgagtgttt caaagtctaa 480
ataaggaagc tccacagata atattaacat ttctctgatc tagtcatatt tattattgtg 540
tttcaattag aagtggctgt aggctctgaa agacacacta taaataaagc ctcccccctca 600 tacaccctca ctcacaccca cacttacacc aatgcaattt ttagacagaa acacaagcaa 660
gaaataggat agattttttt taaaaaatgg gcattggtta aattttctgg tcatattaaa 720
aaanntnttt nagaactccc aangggggggc cattaataga gacctnattc nctgnnggaa 780
nnaaannggn aaattncnan aattnctnac aatntttagg ganttgangn aaaatnttnn 840
gtnnntgnna ctttcctagn ggncnnnttn ngccctatnc ccaggnnttt tatnctaaac 900 cccntc 906

<210> SEQ ID NO 77
<211> LENGTH: 909
<212> TYPE: DNA
<213> ORGANISM: Cercopithecus aethiops
<220> FEATURE:
<221> NAME/KEY: misc_feature
<222> LOCATION: (1)..(909)
<223> OTHER INFORMATION: n is a, g, c, or t

<400> SEQUENCE: 77
cntcttnngg gngttnaanc tgncntnnaa tgcntcacat tnattnnggg gaaaaccgta 60
ctgacttatt atgagaggtt tctgctcttg ttaggatcca gtaggtttga ggtgcaacta 120
ttcctctact ttactcttcc acctcccaga gaactctgcc aagaaccatg ttaagactgc 180
tttctgcttt aactactaat agtcttgatt ataggaacgg aatttgtgta tcaagtaggt 240
tctaagaact taacataaaa actggctatt aatgcatttg caaaatttgc attttaaatc 300
caaggcaaga acaggtcagg caaaaatgga atccaaacac caaattgtta aaagttttaa 360
gtccatttct cttgttagtt tgcaacttaa attactaatt ctctaatgtt ttagagcaga 420
agttggtaaa ttgtttctgt aaaaaaattg tttctttaaa ttgtttcata atcaaaattt 480
taggttgtgt aggtgatact gtttctgttg aaattattta atctaaataa atggacatag 540
ctgtgttcta acaaaacttt atgattaacc tgacaggcca gatttgaaat gttagcaggt 600
ttgcacaccc ctactttaga aaaactcagt ctttatagct tccagttaca agatgtatct 660 ttttttttt tttttttaaa taagacagta ttattncaaa tgtcgggtgg ctcataccna 720
aatttgtttc cccnttcttn anttttcnaa angtggggcc caaanacttn aaaaggtngn 780
anncntttnn nntaanaaaa nanccattta ggggnttntn caacccctnn aaaaantttt 840
tttcttnaaa aanaantnca naaaannntn ctnaaaaaan naaaggggcc cacccnttnt 900
ttttaaaac 909

<210> SEQ ID NO 78
<211> LENGTH: 890
<212> TYPE: DNA
<213> ORGANISM: Cercopithecus aethiops
<220> FEATURE:
<221> NAME/KEY: misc_feature
<222> LOCATION: (1)..(890)
<223> OTHER INFORMATION: n is a, g, c, or t

<400> SEQUENCE: 78
gnnntncnnc tttnnnngat cagccgcncc ncagnncccc accaatccna cttggtgtaa 60
accccccagc agggtcttgg gctttctttc tgcttctcca aaatgggcct ggcttcccag 120
gagacagccg agagcgcctc gcccctgctg gaagggcagc ctgggagctg gagttggcaa 180
acgggagggg acgggaggag gcccagggga gggggcgtct tcccttagct ttcagcgaca 240
tctgctggcc gtgcgctgaa ctgccgctac cccagaggcc agctggagac caattttgag 300
ttgtgagcag ggaaagagag gaggggttcc aggacaatca ggtctggagc ttccagaaac 360
attccaaaaa cacagtttag gctttttaat tgttcactca gtcattctcc cggggtctag 420
ggagaaatcg gactcagact cggatctttg gggacctacc gcagcatgat aacccaggtg 480
tacctggggc tcatgggggc ctggggatca gggaggcccc tcacctgcat tcactgtgtg 540
ccaagcactg gcctacatca ctgacatttg ctgtctcgct gcgggtgctg tgatcttgct 600
gctgtgctca tttgacagat gaaaacgctc aggttgtgag agaaccccaa agccagagga 660
ttcccttgat cactcccctt ccttcatgcc catagtcaat ccttcttcaa agcctatccg 720
tcccacctcc aaagcacacc atggatgccc atccttggcc catcatcgtt accctctnag 780
tgccagcctg cctgancccc tcanttnaag tcccgctccc tggccttttg cagaagcatc 840
ccaccagaat ctncaagcca cccctcccna ntttnttntt cccaaatggc 890

<210> SEQ ID NO 79
<211> LENGTH: 965
<212> TYPE: DNA
<213> ORGANISM: Cercopithecus aethiops
<220> FEATURE:
<221> NAME/KEY: misc_feature
<222> LOCATION: (1)..(965)
<223> OTHER INFORMATION: n is a, g, c, or t

<400> SEQUENCE: 79
ntttctggnn gtnacagang gggngccnnn cccccccatn aactgggggn aaacncnccc 60
agccccaagg tggccattgt cagggaggtg cttgctatgc agatgtgccg ttcaaaggca 120
tgcagatatg aaagcatcgc tccctcaggt gggagacaat gggaaggtcg agagcactgt 180
ggttaggagc aaggctttgg aattagcagt ccctgcattc aaatcctagc tttacttgcc 240
tcatgacagc cgtctgtcct tgagcaaaat tgtttaacct ctctggacct gtctatatct 300
gtaaaaaggg ccaacatggt gtacccaaaa gccttgtcgt ggtgatctca ttaagatatt 360
tcatgtgaat atgtgctgag tggcctcacg taggaggtgc ttactgactt ctcccaagcc 420
ccctcctctt catcgctact gcccgtctgc gtatcctcca gcctcctccc acgctttctc 480
tcactgcact ttttgggggt gagggaggcc atttctgagt cacttgctcc tggacttgat 540
gaattccatt cgtgtggcgg gggcagcagg gcccagtgtg aaccagcagc tccccaaccc 600
tgcccactat accactcaag tgagtccaag ctgtgatgcc cctggctgcc tcccccactt 660
cccttgagcg agctgggagg acaaagattg gactctgagg atcagcctga gacttaagat 720
ggaggctgtg ttcccgagag cccagggtgg gcatgccagg aagcactctg gctccacgga 780
atgctgcact gccccggggc tggcanacca ncacttcctt gtnttnctgg gtctnacagn 840
cncancctgg cctgggctgt ttttgcntgn tgnacctgcc tnaaannggn aaancctggn 900
ancctggagn cttccnaggt ttngnttttc caancnccca aaattangnc naaccngnct 960 nnggc 965

<210> SEQ ID NO 80
<211> LENGTH: 891
<212> TYPE: DNA
<213> ORGANISM: Cercopithecus aethiops
<220> FEATURE:
<221> NAME/KEY: misc_feature
<222> LOCATION: (1)..(891)
<223> OTHER INFORMATION: n is a, g, c, or t

<400> SEQUENCE: 80
tttggtaact gtcagaccaa gttttactca tatcggatcc tctctatcag attgatctgc 60
aggtgagggt gtccagagat gtcttgcaaa tggcaatgtc ccaggccatg gaaacaggaa 120
tatgggctca aatccattta tggccaggca tggtggctca tgcctgtaat cccaacactt 180
tgggaggtca aggcaggagg attgcttaag cccaggagtt caagaccgtc tgggcaacgg 240
agaggagacc ctgtctctac aaataattaa aaaattatct gagcatagtg gcacatgcgt 300
gtggtcccag ctactcggga ggctgaagtg ggaggatcgc ttgaggccaa gaggtcaagg 360
ctgcagtgaa ctgtgatcat accacggcac ttgagcctgg gcgacagagc aagaccctgt 420
ctttcttttt tttttcaaa aaaaaaaaat ccatttataa tttaacatgg gagcctcacg 480
ggaaagagtt cttgtcttgt tgagtggtcc agtgttttgg atgggctgga actttgcact 540
tgatgtgttg taattcattt tctagagtct atgtcgtgaa ggtccttggg gtgatagagc 600
cttggaaaaa tgttgtttcc ctgtggatta tctaaactag atccaagaac atgaaagacc 660
atccctcagg gagctggcat ttgtctaaaa accancattn cctgggccat ttgattgggg 720
ntcttgcttc actgcaaang ggggacttgc aaaattttac tnatgncccn nttgttnttt 780
ttntccaagg ggnttttana aaatttttct tnncnntttt ncnnaanacc ccnttnnant 840
tntnttttnc nnccccnttt nttntaacna ngggggggntt ttnaacnncc n 891

<210> SEQ ID NO 81
<211> LENGTH: 803
<212> TYPE: DNA
<213> ORGANISM: Cercopithecus aethiops
<220> FEATURE:
<221> NAME/KEY: misc_feature
<222> LOCATION: (1)..(803)
<223> OTHER INFORMATION: n is a, g, c, or t

<400> SEQUENCE: 81
tggtaactgt cagaccaagt ttactcatat cggatccctt ctggtcccac atcactcagg 60
caactctctc ttcccacctg ccccccaaac tcccttccac ctccctccac atgtatcctc 120
ccacttcctt ccactcatgt aatgagaggt gctgatgagt cacaggagag gtagccctag 180
ataaccaaca gactgcaaaa cggacagtcc ctggatgtct gagccagtgt ttgtgcactg 240
cattgactgg ctcctcgtag ttttttcctg tagttgctaa agcctgtaag gtctgtgtga 300
tgaatatttt ctaacacatc ttagaagaac ataatgcaag acagaatgaa aaactagaga 360
ggcagaaacc cccaaagtaa gtagtgggaa attaccaggt atataatagg tcaagcctgc 420
tctgcaggag ctcaagggat tgtagcattc ttatcccaaa ccactgaatc ctgggcaaaa 480
ataagaagtc gcctaatttt agtattacca gcttcccaac cccgggcatt cttcatctta 540
ctcaagctgt ccagaggccc cagggtgact ccctataagt cccatgggtg gctgagatct 600
atttagaggc acaagggtat ctccttataa gtcccatggg tggctgagat ctatgagaag 660
catcttgggg agagtgcctc tggccaccag catgtggccc tgaatctttc atgtgcaact 720
ggccagggaa ggaaattatg gaaatagtca tcctgcacat ntgcaaatga gatgcaaatc 780
ctggaagctc ttctaaaaaa aaa 803

<210> SEQ ID NO 82
<211> LENGTH: 763
<212> TYPE: DNA
<213> ORGANISM: Cercopithecus aethiops
<220> FEATURE:
<221> NAME/KEY: misc_feature
<222> LOCATION: (1)..(763)
<223> OTHER INFORMATION: n is a, g, c, or t

<400> SEQUENCE: 82
tcgtgcttta cggtatcgcc gctcccgatt cgcagcgcat cgccttctat cgccttcttg 60
acgagttctt ctgagcggga ctctggggtt cgaaatgagc tagcccttaa gtaacgccat 120
tttgcaaggc atggaaaaat acataactga gaatagaaaa gttcagatcg aggtcaggaa 180
cagatggaac agggtcgacc ggtcgaccgg tcgaccctag agaaccatca gatgtttcca 240

```
gggtgcccca aggacctgaa atgaccctgt gccttatttg aactaaccaa tcagttcgct      300

tctcgcttct gttcgcgcgc ttctgctccc cgagctcaat aaaagagccc acaaccctc       360

actcggggcg ccagtcctcc gattgactga gtcgcccggg tacccgtgta tccaataaac      420

cctcttgcag ttgcatccga cttgtggtct cgctgttcct tgggagggtc tcctctgagt      480

gattgactac ccgtcagcgg gggtctttca gtagcccttc ctttgtagca aagacagaca      540

gatggtgatc caagagatac gcaagaagag gaccgtgtgt gtaatggttg agctctaaaa      600

agagaaatca cttggatgga aatgaaggag aggaaaaggc tgatgtggat ggctgggaag      660

aggttcgatg gttaccttgg caaccgagct tctttctcat cccatccctt ccctagtcct      720

tgtcttaaaa gatttttttn tatgtccctt ccctcccaag ggg                        763
```

<210> SEQ ID NO 83
<211> LENGTH: 861
<212> TYPE: DNA
<213> ORGANISM: Cercopithecus aethiops
<220> FEATURE:
<221> NAME/KEY: misc_feature
<222> LOCATION: (1)..(861)
<223> OTHER INFORMATION: n is a, g, c, or t

<400> SEQUENCE: 83

```
ttggggganc ctgtcagnac canttttact catatccgga tcctgaccta cattcagtgt       60

tctagattga aatcacagat tttggataga gaaaaaaaaa tattctctgc aatctaataa      120

aaccaacttt tttttttttt tttttttttt ttgagacaga gtcttgctcc atggcccagg      180

ctagagtgca gtagcacgat ctcggcttgc tgcaacctct gcctgtcggg ttcaaccgat      240

tctcctgcct cctgtctcct gccccagcct ntcaagtagc agggattaca ggcatgtgcc      300

atgatgccca gctagttttt tgtattttta gtagagatgg ggtcttgcca tgttgcccag      360

gctggacttg aactcctgac ctcaggtgat caggccatct tggcctccca aagtgttggg      420

attacaggcg tgagccatcc tgcctggcca aaaccagcat attttatgga taggaaattg      480

aggcttagat ggggggagaa aaacattaca cagattaaac cacagctaat gtcaagtggt      540

gaccaaaggc gaatctttta ttgcaggctg tgggnttttt ccatgtggct ggtggnacac      600

tgcaccaagc agcacacaca ctaggccagt ttncttttgca gacccagttg caatcccatc      660

tntnagccag gattctatta ggtctcnaca accnatggga atttaggggng ctcanagntt      720

nngggtggga aaaggggact aacctncntg ggttnanggn tttnnaantg gncncnncct      780

ttggancngg ganatttatt nccaaaanng gnngggntng tnttngggnn anaaaccaaa      840

ttttgggaaa aaancntttt t                                                861
```

<210> SEQ ID NO 84
<211> LENGTH: 767
<212> TYPE: DNA
<213> ORGANISM: Cercopithecus aethiops
<220> FEATURE:
<221> NAME/KEY: misc_feature
<222> LOCATION: (1)..(767)
<223> OTHER INFORMATION: n is a, g, c, or t

<400> SEQUENCE: 84

```
ggnattgncn agcggntaac aatttcacac agnaattccg tatttgaaat ttggggacaa       60

acaaacataa ctctttctct ttccttgaag ggttaatgct ccaaccagcc tcagattggt      120

tcgcttgaat cttaaaatta cttttctggt cacgcgcgcc gaaggtctaa gcatttgtga      180

aatgtctttt ttcccccccc ccacccctttg atgctgttct ctttgggctg tcttaattac      240
```

acaggggttg agaaaccaaa ttaaaattag gcgtgtctgg tcaacagtga tcacgttgca 300
tgcttttagc tttgcttgtt gaagttgctt ctcctccctg agtggctttc ctcctttttt 360 ttttttttt tttattttaa aaaggaaata tcataagctc tttcagaaat actcacagga 420
agtgagtgtc cgtatgctgg ttactcacca gcaactgant gttggcaggt ggagaatgct 480
accgcanccn cccanacaga tctgcaaact ggcccnttnc agangatnaa aacagggtgc 540
gtggaantan ggtttttgnn naaangcant ttnaaagnaa atgggcactg cattnnnttc 600 naggggggg anttaagnaa cangnttggg gtnaaaaagn ncntgnttcc attnnggngg 660
tnctgctcct ttnaaanggg nggnnggttt naaaaaaaag ggccccncnc cccanaaaaa 720
aattttttgg nggaaaacct nccaaaaaaa anaccccncn tttttgn 767

<210> SEQ ID NO 85
<211> LENGTH: 761
<212> TYPE: DNA
<213> ORGANISM: Cercopithecus aethiops
<220> FEATURE:
<221> NAME/KEY: misc_feature
<222> LOCATION: (1)..(761)
<223> OTHER INFORMATION: n is a, g, c, or t

<400> SEQUENCE: 85
cngcttgcca acctacaggt ggggtctttc aaaatattgc gttacaaata tcattttggt 60
gtatgtatgt caaaaccaaa actgccttta tgtcaatatg ctgtaaaaat ctatcagaat 120
atatcttaat tcttaacttt cattgttgtc tgtgggttgt cttgtataat tattatcaca 180
tctacagtat tttctgtagg taaatatgaa atgtattata aatgtaccag gggaaaaatg 240
ccctttaata agcctttccc tagacaaagc accatttagg cgtttagaag caagaactag 300
tgaaatcaga aattgctgtc atacatactc acctgtgaat ggtcgtacaa aggatcccaa 360
gcgcaggact tgtcctggaa gcagaggatc ggattccacc aggaaaagag gcaagtagaa 420
atgccaaatg ccagcgctcc ctttncccag ctcatcttat ttgtaggcac tcagattttg 480
gaatcctcca ggactaacat taaaacccca ctagggngtt tncctaatnc cgggaaanga 540
gncagtaggn caaacaactt atccccncna nanaggaaca attccttgag ctccccncct 600
gtttcngaaa ccctnttccc ttntgggncc ctgnanaagg nctgcccnaa tgctngggag 660
nccnccnggt tttnatgaaa accatntnaa aatncccnaa agttnccccc ccaaggnaan 720
nttccnttta aanttttggg aaaaaaancc ccntnanaaa n 761

<210> SEQ ID NO 86
<211> LENGTH: 791
<212> TYPE: DNA
<213> ORGANISM: Cercopithecus aethiops
<220> FEATURE:
<221> NAME/KEY: misc_feature
<222> LOCATION: (1)..(791)
<223> OTHER INFORMATION: n is a, g, c, or t

<400> SEQUENCE: 86
tnggggacca gcttgccaaa tctacaggtg gggtctttca aaatattgcg ttacaaatat 60
cattttggtg tatgtatgtc aaaaccaaaa ctgcctttat gtcaatatgc tgtaaaaatc 120
tatcagaata tatcttaatt cttaactttc attgttgtct gtgggctgtc ttgtataacn 180
attatcacat ctacagtatt ttctgtaggt aaatatgaaa tgtattataa atgtaccagg 240
gggaaaatgc cctttaataa gcctttccct agacaaagca ccatttaggc gtttagaagc 300
aagaactagt gaaatcagaa attgctgtca tacatactca cctgtgaatg gtcgtacaaa 360

```
ggatcccaag cgcaggactt gtcctggaag cagaggatcg gattccacca ggaaaagagg    420

caagtagaaa tgccaaatgc cagcgctccc tttccccagc tcatcttatt tgtaggcact    480

cagattttgg aatcctccag gactaacaat aaaaaccaca ctaggttgtt ttcctaattc    540

ctgtgaaatg agtcagtagg tcaaacaact tatccactcc agagagagaa caattccttg    600

agctacactc cctgtttcca gtaaccctat tccctctctg tgtccctgga taaagtgctg    660

ncnacaatgc atggaṅagcc cccgggttct gatgaaancn atngaaagat ngcanaaagt    720

agctgcctta agggaangtt cccttngaaa tttaggnaaa aaaanccnnt aaaaanacng    780

gnggtcggtt t                                                         791
```

```
<210> SEQ ID NO 87
<211> LENGTH: 783
<212> TYPE: DNA
<213> ORGANISM: Cercopithecus aethiops
<220> FEATURE:
<221> NAME/KEY: misc_feature
<222> LOCATION: (1)..(783)
<223> OTHER INFORMATION: n is a, g, c, or t

<400> SEQUENCE: 87

ttggggganca gcttgccaan tctacaggtg gggtctttca aaatattgcg ttacaaatat     60

cattttggtg tatgtatgtc aaaaccaaaa ctgcctttat gtcaatatgc tgtaaaaatc    120

tatcagaata tatcttaatt cttaactttc attgttgtct gtgggttgtc ttgtataatt    180

attatcacat ctacagtatt ttctgtaggt aaatatgaaa tgtattataa atgtaccagg    240

gggaaaatgc cctttaataa gcctttccct agacaaagca ccatttaggc gtttagaagc    300

aagaactagt gaaatcagaa attgctgtca tacatactca cctgtgaatg gtcgtacaaa    360

ggatcccaag cgcaggactt gtcctggaag cagaggatcg gattccacca ggaaaagagg    420

caagtagaaa tgccaaatgc cagcgctccc tttccccagc tcatcttatt tgtaggcact    480

cagattttgg aatcctccag gactaacaat aaaaccacac taggtnggtt tcctaattcc    540

tgtgaaatga gtcagtaggn caannantta tncnctccag agagagaaca attccttgng    600

ctacactccc tgtttcnnna acccnattnc ctttctgngn ccctgganaa aggggtgccc    660

anaatgcntg gggnnncccc ccggntcttg annaaaaacn tnttaaaaan ngccnaaagt    720

ancctccntc nanggaagnt tcccctttta aattttnggn naaaaaannc ccttnaanta    780

ann                                                                  783
```

```
<210> SEQ ID NO 88
<211> LENGTH: 769
<212> TYPE: DNA
<213> ORGANISM: Cercopithecus aethiops
<220> FEATURE:
<221> NAME/KEY: misc_feature
<222> LOCATION: (1)..(769)
<223> OTHER INFORMATION: n is a, g, c, or t

<400> SEQUENCE: 88

ttggnattgn ccagcggnta acaatttcac acagnaattc cgtatttgaa atttggggac     60

aaacaaacat aactctttct ctttccttga agggttaatg ctccaaccag cctcagattg    120

gttcgcttga atcttaaaat tacttttctg gtcacgcgcg ccgaaggtct aagcatttgt    180

gaaatgtctt ttttcccccc ccccacccct tgatgctgtt ctctttgggc tgtcttaatt    240

acacaggggt tgagaaacca aattaaaatt aggcgtgtct ggtcaacagt gatcacgttg    300

catgctttta gctttgcttg ttgaagttgc ttctcctccc tgagtggctt tcctcctttt    360
```

tttttttttt tttttatttt aaaaaggaaa tatcataagc tctttcagaa atactcacag 420
gaagtgagtg tccgtatgct ggttactcac cagcaactga gtgttggcag gtggagaatg 480
ctaccgcagc cgcccagaca gatctgcaga ctggccccat tgcagangat tagacacagg 540
gtgcgtggat catangggtt tttgtacaga aggcagtttt aagangaaan tgggcactgc 600
atgtcatctc nangggggngg tgattcangg ancanggctg ggggtnaaaa gcacctggct 660
gccattnngg agntcctgct aatttttaaa nggcagggtg gttttaaaaa aaaagctccc 720 cccccccccaa aaannnnttt tttggaggna naacttccaa aangaanga 769

<210> SEQ ID NO 89
<211> LENGTH: 754
<212> TYPE: DNA
<213> ORGANISM: Cercopithecus aethiops
<220> FEATURE:
<221> NAME/KEY: misc_feature
<222> LOCATION: (1)..(754)
<223> OTHER INFORMATION: n is a, g, c, or t

<400> SEQUENCE: 89
cagcttgcca acctacaggt ggggtctttc aaaatattgc gttacaaata tcattttggt 60
gtatgtatgt caaaaccaaa actgccttta tgtcaatatg ctgtaaaaat ctatcagaat 120
atatcttaat tcttaacttt cattgttgtc tgtgggttgt cttgtataat tattatcaca 180
tctacagtat tttctgtagg taaatatgaa atgtattata aatgtaccag ggggaaaatg 240
ccctttaata agcctttccc tagacaaagc accatttagg cgtttagaag caagaactag 300
tgaaatcaga aattgctgtc atacatactc acctgtgaat ggtcgtacaa aggatcccaa 360
gcgcaggact tgtcctggaa gcagaggatc ggattccacc aggaaaagag gcaagtagaa 420
atgccaaatg ccagcgctcc ctttccccag ctcatcttat ttgtaggcac tcagattttg 480
gaatcctcca ggactaacaa taaaaaccac actaggttgt tttcctaatt cctgtgaaat 540
gagtcagtag gtcaaacaac ttatccactc cagagagaga acaattcctt gagctacact 600
ccctgtttnc agtaacccta ttccctctct gtgtccctgg ataaagtgct gcnacaatgc 660
atggggagnc caccgggttc tgaatgagac aatcgtaaan atngccaaaa nttagctgcc 720
ntcangggaa anttnccntt tgaaatttaa gnaa 754

<210> SEQ ID NO 90
<211> LENGTH: 866
<212> TYPE: DNA
<213> ORGANISM: Cercopithecus aethiops
<220> FEATURE:
<221> NAME/KEY: misc_feature
<222> LOCATION: (1)..(866)
<223> OTHER INFORMATION: n is a, g, c, or t

<400> SEQUENCE: 90
tnggggaacc ctgnccagna cctttttac tcatatccgg atcctgacct acattcagtg 60
ttctagattg aaatcacaga ttttggatag agaaaaaaaa atattctctg caatctaata 120
aaaccaactt tttttttttt tttttttttt tttgagacag agtcttgctc catggcccag 180
gctagagtgc agtagcacga tctcggcttg ctgcaacctc tgcctgtngg gttcaaccga 240
ttctcctgcc tcctgtctcc tgccccagcc tntcaagtag cagggattac aggcatgtgc 300
catgatgccc agctagtttt ttgtattttt agtagagatg gggtcttgcc atgttgccca 360
ggctggactt gaactcctga cctcaggtga tcaggccatc ttggcctccc aaagtgttgg 420
gattacaggc gtgagccatc ctgcctggcc aaaaccagca tattttatgg ataggaaatt 480
gaggcttaga tggggggaga aaaacattac acagattaaa ccacagctaa tgtcaagtgg 540
tgaccaaagg cgaatctttt attgcaggct gtgggttttt ccatgtggct ggtggtacac 600
tgcaccaagc agcacacaca ctaggccagt ttcctttgca gacccagttg caatcccatc 660
tntaanccag gatactatta ggtctcnaca ncctatggna ttttagggtg ctcanagttt 720
agggtgggaa aaggggacta anctncttgg nttaaggtnt ntccactggn ccctcncttt 780
nggnccnggg antttnatgc ccaaaancgg tngggctttt ttgggggnan aannccaanc 840
cnngggaaaa aaacnttttt gttang 866

<210> SEQ ID NO 91
<211> LENGTH: 783
<212> TYPE: DNA
<213> ORGANISM: Cercopithecus aethiops
<220> FEATURE:
<221> NAME/KEY: misc_feature
<222> LOCATION: (1)..(783)
<223> OTHER INFORMATION: n is a, g, c, or t

<400> SEQUENCE: 91
tgggnntgnc cagcggntaa cantttcaca cagaattccg tatttgaaat ttggggacaa 60
acaaacataa ctctttctct ttccttgaag ggttaatgct ccaaccagcc tcagattggt 120
tcgcttgaat cttaaaatta cttttctggt cacgcgcgcc gaaggtctaa gcatttgtga 180
aatgtctttt ttcccccccc ccaccccttg atgctgttct ctttgggctg tcttaattac 240
acaggggttg agaaaccaaa ttaaaattag gcgtgtctgg tcaacagtga tcacgttgca 300
tgcttttagc tttgcttgtt gaagttgctt ctcctccctg agtggctttc ctcctttttt 360
tttttttttt tttattttaa aaaggaaata tcataagctc tttcagaaat actcacagga 420
agtgagtgtc cgtatgctgg ttactcacca gcaactgagt gttggcaggt ggagaatgct 480
accgcagccg cccagacaga tctgcagact ggccccattg cagaggatta gacacagggt 540
gcgtggatca tanggttttt gtacagaagg cagttttaag aggaaattgg tcactgcatg 600
tcatctcgag gggtggtgat tcaaggagca gggctngggg gtcanaangc acntggctgc 660
catctcgggg gttcctgctc acttntnaaa gggcaggctg gcttntaaaa anaaatgctn 720
ccttcacccc caaanaggga tttttttgc agngaataac ttcccaaaaa tgaatngccc 780 cna 783

<210> SEQ ID NO 92
<211> LENGTH: 775
<212> TYPE: DNA
<213> ORGANISM: Cercopithecus aethiops
<220> FEATURE:
<221> NAME/KEY: misc_feature
<222> LOCATION: (1)..(775)
<223> OTHER INFORMATION: n is a, g, c, or t

<400> SEQUENCE: 92
ttggggaanc agcttgccaa anctacaggt ggggtctttc aaaatattgc gttacaaata 60
tcattttggt gtatgtatgt caaaaccaaa actgccttta tgtcaatatg ctgtaaaaat 120
ctatcagaat atatcttaat tcttaacttt cattgttgtc tgtgggttgt cttgtataat 180
tattatcaca tctacagtat tttctgtagg taaatatgaa atgtattata aatgtaccag 240
ggggaaaatg ccctttaata agcctttccc tagacaaagc accatttagg cgtttagaag 300
caagaactag tgaaatcaga aattgctgtc atacatactc acctgtgaat ggtcgtacaa 360
aggatcccaa gcgcaggact tgtcctggaa gcagaggatc ggattccacc aggaaaagag 420
gcaagtagaa atgccaaatg ccagcgctcc ctttccccag ctcatcttat ttgtaggcac 480
tcagattttg gaatcctcca ggactaacaa taaaaaccac actaggttgt tttcctaatt 540
cctgtgaaat gagtcagtag gtcaaacaac ttatccactc cagagagaga acaattcctt 600
gagctacact ccctgtttcc agtaacccta ttccctctct gtgtccctgg ataaagtgct 660
gccaanaatg catggagagn cccccgggtt ttgaatgana cccatcgtaa agatngccaa 720
aagntagctg ccttcaaggg aagttnccnt ttganattta gnagaaaaag tccnt 775

<210> SEQ ID NO 93
<211> LENGTH: 837
<212> TYPE: DNA
<213> ORGANISM: Cercopithecus aethiops
<220> FEATURE:
<221> NAME/KEY: misc_feature
<222> LOCATION: (1)..(837)
<223> OTHER INFORMATION: n is a, g, c, or t

<400> SEQUENCE: 93 ttnggggганc tagcttgcca aanctacagg tggggtcttt caaaatattg cgttacaaat 60
atcattttgg tgtatgtatg tcaaaaccaa aactgccttt atgtcaatat gctgtaaaaa 120
tctatcagaa tatatcttaa ttcttaactt tcattgttgt ctgtgggttg tcttgtataa 180
ttattatcac atctacagta ttttctgtag gtaaatatga aatgtattat aaatgtacca 240
gggggaaaat gccctttaat aagcctttcc ctagacaaag caccatttag gcgtttagaa 300
gcaagaacta gtgaaatcag aaattgctgt catacatact cacctgtgaa tggtcgtaca 360
aaggatccca agcgcaggac ttgtcctgga agcagaggat cggattccac caggaaaaga 420
ggcaagtaga aatgccaaat gccagcgctc cctttnccca gctcatctta tttgtaggca 480
ctcagatttt ggaatcctcc aggactaaca ntaaaacccc actagggggn ttncnnantc 540
ctgngaaatg agtcagtagg ncaaacannt ttncnctcca nanannnaan antccntggn 600
ntacnctccc tgnttcagna acccnattcc ctncntgggn ccnggnaaaa gggcgnccca 660
aatggnnggg ngncccccgg nttntnanga aacccatnnt aaaattnccc aaaantttnc 720
nccccnnann gaaannnncc nttttaaatt ttngganaaa aaanccccnt naaaaaaana 780
ngggggcggn tttntttttn aaagaaanaa anattttttt ttnngggagg ggttnnt 837

<210> SEQ ID NO 94
<211> LENGTH: 837
<212> TYPE: DNA
<213> ORGANISM: Cercopithecus aethiops
<220> FEATURE:
<221> NAME/KEY: misc_feature
<222> LOCATION: (1)..(837)
<223> OTHER INFORMATION: n is a, g, c, or t

<400> SEQUENCE: 94
ttggggnacc ctgncagncc antttactc atatcggatc ctgacctaca ttcagtgttc 60
tagattgaaa tcacagattt tggatagaga aaaaaaaata ttctctgcaa tctaataaaa 120
ccaacttttt tttttttttt tttttttttt gagacagagt cttgctccat ggcccaggct 180
agagtgcagt agcacgatct cggcttgctg caacctctgc ctgtcgggtt caaccgattc 240
tcctgcctcc tgtctcctgc cccagcctct caagtagcag ggattacagg catgtgccat 300
gatgcccagc tagtttttg tatttttagt agagatgggg tcttgccatg ttgcccaggc 360
tggacttgaa ctcctgacct caggtgatca ggccatcttg gcctcccaaa gtgttgggat 420
tacaggcgtg agccatcctg cctggccaaa accagcatat tttatggata ggaaattgag 480
gcttagatgg ggggggaaaa ancnttnccc aaattaancc acagcttatg tnaagtggtg 540
ancnanggcg aatcttttat tgnaggctgg gggnttttcc atngggntgg ggggnncctt 600
gncccaggcg gnccnnnctt tggnccnttt tcttttggaa cccngntgca atcccctttt 660
taanccggga atcttttggg tttcncnccc cttgggnatt nngggggccc caanttnngn 720
nggggnaagg ggnaaaaacc cctttggntn agggntttaa aangggnccc ccctttggnc 780
cngggnnttt tntnccnaan ngggnggggt ttttttgngg annaacncnn acnnggn 837

<210> SEQ ID NO 95
<211> LENGTH: 812
<212> TYPE: DNA
<213> ORGANISM: Cercopithecus aethiops
<220> FEATURE:
<221> NAME/KEY: misc_feature
<222> LOCATION: (1)..(812)
<223> OTHER INFORMATION: n is a, g, c, or t

<400> SEQUENCE: 95
ttggggttgc gagcggntaa cantttcaca cagaattccg tatttgaaat ttggggacaa 60
acaaacataa ctctttctct ttccttgaag ggttaatgct ccaaccagcc tcagattggt 120
tcgcttgaat cttaaaatta cttttctggt cacgcgcgcc gaaggtctaa gcatttgtga 180
aatgtctttt ttcccccccc ccaccccttg atgctgttct ctttgggctg tcttaattac 240
acaggggttg agaaaccaaa ttaaaattag gcgtgtctgg tcaacagtga tcacgttgca 300
tgcttttagc tttgcttgtt gaagttgctt ctcctccctg agtggctttc ctcctttttt 360
tttttttttt tttattttaa aaaggaaata tcataagctc tttcagaaat actcacagga 420
agtgagtgtc cgtatgctgg ttactcacca gcaactgagt gttggcaggt ggagaatgct 480
accgcagccg cccagacaga tctgcagact ggccccattg cagaggatta gacacagggt 540
gcgtggatca tagggttttt gtacagaagg cagttttaag angaaattgg tcactgcatg 600
tcatctcgag gggtggtgat tcanggagca gggctggggg tcanaangca cgtggctgca 660
tctcggnggt nctgctcant tttaaagggn ngctggnttt aaaaataang ntncttcacc 720
ccaaaangaa ttttttgcag gnaaannttc naaaaganna cccnantttt tgnnaaaacn 780
tgggaaancc ccntttnaan ggnggnttta an 812

<210> SEQ ID NO 96
<211> LENGTH: 805
<212> TYPE: DNA
<213> ORGANISM: Cercopithecus aethiops
<220> FEATURE:
<221> NAME/KEY: misc_feature
<222> LOCATION: (1)..(805)
<223> OTHER INFORMATION: n is a, g, c, or t

<400> SEQUENCE: 96
ttggggancn gcttgccaan tctacaggtg gggtctttca aaatattgcg ttacaaatat 60
cattttggtg tatgtatgtc aaaaccaaaa ctgcctttat gtcaatatgc tgtaaaaatc 120
tatcagaata tatcttaatt cttaactttc attgttgtct gtgggttgtc ttgtataatt 180
attatcacat ctacagtatt ttctgtaggt aaatatgaaa tgtattataa atgtaccagg 240
gggaaaatgc cctttaataa gcctttccct agacaaagca ccatttaggc gtttagaagc 300
aagaactagt gaaatcagaa attgctgtca tacatactca cctgtgaatg gtcgtacaaa 360
ggatcccaag cgcaggactt gtcctggaag cagaggatcg gattccacca ggaaaagagg 420
caagtagaaa tgccaaatgc cagcgctccc tttccccagc tcatcttatt tgtaggcact 480
cagattttgg aatcctccag gactaacaat aaaaaccaca ctaggttgtt ttcctaattc 540
ctgtgaaatg agtcagtagg tcaaanaact tatccactcc agagagngaa caattccttg 600
agctacactc cctgtttcag naaccctatt ccctctctgg gtccctggat aaagggctgc 660
cacaatgcat ggggagcccc cnggntnttg atggnaacac tcntaaaaat tgccaaaagn 720
tnnctgcctn aangaaaant nccctttnaa tttttggana aaaaanccct tnaanaaacn 780 gggggcggt ttttcnttaa agaaa 805

<210> SEQ ID NO 97
<211> LENGTH: 854
<212> TYPE: DNA
<213> ORGANISM: Cercopithecus aethiops
<220> FEATURE:
<221> NAME/KEY: misc_feature
<222> LOCATION: (1)..(854)
<223> OTHER INFORMATION: n is a, g, c, or t

<400> SEQUENCE: 97
ttggggaacn ngcttgccaa ntctacaggt ggggtctttc aaaatattgc gttacaaata 60
tcattttggt gtatgtatgt caaaaccaaa actgccttta tgtcaatatg ctgtaaaaat 120
ctatcagaat atatcttaat tcttaacttt cattgttgtc tgtgggttgt cttgtataat 180
tattatcaca tctacagtat tttctgtagg taaatatgaa atgtattata aatgtaccag 240
ggggaaaatg ccctttaata agcctttccc tagacaaagc accatttagg cgtttagaag 300
caagaactag tgaaatcaga aattgctgtc atacatactc acctgtgaat ggtcgtacaa 360
aggatcccaa gcgcaggact tgtcctggaa gcagaggatc ggattccacc aggaaaagag 420
gcaagtagaa atgccaaatg ccagcgctcc ctttccccag ctcatcttat ttgtaggcac 480
tcagattttg gaatcctcca ggactaacaa taaaaaccac actaggttgn tttcctaatt 540
cctgtgaaat gagtcagtag gtcaaacaac ttatccactc cagagagaga acatttcctt 600
gagctacact ncctgnttcc agtaacccta ttccctctct gggtccctgg ataaagggct 660
gccnacaatg catngggggg ccccccgggt tntgaangaa aannntnntt aaaaatngcc 720
aaaanntaac tnccctcaan ggnnannnnc cccttttnaa ntttttgggn aaaaaaaanc 780
cccntnaaaa aananagggg gggnggnttt ttttttnnaa aanaanaann aanntttttt 840
tttggggnan annt 854

<210> SEQ ID NO 98
<211> LENGTH: 912
<212> TYPE: DNA
<213> ORGANISM: Cercopithecus aethiops
<220> FEATURE:
<221> NAME/KEY: misc_feature
<222> LOCATION: (1)..(912)
<223> OTHER INFORMATION: n is a, g, c, or t

<400> SEQUENCE: 98
ttttgttgtt ggggnntgna gcgncggctn aactttttttg cacacagaaa ntcacaggaa 60
cacaggagtc agtttcttca gcaangtctt gcttgtccng ttntgaacgg taggatnttg 120
tcgctatatt tgnacacatg agggacctnt gtggagcttc caaatagtgc gctnggcgca 180
atatnnacaa ganacagccc ttagcgantg gcttgttgnt gggngagatg ntgctctgtg 240
ngatgaattn acanatcaca gagtttttttn tttgnntgct tgtttcctgt tntnaacggt 300
ggatttgtgn ttttggacca tgggatntct atgggctnan agangtccta tgtgngaata 360
nggcaatgta ctgcctttna naactggaat gangctnggt gagaanctgc tctgtgttct 420
gtganttccg tactntgaaa tttggggacn aacaaacata nctctttttt cttttccttg 480
aagggntaat tgctccaacc ccgccncaga ttgggntngc ttgaatctta naattncttt 540
tctggtcccg cccgccgang gntnagcttt tgngnaaatg gtnttttttc cccccccca 600 cccttggtg gngggtnttt ttgggcttgg nnttnanntn cccccggggg nntngnnnna 660
ccnattttnn attttgggnn nttttgggnc ncangggttc cnnnnnnnnn gnctntnann 720
cttggcttgn nngaangntg nttntccccc cccgggggggg ttccccccnt tttttttttt 780
tttntttttt tttnnagggg anttttntng tctttttnna anncncncgg gntgggggn 840 tcnnttttttt gtttttnncn nnnnttggnn nnggggggggg ggannttttct ctnnnncccc 900 cnnnntttnn gc 912

<210> SEQ ID NO 99
<211> LENGTH: 807
<212> TYPE: DNA
<213> ORGANISM: Cercopithecus aethiops
<220> FEATURE:
<221> NAME/KEY: misc_feature
<222> LOCATION: (1)..(807)
<223> OTHER INFORMATION: n is a, g, c, or t

<400> SEQUENCE: 99
ctgcttgcca anctacaggt ggggtctttc aaaatattgc gttacaaata tcattttggt 60
gtatgtatgt caaaaccaaa actgccttta tgtcaatatg ctgtaaaaat ctatcagaat 120
atatcttaat tcttaacttt cattgttgtc tgtgggttgt cttgtataat tattatcaca 180
tctacagtat tttctgtagg taaatatgaa atgtattata aatgtaccag gggaaaaatg 240
ccctttaata agcctttccc tagacaaagc accatttagg cgtttagaag caagaactag 300
tgaaatcaga aattgctgtc atacatactc acctgtgaat ggtcgtacaa aggatcccaa 360
gcgcaggact tgtcctggaa gcagaggatc ggattccacc aggaaaagag gcaagtagaa 420
atgccaaatg ccagcgctcc ctttncccag ctcatcttat ttgtaggcac tcagattttg 480
gaatcctcca ggactaacan taaaacccca ctaggttgnt ttcctaattc ctgtgaaatg 540
agtcagtagg tcaaanannt ttncnctcca ganaggaaca attccttgag ctanctccct 600
gtttcaggaa ccctattccc ttntgggncc ctggaaaang gctgccacan tgctgggaag 660
cccccgggtt tnaangnaaa aatcnnaaaa ttgccaaaan tancnnnccn agggnnggtn 720
cccttanant tttnggaaaa aanccccnta aaaaancngg ggncgnnttt tnttaaaana 780
aaanaaattt ttnttngggn gntttnn 807

<210> SEQ ID NO 100
<211> LENGTH: 814
<212> TYPE: DNA
<213> ORGANISM: Cercopithecus aethiops
<220> FEATURE:
<221> NAME/KEY: misc_feature
<222> LOCATION: (1)..(614)
<223> OTHER INFORMATION: n is a, g, c, or t
<220> FEATURE:
<221> NAME/KEY: misc_feature
<222> LOCATION: (1)..(814)
<223> OTHER INFORMATION: n is a, g, c, or t

<400> SEQUENCE: 100
ttggnattgn ccagcggnta acaatttcac acagnaattc caggcacagt tggctgttaa 60
ctagaatagt aagtggcttc ctaggctctg tcactcctaa actgtagggg gcttccagcc 120
tcggagatta cggaagtagt acttttcatt agcaagctca agaagaagtg tcaaaatagg 180

```
atgacacttt cctagtcgct ctgcaaaaac ccaaaaaacc agaaggggtg tcatctagac    240
actcctaagt ctatgcaggt gtcagcctgc cctcacccaa caccagccag cagcgtgcac    300
cattcaacca tatcttaact tgccccttac aaattgacac ttacactaac aagccctttg    360
atctcatttg tttaaaatga cagatataca accctcacgg gggttcccac tcaaggcctt    420
ncagcctncg ncctgcccct gnccaccccc aaacctacac acgtgttagc ccgacaccgg    480
ccccaccggg tcccacgtgc acctggtcta acacactncc cacgtgtggg cgccccacgg    540
gctttctnan gtagctgang gncccccat gacccccggt tntccaaaan aaaaaaacgg    600
gaaggacaag ggccctttc nccgnggncc caaccntngg gggggngggt ccaacccctt    660
tnttnnntat aaaccccaaa aaanananaaag ggcccggggn ccnncccccc ccttnaaaaa    720
ncccgncccc cnttttnccc cccnaaaaaa ngggggggaaa aaaaaaattt aaaaaaannc    780
nttttttnt tttnnccccc ccnncatnta nata                                  814
```

```
<210> SEQ ID NO 101
<211> LENGTH: 756
<212> TYPE: DNA
<213> ORGANISM: Cercopithecus aethiops
<220> FEATURE:
<221> NAME/KEY: misc_feature
<222> LOCATION: (1)..(756)
<223> OTHER INFORMATION: n is a, g, c, or t

<400> SEQUENCE: 101

ggntctttac aaccttcaca tagacatcta actatgctct tacctaacct ctagcgctct     60
tggtcccaga gtctaaatag gagccccaaa ctaatcactg tatggtagtc gaacttcccg    120
gcacttcccc gacaatctac aaccccatcc aaaggggtca gaaactggta ataaaatacc    180
agctatgagc ctntccttcc cctcaagaga tctatcaatt cggcctcacc ttcccacctc    240
tagcctgcgg gaacaaacat cccaggatcc cgggcggttt cgattgacgt tacttccggg    300
aaaagtaacc ttgcttcggc ggttgcgggc ctgaaaagct ctcgcgacat ttcctcccgc    360
nagatctgct tgctcactgt agcgatgaca tcctcctcct cctccccgcc gcctttcggc    420
aatcttcgcc agtcccagcc ccgaccaatc tgtactcaga tggcatggat cagggtctcc    480
cctcgaaccc cggttcgcac ggggcgtcag gtggcagcgg cggggtgcga gctgcgcgag    540
gccnacngca gcggcactgc gggtggccng gggcaggcca caagcantga ntgtnggccg    600
ggccgggggn aacccacccg ngtagcggct cnantgnttc tggcctggct ttngngccct    660
tttctccccc ccncangggt tcccgggnnc ctgttncgnt tcttttaann ggggaaaggg    720
gccccccccc ccccngncca angccccnnn acnnnt                               756
```

```
<210> SEQ ID NO 102
<211> LENGTH: 804
<212> TYPE: DNA
<213> ORGANISM: Cercopithecus aethiops
<220> FEATURE:
<221> NAME/KEY: misc_feature
<222> LOCATION: (1)..(804)
<223> OTHER INFORMATION: n is a, g, c, or t

<400> SEQUENCE: 102

tgggntgncc agcggntaac antttcacac agaattccaa ttatggggaa caagacatct     60
gaattggcta aaactccttg cagcagcaaa aaggaaaagc aaaacaaaac catacatgtg    120
gtttctgtct ttgcttcctg tcttttcttc caccttactc ctccttcccc ttccccttcc    180
ccttcccctt ccccatcttt gctaccaaaa aaaaatctag agaagccttc tattaacctg    240
```

aaccccttaa agaagtcaga acaaaggcac cacttgccgc tttttgggat gtcgtgtttt 300
ctttatggag ttttcaagag taatgggcag atgcttttag gtctacagtt ctgctttcct 360
gtattgcact acctgattct ttgacttttg gagataccag aaattacctt gtaccatgag 420
aggatttggc tttggcatgt gtaatggcag atgagagcta caaagttaag agtggctgaa 480
gatggtttac atgaagtggt cttaggtggt ttagctgagc tcccaggaag ttgttgtcta 540
ggatcccaat tctagttcag aggtgcattc ctattattat tatcattact attggtggtg 600
ntgntattat tttgagacag agtcttgctc tgttacccca ggctggagtc ctctggcacc 660
attacgggtn actggagcct naanttccag gctncagaga tcctcctttt annttcnnag 720
tagtgggacn canangnngg nnccccccaa cnnannnatt tttgnncttt tgnaanaann 780
gggtttgntt tttngncnnn ntgn 804

<210> SEQ ID NO 103
<211> LENGTH: 795
<212> TYPE: DNA
<213> ORGANISM: Cercopithecus aethiops
<220> FEATURE:
<221> NAME/KEY: misc_feature
<222> LOCATION: (1)..(795)
<223> OTHER INFORMATION: n is a, g, c, or t

<400> SEQUENCE: 103
ggnattgncn agcggntaac aatttcacac agnaattctg gagttaggtt gtctgggcta 60
ttcaattagt ttctatgtgt ctgacacatg gcagaaactt attaaatgct tgaatgaata 120
cataaagcaa gatgacagtt tcagaatgna ccaggtaatt caaagtactg aatccatatt 180
aaatttattt tagtctacac agaagtgaag taacactaaa atctgggcat ttaccaggtg 240
atggcaagta ttcatttcca tcatccagcc cgttacctgg cacatagtta ctgccctatg 300
taaatgctta tcacagcaat caatcaatga aatgttttc tcatagagtt cggtgaataa 360
ctcacgacag catactcaca gaggattcaa agagtatttg acttgtatat attgttttaa 420
acagttggaa cctgataatg cagttttcta aaatacagtg aaagggcttg tcctaaaggg 480
catgtcagga tatgtgtgag aaaggatgaa cttgtcctgt gaagacaacc ttgcattagc 540
tctagcagaa tgagccattg cctacctggg ctggggaagg cggcacctca gtatctccct 600
cacctgctcc ctggcacttt aaatccctct gtgaagangt cagttgtaat tttcagtaag 660
attgaaggtt tcaaagcact gacccctggg gggaatggat tngcttaagt tggctctgaa 720
ngaagnggct gggatnngct ntctganaaa cccgggattg tgaggnaatg gagacngccg 780
ggagggtnna anaaa 795

<210> SEQ ID NO 104
<211> LENGTH: 641
<212> TYPE: DNA
<213> ORGANISM: Cercopithecus aethiops
<220> FEATURE:
<221> NAME/KEY: misc_feature
<222> LOCATION: (1)..(641)
<223> OTHER INFORMATION: n is a, g, c, or t

<400> SEQUENCE: 104
tgggggnacc cagcggntaa cattttcaca cagaaatctc attcaatgaa ctgttatggg 60
gtctcacatt gtaccaggca ctggggattc agcttccagt tcatagtctg catgcaaacc 120
gacatgcagg tagacatgca gacagaaaat cggaacgcaa cacggtaagt gctatgctag 180
agaatgagaa ggactgtcag taatcacaac cacctttcac tgggttcctt cagtgtgcca 240

```
ggctcgtgta cattattttg tttagtgctc acaattgtat ggactgtgta ctatcatttg    300

ccagattata tggatgaaga aactagactg agggggttaa ataactcgtc caagatcatg    360

cagacaaaaa accacagaga ttattttcca atacaaactc tctggctgta cagctcaagt    420

tcttaaacac tgggccaacc agtctgaatc tgagaggagg cattctaagg cttacaggta    480

agtgggaatt gaaagggttg agggaagcct tctggaggag atgccattac actgaatgtt    540

gaatgagtag gagttagcta tctccagagg ggtagtggct gtgaaggggc gaggggtana    600

gggtgggaag gggatgatgg aaggtggtag agtggnnaca g                        641
```

<210> SEQ ID NO 105
<211> LENGTH: 757
<212> TYPE: DNA
<213> ORGANISM: Cercopithecus aethiops
<220> FEATURE:
<221> NAME/KEY: misc_feature
<222> LOCATION: (1)..(757)
<223> OTHER INFORMATION: n is a, g, c, or t

<400> SEQUENCE: 105

```
cngncttgcc aacctacagg tggggtcttt caagatctgc tgacagtgaa gctaaatctg     60

gcggaagcaa aggattcact ttctcataat ggattaactc atcctatttg cctcttaaac    120

aatgggtatt ttaaagacag aagttgaagg aagtccaagt atccaatttt aaggatgcct    180

attagagcag ttataagaga gtgtctctct ttctctctct tctttctttc tcttggtagg    240

agtatgcagg aggtcattta aaagccagat agtgatacaa atcacaatgc agaaaaacat    300

ccccgtggac tcctccctgt cctatgtttg acattcttaa aatctatgtc ccaggtcttg    360

aaatctttaa ataatctacc atgttctttg gcctgccctg ggaaatctat ttcagtacca    420

gagctatgct ggttacacac cttttctgac tcatgttccc aagtgatttt attccagata    480

cgatttgggg acagttacgt gtactgttct gatatcttcc taaaaggaaa ttatttttgg    540

aagtaaagtc actgataaaa tcanctcagg aaaatgcact ttgtaaatat taaaatataa    600

actttttnaa ggncntgctg gaaaanacta attgattttc ctgggnagca gttccatnga    660

acancgatng atctttaggg ggnagtgaan ggccccnatt tgaaaaangg gggcgggaaa    720

ngttcaaata ntttttccaa angggnncct anntnnt                             757
```

<210> SEQ ID NO 106
<211> LENGTH: 640
<212> TYPE: DNA
<213> ORGANISM: Cercopithecus aethiops
<220> FEATURE:
<221> NAME/KEY: misc_feature
<222> LOCATION: (1)..(640)
<223> OTHER INFORMATION: n is a, g, c, or t

<400> SEQUENCE: 106

```
ttggggnanc gagcggntaa cattttcaca cagaaattca ttcaatgaac tgttatgggg     60

tctcacattg taccaggcac tggggattca gcttccagtt catagtctgc atgcaaaccg    120

acatgcaggt agacatgcag acagaaaatc ggaacgcaac acggtaagtg ctatgctaga    180

gaatgagaag gactgtcagt aatcacaacc acctttcact gggttccttc agtgtgccag    240

gctcgtgtac attattttgt ttagtgctca caattgtatg gactgtgtac tatcatttgc    300

cagattatat ggatgaagaa actagactga gggggttaaa taactcgtcc aagatcatgc    360

agacaaaaaa ccacagagat tattttccaa tacaaactct ctggctgtac agctcaagtt    420

cttaaacact gggccaacca gtctgaatct gagaggaggc attctaaggc ttacaggtaa    480
```

gtgggaattg aaagggttga gggaagcctt ctggaggaga tgccattaca ctgaatgttg 540
aatgagtagg agttagctat ctccanaggg gtagtggctg tgaangggcn aggggtaaag 600
ggtgggaagg ggatnatgga aggggtnnaa tnggnncnng 640

<210> SEQ ID NO 107
<211> LENGTH: 818
<212> TYPE: DNA
<213> ORGANISM: Cercopithecus aethiops
<220> FEATURE:
<221> NAME/KEY: misc_feature
<222> LOCATION: (1)..(818)
<223> OTHER INFORMATION: n is a, g, c, or t

<400> SEQUENCE: 107
ttggggacca gcttgccaat tctacaggtg gggtctttca agatctgctg acagtgaagc 60
taaatctggc ggaagcaaag gattcacttt ctcataatgg attaactcat cctatttgcc 120
tcttaaacaa tgggtatttt aaagacagaa gttgaaggaa gtccaagtat ccaattttaa 180
ggatgcctat tagagcagtt ataagagagt gtctctcttt ctctctcttc tttctttctc 240
ttggtaggag tatgcaggag gtcatttaaa agccagatag tgatacaaat cacaatgcag 300
aaaaacatcc ccgtggactc ctccctgtcc tatgtttgac attcttaaaa tctatgtccc 360
aggtcttgaa atctttaaat aatctaccat gttctttggc ctgccctggg aaatctattt 420
cagtaccaga gctatgctgg ttacacacct tttctgactc atgttcccaa gtgattttat 480
tccagatacg atttggggac agttacgtgt actgttctga tatcttccta aaaggaaatt 540
attttggaag taaagtcact gataaaatca actcaggaaa atgcactttg taaatattaa 600
aatataaaca ttattaaagg ccatgctgta aaaatactaa ttgattttcc tgggtagcag 660
ttacaataga acancgatng atctctaagg ggagagtgaa aggacctcan tttganaaac 720
gtgaggcagg aaaagnttca aatnattatt tncaanaggg ntccctaagt tgttncttaa 780
anaaaatttt tttcntnaaa aaaaaacnnt aanggcca 818

<210> SEQ ID NO 108
<211> LENGTH: 608
<212> TYPE: DNA
<213> ORGANISM: Cercopithecus aethiops
<220> FEATURE:
<221> NAME/KEY: misc_feature
<222> LOCATION: (1)..(608)
<223> OTHER INFORMATION: n is a, g, c, or t

<400> SEQUENCE: 108
ttgggaccct gtcagaccan ttttactcat atcggatccc ctgaggtcgg gagatcaaga 60
ccaccctggc caacatggtg aaaccctgtc tctactaaaa tacaaaaatt agccaggcgt 120
ggtggcaggc gcctgtaatc ccagctactc aaaggctgag gcaggagaat cgcttgaacc 180
taggaggcag aggtggaagt gagccgagat cataccactg cactccagcc tgggcatcag 240
agccagactc tgtcgcaaaa aaaaaaaaaa aaaaaaaaaa attagctacc tctcccatcc 300
anaaatgaga gtcgaggctt ctgacttccc gggctcaatt tatcctcccg cctcagcctc 360
ttgaggaact gggactacag acgtgcacta tcacacttgg ctaatttttt tgagatgatg 420
tcttgctctg tgcccaggct ggagtacagt gacacaatct cagctcactg caacctccgc 480
ctnctgggtt caaccgattc tnttgcttca gcctcccaag tagctgggat tacaggcgtg 540
ccccacaacg tccagntatt tttgtatttn aagnagagac nggggnnncc cctgttggnc 600 ngggnggg 608

<210> SEQ ID NO 109
<211> LENGTH: 516
<212> TYPE: DNA
<213> ORGANISM: Cercopithecus aethiops
<220> FEATURE:
<221> NAME/KEY: misc_feature
<222> LOCATION: (1)..(516)
<223> OTHER INFORMATION: n is a, g, c, or t

<400> SEQUENCE: 109

```
ngggancctg nccagnacct ttttactgca tatcggatcc tgagaagctc ctgattttcc     60

ctcaagccta aggcaaagta gtattcagaa cctcctatcc cactgactcc gagagcctgt    120

cctccgatat ctccaagaga gcctatcctc cgataggagg ggaagcccct ccaacctgca    180

ggtatcctcc ccagactcac catttctccc accccacact ggtggcttcc aaactttccc    240

tctcataaca aggcgccctg tcacccagac tgcttccctc ggcttgagga ggaggggaag    300

gcgcacgaag taggaaggaa cttggggaga gggcgggcgg agggtgggcg aagcactgag    360

gggagggcgg tgaagaaggc agaagtcagg cagtgagagg gagaagcggc gggggcaggt    420

gagggcgggg gagtggggat ggggccgggg aaaggggccg agaggacgcg gagggggcag    480

aggtagggna caggagggga ggggaggggg agggcc                               516
```

<210> SEQ ID NO 110
<211> LENGTH: 802
<212> TYPE: DNA
<213> ORGANISM: Cercopithecus aethiops
<220> FEATURE:
<221> NAME/KEY: misc_feature
<222> LOCATION: (1)..(802)
<223> OTHER INFORMATION: n is a, g, c, or t

<400> SEQUENCE: 110

```
tnggggaacc tgccagacct tttttactca tatcggatcc ttattgcctg gctatttcag     60

cctgggaggg gtttggctgg aatatccctg gggaggcagg ctctcagggc taaaatagtg    120

ggagaaaaga ttaaaccttt aggaaactgg tacacatcag cgctaagtgt gactcaggga    180

gaaacaagaa ctaggacact tattactcca aaggagttgt atttggttca actcttgtat    240

tttcttatta aaacttttgc aaagtgggtt gagaagaaag tgttacttcc agtgttacac    300

cctcaacact ttttcctgtg gagactccag catgttcatt atgttttctg aagccatggc    360

actgtagtac tctttcattg ttgttattat tatttaataa tataaaatga gacatttttg    420

ctccattttt cattcatatt tttgtcctaa ttacttttta aatatattct ggtgtcaggt    480

caatatttat agtctaacgt ttaagactta gactttggtt cttaggatgt tatttttgaa    540

tcagctgcgt ctggtaaggt aatagatatt gaaagtgcct tgtaaattgt ccagtggcat    600

aaaagtattg tcatatcttt atgacataaa agaaaantgt tttcttcttt ttagcatgga    660

aaactttaca anccatttgc tggtgacngg ngangncctn ggggttggat ttcatgattt    720

tggggtccct tgagggtcca aantaccntt ctaanagngg aaantttca nnaattcatg     780

antgncctna ttnaaanann tt                                              802
```

<210> SEQ ID NO 111
<211> LENGTH: 851
<212> TYPE: DNA
<213> ORGANISM: Cercopithecus aethiops
<220> FEATURE:
<221> NAME/KEY: misc_feature
<222> LOCATION: (1)..(851)
<223> OTHER INFORMATION: n is a, g, c, or t

<400> SEQUENCE: 111
tacttttttt tgggggnncc aagncggnta acattttcac acagaaatct ccaagttccn 60
naggaccgca gnatcctccc cagaacccct gngaccaagt cactgtggtt ggntgtgctg 120
ggcatccctg aggcccagcc actcaacttt actggctcca ggattctata gaaagggaaa 180
ggggtagaaa atctcaaaag gcttcttcct ttcagggagg gggttccctc tcagcggctt 240
ctggaatctc tacccactcc agccgacttt tgaggccatg tggtcctgga acaaggcccc 300
tctgagggcg gcagatgggg caggcggccc aggcacacag catggttggc tctgcggccc 360
agggcccaca aaagccttat tgagtcacca ccagcccccg gcagaggctg aggtggcagt 420
ggcgccgagc gcctgccacc taatgactgt cctggcacag ccagatgttc cgcagacctc 480
cggagcagcg ggaccaaggg cccgcccggg ccagccggca ccngannagg ccacttttaa 540
tttccaatta accagntttc agnntgancn aaanaggggg gcagtnggtg gncccacccc 600
cgggcnagta ngccccggcc cnnaaaannc cttncgaagt tntaanactn ccanatntga 660
aaccnccacc ncccngaatt cccnatggaa aaantggccc ccagccangg gcaagggntt 720
gggncctttc ttttctttgg aaaaggaaat tttggttntt ttnacnaagg ccccccaang 780
ggncttnnnt gcccaantnt nccnngnttt ggggggnaat cnttnnnaaa nttttnttaa 840
aaccccnatt t 851

<210> SEQ ID NO 112
<211> LENGTH: 773
<212> TYPE: DNA
<213> ORGANISM: Cercopithecus aethiops
<220> FEATURE:
<221> NAME/KEY: misc_feature
<222> LOCATION: (1)..(773)
<223> OTHER INFORMATION: n is a, g, c, or t

<400> SEQUENCE: 112
cagcttgcca antttacagg tgggantctt tcaagagcag taaaacgacc tatccaagga 60
aactcagcta gtaaaggcag ggacagggta tcgcaggctc tcggaactca cgagtccccg 120
ccaggcgcat ggccgctcct ttcccccggt gggcgtggcc aggccaggcc cgtcccctcc 180
cctgagcgcg ttcctggcag cccggccggc cgtttnctgc ctgcgtcgct gggcgcgcgg 240
gcgggcgggc agcccatctg gcggcccccg cggggcggcg cggggaggcg gcccagactt 300
gctggagcca ggcgcctgcc cgggggcccc cctgcccgcc tggagaaccc aggtgtggcc 360
gcggcggggg tggggggtgg tgctttcctt cccgctcgct cggctcttnc tgacgcacga 420
gggcaggatg cagcctcctc ccgtcctctc ctcggcctcc gcctcccgcg ccctggcccg 480
gaatcctgga gggaatccaa acgcggggcg gggaggccgg ggcaggcccc tgaggccccg 540
cccctgatag ccatttaata ccaccgcaag tcttgaccgt atttttgggg tgacccanct 600
tccctgcttg ggcaagacca gctgaactct gacctnctgg anggccgatt ttaccttgct 660
cctcagggac ccnnaaatga tcgtaggaac cngnntcact actgctgtaa gccanancgc 720
ttganatatn caattattca gcggnttcaa gtcccggaag cggnttttna cna 773

<210> SEQ ID NO 113
<211> LENGTH: 807
<212> TYPE: DNA
<213> ORGANISM: Cercopithecus aethiops
<220> FEATURE:
<221> NAME/KEY: misc_feature
<222> LOCATION: (1)..(807)
<223> OTHER INFORMATION: n is a, g, c, or t

<400> SEQUENCE: 113
ttggggttgc gagcggntaa cantttcaca cagaattctt cagtgaattt cttaagccct 60
gagcatcttc tttgtattct gctttaagaa cttgtttgtt tctgtatttc atactcagtg 120
gctctggcgc ttggatgccc tggtcccaca gaaggccttg aatactgaat ctgaggatgg 180
ggcttgctta taaggacctt actccctgtc ttaaccagat tgtgttttaa cctttcatct 240
cactttttac ttttcattca tggatagtgt ttgtcactgt gtgtgtgtgt gtgtgtgtat 300
gaatgagtga atgaatatct ctcacactct aaattctttt aaaggcagga agtactgttc 360
tcttgtttgc tattttatcc actctgcctc tactgggtct ggcacataat aaagaaagaa 420
tgaacaggac aaacacccat tctgaaagtg aacttctctg gcaattgtcg tttgtacata 480
ccagctggag catagacaat tggcttttaa tgtggtaagg gaaaaggtca aaaaaagaat 540
cgtcattgac caagggcttc accagatgat tttataatca ntccnaaagg gnctttnaan 600
aaaaaaggcc ttngaggaac aaatttnttc cnnntggaaa antgntttna aatttttntn 660
gaaaaagttt tnanaatttt tgnaaaaccc ccnccccnnt gaaaacntnt aaancnngna 720
annngnnnng ggcggggttt naaaaaaaaa aantnccccc cnnnnaanng ggnctttnaa 780
aaannnnngn ntnctaaaaa aangggg 807

<210> SEQ ID NO 114
<211> LENGTH: 836
<212> TYPE: DNA
<213> ORGANISM: Cercopithecus aethiops
<220> FEATURE:
<221> NAME/KEY: misc_feature
<222> LOCATION: (1)..(836)
<223> OTHER INFORMATION: n is a, g, c, or t

<400> SEQUENCE: 114
ttggggacca gcttgccaan tctacaggtg gggtctttca gtatgtgtca agagtcagaa 60
tttaaagaag ataagaaaat taaatacact gagaacaatg catctcntga cattcaaaat 120
atgtaagtgc agcaaccagc agtaattcca taggcctttt atcaaccttt gccaaaacct 180
ataaaaagaa tatctaaaat tgctttttta tgaaagttcc tatttattct tgtttccctt 240
accagagagc ctgctttccc cttactgatg agaacacagg gggtcctggg taaagagtcc 300
ataanattta aaaaggagta tgccttggcc tcccatgacc ctcttacttc acaataaggc 360
catcttttac ctggtttaga tttgcagact aggtccatta gatacgttgt cattaaatac 420
ctatactata ccctaatatt tgtaatcttg acaggtatta ttttcatttt atagacagat 480
ctaggaaaat tacatgactt atcggaatcc cttcaaatat cacagagcaa agtcatgatt 540
ttaacttgtg tttgccactc tgaaactcac actggaattc gagactagtg tgcgtaacat 600
ggcgaaaccc catctctatt tnttnttttc aaaatntntt tttccaaaat ttgctggggg 660
tgttggtgtg tgcctgtant ncagcctnct tgggaggctn aannggngga cngcttgacc 720
ctgggngnaa aggctaaatn gnctttnttn gcccctggan ttaaccnngg ggaaaaangg 780
aacccttntc aaaataaatt ttaaattaaa naangccnag gtttccccna aaaaat 836

<210> SEQ ID NO 115
<211> LENGTH: 839
<212> TYPE: DNA
<213> ORGANISM: Cercopithecus aethiops
<220> FEATURE:
<221> NAME/KEY: misc_feature
<222> LOCATION: (1)..(839)
<223> OTHER INFORMATION: n is a, g, c, or t

<400> SEQUENCE: 115
ttgggananc gagcggntaa cattttcaca cagaantcca gtgtgagttt cagagtggca 60
aacacaagtt aaaatcatga ctttgctctg tgatatttga agggattccg ataagtcatg 120
taattttcct agatctgtct ataaaatgaa aataatacct gtcaagatta caaatattag 180
ggtatagtat aggtatttaa tgacaacnta tctaatggac ctagtctgca aatctaaacc 240
aggtaaaaga tggccttatt gtgaagtaag agggtcatgg gaggccaagg catactcctt 300
tttaaatttt atggactctt tacccaggac cccctgtgtt ctcatcagta aggggaaagc 360
aggctctctg gtaagggaaa caagaataaa taggaacttt cataaaaaag caattttaga 420
tattcttttt ataggttttg gcaaaggttg ataaaaggcc tatggaatta ctgctggttg 480
ctgcacttac atattttgaa tgtcttgaga tgcattgttc tcagtgtatt taattttctt 540
atcttcttta aattctgact cttgacacat actgaaagac cccacctgta ggtttggcaa 600
gctagctgag gatcgtttcg catgattgaa caagatggat tgcacgctgg ttctccggcc 660
gcttgggtgg agaggctatt cggctatgac tgggcacaca gacantcggn tgctctgatg 720
ccgccgtgtt cggctgtcan cncagggcnc ccgntttttt tgnaanaccn nctgnccggg 780
ccctnatgaa ctgnngacaa ggcacccggt ttntnggttg ncnaaanggn gtttnttgc 839

<210> SEQ ID NO 116
<211> LENGTH: 815
<212> TYPE: DNA
<213> ORGANISM: Cercopithecus aethiops
<220> FEATURE:
<221> NAME/KEY: misc_feature
<222> LOCATION: (1)..(815)
<223> OTHER INFORMATION: n is a, g, c, or t

<400> SEQUENCE: 116
tnggggacca gcttgccant tctacaggtg gggtctttca gtatgtgtca agagtcagaa 60
tttaaagaag ataagaaaat taaatacact gagaacaatg catctcaaga cattcaaaat 120
atgtaagtgc agcaaccagc agtaattcca taggcctttt atcaaccttt gccaaaacct 180
ataaaaagaa tatctaaaat tgcttttta tgaaagttcc tatttattct tgtttccctt 240
accagagagc ctgctttccc cttactgatg agaacacagg gggtcctggg taaagagtcc 300
ataaaattta aaaaggagta tgccttggcc tcccatgacc ctcttacttc acaataaggc 360
catcttttac ctggtttaga tttgcagact aggtccatta gatacgttgt cattaaatac 420
ctatactata ccctaatatt tgtaatcttg acaggtatta ttttcatttt atagacagat 480
ctaggaaaat tacatgactt atcggaatcc cttcaaatat cacagagcaa agtcatgatt 540
ttaacttgtg tttgncactc tgaaactcac actggaattn tgngggaaat nntatccgnt 600
canaattccc ccnacatgag cgtnanaccc cgaaaaaaga acaangatnt ttttggaacc 660
nttttttttg gggnnaanng gngnngnaaa aaaaaaccnc cnntncnacg ggggtttgtt 720
ggcgganaan aacnccacct tttttccnaa ggaaangntt tnaaaangcg aanaccaaaa 780
ntgtcntttt gnnnggccgg gttggncccn cttna 815

<210> SEQ ID NO 117
<211> LENGTH: 792
<212> TYPE: DNA
<213> ORGANISM: Cercopithecus aethiops
<220> FEATURE:
<221> NAME/KEY: misc_feature
<222> LOCATION: (1)..(792)
<223> OTHER INFORMATION: n is a, g, c, or t

<400> SEQUENCE: 117 ttgggggane gagcggntaa cattttcaca cagaaattcc cgacctcaag tgatatatcc 60
accttggcct ccaaaagtgc tgggattaca ggcatgagcc accgcgcccg gccccttcat 120
gcagtttctc tcactccttt cagaatcgag gagtctgcta ttccatcgac atctaaccca 180
ctcctctaaa ccagcctgca atcccagctg gagaactaca atccaatcag ggattaaatc 240
taaattcctc ccatctgatc actgggatcc ctacccattc aactcccctc ctcctccaga 300
aatgttacca atcccctaaa gcctccaatc acctgttgag ccaccagcca agcgcttact 360
aatccctgtc tcccaagctc agacactccc tgtaattgat ggacacgcag cattgggagc 420
tttcacattg agctcttact ttgaaacttt gaataagaaa agagctgaaa aaagcagatc 480
tcccaatctc ggtgaaactg tagttaaact ccaagtagaa taccccaata aatggatang 540
aatganaaat ctcatatggg ttatatangc antatttana aattttggaa ttataggnnt 600
anggatncaa acttnnanan tantattcca ttggnntttg gngcncccna ngntaaanaa 660
gttnnccnct canaaggaaa nggggngggt nangggctan nccnnaancc anntttggn 720 ggntnggnnn aaanttttn ggnccaantt naaanaaann tnntnaaaaa aanggnnccn 780
tttttnaaaa aa 792

<210> SEQ ID NO 118
<211> LENGTH: 838
<212> TYPE: DNA
<213> ORGANISM: Cercopithecus aethiops
<220> FEATURE:
<221> NAME/KEY: misc_feature
<222> LOCATION: (1)..(838)
<223> OTHER INFORMATION: n is a, g, c, or t

<400> SEQUENCE: 118
gggnaaccga gcggntaaca ttttcacaca gaaantcgga aagtaaagcc aatcttagag 60
gctgcaggag gtttgggggc agtatctgat tcagacgctg gctaacgttt cacgatcgcg 120 ttccctttt tcttccaact cggtaagtaa aaaggcaaga tgagaaattt acgtgctgaa 180
cttaataaat agttggtgga cgtattgcct tttttttttt ttttttggta agggatgaca 240
catctcgtga ctacagttct tttgaggaat aacttttctg ctagtttcca aatcggcacg 300
tgaccaaagt cttttcatag gattttagcg tcctgataaa aatcaatggg cagaatttga 360
ttgcttttta aaaaatgtgt ttgtcctttg gtctctggca ccattgtaat ggaaaatccc 420
tacattgcct gtactctcag aagctgtcca gtggagcaaa actagagata aagaaacctg 480
gaacgattca gttaggaact tttaagaagc cagcctttag tttttccttt agaagattat 540
gcagttatca tgattgcttc tctagaactt cagtgtgtta tttggattcc taaatctaag 600
acaatgctgn ggaagtctgg ggcttttagn attttngggt ctgctgnaga aaatcctcgt 660
ttatactaca aagtttctnt tttggaactt tnggaattgg gcatttttn nnttattatt 720 ngnatgntng antnanngge aaaactnagn naacccttt nggtttgcct cnanccggtt 780
nttaaanaaa ngggaaaaan cctnanttta aanttttttc cacccttttt tnttttnt 838

<210> SEQ ID NO 119
<211> LENGTH: 820
<212> TYPE: DNA
<213> ORGANISM: Cercopithecus aethiops
<220> FEATURE:
<221> NAME/KEY: misc_feature
<222> LOCATION: (1)..(820)
<223> OTHER INFORMATION: n is a, g, c, or t

<400> SEQUENCE: 119 ttggggganct agcttgccaa ntctacaggt ggggtctttc agtggggggc tgtcctgtag 60
gttatagaat gtttagcagc aaaaattaaa aattaaataa caaaaataaa aataaaaaag 120
aatgtttagc agcatccctg gcctctaccc actagatgtc agcagcacct cccttgcccc 180
caggtgtgaa ccaaaaatgc ctgcagacat tgccaaatat ctcctaggag gacaaaattg 240
tcctctcttc cacttgagaa ctattactct aaaattaccc agatctgctt tgaatccccg 300
ctccacccca tcacaacctg ggtcatcttg gaaaacagac tgaaccttcc tatgcccccc 360
gcaaattcct caactgtaac atggagctct tgctgaagaa atgctatgaa aattaaatga 420
aatgatgtac gtacaggatt tacacgcaca gaatattcac cgcgccagag tgagtgctca 480
ataaatggtc agaaatgagg ggaggctaaa aaaaaataat ttcgagaact caaaaatctt 540
atctttaggc ctccagagta ctgtagtcta gacagaagaa atggttgaga tagaancaaa 600
agagatgaga gaggttggaa aagaagtgat agaactaagg tattattccc cttatctctt 660
aagaacccgg cttggagtca aagccaatag agggtctact tagttttgnc tattactcta 720
ctttcaaata taacgaaaat tgcccaaacc caaagtntcc aaaaaaaact ttnnnttnan 780
cggggatttc tncncggncn aaaatctaan nccccnctnc 820

<210> SEQ ID NO 120
<211> LENGTH: 797
<212> TYPE: DNA
<213> ORGANISM: Cercopithecus aethiops
<220> FEATURE:
<221> NAME/KEY: misc_feature
<222> LOCATION: (1)..(797)
<223> OTHER INFORMATION: n is a, g, c, or t

<400> SEQUENCE: 120
ttggggttgc gagcggntaa cantttcaca cagnaattca gctgatgaat gcagatatga 60
accgatggtt caagagctgt agacatacat acctagttta ccacactgat cttcttagta 120
taaaaaaaca agcgttacta agaaacatct actttcagca aatggacatg accagaatga 180
tacatagaat gatgcaagaa atttcactct accattcatt ttaatcttta cagtaacagg 240
atgattgcta tctcaatctg tcattttacc tttttttttt ttttcagaag ttaaagtgta 300
tccatacaag ttcaacttaa cattgttaag tgcaaagtta acagtgtaca ctttggagat 360 accttttttag gtagaaaatg attttttgtt ttctaataag ttttcccaag taatattaaa 420
gaaggttaaa tatgtcattt acttggagaa aacagaaaac catgagaaag tttgggaaaa 480
tgctatattt cagagcttaa tatattgaaa cagtaagtaa gacaggaatt ggctaccttt 540
taagaacgtt tacaaaaata caaactgann ggaatgcttt tggcaatnaa aatntgacnt 600
gaaacattca atggcnnaac attcaanaan gnttnagana tcnttnccttt tancatccaa 660 natngttttg ncgncntctc aaaaaantgt ntntttttaaa aaanttaggg ntaaaanttt 720
ctggnagntt nattaanctt tttttgnncc ctnaaatttt nnccnaaagt tcnttnanca 780
aaaaaaaatn cttttttt 797

<210> SEQ ID NO 121
<211> LENGTH: 828
<212> TYPE: DNA
<213> ORGANISM: Cercopithecus aethiops
<220> FEATURE:
<221> NAME/KEY: misc_feature
<222> LOCATION: (1)..(828)
<223> OTHER INFORMATION: n is a, g, c, or t

<400> SEQUENCE: 121
ttggggancn gcttgccaan tntacaggtg gggtctttca ccttcttgcc agaaacataa 60
aatgcgatgg agctacggcg accgctgccg agacaaaatg gcgccgagaa cctggtttag 120
cgcaggcgcc ttggaaagac cctgccccgc ccccgtgcaa gcccctggct gcaattctgg 180
gttccgtttc catgggacac tccgccgcca atcctcgtgc cgaactgctc ttcctgaccc 240
ctcaattcac caatcagtgc ccagtcaagc acatccggag tcgtctctac caatcatttc 300
tcaagacttg cttactcaat aaccaactct ccaataacgt tggtcttcgg aaaaagccaa 360
tcataagtgg aagatgtcct acctgctgtt tttcgcacca atccatgaag tttcagagct 420
acatccaatg aggacggcag gtagcgaggt cctatccgaa gctcttcggc gtcatgaaca 480
gccaatagga gttcgtgtag aagcgagtct gctcaacagc ttgttatttg gtggattgtg 540
gcagtaaatc ggggcgagtg gggaaccggg cgcaggaact gcagccgcgg ttgggagtgg 600
tgctgcccgg acgggggccc acggaggtca gaggggagga ggactctgga gctgacagcg 660
cgcacttnac ccgcanttgg taggtggggg agaggggaat cngggggatn ctgaatggac 720
aaancggnan cggcagcaan tgntgntgcc cgggtncccg tgcaantnga aacntttggn 780
gtggggaang ggattctagg caanggnccc gcnancccna aaaaaggc 828

<210> SEQ ID NO 122
<211> LENGTH: 842
<212> TYPE: DNA
<213> ORGANISM: Cercopithecus aethiops
<220> FEATURE:
<221> NAME/KEY: misc_feature
<222> LOCATION: (1)..(842)
<223> OTHER INFORMATION: n is a, g, c, or t

<400> SEQUENCE: 122
ttggggancc tagcttgcca antctacagg tggggtcttt caccttcttg ccagaaacat 60
aaaatgcgat ggagctacgg cgaccgctgc cgagacaaaa tggcgccgag aacctggttt 120
agcgcaggcg ccttggaaag accctgcccc gcccccgtgc aagcccctgg ctgcaattct 180
gggttccgtt tccatgggac actccgccgc caatcctcgt gccgaactgc tcttcctgac 240
ccctcaattc accaatcagt gcccagtcaa gcacatccgg agtcgtctct accaatcatt 300
tctcaagact tgcttactca ataaccaact ctccaataac gttggtcttc ggaaaaagcc 360
aatcataagt ggaagatgtc ctacctgctg tttttcgcac caatccatga agtttcagag 420
ctacatccaa tgaggacggc aggtagcgag gtcctatccg aagctcttcg gcgtcatgaa 480
cagccaatag gagttcgtgt agaagcgagt ctgctcaaca gcttgttatt tggtggattg 540
tggcagtaaa tcggggcgag tggggaaccg ggcgcaggaa ctgcagccgc ggttgggagt 600
ggtgctgccc ggacgggggc cccacggagg tcagagggga ggaggactct ggagctgaca 660
gcgcgcactt cacccgcagt tggtaggtgg gggagagggg aatcgggggn annctgaatg 720
gacaaancgg cacgggnagc aantgntgnt gcccngggtt cccggngcaa ttggaanctt 780
ttggaggtgg gggnanggna ttctagccaa ngggcccnnc nagcccaaaa aaangggncc 840
nc 842

<210> SEQ ID NO 123
<211> LENGTH: 815
<212> TYPE: DNA
<213> ORGANISM: Cercopithecus aethiops
<220> FEATURE:
<221> NAME/KEY: misc_feature
<222> LOCATION: (1)..(815)
<223> OTHER INFORMATION: n is a, g, c, or t

<400> SEQUENCE: 123
ttgggnaacc gagcggntaa cnttttcaca cagaaantcc caggctccat gcctgaatag 60
ctgggactac aggcacacag aatcatgccc atctaccttt ttattttttg tagagaagag 120
gtctcactat gatgcccagg ttggtctcaa acacctgtac tcaagagatc ttcccacctt 180
ggcctcccaa agtgccagct ttacaaatgt gagccactgt gggtggccat gaactcttcc 240
aatgaccctt tttcaaaaaa atatttcaac tattcaatgt gagccaagga tgtgccagac 300
atttgctaga tgctatgaat aaaatatgac aaagattcag tctttgtccc catggacttt 360
atagtctagt agtagatgag actcataagt aatatctagc caaaaataaa aattactgta 420
ttatgggaga ataagaatat ggtactaatt tcttcagtgc caatgtatat cttttcatgt 480
tcttgttcct tggattctca caacaattga tgaaaaatgt aacactggat ttgagtttgt 540
agtcttattt tccaacatga tgaagttgtt attaagtgtg agatgatcaa gggagactca 600
ggaagcagtg ggtaacctca gctaaaagca aacagatagt atattggaag atgaggtaaa 660
caaagagagc aaagctttat gaatctgggc taaaantcag ctataagtnt tcgcanatcc 720
angagaactt tncaacagnt tncaattgaa ancctttnag tttttaaann cctntttttn 780
caaantgncn aaannnttaa caggnttgna atncc 815

<210> SEQ ID NO 124
<211> LENGTH: 823
<212> TYPE: DNA
<213> ORGANISM: Cercopithecus aethiops
<220> FEATURE:
<221> NAME/KEY: misc_feature
<222> LOCATION: (1)..(823)
<223> OTHER INFORMATION: n is a, g, c, or t

<400> SEQUENCE: 124
ggnnttgcga gcggntaaca atttcacaca gaattcaaac tccagcttta ctaccctgtg 60
accttgggca ggtcacttca catttctcag gctggtttcc agtctggctg cctttgggga 120
ggggacctgg gtttgcagga agaaaacttc cttacactga ataattattg ccttgttaga 180 aatttttac catgtgcaca tattactttt cctaaatatt tgcacccaat ttaattgatt 240
taattgggga aaaatgaaca taggaaaaat aatgacctct tcctcagggt tattaaaagg 300
tttcaaaata aagtatgtag ctagtaaagg tgcatagtat atgcttaatc aatagagtgg 360
tgacagggtg gagggaggtg ggaggcaggc tcattcctgc cctggggccc agaggagaac 420
atgtggtaca gaagtcccag cctacagcca gctcctagca ttaaggcagg tgcccattca 480
gctagagcct canggggtg cnagttgagg gagctgctcc tancctggnc cccatgccct 540
ttnctttgtg gtgganccttt aagaagcccn ttttcctgan naanncctgg gnttananaa 600
ttcacctttg ncaattncca agnncccggn gnaattntcc ntnttgggng aaacccnttn 660
nntttaaggg tgnntnttng ggattngnac cnnnnttttg gggcncnccc ngntttttnn 720
tttttnttnn aaannccnnn aaaanaaaaa aaaaaanntnn gngnccnnaa anncccccnn 780
ggggggggaa aaaaaaaaaa anttttccc cccccccncc cnc 823

<210> SEQ ID NO 125
<211> LENGTH: 691
<212> TYPE: DNA
<213> ORGANISM: Cercopithecus aethiops

<400> SEQUENCE: 125

-continued

```
cctaatccac caacccccaa ctactatagt gggagcctga ggtcacagca tggccccccc     60

gtgttgtgag aaaaatctcc acaggattct cccactgttt cctaagtgtg ctctgggatc    120

ctccgtgact agtgtggaat tttgagccag tgatttctcc ccacaggttt caattaaatc    180

atctgtcaaa tgaggatgac cacatcttct ttacctcacc actgagctgt gaaatgaacc    240

agaggcctta ccttttcccc ctgaactccc agtcatccct ggaacaccaa tttgaacatc    300

atctcccact ttcccagcca gttagcagct ctgtcctctg gatttcaaag agaaatgtct    360

ctagcatcat ccctgtttcc ttgcactgtc ctactttctt tttcccccca gagccaggaa    420

tgtcttaaac agaatgagat gctcccaagg ggccaccaac tcacaattag gagttcaata    480

aatactgact taagagtgaa tgaacgatcc ccgtgtcttt gtccacattt gtacatgctt    540

acatgattct gcaaagaatc taaatttctc tttacattaa caaacaaggg ggctgggcat    600

ggtggctcat gactgtaatc tcagcatttt tgttaaccag gacagtcctg atgaaataac    660

tgggaaagtt cctttttggg gggtggggtg g                                    691
```

<210> SEQ ID NO 126
<211> LENGTH: 748
<212> TYPE: DNA
<213> ORGANISM: Cercopithecus aethiops

<400> SEQUENCE: 126

```
ccatcgcctt actattgcct tcttgacgag ttcttctgag cgggactctg gggttcgaaa     60

tgagctagcc cttaagtaac gccattttgc aaggcatgga aaaatacata actgagaata    120

gaaaagttca gatcgaggtc aggaacagat ggaacagggt cgaccggtcg accggtcgac    180

cctagagaac catcagatgt ttccagggtg ccccaaggac ctgaaatgac cctgtgcctt    240

atttgaacta accaatcagt tcgcttctcg cttctgttcg cgcgcttctg ctccccgagc    300

tcaataaaag agcccacaac ccctcactcg gggcgccagt cctccgattg actgagtcgc    360

ccgggtaccc gtgtatccaa taaaccctct tgcagttgca tccgacttgt ggtctcgctg    420

ttccttggga gggtctcctc tgagtgattg actacccgtc agcgggggtc tttcagcagg    480

gcccggggcc acagaaggaa aacatctctg tggaatgtgg aaatgcagaa ctctactggg    540

cccgtttaga aagcacagaa aagcatggaa gaaagggaga ggcgagaagc ctagaaaatt    600

accctagatc ttaggtatgg atatatcgac ctaaaagaaa gaagatgggg caaagttaat    660

gcaagcagag agtttatttg ggtcaagct tgaggattgc accccaggag catagattca    720

agttgccctg aatttacact gattagca                                       748
```

<210> SEQ ID NO 127
<211> LENGTH: 708
<212> TYPE: DNA
<213> ORGANISM: Cercopithecus aethiops

<400> SEQUENCE: 127

```
gccaaaccta caggggggt tctttcactg ccagtcagcg aaccgcgaag ccggcaggca      60

cttcggcggt ctccagcctt tgcctgaaaa gagctcggca agctagctag aggtcagacc    120

ccaggaccca gtcgttttag ctcagggaaa ggaagcgccg gacgccagcc tgcaagcttc    180

actgcgcagc cgtggacacc gccccacgtc gtagggccgt ggaccctgac aacgccggaa    240

cccggcgtcc ggtgcgtgcg cttggcggac cagaatggct aacgtaccgc catgccgcga    300

ggcccacgta gaggcggaag ttgatgggac ggacgcagat gggggaacct tgcctcgatg    360

gcactttcct gtccgcgact ccgccccgc cagaggggct aggctccggg tttcaagatg    420
```

gaggcgctga gtcgagctgg gcaggagatg agcctggcgg ccctgaagca acacgaccct 480
tacatcacca gcatcgcaga cctcacgggc caggttgctc tgtacacctt ctgccccaag 540
gccaaccagt gggtgagtgc cgcctggctc tgaggacggc cgcccggccg ctgcggtctc 600
ttaaaggggc cgtgcgtgtt gctgtggggt gggggacaca gcaagagcca gggaggtgaa 660
gacggggcca gggactgccg agaagccgac cagaaccaga ggggttgt 708

<210> SEQ ID NO 128
<211> LENGTH: 741
<212> TYPE: DNA
<213> ORGANISM: Cercopithecus aethiops
<220> FEATURE:
<221> NAME/KEY: misc_feature
<222> LOCATION: (1)..(741)
<223> OTHER INFORMATION: n is a, g, c or t

<400> SEQUENCE: 128
taacaatttt cacacagaaa ttcaatccaa caaacaanta catattattt tctaagttgt 60
aaagcctgta accgaatgag ttaattagga agggtcaatt acaagaaagt gggaaattat 120
gctagttgtt tttaaacaac taacaaagct tcaagcaggg gctaacgaga atcagtgaac 180
agactgaatg taacttttcg gaccctctcc agtgcacgaa aagccagaaa gtactgagtc 240
tgaggggaac attcagagat gacatcacca gcatcatagg tggaacaaaa cacatttaca 300
gggtctctct tgtttgtaca aaggtcttcg gggatctagt gaacatggaa gcccttttcc 360
taagtgcctt gaaatctttt ccgaaactgt gtagttcgat taaagccgga cccaccgcac 420 tccccccttcc aagaatcgaa actaattgga ttttaagctt taaatccaaa tgacctctga 480
gaaaggggct ctcatttacg tctgccgggg gagaggagga gtgtttattt tatagacaat 540
gtatatgcaa tttatctaat aatccgcaaa gcctcaaaca caagctttca ggcactcttt 600
tgaccccacc ggtctcataa ctcccaatgt atctgcaaag aaggcaggtc gcccacgtcc 660
ccaaacccga cgccaaggga ctgatcctgc tccaatcctc cctcactggc ttttccttgg 720
ggatgtgtnc agcccacttc t 741

<210> SEQ ID NO 129
<211> LENGTH: 694
<212> TYPE: DNA
<213> ORGANISM: Cercopithecus aethiops
<220> FEATURE:
<221> NAME/KEY: misc_feature
<222> LOCATION: (1)..(694)
<223> OTHER INFORMATION: n is a, g, c or t

<400> SEQUENCE: 129
ccgccaacct acagggtggg gttctttcac tgccagtaca gcgaaccgcg aagccggcag 60
gcacttcggc ggtctccagc ctttgcctga aaagagctcg gcaagctagc tagaggtcag 120
accccaggac ccagtcgttt tagctcaggg aaaggaagcg ccggacgcca gcctgcaagc 180
ttcactgcgc agccgtggac accgccccac gtcgtagggc cgtggaccct gacaacgccg 240
gaacccggcg tccggtgcgt gcgcttggcg gaccagaatg gctaacgtac cgccatgccg 300
cgaggcccac gtagaggcgg aagttgatgg gacggacgca gatgggggaa ccttgcctcg 360
atggcacttt cctgtccgcg actccgcccc cgccagaggg gctaggctcc gggtttcaag 420
atggaggcgc tgagtcgagc tgggcaggag atgagcctgg cggccctgaa gcaacacgac 480
ccttacatca ccagcatcgc agacctcacg ggccaggttg ctctgtacac cttctgcccc 540
aaggccaacc agtgggtgag tgccgcctgg ctctgaggac ggccgctccg gccgctgcgg 600
tctcttaaag gggccgtgcg tgttgctgtg gggtggggga cacagcaaga ggccagggga 660
ggtgaagacg gggccaaggg actgncgaaa agcc 694

<210> SEQ ID NO 130
<211> LENGTH: 678
<212> TYPE: DNA
<213> ORGANISM: Cercopithecus aethiops

<400> SEQUENCE: 130
ccctttactg ccagacagcg aaccgcgaag ccggcaggca cttcggcggt ctccagcctt 60
tgcctgaaaa gagctcggca agctagctag aggtcagacc ccaggaccca gtcgttttag 120
ctcagggaaa ggaagcgccg gacgccagcc tgcaagcttc actgcgcagc cgtggacacc 180
gccccacgtc gtagggccgt ggaccctgac aacgccggaa cccggcgtcc ggtgcgtgcg 240
cttggcggac cagaatggct aacgtaccgc catgccgcga ggcccacgta gaggcggaag 300
ttgatgggac ggacgcagat gggggaacct tgcctcgatg gcactttcct gtccgcgact 360
ccgcccccgc cagaggggct aggctccggg tttcaagatg gaggcgctga gtcgagctgg 420
gcaggagatg agcctggcgg ccctgaagca acacgaccct tacatcacca gcatcgcaga 480
cctcacgggc caggttgctc tgtacacctt ctgccccaag gccaaccagt gggtgagtgc 540
cgcctggctc tgaggacggc cgcccggccg ctgcggtctc ttaaaggggc cgtgcgtgtt 600
gctgtggggt gggggacaca gcaagaggcc agggaagttg aagacggggc caagggaact 660
ggccgaaaag ccaagcca 678

<210> SEQ ID NO 131
<211> LENGTH: 712
<212> TYPE: DNA
<213> ORGANISM: Cercopithecus aethiops

<400> SEQUENCE: 131
cccgccagcc tacaggtggg gtctttcact gccagtacag cgaaccgcga agccggcagg 60
cacttcggac ggtctccagc ctttgcctga aaagagctcg gcaagctagc tagaggtcag 120
accccaggac ccagtcgttt tagctcaggg aaaggaagcg ccggacgcca gcctgcaagc 180
ttcactgcgc agccgtggac accgccccac gtcgtcgggc cgtggaccct gacaacgccg 240
gaacccggcg tccggtgcgt gcgcttggcg gaccagaatg gctaacgtac cgccatgccg 300
cgaggcccac gtagaggcgg aagttgatgg gacggacgca gatgggggaa ccttgcctcg 360
atggcacttt cctgtccgcg actccgcccc cgccagaggg gctaggctcc gggtttcaag 420
ttggaggcgc tgagtcgagc tgggcaggag atgagcctgg cggccctgaa gcaacacgac 480
ccttacatca ccagcatcgc agacctcacg ggccaggttg ctctgtacac cttctgcccc 540
aaggccaacc cagtgggtga gtgccgcctg gctctgagga cagccgcccg gccgctgcgg 600
tctcttaaag gggcccgtgc gtgttgctgt gggggtgggg gaacacagca agaggccagg 660
ggaggtgaag accggggcca gggacctggc gaaaagcccg aaccagaagc cc 712

<210> SEQ ID NO 132
<211> LENGTH: 738
<212> TYPE: DNA
<213> ORGANISM: Cercopithecus aethiops
<220> FEATURE:
<221> NAME/KEY: misc_feature
<222> LOCATION: (1)..(738)
<223> OTHER INFORMATION: n is a, g, c or t

<400> SEQUENCE: 132
gccagcctac agggggggt ctntcactgc acagtacagc gaaccgcgaa gccggcaggc 60
acttcggcgg tctccagcct ttgcctgaaa agagctcggc aagctagcta gaggtcagac 120
cccaggaccc agtcgtttta gctcagggaa aggaagcgcc ggacgccagc ctgcaagctt 180
cactgcgcag ccgtggacac cgccccacgt cgtagggccg tggaccctga caacgccgga 240
acccggcgtc cggtgcgtgc gcttggcgga ccagaatggc taacgtaccg ccatgccgcg 300
aggcccacgt agaggcggaa gttgatggga cggacgcaga tgggggaacc ttgcctcgat 360
ggcactttcc tgtccgcgac tccgcccccg ccagaggggc taggctccgg gtttcaagat 420
ggaggcgctg agtcgagctg ggcaggagat gagcctggcg gccctgaagc aacacgaccc 480
ttacatcacc agcatcgcag acctcacggg ccaggttgct ctgtacacct tctgccccaa 540
ggccaaccag tgggtgagtg ccgcctggct ctgaggacgg ccgcccggcc gctgcggtct 600
cttaaagggg ccgtgcgtgt ttgctgtggg gtgggggaca cagcaagagg ccagggaggt 660
gaagacnggg gccagggnac tggcgaagag ccgagccaaa gccagagggg tgtcgggtcc 720
acctgggaat tgggggaa 738

<210> SEQ ID NO 133
<211> LENGTH: 757
<212> TYPE: DNA
<213> ORGANISM: Cercopithecus aethiops

<400> SEQUENCE: 133
cgccaaacct acaggggggg tctttcactg ccagacagcg aaccgcgaag ccggcaggca 60
cttcggcggt ctccagcctt tgcctgaaaa gagctcggca agctagctag aggtcagacc 120
ccaggaccca gtcgttttag ctcagggaaa ggaagcgccg gacgccagcc tgcaagcttc 180
actgcgcagc cgtggacacc gccccacgtc gtagggccgt ggaccctgac aacgccggaa 240
cccggcgtcc ggtgcgtgcg cttggcggac cagaatggct aacgtaccgc catgccgcga 300
ggcccacgta gaggcggaag ttgatgggac ggacgcagat gggggaacct tgcctcgatg 360
gcactttcct gtccgcgact ccgcccccgc cagaggggct aggctccggg tttcaagatg 420
gaggcgctga gtcgagctgg gcaggagatg agcctggcgg ccctgaagca acacgaccct 480
tacatcacca gcatcgcaga cctcacgggc caggttgctc tgtacacctt ctgccccaag 540
gccaaccagt gggtgagtgc cgcctggctc tgaggacggc cgcccggccg ctgcggtctc 600
ttaaaggggc cgtgcgtgtt gctgtggggt gggggacaca gcaagaggcc aggggaggtg 660
aagacggggg ccaggggact ggcgaagagc ccgagccaga gccagagggg tgtcgggtcc 720
acctgggatt ggggggatag gaagtgagaa gaagtgg 757

<210> SEQ ID NO 134
<211> LENGTH: 668
<212> TYPE: DNA
<213> ORGANISM: Cercopithecus aethiops
<220> FEATURE:
<221> NAME/KEY: misc_feature
<222> LOCATION: (1)..(668)
<223> OTHER INFORMATION: n is a, g, c or t

<400> SEQUENCE: 134
ccagcctaca ggggggggtt ctttcactgc cagtacagcg aaccgcgaag ccggcaggca 60
cttcggcggt ctccagcctt tgcctgaaaa gagctcggca agctagctag aggtcagacc 120
ccaggaccca gtcgttttag ctcagggaaa ggaagcgccg gacgccagcc tgcaagcttc 180
actgcgcagc cgtggacacc gccccacgta gtagggccgt ggaccctgac aacgccggaa 240

```
cccggcgtcc ggtgcgtgcg cttggcggac cagaatggct aacgtaccgc catgccgtga    300

ggcccacgta gaggcggaag ttgatgggac ggacgcagat gggggaacct tgcctcgatg    360

gcactttcct gtccgcgact ccgcccccgc cagaggggct aggctccggg tttcaagatg    420

gaggcgctga gtcgagctgg gcaggagatg agcctggcgg ccctgaagca acacgaccct    480

tacatcacca gcatcgcaga cctcacgggc caggttgctc tgtacacctt ctgccccaag    540

gccaaccagt gggtgagtgc cgcctggctc tgaggacggc ccgcccggcc gctgncggtc    600

ntcttaaaag gggcccganc gtgtttgctg tgggggtggg gggacncaag caagaaggcn    660

cagggagg                                                             668
```

<210> SEQ ID NO 135
<211> LENGTH: 752
<212> TYPE: DNA
<213> ORGANISM: Cercopithecus aethiops
<220> FEATURE:
<221> NAME/KEY: misc_feature
<222> LOCATION: (1)..(752)
<223> OTHER INFORMATION: n is a, g, c or t

<400> SEQUENCE: 135

```
gcttgccaaa cctacagggg gggtctttca ctgccagaca gcgaaccgcg aagccggcag     60

gcacttcggc ggtctccagc ctttgcctga aaagagctcg gcaagctagc tagaggtcag    120

accccaggac ccagtcgttt tagctcaggg aaaggaagcg ccggacgcca gcctgcaagc    180

ttcactgcgc agccgtggac accgccccac gtcgtagggc cgtggaccct gacaacgccg    240

gaacccggcg tccggtgcgt gcgcttggcg gaccagaatg gctaacgtac cgccatgccg    300

cgaggcccac gtagaggcgg aagttgatgg gacggacgca gatgggggaa ccttgcctcg    360

atggcacttt cctgtccgcg actccgcccc cgccagaggg gctaggctcc gggtttcaag    420

atggaggcgc tgagtcgagc tgggcaggag atgagcctgg cggccctgaa gcaacacgac    480

ccttacatca ccagcatcgc agacctcacg ggccaggttg ctctgtacac cttctgcccc    540

aaggccaacc agtgggtgag tgccgcctgg ctctgaggac ggccgcccgg ccgctgcggt    600

ctcttaaagg ggccgtgcgt gttgctgtgg ggtgggggac acagccagga ggccaaggga    660

ggtgaagacn ggggccaggg actggcgaag agccgagcca ganccagagg ggtgtcgggt    720

tcacctggga ttgggggata ggagtgagag aa                                  752
```

<210> SEQ ID NO 136
<211> LENGTH: 739
<212> TYPE: DNA
<213> ORGANISM: Cercopithecus aethiops
<220> FEATURE:
<221> NAME/KEY: misc_feature
<222> LOCATION: (1)..(739)
<223> OTHER INFORMATION: n is a, g, c or t

<400> SEQUENCE: 136

```
ctttcactgc cagnacagcg aaccgcgaag ccggcaggca cttcggcggt ctccagcctt     60

tgcctgaaaa gagctcggca agctagctag aggtcagacc ccaggaccca gtcgttttag    120

ctcagggaaa ggaagcgccg gacgccagcc tgcaagcttc actgcgcagc cgtggacacc    180

gccccacgtc gtagggccgt ggaccctgac aacgccggaa cccggcgtcc ggtgcgtgcg    240

cttggcggac cagaatggct aacgtaccgc catgccgcga ggcccacgta gaggcggaag    300

ttgatgggac ggacgcagat gggggaacct tgcctcgatg gcactttcct gtccgcgact    360

ccgcccccgc cagaggggct aggctccggg tttcaagatg gaggcgctga gtcgagctgg    420
```

gcaggagatg agcctggcgg ccctgaagca acacgaccct tacatcacca gcatcgcaga 480
cctcacgggc caggttgctc tgtacacctt ctgccccaag gccaaccagt gggtgagtgc 540
cgcctggctc tgaggacggc cgcccggccg ctgcggtctc ttaaaggggc cgtgcgtgtt 600
gctgtggggt gggggacaca gcaagaggcc agggaggtga agacggggcc agggactggc 660
gaagagccga gccagagcca gaggggtgtc gggtccacct gggattgggg gataggggtg 720
agagaagngg ctgganaat 739

<210> SEQ ID NO 137
<211> LENGTH: 707
<212> TYPE: DNA
<213> ORGANISM: Cercopithecus aethiops
<220> FEATURE:
<221> NAME/KEY: misc_feature
<222> LOCATION: (1)..(707)
<223> OTHER INFORMATION: n is a, g, c or t

<400> SEQUENCE: 137
gccaaaccta caggtgggat ctttcactgc cagacagcga accgcgaagc cggcaggcac 60
ttcggcggtc tccagccttt gcctgaaaag agctcggcaa gctagnttag aggtcagacc 120
ccaggaccca gtcgttttag ctcagggaaa ggaagcgccg gacgccagcc tgcaagcttc 180
actgcgcagc cgtggacacc gccccacgtc gtagggccgt ggaccctgac aacgccggaa 240
cccggcgtcc ggtgcgtgcg cttggcggac cagaatggct aacgtaccgc catgccgcga 300
ggcccacgta gaggcggaag ttgatgggac ggacgcagat gggggaacct tgcctcgatg 360
gcactttcct gtccgcgact ccgccccgc cagaggggct aggctccggg tttcaagatg 420
gaggcgctga gtcgagctgg gcaggagatg agcctggcgg ccctgaagca acacgaccct 480
tacatcacca gcatcgcaga cctcacgggc caggttgctc tgtacacctt ctgccccaag 540
gccaaccagt gggtgagtgc cgcctggctc tgaggacggc cgcccggccg ctgcggtctc 600
ttaaaggggc cgtgcgtgtt gctgtggggt gggggacaca gcaagaggcc agggaggtga 660
agacggggcc agggactggc gaagagccga gccagagcca gaggggt 707

<210> SEQ ID NO 138
<211> LENGTH: 818
<212> TYPE: DNA
<213> ORGANISM: Cercopithecus aethiops
<220> FEATURE:
<221> NAME/KEY: misc_feature
<222> LOCATION: (1)..(818)
<223> OTHER INFORMATION: n is a, g, c or t

<400> SEQUENCE: 138
tcacacagaa ttcagnaaag cacagctgtc taggcgtttg gctcctgaca aatggttgcc 60
tgcccctcac ctcaccagcc tctccagaca cctctgcatc acacagcact gatgaccgcc 120
tcccagccca acacccactc tgcttactct gtgccgccag gctctgattg tgtttgggag 180
gtaaagtgct cagccccaag actggccaaa cttggccctc atcatcccat tcctccttgc 240
cagtggttta tctaggaata gatatggggc cctgttcagg tcagtgaaat gtaagggtga 300
gttagttcag gaatttctga gaaagattct cctctgtaat aaagcagaga gtcacatgac 360
tagaaaatct ttttgttgtt gttgttgttt taccaccacc ccttccttcc tgctttggaa 420
atcggtttat gatgtgatgc ctggagctgt ggcagctgtt ttatgaccat gagagaaggc 480
ttctccagtg tgctaggatt caggggagga aatacagaat gaatgtcagc cctcgatgac 540
actgccgagc cctaaaccaa ctctgagaat ttaagacttt ttgttctgta agaaatgaga 600
tttatttatt gtttaagact ctgttgggta ttctgttatc tgtggcccan aatattttaa 660
ataatataat ttctttttgc aataatacat ctcagatgga cattccccaa agtctaagac 720
tttgagagaa gtcatctctg aagagccaag cattcataat tagaaacttg gccaggtgca 780
gtggctcacg cctgtgatcc cagcactttg ggaggcca 818

<210> SEQ ID NO 139
<211> LENGTH: 581
<212> TYPE: DNA
<213> ORGANISM: Cercopithecus aethiops
<220> FEATURE:
<221> NAME/KEY: misc_feature
<222> LOCATION: (1)..(581)
<223> OTHER INFORMATION: n is a, g, c or t

<400> SEQUENCE: 139
cacacaaatt agnncaggtc atcctcctgg tggttcctgt accagtcctc gatcacctcc 60
tcaaactctt ccaccagcac gtcgcactgt taatcgtaac acctcacgtt ggcaaagccc 120
cagcacctta ctcactccta gaggagctca gctaagcctt gcaacccact gcaaggtagt 180
ggcagtggtt cacctaagga aactgaggct agagaggtga aatgacgtga ccaaagccac 240
cctggcctgg gtggccctcc tcagagcaga cccaatcccc accggcccct cactgggcac 300
agcaaccctt ccaagggctg aagggcctgt acctgcttct tgaggtcagc cacctctgca 360
gaagtctcgt tccacagctc ataggggatg tccatcacca ccttgacccc tttgtgtacc 420
aggttgtgta atgtctcaaa ggtctctgac atgccctgga agaagcgacc agacatggga 480
ggcagagctc ccttctctcc ctcctaccct cctctcccag tggggcctat gaactcagct 540
gtaagaccaa tgcccaatgc cctctgagga tcctcaaacc t 581

<210> SEQ ID NO 140
<211> LENGTH: 630
<212> TYPE: DNA
<213> ORGANISM: Cercopithecus aethiops

<400> SEQUENCE: 140
tcacacagaa ttccatgttc agtaaccagg tgctacaaat gcagttcaag gctctaggtc 60
atgacaatgt cacagatatc tcaggtccag tcaccaaggc aacatgtggc ttgggtcttt 120
ttctggtttc aagactgcat ctgtattctc tcacctccct gggcccacag attccctaaa 180
tcatagcttg gtctaagagc aatgcttcaa attcaggtcc cttgtctcag gtgggtagac 240
ttcctgtcac ccagccaccg ccacctgatt ctggacctgg agccggcagg cccgtggctt 300
cagcccgact cactcttttg tattctgttg cttactatca tctttttttt ttttggtctt 360
gaactccgca gtgtcatttt ttttttctag tttatccatc tttgccatgt gtttggggaa 420
gaatggcaat gcgaaagtgt gaacttccag tcccggctta ttagaagccc acagctgttt 480
taaaaaaaat ctaccttgct atcctttccc ttttctgtga cacacaagtg actgttaatt 540
agtacctagg ccatgggctg tcatgcttaa aaactgaatg gaatttttttg ttcttttagc 600 aatgttagga tgactggctg attataaaaa 630

<210> SEQ ID NO 141
<211> LENGTH: 737
<212> TYPE: DNA
<213> ORGANISM: Cercopithecus aethiops
<220> FEATURE:
<221> NAME/KEY: misc_feature
<222> LOCATION: (1)..(737)
<223> OTHER INFORMATION: n is a, g, c or t

<400> SEQUENCE: 141
acacagaatt cttacttaat acatataaac agaacatttc taggtcagtg aacaaaaata 60
taacctgaat cataaaaaca gagttataac tcctccatca atttccagac atcagccagt 120
ttacaaatcc agaacccctt aaatgaagaa caagcttgat gcccttgagg aagggcccta 180
gtacactgcc caaaatctgt acatttaatt ttcctcctaa tcttcccaaa agggacatat 240
gtccttttac cagtgaaact gctcatttgg gtaattgaaa ataatcaaat caggtactac 300
tggaccctgg ctacgaactg atgcaaattc caggagacct aacatgccat ggtggtccac 360
aaagacagtg cttatgggaa tcaggtgatc catggagttt taagttgggt ccaactcaca 420
gtgggtccac attgtccctc atgtaccctg tagttatgta ctcagttctg gaatgcatat 480
tttgaataaa tatactcatg ctgacagaat ctccataatg gttccctgac ctgtaaagtg 540
aggtgcatta tggtgggtaa tggcaaatgg aagccagtag aaacacctct atctaggaaa 600
aatagtaaag caaatgcaat attttcatct ccgtagggat tgcagacatt agttgccacc 660
atcaagggct tgaaaaatga ccagggggtg attcccacca acattctnca ttcagctttg 720
tctattnggg ccttgcc 737

<210> SEQ ID NO 142
<211> LENGTH: 768
<212> TYPE: DNA
<213> ORGANISM: Cercopithecus aethiops

<400> SEQUENCE: 142
tttcacacag aattcagtgg atgctatgaa acatatcttc actgttcgtg tttgtctctt 60
tctgaatcca caagtgatgg acacatgaat ctactactac tgttctcttt tcttcttttt 120
ccgtctttct ctcccttccc acccctagtt cctgacgttt gcctactcta tcatgtctgc 180
tgaggtcagg aatattcatt tatcttcatg ctcaaggtaa gtgaagccat taatgctgaa 240
agtgttgcat accactctgc atcctcatct gtctgagaca cattcaacca ctaggtcctc 300
agctgcttca ctgctgcctg atgttctttg aagtccagta taagagagaa cattctattt 360
tgctaaaact aaaagactac cctttatctt tgctgagaat atgtaaagaa aaggggaatg 420
actagatcag aaggcttatt ctgaggtata tagtaatgtt aatttttaaa taattgttag 480
gtgttcttct tcattaggta ttcaccttca gttttccaag actatggaaa gcaccattgg 540
tgcatgtagt taacagcagc ttgactcaga cgtagaactg cagccaggac ccatctgttc 600
cccattactc cctgctgcca gttttgcaac cagaacctag gagtgattta tcccatcctc 660
aattttgctc aggactcagc agaagaagga tcctgggaca caagactttt cagtggcttc 720
aaacttggga gagttctttg gcaatgcaca ggtttgacct atgaactg 768

<210> SEQ ID NO 143
<211> LENGTH: 450
<212> TYPE: DNA
<213> ORGANISM: Cercopithecus aethiops
<220> FEATURE:
<221> NAME/KEY: misc_feature
<222> LOCATION: (1)..(450)
<223> OTHER INFORMATION: n is a, g, c or t

<400> SEQUENCE: 143
gcctgtgaaa ccatctggnc ctggactttt tttggttggn aggctatcaa cttattgcct 60
caatttcaga gcctactatt ggtctattca gggatctcaa ctncttcctg gctttagtct 120
tggaagagtg taagtgtcca ggaaatctat ccatcttctt ctagattttc cagtttattn 180

```
cgcgcagagg cgttcacagc agcctctgat ggtagttcga atttctgagg ggncggcggn    240

gatatcccct ttatcattnt naatngcgnc gatnagacnc ttctctcttn tcttctttat    300

aagcactcng ctagccggcc ngccaatntc gnngangctt ntcaaaaaac caactcctgg    360

attcatcgat tncnntggag ggtctntttg ngtctctatc tccttcagtn actgcnctga    420

tcttagnata tttcntgccn tctgctagct                                      450
```

<210> SEQ ID NO 144
<211> LENGTH: 729
<212> TYPE: DNA
<213> ORGANISM: Cercopithecus aethiops
<220> FEATURE:
<221> NAME/KEY: misc_feature
<222> LOCATION: (1)..(729)
<223> OTHER INFORMATION: n is a, g, c or t

<400> SEQUENCE: 144

```
cacacagaat taccctttc gccttccaag gggaaaccag gccactttgc tcttcttggg      60

gaaggaggat aattgtccag tgctgggagg tgacagcagc tactgccagc acgaggtggg    120

gcccctgcag tgtggttcct caggtctgag aggggttccc tctgccttcc tccctcctgc    180

tccccttcc tctttcctct acctgttttt tccttctctc acatctctcc tgcttcccca      240

caatccctga catttactgc aggctcccga agagccatga cactttatac cctcaacctc    300

atttaattct caggaaaccc cacaaggccg tgcaattctc accccaggta ccaagtgagc    360

cagttcaggt gcacagagac tgccccttgc ccagagatcc tagcacgagg gctctgtact    420

ggttagggtc tccagagaaa cagctccaat agaatgtgca gatgctgggt gcagtggctc    480

acccctgtaa tcccagcact ttgggaggcc gaggcgggcg gatcatgagg tcaggagatc    540

gagaccatcc tggctaacac ggtgaaaccc catctctact aaaaatacaa aaacattagc    600

cgggccgtgg tggcgggncg cctgtagtcc cagctacttg ggaggctgag ggcaggagaa    660

tggcatgaag ccganaggca nagcttgcag tgagccaaga tcacatggca ctccaacctg    720

ggcgacaaa                                                             729
```

<210> SEQ ID NO 145
<211> LENGTH: 755
<212> TYPE: DNA
<213> ORGANISM: Cercopithecus aethiops
<220> FEATURE:
<221> NAME/KEY: misc_feature
<222> LOCATION: (1)..(755)
<223> OTHER INFORMATION: n is a, g, c or t

<400> SEQUENCE: 145

```
aacaattttc acacagaatt acctggtctc aaagtgtatc ctccatgctt cggcctccca     60

aagtattgtg attacaggag tgacccaccc tgcccggccc tctagcttat ggtggaagct    120

taaataatca gttttagaca tttcttcttc cttttttcc caagaaacag ggtcttgctc     180

tgccacccac gctggaatga agtggtgcaa tcatagctga ttgcaacctc aaactcctta    240

actcaatcaa tcctcccacc tcagcctttc aaatagctgg gactacagtg cgtaagccac    300

cgcacctggc ctcttctttc taatataagt atttaatatt ataaaatttc ctctaagatc    360

taaacactgc tttagctgca actcacaaat tttgatatgt tgtattttta tttatatccc    420

attaaaaata cagtattagt tcccgtgtga tttcttcttt gacccatggc ttagaagtgt    480

gttgtttagt ttccaaattt gggggcattt tccagatatc tttctcttat ttatttgtaa    540

tttaattctg ttgtggtcga ggagcacgtt ctgtttgctt acaatcctcg taaatttatt    600
```

atgacttgtt ttatggccca gcatagggtc tgtttggcga gtgttccatg tgcatctgaa 660
aagaatgtgt attctgtagt tgtgcagggt atttttaaaa ttttattctt ttcactgana 720
caaaatagct gtncatattt agagggtaca tgcga 755

<210> SEQ ID NO 146
<211> LENGTH: 795
<212> TYPE: DNA
<213> ORGANISM: Cercopithecus aethiops

<400> SEQUENCE: 146
ctaccagtat atacaaagaa aagctcgtac cattcatgct gaaactactc caaaaagttg 60
aggagaagga aatcctccct agcttattct acaaagctag catcacactg ctaccaaaac 120
ctgacagagt cacaacaaca aaaatttcag acatatattc ttgatgaaca ttgatgcaaa 180
gtagtcaaca aaatacttgc aaaccaaatt cagcagcaca tcaaaaagct tatccatcat 240
gatcaagtag gctttatccc tgggatgcaa ggttggttca acatctgcaa atcaataaat 300
gtgattcatc acataaatac cactaaagac aaaaaaacca catgattatc tcaacagatg 360
cagaaaaggc ttttgataaa atccaatacc ccttcatgtt aaaaactctc aataaactag 420
gtattgaagg aacatacctc aaagtaataa gaaccaccta taaaaaaccc acagccaaca 480
tcatattgaa tgggcaaaag ctggaagcaa tccccttgaa aactggagga agacaagaat 540
accctttctt accactccta ttcaacataa tattggaagt cctggccagg acaagcaggc 600
aagagaaaga aagaaaggca tcccaatagg aagaaaggga agtcaaacta tccctgtttg 660
cagacaaaat gatcctatag ctagaaaccc catagtctca gcccaaagct tttaagctga 720
taaacacttt cagcaagcct cagcatacaa aatcatgtgc aaaagtcagt acattttgta 780
caccaccaac agtca 795

<210> SEQ ID NO 147
<211> LENGTH: 704
<212> TYPE: DNA
<213> ORGANISM: Cercopithecus aethiops
<220> FEATURE:
<221> NAME/KEY: misc_feature
<222> LOCATION: (1)..(704)
<223> OTHER INFORMATION: n is a, g, c or t

<400> SEQUENCE: 147
gcatcctccc tcctcggcct gggcgtgggc tcgcaaaacg ctgggattcc cggtattaca 60
ggcgggcgcg ccacgccagg agcaaacact tcctgcttta aaaattcagt gttgtgattg 120
gctgccattc agcattatgc taattaagca tgcctgtttt ttttaagctt cttaaaacaa 180
ttttttaaaa ttccgtttcc acctaaaacg ttaaaatttg tcaagtgata atattcgaga 240
agatgttgtt gccaaactat ttttctattt gtttcctaat ggcatcggaa atagcgaaag 300
tatctcgcca ttagttaaaa gttggcagca gatgtagacc ccgcagaggc tgcgagtggg 360
ctgttaagac tatactttca gggatcattt ctatagtttg ttactagaga agttctctct 420
gaacgtgtag agcaccgaaa accacgagga agagacgtag cgttttctcc tgagcgtgaa 480
gcgggcgttt ggtgttgctt cgctgcaact gccatcagcc attgatgatc gttcttctct 540
ccgctttgga gagnaagagg gagagaacgc ggtctgagtg gtttttcttt tttgcgnggt 600
tagaacgaca gactgtacag cgaccgtntc ccggcttgnc tntgtgcttg nntgnccncc 660
ngaggccnaa gngagttgcc ttattttgtt tcacnanccg ntgt 704

<210> SEQ ID NO 148
<211> LENGTH: 650
<212> TYPE: DNA
<213> ORGANISM: Cercopithecus aethiops
<220> FEATURE:
<221> NAME/KEY: misc_feature
<222> LOCATION: (1)..(650)
<223> OTHER INFORMATION: n is a, g, c or t

<400> SEQUENCE: 148
atcgccttct atcgccttct tgacgagttc ttctgagcgg gactctgggg ttcgaaatga 60
gctagccctt aagtaacgcc attttgcaag gcatggaaaa atacataact gagaatagaa 120
aagttcagat cgaggtcagg aacagatgga acagggtcga ccggtcgacc ggtcgaccct 180
agagaaccat cagatgtttc cagggtgccc caaggacctg aaatgaccct gtgccttatt 240
tgaactaacc aatcagttcg cttctcgctt ctgttcgcgc gcttctgctc cccgagctca 300
ataaaagagc ccacaacccc tcactcgggg cgccagtcct ccgattgact gagtcgcccg 360
ggtacccgtg tatccaataa accctcttgc agttgcatcc gacttgtggt ctcgctgttc 420
cttgggaggg tctcctctga gtgattgact acccgtcagc gggggtcttt cagttaagac 480
tatactttca gggatcattt ctatagtttg ttactagaga agtttctctg aacgtgtaga 540
gcaccgaaaa ccacgaggaa gagacgtagc gttttctcct gagcgtgaag cgggcgtttg 600
gtgttgcttc gctgcactgc catcanccat tgatgatcgt tttntntccg 650

<210> SEQ ID NO 149
<211> LENGTH: 671
<212> TYPE: DNA
<213> ORGANISM: Cercopithecus aethiops
<220> FEATURE:
<221> NAME/KEY: misc_feature
<222> LOCATION: (1)..(671)
<223> OTHER INFORMATION: n is a, g, c or t

<400> SEQUENCE: 149
aactttaact aatggcgaga taccttcgct attgccgatg ccattaggaa acaaatagaa 60
aaatagtctg gcaacaacat cttctcgaat attatcactc gacaaattat aacgttttag 120
gtggaaacgg aactttaaaa aattgtttta agaagcggaa aaaaaacagg catgcataat 180
tagcataatg ctgaatggca gccaatcaca aactgaatct ccaaagcagg aagtgtttgc 240
tcctggcgtg gcgcgcccgc ctgtaatccg ggaatcccag cgtttagcga gcccacgccc 300
aggccgagga gggaggatcc tttgttccac gagatcgaca ccagcctagg caatatagca 360
gaatcctggt ggtgacggaa atgccctatc ttgagcttat caatgccaaa accccggtca 420
tataacttta ttggatatca gtggggaaaa ctgagtaaaa ggtgcaaatg tataactcag 480
tataaacccc aagaacgaaa cgcaaaacct accattctct gaaagaaatg ttttgtacat 540
atatttacac agaaacacat acatcatgat caaaaaatga catcattcgt aaaaaaaaat 600
aacaaaaagt gtaaaagaac ccatcgcccg gaaaggaagg gccctgtgag accggatccc 660
caaaaccaaa c 671

<210> SEQ ID NO 150
<211> LENGTH: 704
<212> TYPE: DNA
<213> ORGANISM: Cercopithecus aethiops
<220> FEATURE:
<221> NAME/KEY: misc_feature
<222> LOCATION: (1)..(704)
<223> OTHER INFORMATION: n is a, g, c or t

<400> SEQUENCE: 150

```
tcattaacag cccactcgca gcctctgcgg ggtctacatc tgctgccaac ttttaactaa     60

tggcgagata ctttcgctat ttccgatgcc attaggaaac aaatagaaaa atagtttggc    120

aacaacatct tctcgaatat tatcacttga caaattttaa cgttttaggt ggaaacggaa    180

ttttaaaaaa ttgttttaag aagcttaaaa aaaacaggca tgcttaatta gcataatgct    240

gaatggcagc caatcacaaa ctgaattttt aaagcaggaa gtgtttgctc ctggcgtggc    300

gcgcccgcct gtaatccggg aatcccagcg ttttgcgagc ccacgcccag gccgaggagg    360

gaggatcctt tgttccacga gttcgacacc agcctaggca atatagcaga attctgtgtg    420

aaattgttat ccgctcacaa ttccacacaa catgagcgtc agaccccgaa gaaaagatca    480

aaggatcttc ttgagatcct ttttttctgc gcgtaatctg ctgcttgcaa acaaaaaaac    540

caccgctacc agcggtggtt tgtttgccgg atcaagagct accaactctt tttccgaagg    600

taactggctt cagcagagcg cagataccaa atactgtcct tctagtgtag ccgtagttag    660

gcccnccact tcaagaactc tgtagcaccg cctacatacc tcga                     704
```

<210> SEQ ID NO 151
<211> LENGTH: 705
<212> TYPE: DNA
<213> ORGANISM: Cercopithecus aethiops

<400> SEQUENCE: 151

```
gctatattgc ctaggctggt gtcgaactcg tggtaacaaa ggatcctccc tcctcggcct     60

gggcgtgggc tcgcaaaacg ctgggattcc cggattacag gcgggcgcgc cacgccagga    120

gcaaacactt cctgctttaa aaattcagtt tgtgattggc tgccattcag cattatgcta    180

attaagcatg cctgtttttt ttaagcttct taaaacaatt ttttaaaatt ccgtttccac    240

ctaaaacgtt aaaatttgtc aagtgataat attcgagaag atgttgttgc caaactattt    300

ttctatttgt ttcctaatgg catcggaaat agcgaaagta tctcgccatt agttaaaagt    360

tggcagcaga tgtagacccc gcagaggctg cgagtgggct gttaatgaaa gaccccacct    420

gtaggtttgg caagctagct gaggatcgtt tcgcatgatt gaacaagatg gattgcacgc    480

tggttctccg gccgcttggg tggagaggct attcggctat gactgggcac aacagacaat    540

cggctgctct gatgccgccg tgttccggct gtcagcgcag gggcgcccgg ttctttttgt    600

caagaccgac ctgtccggtg ccctgaatga actgcaggac gaggcagcgc ggctatcgtg    660

gctggccacg acgggcgttc cttgcgcacc tgtgctcgac gttgt                    705
```

<210> SEQ ID NO 152
<211> LENGTH: 673
<212> TYPE: DNA
<213> ORGANISM: Cercopithecus aethiops

<400> SEQUENCE: 152

```
tttcattaac agcccactcg cagcctctgc ggggtctaca tctgctgcca acttttaact     60

aatggcgaga tactttcgct atttccgatg ccattaggaa acaaatagaa aaatagtttg    120

gcaacaacat cttctcgaat attatcactt gacaaatttt aacgttttag gtggaaacgg    180

aattttaaaa aattgtttta agaagcttaa aaaaaacagg catgcttaat tagcataatg    240

ctgaatggca gccaatcaca aactgaattt ttaaagcagg aagtgtttgc tcctggcgtg    300

gcgcgcccgc ctgtaatccg ggaatcccag cgttttgcga gcccacgccc aggccgagga    360

gggaggatcc tttgttccac gagttcgaca ccagcctagg caatatagca gaattcatct    420

cacagagtta catctttccc ttcaagaagc ctttcgctaa ggctgttctt gtggaattgg    480
```

caaagggata tttggaagcc catagagggc tatggtgaaa aaggaaatat cttccgttca 540
aaactggaaa gaagctttct gagaaactgc tctgtgttcc tctgaattct ggaagaaaac 600
aaacacatca ttcttgtctc caagagctta aatttctgtt tgggcaattt atttataaaa 660
acacaactta gcc 673

<210> SEQ ID NO 153
<211> LENGTH: 709
<212> TYPE: DNA
<213> ORGANISM: Cercopithecus aethiops
<220> FEATURE:
<221> NAME/KEY: misc_feature
<222> LOCATION: (1)..(709)
<223> OTHER INFORMATION: n is a, g, c or t

<400> SEQUENCE: 153
tttcattaac agcccactcg cagcctctgc ggggtctaca tctgctgcca acttttaact 60
aatggcgaga tactttcgct atttccgatg ccattaggaa acaaatagaa aaatagtttg 120
gcaacaacat cttctcgaat attatcactt gacaaatttt aacgttttag gtggaaacgg 180
aattntaaaa aaagttttta agaagcttaa aaaaaacagg catgcttaat tagcataatg 240
ctgaatggca gccaatcaca aactgaattt ttaaagcagg aagtgtttgc tcctggcgtg 300
gcgcgcccgc ctgtaatccg ggaatcccag cgttttgcga gcccacgccc aggccgagga 360
gggaggatcc tttgttccac gagttcgaca ccagcctagg caatatagca gaattctgtg 420
tgaaattgtt atccgctcac aattccacac aacatgagcg tcagaccccg aagaaaagat 480
caaaggatct tcttgagatc cttttttttc tgcgcgtaat ctgctgcttg caaaacaaaa 540
aaaccaccgc taccagcggt ggtttgtttg cncgggatca agagtctacc aacctctttt 600
ttacgaaagg tnactgggct tcaggcagga gccgcanatt nccaaaataa ttggnccctt 660
ccaagnggnn ancccgcnag gnttagggcc cncccaactt tcnaaggac 709

<210> SEQ ID NO 154
<211> LENGTH: 574
<212> TYPE: DNA
<213> ORGANISM: Cercopithecus aethiops
<220> FEATURE:
<221> NAME/KEY: misc_feature
<222> LOCATION: (1)..(574)
<223> OTHER INFORMATION: n is a, g, c or t

<400> SEQUENCE: 154
cctcggcctg ggcgtgggct cgcaaaacgc tgggattccc ggattacagg cgggcgcgcc 60
acgccaggag caaacacttc ctgctttaaa aattcagttt gtgattggct gccattcagc 120
attatgctaa tnaagcatgc ctgttttttt taagcttctt aaaacaattt tttaaaattc 180
cgttaccacc taaaacgtta aaatttgtca agtgataata ttcgagaaga tgttgttgcc 240
aaactatttt tctatttgnt tcctaatggc atcggaaata gcgaaagtat ctcgccatta 300
gttaaaagtt ggcagcagat gtagaccccg cagaggctgc gagtgggctg ttaatgaaag 360
accccacctg taggtttggc aagcatagct gaggatcgtt tcgcatgntt gaacaagatg 420
gattgcacgc tggntctccg gccgctngng tggagaggct attcggntat gactgggcac 480
aacagacaaa tcgggctgnt ctgatgccgc cgtgttccgg ntgtaagcgc aggggcgccc 540
cngtttcttt tttgnaaaga ccganctgta acgg 574

<210> SEQ ID NO 155
<211> LENGTH: 794

<212> TYPE: DNA
<213> ORGANISM: Cercopithecus aethiops
<220> FEATURE:
<221> NAME/KEY: misc_feature
<222> LOCATION: (1)..(794)
<223> OTHER INFORMATION: n is a, g, c or t

<400> SEQUENCE: 155

```
actccggaga tatgaggcct agctccatcc ttcttttctt atcactcagt cattcaatct     60

ttgcttggaa tacatgaact aataatttcc aatattacct gacatggatc cactttaggg    120

aagacacaag atatgaaaga aaggataaag tctgaaagtt agaagtaaca caactacaga    180

aaatagatta atgtggattg ttatagccat tcatacaatg acatcctcaa cgtcaaaacc    240

tttttgtact ctttacagat tccacatcca agcagaattc tatttaatgt gctttctaac    300

aatcagattc ctgacaaatg tgttcataaa gtaataaaag cagcaaaatc ttaaatgttt    360

tatactaaca tagtagacaa aatacaaata ctctgaacac taatatcaca gaaaccctta    420

aaaaaaagat tgaggggagg taataacata cctaatacaa atagaaataa ggaggaacct    480

ttgaggtttg ctatgctttg aacgtgtccc caaggttcac atgttggaaa cttaatccct    540

gaagcaacag tgatgagaag tgggaccttt aagaggtgag taggtcacga gggctctgct    600

ctgccacatg aatggattaa tgctattacc agaggagtgg ggaatgggtt ccagatagaa    660

gaccgagttt ggcctcctcc ttatntntcg ctctctngcc ttccgccttc taccatggga    720

tgatacagca ggaagaccct agataccaca ccttgatatg gacttccngt cccnanacct    780

tgantaaata ccag                                                      794
```

<210> SEQ ID NO 156
<211> LENGTH: 831
<212> TYPE: DNA
<213> ORGANISM: Cercopithecus aethiops
<220> FEATURE:
<221> NAME/KEY: misc_feature
<222> LOCATION: (1)..(831)
<223> OTHER INFORMATION: n is a, g, c or t

<400> SEQUENCE: 156

```
cgcatcgcct tctatcgcct tcttgacgag ttcttctgag cgggactctg gggttcgaaa     60

tgagctagcc cttaagtaac gccattttgc aaggcatgga aaaatacata actgagaata    120

gaaaagttca gatcgaggtc aggaacagat ggaacagggt cgaccggtcg accggtcgac    180

cctagagaac catcatatgt ttccagggtg ccccaaggac ctgaaatgac cctgtgcctt    240

atttgaacta accaatcagt tcgcttctcg cttctgttcg cgcgcttctg ctccccgagc    300

tcaataaaag agcccacaac ccctcactcg gggcgccagt cctccgattg actgagtcgc    360

ccgggtaccc gtgtatccaa taaaccctct tgcagttgca tccgacttgt ggtctcgctg    420

ttccttggga gggtctcctc tgagtgattg actacccgtc agcgggggtc tttcaaggtc    480

aactgacttt aaacttgccg tttgatttgt gactttagaa agtagagtta actatattta    540

gcaatatgct taagcatgtg catatcacct catgaaacgt gtgtgtgcat gagaaaagct    600

gcctccagta catatacata tgtatataaa cacacataca cacaagcata tatatgtatg    660

tatttcttgn aggaccagtc tcattgtata taatttcaag tgcaggttcc tgatctccan    720

ggatgcgtaa aagactcact gaagttngga agaaanttta nggctactat tntgttggng    780

atcncaccct tcaagtttaa atttgatntg attattctta cngnttgcng g             831
```

<210> SEQ ID NO 157
<211> LENGTH: 637

<212> TYPE: DNA
<213> ORGANISM: Cercopithecus aethiops
<220> FEATURE:
<221> NAME/KEY: misc_feature
<222> LOCATION: (1)..(637)
<223> OTHER INFORMATION: n is a, g, c or t

<400> SEQUENCE: 157
caacctaaga aaaactcaca gccactttta aagcagtaac acatgtataa agtatagttt 60
ggatcctttt gtacacagct cctgaaagag agaaattttt ttttcaccta ccgacagaca 120
tattggaagg ctgctaatat tctgactttt acggactgta ctccctttaa cctgggtaca 180
taccataata ttctttcagt tgnccacagc tatagatacc cctagcataa cacttcagga 240
ttcagaagac gaatgtacct ttctgtatct taacctctct actccacact tcccacctct 300
gaaaaaacaa caggccaaat tctcagaacc taaaaccaag tcagagtaaa cactgctaat 360
acaatactga cacttacata tttacctggc ataatctcta ggattccacc cacaacctaa 420
cagatcctaa ctctctcata gagngagaaa atctgctaaa atctgacaga agtccaaatg 480
aatcctttca gatatatgta gcttgctaca cactcagaaa gnnaagttct cggaacttga 540
aagctctctg aaactnttac cagntacaag angttncagc nnatcacact agcagcatgg 600
ntaanggcaa accagagcag ctaccggaan attaaag 637

<210> SEQ ID NO 158
<211> LENGTH: 656
<212> TYPE: DNA
<213> ORGANISM: Cercopithecus aethiops
<220> FEATURE:
<221> NAME/KEY: misc_feature
<222> LOCATION: (1)..(656)
<223> OTHER INFORMATION: n is a, g, c or t

<400> SEQUENCE: 158
tccatacctt taaaattcaa gaatgttgtg ttctaatggc agtttgaccg ttgagatatt 60
aacataggaa catcatttag cctcttaagc ttgaacatcc attaagcggg aaaaatagtg 120
cttatttcct agaggtttgc agacattggc taaccaatag ttntgattnt gctggaaagc 180
aatgtgcaaa ttttcttaga tgtgatcgct tcattttctc ttacatttta gattggcagc 240
agccaaatgg gcgttccagc ccctnatctc ctgcaagatt cttctcagtt tcataaatct 300
ggtaattttt gagctctttt cccaacaggg tgctgcagct caccaagtgg aatctacaac 360 atttctgct accaggatag cagcttgcca gcaggatata ctgaaattac tgggtttcag 420
tatgatgttg gctggtacga acntcaatca tncgaatcga catgcgccca gccattctca 480
taatgaaatg tntccttctc ctttcaacat gttccgcttt ccagcccccc atcctccntt 540
tattatnttt tttctttcan nnaaaagaag ctttnagnaa acacnnaaac ctcttactcc 600
ctntagngaa aggaaaacnt tctttccnnt nctncntccc ctttnganne ncccta 656

<210> SEQ ID NO 159
<211> LENGTH: 654
<212> TYPE: DNA
<213> ORGANISM: Cercopithecus aethiops
<220> FEATURE:
<221> NAME/KEY: misc_feature
<222> LOCATION: (1)..(654)
<223> OTHER INFORMATION: n is a, g, c or t

<400> SEQUENCE: 159
cattttaatt tttatatagg atggtattta tgaacatccc actaactatt ctgccgctga 60
ttgatatttg gatgtgtaca gtttgatgct attataaaat tcttctaaga acattcttgt 120
acatgttcat tttgtttcgc taggtcctag agtctaaggt atatatccag aagaggaata 180
gctgggtatt atgatagaat aatgacaaac tagtttctaa agtgattgta ccaattagtg 240
tttccatagg agaaaagtgt acagctactg gaaaaacagt ttggaatgat ctgaagtata 300
agaatgttca tagcaacaga atgtgtttct tgtattccaa atgttcacct acagttggtg 360
tggtcagtat aagttgttgt ttttgttttt attgtgtgtg tgttttttttt atcctttggg 420 acagggcctc actttgttat ccaggctaga gagcagtggt acaaacatga ctcactgcag 480
ccttagcctc ccaggctcaa gcagtcctcc tgcctcagcc tcctaagtac ctgggactac 540
aggcatgtgc caccacacct ggctaatttt tgtattttnt tgtagagaca gggtttcacc 600
atgttngccc agtctggtct agttttaaac aaagttgtng cctgnggaaa tgat 654

<210> SEQ ID NO 160
<211> LENGTH: 683
<212> TYPE: DNA
<213> ORGANISM: Cercopithecus aethiops

<400> SEQUENCE: 160
ttactgcatc tgcacacaaa aacccaccga agaaaaaaag tgtgaatgcc atacaatttt 60
tttcaatgca agtatggaac actgtacatc actgaaaaac agggggaaaa aaaaaaagga 120
aaaagaggag aaccattgaa gaaagcataa aatagcagct agctttctta cgtgtgctgg 180
aattgtgtct ttcgggttaa ccccaaattt tcctatgcta tacactcttc tcacattttg 240
gtcaatacta gcttctgaat tggaagaggc attatcaatt gctttaaaat gttataccta 300
aaataaagaa acactgagtt agactgtcac cactttgaat acccatcagg agagtgtggc 360
attgcatgcg aaaatgtatg tgttcctctt aggagatgaa gatcaagtca gctaacagct 420
gtcaacaaac ttctagtgta ggcaagaatt ttatggccaa gttgggcttt cctttattcc 480
ttactggaag aaagtattca gaaaatagca ttttagggga aaaaagtgtt aagtaaacag 540
aatcctttta agcacacaaa caaaagttga gcagtgtaaa ttttgaaact tagtgccttt 600
tagtatctga agcaaaatga taacaagtta taggattttt tctttatgaa gaatgatgta 660
agctcactta tgaaagaaga acc 683

<210> SEQ ID NO 161
<211> LENGTH: 811
<212> TYPE: DNA
<213> ORGANISM: Cercopithecus aethiops
<220> FEATURE:
<221> NAME/KEY: misc_feature
<222> LOCATION: (1)..(811)
<223> OTHER INFORMATION: n is a, g, c or t

<400> SEQUENCE: 161
ctttcacgag aattctgtct caaaaaaaaa aaaaaagcca aagtcctcaa aatggcctgc 60
atggcactac attctctggc cctttatcag cactctgaca gctctctcct ttgcttattt 120
tgctcctcat tctagcctct ggatctttgc ccttgctgtt ccttacgctc ttctcccagg 180
gatctgaaag gctcacaccc tcacctcctt cagaggtttg ctaaaatgtc ttctacccag 240
tgaagccttc cccaaccacc acattaaaaa cacacaacca gcacccgttc tctatcttcc 300
ttcactttgc atttgtccat tgtgtaacat cacttacata cctttaattt ttagtttatt 360
aattcatact gcaaaacaac ttagtttnta ccatgtgcca ggcattgtcc ctagttgctg 420
acaatacagt tgaaaataaa atagacaaaa atcccatctt ttgaatcttt tgaaccttac 480
attgggagtg acaggcaaaa acgaggtaaa tcagtaaaat acgtgagaca gaacgctaaa 540

-continued agaaaaaaaa gaggaaaggg ctgatttttg tgtctttccc tccanaatgc aagctccctt 600
gaggatacag atttgngtgt tttttaacta ctgnaatnct ccctgacaat agcgccccag 660
tnacatagta agggcatttc gannccaatt ttttaaaaat gaagaaaact aggccagtta 720
ccncagtttc ctggggccca attttcaact ttttagganc ntnaantacc gatataaana 780
aaattcggtt acagctaggg ctccgnatna a 811

<210> SEQ ID NO 162
<211> LENGTH: 757
<212> TYPE: DNA
<213> ORGANISM: Cercopithecus aethiops
<220> FEATURE:
<221> NAME/KEY: misc_feature
<222> LOCATION: (1)..(757)
<223> OTHER INFORMATION: n is a, g, c or t

<400> SEQUENCE: 162
ctttcacgag aattctgtct caaaaaaaaa aaaaaagcca aagtcctcaa aatggcctgc 60
atggcactac attctctggc cctttatcag cactctgaca gctctctcct ttgcttattt 120
tgctcctcat tctagcctct ggatctttgc ccttgctgtt ccttacgctc ttctcccagg 180
gatctgaaag gctcacaccc tcacctcctt cagaggtttg ctaaaatgtc ttctacccag 240
tgaagccttc cccaaccacc acattaaaaa cacacaacca gcacccgttc tctatcttcc 300
ttcactttgc atttgtccat tgtgtaacat cacttacata cctttaattt ttagtttatt 360
aattcatact gcaaaacaac ttagttttta ccatgtgcca ggcattgtcc ctagttgctg 420
acaatacagt tgaaaataaa atagacaaaa atcccatctt ttgaatcttt tgaaccttac 480
attgggagtg acaggcaaaa acgaggtaaa tcagtaaaat acgtgagaca gaacgctaaa 540
agaaaaaaaa gaggaaaggg ctgatttttg tgtcttccct ccagaatgca agctccttga 600
ggatacagat ttgtgtgttt tttactactg tatctcctga caatagcgcc cagtacatag 660
taggcattcg atccaatttt aaaatgagat actaggcagt tactcagttt tctgggcaca 720
tttcaacttt tagacaataa taccgataag aaaanta 757

<210> SEQ ID NO 163
<211> LENGTH: 749
<212> TYPE: DNA
<213> ORGANISM: Cercopithecus aethiops
<220> FEATURE:
<221> NAME/KEY: misc_feature
<222> LOCATION: (1)..(749)
<223> OTHER INFORMATION: n is a, g, c or t

<400> SEQUENCE: 163
ctttcacgag aattctgtct caaaaaaaaa aaaaaagcca aagtcctcaa aatggcctgc 60
atggcactac attctctggc cctttatcag cactctgaca gctctctcct ttgcttattt 120
tgctcctcat tctagcctct ggatctttgc ccttgctgtt ccttacgctc ttctcccagg 180
gatctgaaag gctcacaccc tcacctcctt cagaggtttg ctaaaatgtc ttctacccag 240
tgaagccttc cccaaccacc acattaaaaa cacacaacca gcacccgttc tctatcttcc 300
ttcactttgc atttgtccat tgtgtaacat cacttacata cctttaattt ttagtttatt 360
aattcatact gcaaaacaac ttagttttta ccatgtgcca ggcattgtcc ctagttgctg 420
acaatacagt tgaaaataaa atagacaaaa atcccatctt ttgaatcttt tgaaccttac 480
attgggagtg acaggcaaaa acgaggtaaa tcagtaaaat acgtgagaca gaacgctaaa 540
agaaaaaaaa gaggaaaggg ctgatttttg tgtcttccct ccagaatgca agctccttga 600
ggatacagat ttgggtgttt tntactactg natctcctga acaatagcgc cccagtacnt 660
aggtaggnca ttcgatccaa nttttnaaaa agaggancct agggccagtt aactnaagtt 720
ttctggggcc ccatttccaa acttttaga 749

<210> SEQ ID NO 164
<211> LENGTH: 741
<212> TYPE: DNA
<213> ORGANISM: Cercopithecus aethiops
<220> FEATURE:
<221> NAME/KEY: misc_feature
<222> LOCATION: (1)..(741)
<223> OTHER INFORMATION: n is a, g, c or t

<400> SEQUENCE: 164
ctttcacgag attctgtctc aaaaaaaaaa aaaaagccaa agtcctcaaa atggcctgca 60
tggcactaca ttctctggcc ctttatcagc actctgacag ctctctcctt tgcttatttt 120
gctcctcatt ctagcctctg gatctttgcc cttgctgttc cttacgctct tctcccaggg 180
atctgaaagg ctcacaccct cacctccttc agaggtttgc taaaatgtct tctacccagt 240
gaagccttcc ccaaccacca cattaaaaac acacaaccag cacccgttct ctatcttcct 300
tcactttgca tttgtccatt gtgtaacatc acttacatac ctttaatttt tagtttatta 360
attcatactg caaaacaact tagtttttac catgtgccag gcattgtccc tagttgctga 420
caatacagtt gaaaataaaa tagacaaaaa tcccatcttt tgaatctttt gaaccttaca 480
ttgggagtga caggcaaaaa cgaggtaaat cagtaaaata cgtgagacag aacgctaaaa 540
gaaaaaaaaa gaggaaaggg ctgatttttg tgtcttccct nccagaatgc aagctccttg 600
aggatacaga attngtgtgt tttttnacta ctgnatctcc tgacaatagc ncccagtaca 660
tagtaggcat tcgatccaat tttnaaaaga ganactaggc angtactaag tttntgggcc 720
cattnnactt ttaagacaat a 741

<210> SEQ ID NO 165
<211> LENGTH: 727
<212> TYPE: DNA
<213> ORGANISM: Cercopithecus aethiops
<220> FEATURE:
<221> NAME/KEY: misc_feature
<222> LOCATION: (1)..(727)
<223> OTHER INFORMATION: n is a, g, c or t

<400> SEQUENCE: 165
ctacgataca tgtaacattc tacgaacaac catggtgagt agaaccatct ggattttcca 60
tcactttcat ttaaaagact ctgttgatat tctaggtact gattccatat atcagtatca 120
acaaatttct caaccaaggg gataattggt ttatctgttt gcaattcatt ccgtaattta 180
gaaaggagag aaatagcttt cttttcagct tccacgcctt cctgcaaaaa tacaagaaaa 240
atcaattgtg tgtgtgtctg tgtctgtgtt tgtgtgtgcg tgtctatgca attcctctag 300
ggtaacatat ttttacagac ttaagaagaa aagaaaaatg ttcaaactac attatacttc 360
tttaaacatt acatttagaa ctcttaaact gaaaatcaaa aaacacacac agatctcata 420
tgaacataat catgccttat ctatctaagt tctggccttt ctgtgtcttc ggtgatcatt 480
actacagagg gaaaggaacc cctgacagat tttccatgtc tttcatgctt ccatacacat 540
tcttctttca ccattgacac cactagaaaa gaaactgtgg cctttctgag gtttcttttg 600
gtagctcaat tttttttttt aacttgtttt ccactgagtt ctagctaggt gagagatgag 660
atatgctgac atacaaggcg ctacaatata tctcacatga caggccantg ggagtgggga 720 naaatgt 727

<210> SEQ ID NO 166
<211> LENGTH: 713
<212> TYPE: DNA
<213> ORGANISM: Cercopithecus aethiops
<220> FEATURE:
<221> NAME/KEY: misc_feature
<222> LOCATION: (1)..(713)
<223> OTHER INFORMATION: n is a, g, c or t

<400> SEQUENCE: 166
cacgagaatt ctgtctcaaa aaaaaaaaaa aagccaaagg tcctctaaaa tggcctgcat 60
ggcactacat tctctggccc tttatcagca ctctgacagc tctctccttt gcttattttg 120
ctcctcattc tagcctctgg atctttgccc ttgctgttcc ttacgctctt ctcccaggga 180
tctgaaaggc tcacaccctc acctccttca gaggtttgct aaaatgtctt ctacccagtg 240
aagccttccc caaccaccac attaaaaaca cacaaccagc acccgttctc tatcttcctt 300
cactttgcat ttgtccattg tgtaacatca cttacatacc tttaattttt agtttattaa 360
ttcatactgc aaaacaactt agtttttacc atgtgccagg cattgtccct agttgctgac 420
aatacagttg aaaataaaat agacaaaaat cccatctttt gaatcttttg aaccttacat 480
tgggagtgac aggcaaaaac gaggtaaaat cagtaaaata cgtgagacag aacgctaaaa 540
gaaaaaaaag aggaaagggc tgatttttgt gtcttcccct ccagaatgca agctcccttg 600
aggatacaga tttnggntgt ttttttacta ctgtatctcc tgacaanagg cgcccagtaa 660
cataggtang gcattcgatn ccaatttttn aaaatgagan actaggcagt tac 713

<210> SEQ ID NO 167
<211> LENGTH: 714
<212> TYPE: DNA
<213> ORGANISM: Cercopithecus aethiops
<220> FEATURE:
<221> NAME/KEY: misc_feature
<222> LOCATION: (1)..(714)
<223> OTHER INFORMATION: n is a, g, c or t

<400> SEQUENCE: 167
ctttcacgag aattctgtct caaaaaaaaa aaaaaagcca aagtcctcaa aatggcctgc 60
atggcactac attctctggc cctttatcag cactctgaca gctctctcct ttgcttattt 120
tgctcctcat tctagcctct ggatctttgc ccttgctgtt ccttacgctc ttctcccagg 180
gatctgaaag gctcacaccc tcacctcctt cagaggtttg ctaaaatgtc ttctacccag 240
tgaagccttc cccaaccacc acattaaaaa cacacaacca gcacccgttc tctatcttcc 300
ttcactttgc atttgtccat tgtgtaacat cacttacata cctttaattt ttagtttatt 360
aattcatact gcaaaacaac ttagttttta ccatgtgcca ggcattgtcc ctagttgctg 420
acaatacagt tgaaaataaa atagacaaaa atcccatctt ttgaatcttt tgaaccttac 480
attgggagtg acaggcaaaa acgaggtaaa tcagtaaaat acgtgagaca gaacgctaaa 540
agaaaaaaaa gaggaaaggg ctgatttttg tgtcttccct ccaaaatgca agctccttga 600
ggatacagat ttngtgtgtt ttttanttac tgtatctcct gacaatagcg ccccagntcc 660
atagtaaggc attcgatcca atttttaaaa atggagatac tagggcagtt tact 714

<210> SEQ ID NO 168
<211> LENGTH: 792
<212> TYPE: DNA
<213> ORGANISM: Cercopithecus aethiops
<220> FEATURE:
<221> NAME/KEY: misc_feature
<222> LOCATION: (1)..(792)
<223> OTHER INFORMATION: n is a, g, c or t

<400> SEQUENCE: 168
ctttcacgag attctgtctc aaaaaaaaaa aaaaagccaa agtcctcaaa atggcctgca 60
tggcactaca ttctctggcc ctttatcagc actctgacag ctctctcctt tgcttatttt 120
gctcctcatt ctagcctctg gatctttgcc cttgctgttc cttacgctct tctcccaggg 180
atctgaaagg ctcacaccct cacctccttc agaggtttgc taaaatgtct tctacccagt 240
gaagccttcc ccaaccacca cattaaaaac acacaaccag cacccgttct ctatcttcct 300
tcactttgca tttgtccatt gtgtaacatc acttacatac ctttaatttt tagtttatta 360
attcatactg caaaacaact tagtttttac catgtgccag gcattgtccc tagttgctga 420
caatacagtt gaaaataaaa tagacaaaaa tcccatcttt tgaatctttt gaaccttaca 480
ttgggagtga caggcaaaaa cgaggtaaat cagtaaaata cgtgagacag aacgctaaaa 540
gaaaaaaaag aggaaagggc tgatttttgt gtcttccctc cagaatgcaa gctccttgag 600
gatacagatt tgtgtgtttt ttactactgt atctcctgac aatagcgccc agtacatagt 660
aggcattcga tccaattttt aaaatgtgat actaggcagt tactcagttt ctgggcacat 720
ttnaactttt agacnataat accgattaaa aaaancggtt ncagctaggc tacgatncaa 780
gananaactg tn 792

<210> SEQ ID NO 169
<211> LENGTH: 691
<212> TYPE: DNA
<213> ORGANISM: Cercopithecus aethiops
<220> FEATURE:
<221> NAME/KEY: misc_feature
<222> LOCATION: (1)..(691)
<223> OTHER INFORMATION: n is a, g, c or t

<400> SEQUENCE: 169
ctacgaacaa ccatggtgag tagaaccatc tggattttcc atcactttca tttaaaagac 60
tctgttgata ttctaggtac tgattccata tatcagtatc aacaaatttc tcaaccaagg 120
ggataattgg tttatctgtt tgcaattcat tccgtaattt agaaaggaga gaaatagctt 180
tcttttcagc ttccacgcct tcctgcaaaa atacaagaaa aatcaattgt gtgtgtgtct 240
gtgtctgtgt ttgtgtgtgc gtgtctatgc aattcctcta gggtaacata tttttacaga 300
cttaagaaga aaagaaaaat gttcaaacta cattatactt ctttaaacat tacatttaga 360
actcttaaac tgaaaatcaa aaaacacaca cagatctcat atgaacataa tcatgcctta 420
tctatctaag ttctggcctt tctgtgtctt cggtgatcat tactacagag ggaaaggaac 480
ccctgacaga ttttccatgt ctttcatgct tccatacaca ttcttctttc accattgaca 540
ccactagaaa agaaactgtg gcctttctga ggtttctttt ggtagctcaa ttttttttn 600 aacttgtttt ccactgagtt ctagctaggt gagagatgag atatgctgac atacaaggcg 660
ctncaatatt atctnacatg acaggccaat t 691

<210> SEQ ID NO 170
<211> LENGTH: 699
<212> TYPE: DNA
<213> ORGANISM: Cercopithecus aethiops
<220> FEATURE:
<221> NAME/KEY: misc_feature
<222> LOCATION: (1)..(699)
<223> OTHER INFORMATION: n is a, g, c or t

<400> SEQUENCE: 170
ctcaaaaaaa aaaaaaaagc caaagtcctc aaaacggcct gcatggcact acattctctg 60
gccctttatc agcactctga cagctctctc ctttgcttat tttgctcctc attctagcct 120
ctggatcttt gcccttgctg ttccttacgc tcttctccca gggatctgaa aggctcacac 180
cctcacctcc ttcagaggtt tgctaaaatg tcttctaccc agtgaagcct tccccaacca 240
ccacattaaa aacacacaac cagcacccgt tctctatctt ccttcacttt gcatttgtcc 300
attgtgtaac atcacttaca tacctttaat ttttagttta ttaattcata ctgcaaaaca 360
acttagtttt taccatgtgc caggcattgt ccctagttgc tgacaataca gttgaaaata 420
aaatagacaa aaatcccatc ttttgaatct tttgaacctt acattgggag tgacaggcaa 480
aaacgaggta aatcagtaaa atacgtgaga cagaacgcta aaagaaaaaa aagaggaaag 540
ggctgatttt tngtgtcttc cctccagaat gcaagctcct ttgaggatac agatttgngt 600
gtttattact actgaatctc cnggacaaat agcgcccagc acatnagtan gccattcnat 660
ccaatttttn aaaatgagat actagggcag tnactccaa 699

<210> SEQ ID NO 171
<211> LENGTH: 767
<212> TYPE: DNA
<213> ORGANISM: Cercopithecus aethiops
<220> FEATURE:
<221> NAME/KEY: misc_feature
<222> LOCATION: (1)..(767)
<223> OTHER INFORMATION: n is a, g, c or t

<400> SEQUENCE: 171
catctcacag agttacatct ttcccttcaa gtaatccttt cgctaaggct gttcttgtgg 60
aattggcaaa gcgatatttg gaagcccgta gagggctatg gtgaaaaagg aaatatcttc 120
cgttcaaaac tggaaagaag ctttccgaga aactgctctg tgttctgtga attcctcttt 180
tagaattttc ttcagaactt gtggcacatc attaaacctc cgtcagtgat cacatatctt 240
catcctttgg agtcaattta tttttggaaa cagtcaaaag tcactcggag tgacttcagt 300
agaatgaagt gtgtgatcaa attggataaa aacttttttt tttaatcaaa aatgagtaac 360
taaaaaaaac agaagactaa attttctttt tgaggcatgt aaactggctc tgaaagaagt 420
tccaaataat tcaaagatgg ttttagcaat ggcagcactg ctgaaatcca tcagtctctc 480
aaggtgactt aaaaggataa atatcattcg gatgcataga gccaatccgg tccaccacct 540
gttttgtctg actcacatgc taagagtggt ttttatattt ttgaatggct gaaaacaaaa 600
gtgaaagaaa agtagtattt tgtgatacat gaaattcaaa tttcagtgtt cattaaataa 660
agntttcttt agaacacagc catgctcatt cttacatatt atttaaggct gcttttcaca 720
ctacaacgac aggnttcagc agctgcaana aaaaccacat ggcccca 767

<210> SEQ ID NO 172
<211> LENGTH: 769
<212> TYPE: DNA
<213> ORGANISM: Cercopithecus aethiops
<220> FEATURE:
<221> NAME/KEY: misc_feature
<222> LOCATION: (1)..(769)
<223> OTHER INFORMATION: n is a, g, c or t

<400> SEQUENCE: 172
ctttcacgag attctgtctc aaaaaaaaaa aaaaagccaa agtcctcaaa atggcctgca 60
tggcactaca ttctctggcc ctttatcagc actctgacag ctctctcctt tgcttatttt 120

```
gctcctcatt ctagcctctg gatctttgcc cttgctgttc cttacgctct tctcccaggg    180

atctgaaagg ctcacaccct cacctccttc agaggtttgc taaaatgtct tctacccagt    240

gaagccttcc ccaaccacca cattaaaaac acacaaccag cacccgttct ctatcttcct    300

tcactttgca tttgtccatt gtgtaacatc acttacatac ctttaatttt tagtttatta    360

attcatactg caaaacaact tagtttttac catgtgccag gcattgtccc tagttgctga    420

caatacagtt gaaaataaaa tagacaaaaa tcccatcttt tgaatctttt gaaccttaca    480

ttgggagtga caggcaaaaa cgaggtaaat cagtaaaata cgtgagacag aacgctaaaa    540

gaaaaaaaag aggaaagggc tgatttttgt gtcttccctc cagaatgcaa gctccttgag    600

gatacagatt tgtgtgtttt ttactactgt atctcctgac aatagcgccc agtacatagt    660

aggcattcga tccnattttt taaatgagat actaggcagt tactcagttt nctgggccca    720

tttcaacttt tagacaataa taccgatnag aaaaacggtt acagctagg                769
```

```
<210> SEQ ID NO 173
<211> LENGTH: 769
<212> TYPE: DNA
<213> ORGANISM: Cercopithecus aethiops
<220> FEATURE:
<221> NAME/KEY: misc_feature
<222> LOCATION: (1)..(769)
<223> OTHER INFORMATION: n is a, g, c or t

<400> SEQUENCE: 173

cagagaacac agnagtcagt ttctcagaaa gcttctttcc agttttgaac ggcaagatat     60

ttcctttttc accatagccc tctatgggct tccaaatatc gctttgccaa ttccacaaga    120

acagccttag cgaaaggctt cttgaaggga aatatgtaac tctgtgagat gaattctacg    180

atacatgtaa cattctacga acaaccatgg tgagtagaac catctggatt ttccatcact    240

ttcatttaaa agactctgtt gatattctag gtactgattc catatatcag tatcaacaaa    300

tttctcaacc aaggggataa ttggtttatc tgtttgcaat tcattccgta atttagaaag    360

gagagaaata gctttctttt cagcttccac gccttcctgc aaaaatacaa gaaaaatcaa    420

ttgtgtgtgt gtctgtgtct gtgtttgtgt gtgcgtgtct atgcaattcc tctagggtaa    480

catattttta cagacttaag aagaaaagaa aaatgttcaa actacattat acttctttaa    540

acattacatt tagaactctt aaactgaaaa tcaaaaaaca cacacagatc tcatatgaac    600

ataatcatgc cttatctatc taagttctgg cctttctgtg tcttcggtga tcattactac    660

agagggaaag gaacccctga cagattttcc atgtctttca tgcttccata cacattcttt    720

tttcaccatt gacaccactn gaaaagaaac tgtggccttt ctgaggttt                769
```

```
<210> SEQ ID NO 174
<211> LENGTH: 784
<212> TYPE: DNA
<213> ORGANISM: Cercopithecus aethiops
<220> FEATURE:
<221> NAME/KEY: misc_feature
<222> LOCATION: (1)..(784)
<223> OTHER INFORMATION: n is a, g, c or t

<400> SEQUENCE: 174

catggggtga ttttgagaaa aataaaaaat atttgccccc aggagatttg tctttttgtt     60

cttcaaatgt tgaaaaagag ctgaaatgct gcacagctga atgaaggatc ttctcaaggc    120

tctcctggcg cgagccaatc ccagcctcat gaacgagaga gatcctgaca cccacagatg    180

ggcacctcac agccacatgg agacagagac aggctcggtg accagccacc ctcacagcca    240
```

```
cacggggaca ggctcggtga ccagccaccc tcacagtcac acggggacag cctcggtgac    300

cagccaccct cacagccaca tgggacaggc tcggtgacca gccaccctca cagccacacg    360

gggacaggct cggtgaccag ccaccctcac agccacacgg ggacaggctc ggtgaccagc    420

caccctcaca gtcacacggg gacagcctcg gtgaccagcc accctcagag ccacacgggg    480

acaggctcgg tgaccaggca ccctcacagc cacacgggga caggcttggt gaccagccac    540

cctcacagcc acacggggaa cagctctcgg tgaccagcca ccctnagagt aacatgggga    600

caggctcggt tanccagcca cccctcacag ncacacgggg gacngggctc ggtgaccagc    660

cnacnctnac agncacaccg gggacagggc tnngtttacc agcccacccc tcacagaccn    720

cacgggggac agggtttcgt ngaccagccc accccttaca ntccacacgg nggnacagcc    780

ctcg                                                                784
```

<210> SEQ ID NO 175
<211> LENGTH: 733
<212> TYPE: DNA
<213> ORGANISM: Cercopithecus aethiops
<220> FEATURE:
<221> NAME/KEY: misc_feature
<222> LOCATION: (1)..(733)
<223> OTHER INFORMATION: n is a, g, c or t

<400> SEQUENCE: 175

```
aatgtgggaa atgcatcatt tgaaacattt taatggagag actagtattt gatatattaa     60

tgttaggttc ctcccagaac ttaattttta aaatttttat ccaaacttat tttacttaat    120

tatcaccatt tattgaatac attaattgaa atagctcagc tcttctgacc tgtggagcaa    180

aggnntgacc ctcaggatct cctggaagct gccctcaact aagcagaact cagaggaaac    240

ttttgactga gaaactgagg tggtcaaatt gtgctaatgt taaaatacat aaaatagaac    300

atttctttca atcagaacta ctgacactat tacatggcac aggttgccag ttactctgat    360

tagaaatact aaacagaaaa aagaaaacac ttggcttgga tccttaaaga ggtatttacg    420

gaaggtgttg ccaacacagc ccatcccaat gtctggtgag atttcctgtc tgggagaggt    480

ctatgggatc tcacccaaac accacagacc ccagtagcat ttcctggact aatgttcttg    540

tcttttcaca gtgctctgct gatttggtct ttagataacn tggtcttcct tcctcttcat    600

aggnatctat accccctgaa gtgtgggtcc ttagactcag gggcttctt caaaagccct    660

tttggattca gnanaaaaag aancctgggc acttaactgg ggctnaaaga aacacttctn    720

ccgggttccn caa                                                       733
```

<210> SEQ ID NO 176
<211> LENGTH: 729
<212> TYPE: DNA
<213> ORGANISM: Cercopithecus aethiops
<220> FEATURE:
<221> NAME/KEY: misc_feature
<222> LOCATION: (1)..(729)
<223> OTHER INFORMATION: n is a, g, c or t

<400> SEQUENCE: 176

```
catgtccttt tcagtaacat ggatgtaatt ggaagccatt attctaagcg acattaatgc     60

aggaaaagaa aatccaatac cacatgttct ctcctgtaaa tcggagctaa acattgggta    120

cccagggaca caaagatggg aacaatagac attggggatt ccaaaatatg ggatgtaggg    180

aggagggaaa ggatttataa agtgtctatt gggtactacg tttagtacct gggtgtcgag    240

atcatttgta ccctaaacgt cagcattatg caacatacca atgtaacaaa cctgcacatg    300
```

tagactctga atctgaaagt tgaaatactt tttaaaagtc tattatatta tcacacaatg 360
accccataaa caacaacaaa aaaaagtgaa agtaaaaaaa cgcaaggtct ttagacgtag 420
gaatcagaat gatataaaga aggaaaagag atttatacta atatagaacc tttttagaca 480
tgaattttaa aaaaatgata cctaggttat caagttactt ttgtgtccac ctaatattta 540
tacactgtat ccctaaccac aattggctgt attttgaaga cagagccctc aaaggaagta 600
attcaggttn tggtgtccct ataaggagga gaacactagn agnatctcag cttctctcca 660
ccccaccccc aacccccaca aaaacatgtt aaagaaagnc tttatnttgn gggacacagt 720 nggagaaaa 729

<210> SEQ ID NO 177
<211> LENGTH: 679
<212> TYPE: DNA
<213> ORGANISM: Cercopithecus aethiops
<220> FEATURE:
<221> NAME/KEY: misc_feature
<222> LOCATION: (1)..(679)
<223> OTHER INFORMATION: n is a, g, c or t

<400> SEQUENCE: 177
catgcaaggt caggtgcagg catctcttcc aatagggcag tgtctaccag gtagggtctt 60
tctcctctta gaatcattna tggaaatata attcacacaa cataaaattc accctttaaa 120
actatactac acacacacac acacacacac acacacgaat aaaccatatc ccattagcag 180
ttattcaaca cactctgccc ctttgacccc tggaaataat cactaatcta ctggctggta 240
ttatggattt gcttattctg gacaaatcat agaaattgaa tcattaaaca tttggttatt 300
ttgaatctat cttctttcac ttggcataat gtttgcaagg tttatccatg ttgcagcaag 360
taccaatact cattcctttt tatgcttcca taatattcca tggatatatt ataattttag 420
tcaattttta agtcggtgaa catttacact gtttctcctt tttagctatt atgaataatc 480
ttgctatgaa tattcatgta caagtttttg cataaacacg tttncaattc tctattatgc 540
acctagaagt ggaattggta ggtcatatgg taattctatg ntnaactttt gngaatatat 600
gccaaactat tttccaaagc aactgcaccc atttngtatt accaccatta aggnataaaa 660
ngttcctact ttcttcaca 679

<210> SEQ ID NO 178
<211> LENGTH: 737
<212> TYPE: DNA
<213> ORGANISM: Cercopithecus aethiops
<220> FEATURE:
<221> NAME/KEY: misc_feature
<222> LOCATION: (1)..(737)
<223> OTHER INFORMATION: n is a, g, c or t

<400> SEQUENCE: 178
ctttcataat gaaaagaaaa aaatgaattt caactagtat cgatttttcg gtgtgtgggg 60
gcagggcatt taagggtatt atttcctagt aatgatcact tagattctaa gccttaaaca 120
tgattcaaat gcagcagaaa tcaggaaaga agcaacagat acggtggtgc atatcgaatg 180
tctagactac aaggcaaaac ccaaatacca aagaagcatc catgtgtcaa accagcataa 240
tttctaagct atgcctgggg ccacatacaa aaaaaaaaaa aaaaaggtta gtttgaaaga 300
aaaatctagg aggggtaacc agaaggtcaa ccccagttca caggaactgg gaagaagcta 360
gccgttaccc tgtgacatct tcctgagcag cttcctccgc agccagctcc ccagcctcct 420
tacaatgttt ccaaaaggcc caactcccta aacatttgct tcttcaaggt catcctaaga 480
taaggcagtg aataaccacc aaacactgag tcacggatac ctttcggcta aaaaagatcc 540
cccttcccaa aatcattaca taaatacttt aaatgccaag agggttttct ccggaactcc 600
accagaaact cccagnactt taatttagat tgggcaacta aatgtgttca anttttgcgc 660
cataaaatat taaaggcttt tcaggtctgg caantncagt tcaaaacagg tgctttcagt 720
gtacgctgaa taacagg 737

<210> SEQ ID NO 179
<211> LENGTH: 759
<212> TYPE: DNA
<213> ORGANISM: Cercopithecus aethiops
<220> FEATURE:
<221> NAME/KEY: misc_feature
<222> LOCATION: (1)..(759)
<223> OTHER INFORMATION: n is a, g, c or t

<400> SEQUENCE: 179
cagatttttc tttaagaatt ttgtttattg caataggatt atcaaagtaa aaattaaaaa 60
gtaatgaaaa aattaaaaaa ataattttgt agctaccctt cctataaaac ttatccagat 120
tacttcttga cctatacttt gagagcagag gaaatctagc tacattaact cagtagctct 180
gcaacttcta ggtaatttct tacctgaaca gtatatccta agtactgtaa ttcctgcatt 240
gcttgcacat ttgagtttat tattccatcc ctgtattaca ataaatattc tttacataaa 300
ctttcaagag aaaaagcatt caaggtatat gtgtgtgtac acacttatat atatgtgtat 360
atatactcct gtaaaccata attggagttt aaaaaatata tggtatttgc aattttctct 420
tctttctctc tgtctctctc tctctctctc tctctctctc tctctctttc tttcgatgga 480
gtcttgctct gtcacccagg ttggagtgca gtggtgtgat ttcagcttac tgcaacctcc 540
aactcctggg ttcaagtgat tctcctgcct cagactccca agtagctagg actacaggtg 600
cgtgccacca tgcccggcta atttttttgt atttttagta gagatggggt ttcaccatgc 660
tgnccagact gntcttgaac tccctgacct tctgatccac ccgcctcgtc ctccnaagtg 720
ctgggataca ggncatgagc caccaccccc gccggtatt 759

<210> SEQ ID NO 180
<211> LENGTH: 770
<212> TYPE: DNA
<213> ORGANISM: Cercopithecus aethiops
<220> FEATURE:
<221> NAME/KEY: misc_feature
<222> LOCATION: (1)..(770)
<223> OTHER INFORMATION: n is a, g, c or t

<400> SEQUENCE: 180
cagcttttat atatgctgag ttcaagacac ataagtacat atagataant aatgtacact 60
tcttctgtaa gaagacatat aagactgtaa tccatgagag agggaagtct aagatgacat 120
gtttgggaat cctttatatg gacatgatag atgaagccaa agagaacaat gaaatgattc 180
atgttgagtt atttgacatt ttaaaaagta tataagtatt ttaatagtgt gaccatttgt 240
gtctggaaat tttgaaaagc acaaagatct acaatgattt atttatctct atactgatct 300
gtaggaagtt tttggcatgg gaaattgtgc taatgagtat ttggaaacaa gtgtattaag 360
taagggttta caagatcatt agactttcat tttgcagact caatcagatc tgttcactat 420
agtctcctgt tggcataatt ggtttcctga ggacttatta cctgtagatg cacaattttt 480
cattccaaca atgttctgca ttccttttgg actttcctgt cttgaggatc tctttaaaga 540
gctaaaacct caggaacttc ttctacttgt ttctttaaag tcaggatgag agacagaata 600
aggcatccag ccatgatggt ttttccccag gttcttctct catgctaagc cctttatggt 660
acgatgtgcc tctcaaagga gaatgcagat ctaatactat tgcaccactc tgaaagaagt 720
atgaggagaa ggcanaagag ctatgaaaag aaaaacatcc tgatcttttt 770

<210> SEQ ID NO 181
<211> LENGTH: 706
<212> TYPE: DNA
<213> ORGANISM: Cercopithecus aethiops
<220> FEATURE:
<221> NAME/KEY: misc_feature
<222> LOCATION: (1)..(706)
<223> OTHER INFORMATION: n is a, g, c or t

<400> SEQUENCE: 181
ctttcatgcc tagtaaagag tggggcttgg cctggagagg gaggcctcat gggccagata 60
agggagatgc tggcccatct gggcacgcat gtgcccgtag gctttccctg tcgagatgat 120
caactggaaa ggcagagaat gcggcctgga ggctcagaaa catccttgaa gccatatccc 180
caggtcctag tcctaactgc cactcttttc ttttttgaa atggggtctt gctatgttgc 240
tcaggctgga ctccaactcc tgggcttaag cgttcctcct gcctcaactg cccaagcagc 300
cacaaaccac acctggcctc ttcctgccac ttctagctta gcaggtggct tcatctgtat 360
acggggatga cgtgactgct tgggggaatg agctgagccc ttggtggaat catggttcat 420
gcaagaggtc tccggcaaaa tgctccaggc ttggagtctg ctgggcgctt ctacccctga 480
caatccgttt acttaccacc accctctgtt cagacaggga agttctttcc atcaggatta 540
tagcgaggat tggtcttcat ggcacccttg gcatccgagc acgtgttgtt ggagctgttc 600
tacgagccag gacacaccag ggaacggttn cccgcaataa acacccgtct cttcctcgta 660
ctcaagttct tcggggttgc aacattctga gagcttgtcc ttcatt 706

<210> SEQ ID NO 182
<211> LENGTH: 740
<212> TYPE: DNA
<213> ORGANISM: Cercopithecus aethiops
<220> FEATURE:
<221> NAME/KEY: misc_feature
<222> LOCATION: (1)..(740)
<223> OTHER INFORMATION: n is a, g, c or t

<400> SEQUENCE: 182
cngngnctcg atcgttcctc ccacctcagc ctcccaaagt gctgtgttac aggtgggagc 60
cactagaccc agctgaatta tggattttta aggctgcttt atgtcaaaca ttgcgggttc 120
ttttaatatt gttttccaga tttaagattt ttttctttta agctttgtat aatttatagt 180
aatttggtaa agtacttttg aaaacaaaaa tgaaaacatt tgcttttctt ctctacctga 240
accctccaga atttagaagc aatttatgat tattcttatt tttacagcaa catggttatt 300
tgcataggtt cagtaagaat ctgttctctg tccaggcaca gtggctcaca cctataatcc 360
cagaactttg ggaggctgag gcaggcagat cacttgagat caggagttca agactagcct 420
ggccaacatg gcgaaaccct gtctctaccg aaaatacaaa aattagcctg gcgtgttggg 480
catgtgcctg gaatcccagc tactagggag gctgagtcag gagaatcact tgaacctgcg 540
aggtggaggt tgctgtaagc tgagattgta ccactgcact ccagcctggg tgacagagtg 600
agattttgtc tcaaaaaaaa aaggagggcc aggcatagtg gctcatgcct gtaattccag 660
cactttggga gaccanggggg agcgaatcac anggtcagtt cgaggtgact ntaggganaa 720
aattatgttt naatagaaaa 740

<210> SEQ ID NO 183
<211> LENGTH: 720
<212> TYPE: DNA
<213> ORGANISM: Cercopithecus aethiops
<220> FEATURE:
<221> NAME/KEY: misc_feature
<222> LOCATION: (1)..(720)
<223> OTHER INFORMATION: n is a, g, c or t

<400> SEQUENCE: 183
aaacagtaaa aaataaggaa ttttactttc tctggggctc ccaggctctc tggttgggtc 60
agggcccaag tggagcaggg aagaaggggc cactctttct gaagtctccc tgcatgaatg 120
aaaataacag ttgagtggca gtcacacact tagaagcaaa tcattctgat tttgccttct 180
agagcagaga tgtctcccct aagatccatt ttaccccagc agaaaaagcc cgggttgtct 240
ggattgtagc aacgctgttt tgacagaaag ccctatgatt tttctcacaa acttccctaa 300
ggatgctatc tttcagctac acatacttag attatttctt ctccctcacc aactcaatct 360
aatgttgcta aggggttcag tactttctct ctgctgctta cctcgtccca acccccaagt 420
tctttcccaa attccagcag ctgggaccag tctctgggac agagcagaaa taacatggaa 480
attgggggta gggttaaaca catctatcag tctaggaaca ggtagaaaag caacaccccc 540
gtgactacaa gtttggtagt gggcaacaat tttcttatcc atcatgggtg gtggtgtggg 600
tagtnattga gcataanttt atttgtagag gtgaatttgt ttactgggct ntnaagggtc 660
acatggaggc tgtccaagga aaganattcn ataatnaatg gaaatttatt ataatttaat 720

<210> SEQ ID NO 184
<211> LENGTH: 775
<212> TYPE: DNA
<213> ORGANISM: Cercopithecus aethiops
<220> FEATURE:
<221> NAME/KEY: misc_feature
<222> LOCATION: (1)..(775)
<223> OTHER INFORMATION: n is a, g, c or t

<400> SEQUENCE: 184
annnnactna nnnnnnnnat cggctnnttn nnttgggggg naanccagta cttcaaaact 60
ttgtattatt taataaatga tactgactag ttggctaaac atttgaacaa aagataaatc 120
tccaaaccat tctacccacc aaaataaatt ctagaaatga acaaagattt caaagtaaga 180
agtaatccac aaaagtacgg aagaaaacaa tcttaaattg gagaaggact ttctaaacat 240
ggcaccaaag gtagaaacca aaaggaatca cttgcaggtt tcatcacata aagattttaa 300
aatttctata catccaaagc actacaatgt tcagctcaag atggcaggct aggcacattt 360
gcctttcatc tttagagaac catttaaata aaaagacgga ggtacaatga ggaaaaactg 420
taacagggaa gagacgggct ggaacgacag gaagcagatg agccagctgg gagatgaacc 480
agctgaaaga gctgcagtgg agatgaaagc ctgtcctgtg canactgtgg aggaaggagt 540
gaaagacccc acctgtaggt ttggcaagct agctgaggat cgttncncat gattgaacaa 600
natggattgc acnctggttn tccngccnnt tgggtggana ggctnttnnn ntttnantgg 660
nccaacanac antnnnntgt ttnatnccnc cnnntncngn tnnnannnan gggcncccnn 720
tttttnttnn ananccacct nnncnnnncc cnnatnaact nnnnncnang nnnnn 775

<210> SEQ ID NO 185
<211> LENGTH: 400
<212> TYPE: DNA
<213> ORGANISM: Cercopithecus aethiops
<220> FEATURE:
<221> NAME/KEY: misc_feature
<222> LOCATION: (1)..(400)
<223> OTHER INFORMATION: n is a, g, c or t

<400> SEQUENCE: 185
tttttcccgg ngggngnnnn nnnnnnnnnn nnnnnnnncc cccccccttn nnnnttgggg 60
ggggggaaan nncccccccc ctttnnnnnn tttttnnnng nnnnngnnac aggtttttttg 120 ncgnggggat nntnttancc ccannntttt nnncagnnng gnnnncannc nnnccagcnn 180
ggnngnannn tgctnncctg cncgnnncca gcccgnctct tnncctgnta cagnnnnntc 240
ctnattgnac ctccgnctnt ntatntaaat ggntctctaa agangaaagg caaatntttt 300
tttcctgcca ttttgagcng aacattgnng ngctnnggat gnatagaaat tntaaaanct 360
tnntgtgang aaaccngcaa gtgntttttt tnnggnncct 400

<210> SEQ ID NO 186
<211> LENGTH: 951
<212> TYPE: DNA
<213> ORGANISM: Cercopithecus aethiops
<220> FEATURE:
<221> NAME/KEY: misc_feature
<222> LOCATION: (1)..(951)
<223> OTHER INFORMATION: n is a, g, c or t

<400> SEQUENCE: 186
ccgccnggtg ntgggaaaga cnnnggacgc ttcagaccac aggnaggtac catcctggaa 60
cctggaatct ggaacctcag gggctgacct ggcactgggt gggcctggaa cctgtatctg 120
cagcccagaa gcagggtctg caggtgcaag cctgatgcca ggctgcaggg gacagccgng 180
agcnggtttt tnttgaggca ggggntgata angccagcag gcccaaagca aagnctaggg 240
cnnatntntg tctcctaccc ccatgcngag gatacctnnn ttnaagctgc ggagccngag 300
gaagggaggg ggcgcangca agagaatgtc anaactancc ttncnnacct nctncagngc 360
nacctccagg ngctgtaanc actcactagg anacccttaa ggncnnactg aaaggagcnt 420
ccctangagn gatggnagca aaaaananga nacgacactn cgactgcnng gngacgtgca 480
acntggaaag actctgnncc ctncancacc tcgggnanac tatnacaaag angnccccca 540
ncacctncan aatgaaagna aangtgancg ngcnanacca acnncgacnn ccctnggcca 600
agagaacacc aataacnaga ntagganatc caaaagcggn aaanacnaca gngctatnng 660
gaatgcncaa gccaccatnn cttgcantgg nncaacagnt gnaatcnaaa nctacnnccn 720
cnatacactg gagagacaan naccnagcnc cantaaagcg nnaaaaanga gaaaacgnaa 780
aaaancgcgc anngnngcng ncnaatngcc cnnaccntaa ccctccnnan aaaaannaat 840
cnngaacctg gnnacgacnn ncnaagnggc ncaanccncc cncaggcgnc tcnnccncct 900
gccacnanca ccccngagcc ncnncagagn caccngcctn acncacccan c 951

<210> SEQ ID NO 187
<211> LENGTH: 450
<212> TYPE: DNA
<213> ORGANISM: Cercopithecus aethiops
<220> FEATURE:
<221> NAME/KEY: misc_feature
<222> LOCATION: (1)..(450)
<223> OTHER INFORMATION: n is a, g, c or t

<400> SEQUENCE: 187
tnctnntttn ggggtnnnan nnnnnnnnnn anntccncca atnnnnntgg gggggaannc 60
ctggtttcct gcactctccc tcttttccac tcatgtcgcc aggcttccca aatgttccct 120
gactattctt tccctttttt gtgcccacct gtgccccagg cacagcatgt gacctagtcc 180
tgggagtccg cggtggcaga actgcaggcc gttggggcct ccaagtagac catgcaagtt 240
tcacagccat attnctctga tatcagaagc taaggagtcg tgcctggcca gtactaggat 300
gggggtccgn ctgggaacac tgggtgatgt aggctttttg cttacagnnc cctccctctn 360
tccccctnca gnngnctnga tncacaacca tnccctgact ntnntntncn ntnnnnncac 420
ccaactgcat ncnanacaca nncngngact 450

<210> SEQ ID NO 188
<211> LENGTH: 338
<212> TYPE: DNA
<213> ORGANISM: Cercopithecus aethiops
<220> FEATURE:
<221> NAME/KEY: misc_feature
<222> LOCATION: (1)..(338)
<223> OTHER INFORMATION: n is a, g, c or t

<400> SEQUENCE: 188
tncnncttnt ggnggannna nncnnnnnnn nnnntcccnc ctnnnntggg gggggaannc 60
gnncacntnc nntttangaa agagacgacg cttncgagga agaaggtttn tgggacgcgg 120
gactgggnag agctccagag ccccagcagc ccggctcaag gnccccctgcg cataggcgcc 180 ccaccgngac gncagggacg cgactnccgn gangccccgc gcgccgnnng ancccaggcg 240
cgggcnnaga ctgngatcnn ggagnngccc ngngccnnnc ngacggngcg nnnnggnggn 300
cnngggcgcg ggcnnngnga nnggacagnc nggagcnt 338

<210> SEQ ID NO 189
<211> LENGTH: 936
<212> TYPE: DNA
<213> ORGANISM: Cercopithecus aethiops
<220> FEATURE:
<221> NAME/KEY: misc_feature
<222> LOCATION: (1)..(936)
<223> OTHER INFORMATION: n is a, g, c or t

<400> SEQUENCE: 189
ttttnngggg gaannnnnnn nggngtangn nnnnnnnccn ccgcggttnn nccttggggg 60
gggaannncc nnnccangtn nctttttcat gnaaagngna cgacgntctc cgaggaagaa 120
ggctccggga cgcgggactg ggtagagctc cagagcccca gcagcccggc tcaaggtccc 180
ctgcgcatag gcgccccacc gtgacgtcag ggacgcgact cccgcgatgc cccgcgcgcc 240
gtctgatccc aggcgcgggc tcannntttt atctcggagt tcccctgcgc cttcctgacg 300
gtgcgttctg gcggcctcgg gcgcgggctc tgcgatcgga cagcctggag cctttggcct 360
cgatttacat gggaggcccc tcgaaacagg gcacgtcact tgcccccggt cacctgcgga 420
cggggagact ctcgggttga ctccaaggcc tgacattccc ctccggtttt caccgaggag 480
gatgaggatg ttgtcaggag ctgcggcaag gctggaggag cttgcgttgn gtccacccnc 540
ctctgnacag gccttagcat ncacccncag tttctccctt gacttntgaa cccnaactcc 600
ttacccccgc aagtnncnnc cctgtttnga ttgctgaaac tgcaagtgac ggaagantaa 660
aatgtttgcc naagcntnat gcttnanggn ggntgccngg gtataaggtc angggttggg 720
ggcccttnnc cctgnngggt nggcnttaag ntaacccagg gnncntggca nttnantnnt 780
attcaanana tgccanggnn ntcggnntnn aanggntntt tnnanaaaat nnttnccctt 840
nttannctnt annccnnagg gaaanccntn gggtcttgtt tngccctgna aanacnatna 900
aaggggtaat nncccncnct tnaatntnnn gncncc 936

<210> SEQ ID NO 190
<211> LENGTH: 936
<212> TYPE: DNA
<213> ORGANISM: Cercopithecus aethiops
<220> FEATURE:
<221> NAME/KEY: misc_feature
<222> LOCATION: (1)..(936)
<223> OTHER INFORMATION: n is a, g, c or t

<400> SEQUENCE: 190

```
tttttnngng gannncnnnn gtttntngnn nncccccccc ccatnnnttt ngggggggaa     60
nncccnnnca cgtcctcntn atgaaagaga cgacgcctcc gagaagaagg ctctgggtac    120
gcgggactgg gtagagctcc agagccccag cagcccggct caaggtcccc tgcgcatagg    180
cgccccaccg tgacgtcagg gacgcgactc ccgcgatgcc ccgcgcgccg tctgatccca    240
ggcgcgggct cagantnnna tctcggagtt cccctgcgcc ttcctgacgg tgcgttctgg    300
cggcctcggg cgcgggctct gcgatcggac agcctggagc ctttggcctc gatttacatg    360
ggaggcccct cgaaacaggg cacgtcactt gcccccggtc acctgcggac ggggagactc    420
tcgggttgac tccaaggcct gacattcccc tccggttttc accgaggagg atgaggatgt    480
tgtcaggagc tgcggcaagg ctggaggagc ttgcgttggg tccacccgcc tctggacagg    540
ccttagcatt cacccgcagt ttctccctga ctttgaaccc aaactcccta cccccgcaag    600
tccttccctg ttttgattgc tgaactgcaa gtgacggaag aattaagtgt tggccgaaag    660
ctgatgcttc agggggtgca ggntagaggt caggggtggg ggcctngcct tgnggngngc    720
atantgtanc ccanggtccn gcactgantn ttnnaggaat gcanggaatn gnatannang    780
gtnctaanaa antntccccc tannaactga taccnnagna accntngggc tgnntgancn    840
tgaaaaaccc annagggtaa ngcctnnctt atnngggccc cnntntcnag annaaangcc    900
ctggggtttc anngaaaacc cnnnnanaaa ntntgg                              936
```

<210> SEQ ID NO 191
<211> LENGTH: 951
<212> TYPE: DNA
<213> ORGANISM: Cercopithecus aethiops
<220> FEATURE:
<221> NAME/KEY: misc_feature
<222> LOCATION: (1)..(951)
<223> OTHER INFORMATION: n is a, g, c or t

<400> SEQUENCE: 191

```
tttttnngng gancnnncng gttgttgnnc cntcccgcgc attcccttgg gggggnaacc     60
cccnnncang tncctnttna tgaaagagac gacgcntccg agaagaaggc tctgggacgc    120
gggactgggt agagctccag agccccagca gcccggctca aggtcccctg cgcataggcg    180
ccccaccgtg acgtcaggga cgcgactccc gngatgcccc gcgcgccgtc tgatcccagg    240
cgcgggctca nanttnnatc tcggagttcc cctgcgcctt cctgacggtg cgttctggcg    300
gcctcgggcg cgggctctgc gatcggacag cctggagcct ttggcctcga tttacatggg    360
aggcccctcg aaacagggca cgtcacttgc ccccggtcac ctgcggacgg ggagactctc    420
gggttgactc caaggcctga cattcccctc cggttttcac cgaggaggat gaggatgttg    480
tcaggagctg cggcaaggct ggaggagctt gcgttgggtc cacccgcctc tggacaggcc    540
ttagcattca cccgcagttt ctccctgact ttgaacccaa actccctacc cccgcaagtc    600
cttccctgtt tgattgctga actgcaagtg acggaagaat taagtgttgg cgaaagctga    660
tgcttcaggg ggntgcaggg tagaggtcag ggtgggggc ctcgccttgt ggngtgcata    720
```

tgtagcccag ggtcntggca ctgattntta ttaggaatgc aggganttng attagatggt 780
ttcttagaaa atatcccctn tgnanctgnt acctgagnaa ccgctgggct ggcatnacct 840
tgnaaaaccc agaanggtta nngccctttc ttantngtgg cccnattttt tcaggacnaa 900
angggccntg gntttncaat gnaatcncnt ttgcncaaan nnctggtttc t 951

<210> SEQ ID NO 192
<211> LENGTH: 938
<212> TYPE: DNA
<213> ORGANISM: Cercopithecus aethiops
<220> FEATURE:
<221> NAME/KEY: misc_feature
<222> LOCATION: (1)..(938)
<223> OTHER INFORMATION: n is a, g, c or t

<400> SEQUENCE: 192
ttcnnggntc ttnntgntan attttccccc ccatttttg gggggggaanc cnacncanca 60 aaaggtagaa attattgata aantntaaat gttacaaact gcngctaaaa gaagcaaaag 120
agaacatgct gtatgatcct tttttttttt tttttttttt tttttttgag gcggagtttc 180
actcttgttg cccaggctgg agtacaatgg cacaatctcg gctcaccaca acctctgcct 240
cnnnttttca agcaattttt ntnnncttann ctccctagta gctgggatta taggcatgtg 300
ccaccaggcc cagctaattt tgtattttta gtagagacgg ggtttctcca tgttggtcag 360
gctggtcttg aactcccgac ctcaggtgat ccaaccgcct cggcctccca aagtgctggg 420
attacagacg tgagccactg tgcccggcaa tctttttttct taattttaaa tttttttagag 480 acaaagtctg gcttttctag tnccaggctg gagggcagtg gagccatcct ggctcactgc 540 anccttttnnc tcccaggctc aagccatcct nctaccttaa ncttcctgag tngctggnaa 600
ctacaggtac acaccaccat gtcagnctaa tttttttttt tttttttttt ttgaaaccna 660
attttttcnt tgttcacccc tnntggganan ncaggnngna nnanctctnn ccncntcnac 720
cccttacnnc naagnncaat atnaantatc nncctacnnn cccnagntct tnnnnnttta 780
annnannttn tatttttntt nnttatantt tacctnnntn tttcntnntn ctnanccctn 840
ntncactnnt nnactantct ttttccacnt attcttctct ncnnctntnc tnatatcncn 900
nnccnnnctc tctcttntnc ttctttnttt ctnnnatn 938

<210> SEQ ID NO 193
<211> LENGTH: 804
<212> TYPE: DNA
<213> ORGANISM: Cercopithecus aethiops
<220> FEATURE:
<221> NAME/KEY: misc_feature
<222> LOCATION: (1)..(804)
<223> OTHER INFORMATION: n is a, g, c or t

<400> SEQUENCE: 193 tntnggggggt nnnaaaacnt tncnnacata atcgccncaa tacaanttgg gnggggaaaa 60
annctgnntc attcctccnt gnacccatct ccatgccgtg naagcatctc ctncttggac 120
ttgcactatc tggtcccata gcccttgctt attcttaaat gggagtcact ctgacttgca 180
ttgtggggaa gggtatacct ggggcacagt cctctgggat ggacacttcc ataggaaggg 240
gcagttatac gtggacttat gtcctcctac actctcatcc agaaccatcc acccagaagc 300
aggagttgtt tcttttagaa accagccggc ccaatcagcc cattttatag gtgaaggcag 360
tgaagcccag agagataaag catcttgtcc aaggtcacag agccagacct agactaggct 420
gcctggctcc tagttcaggg ctcatcccac cctagccggc ttctggctag acagaatcta 480
cccatcctgg cccagactct ctggtgggaa gtcagggatg cagnggtcag gatgggcatc 540
agagccagca ggccctgagc acggntcacc caagtggaac atgaacttcc taaactccag 600
nggaagttag aaatggcana ttgatcagng ctaatgagct taaaacaccc agggattaaa 660
aaaaaaaaca tgaanaagct ntacttnaag cataaatntg ntnaacanaa agganaccng 720
gctncncnnt ntntnanann nacnnnntgg aggctnaggg ggnnngnnca tnnggggngn 780
ganattngnn ttngnaaggg gnnt 804

<210> SEQ ID NO 194
<211> LENGTH: 560
<212> TYPE: DNA
<213> ORGANISM: Cercopithecus aethiops
<220> FEATURE:
<221> NAME/KEY: misc_feature
<222> LOCATION: (1)..(560)
<223> OTHER INFORMATION: n is a, g, c or t

<400> SEQUENCE: 194
ttctanttnn nnnggtnnna ancannnnnn ncatnntcgn cncatnnnnn ttgggaggga 60
aannnaatna ataatcaaan ttagnaattg aatttagaat ttcatttatg aataaaaagg 120
ctgggaggaa acacacccca accgacacag tggatgcgat aggataagac tatgagcaga 180
ttttgttctt ccttttcacc gtctgtattt tccatcaatt atttgtatga ttaaaatcaa 240
tcatttcaga caagagggac attgtgagct atctgtgaga aatgtcttct atctgtttcc 300
agatagaagg ggctccagct cggtttgggg aaagtcccaa tgccattctc ttaaccaaga 360
ggtttcctac ctcatctaat gtggagattc tacttacccg ggaagactcc cctcctgtta 420
cctcaagtct gcagccggcc tcccagactt ctgcctnctn ctaaccacag cctgcctggn 480
tgcaggncgg ngggaaagga gggcatangg ggctgnatnc cgnanaggcc ctnncactcc 540
tngactnang cagggnnctg 560

<210> SEQ ID NO 195
<211> LENGTH: 977
<212> TYPE: DNA
<213> ORGANISM: Cercopithecus aethiops
<220> FEATURE:
<221> NAME/KEY: misc_feature
<222> LOCATION: (1)..(977)
<223> OTHER INFORMATION: n is a, g, c or t

<400> SEQUENCE: 195
cnncccccng gntncccncg ggnnnnnnnn nnnnccccccc ccnanncttt gggggggaan 60
nncnnncctt tnggngnatt gnngggnana anncngtnct tccnnaatag natgnggcng 120
canttcaact ncgctaatta acggaacagc aggctngnaa ttctgacaac agcaggacac 180
aaanggggcn gggatcagca ctgaatgccg gcgaagcatg ccncccccccc ttaagaagaa 240 gcacaacacc cacgacccac attnnntntn gggncaggtc catgaaggng cnaccctnga 300
tttagttana ngcnctnccc tgcagcaact ccaagggcnc agggttttta aaatgncncc 360
tcaggccttc ttnagaggna gcaagccngc cccaactggc ctttttcnna aaaaaganggg 420 aaacaggnct gngattggtc nagagcagga nncgcccagc ccnttnggct ccccngggcc 480
acacngnaag aaaaagaatn gnnttggacc acacagaaaa cacaccaana ctaangacag 540
ctgaaaagct caaaaaaaaa atcgcnaaaa aatccctcaa tgctcnaaga agtccncaaa 600
nncgccgngn gacngnnaca cagctnccng gccngcanga cnncngggggn ncacaggnng 660 cnacacccag gaccagnagn taatatcnna aaagggtaac aanaaaancc ctaataccaa 720
aaangcnatg anaatggaag cnnnacntcc tncaaaagac aagccctang gaaancntcn 780
cncnacccnn nccccaaccn ggcanncggg cccccaccca aaagggggn nccgccccgg 840 aannnaaaan ccnacnnngg ggaaaaanng accnnaancc ngaaanngtc tatanccca 900 cngnccnaaa acctcccang ncaatnaccc cnccctccta aaaggntagg annaanacnc 960
nggngcaaag ncnncca 977

<210> SEQ ID NO 196
<211> LENGTH: 868
<212> TYPE: DNA
<213> ORGANISM: Cercopithecus aethiops
<220> FEATURE:
<221> NAME/KEY: misc_feature
<222> LOCATION: (1)..(868)
<223> OTHER INFORMATION: n is a, g, c or t

<400> SEQUENCE: 196
gaannccnnc nnaaaaaacn nnnnnccccc nccccatann ncttgggggg gaaannnccc 60
ccccacaagn natantnagn aggnaggaaa acacanttaa tatatctcac tagcnctcat 120
ttccctcccc caccctcatc ccactccact gctaagagag agaaatnnca gcactgctat 180
cctgttntat tatacattnt cccttnngag tnaaggattn naagattnng aaagtaacag 240
aatagaaacc aaaagtnnta ctcaactncc aatttggctt aaaaagagag aaataatnat 300
tattncctat gnnacccaaa actnattctg nnaataacag ntataattat atattcaaan 360
naataaatga agatcgccaa aatcacctna atataatngn nagcagctaa agaacaaaaa 420
tnnnnnncat nngctnctat aagnagacat cacatganna ctnctatnga ccagnaagaa 480
actagnaaaa ncaggcagnc acccaccatn cnnnnctaac anncnnnnnc nnannctatn 540
caaccnnnnc ggnatanncn naagaagcca aatcaagaaa nnagaccnnc atgcctaaaa 600
aaaaanngng nnatcnnaan acatcangaa caggaaccng nngnanataa cacaggnann 660
caaagcnnna ncgncaannn cnagaacccn naaacanaaa ggcagcnnan anncaagann 720
agaaacngaa nncacanaac acanagcann nncncanaaa gcnnnnnnca nnnnngaacg 780
aagaaannnc nnnnnaccaa aggccncaag ggcnnncaaa nnccnnngcc aannnaaaaa 840
aaaccnanca aaggcncnng anggaaaa 868

<210> SEQ ID NO 197
<211> LENGTH: 260
<212> TYPE: DNA
<213> ORGANISM: Cercopithecus aethiops
<220> FEATURE:
<221> NAME/KEY: misc_feature
<222> LOCATION: (1)..(260)
<223> OTHER INFORMATION: n is a, g, c or t

<400> SEQUENCE: 197
ttttcnggng gannnnnnnn nnnnnnnnnn nccncnccgn tnnnnttggg ggggaaannc 60
nnnncacang nnatnttngn ggaggaaaac acatttaata nanctcatta gccctcattt 120
ccctccccca ccctcatccc actccacngn taagagagag aaatnncagc actgntatcc 180
tgnnnnatna tacatttncc ctnnngagtn aaggatnnna agatnnngaa agnaacagaa 240
nagaaaccaa atnttttttt 260

<210> SEQ ID NO 198
<211> LENGTH: 901
<212> TYPE: DNA
<213> ORGANISM: Cercopithecus aethiops
<220> FEATURE:
<221> NAME/KEY: misc_feature
<222> LOCATION: (1)..(901)
<223> OTHER INFORMATION: n is a, g, c or t

<400> SEQUENCE: 198
gggnancnnn agnngnaana nnccaacccc gccaanatnt angggggggan actntcacaa 60 gtatacaaga ggaggaaaac acaattaata tatctcacta gcattcattt ccctccccca 120
ccctcatccc actccactgc taagagagag aaatttnggc actgctatcc tgttntatna 180
tacatnttcc cttttgagtn aaggattnna agattntgaa agtaacagaa tagaaaccaa 240
aagtttnctc aactnccaan nnggctaaaa agagagaaat aatnattatt tcctatgnna 300
cccaaaactn annncgnnaa taacagntat aattatatat ncaaatcaat aaatgaagan 360
cgccaaaatc accttaatat aattgncagc agctaaagaa caaaaanncn ncncannngc 420
nncnataagn anacatcaca tgatnactnc tatngaccag naagaaacta gnaaaancag 480
gcagncaccc acccacncnn nnctaacatt cnnnnncnna nncnanccaa cctnnnncgg 540
natatncnna agaagccaaa ncaagaaaan nagaccnnca ngccnaaaaa aaaacngngn 600
nancnnaaac atcangaaca ggaaaccagn ngnaaaataa cacagggnat ncaaaagcnn 660
tanccggcan nnnnccaaaa acccctaaac anaaaaggcn gncccagaac ccangaaana 720
gaaaaccnga aanncccngg nnaancccgg cancnncccc caatccacaa ccccccgnna 780
naancncccn aaacccancc aaaacanaaa acccngnggc naaaaaggcn ccccnaaaaa 840
aanggnnccc cggnccggcg gncgaacncc cnagggncaa nanngggggng nagncaaaaa 900 a 901

<210> SEQ ID NO 199
<211> LENGTH: 885
<212> TYPE: DNA
<213> ORGANISM: Cercopithecus aethiops
<220> FEATURE:
<221> NAME/KEY: misc_feature
<222> LOCATION: (1)..(885)
<223> OTHER INFORMATION: n is a, g, c or t

<400> SEQUENCE: 199
ttttttnggn ggntttnnnc nnttttnntc nnnnnncccc cccgattnnn nttnggggggg 60 aaannnccnn nccanaagnn atnttagnag gaggaaaaca canttaatat atctcactag 120
cattcatttc cctcccccac cctcatccca ctccactgct aagagagaga aatttcagca 180
ctgctatcct gttttattat acattttccc ttttgagtta aggattttaa gattttgaaa 240
gtaacagaat agaaaccaaa attttnntca acttccaatt tggctnaaaa agagagaaat 300
aattattatt tcctatgtta cccaaaactt attctgttaa taacagttat nattatatat 360
tcaaattaat aaatgaagat cgccaaaatc accttaatat aattgttagc agctaaagaa 420
caaaaatttt tttcatttgc ttctataagt agacatcaca tgattacttc tattgaccag 480
taagaaacta gtaaaatcag gcagtcaccc accattcttt tctaacattc ttttncttat 540
tctatncaac ctttncngta tattcttaan aagccaaatc aanaaatnan accttcatgc 600
ctaaaataaa attgtgntat cttatacatn atgaacagga acctgtngta tataacacaa 660
nntatnncaa agctttatcn cantttctan aaccottaaa caaaaangca nnctcanatt 720
nnaanattan aaaactnaat tctggaccca antgtanatt aactctnnan acatttttnn 780
gtgnattaan naaaaactgg nnncctatcc ttaactttaa naggtcancc caaanttntn 840
nnanaacaan ncctnnnnan aancaantta tatnaaacca nctan 885

<210> SEQ ID NO 200
<211> LENGTH: 941
<212> TYPE: DNA
<213> ORGANISM: Cercopithecus aethiops
<220> FEATURE:
<221> NAME/KEY: misc_feature
<222> LOCATION: (1)..(941)
<223> OTHER INFORMATION: n is a, g, c or t

<400> SEQUENCE: 200 ttttngggggg anntananng nnnnnnnnnn nnccnngnnn nnattggggg gaaannnccn 60
nncttngnat ttagaggagg aaaacacntt taatggatct tattagcttc atttccctcc 120
cccaccctca tcccactcca cngntaagag agagaaattt cagcactgct atcctgtttt 180
atnatacatt ttccctttg agtnaaggat nntaagattn ngaaagtaac agaanagaaa 240 ccaannttt ttttcaactg gnaattnggc tcaaaaagag agaaataatt atnatntcct 300
atgttaccca aaactnatcc tgnnaataac agttatnttt atatattcaa attaataaat 360
gaagatcgcc aaaatcacct taatataatn gncagcanan aaagaacaaa aatnctttca 420
nncngcttna ataangnnga catcnccatg atcacctnct attgaccagn aagnaaacta 480
gnnnnaatna ggcnanncac ncacnanann nanncnaanc accannnnna cnaannncna 540
ttcaacannt nanngggnana ntnncnnaat aagccnaaat aanananann gccccnanan 600
gcctaannan nancgaggna atgcnnnncc caannttnaa caggnatncc nggcagngnt 660
tntaacanng annatttcan angnnnnanc cggnaatact nnnanaannc cnannaaann 720
naaaggnnan tcnnaatnca angttnaana aaangnaatn cncccnnnnn antantaaat 780
aangncnnna ntannannnn nctancatcn cncncnatgc acnnnnnaaa ntnnnnnntn 840
acnnncnnnc nnngnnaaan nttnaangga nnncnnnntn ancacannnn cncannaang 900
nnnnnnaana nccacaannc aacacatnan caancacnaa t 941

<210> SEQ ID NO 201
<211> LENGTH: 886
<212> TYPE: DNA
<213> ORGANISM: Cercopithecus aethiops
<220> FEATURE:
<221> NAME/KEY: misc_feature
<222> LOCATION: (1)..(886)
<223> OTHER INFORMATION: n is a, g, c or t

<400> SEQUENCE: 201
ttttcccnng gntnnnnnnt nnnnannnnn nntccccccc catnnnnttt gggggggaaa 60
ancacagnaa cacagngttt nngnnctcag naaagctttt ttccagtttt gaacgtaaga 120
tatttccttt ttcaccatat ccctctatgg gcttccaaat atccctttgc caattccaca 180
agaacagcct tagcgaaagg cttcttgaag ggaaagatgt aactctgtga gatgaattca 240
cagaacacaa agcagttttt ttagaaagct tctttctagt tttgatctga gaatatttcc 300
cttttcacca tagacctcta tgggcttcca aatatcacgt tggaaatttc acaagaacag 360
tgttagcgaa aagcttcttg agggaaaagc tataactctg tgagatgaat tctacgatac 420
atgtaacatt ctacgaacaa ccatggtgag tagaaccatc tggattttcc atcactttca 480
tttaaaagac tctgttgata ttctaggtac tgattccata tatcantatc aacaaatttc 540
tcaaccaagg ggataattgg ttnatctgnt tgcaaantca ttccgtnatt tnanaaaagg 600
agagaaaata gctttctntt cancttncca cgccttncct gccaaaaatn ccaanaaaaa 660
ancaatngng nngnggngcc ncgnntnntg nngnttngng tgtnccntgn nctntccnan 720
tcccnntnag ggnnaacnaa tttttncnga ctttaanaaa naaaanaaaa aanngnncaa 780
accacnttnn aaactnnttt aaanntncca tnnnaaacct taaancnnaa aaccaaaaaa 840
ancccccacn ancnnnnnnn nanananann nnncccntan ttntttt 886

<210> SEQ ID NO 202
<211> LENGTH: 925
<212> TYPE: DNA
<213> ORGANISM: Cercopithecus aethiops
<220> FEATURE:
<221> NAME/KEY: misc_feature
<222> LOCATION: (1)..(925)
<223> OTHER INFORMATION: n is a, g, c or t

<400> SEQUENCE: 202
ttttntggng gannnctnnt nnnnnnnttn nnccccncct annncttngg ggggaannnn 60
cnncccactt agnatttttt ncncaaaaaa aaaaaaatag ccaaagtcct caaaacggcc 120
tgcatggcac tacattctct ggccctttat cagcactctg acagctctct cctttgctta 180
ttttgctcct cattctagcc tctggatctt tgcccttgct gttccttacg ctcttctccc 240
agggatctga aanntttttt tccctcacct ccttcagagg tttgctaaaa tgtcttctac 300
ccagngaagc cttccccaac caccacatta aaaacacaca accntttccc gttctctatc 360
ttccttcact tngcatatgt ccattgngta acatcactta catacettna attntnagct 420 natnaatnca tactncaaaa caccttatnt nttaccatgt nccaagcatt gncccntant 480
tgcttnacan tacancncna anatnaaatt cnacanaaaa tcccatnctt tttgaatntt 540
tttgaacctt acattngnaa gtnncannca aaatccnang ttaaancata aaaatncccn 600
tgnanacnna acccctnaaa naaanaaaat angaaganag gggcctgaat tnnngngcnc 660
tttcccctcc caaantncan acntcctngn angnaaccnn atctnnnnng nnntnnnntc 720
actnccgtnt nttcccgaca anaancnccc cnnnncccctn ntnngccctt ccatnccnat 780
tnttnaaana ttaaaanccc cccncnctcn ctaanttnct ngggnccnat ttcaaacttt 840
tnaacnaann anncccnncc nnnaaaaacn ncnnccnccc tnngnnnccc anncnaaatc 900
atccnncntc nnctcctcnt ctccn 925

<210> SEQ ID NO 203
<211> LENGTH: 895
<212> TYPE: DNA
<213> ORGANISM: Cercopithecus aethiops
<220> FEATURE:
<221> NAME/KEY: misc_feature
<222> LOCATION: (1)..(895)
<223> OTHER INFORMATION: n is a, g, c or t

<400> SEQUENCE: 203
ttttttcgng gattnctnnt ntnnnnntnn ntccccccat tnnncttggg gggnaannnc 60
nacgattcan gtnttatnnc tacgaacaac cattgtgagt agaaccatct ggattttnca 120
tcactttcat ttaaaagact ctgttgatat tctaggtact gattccatat atcagtatca 180
acaaatttct caaccaaggg gataattggt ttatctgttt gcaattcatt ccgtaattta 240
gaaaggagan anntttcttt cttttcagct tccacgcctt cctgcaaaaa tacaagaaaa 300
atcaattgtg tgtgtgtctg tgtctgtgtt tgtgtgtgcn tgtctatgca attcctctag 360
ggtaacatat ttttacagac ttaagaagaa aagaaaaatg ttcaaactac attatacttc 420
tttaaacatt acatttagaa ctcttaaact gaaaatcaaa aaacacacac agatctcata 480
tgaacataat catgccttat ctatctaagt tctggccttt ctgtgtcttc ggtgatcatt 540

```
actacagagg gaaaggaacc cctgacagat tttccatgtn ttttcatgct tccatacaca    600

ttnttctttc accattgaca ccnactanaa aaagaaaccn gtggnccttt ctgaggtttt    660

ttttttngnn anntnaattn nttttttttta aacttggntt ttccncctna attnttancn    720

taggntnana aaangaaana ntgcctnnna tnaaaanggn ncctncaatn ntatnttacn    780

cnnanaagnc cnattggnna gggngcanaa antntnanng ggnnacnaaa ataaaannaa    840

aaataactct nnnanccttt ggttttacat taacnaaana nntctncccc caana        895
```

<210> SEQ ID NO 204
<211> LENGTH: 887
<212> TYPE: DNA
<213> ORGANISM: Cercopithecus aethiops
<220> FEATURE:
<221> NAME/KEY: misc_feature
<222> LOCATION: (1)..(887)
<223> OTHER INFORMATION: n is a, g, c or t

<400> SEQUENCE: 204

```
ttttcnngng gntnnnnnnn nnnnnnnnnn nnaccccncg tnnnnntngg ggggaannnc     60

cnncccacga gnatttttnn ctcaaaaaaa aaaaaaaagc caaagtcctc aaaatggcct    120

gcatggcact acattctctg gccctttatc agcactctga cagctctctc ctttgcttat    180

tttgctcctc attctagcct ctggatcttt gcccttgctg ttccttacgc tcttctccca    240

gggatctgaa aggnttacac cctcacctcc ttcagaggtt tgctaaaatg tcttctaccc    300

agngaagcct tccccaacca ccacattaaa aacacacaac cagcacccgt tctctatctt    360

ccttcacttt gcattngncc attgngtaac atcacttaca taccttnaat tnttagttna    420

ttaattcata ctgcaaaaca acttantttt taccatgtgc caggcattgn ccctagttgc    480

tgacaataca gnngaaaata aaatagacaa aaatcccatc tttngaatct ttngaacctt    540

acattgggag tgacaggcaa aaacgaggna aatcagnaaa atacgtgaga cagaacgcta    600

aaagaaaaaa aagaggaaag ggctganntt ngngncttcc ctccanaatg caagctcctn    660

gagaatacag annngngngn nnnnnacnac ngnatctccn gacaatagcn cccannacan    720

annangcatt ncnacccaan tnnaaaaang annaacnang gcannnnccn aannncnggc    780

cacatnncaa ccntaaaaca anaanaccca anaaaaaaac ngnnncagcn aggncacnaa    840

nnaagaaana nccgnncnna attnnnggng caggccntna aanncca                  887
```

<210> SEQ ID NO 205
<211> LENGTH: 843
<212> TYPE: DNA
<213> ORGANISM: Cercopithecus aethiops
<220> FEATURE:
<221> NAME/KEY: misc_feature
<222> LOCATION: (1)..(843)
<223> OTHER INFORMATION: n is a, g, c or t

<400> SEQUENCE: 205

```
acccccccca tnnnnttggg ggggaaaaac canccagtaa nagttttgnn gcaaggnngg     60

tggctcttaa tcatcagggg caaggtagat ttaattctcc attatccatt aattatttaa    120

tgaacaccaa cagtgggatt gcaagtggga ggtttagaac aacagggctc tgtggcaaag    180

actactagac catggtatca ctagggacag ctagttgggg aggcnttnng ggtattactt    240

ggcttataaa accaaaatag accaacagca gattattaaa atgctggtgt tggctgccaa    300

gtggaacgta ataatcacac atctggtttt ccaaattgaa cagttcttag atccagaatc    360

ctgtgattga tagagatgct agatcctttt gcagaaaatc ttataatgcc ccaatgaatt    420
```

```
tatagtagta atttccccaa tccttctcca aaagaatcta tgctgcagaa aataaaatac    480

ctgnacagng ngcattacat tgngcactac agagatgaaa gtagccaaat atttcaagtg    540

ctgnngaatc canagttnga gatgacacca ataccagaga aaacaaaaac catcatgatg    600

ccctggntag ggngggtgtg ngaaanccan gnggaaaaan aaagncttgg gcccnacant    660

ncanatataa atgnncaaag agncnggcna cccnccccgn naanaaggnn agggncnctg    720

nnggccnaaa nnaggnnngg aagcaccnaa anaannngaa anaacccccc accaaaaccc    780

ccgngcnccn gaccnggana ggggggnncc cntncncann ccaaaanggc ccanngqnnn    840

ncc                                                                  843
```

<210> SEQ ID NO 206
<211> LENGTH: 927
<212> TYPE: DNA
<213> ORGANISM: Cercopithecus aethiops
<220> FEATURE:
<221> NAME/KEY: misc_feature
<222> LOCATION: (1)..(927)
<223> OTHER INFORMATION: n is a, g, c or t

<400> SEQUENCE: 206

```
ncncccccng gnaancccon ggngtaannn nnnncccccc ccaatanntt tggggggggna     60

annncccnnn canagtgnaa tantaagnaa ncaaaggcag cngagtcagn accaaaacta    120

acagnanaat aacagnaaaa nnnccaccac catatgaaag caggggaaaa atatatggaa    180

acagatatgg ccaaaaaaaa ggatgcagac aacgaagnaa gcggacagaa gcccgagaag    240

aaaaacgggg ncgggggaga aaggagacta tnaataggaa aaangaaaaa gcanacacag    300

ggcgactgag caatacagaa agcaaagang cnggataaaa agcagggccc tagagtggga    360

gtggcncaac acgaagaggg gcatccagag ggggaacaca gcgcngggng acaggagggg    420

gnccaaaang gaggaaaagc gcccnncnca gagaaccanc aggcgcggcc caccccgggg    480

cggcagccgg ggagggggcc cacagangng ggngagaagc caagaaacnc agcgganggn    540

agggaancac nggcccangc gcaggggaca ccccccagaa gccnaggaca gagggagggg    600

caaggngcac actaagganc cnnnaangaa cggccagagg ngcagganco cacannagaa    660

gnacccngaa ggggcaggng caggcaagnc cccgcngcan gaggacaaaa cnggccngcn    720

gaaaanggnc gccccnncac cccnccngnc cnnaacccac ngcaaccacc agncnnnnac    780

annaanccon aaaacacaaa ngnccccacn nnanccancc cganaaaagg cnaanaacca    840

ggngnaancc nacccaccng gnccgnanga cccnggaaac cnnnanncca nncnnaannn    900

nnacccnaaa ccaaaagnnc gannacc                                        927
```

<210> SEQ ID NO 207
<211> LENGTH: 940
<212> TYPE: DNA
<213> ORGANISM: Cercopithecus aethiops
<220> FEATURE:
<221> NAME/KEY: misc_feature
<222> LOCATION: (1)..(940)
<223> OTHER INFORMATION: n is a, g, c or t

<400> SEQUENCE: 207

```
ccccggnatc ntttctgtnt nntnctnnnc ccccccctta ttttgggggg ggaannnccn     60

nnncntnnnn nnntttncca ccnaaaacta tttnttntnc tnncccgcct atcctccaaa    120

ctagcaatan ttcggttctt ccctcttgct ctcgggcgga ttcctgaaag tcgtttattc    180

tcttaattaa tacgccgctc cagccccgcc cgttcagctc attctcttaa tcgcattacc    240
```

```
ctggctgcng nnnctttttt tttttttccac ctgctgccac ccacccagac accgcctncg    300

gctctttccg gaccatctca gtttctcctc cttccccngn cccaattttc tttaggctat    360

ttctggctcc cgtaggtttn tcatgctctc gttagcccca ccccatcacc accancggct    420

ctttttcggc tctctcccgn cncctcctgt ctcctgctca ggctcttttc cagctattnn    480

cgactcccct cntactcacc ctttgccttc ngaaactntc ccaccngccc ttcaggcaaa    540

tcngtctcna ccccctantc ccgcacgtga acacagncct ncccccctccg ccttcttaga    600

nacccccctct caccnnnncc ctttccnncc catcctcaaa actananggn tgggtacngg    660

ccnanccncc cnttttggtg nnnaannccn gaatcgccgn caaggncccg gtncntnccc    720

ngaaaanccct atngncnggn cacaaacang ggaaacannn ttcncacccn ttntccactg    780

ancccncttcc cccntcaccc ttnaaanaca ttntttnnnt ttatctaaaa ccnttcancc    840

cccncctcct tcggncacct cnttnctant ncccatatan ccccntagnt natncntnca    900

atnccngcac cnnntntnta tctaatnaaa ccccaacccc                          940
```

<210> SEQ ID NO 208
<211> LENGTH: 881
<212> TYPE: DNA
<213> ORGANISM: Cercopithecus aethiops
<220> FEATURE:
<221> NAME/KEY: misc_feature
<222> LOCATION: (1)..(881)
<223> OTHER INFORMATION: n is a, g, c or t

<400> SEQUENCE: 208

```
tttttccnng gnnattcnnt gtnnaatntn ntntcccccc cattntttgg gggggaanac     60

ccgnanttga aatttnggga caaacaaaca tanctctttc tctttccttg aagggttaat    120

gctccaacca gcctcagatt ggttcgcttg aatcttaaaa ttacttttct ggtcacgcgc    180

gccgaaggtc taagcatttg tgaaatgtct tttttccccc cccccacccc ttgatgctgt    240

tctctttggn nttttttaat tacacagggg ttgagaaacc aaattaaaat taggcgtgtc    300

tggtcaacag tgatcacgtt gcatgctttt agctttgntt gttgaagttg cttctcctcc    360

ctgagtggct ttcctccttt tttttttttt tttttttattt taaaaaggaa atatcataag    420

ctctttcaga aatactcaca ggaagtgagt gtccgtatgc tggttactca ccancaactg    480

agtgttggca ggtggagaat gctaccgcag ccgcccagac agatctgcag actggcccca    540

ttgcagagga ttagacacag ggtgcgtgga tcatagggtt tttgtacaga angcagtttt    600

aagaggaaat tggtcactgc atgtcatctc gaggggtggt gattcangga gccaggcctn    660

ggggttcana aagnacgttg ctngccatct tnggaggttt cctgctcact tntcaaangg    720

ncaggctngc cttttaaaaa tcaatgttcc ttccaccccc aaaagggntt ctttttgcag    780

tgaatcanct nccaaaataa atagcccccn tttttttgga aaagaacgtt tgnaaatccc    840

ncnttttaat ggnangtttt naattngggg gttnantcaa a                        881
```

<210> SEQ ID NO 209
<211> LENGTH: 896
<212> TYPE: DNA
<213> ORGANISM: Cercopithecus aethiops
<220> FEATURE:
<221> NAME/KEY: misc_feature
<222> LOCATION: (1)..(896)
<223> OTHER INFORMATION: n is a, g, c or t

<400> SEQUENCE: 209

```
tttttccngg atnttnattt ntanacttat ccccnccatt attttanggg ggnaanccct     60
```

nncanaatat tgtnttacaa atatcatttt ngtgtatgta tgtcaaaacc aaaactgcct 120
ttatgtcaat atgctgtaaa aatctatcag aatatatctt aattcttaac tttcattgtt 180
gtctgtgggt tgtcttgtat aattattatc acatctacag tattttctgt aggtaaatat 240
gaaatgtttt tttnatgtac cagggggaaa atgcccttta ataagccttt ccctagacaa 300
agcaccattt aggcgtttag aagcaagaac tagtganntc agaaattgct gtcatacata 360
ctcacctgtg aatggtcgta caaaggatcc caagcgcagg acttgtcctg gaagcagagg 420
atcggattcc accaggaaaa gaggcaagta gaaatgccaa atgccagcgc tccctttccc 480
cagctcatct tatttgtagg cactcagatt tttggaatcc tccaggacta acaaatanaa 540
accacactag gttgtttttc ctaattncct gtgaaatgag tcangtangt caaacanctt 600
atccactcca gagagagaac caattccttt gagctacact ccctgttttc cagtnaccct 660
aatnccctct ntggtgtccc ttgaanaaag ggnntgccna ccantgcatt ggagagccca 720
ccgggtttnt gaatgaagan nattgtnaaa antnnccaaa aagttaannn gccttcaagg 780
gganagtttn cctttntgaa nattnaagna ggaaaaatcc cannttaaaa tacctgggnt 840
ccngtttttt nntaaaaaan cnnnnnactt ttttttggnc naangntttt tttttt 896

<210> SEQ ID NO 210
<211> LENGTH: 869
<212> TYPE: DNA
<213> ORGANISM: Cercopithecus aethiops
<220> FEATURE:
<221> NAME/KEY: misc_feature
<222> LOCATION: (1)..(869)
<223> OTHER INFORMATION: n is a, g, c or t

<400> SEQUENCE: 210
nnccttctaa ttttntagtt tnnnagctca cttataaanc aggctacagt gttattctta 60
agtattcatt gttgtataac acactacccc caaaatttag gagcttaaaa taacagcaaa 120
cacttattat ctctcatggt tctgtgtgtt gactagacat ttcggctcct gtgcagatgg 180
ctggagcact gagctntttt ttnggtctac agtgctctcg cttacatagt aggcactagt 240
gttggctgct ggtagcaagc tcagttgggt gtgttgacca gannnnttgg ttctgctcta 300
tagaggccac tgtacattgt tacttaaatt ctcacagcac agcaatttgg ttccaagaaa 360
gagcattgta atantgagca tttcaacagt attaacccaa catgcaaaca ctcactatag 420
taagcaaaat aaaataaaat aaagcccccc cccagatatc tatgctctaa aacttccaaa 480
cgtatgaata tgtnacctta aatagcaaaa ggcactntgc agtgtgattn angcaagatg 540
gggcagagtg tctgggaata tccangtgga acccaataat gcaaataaaa aaaatcnttt 600
tataanangg naggtaggaa ntaanacatc tgntcancat taccgctgcc nggtttttng 660
aaaaanaaaa ttnggaagaa aggggccnca agccaaggga atnccaggca tttcnctaan 720
tnggccaaaa caanannatn aaaantcntc ccccnnnnnc cnncnanaaa aaantgnaac 780
cctgggcgnc cncnttgatt tttnnnccca angancctnc ctnaccaana nantnaaaaa 840
aaaatctntt gntcgnnttt nancnaaan 869

<210> SEQ ID NO 211
<211> LENGTH: 874
<212> TYPE: DNA
<213> ORGANISM: Cercopithecus aethiops
<220> FEATURE:
<221> NAME/KEY: misc_feature
<222> LOCATION: (1)..(874)
<223> OTHER INFORMATION: n is a, g, c or t

<400> SEQUENCE: 211
tttttngggg atttcccttn tanantnnan cccccccctt anttgggggg gaaatacnnc 60
ccattaacag ttttactcgc agcctctgct tngtctacat ctgctgccaa cttttaacta 120
atggcgagat actttcgcta tttccgatgc cattaggaaa caaatagaaa aatagtttgg 180
caacaacatc ttctcgaata ttatcacttg acaaatttta acgttttagg tggaaacgga 240
attttaannt tttgttttaa gaagcttaaa aaaaacaggc atgcttaatt agcataatgc 300
tgaatggcag ccaatcacaa actgaatttt taaagcnnga agtgtttgct cctggcgtgg 360
cgcgcccgcc tgtaatccgg gaatcccagc gttttgcgag cccacgccca ggccgaggag 420
ggaggatcct ttgttccacg agttcgacac cagcctaggc aatatagcag aattcagttc 480
aatgactcta ggctttagcc atgcagtatt aacaaatggg atattaacaa tattaacaaa 540
tgggataaaa accaagaact tgacaaatgt gttaatttcc tatttctgtt ttaatacatt 600
acacaaaact aactgcctga aaacaaaaca aaagntntta tttttatagt tctctaaatc 660
agaanttttc attggggcnt aaaatcaagg tnntctgcaa ggctgcattc tttntgnagg 720
ctgtagggga naaatttcat tgtccttgnt ngncctttaa naaagcctgt tttnccttgg 780
cttggngncc cctttttcaa ttcattttta aaaccccnan nnnatnngnn ccnntttctn 840
cctccncctc cncnttaaaa nattttttnt gngn 874

<210> SEQ ID NO 212
<211> LENGTH: 866
<212> TYPE: DNA
<213> ORGANISM: Cercopithecus aethiops
<220> FEATURE:
<221> NAME/KEY: misc_feature
<222> LOCATION: (1)..(866)
<223> OTHER INFORMATION: n is a, g, c or t

<400> SEQUENCE: 212
annnncnnnn nnnnnnnncc cccngatann ttggggggga aanncncnca tttgagtgnt 60
ncagggcaaa accaacagta aaccagacta ctaaagattt acttgtggaa tttttttgca 120
aagtgtcaaa gggcttatag agaaaatgaa acagttcttt aaagatgttc ttgagcgagg 180 ttttttttt tttaacttac taaaagactt tatgttttag aacagttttt gtttacgttn 240
agcacgtagg acgtccccac tacacacaca gnttctctta ttaatagata ttagtatggt 300
acattngntg caactaatga accagtaatg ataaattatt aactaagatc catagntnat 360
tcctgcttcc tcacattnta tctaaagncc tttntctgnt ccaggatccc agctaggaga 420
tngaaagacc ccacctgnag gttnggcaag ctagctgagg atcgnnncgc atgatngaac 480
aagatggatn gcacgctggn tctccggccg ctngggngga gaggctatnc ggctatgact 540
gggcacaaca gacaancggc tgctctgatg ccgccgngnn ccggctgnca gcgcaggggc 600
gcccggnncn tttnggnaan accgaccngn ccggngcccn gaangaacng caggacnagg 660
canngcggnn atcgnggntg gccacgacgg gcgnnccnng cgcannnggg cncnacgnng 720
nnacngaaac gggaagggna ccggcngnna nngggncaaa angccggggc aggaaccncn 780
gnnaannaaa ccnggnnccn gccnnnaang aaccanaang ggngnnnnaa agnggngggn 840
ngnananccc ngnaaccggn nncccc 866

<210> SEQ ID NO 213
<211> LENGTH: 998
<212> TYPE: DNA
<213> ORGANISM: Cercopithecus aethiops
<220> FEATURE:
<221> NAME/KEY: misc_feature
<222> LOCATION: (1)..(998)
<223> OTHER INFORMATION: n is a, g, c or t

<400> SEQUENCE: 213
ttcgggggtc tanaangtnt nntnntncan nccccccccn tttttggggg gnaannncnn 60
nccagtttnn natttggnnn nggagcataa attnagtcgn ctctctcacc taaaactcat 120
ggtctggtgg aggctccgcc tcctttgtcc cctttcatgt ttctgtctca gcatgcctgg 180
ctccttaagg ntcttcatct tttgcaggtt tatctcaagn ctcaattgaa ccgccncctc 240
ctgncaggcn tttttnnnct gggaggtgag cagnngggtc cgggaatgtg ggagctaagg 300
gcatagatgt gaggaccncc ctatgaanag gaaaaggann cnnctggaat gcanacctgg 360
gactgtctgt atacctgcct ggtcactaaa tttctctgag aggcatcaac agnnaaaanc 420
ctganagggt tatngccaag agcatngatg gggtctgctt tctgggangc agggaataaa 480
ggnngtgata cccanaggga ttatntctca gccaggnccc tccttcccnt gtanganag 540 tcccttgagc cnccnnncna ctnancnntn ttttnaatna aacncccctn tnnncgggac 600
aacgggaann tccctatann cctcccannc tnggttgnnn aannccccggn gctaaaagca 660 atcnnncntn nccntnggtc tncacaaaan ggctnagaat naccangttg nagccccntn 720
ntnccctant cccccctgna nnnctatnat ttnttccaan taaccaatna nacccccccan 780 aacccannat acancacaac atngaccccc ntcaaaacca acanccnnnt agacnttntn 840
ccnacntnnt aggncatnng cnaaccgnaa gcntttgttn tngaanctan ccaagggcct 900
cncnaacaan ttcaaaaana agtggtgntt cccccancct naaccccgng cccccacnnt 960
caacanannt aaaaannaan acccacnncc nntngtng 998

<210> SEQ ID NO 214
<211> LENGTH: 956
<212> TYPE: DNA
<213> ORGANISM: Cercopithecus aethiops
<220> FEATURE:
<221> NAME/KEY: misc_feature
<222> LOCATION: (1)..(956)
<223> OTHER INFORMATION: n is a, g, c or t

<400> SEQUENCE: 214 tttttcggn ggattnctnn tttnnttnnt tnnncccccc ngttnnttgg gggggaannc 60
cancgttctn nctatttcct tcttgacgag ttnttctgag cgggactctg ggttcnaaa 120 tgagctagcc cttaagtaac gccattttgc aaggcatgga aaaatacata actgagaata 180
gaaaagttca gatcgaggtc aggaacagat ggaacagggt cgaccggtcg accggtcgac 240
cctagagaac nnttttntgt ttccagggtg ccccaaggac ctgaaatgac cctgtgcctt 300
atttgaacta accaatcagt tcgcttctcg cttctgttct ntcgcttctg ctccccgagc 360
tcaataaaag agcccacaac ccctcactcg gggcgccagt cctccgattg actgagtcgc 420
ccgggtaccc gtgtatccaa taaaccctct tgcagttgca tccgacttgt ggtctcgctg 480
ttccttggga gggtctcctc tgagtgattg actacccgtc agcgggggtc tttcaatctg 540
attgcctctt gcttgacggc aaggagtccc gaccactgaa cactgatgac ctcatctggt 600
gtgattgtct cttgcttgac ggcgaggagc cccgacgact gaacatggat agtcgccgcc 660
acagcacggt gatcanaagg ctttcgttcg acttatgant ccgacgntcc ggggagttca 720
agtcgatann cttggcgcct gaggcgacna cnaggcntct naactcaccc tacccttggg 780 aagcccctttt tcnactccnt gggnccttt ngtnnttntc ttgnccacct ttcttgactt 840
cttnaanttt gcttctggan tgntaatncn natcnnaaan ccttgtttgn aaaancntgg 900
ccccnggncc cngnttcntt nacccccann tantgnttta ngncccnttt tggaaa 956

<210> SEQ ID NO 215
<211> LENGTH: 915
<212> TYPE: DNA
<213> ORGANISM: Cercopithecus aethiops
<220> FEATURE:
<221> NAME/KEY: misc_feature
<222> LOCATION: (1)..(915)
<223> OTHER INFORMATION: n is a, g, c or t

<400> SEQUENCE: 215
ccncaacctt ngagacccta aagacattgg agcagcccca tacacctcct cccagggcac 60
acaaaggccc ctgacatgcc catggcagtc caaggcctcc aattggagcc atctttggta 120
aatctggggc ccatcagccc ccactgccct tcctggtacc ctgagcatgc tggcaagggg 180
actnnttttt gcatcccatc ttgtntcata tacccacagn acctgatgtg gacatgactc 240
accctggggt cctgtgagtc aataagggtg tntgantaag gggcagagca tttcaactta 300
gtcccataac ccatgagctc attaagcaaa tattacccat gcctagattt ggggccagtc 360
actacccact ggaggctgtg ggctccaagg tatggcagca ggggaggcca gccaggcntc 420
tgcccagctc acccttccct gtgaggatgg acnccagcca ggcctcccac ctccacccct 480
agactggggg acccggggtt ggggggcaag aaaggggacc tgaaagtggn tgtctnggag 540
ntaagcccat ttncttnata ctccnccaat aggganccaa gaaggngggt tnagagttac 600
cccaanaact caccccaacc cantntnaac gctgtggggt ctcaangggg acangcnaaa 660
acnaaaantn anacnggccc aaaaaagaac aggtncggnc ctnccccnan ggaccttttn 720
ttttctacca ccttacccan nanaatnctt gaccaggggc ntttccccaa acncngnaaa 780
anctttcaag cntngncact ntnnanaccc ngggcnnnnn aaggnttagn gcctcttnnn 840
ancnctntgn cnggttncca tngnntaaaa accccaangn aactcctcca aanaacaagn 900
anccnntctn ggttn 915

<210> SEQ ID NO 216
<211> LENGTH: 949
<212> TYPE: DNA
<213> ORGANISM: Cercopithecus aethiops
<220> FEATURE:
<221> NAME/KEY: misc_feature
<222> LOCATION: (1)..(949)
<223> OTHER INFORMATION: n is a, g, c or t

<400> SEQUENCE: 216
tttncngngg nanntttntg nggaannctt nncnnccccg gntttttggg ggggnaannc 60
ncatcgttct tactattgcc ttcttgacga gttnttctga gcgggactct ggggttcgaa 120
atgagctagc ccttaagtaa cgccattttg caaggcatgg aaaaatacat aactgagaat 180
agaaaagttc agatcgaggt caggaacaga tggnacaggg tcgaccggtc gaccggtcga 240
ccctagagaa cctttntatg tttccagggt gccccaagga cctgaaatga ccctgtgcct 300
tatttgaact aaccaatcnn ttcgcttctc gcttctgttc ncgcgcttct gctccccgag 360
ctcaataaaa gagcccacaa cccctcactc ggggcgccag tcctccgatt gactgagtcg 420
cccgggtacc cgtgtatcca ataaaccctc ttgcagttgc atccgacttg tggtctcgct 480
gttccttggg agggtctcct ctgagtgatt gactacccga gtggggaacg ggggcagggc 540
gggtgggagg agggcgcagg aggctgagac agcccaggtg agagagggcc aagcttgaaa 600
ggttttccca ggcttgggga gaggccctgg tcaggatgtg tatgggtaag gggtgagaga 660
cagaggtncn tggggcangc ccggacctgt ttttttngnc cagtntcagt tctgnttcnc 720
ttgnccctga gaccccacgt tcanagaggg ttggnncggt tgnggggnga cnnttanccc 780
catctgatcc catggtggnn ntganganan gggctaannc nnancccntn cagtcccttn 840
ttgcccncac ccgggccccn atcnnggnga agagggagnc cgctcgnccc ncccccagga 900
agggnncngg nanaccggnn gnccccgnng caaccngnaa ccaacnnan 949

<210> SEQ ID NO 217
<211> LENGTH: 999
<212> TYPE: DNA
<213> ORGANISM: Cercopithecus aethiops
<220> FEATURE:
<221> NAME/KEY: misc_feature
<222> LOCATION: (1)..(999)
<223> OTHER INFORMATION: n is a, g, c or t

<400> SEQUENCE: 217
ttttcccgng gannnnnntg nnnnttnnnn nttncccccc cccatnnnnc attggggggg 60
aaatnccccc catntaggcc tttnngcnaa agacccagtn ntctgcccct gggtncccnc 120
agganctctg caatggggaa gtgagccctc ctgaggcctg gctggcagga ggctcttcaa 180
ggtcatgtgg acttccccca acacctcgag tttctgcaca gcagccacgg agacgggcct 240
gggggctggc gggaaatttt tnnnaaggca atgtttncct gagtgggctg aaacctgaga 300
tgaggaaatg agaagacgtc aggtggctgg aggacacggg ctttaggaca gccagcaccc 360
agccctgtag ctgaggcctc cggagggagc cagagggaaa gggagtcccc tccccgcggc 420
ctgagtctct gccagtgccc agcactccca aaggatccac cccaacctga gagaccctaa 480
agacattgga gcagccccag acacctcctc ccagggccac aaaggcccct gacatgccca 540
tggcagtcca aggcctncaa ttggagccat cttttggtaa atctggggcc catcagcccc 600
cactgcncct tcctggtacc ctgagcatgc tggcaagggg actggaaact gcatcccatc 660
ttgtctcana tacccacagn acctgatgtg ggacatgact caccctgggg tcctgtgagt 720
caataagggt gtttgantaa ngggcagaac nnttnaactt antnccanaa acccatgagc 780
tcattaannc aaanttaccc tgcctanaat nggggccant nactaccnac tggaaggttg 840
tggcttcang natggntnag ggaagnccnc nggctttccc aannnnncct tnccttngag 900
gnggacccac cagcctccan cncccccnna actgggaacc nngngnggca anaagggcng 960
aaanggtttt gantaaccna tttntanncc cnnggnaaa 999

<210> SEQ ID NO 218
<211> LENGTH: 962
<212> TYPE: DNA
<213> ORGANISM: Cercopithecus aethiops
<220> FEATURE:
<221> NAME/KEY: misc_feature
<222> LOCATION: (1)..(962)
<223> OTHER INFORMATION: n is a, g, c or t

<400> SEQUENCE: 218 nnncccccggn actttcnnnt anngnanncc cccccctnat ttggggggna anncacannn 60
ttannnattt nnnnnngaca aagctttttt ccagggnntg aacngcngga tatttcctnn 120
ancaccatag ccgnctatgg gcttccaaat atccctttgc catttccaca agaactgcct 180
tatcgaaagg cttcttgaag ggaaagatgt aactctgnga gatgaatnct ccagaggaat 240
cctggatnnt nnccataggn angnctnaac ctgttcactc cnganctttng ggagggtgca 300 cctggaagca agctctgggg tccctgggag agaaagcaca gcccctgccc tggagacact 360
caaagcctgg aagggaaggg cagngggctg gacagagacc acaggtgtga cggtcctagg 420
tgggaggtgg gagctcagag ggggcaccta accccattgg gcagagtgct canggaaggc 480
tttgagtagc gccncagagg atgcngnaga anancccag gaggagagcg acngnatgna 540
gagggaanag catttaccgn ngcctgggag tgngagaggg ctggcnggag aaaaaagagc 600
tccangaagc cacaaancct cannagnngc gtccacagcn cgatnctcna ncaccnacaa 660 canancccg ccncatanaa agngcnccaa nccatcnntc acngaangaa nnaacaaaat 720
gaaanaaggg agatcaccna agggaganac gcngacaccc ccccnncccn accnganaac 780
cacnncanaa cntnnacccc gcanaccnaa ganccatgaa ganttnagca cggnanggcc 840
cannnaaaag ncataaanan aacngnagga aaagggaccg gacacccnan tnactacccc 900
cacnnntacc caaaaccaca ncnncngccn gggcgnaacn cccnacnacc aaccanccc 960 ng 962

<210> SEQ ID NO 219
<211> LENGTH: 891
<212> TYPE: DNA
<213> ORGANISM: Cercopithecus aethiops
<220> FEATURE:
<221> NAME/KEY: misc_feature
<222> LOCATION: (1)..(891)
<223> OTHER INFORMATION: n is a, g, c or t

<400> SEQUENCE: 219
tttttngggg ntnnnnnggg gnnngnnnnt cccgcctnnc cttngggggn anncctnnnc 60
agttgggaat tnatttaaag aagggactta agggagatta ttaaagagcc agnaacgcaa 120
aggagagctg cggcaatcga caactaccga agacgcgaag cacattcacg aagcgttccc 180
ttcaatccgc acactacact cccacgaccc gccccttccg cccacagagc ccgccacttc 240
cgcctcanan ntnacgcccg ctctgtgctc ctaagggcct tcccgcggct gatcagacgc 300
cccgcccctt agccgcaaca gaagccgtaa agctttctcc cgtcgcgatg cagcgctcaa 360
ggcgcctgcg cagaccctga aaagcggcca gggtggcccc gagcttccct tttccggttg 420
cagcgccgcg cggttaggtt ctctcgttct cgctcgcagc catgccgtcc aagggcccgc 480
tgcagtcggt gcaggtcttc ggacgcaagg tgagctagac gccagatggg aaggggaggg 540
gaaggagaag gtcagggtct gggagaggac ggtgggcagg aatacagggg gcaacatggg 600
agctggatcc cgagctcacg gggccacact ctcttgtatc ccacagaaga cagccacagc 660
tgtggcgcac tgcaaacgcg gcaatggtct catcaaggtg aacgggcggc ccctggagat 720
gattgagccn cgcacgctnc aatacaaggt gnttggcatt gggncattcg ncgttgantt 780
ggattggagg acctntngga nataatagta gctnnttgaa agcttgaggg ggcnggntnt 840
cancanccgg gnttttnana anttngnttn gtntnnnnaa aagggggttt t 891

<210> SEQ ID NO 220
<211> LENGTH: 902
<212> TYPE: DNA
<213> ORGANISM: Cercopithecus aethiops
<220> FEATURE:
<221> NAME/KEY: misc_feature
<222> LOCATION: (1)..(902)
<223> OTHER INFORMATION: n is a, g, c or t

<400> SEQUENCE: 220
tttttnnngg nntataattt ganntatnta tcccncccat aaaccttggg ggggaanaca 60
aggnctnaag ttttttagga ttgtgctact gtactccagg gtgagtgaca gcaagtatac 120
tgttcttaaa aaaagaacct tatatattaa aaaaaaattt ttttttaact gaccctgcaa 180
tgcacatatg cttcctttta aaagtagtaa acttcagaag gggcagaaat cagactctgg 240
tttctttcca ttttnagcca aagaaactga nagtnccaaa cagggaacag aagaacccct 300
ttcacaagca agcatttaaa cagacccaaa ttcggccgcg cggctcacca ggctggtcag 360
gagttctaga ccagcctggc cgacatggtg aaaccacgtc tctcctgaaa atacaaacat 420
tagccggccg tggtggtgtg cgcctatagt cccagccacc cgggaggctg aggcaagaga 480
attgcttgaa cccggagggt ggaggttgca gcgatccgag atcgtgccac tgcactctcc 540
agcctgggcg acagagcgag actccctctc aaacaaataa atngaaaaaa aaataaacag 600
acccaaattc aagctatttc aatacttact gagcacttac aatgtctaaa acgctgcttt 660
tagacgcctt ggggttttnt taaggatnaa aacacttgnt ncttngtgaa aatnaaanct 720
atgaaaactg ggtgttcctt caanccttttn gggntccccc ccggnttccc cnnttnaaat 780
gaaccttnct aaacattncc aattttnaaa agncanccccc nttaattntt taanacnccc 840
ccaatttnaa nnttttaaan tttttntnaa acnntaaanc cccgggtttt ttttnncnaa 900
aa 902

<210> SEQ ID NO 221
<211> LENGTH: 907
<212> TYPE: DNA
<213> ORGANISM: Cercopithecus aethiops
<220> FEATURE:
<221> NAME/KEY: misc_feature
<222> LOCATION: (1)..(907)
<223> OTHER INFORMATION: n is a, g, c or t

<400> SEQUENCE: 221
ccncannggt agntccgctc gccttccgcc ttgtaagcng gaaaggtgct tcgcgaggtc 60
tcgccttcgg ggtccgacat ggtgaccgga tttagagacg ctaaagcaga gacaatcgaa 120
gaaaagctgg agaacctcta tctggttctg gtttgtggaa gctccgtctc ttagcaaccg 180
cgagacgann ttttcagcga tttccggttc cgtccctgtc tggcaagggc ccggattctg 240
ggtgcaacct gccggcgtgc gcgtgcgcca gttctntnnn gcaccgggcc ggagagtgat 300
gagtgcgtgg ctggcggctg agctccttag tgtttgctgt tgcacgctcc ttcggttctc 360
tctggagtta ctgcgtgaaa aggctgcctt gtaagacagc caagaaaaca ggaagagggt 420
tggaggcaaa gttccnaata gggattgaaa gaccccacct gtnggttttg gcaagctagc 480
tgaggatcgt tcgcatgatt gaacaagatg gattgcacgc tggtttcttc ggccgcttgg 540
gtggagaggc tatttcggct atgactgggc acacagacat tcggctnctt ttantgccnc 600
cngngtncng gctgtnagcg naggggacgn cccgggttct ttnttgnaaa gacccnaccg 660
ttccggtgcc cttaatnaan ctgnanggac gagnnnancc cngntttatt ttgntgggcn 720
ncaacggncn ttccttnnac anctngntcn ncancnttgt nanttaaccn gnaanggnnc 780
tngntngttt tggncnaaat annccgggca aggaactccn nnnnanncce ccgtgtnnnt 840 ncccacaaan tatcnattng ggtancnaan cngggnnnnn tnaccnnnac ccgnnnnccg 900 ccnanct 907

<210> SEQ ID NO 222
<211> LENGTH: 955
<212> TYPE: DNA
<213> ORGANISM: Cercopithecus aethiops
<220> FEATURE:
<221> NAME/KEY: misc_feature
<222> LOCATION: (1)..(955)
<223> OTHER INFORMATION: n is a, g, c or t

<400> SEQUENCE: 222

```
tttttccggg ggaannnnnn nnggnnnnaa nnnnntcccc nccccatnnn ccttnggggg     60
gnaanacccc nnncaattcc ctatttggna actttgcctc caaccctctt cctgttttct    120
tggctgtctt acaaggcagc cttttcacgc agtaactcca gagagaaccg aaggagcgtg    180
caacagcaaa cactaaggag ctcagccgcc agccacgcac tcatcactct ccggcccggt    240
gcgcggcaga actggcgcac nnttnnnccg gcaggttgca cccagaatcc gggcccttgc    300
cagacaggga cggaaccgga aatcgctgta cgtctcgtct cacggttgct aagagacgga    360
gcttccacaa accagaacca gatagaggtt ctccagcttt tcttcgattg tctctgcttt    420
agcgtctcta aatccggtca ccatgtcgga ccccgaaggc gagacctcgc gaagcacctt    480
tccctcttac atggcggaag gcgagcggct ctacctgtgc ggagaattct gtgtgaaatt    540
gttatccgct cacaattccc acacaacatg agcgtcagac cccgaagaaa agatcaaagg    600
atcttctttg agatcccttt ttttctgcgc gtaatctgct gcttgcaaac aaaaaaaacca    660
ccgntaccag cggnggtttt gnttngccgg atcaagagnt accaaantnt tttttcnnaa    720
gnaacttggc ttnagcanaa cccnaanacc aaatactgnc ntttngngta cccgtantta    780
ggcccccccct taaaaanttn nnanccncta atanccngtt ttntaatttn ttacaanggg    840
tnttgcnagg gnaaaaattn gttttaccgg ttgnctnaaa aaaattttcc gaaaggcccn    900
ngtnngntaa aggggntctg cccaacccat tgggnnannt ccncccannt naatc         955
```

<210> SEQ ID NO 223
<211> LENGTH: 927
<212> TYPE: DNA
<213> ORGANISM: Cercopithecus aethiops
<220> FEATURE:
<221> NAME/KEY: misc_feature
<222> LOCATION: (1)..(927)
<223> OTHER INFORMATION: n is a, g, c or t

<400> SEQUENCE: 223

```
nnnnnnttta aanacnnanc ccccccanta ntttgggggg gaaaacccccc agcatgccca     60
cntatcatnn cccatcactg ggtaatattc acagnatcaa attatcctcc ctaacccagt    120
cctgtgaata ttctcattga tcctcaaact cactttggcc tcagtgatcc ccaacagcct    180
cctttacaac cttacaacat ccaagttcct gttctgtgag agtttcctct cgaaacacaa    240
cattccgtac aattcagtct ctcactccgt caatcctcta cattggcagt gagaccttat    300
tttgtgaccc tttactttac agcagccatt tcaaagagac attctctagc ctgaaagggc    360
tccagattct ttcaactttc tattatgtat gcattgccaa tattgaattt gcactatctt    420
atcaactatt ctaaaactac tgacatttgc agaaactggt catttgttct tagggaaaat    480
gtctgtgtta tccaaaaatg gagattaaaa acttgcacac attcctactt gatttccaca    540
gngacctgat ctatggtatc tagcntcctt cccctctgcc ccaagttcac atttccatca    600
gctcatatat actcttccct ttctactcct gctgacaggg tccaaggata ctgcctcaaa    660
aactctataa aaganaataa aaactnatta actggctttn ctatcnaaaa nctttcnact    720
agnaatatta anaaangntt ttcaaccggt nggatccgaa ancatccnaa gnagggntna    780
ngccnaaaaa aaaaataatn nntttccccn aaaaannaaa aaatagnntn tnangggggc    840
ccngnncntn gnaaaagaaa naannccggn cntnnaaana nnannaaaaa nntccncngg    900
```

nttnannnnn aaaaancatn aancnnn 927

<210> SEQ ID NO 224
<211> LENGTH: 936
<212> TYPE: DNA
<213> ORGANISM: Cercopithecus aethiops
<220> FEATURE:
<221> NAME/KEY: misc_feature
<222> LOCATION: (1)..(936)
<223> OTHER INFORMATION: n is a, g, c or t

<400> SEQUENCE: 224
tttttccgng gnanntannn ntttanactt nncccccccc atttcttggg gggggaanac 60
ccccccacag nnccacttcg cggctgccag gcagtcaggc aaagnaggcc gaagcaaagc 120
cctagaagca aagccacagg aataagtcag ctttcccaga ggtcaaagaa ggctgtaggg 180
ccacctgcca cgcctcccga ccccggccgc gcggcctggg cccgctcccc aaccaaagag 240
gcccgaattc agagannttt tagcagtttc acagaaagct tctttccagt tttgaacgga 300
agatatttcc tttttcaccg taggcctcta tgggcttcca aatatccctt tgccaattcc 360
acaagaacag ccttagcgaa aggcttcttg aagggaaaga tgtaactctg tgaaatgaat 420
tctgcttata ggtcttgaga taaagtcacc gatctcatat catggattat aaggttttcc 480
ttctattttc tggcattttg gatatgtaat gatgagcatc agaaagttta atcatattta 540
atttttagaa ttattaaata ctcctgaggt cattttggtt gattttgngt ggctttcaac 600
cataaagaga tcaatgcctt gcagatataa agctttcctt ttccttcttt aataattnta 660
aactctgaat tnatgnctac agatatntaa tngatcataa atganaaatg ngatactatt 720
cnctacctcc ttatctgttc tcggaanaga ctatacancc ctgcaannat ngaagttnan 780
gattgcttnt acgaaannna aaaaaaattn acttnttttt nggcaanana aaatgcttcc 840
tccgttgnna actcccctca nggngtntta gggggnannc taccttnaan ttccntngnc 900
ctggnnncng tnnnaggnan tgcaaanngn tttctt 936

<210> SEQ ID NO 225
<211> LENGTH: 605
<212> TYPE: DNA
<213> ORGANISM: Cercopithecus aethiops
<220> FEATURE:
<221> NAME/KEY: misc_feature
<222> LOCATION: (1)..(605)
<223> OTHER INFORMATION: n is a, g, c or t

<400> SEQUENCE: 225
ttttnccnng nnntacnnct tnnnnanttn anncccccccc attattttng gggggaaacc 60
tagnaaaaat aatantgtac aagattttat ttttgtcttt aaccagaatg atgtatttgg 120
ttaagaagat agtccaagtt aaaggcatac attcaagcta gtggcacatt cggaagagca 180
gacaaagata gttggttgca aatgggaaat ttaagccatg atcttaaaag gacagaatgg 240
atatttgtta cttttnctat gggaataatt gattttttc accttccctt tcttggattt 300
tttttttttt ttaaattagt ttggttactt taaccttact gtcggttata ttggttctct 360
ttttatgtct gagttttttt ttttttttga gacggagtct tgctctgtcg cccaggctgg 420
agtgcagtgg ccggatctca gctcactgca agctctgcct cccgggttta caccattctc 480
ctgcctcagc ctnctgagta gctaggacta caggcgcccg ccacctngcc cggctagttt 540
tttgtatttt ttagtagaga cgggtttnna cccnnntnnn ncanatggtt tnnntctnct 600 ntcct 605

<210> SEQ ID NO 226
<211> LENGTH: 654
<212> TYPE: DNA
<213> ORGANISM: Cercopithecus aethiops
<220> FEATURE:
<221> NAME/KEY: misc_feature
<222> LOCATION: (1)..(654)
<223> OTHER INFORMATION: n is a, g, c or t

<400> SEQUENCE: 226

```
tttntngggg nnnnnnnngn attgnnnntc cccccgtnn nttggggggn aannccnncc      60

antactgttt gaggaaagac tgaggntcag atggcagagg ctccntagag gaaggaggct    120

acagccttga gggcatcagc ttcccacact cccaacctgc tgcctctctc tgctggaatg    180

aggaggggcc tcctggctgg gggtctccag ggtggaggga ggagctcaca ttcttagcat    240

tcctnttncc ctgagttgca aggaagacct ggtgagcatg ctgaccccag aggagtgact    300

caggcccatg gctcgagtgc ctgaggaggg accagggtcg gggatggggc atgagtcagc    360

ctggcaggtc ccataagaag ggaagggaag ggagagaaat gggggctgca caggtgtgag    420

ggtctgtgca tgtctgtgtg gtgtggtggg gtgtctggat atccgngtgt tctggatctg    480

agtgttagtg tatccgncag cacaacctct gtgtgagggt gtgtctnggc gagggtgggc    540

ttctgtggat gtcccntgtg tggnatgtgt gngtgtgtgt gtgngngact aanntatnnc    600

cttcaacnng ggntctnncc caangngnnt ntggatctnc atannatgtc tctc          654
```

<210> SEQ ID NO 227
<211> LENGTH: 2635
<212> TYPE: DNA
<213> ORGANISM: homo sapiens
<220> FEATURE:
<221> NAME/KEY: CDS
<222> LOCATION: (285)..(1679)

<400> SEQUENCE: 227

```
ggccgacgcg agcgccgcgc ttcgcttcag ctgctagctg gcccaaggga ggcgaccgcg      60

gagggtggcg aggggcggcc aggacccgca gccccggggc cgggccggtc cggaccgcca    120

gggagggcag gtcagtgggc agatcgcgtc cgcgggattc aatctctgcc cgctctgata    180

acagtccttt tccctggcgc tcacttcgtg cctggcaccc ggctgggcgc ctcaagaccg    240

ttgtctcttc gatcgcttct ttggacttgg cgaccatttc agag atg tct tcc aga     296
                                                 Met Ser Ser Arg
                                                 1

agt acc aaa gat tta att aaa agt aag tgg gga tcg aag cct agt aac      344
Ser Thr Lys Asp Leu Ile Lys Ser Lys Trp Gly Ser Lys Pro Ser Asn
5                   10                  15                  20

tcc aaa tcc gaa act aca tta gaa aaa tta aag gga gaa att gca cac      392
Ser Lys Ser Glu Thr Thr Leu Glu Lys Leu Lys Gly Glu Ile Ala His
                25                  30                  35

tta aag aca tca gtg gat gaa atc aca agt ggg aaa gga aag ctg act      440
Leu Lys Thr Ser Val Asp Glu Ile Thr Ser Gly Lys Gly Lys Leu Thr
            40                  45                  50

gat aaa gag aga cac aga ctt ttg gag aaa att cga gtc ctt gag gct      488
Asp Lys Glu Arg His Arg Leu Leu Glu Lys Ile Arg Val Leu Glu Ala
        55                  60                  65

gag aag gag aag aat gct tat caa ctc aca gag aag gac aaa gaa ata      536
Glu Lys Glu Lys Asn Ala Tyr Gln Leu Thr Glu Lys Asp Lys Glu Ile
    70                  75                  80

cag cga ctg aga gac caa ctg aag gcc aga tat agt act acc gca ttg      584
Gln Arg Leu Arg Asp Gln Leu Lys Ala Arg Tyr Ser Thr Thr Ala Leu
```

-continued

```
85                  90                  95                  100

ctt gaa cag ctg gaa gag aca acg aga gaa gga gaa agg agg gag cag      632
Leu Glu Gln Leu Glu Glu Thr Thr Arg Glu Gly Glu Arg Arg Glu Gln
                105                 110                 115

gtg ttg aaa gcc tta tct gaa gag aaa gac gta ttg aaa caa cag ttg      680
Val Leu Lys Ala Leu Ser Glu Glu Lys Asp Val Leu Lys Gln Gln Leu
            120                 125                 130

tct gct gca acc tca cga att gct gaa ctt gaa agc aaa acc aat aca      728
Ser Ala Ala Thr Ser Arg Ile Ala Glu Leu Glu Ser Lys Thr Asn Thr
        135                 140                 145

ctc cgt tta tca cag act gtg gct cca aac tgc ttc aac tca tca ata      776
Leu Arg Leu Ser Gln Thr Val Ala Pro Asn Cys Phe Asn Ser Ser Ile
    150                 155                 160

aat aat att cat gaa atg gaa ata cag ctg aaa gat gct ctg gag aaa      824
Asn Asn Ile His Glu Met Glu Ile Gln Leu Lys Asp Ala Leu Glu Lys
165                 170                 175                 180

aat cag cag tgg ctc gtg tat gat cag cag cgg gaa gtc tat gta aaa      872
Asn Gln Gln Trp Leu Val Tyr Asp Gln Gln Arg Glu Val Tyr Val Lys
                185                 190                 195

gga ctt tta gca aag atc ttt gag ttg gaa aag aaa acg gaa aca gct      920
Gly Leu Leu Ala Lys Ile Phe Glu Leu Glu Lys Lys Thr Glu Thr Ala
            200                 205                 210

gct cat tca ctc cca cag cag aca aaa aag cct gaa tca gaa ggt tat      968
Ala His Ser Leu Pro Gln Gln Thr Lys Lys Pro Glu Ser Glu Gly Tyr
        215                 220                 225

ctt caa gaa gag aag cag aaa tgt tac aac gat ctc ttg gca agt gca     1016
Leu Gln Glu Glu Lys Gln Lys Cys Tyr Asn Asp Leu Leu Ala Ser Ala
    230                 235                 240

aaa aaa gat ctt gag gtt gaa cga caa acc ata act cag ctg agt ttt     1064
Lys Lys Asp Leu Glu Val Glu Arg Gln Thr Ile Thr Gln Leu Ser Phe
245                 250                 255                 260

gaa ctg agt gaa ttt cga aga aaa tat gaa gaa acc caa aaa gaa gtt     1112
Glu Leu Ser Glu Phe Arg Arg Lys Tyr Glu Glu Thr Gln Lys Glu Val
                265                 270                 275

cac aat tta aat cag ctg ttg tat tca caa aga agg gca gat gtg caa     1160
His Asn Leu Asn Gln Leu Leu Tyr Ser Gln Arg Arg Ala Asp Val Gln
            280                 285                 290

cat ctg gaa gat gat agg cat aaa aca gag aag ata caa aaa ctc agg     1208
His Leu Glu Asp Asp Arg His Lys Thr Glu Lys Ile Gln Lys Leu Arg
        295                 300                 305

gaa gag aat gat att gct agg gga aaa ctt gaa gaa gag aag aag aga     1256
Glu Glu Asn Asp Ile Ala Arg Gly Lys Leu Glu Glu Glu Lys Lys Arg
    310                 315                 320

tcc gaa gag ctc tta tct cag gtc cag ttt ctt tac aca tct ctg cta     1304
Ser Glu Glu Leu Leu Ser Gln Val Gln Phe Leu Tyr Thr Ser Leu Leu
325                 330                 335                 340

aag cag caa gaa gaa caa aca agg gta gct ctg ttg gaa caa cag atg     1352
Lys Gln Gln Glu Glu Gln Thr Arg Val Ala Leu Leu Glu Gln Gln Met
                345                 350                 355

cag gca tgt act tta gac ttt gaa aat gaa aaa ctc gac cgt caa cat     1400
Gln Ala Cys Thr Leu Asp Phe Glu Asn Glu Lys Leu Asp Arg Gln His
            360                 365                 370

gtg cag cat caa ttg ctt gta att ctt aag gag ctc cga aaa gca aga     1448
Val Gln His Gln Leu Leu Val Ile Leu Lys Glu Leu Arg Lys Ala Arg
        375                 380                 385

aat caa ata aca cag ttg gaa tcc ttg aaa cag ctt cat gag ttt gcc     1496
Asn Gln Ile Thr Gln Leu Glu Ser Leu Lys Gln Leu His Glu Phe Ala
    390                 395                 400

atc aca gag cca tta gtc act ttc caa gga gag act gaa aac aga gaa     1544
Ile Thr Glu Pro Leu Val Thr Phe Gln Gly Glu Thr Glu Asn Arg Glu
```

```
405                 410                 415                 420

aaa gtt gcc gcc tca cca aaa agt ccc act gct gca ctc aat gaa agc      1592
Lys Val Ala Ala Ser Pro Lys Ser Pro Thr Ala Ala Leu Asn Glu Ser
                425                 430                 435

ctg gtg gaa tgt ccc aag tgc aat ata cag tat cca gcc act gag cat      1640
Leu Val Glu Cys Pro Lys Cys Asn Ile Gln Tyr Pro Ala Thr Glu His
            440                 445                 450

cgc gat ctg ctt gtc cat gtg gaa tac tgt tca aag tag caaaataagt       1689
Arg Asp Leu Leu Val His Val Glu Tyr Cys Ser Lys
        455                 460

atttgttttg atattaaaag attcaatact gtattttctg ttagcttgtg ggcattttga   1749

attatatatt tcacattttg cataaaactg cctatctacc tttgacactc cagcatgcta   1809

gtgaatcatg tatcttttag gctgctgtgc atttctcttg gcagtgatac ctccctgaca   1869

tggttcatca tcaggctgca atgacagaat gtggtgagca gcgtctactg agactactaa   1929

cattttgcac tgtcaaaata cttggtgagg aaaagatagc tcaggttatt gctaatgggt   1989

taatgcacca gcaagcaaaa tattttatgt tttgggggtt tgaaaaatca aagataatta   2049

accaaggatc ttaactgtgt tcgcattttt tatccaagca cttagaaaac ctacaatcct   2109

aattttgatg tccattgtta agaggtggtg atagatacta ttttttttt catattgtat    2169

agcggttatt agaaaagttg ggattttct tgatctttat tgctgcttac cattgaaact    2229

taacccagct gtgttcccca actctgttct gcgcacgaaa cagtatctgt ttgaggcata   2289

atcttaagtg gccacacaca atgttttctc ttatgttatc tggcagtaac tgtaacttga   2349

attacattag cacattctgc ttagctaaaa ttgttaaaat aaactttaat aaacccatgt   2409

agccctctca tttgattgac agtattttag ttatttttgg cattcttaaa gctgggcaat   2469

gtaatgatca gatctttgtt tgtctgaaca ggtattttta tacatgcttt ttgtaaacca   2529

aaaactttta aatttcttca ggttttctaa catgcttacc actgggctac tgtaaatgag   2589

aaaagaataa aattatttaa tgttttaaaa aaaaaaaaaa aaaaaa                  2635


<210> SEQ ID NO 228
<211> LENGTH: 464
<212> TYPE: PRT
<213> ORGANISM: homo sapiens

<400> SEQUENCE: 228

Met Ser Ser Arg Ser Thr Lys Asp Leu Ile Lys Ser Lys Trp Gly Ser
1               5                   10                  15

Lys Pro Ser Asn Ser Lys Ser Glu Thr Thr Leu Glu Lys Leu Lys Gly
            20                  25                  30

Glu Ile Ala His Leu Lys Thr Ser Val Asp Glu Ile Thr Ser Gly Lys
        35                  40                  45

Gly Lys Leu Thr Asp Lys Glu Arg His Arg Leu Leu Glu Lys Ile Arg
    50                  55                  60

Val Leu Glu Ala Glu Lys Glu Lys Asn Ala Tyr Gln Leu Thr Glu Lys
65                  70                  75                  80

Asp Lys Glu Ile Gln Arg Leu Arg Asp Gln Leu Lys Ala Arg Tyr Ser
                85                  90                  95

Thr Thr Ala Leu Leu Glu Gln Leu Glu Glu Thr Thr Arg Glu Gly Glu
            100                 105                 110

Arg Arg Glu Gln Val Leu Lys Ala Leu Ser Glu Glu Lys Asp Val Leu
        115                 120                 125

Lys Gln Gln Leu Ser Ala Ala Thr Ser Arg Ile Ala Glu Leu Glu Ser
    130                 135                 140
```

Lys Thr Asn Thr Leu Arg Leu Ser Gln Thr Val Ala Pro Asn Cys Phe
145 150 155 160

Asn Ser Ser Ile Asn Asn Ile His Glu Met Glu Ile Gln Leu Lys Asp
165 170 175

Ala Leu Glu Lys Asn Gln Gln Trp Leu Val Tyr Asp Gln Gln Arg Glu
180 185 190

Val Tyr Val Lys Gly Leu Leu Ala Lys Ile Phe Glu Leu Glu Lys Lys
195 200 205

Thr Glu Thr Ala Ala His Ser Leu Pro Gln Gln Thr Lys Lys Pro Glu
210 215 220

Ser Glu Gly Tyr Leu Gln Glu Glu Lys Gln Lys Cys Tyr Asn Asp Leu
225 230 235 240

Leu Ala Ser Ala Lys Lys Asp Leu Glu Val Glu Arg Gln Thr Ile Thr
245 250 255

Gln Leu Ser Phe Glu Leu Ser Glu Phe Arg Arg Lys Tyr Glu Glu Thr
260 265 270

Gln Lys Glu Val His Asn Leu Asn Gln Leu Leu Tyr Ser Gln Arg Arg
275 280 285

Ala Asp Val Gln His Leu Glu Asp Asp Arg His Lys Thr Glu Lys Ile
290 295 300

Gln Lys Leu Arg Glu Glu Asn Asp Ile Ala Arg Gly Lys Leu Glu Glu
305 310 315 320

Glu Lys Lys Arg Ser Glu Glu Leu Leu Ser Gln Val Gln Phe Leu Tyr
325 330 335

Thr Ser Leu Leu Lys Gln Gln Glu Glu Gln Thr Arg Val Ala Leu Leu
340 345 350

Glu Gln Gln Met Gln Ala Cys Thr Leu Asp Phe Glu Asn Glu Lys Leu
355 360 365

Asp Arg Gln His Val Gln His Gln Leu Leu Val Ile Leu Lys Glu Leu
370 375 380

Arg Lys Ala Arg Asn Gln Ile Thr Gln Leu Glu Ser Leu Lys Gln Leu
385 390 395 400

His Glu Phe Ala Ile Thr Glu Pro Leu Val Thr Phe Gln Gly Glu Thr
405 410 415

Glu Asn Arg Glu Lys Val Ala Ala Ser Pro Lys Ser Pro Thr Ala Ala
420 425 430

Leu Asn Glu Ser Leu Val Glu Cys Pro Lys Cys Asn Ile Gln Tyr Pro
435 440 445

Ala Thr Glu His Arg Asp Leu Leu Val His Val Glu Tyr Cys Ser Lys
450 455 460

<210> SEQ ID NO 229
<211> LENGTH: 2635
<212> TYPE: DNA
<213> ORGANISM: homo sapiens
<220> FEATURE:
<221> NAME/KEY: CDS
<222> LOCATION: (285)..(1679)

<400> SEQUENCE: 229
ggccgacgcg agcgccgcgc ttcgcttcag ctgctagctg gcccaaggga ggcgaccgcg 60
gagggtggcg aggggcggcc aggacccgca gccccggggc cgggccggtc cggaccgcca 120
gggagggcag gtcagtgggc agatcgcgtc cgcgggattc aatctctgcc cgctctgata 180
acagtccttt tccctggcgc tcacttcgtg cctggcaccc ggctgggcgc ctcaagaccg 240

```
ttgtctcttc gatcgcttct ttggacttgg cgaccatttc agag atg tct tcc aga      296
                                                 Met Ser Ser Arg
                                                 1

agt acc aaa gat tta att aaa agt aag tgg gga tcg aag cct agt aac      344
Ser Thr Lys Asp Leu Ile Lys Ser Lys Trp Gly Ser Lys Pro Ser Asn
5                   10                  15                  20

tcc aaa tcc gaa act aca tta gaa aaa tta aag gga gaa att gca cac      392
Ser Lys Ser Glu Thr Thr Leu Glu Lys Leu Lys Gly Glu Ile Ala His
                25                  30                  35

tta aag aca tca gtg gat gaa atc aca agt ggg aaa gga aag ctg act      440
Leu Lys Thr Ser Val Asp Glu Ile Thr Ser Gly Lys Gly Lys Leu Thr
            40                  45                  50

gat aaa gag aga cac aga ctt ttg gag aaa att cga gtc ctt gag gct      488
Asp Lys Glu Arg His Arg Leu Leu Glu Lys Ile Arg Val Leu Glu Ala
        55                  60                  65

gag aag gag aag aat gct tat caa ctc aca gag aag gac aaa gaa ata      536
Glu Lys Glu Lys Asn Ala Tyr Gln Leu Thr Glu Lys Asp Lys Glu Ile
    70                  75                  80

cag cga ctg aga gac caa ctg aag gcc aga tat agt act acc gca ttg      584
Gln Arg Leu Arg Asp Gln Leu Lys Ala Arg Tyr Ser Thr Thr Ala Leu
85                  90                  95                  100

ctt gaa cag ctg gaa gag aca acg aga gaa gga gaa agg agg gag cag      632
Leu Glu Gln Leu Glu Glu Thr Thr Arg Glu Gly Glu Arg Arg Glu Gln
                105                 110                 115

gtg ttg aaa gcc tta tct gaa gag aaa gac gta ttg aaa caa cag ttg      680
Val Leu Lys Ala Leu Ser Glu Glu Lys Asp Val Leu Lys Gln Gln Leu
            120                 125                 130

tct gct gca acc tca cga att gct gaa ctt gaa agc aaa acc aat aca      728
Ser Ala Ala Thr Ser Arg Ile Ala Glu Leu Glu Ser Lys Thr Asn Thr
        135                 140                 145

ctc cgt tta tca cag act gtg gct cca aac tgc ttc aac tca tca ata      776
Leu Arg Leu Ser Gln Thr Val Ala Pro Asn Cys Phe Asn Ser Ser Ile
    150                 155                 160

aat aat att cat gaa atg gaa ata cag ctg aaa gat gct ctg gag aaa      824
Asn Asn Ile His Glu Met Glu Ile Gln Leu Lys Asp Ala Leu Glu Lys
165                 170                 175                 180

aat cag cag tgg ctc gtg tat gat cag cag cgg gaa gtc tat gta aaa      872
Asn Gln Gln Trp Leu Val Tyr Asp Gln Gln Arg Glu Val Tyr Val Lys
                185                 190                 195

gga ctt tta gca aag atc ttt gag ttg gaa aag aaa acg gaa aca gct      920
Gly Leu Leu Ala Lys Ile Phe Glu Leu Glu Lys Lys Thr Glu Thr Ala
            200                 205                 210

gct cat tca ctc cca cag cag aca aaa aag cct gaa tca gaa ggt tat      968
Ala His Ser Leu Pro Gln Gln Thr Lys Lys Pro Glu Ser Glu Gly Tyr
        215                 220                 225

ctt caa gaa gag aag cag aaa tgt tac aac gat ctc ttg gca agt gca     1016
Leu Gln Glu Glu Lys Gln Lys Cys Tyr Asn Asp Leu Leu Ala Ser Ala
    230                 235                 240

aaa aaa gat ctt gag gtt gaa cga caa acc ata act cag ctg agt ttt     1064
Lys Lys Asp Leu Glu Val Glu Arg Gln Thr Ile Thr Gln Leu Ser Phe
245                 250                 255                 260

gaa ctg agt gaa ttt cga aga aaa tat gaa gaa acc caa aaa gaa gtt     1112
Glu Leu Ser Glu Phe Arg Arg Lys Tyr Glu Glu Thr Gln Lys Glu Val
                265                 270                 275

cac aat tta aat cag ctg ttg tat tca caa aga agg gca gat gtg caa     1160
His Asn Leu Asn Gln Leu Leu Tyr Ser Gln Arg Arg Ala Asp Val Gln
            280                 285                 290

cat ctg gaa gat gat agg cat aaa aca gag aag ata caa aaa ctc agg     1208
His Leu Glu Asp Asp Arg His Lys Thr Glu Lys Ile Gln Lys Leu Arg
        295                 300                 305
```

```
gaa gag aat gat att gct agg gga aaa ctt gaa gaa gag aag aag aga      1256
Glu Glu Asn Asp Ile Ala Arg Gly Lys Leu Glu Glu Glu Lys Lys Arg
    310                 315                 320

tcc gaa gag ctc tta tct cag gtc cag ttt ctt tac aca tct ctg cta      1304
Ser Glu Glu Leu Leu Ser Gln Val Gln Phe Leu Tyr Thr Ser Leu Leu
325                 330                 335                 340

aag cag caa gaa gaa caa aca agg gta gct ctg ttg gaa caa cag atg      1352
Lys Gln Gln Glu Glu Gln Thr Arg Val Ala Leu Leu Glu Gln Gln Met
                345                 350                 355

cag gca tgt act tta gac ttt gaa aat gaa aaa ctc gac cgt caa cat      1400
Gln Ala Cys Thr Leu Asp Phe Glu Asn Glu Lys Leu Asp Arg Gln His
            360                 365                 370

gtg cag cat caa ttg ctt gta att ctt aag gag ctc cga aaa gca aga      1448
Val Gln His Gln Leu Leu Val Ile Leu Lys Glu Leu Arg Lys Ala Arg
        375                 380                 385

aat caa ata aca cag ttg gaa tcc ttg aaa cag ctt cat gag ttt gcc      1496
Asn Gln Ile Thr Gln Leu Glu Ser Leu Lys Gln Leu His Glu Phe Ala
    390                 395                 400

atc aca gag cca tta gtc act ttc caa gga gag act gaa aac aga gaa      1544
Ile Thr Glu Pro Leu Val Thr Phe Gln Gly Glu Thr Glu Asn Arg Glu
405                 410                 415                 420

aaa gtt gcc gcc tca cca aaa agt ccc act gct gca ctc aat gaa agc      1592
Lys Val Ala Ala Ser Pro Lys Ser Pro Thr Ala Ala Leu Asn Glu Ser
                425                 430                 435

ctg gtg gaa tgt ccc aag tgc aat ata cag tat cca gcc act gag cat      1640
Leu Val Glu Cys Pro Lys Cys Asn Ile Gln Tyr Pro Ala Thr Glu His
            440                 445                 450

cgc gat ctg ctt gtc cat gtg gaa tac tgt tca aag tag caaaataagt      1689
Arg Asp Leu Leu Val His Val Glu Tyr Cys Ser Lys
        455                 460

atttgttttg atattaaaag attcaatact gtattttctg ttagcttgtg ggcattttga   1749

attatatatt tcacattttg cataaaactg cctatctacc tttgacactc cagcatgcta   1809

gtgaatcatg tatcttttag gctgctgtgc atttctcttg gcagtgatac ctccctgaca   1869

tggttcatca tcaggctgca atgacagaat gtggtgagca gcgtctactg agactactaa   1929

cattttgcac tgtcaaaata cttggtgagg aaaagatagc tcaggttatt gctaatgggt   1989

taatgcacca gcaagcaaaa tattttatgt tttggggggtt tgaaaaatca aagataatta   2049

accaaggatc ttaactgtgt tcgcattttt tatccaagca cttagaaaac ctacaatcct   2109

aattttgatg tccattgtta agaggtggtg atagatacta ttttttttttt catattgtat   2169

agcggttatt agaaaagttg gggattttct tgatctttat tgctgcttac cattgaaact   2229

taacccagct gtgttcccca actctgttct gcgcacgaaa cagtatctgt ttgaggcata   2289

atcttaagtg gccacacaca atgttttctc ttatgttatc tggcagtaac tgtaacttga   2349

attacattag cacattctgc ttagctaaaa ttgttaaaat aaactttaat aaacccatgt   2409

agccctctca tttgattgac agtattttag ttatttttgg cattcttaaa gctgggcaat   2469

gtaatgatca gatctttgtt tgtctgaaca ggtattttta tacatgcttt ttgtaaacca   2529

aaaactttta aatttcttca ggttttctaa catgcttacc actgggctac tgtaaatgag   2589

aaaagaataa aattatttaa tgttttaaaa aaaaaaaaaa aaaaaa                  2635
```

<210> SEQ ID NO 230
<211> LENGTH: 464
<212> TYPE: PRT
<213> ORGANISM: homo sapiens

<400> SEQUENCE: 230

```
Met Ser Ser Arg Ser Thr Lys Asp Leu Ile Lys Ser Lys Trp Gly Ser
1               5                   10                  15

Lys Pro Ser Asn Ser Lys Ser Glu Thr Thr Leu Glu Lys Leu Lys Gly
            20                  25                  30

Glu Ile Ala His Leu Lys Thr Ser Val Asp Glu Ile Thr Ser Gly Lys
        35                  40                  45

Gly Lys Leu Thr Asp Lys Glu Arg His Arg Leu Leu Glu Lys Ile Arg
    50                  55                  60

Val Leu Glu Ala Glu Lys Glu Lys Asn Ala Tyr Gln Leu Thr Glu Lys
65                  70                  75                  80

Asp Lys Glu Ile Gln Arg Leu Arg Asp Gln Leu Lys Ala Arg Tyr Ser
                85                  90                  95

Thr Thr Ala Leu Leu Glu Gln Leu Glu Glu Thr Thr Arg Glu Gly Glu
            100                 105                 110

Arg Arg Glu Gln Val Leu Lys Ala Leu Ser Glu Glu Lys Asp Val Leu
        115                 120                 125

Lys Gln Gln Leu Ser Ala Ala Thr Ser Arg Ile Ala Glu Leu Glu Ser
    130                 135                 140

Lys Thr Asn Thr Leu Arg Leu Ser Gln Thr Val Ala Pro Asn Cys Phe
145                 150                 155                 160

Asn Ser Ser Ile Asn Asn Ile His Glu Met Glu Ile Gln Leu Lys Asp
                165                 170                 175

Ala Leu Glu Lys Asn Gln Gln Trp Leu Val Tyr Asp Gln Gln Arg Glu
            180                 185                 190

Val Tyr Val Lys Gly Leu Leu Ala Lys Ile Phe Glu Leu Glu Lys Lys
        195                 200                 205

Thr Glu Thr Ala Ala His Ser Leu Pro Gln Gln Thr Lys Lys Pro Glu
    210                 215                 220

Ser Glu Gly Tyr Leu Gln Glu Glu Lys Gln Lys Cys Tyr Asn Asp Leu
225                 230                 235                 240

Leu Ala Ser Ala Lys Lys Asp Leu Glu Val Glu Arg Gln Thr Ile Thr
                245                 250                 255

Gln Leu Ser Phe Glu Leu Ser Glu Phe Arg Arg Lys Tyr Glu Glu Thr
            260                 265                 270

Gln Lys Glu Val His Asn Leu Asn Gln Leu Leu Tyr Ser Gln Arg Arg
        275                 280                 285

Ala Asp Val Gln His Leu Glu Asp Asp Arg His Lys Thr Glu Lys Ile
    290                 295                 300

Gln Lys Leu Arg Glu Glu Asn Asp Ile Ala Arg Gly Lys Leu Glu Glu
305                 310                 315                 320

Glu Lys Lys Arg Ser Glu Glu Leu Leu Ser Gln Val Gln Phe Leu Tyr
                325                 330                 335

Thr Ser Leu Leu Lys Gln Gln Glu Glu Gln Thr Arg Val Ala Leu Leu
            340                 345                 350

Glu Gln Gln Met Gln Ala Cys Thr Leu Asp Phe Glu Asn Glu Lys Leu
        355                 360                 365

Asp Arg Gln His Val Gln His Gln Leu Leu Val Ile Leu Lys Glu Leu
    370                 375                 380

Arg Lys Ala Arg Asn Gln Ile Thr Gln Leu Glu Ser Leu Lys Gln Leu
385                 390                 395                 400

His Glu Phe Ala Ile Thr Glu Pro Leu Val Thr Phe Gln Gly Glu Thr
                405                 410                 415

Glu Asn Arg Glu Lys Val Ala Ala Ser Pro Lys Ser Pro Thr Ala Ala
            420                 425                 430
```

```
Leu Asn Glu Ser Leu Val Glu Cys Pro Lys Cys Asn Ile Gln Tyr Pro
        435                 440                 445

Ala Thr Glu His Arg Asp Leu Leu Val His Val Glu Tyr Cys Ser Lys
    450                 455                 460


<210> SEQ ID NO 231
<211> LENGTH: 6829
<212> TYPE: DNA
<213> ORGANISM: HOMO SAPIENS
<220> FEATURE:
<221> NAME/KEY: CDS
<222> LOCATION: (89)..(6274)

<400> SEQUENCE: 231

cttctctccc agggcggtgc gacccggagc tccagcgccc gagtctccac ttcgtttgct      60

gaaacttgct ttctaccagc taagaacc atg ctg cga gtg att gtg gaa tct        112
                               Met Leu Arg Val Ile Val Glu Ser
                               1               5

gcc agc aat atc cct aaa acg aaa ttt ggc aag ccg gat cct att gtt       160
Ala Ser Asn Ile Pro Lys Thr Lys Phe Gly Lys Pro Asp Pro Ile Val
    10                  15                  20

tct gtc att ttt aag gat gag aaa aag aaa aca aag aaa gtt gat aat       208
Ser Val Ile Phe Lys Asp Glu Lys Lys Lys Thr Lys Lys Val Asp Asn
25                  30                  35                  40

gaa ttg aac cct gtc tgg aat gag att ttg gag ttt gac ttg agg ggt       256
Glu Leu Asn Pro Val Trp Asn Glu Ile Leu Glu Phe Asp Leu Arg Gly
                45                  50                  55

ata cca ctg gac ttt tca tct tcc ctt ggg att att gtg aaa gat ttt       304
Ile Pro Leu Asp Phe Ser Ser Ser Leu Gly Ile Ile Val Lys Asp Phe
            60                  65                  70

gag aca att gga caa aat aaa tta att ggc acg gcg act gta gcc ctg       352
Glu Thr Ile Gly Gln Asn Lys Leu Ile Gly Thr Ala Thr Val Ala Leu
        75                  80                  85

aag gac ctg act ggt gac cag agc aga tcc ctg ccg tac aag ctg atc       400
Lys Asp Leu Thr Gly Asp Gln Ser Arg Ser Leu Pro Tyr Lys Leu Ile
    90                  95                  100

tcc ctg cta aat gaa aaa ggg caa gat act ggg gcc acc att gac ttg       448
Ser Leu Leu Asn Glu Lys Gly Gln Asp Thr Gly Ala Thr Ile Asp Leu
105                 110                 115                 120

gtg atc ggc tat gat ccg cct tct gct cca cat cca aat gac ctg agc       496
Val Ile Gly Tyr Asp Pro Pro Ser Ala Pro His Pro Asn Asp Leu Ser
                125                 130                 135

ggg ccc agc gtg cca ggc atg gga gga gat ggg gaa gaa gat gaa ggt       544
Gly Pro Ser Val Pro Gly Met Gly Gly Asp Gly Glu Glu Asp Glu Gly
            140                 145                 150

gat gaa gac agg ttg gac aat gca gtc agg ggc cct ggg ccc aag ggg       592
Asp Glu Asp Arg Leu Asp Asn Ala Val Arg Gly Pro Gly Pro Lys Gly
        155                 160                 165

cca gtt ggg acg gtg tcg gaa gct cag ctt gct cgg agg ctc acc aaa       640
Pro Val Gly Thr Val Ser Glu Ala Gln Leu Ala Arg Arg Leu Thr Lys
    170                 175                 180

gta aag aac agc cgg cgg atg ctg tca aat aag cca cag gac ttc cag       688
Val Lys Asn Ser Arg Arg Met Leu Ser Asn Lys Pro Gln Asp Phe Gln
185                 190                 195                 200

atc cgc gtc cga gtg att gag ggc cga cag tta agt ggt aac aac ata       736
Ile Arg Val Arg Val Ile Glu Gly Arg Gln Leu Ser Gly Asn Asn Ile
                205                 210                 215

agg cct gtg gtc aaa gtt cac gtc tgt ggc cag aca cac cga aca aga       784
Arg Pro Val Val Lys Val His Val Cys Gly Gln Thr His Arg Thr Arg
            220                 225                 230
```

```
atc aag aga gga aac aac cct ttt ttt gat gag ttg ttt ttc tac aat      832
Ile Lys Arg Gly Asn Asn Pro Phe Phe Asp Glu Leu Phe Phe Tyr Asn
        235                 240                 245

gtc aac atg acc cct tct gaa ttg atg gat gag atc atc agc atc cgg      880
Val Asn Met Thr Pro Ser Glu Leu Met Asp Glu Ile Ile Ser Ile Arg
    250                 255                 260

gtt tat aat tct cac tct ctg cgg gca gat tgt ctg atg ggg gaa ttt      928
Val Tyr Asn Ser His Ser Leu Arg Ala Asp Cys Leu Met Gly Glu Phe
265                 270                 275                 280

aag att gat gtt gga ttt gtt tat gat gaa cct ggc cat gct gtc atg      976
Lys Ile Asp Val Gly Phe Val Tyr Asp Glu Pro Gly His Ala Val Met
                285                 290                 295

aga aag tgg ctt ctt ctc aat gac ccg gaa gat acc agt tca ggt tct     1024
Arg Lys Trp Leu Leu Leu Asn Asp Pro Glu Asp Thr Ser Ser Gly Ser
            300                 305                 310

aaa ggt tat atg aaa gtc agc atg ttt gtc ctg gga acc gga gat gag     1072
Lys Gly Tyr Met Lys Val Ser Met Phe Val Leu Gly Thr Gly Asp Glu
        315                 320                 325

cct cct cct gag aga cga gat cgt gat aat gac agt gat gat gtg gag     1120
Pro Pro Pro Glu Arg Arg Asp Arg Asp Asn Asp Ser Asp Asp Val Glu
    330                 335                 340

agt aat ttg tta ctc cct gct ggc att gcc ctc cgg tgg gtg acc ttc     1168
Ser Asn Leu Leu Leu Pro Ala Gly Ile Ala Leu Arg Trp Val Thr Phe
345                 350                 355                 360

ttg ctg aaa atc tac cga gct gag gac atc ccc cag atg gat gat gcc     1216
Leu Leu Lys Ile Tyr Arg Ala Glu Asp Ile Pro Gln Met Asp Asp Ala
                365                 370                 375

ttc tca cag aca gta aag gaa ata ttt gga ggc aat gca gat aag aaa     1264
Phe Ser Gln Thr Val Lys Glu Ile Phe Gly Gly Asn Ala Asp Lys Lys
            380                 385                 390

aat ctc gtg gat cct ttt gta gaa gtt tcc ttt gct gga aaa aag gtt     1312
Asn Leu Val Asp Pro Phe Val Glu Val Ser Phe Ala Gly Lys Lys Val
        395                 400                 405

tgt aca aac ata att gag aaa aat gca aac cca gag tgg aat cag gtc     1360
Cys Thr Asn Ile Ile Glu Lys Asn Ala Asn Pro Glu Trp Asn Gln Val
    410                 415                 420

gtc aat ctt cag atc aag ttt cct tca gtg tgt gaa aaa ata aaa cta     1408
Val Asn Leu Gln Ile Lys Phe Pro Ser Val Cys Glu Lys Ile Lys Leu
425                 430                 435                 440

aca ata tat gac tgg gac cgt ctt act aaa aat gat gta gtt gga aca     1456
Thr Ile Tyr Asp Trp Asp Arg Leu Thr Lys Asn Asp Val Val Gly Thr
                445                 450                 455

aca tat cta cac ctc tct aaa att gct gcc tct ggt ggg gaa gtg gaa     1504
Thr Tyr Leu His Leu Ser Lys Ile Ala Ala Ser Gly Gly Glu Val Glu
            460                 465                 470

gat ttc tca tct tcg gga act ggg gct gca tca tat aca gta aac aca     1552
Asp Phe Ser Ser Ser Gly Thr Gly Ala Ala Ser Tyr Thr Val Asn Thr
        475                 480                 485

gga gaa aca gag gta ggc ttt gtt cca acg ttt gga cct tgt tac ctg     1600
Gly Glu Thr Glu Val Gly Phe Val Pro Thr Phe Gly Pro Cys Tyr Leu
    490                 495                 500

aat ctt tat gga agc ccc agg gag tac acg gga ttc cca gac ccc tat     1648
Asn Leu Tyr Gly Ser Pro Arg Glu Tyr Thr Gly Phe Pro Asp Pro Tyr
505                 510                 515                 520

gat gag ctg aat act gga aag ggg gaa gga gtt gcc tac aga ggc agg     1696
Asp Glu Leu Asn Thr Gly Lys Gly Glu Gly Val Ala Tyr Arg Gly Arg
                525                 530                 535

atc ttg gtt gaa tta gcc act ttt ctt gag aag aca cca cca gat aaa     1744
Ile Leu Val Glu Leu Ala Thr Phe Leu Glu Lys Thr Pro Pro Asp Lys
            540                 545                 550
```

-continued

```
aag ctt gag ccc att tca aat gat gac ctg ctg gtt gtt gag aaa tac      1792
Lys Leu Glu Pro Ile Ser Asn Asp Asp Leu Leu Val Val Glu Lys Tyr
        555                 560                 565

cag cga agg cgg aag tac agc ctg tct gcc gtg ttt cat tca gcc acc      1840
Gln Arg Arg Arg Lys Tyr Ser Leu Ser Ala Val Phe His Ser Ala Thr
    570                 575                 580

atg ttg caa gat gtt ggt gag gcc att cag ttt gaa gtc agc att ggg      1888
Met Leu Gln Asp Val Gly Glu Ala Ile Gln Phe Glu Val Ser Ile Gly
585                 590                 595                 600

aac tat ggc aac aag ttt gac acc acc tgt aag cct ttg gca tca aca      1936
Asn Tyr Gly Asn Lys Phe Asp Thr Thr Cys Lys Pro Leu Ala Ser Thr
                605                 610                 615

act cag tac agc cgt gct gta ttt gat ggc aac tac tat tat tac ttg      1984
Thr Gln Tyr Ser Arg Ala Val Phe Asp Gly Asn Tyr Tyr Tyr Tyr Leu
            620                 625                 630

cct tgg gcc cac acc aag cca gtt gtt acc ctg act tca tac tgg gag      2032
Pro Trp Ala His Thr Lys Pro Val Val Thr Leu Thr Ser Tyr Trp Glu
        635                 640                 645

gat att agt cat cgc ctg gat gcg gtg aac act ctc cta gct atg gca      2080
Asp Ile Ser His Arg Leu Asp Ala Val Asn Thr Leu Leu Ala Met Ala
    650                 655                 660

gaa cgg ctg caa aca aat ata gaa gct cta aaa tca ggg ata caa ggt      2128
Glu Arg Leu Gln Thr Asn Ile Glu Ala Leu Lys Ser Gly Ile Gln Gly
665                 670                 675                 680

aaa att cct gca aac cag ctg gct gaa ttg tgg ctg aag ctg ata gat      2176
Lys Ile Pro Ala Asn Gln Leu Ala Glu Leu Trp Leu Lys Leu Ile Asp
                685                 690                 695

gaa gtt ata gaa gac acg aga tac acg ttg cct ctc aca gaa gga aaa      2224
Glu Val Ile Glu Asp Thr Arg Tyr Thr Leu Pro Leu Thr Glu Gly Lys
            700                 705                 710

gcc aac gtc aca gtt ctc gat act cag atc cga aag ctg cgg tcc agg      2272
Ala Asn Val Thr Val Leu Asp Thr Gln Ile Arg Lys Leu Arg Ser Arg
        715                 720                 725

tct ctc tcc caa ata cat gag gcg gct gtg agg atg agg tcg gaa gcc      2320
Ser Leu Ser Gln Ile His Glu Ala Ala Val Arg Met Arg Ser Glu Ala
    730                 735                 740

aca gat gtg aag tcc aca ctg gca gaa att gag gac tgg ctt gat aaa      2368
Thr Asp Val Lys Ser Thr Leu Ala Glu Ile Glu Asp Trp Leu Asp Lys
745                 750                 755                 760

tta atg cag ctg act gaa gag cca cag aac agc atg cct gac atc atc      2416
Leu Met Gln Leu Thr Glu Glu Pro Gln Asn Ser Met Pro Asp Ile Ile
                765                 770                 775

atc tgg atg atc cgg gga gag aag aga ctg gcc tat gca cga att ccc      2464
Ile Trp Met Ile Arg Gly Glu Lys Arg Leu Ala Tyr Ala Arg Ile Pro
            780                 785                 790

gca cat cag gtc ttg tac tcc acc agt ggt gag aat gca tct gga aaa      2512
Ala His Gln Val Leu Tyr Ser Thr Ser Gly Glu Asn Ala Ser Gly Lys
        795                 800                 805

tac tgt ggg aaa acc caa acc atc ttt ctg aag tat cca cag gag aaa      2560
Tyr Cys Gly Lys Thr Gln Thr Ile Phe Leu Lys Tyr Pro Gln Glu Lys
    810                 815                 820

aac aac ggg cca aag gtg cct gtg gag ttg cga gtg aac atc tgg cta      2608
Asn Asn Gly Pro Lys Val Pro Val Glu Leu Arg Val Asn Ile Trp Leu
825                 830                 835                 840

ggc tta agt gct gtg gag aag aag ttt aac agc ttc gca gaa gga act      2656
Gly Leu Ser Ala Val Glu Lys Lys Phe Asn Ser Phe Ala Glu Gly Thr
                845                 850                 855

ttc acc gtc ttt gct gaa atg tat gaa aat caa gct ctc atg ttt gga      2704
Phe Thr Val Phe Ala Glu Met Tyr Glu Asn Gln Ala Leu Met Phe Gly
            860                 865                 870
```

-continued

```
aaa tgg ggt act tct gga tta gta gga cgt cat aag ttt tct gat gtc      2752
Lys Trp Gly Thr Ser Gly Leu Val Gly Arg His Lys Phe Ser Asp Val
        875                 880                 885

aca gga aaa ata aaa ctc aag agg gaa ttt ttt ctg cct cca aaa ggc      2800
Thr Gly Lys Ile Lys Leu Lys Arg Glu Phe Phe Leu Pro Pro Lys Gly
    890                 895                 900

tgg gaa tgg gaa gga gag tgg ata gtt gat cct gaa aga agc ttg ctg      2848
Trp Glu Trp Glu Gly Glu Trp Ile Val Asp Pro Glu Arg Ser Leu Leu
905                 910                 915                 920

act gag gca gat gca ggt cac acg gag ttc act gat gaa gtc tat cag      2896
Thr Glu Ala Asp Ala Gly His Thr Glu Phe Thr Asp Glu Val Tyr Gln
                925                 930                 935

aac gag agc cgc tac ccc ggg ggc gac tgg aag ccg gcc gag gac acc      2944
Asn Glu Ser Arg Tyr Pro Gly Gly Asp Trp Lys Pro Ala Glu Asp Thr
            940                 945                 950

tac acg gat gcg aac ggc gat aaa gca gca tca ccc agc gag ttg act      2992
Tyr Thr Asp Ala Asn Gly Asp Lys Ala Ala Ser Pro Ser Glu Leu Thr
        955                 960                 965

tgt cct cca ggt tgg gaa tgg gaa gat gat gca tgg tct tat gac ata      3040
Cys Pro Pro Gly Trp Glu Trp Glu Asp Asp Ala Trp Ser Tyr Asp Ile
    970                 975                 980

aat cga gcg gtg gat gag aaa ggc tgg gaa tat gga atc acc att cct      3088
Asn Arg Ala Val Asp Glu Lys Gly Trp Glu Tyr Gly Ile Thr Ile Pro
985                 990                 995                 1000

cct gat cat aag ccc  aaa tcc tgg gtt gca  gca gag aaa atg tac       3133
Pro Asp His Lys Pro  Lys Ser Trp Val Ala  Ala Glu Lys Met Tyr
                1005                 1010                 1015

cac act cat aga cgg  cga agg ctg gtc cga  aaa cgc aag aaa gat       3178
His Thr His Arg Arg  Arg Arg Leu Val Arg  Lys Arg Lys Lys Asp
                1020                 1025                 1030

tta aca cag act gct  tca agc acc gca agg  gcc atg gag gaa ttg       3223
Leu Thr Gln Thr Ala  Ser Ser Thr Ala Arg  Ala Met Glu Glu Leu
                1035                 1040                 1045

caa gac caa gag ggc  tgg gaa tat gct tct  cta att ggc tgg aaa       3268
Gln Asp Gln Glu Gly  Trp Glu Tyr Ala Ser  Leu Ile Gly Trp Lys
                1050                 1055                 1060

ttt cac tgg aaa caa  cgt agt tca gat acc  ttc cgc cgc aga cgc       3313
Phe His Trp Lys Gln  Arg Ser Ser Asp Thr  Phe Arg Arg Arg Arg
                1065                 1070                 1075

tgg agg aga aaa atg  gct cct tca gaa aca  cat ggt gca gct gcc       3358
Trp Arg Arg Lys Met  Ala Pro Ser Glu Thr  His Gly Ala Ala Ala
                1080                 1085                 1090

atc ttt aaa ctt gaa  ggt gcc ctt ggg gca  gac act acc gaa gat       3403
Ile Phe Lys Leu Glu  Gly Ala Leu Gly Ala  Asp Thr Thr Glu Asp
                1095                 1100                 1105

ggg gat gag aag agc  ctg gag aaa cag aag  cac agt gcc acc act       3448
Gly Asp Glu Lys Ser  Leu Glu Lys Gln Lys  His Ser Ala Thr Thr
                1110                 1115                 1120

gtg ttc gga gca aac  acc ccc att gtt tcc  tgc aat ttt gac aga       3493
Val Phe Gly Ala Asn  Thr Pro Ile Val Ser  Cys Asn Phe Asp Arg
                1125                 1130                 1135

gtc tac atc tac cat  ctg cgc tgc tat gtc  tat caa gcc aga aac       3538
Val Tyr Ile Tyr His  Leu Arg Cys Tyr Val  Tyr Gln Ala Arg Asn
                1140                 1145                 1150

ctc ttg gct tta gat  aag gat agc ttt tca  gat cca tat gct cat       3583
Leu Leu Ala Leu Asp  Lys Asp Ser Phe Ser  Asp Pro Tyr Ala His
                1155                 1160                 1165

atc tgt ttc ctc cat  cgg agc aaa acc act  gag atc atc cat tca       3628
Ile Cys Phe Leu His  Arg Ser Lys Thr Thr  Glu Ile Ile His Ser
                1170                 1175                 1180
```

-continued

```
acc ctg aat ccc acg  tgg gac caa aca att  ata ttc gat gaa gtt        3673
Thr Leu Asn Pro Thr  Trp Asp Gln Thr Ile  Ile Phe Asp Glu Val
                1185                 1190                 1195

gaa atc tat ggg gaa  ccc caa aca gtt cta  cag aat cca ccc aaa        3718
Glu Ile Tyr Gly Glu  Pro Gln Thr Val Leu  Gln Asn Pro Pro Lys
                1200                 1205                 1210

gtt atc atg gaa ctt  ttt gac aat gac caa  gtg ggc aaa gat gaa        3763
Val Ile Met Glu Leu  Phe Asp Asn Asp Gln  Val Gly Lys Asp Glu
                1215                 1220                 1225

ttt tta gga cga agc  att ttc tct cct gtg  gtg aaa ctg aac tca        3808
Phe Leu Gly Arg Ser  Ile Phe Ser Pro Val  Val Lys Leu Asn Ser
                1230                 1235                 1240

gaa atg gac atc aca  ccc aaa ctt ctc tgg  cac cca gta atg aat        3853
Glu Met Asp Ile Thr  Pro Lys Leu Leu Trp  His Pro Val Met Asn
                1245                 1250                 1255

gga gac aaa gcc tgc  ggg gat gtt ctt gta  act gca gag ctg att        3898
Gly Asp Lys Ala Cys  Gly Asp Val Leu Val  Thr Ala Glu Leu Ile
                1260                 1265                 1270

ctg agg ggc aag gat  ggc tcc aac ctt ccc  att ctt ccc cct caa        3943
Leu Arg Gly Lys Asp  Gly Ser Asn Leu Pro  Ile Leu Pro Pro Gln
                1275                 1280                 1285

agg gcg cca aat cta  tac atg gtc ccc cag  ggg atc agg cct gtg        3988
Arg Ala Pro Asn Leu  Tyr Met Val Pro Gln  Gly Ile Arg Pro Val
                1290                 1295                 1300

gtc cag ctc act gcc  att gag att cta gct  tgg ggc tta aga aat        4033
Val Gln Leu Thr Ala  Ile Glu Ile Leu Ala  Trp Gly Leu Arg Asn
                1305                 1310                 1315

atg aaa aac ttc cag  atg gct tct atc aca  tcc ccc agt ctt gtt        4078
Met Lys Asn Phe Gln  Met Ala Ser Ile Thr  Ser Pro Ser Leu Val
                1320                 1325                 1330

gtg gag tgt gga gga  gaa agg gtg gaa tcg  gtg gtg atc aaa aac        4123
Val Glu Cys Gly Gly  Glu Arg Val Glu Ser  Val Val Ile Lys Asn
                1335                 1340                 1345

ctt aag aag aca ccc  aac ttt cca agt tct  gtt ctc ttc atg aaa        4168
Leu Lys Lys Thr Pro  Asn Phe Pro Ser Ser  Val Leu Phe Met Lys
                1350                 1355                 1360

gtg ttc ttg ccc aag  gag gaa ttg tac atg  ccc cca ctg gtg atc        4213
Val Phe Leu Pro Lys  Glu Glu Leu Tyr Met  Pro Pro Leu Val Ile
                1365                 1370                 1375

aag gtc atc gac cac  agg cag ttt ggg cgg  aag cct gtc gtc ggc        4258
Lys Val Ile Asp His  Arg Gln Phe Gly Arg  Lys Pro Val Val Gly
                1380                 1385                 1390

cag tgc acc atc gag  cgc ctg gac cgc ttt  cgc tgt gac cct tat        4303
Gln Cys Thr Ile Glu  Arg Leu Asp Arg Phe  Arg Cys Asp Pro Tyr
                1395                 1400                 1405

gca ggg aaa gag gac  atc gtc cca cag ctc  aaa gcc tcc ctt ctg        4348
Ala Gly Lys Glu Asp  Ile Val Pro Gln Leu  Lys Ala Ser Leu Leu
                1410                 1415                 1420

tct gcc cca cca tgc  cgg gac atc gtt atc  gaa atg gaa gac acc        4393
Ser Ala Pro Pro Cys  Arg Asp Ile Val Ile  Glu Met Glu Asp Thr
                1425                 1430                 1435

aaa cca tta ctg gct  tct aag ctg aca gaa  aag gag gaa gaa atc        4438
Lys Pro Leu Leu Ala  Ser Lys Leu Thr Glu  Lys Glu Glu Glu Ile
                1440                 1445                 1450

gtg gac tgg tgg agt  aaa ttt tat gct tcc  tca ggg gaa cat gaa        4483
Val Asp Trp Trp Ser  Lys Phe Tyr Ala Ser  Ser Gly Glu His Glu
                1455                 1460                 1465

aaa tgc gga cag tat  att cag aaa ggc tat  tcc aag ctc aag ata        4528
Lys Cys Gly Gln Tyr  Ile Gln Lys Gly Tyr  Ser Lys Leu Lys Ile
                1470                 1475                 1480
```

-continued

```
tat aat tgt gaa cta  gaa aat gta gca gaa  ttt gag ggc ctg aca       4573
Tyr Asn Cys Glu Leu  Glu Asn Val Ala Glu  Phe Glu Gly Leu Thr
                1485                 1490                 1495

gac ttc tca gat acg  ttc aag ttg tac cga  ggc aag tcg gat gaa       4618
Asp Phe Ser Asp Thr  Phe Lys Leu Tyr Arg  Gly Lys Ser Asp Glu
                1500                 1505                 1510

aat gaa gat cct tct  gtg gtt gga gag ttt  aag ggc tcc ttt cgg       4663
Asn Glu Asp Pro Ser  Val Val Gly Glu Phe  Lys Gly Ser Phe Arg
                1515                 1520                 1525

atc tac cct ctg ccg  gat gac ccc agc gtg  cca gcc cct ccc aga       4708
Ile Tyr Pro Leu Pro  Asp Asp Pro Ser Val  Pro Ala Pro Pro Arg
                1530                 1535                 1540

cag ttt cgg gaa tta  cct gac agc gtc cca  cag gaa tgc acg gtt       4753
Gln Phe Arg Glu Leu  Pro Asp Ser Val Pro  Gln Glu Cys Thr Val
                1545                 1550                 1555

agg att tac att gtt  cga ggc tta gag ctc  cag ccc cag gac aac       4798
Arg Ile Tyr Ile Val  Arg Gly Leu Glu Leu  Gln Pro Gln Asp Asn
                1560                 1565                 1570

aat ggc ctg tgt gac  cct tac ata aaa ata  aca ctg ggc aaa aaa       4843
Asn Gly Leu Cys Asp  Pro Tyr Ile Lys Ile  Thr Leu Gly Lys Lys
                1575                 1580                 1585

gtc att gaa gac cga  gat cac tac att ccc  aac act ctc aac cca       4888
Val Ile Glu Asp Arg  Asp His Tyr Ile Pro  Asn Thr Leu Asn Pro
                1590                 1595                 1600

gtc ttt ggc agg atg  tac gaa ctg agc tgc  tac tta cct caa gaa       4933
Val Phe Gly Arg Met  Tyr Glu Leu Ser Cys  Tyr Leu Pro Gln Glu
                1605                 1610                 1615

aaa gac ctg aaa att  tct gtc tat gat tat  gac acc ttt acc cgg       4978
Lys Asp Leu Lys Ile  Ser Val Tyr Asp Tyr  Asp Thr Phe Thr Arg
                1620                 1625                 1630

gat gaa aaa gta gga  gaa aca att att gat  ctg gaa aac cga ttc       5023
Asp Glu Lys Val Gly  Glu Thr Ile Ile Asp  Leu Glu Asn Arg Phe
                1635                 1640                 1645

ctt tcc cgc ttt ggg  tcc cac tgc ggc ata  cca gag gag tac tgt       5068
Leu Ser Arg Phe Gly  Ser His Cys Gly Ile  Pro Glu Glu Tyr Cys
                1650                 1655                 1660

gtt tct gga gtc aat  acc tgg cga gat caa  ctg aga cca aca cag       5113
Val Ser Gly Val Asn  Thr Trp Arg Asp Gln  Leu Arg Pro Thr Gln
                1665                 1670                 1675

ctg ctt caa aat gtc  gcc aga ttc aaa ggc  ttc cca caa ccc atc       5158
Leu Leu Gln Asn Val  Ala Arg Phe Lys Gly  Phe Pro Gln Pro Ile
                1680                 1685                 1690

ctt tcc gaa gat ggg  agt aga atc aga tat  gga gga cga gac tac       5203
Leu Ser Glu Asp Gly  Ser Arg Ile Arg Tyr  Gly Gly Arg Asp Tyr
                1695                 1700                 1705

agc ttg gat gaa ttt  gaa gcc aac aaa atc  ctg cac cag cac ctc       5248
Ser Leu Asp Glu Phe  Glu Ala Asn Lys Ile  Leu His Gln His Leu
                1710                 1715                 1720

ggg gcc cct gaa gag  cgg ctt gct ctt cac  atc ctc agg act cag       5293
Gly Ala Pro Glu Glu  Arg Leu Ala Leu His  Ile Leu Arg Thr Gln
                1725                 1730                 1735

ggg ctg gtc cct gag  cac gtg gaa aca agg  act ttg cac agc acc       5338
Gly Leu Val Pro Glu  His Val Glu Thr Arg  Thr Leu His Ser Thr
                1740                 1745                 1750

ttc cag ccc aac att  tcc cag gga aaa ctt  cag atg tgg gtg gat       5383
Phe Gln Pro Asn Ile  Ser Gln Gly Lys Leu  Gln Met Trp Val Asp
                1755                 1760                 1765

gtt ttc ccc aag agt  ttg ggg cca cca ggc  cct cct ttc aac atc       5428
Val Phe Pro Lys Ser  Leu Gly Pro Pro Gly  Pro Pro Phe Asn Ile
                1770                 1775                 1780
```

-continued

```
aca ccc cgg aaa gcc  aag aaa tac tac ctg  cgt gtg atc atc tgg       5473
Thr Pro Arg Lys Ala  Lys Lys Tyr Tyr Leu  Arg Val Ile Ile Trp
                1785                 1790                 1795

aac acc aag gac gtt  atc ttg gac gag aaa  agc atc aca gga gag       5518
Asn Thr Lys Asp Val  Ile Leu Asp Glu Lys  Ser Ile Thr Gly Glu
                1800                 1805                 1810

gaa atg agt gac atc  tac gtc aaa ggc tgg  att cct ggc aat gaa       5563
Glu Met Ser Asp Ile  Tyr Val Lys Gly Trp  Ile Pro Gly Asn Glu
                1815                 1820                 1825

gaa aac aaa cag aaa  aca gat gtc cat tac  aga tct ttg gat ggt       5608
Glu Asn Lys Gln Lys  Thr Asp Val His Tyr  Arg Ser Leu Asp Gly
                1830                 1835                 1840

gaa ggg aat ttt aac  tgg cga ttt gtt ttc  ccg ttt gac tac ctt       5653
Glu Gly Asn Phe Asn  Trp Arg Phe Val Phe  Pro Phe Asp Tyr Leu
                1845                 1850                 1855

cca gcc gaa caa ctc  tgt atc gtt gcg aaa  aaa gag cat ttc tgg       5698
Pro Ala Glu Gln Leu  Cys Ile Val Ala Lys  Lys Glu His Phe Trp
                1860                 1865                 1870

agt att gac caa acg  gaa ttt cga atc cca  ccc agg ctg atc att       5743
Ser Ile Asp Gln Thr  Glu Phe Arg Ile Pro  Pro Arg Leu Ile Ile
                1875                 1880                 1885

cag ata tgg gac aat  gac aag ttt tct ctg  gat gac tac ttg ggt       5788
Gln Ile Trp Asp Asn  Asp Lys Phe Ser Leu  Asp Asp Tyr Leu Gly
                1890                 1895                 1900

ttc cta gaa ctt gac  ttg cgt cac acg atc  att cct gca aaa tca       5833
Phe Leu Glu Leu Asp  Leu Arg His Thr Ile  Ile Pro Ala Lys Ser
                1905                 1910                 1915

cca gag aaa tgc agg  ttg gac atg att ccg  gac ctc aaa gcc atg       5878
Pro Glu Lys Cys Arg  Leu Asp Met Ile Pro  Asp Leu Lys Ala Met
                1920                 1925                 1930

aac ccc ctt aaa gcc  aag aca gcc tcc ctc  ttt gag cag aag tcc       5923
Asn Pro Leu Lys Ala  Lys Thr Ala Ser Leu  Phe Glu Gln Lys Ser
                1935                 1940                 1945

atg aaa gga tgg tgg  cca tgc tac gca gag  aaa gat ggc gcc cgc       5968
Met Lys Gly Trp Trp  Pro Cys Tyr Ala Glu  Lys Asp Gly Ala Arg
                1950                 1955                 1960

gta atg gct ggg aaa  gtg gag atg aca ttg  gaa atc ctc aac gag       6013
Val Met Ala Gly Lys  Val Glu Met Thr Leu  Glu Ile Leu Asn Glu
                1965                 1970                 1975

aag gag gcc gac gag  agg cca gcc ggg aag  ggg cgg gac gaa ccc       6058
Lys Glu Ala Asp Glu  Arg Pro Ala Gly Lys  Gly Arg Asp Glu Pro
                1980                 1985                 1990

aac atg aac ccc aag  ctg gac tta cca aat  cga cca gaa acc tcc       6103
Asn Met Asn Pro Lys  Leu Asp Leu Pro Asn  Arg Pro Glu Thr Ser
                1995                 2000                 2005

ttc ctc tgg ttc acc  aac cca tgc aag acc  atg aag ttc atc gtg       6148
Phe Leu Trp Phe Thr  Asn Pro Cys Lys Thr  Met Lys Phe Ile Val
                2010                 2015                 2020

tgg cgc cgc ttt aag  tgg gtc atc atc ggc  ttg ctg ttc ctg ctt       6193
Trp Arg Arg Phe Lys  Trp Val Ile Ile Gly  Leu Leu Phe Leu Leu
                2025                 2030                 2035

atc ctg ctg ctc ttc  gtg gcc gtg ctc ctc  tac tct ttg ccg aac       6238
Ile Leu Leu Leu Phe  Val Ala Val Leu Leu  Tyr Ser Leu Pro Asn
                2040                 2045                 2050

tat ttg tca atg aag  att gta aag cca aat  gtg taa caaaggcaaa        6284
Tyr Leu Ser Met Lys  Ile Val Lys Pro Asn  Val
                2055                 2060

ggcttcattt caagagtcat ccagcaatga gagaatcctg cctctgtaga ccaacatcca   6344

gtgtgatttt gtgtctgaga ccacacccca gtagcaggtt acgccatgtc accgagcccc   6404
```

-continued

```
attgattccc agagggtctt agtcctggaa agtcaggcca acaagcaacg tttgcatcat   6464

gttatctctt aagtattaaa agttttattt tctaaagttt aaatcatgtt tttcaaaata   6524

tttttcaagg tggctggttc catttaaaaa tcatcttttt atatgtgtct tcggttctag   6584

acttcagctt ttggaaattg ctaaatagaa ttcaaaaatc tctgcatcct gaggtgatat   6644

acttcatatt tgtaatcaac tgaaagagct gtgcattata aaatcagtta gaatagttag   6704

aacaattctt atttatgccc acaaccattg ctatattttg tatggatgtc ataaaagtct   6764

atttaacctc tgtaatgaaa ctaaataaaa atgtttcacc tttaaaaaaa aaaaaaaaaa   6824

aaaaa                                                               6829


<210> SEQ ID NO 232
<211> LENGTH: 2061
<212> TYPE: PRT
<213> ORGANISM: HOMO SAPIENS

<400> SEQUENCE: 232

Met Leu Arg Val Ile Val Glu Ser Ala Ser Asn Ile Pro Lys Thr Lys
1               5                   10                  15

Phe Gly Lys Pro Asp Pro Ile Val Ser Val Ile Phe Lys Asp Glu Lys
            20                  25                  30

Lys Lys Thr Lys Lys Val Asp Asn Glu Leu Asn Pro Val Trp Asn Glu
        35                  40                  45

Ile Leu Glu Phe Asp Leu Arg Gly Ile Pro Leu Asp Phe Ser Ser Ser
    50                  55                  60

Leu Gly Ile Ile Val Lys Asp Phe Glu Thr Ile Gly Gln Asn Lys Leu
65                  70                  75                  80

Ile Gly Thr Ala Thr Val Ala Leu Lys Asp Leu Thr Gly Asp Gln Ser
                85                  90                  95

Arg Ser Leu Pro Tyr Lys Leu Ile Ser Leu Leu Asn Glu Lys Gly Gln
            100                 105                 110

Asp Thr Gly Ala Thr Ile Asp Leu Val Ile Gly Tyr Asp Pro Pro Ser
        115                 120                 125

Ala Pro His Pro Asn Asp Leu Ser Gly Pro Ser Val Pro Gly Met Gly
    130                 135                 140

Gly Asp Gly Glu Glu Asp Glu Gly Asp Glu Asp Arg Leu Asp Asn Ala
145                 150                 155                 160

Val Arg Gly Pro Gly Pro Lys Gly Pro Val Gly Thr Val Ser Glu Ala
                165                 170                 175

Gln Leu Ala Arg Arg Leu Thr Lys Val Lys Asn Ser Arg Arg Met Leu
            180                 185                 190

Ser Asn Lys Pro Gln Asp Phe Gln Ile Arg Val Arg Val Ile Glu Gly
        195                 200                 205

Arg Gln Leu Ser Gly Asn Asn Ile Arg Pro Val Val Lys Val His Val
    210                 215                 220

Cys Gly Gln Thr His Arg Thr Arg Ile Lys Arg Gly Asn Asn Pro Phe
225                 230                 235                 240

Phe Asp Glu Leu Phe Phe Tyr Asn Val Asn Met Thr Pro Ser Glu Leu
                245                 250                 255

Met Asp Glu Ile Ile Ser Ile Arg Val Tyr Asn Ser His Ser Leu Arg
            260                 265                 270

Ala Asp Cys Leu Met Gly Glu Phe Lys Ile Asp Val Gly Phe Val Tyr
        275                 280                 285

Asp Glu Pro Gly His Ala Val Met Arg Lys Trp Leu Leu Leu Asn Asp
    290                 295                 300
```

-continued

```
Pro Glu Asp Thr Ser Ser Gly Ser Lys Gly Tyr Met Lys Val Ser Met
305                 310                 315                 320

Phe Val Leu Gly Thr Gly Asp Glu Pro Pro Pro Glu Arg Arg Asp Arg
                325                 330                 335

Asp Asn Asp Ser Asp Asp Val Glu Ser Asn Leu Leu Leu Pro Ala Gly
            340                 345                 350

Ile Ala Leu Arg Trp Val Thr Phe Leu Leu Lys Ile Tyr Arg Ala Glu
        355                 360                 365

Asp Ile Pro Gln Met Asp Asp Ala Phe Ser Gln Thr Val Lys Glu Ile
    370                 375                 380

Phe Gly Gly Asn Ala Asp Lys Lys Asn Leu Val Asp Pro Phe Val Glu
385                 390                 395                 400

Val Ser Phe Ala Gly Lys Lys Val Cys Thr Asn Ile Ile Glu Lys Asn
                405                 410                 415

Ala Asn Pro Glu Trp Asn Gln Val Val Asn Leu Gln Ile Lys Phe Pro
            420                 425                 430

Ser Val Cys Glu Lys Ile Lys Leu Thr Ile Tyr Asp Trp Asp Arg Leu
        435                 440                 445

Thr Lys Asn Asp Val Val Gly Thr Thr Tyr Leu His Leu Ser Lys Ile
    450                 455                 460

Ala Ala Ser Gly Gly Glu Val Glu Asp Phe Ser Ser Ser Gly Thr Gly
465                 470                 475                 480

Ala Ala Ser Tyr Thr Val Asn Thr Gly Glu Thr Glu Val Gly Phe Val
                485                 490                 495

Pro Thr Phe Gly Pro Cys Tyr Leu Asn Leu Tyr Gly Ser Pro Arg Glu
            500                 505                 510

Tyr Thr Gly Phe Pro Asp Pro Tyr Asp Glu Leu Asn Thr Gly Lys Gly
        515                 520                 525

Glu Gly Val Ala Tyr Arg Gly Arg Ile Leu Val Glu Leu Ala Thr Phe
    530                 535                 540

Leu Glu Lys Thr Pro Pro Asp Lys Lys Leu Glu Pro Ile Ser Asn Asp
545                 550                 555                 560

Asp Leu Leu Val Val Glu Lys Tyr Gln Arg Arg Arg Lys Tyr Ser Leu
                565                 570                 575

Ser Ala Val Phe His Ser Ala Thr Met Leu Gln Asp Val Gly Glu Ala
            580                 585                 590

Ile Gln Phe Glu Val Ser Ile Gly Asn Tyr Gly Asn Lys Phe Asp Thr
        595                 600                 605

Thr Cys Lys Pro Leu Ala Ser Thr Thr Gln Tyr Ser Arg Ala Val Phe
    610                 615                 620

Asp Gly Asn Tyr Tyr Tyr Tyr Leu Pro Trp Ala His Thr Lys Pro Val
625                 630                 635                 640

Val Thr Leu Thr Ser Tyr Trp Glu Asp Ile Ser His Arg Leu Asp Ala
                645                 650                 655

Val Asn Thr Leu Leu Ala Met Ala Glu Arg Leu Gln Thr Asn Ile Glu
            660                 665                 670

Ala Leu Lys Ser Gly Ile Gln Gly Lys Ile Pro Ala Asn Gln Leu Ala
        675                 680                 685

Glu Leu Trp Leu Lys Leu Ile Asp Glu Val Ile Glu Asp Thr Arg Tyr
    690                 695                 700

Thr Leu Pro Leu Thr Glu Gly Lys Ala Asn Val Thr Val Leu Asp Thr
705                 710                 715                 720

Gln Ile Arg Lys Leu Arg Ser Arg Ser Leu Ser Gln Ile His Glu Ala
```

-continued

```
                725                 730                 735

Ala Val Arg Met Arg Ser Glu Ala Thr Asp Val Lys Ser Thr Leu Ala
            740                 745                 750

Glu Ile Glu Asp Trp Leu Asp Lys Leu Met Gln Leu Thr Glu Glu Pro
        755                 760                 765

Gln Asn Ser Met Pro Asp Ile Ile Ile Trp Met Ile Arg Gly Glu Lys
    770                 775                 780

Arg Leu Ala Tyr Ala Arg Ile Pro Ala His Gln Val Leu Tyr Ser Thr
785                 790                 795                 800

Ser Gly Glu Asn Ala Ser Gly Lys Tyr Cys Gly Lys Thr Gln Thr Ile
                805                 810                 815

Phe Leu Lys Tyr Pro Gln Glu Lys Asn Asn Gly Pro Lys Val Pro Val
            820                 825                 830

Glu Leu Arg Val Asn Ile Trp Leu Gly Leu Ser Ala Val Glu Lys Lys
        835                 840                 845

Phe Asn Ser Phe Ala Glu Gly Thr Phe Thr Val Phe Ala Glu Met Tyr
    850                 855                 860

Glu Asn Gln Ala Leu Met Phe Gly Lys Trp Gly Thr Ser Gly Leu Val
865                 870                 875                 880

Gly Arg His Lys Phe Ser Asp Val Thr Gly Lys Ile Lys Leu Lys Arg
                885                 890                 895

Glu Phe Phe Leu Pro Pro Lys Gly Trp Glu Trp Glu Gly Glu Trp Ile
            900                 905                 910

Val Asp Pro Glu Arg Ser Leu Leu Thr Glu Ala Asp Ala Gly His Thr
        915                 920                 925

Glu Phe Thr Asp Glu Val Tyr Gln Asn Glu Ser Arg Tyr Pro Gly Gly
    930                 935                 940

Asp Trp Lys Pro Ala Glu Asp Thr Tyr Thr Asp Ala Asn Gly Asp Lys
945                 950                 955                 960

Ala Ala Ser Pro Ser Glu Leu Thr Cys Pro Pro Gly Trp Glu Trp Glu
                965                 970                 975

Asp Asp Ala Trp Ser Tyr Asp Ile Asn Arg Ala Val Asp Glu Lys Gly
            980                 985                 990

Trp Glu Tyr Gly Ile Thr Ile Pro  Pro Asp His Lys Pro  Lys Ser Trp
        995                 1000                1005

Val Ala  Ala Glu Lys Met Tyr  His Thr His Arg Arg  Arg Arg Leu
    1010                1015                1020

Val Arg  Lys Arg Lys Lys Asp  Leu Thr Gln Thr Ala  Ser Ser Thr
    1025                1030                1035

Ala Arg  Ala Met Glu Glu Leu  Gln Asp Gln Glu Gly  Trp Glu Tyr
    1040                1045                1050

Ala Ser  Leu Ile Gly Trp Lys  Phe His Trp Lys Gln  Arg Ser Ser
    1055                1060                1065

Asp Thr  Phe Arg Arg Arg Arg  Trp Arg Arg Lys Met  Ala Pro Ser
    1070                1075                1080

Glu Thr  His Gly Ala Ala Ala  Ile Phe Lys Leu Glu  Gly Ala Leu
    1085                1090                1095

Gly Ala  Asp Thr Thr Glu Asp  Gly Asp Glu Lys Ser  Leu Glu Lys
    1100                1105                1110

Gln Lys  His Ser Ala Thr Thr  Val Phe Gly Ala Asn  Thr Pro Ile
    1115                1120                1125

Val Ser  Cys Asn Phe Asp Arg  Val Tyr Ile Tyr His  Leu Arg Cys
    1130                1135                1140
```

```
Tyr Val  Tyr Gln Ala Arg Asn  Leu Leu Ala Leu Asp  Lys Asp Ser
    1145                 1150                 1155

Phe Ser  Asp Pro Tyr Ala His  Ile Cys Phe Leu His  Arg Ser Lys
    1160                 1165                 1170

Thr Thr  Glu Ile Ile His Ser  Thr Leu Asn Pro Thr  Trp Asp Gln
    1175                 1180                 1185

Thr Ile  Ile Phe Asp Glu Val  Glu Ile Tyr Gly Glu  Pro Gln Thr
    1190                 1195                 1200

Val Leu  Gln Asn Pro Pro Lys  Val Ile Met Glu Leu  Phe Asp Asn
    1205                 1210                 1215

Asp Gln  Val Gly Lys Asp Glu  Phe Leu Gly Arg Ser  Ile Phe Ser
    1220                 1225                 1230

Pro Val  Val Lys Leu Asn Ser  Glu Met Asp Ile Thr  Pro Lys Leu
    1235                 1240                 1245

Leu Trp  His Pro Val Met Asn  Gly Asp Lys Ala Cys  Gly Asp Val
    1250                 1255                 1260

Leu Val  Thr Ala Glu Leu Ile  Leu Arg Gly Lys Asp  Gly Ser Asn
    1265                 1270                 1275

Leu Pro  Ile Leu Pro Pro Gln  Arg Ala Pro Asn Leu  Tyr Met Val
    1280                 1285                 1290

Pro Gln  Gly Ile Arg Pro Val  Val Gln Leu Thr Ala  Ile Glu Ile
    1295                 1300                 1305

Leu Ala  Trp Gly Leu Arg Asn  Met Lys Asn Phe Gln  Met Ala Ser
    1310                 1315                 1320

Ile Thr  Ser Pro Ser Leu Val  Val Glu Cys Gly Gly  Glu Arg Val
    1325                 1330                 1335

Glu Ser  Val Val Ile Lys Asn  Leu Lys Lys Thr Pro  Asn Phe Pro
    1340                 1345                 1350

Ser Ser  Val Leu Phe Met Lys  Val Phe Leu Pro Lys  Glu Glu Leu
    1355                 1360                 1365

Tyr Met  Pro Pro Leu Val Ile  Lys Val Ile Asp His  Arg Gln Phe
    1370                 1375                 1380

Gly Arg  Lys Pro Val Val Gly  Gln Cys Thr Ile Glu  Arg Leu Asp
    1385                 1390                 1395

Arg Phe  Arg Cys Asp Pro Tyr  Ala Gly Lys Glu Asp  Ile Val Pro
    1400                 1405                 1410

Gln Leu  Lys Ala Ser Leu Leu  Ser Ala Pro Pro Cys  Arg Asp Ile
    1415                 1420                 1425

Val Ile  Glu Met Glu Asp Thr  Lys Pro Leu Leu Ala  Ser Lys Leu
    1430                 1435                 1440

Thr Glu  Lys Glu Glu Glu Ile  Val Asp Trp Trp Ser  Lys Phe Tyr
    1445                 1450                 1455

Ala Ser  Ser Gly Glu His Glu  Lys Cys Gly Gln Tyr  Ile Gln Lys
    1460                 1465                 1470

Gly Tyr  Ser Lys Leu Lys Ile  Tyr Asn Cys Glu Leu  Glu Asn Val
    1475                 1480                 1485

Ala Glu  Phe Glu Gly Leu Thr  Asp Phe Ser Asp Thr  Phe Lys Leu
    1490                 1495                 1500

Tyr Arg  Gly Lys Ser Asp Glu  Asn Glu Asp Pro Ser  Val Val Gly
    1505                 1510                 1515

Glu Phe  Lys Gly Ser Phe Arg  Ile Tyr Pro Leu Pro  Asp Asp Pro
    1520                 1525                 1530

Ser Val  Pro Ala Pro Pro Arg  Gln Phe Arg Glu Leu  Pro Asp Ser
    1535                 1540                 1545
```

```
Val Pro  Gln Glu Cys Thr Val  Arg Ile Tyr Ile Val  Arg Gly Leu
    1550                 1555                 1560

Glu Leu  Gln Pro Gln Asp Asn  Asn Gly Leu Cys Asp  Pro Tyr Ile
    1565                 1570                 1575

Lys Ile  Thr Leu Gly Lys Lys  Val Ile Glu Asp Arg  Asp His Tyr
    1580                 1585                 1590

Ile Pro  Asn Thr Leu Asn Pro  Val Phe Gly Arg Met  Tyr Glu Leu
    1595                 1600                 1605

Ser Cys  Tyr Leu Pro Gln Glu  Lys Asp Leu Lys Ile  Ser Val Tyr
    1610                 1615                 1620

Asp Tyr  Asp Thr Phe Thr Arg  Asp Glu Lys Val Gly  Glu Thr Ile
    1625                 1630                 1635

Ile Asp  Leu Glu Asn Arg Phe  Leu Ser Arg Phe Gly  Ser His Cys
    1640                 1645                 1650

Gly Ile  Pro Glu Glu Tyr Cys  Val Ser Gly Val Asn  Thr Trp Arg
    1655                 1660                 1665

Asp Gln  Leu Arg Pro Thr Gln  Leu Leu Gln Asn Val  Ala Arg Phe
    1670                 1675                 1680

Lys Gly  Phe Pro Gln Pro Ile  Leu Ser Glu Asp Gly  Ser Arg Ile
    1685                 1690                 1695

Arg Tyr  Gly Gly Arg Asp Tyr  Ser Leu Asp Glu Phe  Glu Ala Asn
    1700                 1705                 1710

Lys Ile  Leu His Gln His Leu  Gly Ala Pro Glu Glu  Arg Leu Ala
    1715                 1720                 1725

Leu His  Ile Leu Arg Thr Gln  Gly Leu Val Pro Glu  His Val Glu
    1730                 1735                 1740

Thr Arg  Thr Leu His Ser Thr  Phe Gln Pro Asn Ile  Ser Gln Gly
    1745                 1750                 1755

Lys Leu  Gln Met Trp Val Asp  Val Phe Pro Lys Ser  Leu Gly Pro
    1760                 1765                 1770

Pro Gly  Pro Pro Phe Asn Ile  Thr Pro Arg Lys Ala  Lys Lys Tyr
    1775                 1780                 1785

Tyr Leu  Arg Val Ile Ile Trp  Asn Thr Lys Asp Val  Ile Leu Asp
    1790                 1795                 1800

Glu Lys  Ser Ile Thr Gly Glu  Glu Met Ser Asp Ile  Tyr Val Lys
    1805                 1810                 1815

Gly Trp  Ile Pro Gly Asn Glu  Glu Asn Lys Gln Lys  Thr Asp Val
    1820                 1825                 1830

His Tyr  Arg Ser Leu Asp Gly  Glu Gly Asn Phe Asn  Trp Arg Phe
    1835                 1840                 1845

Val Phe  Pro Phe Asp Tyr Leu  Pro Ala Glu Gln Leu  Cys Ile Val
    1850                 1855                 1860

Ala Lys  Lys Glu His Phe Trp  Ser Ile Asp Gln Thr  Glu Phe Arg
    1865                 1870                 1875

Ile Pro  Pro Arg Leu Ile Ile  Gln Ile Trp Asp Asn  Asp Lys Phe
    1880                 1885                 1890

Ser Leu  Asp Asp Tyr Leu Gly  Phe Leu Glu Leu Asp  Leu Arg His
    1895                 1900                 1905

Thr Ile  Ile Pro Ala Lys Ser  Pro Glu Lys Cys Arg  Leu Asp Met
    1910                 1915                 1920

Ile Pro  Asp Leu Lys Ala Met  Asn Pro Leu Lys Ala  Lys Thr Ala
    1925                 1930                 1935

Ser Leu  Phe Glu Gln Lys Ser  Met Lys Gly Trp Trp  Pro Cys Tyr
```

```
    1940                1945                1950

Ala Glu  Lys Asp Gly Ala Arg  Val Met Ala Gly Lys  Val Glu Met
    1955                1960                1965

Thr Leu  Glu Ile Leu Asn Glu  Lys Glu Ala Asp Glu  Arg Pro Ala
    1970                1975                1980

Gly Lys  Gly Arg Asp Glu Pro  Asn Met Asn Pro Lys  Leu Asp Leu
    1985                1990                1995

Pro Asn  Arg Pro Glu Thr Ser  Phe Leu Trp Phe Thr  Asn Pro Cys
    2000                2005                2010

Lys Thr  Met Lys Phe Ile Val  Trp Arg Arg Phe Lys  Trp Val Ile
    2015                2020                2025

Ile Gly  Leu Leu Phe Leu Leu  Ile Leu Leu Leu Phe  Val Ala Val
    2030                2035                2040

Leu Leu  Tyr Ser Leu Pro Asn  Tyr Leu Ser Met Lys  Ile Val Lys
    2045                2050                2055

Pro Asn  Val
    2060
```

<210> SEQ ID NO 233
<211> LENGTH: 16
<212> TYPE: DNA
<213> ORGANISM: Artificial sequence
<220> FEATURE:
<223> OTHER INFORMATION: primer

<400> SEQUENCE: 233
gcttgccaaa cctaca 16

<210> SEQ ID NO 234
<211> LENGTH: 16
<212> TYPE: DNA
<213> ORGANISM: Artificial sequence
<220> FEATURE:
<223> OTHER INFORMATION: primer

<400> SEQUENCE: 234
tgtaggtctg gcaagc 16

<210> SEQ ID NO 235
<211> LENGTH: 18
<212> TYPE: DNA
<213> ORGANISM: Artificial sequence
<220> FEATURE:
<223> OTHER INFORMATION: primer

<400> SEQUENCE: 235
atcttgttca atcatgcg 18

<210> SEQ ID NO 236
<211> LENGTH: 16
<212> TYPE: DNA
<213> ORGANISM: Artificial sequence
<220> FEATURE:
<223> OTHER INFORMATION: primer

<400> SEQUENCE: 236
gggtctgacg ctcatg 16

<210> SEQ ID NO 237
<211> LENGTH: 16
<212> TYPE: DNA
<213> ORGANISM: Artificial sequence
<220> FEATURE:

<223> OTHER INFORMATION: primer

<400> SEQUENCE: 237
gataggtgcc tcactg 16

<210> SEQ ID NO 238
<211> LENGTH: 19
<212> TYPE: DNA
<213> ORGANISM: Artificial
<220> FEATURE:
<223> OTHER INFORMATION: Rab9 siRNA

<400> SEQUENCE: 238
gggaagagtt cacttatga 19

<210> SEQ ID NO 239
<211> LENGTH: 19
<212> TYPE: DNA
<213> ORGANISM: Artificial
<220> FEATURE:
<223> OTHER INFORMATION: Rab9 siRNA

<400> SEQUENCE: 239
tcacaaagct tccagaact 19

<210> SEQ ID NO 240
<211> LENGTH: 19
<212> TYPE: DNA
<213> ORGANISM: Artificial
<220> FEATURE:
<223> OTHER INFORMATION: Rab9 siRNA

<400> SEQUENCE: 240
gtaacaagat tgacataag 19

<210> SEQ ID NO 241
<211> LENGTH: 19
<212> TYPE: DNA
<213> ORGANISM: Artificial
<220> FEATURE:
<223> OTHER INFORMATION: Rab9 siRNA

<400> SEQUENCE: 241
ggaagtggat ggacatttt 19

<210> SEQ ID NO 242
<211> LENGTH: 19
<212> TYPE: RNA
<213> ORGANISM: Artificial Sequence
<220> FEATURE:
<223> OTHER INFORMATION: RNAi molecule

<400> SEQUENCE: 242
ggucagagcu ggaggauuu 19

<210> SEQ ID NO 243
<211> LENGTH: 19
<212> TYPE: RNA
<213> ORGANISM: Artificial Sequence
<220> FEATURE:
<223> OTHER INFORMATION: RNAi molecule

<400> SEQUENCE: 243
gaaagaagga gacccguua 19

<210> SEQ ID NO 244

<211> LENGTH: 19
<212> TYPE: RNA
<213> ORGANISM: Artificial Sequence
<220> FEATURE:
<223> OTHER INFORMATION: RNAi molecule

<400> SEQUENCE: 244
ccaagaagau cuacaaugg 19

<210> SEQ ID NO 245
<211> LENGTH: 19
<212> TYPE: RNA
<213> ORGANISM: Artificial Sequence
<220> FEATURE:
<223> OTHER INFORMATION: RNAi molecule

<400> SEQUENCE: 245
ggaacugcau gcugaauga 19

<210> SEQ ID NO 246
<211> LENGTH: 27
<212> TYPE: RNA
<213> ORGANISM: Artificial Sequence
<220> FEATURE:
<223> OTHER INFORMATION: RNAi molecule

<400> SEQUENCE: 246
uagaccugcu cagccuucug gauacuu 27

<210> SEQ ID NO 247
<211> LENGTH: 27
<212> TYPE: RNA
<213> ORGANISM: Artificial Sequence
<220> FEATURE:
<223> OTHER INFORMATION: RNAi molecule

<400> SEQUENCE: 247
cuucucauaa uugaaguggu ugucguu 27

<210> SEQ ID NO 248
<211> LENGTH: 27
<212> TYPE: RNA
<213> ORGANISM: Artificial Sequence
<220> FEATURE:
<223> OTHER INFORMATION: RNAi molecule

<400> SEQUENCE: 248
gugugucuuc ucauaauuga agugguu 27

<210> SEQ ID NO 249
<211> LENGTH: 27
<212> TYPE: RNA
<213> ORGANISM: Artificial Sequence
<220> FEATURE:
<223> OTHER INFORMATION: RNAi molecule

<400> SEQUENCE: 249
cgcugugugu ucuucaugug ugacguu 27

<210> SEQ ID NO 250
<211> LENGTH: 27
<212> TYPE: RNA
<213> ORGANISM: Artificial Sequence
<220> FEATURE:
<223> OTHER INFORMATION: RNAi molecule

<400> SEQUENCE: 250
agaccugcuc agccuucugg auacuuu 27

<210> SEQ ID NO 251
<211> LENGTH: 27
<212> TYPE: RNA
<213> ORGANISM: Artificial Sequence
<220> FEATURE:
<223> OTHER INFORMATION: RNAi molecule

<400> SEQUENCE: 251
ccucuugaga ucagguuggc agucauu 27

<210> SEQ ID NO 252
<211> LENGTH: 27
<212> TYPE: RNA
<213> ORGANISM: Artificial Sequence
<220> FEATURE:
<223> OTHER INFORMATION: RNAi molecule

<400> SEQUENCE: 252
gaccugcuca gccuucugga uacuuuu 27

<210> SEQ ID NO 253
<211> LENGTH: 27
<212> TYPE: RNA
<213> ORGANISM: Artificial Sequence
<220> FEATURE:
<223> OTHER INFORMATION: RNAi molecule

<400> SEQUENCE: 253
ccgauuuuaa uccucuugcu ucaauuu 27

<210> SEQ ID NO 254
<211> LENGTH: 27
<212> TYPE: RNA
<213> ORGANISM: Artificial Sequence
<220> FEATURE:
<223> OTHER INFORMATION: RNAi molecule

<400> SEQUENCE: 254
uccgauuuua auccucuugc uucaauu 27

<210> SEQ ID NO 255
<211> LENGTH: 27
<212> TYPE: RNA
<213> ORGANISM: Artificial Sequence
<220> FEATURE:
<223> OTHER INFORMATION: RNAi molecule

<400> SEQUENCE: 255
cagaucauga aucgacucaa accucuu 27

<210> SEQ ID NO 256
<211> LENGTH: 27
<212> TYPE: RNA
<213> ORGANISM: Artificial Sequence
<220> FEATURE:
<223> OTHER INFORMATION: RNAi molecule

<400> SEQUENCE: 256
accugcucag ccuucuggau acuuuuu 27

<210> SEQ ID NO 257
<211> LENGTH: 27
<212> TYPE: RNA
<213> ORGANISM: Artificial Sequence
<220> FEATURE:

<223> OTHER INFORMATION: RNAi molecule

<400> SEQUENCE: 257
agaucuuuuc caccgcugug uguucuu 27

<210> SEQ ID NO 258
<211> LENGTH: 27
<212> TYPE: RNA
<213> ORGANISM: Artificial Sequence
<220> FEATURE:
<223> OTHER INFORMATION: RNAi molecule

<400> SEQUENCE: 258
guguugugag gucacaacag uacacuu 27

<210> SEQ ID NO 259
<211> LENGTH: 27
<212> TYPE: RNA
<213> ORGANISM: Artificial Sequence
<220> FEATURE:
<223> OTHER INFORMATION: RNAi molecule

<400> SEQUENCE: 259
ggccuuccga uuuuaauccu cuugcuu 27

<210> SEQ ID NO 260
<211> LENGTH: 27
<212> TYPE: RNA
<213> ORGANISM: Artificial Sequence
<220> FEATURE:
<223> OTHER INFORMATION: RNAi molecule

<400> SEQUENCE: 260
gcagcuuuug uuucuaugua caguguu 27

<210> SEQ ID NO 261
<211> LENGTH: 27
<212> TYPE: RNA
<213> ORGANISM: Artificial Sequence
<220> FEATURE:
<223> OTHER INFORMATION: RNAi molecule

<400> SEQUENCE: 261
auagacauug gcagauauau cggccuu 27

<210> SEQ ID NO 262
<211> LENGTH: 27
<212> TYPE: RNA
<213> ORGANISM: Artificial Sequence
<220> FEATURE:
<223> OTHER INFORMATION: RNAi molecule

<400> SEQUENCE: 262
gcuguguguu cuucaugugu gacguuu 27

<210> SEQ ID NO 263
<211> LENGTH: 27
<212> TYPE: RNA
<213> ORGANISM: Artificial Sequence
<220> FEATURE:
<223> OTHER INFORMATION: RNAi molecule

<400> SEQUENCE: 263
ugaguguugu gagccuucac aaguguu 27

<210> SEQ ID NO 264

<211> LENGTH: 27
<212> TYPE: RNA
<213> ORGANISM: Artificial Sequence
<220> FEATURE:
<223> OTHER INFORMATION: RNAi molecule

<400> SEQUENCE: 264
ugacguuugu uuuucuuggu ucauuuu 27

<210> SEQ ID NO 265
<211> LENGTH: 27
<212> TYPE: RNA
<213> ORGANISM: Artificial Sequence
<220> FEATURE:
<223> OTHER INFORMATION: RNAi molecule

<400> SEQUENCE: 265
gugacguuug uuuuucuugg uucauuu 27

<210> SEQ ID NO 266
<211> LENGTH: 27
<212> TYPE: RNA
<213> ORGANISM: Artificial Sequence
<220> FEATURE:
<223> OTHER INFORMATION: RNAi molecule

<400> SEQUENCE: 266
ugugacguuu guuuuucuug guucauu 27

<210> SEQ ID NO 267
<211> LENGTH: 27
<212> TYPE: RNA
<213> ORGANISM: Artificial Sequence
<220> FEATURE:
<223> OTHER INFORMATION: RNAi molecule

<400> SEQUENCE: 267
acaacaguac acuuucuuga uccucuu 27

<210> SEQ ID NO 268
<211> LENGTH: 27
<212> TYPE: RNA
<213> ORGANISM: Artificial Sequence
<220> FEATURE:
<223> OTHER INFORMATION: RNAi molecule

<400> SEQUENCE: 268
gccucggaac guguggaccu uaaaguu 27

<210> SEQ ID NO 269
<211> LENGTH: 27
<212> TYPE: RNA
<213> ORGANISM: Artificial Sequence
<220> FEATURE:
<223> OTHER INFORMATION: RNAi molecule

<400> SEQUENCE: 269
uucuauguac aguguuauca agccauc 27

<210> SEQ ID NO 270
<211> LENGTH: 27
<212> TYPE: RNA
<213> ORGANISM: Artificial Sequence
<220> FEATURE:
<223> OTHER INFORMATION: RNAi molecule

<400> SEQUENCE: 270

-continued uucucauaau ugaagugguu gucguug 27

<210> SEQ ID NO 271
<211> LENGTH: 27
<212> TYPE: RNA
<213> ORGANISM: Artificial Sequence
<220> FEATURE:
<223> OTHER INFORMATION: RNAi molecule

<400> SEQUENCE: 271
caguguuauc aagccaucug ucaccag 27

<210> SEQ ID NO 272
<211> LENGTH: 27
<212> TYPE: RNA
<213> ORGANISM: Artificial Sequence
<220> FEATURE:
<223> OTHER INFORMATION: RNAi molecule

<400> SEQUENCE: 272
uguguacguu caauccacag ucugagc 27

<210> SEQ ID NO 273
<211> LENGTH: 27
<212> TYPE: RNA
<213> ORGANISM: Artificial Sequence
<220> FEATURE:
<223> OTHER INFORMATION: RNAi molecule

<400> SEQUENCE: 273
uguacagugu uaucaagcca ucuguca 27

<210> SEQ ID NO 274
<211> LENGTH: 27
<212> TYPE: RNA
<213> ORGANISM: Artificial Sequence
<220> FEATURE:
<223> OTHER INFORMATION: RNAi molecule

<400> SEQUENCE: 274
aguguuauca agccaucugu caccaga 27

<210> SEQ ID NO 275
<211> LENGTH: 27
<212> TYPE: RNA
<213> ORGANISM: Artificial Sequence
<220> FEATURE:
<223> OTHER INFORMATION: RNAi molecule

<400> SEQUENCE: 275
guacaguguu aucaagccau cugucac 27

<210> SEQ ID NO 276
<211> LENGTH: 27
<212> TYPE: RNA
<213> ORGANISM: Artificial Sequence
<220> FEATURE:
<223> OTHER INFORMATION: RNAi molecule

<400> SEQUENCE: 276
uuguguacgu ucaauccaca gucugag 27

<210> SEQ ID NO 277
<211> LENGTH: 27
<212> TYPE: RNA
<213> ORGANISM: Artificial Sequence
<220> FEATURE:

```
<223> OTHER INFORMATION: RNAi molecule

<400> SEQUENCE: 277

ucuauguaca guguuaucaa gccaucu                                           27

<210> SEQ ID NO 278
<211> LENGTH: 27
<212> TYPE: RNA
<213> ORGANISM: Artificial Sequence
<220> FEATURE:
<223> OTHER INFORMATION: RNAi molecule

<400> SEQUENCE: 278

ucauaauuga agugguuguc guugugu                                           27

<210> SEQ ID NO 279
<211> LENGTH: 27
<212> TYPE: RNA
<213> ORGANISM: Artificial Sequence
<220> FEATURE:
<223> OTHER INFORMATION: RNAi molecule

<400> SEQUENCE: 279

ucucauaauu gaagugguug ucguugu                                           27

<210> SEQ ID NO 280
<211> LENGTH: 27
<212> TYPE: RNA
<213> ORGANISM: Artificial Sequence
<220> FEATURE:
<223> OTHER INFORMATION: RNAi molecule

<400> SEQUENCE: 280

aauugaagug guugucguug uguguga                                           27

<210> SEQ ID NO 281
<211> LENGTH: 27
<212> TYPE: RNA
<213> ORGANISM: Artificial Sequence
<220> FEATURE:
<223> OTHER INFORMATION: RNAi molecule

<400> SEQUENCE: 281

cugucaccag aucaugaauc gacucaa                                           27

<210> SEQ ID NO 282
<211> LENGTH: 27
<212> TYPE: RNA
<213> ORGANISM: Artificial Sequence
<220> FEATURE:
<223> OTHER INFORMATION: RNAi molecule

<400> SEQUENCE: 282

acaguguuau caagccaucu gucacca                                           27

<210> SEQ ID NO 283
<211> LENGTH: 27
<212> TYPE: RNA
<213> ORGANISM: Artificial Sequence
<220> FEATURE:
<223> OTHER INFORMATION: RNAi molecule

<400> SEQUENCE: 283

uacaguguua ucaagccauc ugucacc                                           27

<210> SEQ ID NO 284
```

<211> LENGTH: 27
<212> TYPE: RNA
<213> ORGANISM: Artificial Sequence
<220> FEATURE:
<223> OTHER INFORMATION: RNAi molecule

<400> SEQUENCE: 284
uuccaccgcu guguguucuu caugugu 27

<210> SEQ ID NO 285
<211> LENGTH: 27
<212> TYPE: RNA
<213> ORGANISM: Artificial Sequence
<220> FEATURE:
<223> OTHER INFORMATION: RNAi molecule

<400> SEQUENCE: 285
uauguacagu guuaucaagc caucugu 27

<210> SEQ ID NO 286
<211> LENGTH: 27
<212> TYPE: RNA
<213> ORGANISM: Artificial Sequence
<220> FEATURE:
<223> OTHER INFORMATION: RNAi molecule

<400> SEQUENCE: 286
auaauugaag ugguugucgu ugugugu 27

<210> SEQ ID NO 287
<211> LENGTH: 27
<212> TYPE: RNA
<213> ORGANISM: Artificial Sequence
<220> FEATURE:
<223> OTHER INFORMATION: RNAi molecule

<400> SEQUENCE: 287
ucuucucaua auugaagugg uugucgu 27

<210> SEQ ID NO 288
<211> LENGTH: 27
<212> TYPE: RNA
<213> ORGANISM: Artificial Sequence
<220> FEATURE:
<223> OTHER INFORMATION: RNAi molecule

<400> SEQUENCE: 288
gugucuucuc auaauugaag ugguugu 27

<210> SEQ ID NO 289
<211> LENGTH: 27
<212> TYPE: RNA
<213> ORGANISM: Artificial Sequence
<220> FEATURE:
<223> OTHER INFORMATION: RNAi molecule

<400> SEQUENCE: 289
gucuucucau aauugaagug guugucg 27

<210> SEQ ID NO 290
<211> LENGTH: 27
<212> TYPE: RNA
<213> ORGANISM: Artificial Sequence
<220> FEATURE:
<223> OTHER INFORMATION: RNAi molecule

<400> SEQUENCE: 290
ucuggauaga cauuggcaga uauaucg 27

<210> SEQ ID NO 291
<211> LENGTH: 27
<212> TYPE: RNA
<213> ORGANISM: Artificial Sequence
<220> FEATURE:
<223> OTHER INFORMATION: RNAi molecule

<400> SEQUENCE: 291
ucugucacca gaucaugaau cgacuca 27

<210> SEQ ID NO 292
<211> LENGTH: 27
<212> TYPE: RNA
<213> ORGANISM: Artificial Sequence
<220> FEATURE:
<223> OTHER INFORMATION: RNAi molecule

<400> SEQUENCE: 292
auugaagugg uugucguugu gugugag 27

<210> SEQ ID NO 293
<211> LENGTH: 27
<212> TYPE: RNA
<213> ORGANISM: Artificial Sequence
<220> FEATURE:
<223> OTHER INFORMATION: RNAi molecule

<400> SEQUENCE: 293
uugaaguggu ugucguugug ugugagg 27

<210> SEQ ID NO 294
<211> LENGTH: 27
<212> TYPE: RNA
<213> ORGANISM: Artificial Sequence
<220> FEATURE:
<223> OTHER INFORMATION: RNAi molecule

<400> SEQUENCE: 294
guguacguuc aauccacagu cugagca 27

<210> SEQ ID NO 295
<211> LENGTH: 27
<212> TYPE: RNA
<213> ORGANISM: Artificial Sequence
<220> FEATURE:
<223> OTHER INFORMATION: RNAi molecule

<400> SEQUENCE: 295
ccaccgcugu guguucuuca uguguga 27

<210> SEQ ID NO 296
<211> LENGTH: 27
<212> TYPE: RNA
<213> ORGANISM: Artificial Sequence
<220> FEATURE:
<223> OTHER INFORMATION: RNAi molecule

<400> SEQUENCE: 296
gaauuuauuu caguagauau cgaacug 27

<210> SEQ ID NO 297
<211> LENGTH: 27
<212> TYPE: RNA
<213> ORGANISM: Artificial Sequence
<220> FEATURE:

<223> OTHER INFORMATION: RNAi molecule

<400> SEQUENCE: 297
cucgguaaua caagcgaacu ccaaguu 27

<210> SEQ ID NO 298
<211> LENGTH: 27
<212> TYPE: RNA
<213> ORGANISM: Artificial Sequence
<220> FEATURE:
<223> OTHER INFORMATION: RNAi molecule

<400> SEQUENCE: 298
ucaccucauc uauauuacau ucauguu 27

<210> SEQ ID NO 299
<211> LENGTH: 27
<212> TYPE: RNA
<213> ORGANISM: Artificial Sequence
<220> FEATURE:
<223> OTHER INFORMATION: RNAi molecule

<400> SEQUENCE: 299
auuagauguu acaaguccaa gagaauu 27

<210> SEQ ID NO 300
<211> LENGTH: 27
<212> TYPE: RNA
<213> ORGANISM: Artificial Sequence
<220> FEATURE:
<223> OTHER INFORMATION: RNAi molecule

<400> SEQUENCE: 300
aaucaucauu aauuguugga uaguguu 27

<210> SEQ ID NO 301
<211> LENGTH: 27
<212> TYPE: RNA
<213> ORGANISM: Artificial Sequence
<220> FEATURE:
<223> OTHER INFORMATION: RNAi molecule

<400> SEQUENCE: 301
ccucaucuau auuacauuca uguucuu 27

<210> SEQ ID NO 302
<211> LENGTH: 27
<212> TYPE: RNA
<213> ORGANISM: Artificial Sequence
<220> FEATURE:
<223> OTHER INFORMATION: RNAi molecule

<400> SEQUENCE: 302
aauuauauuc accucuucau caagguu 27

<210> SEQ ID NO 303
<211> LENGTH: 27
<212> TYPE: RNA
<213> ORGANISM: Artificial Sequence
<220> FEATURE:
<223> OTHER INFORMATION: RNAi molecule

<400> SEQUENCE: 303
auauucaccu cuucaucaag guuacuu 27

<210> SEQ ID NO 304

```
<211> LENGTH: 27
<212> TYPE: RNA
<213> ORGANISM: Artificial Sequence
<220> FEATURE:
<223> OTHER INFORMATION: RNAi molecule

<400> SEQUENCE: 304

aagauguauc cuauauccuu cacucuu                                              27

<210> SEQ ID NO 305
<211> LENGTH: 27
<212> TYPE: RNA
<213> ORGANISM: Artificial Sequence
<220> FEATURE:
<223> OTHER INFORMATION: RNAi molecule

<400> SEQUENCE: 305

aacuggagug uguggaggaa uuauauu                                              27

<210> SEQ ID NO 306
<211> LENGTH: 27
<212> TYPE: RNA
<213> ORGANISM: Artificial Sequence
<220> FEATURE:
<223> OTHER INFORMATION: RNAi molecule

<400> SEQUENCE: 306

ucgguaauac aagcgaacuc caaguuu                                              27

<210> SEQ ID NO 307
<211> LENGTH: 27
<212> TYPE: RNA
<213> ORGANISM: Artificial Sequence
<220> FEATURE:
<223> OTHER INFORMATION: RNAi molecule

<400> SEQUENCE: 307

gagaacuuca auaauucuug uaucauu                                              27

<210> SEQ ID NO 308
<211> LENGTH: 27
<212> TYPE: RNA
<213> ORGANISM: Artificial Sequence
<220> FEATURE:
<223> OTHER INFORMATION: RNAi molecule

<400> SEQUENCE: 308

ucaaccucug gaaguccauu agauguu                                              27

<210> SEQ ID NO 309
<211> LENGTH: 27
<212> TYPE: RNA
<213> ORGANISM: Artificial Sequence
<220> FEATURE:
<223> OTHER INFORMATION: RNAi molecule

<400> SEQUENCE: 309

gcaguuguua aaauaggaaa ucagauu                                              27

<210> SEQ ID NO 310
<211> LENGTH: 27
<212> TYPE: RNA
<213> ORGANISM: Artificial Sequence
<220> FEATURE:
<223> OTHER INFORMATION: RNAi molecule

<400> SEQUENCE: 310
```

-continued ccagaucauc uuccauuugu aauacuu 27

<210> SEQ ID NO 311
<211> LENGTH: 27
<212> TYPE: RNA
<213> ORGANISM: Artificial Sequence
<220> FEATURE:
<223> OTHER INFORMATION: RNAi molecule

<400> SEQUENCE: 311
aaugaaauca ccagaucauc uuccauu 27

<210> SEQ ID NO 312
<211> LENGTH: 27
<212> TYPE: RNA
<213> ORGANISM: Artificial Sequence
<220> FEATURE:
<223> OTHER INFORMATION: RNAi molecule

<400> SEQUENCE: 312
acugaaauga aaucaccaga ucaucuu 27

<210> SEQ ID NO 313
<211> LENGTH: 27
<212> TYPE: RNA
<213> ORGANISM: Artificial Sequence
<220> FEATURE:
<223> OTHER INFORMATION: RNAi molecule

<400> SEQUENCE: 313
guucuucuuc ugauuuaagc auggauu 27

<210> SEQ ID NO 314
<211> LENGTH: 27
<212> TYPE: RNA
<213> ORGANISM: Artificial Sequence
<220> FEATURE:
<223> OTHER INFORMATION: RNAi molecule

<400> SEQUENCE: 314
gaauggauaa ucguucuucu ucugauu 27

<210> SEQ ID NO 315
<211> LENGTH: 27
<212> TYPE: RNA
<213> ORGANISM: Artificial Sequence
<220> FEATURE:
<223> OTHER INFORMATION: RNAi molecule

<400> SEQUENCE: 315
uucugaaggu ugaucacuug cagaauu 27

<210> SEQ ID NO 316
<211> LENGTH: 27
<212> TYPE: RNA
<213> ORGANISM: Artificial Sequence
<220> FEATURE:
<223> OTHER INFORMATION: RNAi molecule

<400> SEQUENCE: 316
cuaauaaaaa ugugauccaa gaaacuu 27

<210> SEQ ID NO 317
<211> LENGTH: 27
<212> TYPE: RNA
<213> ORGANISM: Artificial Sequence
<220> FEATURE:

<223> OTHER INFORMATION: RNAi molecule

<400> SEQUENCE: 317
ucuuuacaga gaacuucaau aauucuu 27

<210> SEQ ID NO 318
<211> LENGTH: 27
<212> TYPE: RNA
<213> ORGANISM: Artificial Sequence
<220> FEATURE:
<223> OTHER INFORMATION: RNAi molecule

<400> SEQUENCE: 318
cucaucuaua uuacauucau guucuuu 27

<210> SEQ ID NO 319
<211> LENGTH: 27
<212> TYPE: RNA
<213> ORGANISM: Artificial Sequence
<220> FEATURE:
<223> OTHER INFORMATION: RNAi molecule

<400> SEQUENCE: 319
cauuuuucac cucaucuaua uuacauu 27

<210> SEQ ID NO 320
<211> LENGTH: 27
<212> TYPE: RNA
<213> ORGANISM: Artificial Sequence
<220> FEATURE:
<223> OTHER INFORMATION: RNAi molecule

<400> SEQUENCE: 320
uaugaaaaau guugucauuc agaaguu 27

<210> SEQ ID NO 321
<211> LENGTH: 27
<212> TYPE: RNA
<213> ORGANISM: Artificial Sequence
<220> FEATURE:
<223> OTHER INFORMATION: RNAi molecule

<400> SEQUENCE: 321
acucgguaau acaagcgaac uccaagu 27

<210> SEQ ID NO 322
<211> LENGTH: 26
<212> TYPE: RNA
<213> ORGANISM: Artificial Sequence
<220> FEATURE:
<223> OTHER INFORMATION: RNAi molecule

<400> SEQUENCE: 322
uaucgguaau acaagcgaac uccaag 26

<210> SEQ ID NO 323
<211> LENGTH: 27
<212> TYPE: RNA
<213> ORGANISM: Artificial Sequence
<220> FEATURE:
<223> OTHER INFORMATION: RNAi molecule

<400> SEQUENCE: 323
ccauuagaug uuacaagucc aagagaa 27

<210> SEQ ID NO 324

<211> LENGTH: 27
<212> TYPE: RNA
<213> ORGANISM: Artificial Sequence
<220> FEATURE:
<223> OTHER INFORMATION: RNAi molecule

<400> SEQUENCE: 324
uccauuagau guuacaaguc caagaga 27

<210> SEQ ID NO 325
<211> LENGTH: 27
<212> TYPE: RNA
<213> ORGANISM: Artificial Sequence
<220> FEATURE:
<223> OTHER INFORMATION: RNAi molecule

<400> SEQUENCE: 325
aguccauuag auguuacaag uccaaga 27

<210> SEQ ID NO 326
<211> LENGTH: 27
<212> TYPE: RNA
<213> ORGANISM: Artificial Sequence
<220> FEATURE:
<223> OTHER INFORMATION: RNAi molecule

<400> SEQUENCE: 326
aaguccauua gauguuacaa guccaag 27

<210> SEQ ID NO 327
<211> LENGTH: 27
<212> TYPE: RNA
<213> ORGANISM: Artificial Sequence
<220> FEATURE:
<223> OTHER INFORMATION: RNAi molecule

<400> SEQUENCE: 327
gaaguccauu agauguuaca aguccaa 27

<210> SEQ ID NO 328
<211> LENGTH: 27
<212> TYPE: RNA
<213> ORGANISM: Artificial Sequence
<220> FEATURE:
<223> OTHER INFORMATION: RNAi molecule

<400> SEQUENCE: 328
guccauuaga uguuacaagu ccaagag 27

<210> SEQ ID NO 329
<211> LENGTH: 27
<212> TYPE: RNA
<213> ORGANISM: Artificial Sequence
<220> FEATURE:
<223> OTHER INFORMATION: RNAi molecule

<400> SEQUENCE: 329
uuacucggua auacaagcga acuccaa 27

<210> SEQ ID NO 330
<211> LENGTH: 27
<212> TYPE: RNA
<213> ORGANISM: Artificial Sequence
<220> FEATURE:
<223> OTHER INFORMATION: RNAi molecule

<400> SEQUENCE: 330
ucauuaauug uuggauagug uucauaa 27

<210> SEQ ID NO 331
<211> LENGTH: 27
<212> TYPE: RNA
<213> ORGANISM: Artificial Sequence
<220> FEATURE:
<223> OTHER INFORMATION: RNAi molecule

<400> SEQUENCE: 331
accucaucua uauuacauuc auguucu 27

<210> SEQ ID NO 332
<211> LENGTH: 27
<212> TYPE: RNA
<213> ORGANISM: Artificial Sequence
<220> FEATURE:
<223> OTHER INFORMATION: RNAi molecule

<400> SEQUENCE: 332
uucaccucau cuauauuaca uucaugu 27

<210> SEQ ID NO 333
<211> LENGTH: 27
<212> TYPE: RNA
<213> ORGANISM: Artificial Sequence
<220> FEATURE:
<223> OTHER INFORMATION: RNAi molecule

<400> SEQUENCE: 333
cauuaauugu uggauagugu ucauaac 27

<210> SEQ ID NO 334
<211> LENGTH: 27
<212> TYPE: RNA
<213> ORGANISM: Artificial Sequence
<220> FEATURE:
<223> OTHER INFORMATION: RNAi molecule

<400> SEQUENCE: 334
caucauuaau uguuggauag uguucau 27

<210> SEQ ID NO 335
<211> LENGTH: 27
<212> TYPE: RNA
<213> ORGANISM: Artificial Sequence
<220> FEATURE:
<223> OTHER INFORMATION: RNAi molecule

<400> SEQUENCE: 335
ucaucauuaa uuguuggaua guguuca 27

<210> SEQ ID NO 336
<211> LENGTH: 27
<212> TYPE: RNA
<213> ORGANISM: Artificial Sequence
<220> FEATURE:
<223> OTHER INFORMATION: RNAi molecule

<400> SEQUENCE: 336
agauguuaca aguccaagag aauucau 27

<210> SEQ ID NO 337
<211> LENGTH: 27
<212> TYPE: RNA
<213> ORGANISM: Artificial Sequence
<220> FEATURE:

<223> OTHER INFORMATION: RNAi molecule

<400> SEQUENCE: 337
uagauguuac aaguccaaga gaauuca 27

<210> SEQ ID NO 338
<211> LENGTH: 27
<212> TYPE: RNA
<213> ORGANISM: Artificial Sequence
<220> FEATURE:
<223> OTHER INFORMATION: RNAi molecule

<400> SEQUENCE: 338
cauuagaugu uacaagucca agagaau 27

<210> SEQ ID NO 339
<211> LENGTH: 27
<212> TYPE: RNA
<213> ORGANISM: Artificial Sequence
<220> FEATURE:
<223> OTHER INFORMATION: RNAi molecule

<400> SEQUENCE: 339
aggaauuaua uucaccucuu caucaag 27

<210> SEQ ID NO 340
<211> LENGTH: 27
<212> TYPE: RNA
<213> ORGANISM: Artificial Sequence
<220> FEATURE:
<223> OTHER INFORMATION: RNAi molecule

<400> SEQUENCE: 340
ggaaguccau uagauguuac aagucca 27

<210> SEQ ID NO 341
<211> LENGTH: 27
<212> TYPE: RNA
<213> ORGANISM: Artificial Sequence
<220> FEATURE:
<223> OTHER INFORMATION: RNAi molecule

<400> SEQUENCE: 341
accucuggaa guccauuaga uguuaca 27

<210> SEQ ID NO 342
<211> LENGTH: 27
<212> TYPE: RNA
<213> ORGANISM: Artificial Sequence
<220> FEATURE:
<223> OTHER INFORMATION: RNAi molecule

<400> SEQUENCE: 342
auguuacaag uccaagagaa uucauaa 27

<210> SEQ ID NO 343
<211> LENGTH: 27
<212> TYPE: RNA
<213> ORGANISM: Artificial Sequence
<220> FEATURE:
<223> OTHER INFORMATION: RNAi molecule

<400> SEQUENCE: 343
uauauucacc ucuucaucaa gguuacu 27

<210> SEQ ID NO 344

<211> LENGTH: 27
<212> TYPE: RNA
<213> ORGANISM: Artificial Sequence
<220> FEATURE:
<223> OTHER INFORMATION: RNAi molecule

<400> SEQUENCE: 344
uuauauucac cucuucauca agguuac 27

<210> SEQ ID NO 345
<211> LENGTH: 27
<212> TYPE: RNA
<213> ORGANISM: Artificial Sequence
<220> FEATURE:
<223> OTHER INFORMATION: RNAi molecule

<400> SEQUENCE: 345
uaacuggagu guguggagga auuauau 27

<210> SEQ ID NO 346
<211> LENGTH: 27
<212> TYPE: RNA
<213> ORGANISM: Artificial Sequence
<220> FEATURE:
<223> OTHER INFORMATION: RNAi molecule

<400> SEQUENCE: 346
cuucucugug aguugauaag cauucuu 27

<210> SEQ ID NO 347
<211> LENGTH: 27
<212> TYPE: RNA
<213> ORGANISM: Artificial Sequence
<220> FEATURE:
<223> OTHER INFORMATION: RNAi molecule

<400> SEQUENCE: 347
cacuugccaa gagaucguug uaacauu 27

<210> SEQ ID NO 348
<211> LENGTH: 27
<212> TYPE: RNA
<213> ORGANISM: Artificial Sequence
<220> FEATURE:
<223> OTHER INFORMATION: RNAi molecule

<400> SEQUENCE: 348
uucaguuggu cucucagucg cuguauu 27

<210> SEQ ID NO 349
<211> LENGTH: 27
<212> TYPE: RNA
<213> ORGANISM: Artificial Sequence
<220> FEATURE:
<223> OTHER INFORMATION: RNAi molecule

<400> SEQUENCE: 349
cgguaguacu auaucuggcc uucaguu 27

<210> SEQ ID NO 350
<211> LENGTH: 27
<212> TYPE: RNA
<213> ORGANISM: Artificial Sequence
<220> FEATURE:
<223> OTHER INFORMATION: RNAi molecule

<400> SEQUENCE: 350
caaugcggua guacuauauc uggccuu 27

<210> SEQ ID NO 351
<211> LENGTH: 27
<212> TYPE: RNA
<213> ORGANISM: Artificial Sequence
<220> FEATURE:
<223> OTHER INFORMATION: RNAi molecule

<400> SEQUENCE: 351
cugaucauac acgagccacu gcugauu 27

<210> SEQ ID NO 352
<211> LENGTH: 27
<212> TYPE: RNA
<213> ORGANISM: Artificial Sequence
<220> FEATURE:
<223> OTHER INFORMATION: RNAi molecule

<400> SEQUENCE: 352
ugugaguuga uaagcauucu ucuccuu 27

<210> SEQ ID NO 353
<211> LENGTH: 27
<212> TYPE: RNA
<213> ORGANISM: Artificial Sequence
<220> FEATURE:
<223> OTHER INFORMATION: RNAi molecule

<400> SEQUENCE: 353
uugaagauaa ccuucugauu caggcuu 27

<210> SEQ ID NO 354
<211> LENGTH: 27
<212> TYPE: RNA
<213> ORGANISM: Artificial Sequence
<220> FEATURE:
<223> OTHER INFORMATION: RNAi molecule

<400> SEQUENCE: 354
uccuucucag ccucaaggac ucgaauu 27

<210> SEQ ID NO 355
<211> LENGTH: 27
<212> TYPE: RNA
<213> ORGANISM: Artificial Sequence
<220> FEATURE:
<223> OTHER INFORMATION: RNAi molecule

<400> SEQUENCE: 355
cuucucucgu ugucucuucc agcuguu 27

<210> SEQ ID NO 356
<211> LENGTH: 27
<212> TYPE: RNA
<213> ORGANISM: Artificial Sequence
<220> FEATURE:
<223> OTHER INFORMATION: RNAi molecule

<400> SEQUENCE: 356
ucugcuucuc uucuugaaga uaaccuu 27

<210> SEQ ID NO 357
<211> LENGTH: 27
<212> TYPE: RNA
<213> ORGANISM: Artificial Sequence
<220> FEATURE:

<223> OTHER INFORMATION: RNAi molecule

<400> SEQUENCE: 357
guccuucucu gugaguugau aagcauu 27

<210> SEQ ID NO 358
<211> LENGTH: 27
<212> TYPE: RNA
<213> ORGANISM: Artificial Sequence
<220> FEATURE:
<223> OTHER INFORMATION: RNAi molecule

<400> SEQUENCE: 358
gaucauacac gagccacugc ugauuuu 27

<210> SEQ ID NO 359
<211> LENGTH: 27
<212> TYPE: RNA
<213> ORGANISM: Artificial Sequence
<220> FEATURE:
<223> OTHER INFORMATION: RNAi molecule

<400> SEQUENCE: 359
aucauacacg agccacugcu gauuuuu 27

<210> SEQ ID NO 360
<211> LENGTH: 27
<212> TYPE: RNA
<213> ORGANISM: Artificial Sequence
<220> FEATURE:
<223> OTHER INFORMATION: RNAi molecule

<400> SEQUENCE: 360
ugaucauaca cgagccacug cugauuu 27

<210> SEQ ID NO 361
<211> LENGTH: 27
<212> TYPE: RNA
<213> ORGANISM: Artificial Sequence
<220> FEATURE:
<223> OTHER INFORMATION: RNAi molecule

<400> SEQUENCE: 361
uucgugaggu ugcagcagac aacuguu 27

<210> SEQ ID NO 362
<211> LENGTH: 27
<212> TYPE: RNA
<213> ORGANISM: Artificial Sequence
<220> FEATURE:
<223> OTHER INFORMATION: RNAi molecule

<400> SEQUENCE: 362
uuauuuauug augaguugaa gcaguuu 27

<210> SEQ ID NO 363
<211> LENGTH: 27
<212> TYPE: RNA
<213> ORGANISM: Artificial Sequence
<220> FEATURE:
<223> OTHER INFORMATION: RNAi molecule

<400> SEQUENCE: 363
auuauuuauu gaugaguuga agcaguu 27

<210> SEQ ID NO 364

<211> LENGTH: 27
<212> TYPE: RNA
<213> ORGANISM: Artificial Sequence
<220> FEATURE:
<223> OTHER INFORMATION: RNAi molecule

<400> SEQUENCE: 364
ucucuucuug aagauaaccu ucugauu 27

<210> SEQ ID NO 365
<211> LENGTH: 27
<212> TYPE: RNA
<213> ORGANISM: Artificial Sequence
<220> FEATURE:
<223> OTHER INFORMATION: RNAi molecule

<400> SEQUENCE: 365
ucaaccucaa gaucuuuuuu ugcacuu 27

<210> SEQ ID NO 366
<211> LENGTH: 27
<212> TYPE: RNA
<213> ORGANISM: Artificial Sequence
<220> FEATURE:
<223> OTHER INFORMATION: RNAi molecule

<400> SEQUENCE: 366
ugucguucaa ccucaagauc uuuuuuu 27

<210> SEQ ID NO 367
<211> LENGTH: 27
<212> TYPE: RNA
<213> ORGANISM: Artificial Sequence
<220> FEATURE:
<223> OTHER INFORMATION: RNAi molecule

<400> SEQUENCE: 367
uugucguuca accucaagau cuuuuuu 27

<210> SEQ ID NO 368
<211> LENGTH: 27
<212> TYPE: RNA
<213> ORGANISM: Artificial Sequence
<220> FEATURE:
<223> OTHER INFORMATION: RNAi molecule

<400> SEQUENCE: 368
uuugucguuc aaccucaaga ucuuuuu 27

<210> SEQ ID NO 369
<211> LENGTH: 27
<212> TYPE: RNA
<213> ORGANISM: Artificial Sequence
<220> FEATURE:
<223> OTHER INFORMATION: RNAi molecule

<400> SEQUENCE: 369
acuugccaag agaucguugu aacauuu 27

<210> SEQ ID NO 370
<211> LENGTH: 27
<212> TYPE: RNA
<213> ORGANISM: Artificial Sequence
<220> FEATURE:
<223> OTHER INFORMATION: RNAi molecule

<400> SEQUENCE: 370
guuugucguu caaccucaag aucuuuu 27

<210> SEQ ID NO 371
<211> LENGTH: 27
<212> TYPE: RNA
<213> ORGANISM: Artificial Sequence
<220> FEATURE:
<223> OTHER INFORMATION: RNAi molecule

<400> SEQUENCE: 371
ccuucucugu gaguugauaa gcauucu 27

<210> SEQ ID NO 372
<211> LENGTH: 27
<212> TYPE: RNA
<213> ORGANISM: Artificial Sequence
<220> FEATURE:
<223> OTHER INFORMATION: RNAi molecule

<400> SEQUENCE: 372
ucucugugag uugauaagca uucuucu 27

<210> SEQ ID NO 373
<211> LENGTH: 27
<212> TYPE: RNA
<213> ORGANISM: Artificial Sequence
<220> FEATURE:
<223> OTHER INFORMATION: RNAi molecule

<400> SEQUENCE: 373
uugauaagca uucuucuccu ucucagc 27

<210> SEQ ID NO 374
<211> LENGTH: 27
<212> TYPE: RNA
<213> ORGANISM: Artificial Sequence
<220> FEATURE:
<223> OTHER INFORMATION: RNAi molecule

<400> SEQUENCE: 374
aagcauucuu cuccuucuca gccucaa 27

<210> SEQ ID NO 375
<211> LENGTH: 27
<212> TYPE: RNA
<213> ORGANISM: Artificial Sequence
<220> FEATURE:
<223> OTHER INFORMATION: RNAi molecule

<400> SEQUENCE: 375
uaagcauucu ucuccuucuc agccuca 27

<210> SEQ ID NO 376
<211> LENGTH: 27
<212> TYPE: RNA
<213> ORGANISM: Artificial Sequence
<220> FEATURE:
<223> OTHER INFORMATION: RNAi molecule

<400> SEQUENCE: 376
gauaagcauu cuucuccuuc ucagccu 27

<210> SEQ ID NO 377
<211> LENGTH: 27
<212> TYPE: RNA
<213> ORGANISM: Artificial Sequence
<220> FEATURE:

<223> OTHER INFORMATION: RNAi molecule

<400> SEQUENCE: 377
ugauaagcau ucuucuccuu cucagcc 27

<210> SEQ ID NO 378
<211> LENGTH: 27
<212> TYPE: RNA
<213> ORGANISM: Artificial Sequence
<220> FEATURE:
<223> OTHER INFORMATION: RNAi molecule

<400> SEQUENCE: 378
augcgguagu acuauaucug gccuuca 27

<210> SEQ ID NO 379
<211> LENGTH: 27
<212> TYPE: RNA
<213> ORGANISM: Artificial Sequence
<220> FEATURE:
<223> OTHER INFORMATION: RNAi molecule

<400> SEQUENCE: 379
ugcacuugcc aagagaucgu uguaaca 27

<210> SEQ ID NO 380
<211> LENGTH: 27
<212> TYPE: RNA
<213> ORGANISM: Artificial Sequence
<220> FEATURE:
<223> OTHER INFORMATION: RNAi molecule

<400> SEQUENCE: 380
uugcacuugc caagagaucg uuguaac 27

<210> SEQ ID NO 381
<211> LENGTH: 27
<212> TYPE: RNA
<213> ORGANISM: Artificial Sequence
<220> FEATURE:
<223> OTHER INFORMATION: RNAi molecule

<400> SEQUENCE: 381
agcauucuuc uccuucucag ccucaag 27

<210> SEQ ID NO 382
<211> LENGTH: 27
<212> TYPE: RNA
<213> ORGANISM: Artificial Sequence
<220> FEATURE:
<223> OTHER INFORMATION: RNAi molecule

<400> SEQUENCE: 382
ugcgguagua cuauaucugg ccuucag 27

<210> SEQ ID NO 383
<211> LENGTH: 27
<212> TYPE: RNA
<213> ORGANISM: Artificial Sequence
<220> FEATURE:
<223> OTHER INFORMATION: RNAi molecule

<400> SEQUENCE: 383
ucucguuguc ucuuccagcu guucaag 27

<210> SEQ ID NO 384

<211> LENGTH: 27
<212> TYPE: RNA
<213> ORGANISM: Artificial Sequence
<220> FEATURE:
<223> OTHER INFORMATION: RNAi molecule

<400> SEQUENCE: 384
cucguugucu cuuccagcug uucaagc 27

<210> SEQ ID NO 385
<211> LENGTH: 27
<212> TYPE: RNA
<213> ORGANISM: Artificial Sequence
<220> FEATURE:
<223> OTHER INFORMATION: RNAi molecule

<400> SEQUENCE: 385
gcugaucaua cacgagccac ugcugau 27

<210> SEQ ID NO 386
<211> LENGTH: 27
<212> TYPE: RNA
<213> ORGANISM: Artificial Sequence
<220> FEATURE:
<223> OTHER INFORMATION: RNAi molecule

<400> SEQUENCE: 386
ugcugaucau acacgagcca cugcuga 27

<210> SEQ ID NO 387
<211> LENGTH: 27
<212> TYPE: RNA
<213> ORGANISM: Artificial Sequence
<220> FEATURE:
<223> OTHER INFORMATION: RNAi molecule

<400> SEQUENCE: 387
aguugauaag cauucuucuc cuucuca 27

<210> SEQ ID NO 388
<211> LENGTH: 27
<212> TYPE: RNA
<213> ORGANISM: Artificial Sequence
<220> FEATURE:
<223> OTHER INFORMATION: RNAi molecule

<400> SEQUENCE: 388
guugauaagc auucuucucc uucucag 27

<210> SEQ ID NO 389
<211> LENGTH: 27
<212> TYPE: RNA
<213> ORGANISM: Artificial Sequence
<220> FEATURE:
<223> OTHER INFORMATION: RNAi molecule

<400> SEQUENCE: 389
cugugaguug auaagcauuc uucuccu 27

<210> SEQ ID NO 390
<211> LENGTH: 27
<212> TYPE: RNA
<213> ORGANISM: Artificial Sequence
<220> FEATURE:
<223> OTHER INFORMATION: RNAi molecule

<400> SEQUENCE: 390
ucugugaguu gauaagcauu cuucucc 27

<210> SEQ ID NO 391
<211> LENGTH: 27
<212> TYPE: RNA
<213> ORGANISM: Artificial Sequence
<220> FEATURE:
<223> OTHER INFORMATION: RNAi molecule

<400> SEQUENCE: 391
cuugaagaua accuucugau ucaggcu 27

<210> SEQ ID NO 392
<211> LENGTH: 27
<212> TYPE: RNA
<213> ORGANISM: Artificial Sequence
<220> FEATURE:
<223> OTHER INFORMATION: RNAi molecule

<400> SEQUENCE: 392
guaguacuau aucuggccuu caguugg 27

<210> SEQ ID NO 393
<211> LENGTH: 27
<212> TYPE: RNA
<213> ORGANISM: Artificial Sequence
<220> FEATURE:
<223> OTHER INFORMATION: RNAi molecule

<400> SEQUENCE: 393
aagcaaugcg guaguacuau aucuggc 27

<210> SEQ ID NO 394
<211> LENGTH: 27
<212> TYPE: RNA
<213> ORGANISM: Artificial Sequence
<220> FEATURE:
<223> OTHER INFORMATION: RNAi molecule

<400> SEQUENCE: 394
caagcaaugc gguaguacua uaucugg 27

<210> SEQ ID NO 395
<211> LENGTH: 27
<212> TYPE: RNA
<213> ORGANISM: Artificial Sequence
<220> FEATURE:
<223> OTHER INFORMATION: RNAi molecule

<400> SEQUENCE: 395
auucuucucc uucucagccu caaggac 27

<210> SEQ ID NO 396
<211> LENGTH: 27
<212> TYPE: RNA
<213> ORGANISM: Artificial Sequence
<220> FEATURE:
<223> OTHER INFORMATION: RNAi molecule

<400> SEQUENCE: 396
auuacucucc acaucaucac ugucauu 27

<210> SEQ ID NO 397
<211> LENGTH: 27
<212> TYPE: RNA
<213> ORGANISM: Artificial Sequence
<220> FEATURE:

<223> OTHER INFORMATION: RNAi molecule

<400> SEQUENCE: 397
ggaugcugau gaucucaucc aucaauu 27

<210> SEQ ID NO 398
<211> LENGTH: 27
<212> TYPE: RNA
<213> ORGANISM: Artificial Sequence
<220> FEATURE:
<223> OTHER INFORMATION: RNAi molecule

<400> SEQUENCE: 398
agauucaggu aacaaggucc aaacguu 27

<210> SEQ ID NO 399
<211> LENGTH: 27
<212> TYPE: RNA
<213> ORGANISM: Artificial Sequence
<220> FEATURE:
<223> OTHER INFORMATION: RNAi molecule

<400> SEQUENCE: 399
aacguuggaa caaagccuac cucuguu 27

<210> SEQ ID NO 400
<211> LENGTH: 27
<212> TYPE: RNA
<213> ORGANISM: Artificial Sequence
<220> FEATURE:
<223> OTHER INFORMATION: RNAi molecule

<400> SEQUENCE: 400
agauccugcc ucuguaggca acuccuu 27

<210> SEQ ID NO 401
<211> LENGTH: 27
<212> TYPE: RNA
<213> ORGANISM: Artificial Sequence
<220> FEATURE:
<223> OTHER INFORMATION: RNAi molecule

<400> SEQUENCE: 401
cucaagcuuu uuaucuggug gugucuu 27

<210> SEQ ID NO 402
<211> LENGTH: 27
<212> TYPE: RNA
<213> ORGANISM: Artificial Sequence
<220> FEATURE:
<223> OTHER INFORMATION: RNAi molecule

<400> SEQUENCE: 402
aucauaaaca aauccaacau caaucuu 27

<210> SEQ ID NO 403
<211> LENGTH: 27
<212> TYPE: RNA
<213> ORGANISM: Artificial Sequence
<220> FEATURE:
<223> OTHER INFORMATION: RNAi molecule

<400> SEQUENCE: 403
uagauauguu guuccaacua caucauu 27

<210> SEQ ID NO 404

<211> LENGTH: 27
<212> TYPE: RNA
<213> ORGANISM: Artificial Sequence
<220> FEATURE:
<223> OTHER INFORMATION: RNAi molecule

<400> SEQUENCE: 404
uucuuaucug cauugccucc aaauauu 27

<210> SEQ ID NO 405
<211> LENGTH: 27
<212> TYPE: RNA
<213> ORGANISM: Artificial Sequence
<220> FEATURE:
<223> OTHER INFORMATION: RNAi molecule

<400> SEQUENCE: 405
gugucuucuc aagaaaagug gcuaauu 27

<210> SEQ ID NO 406
<211> LENGTH: 27
<212> TYPE: RNA
<213> ORGANISM: Artificial Sequence
<220> FEATURE:
<223> OTHER INFORMATION: RNAi molecule

<400> SEQUENCE: 406
cuugaucuga agauugacga ccugauu 27

<210> SEQ ID NO 407
<211> LENGTH: 27
<212> TYPE: RNA
<213> ORGANISM: Artificial Sequence
<220> FEATURE:
<223> OTHER INFORMATION: RNAi molecule

<400> SEQUENCE: 407
aagccuaccu cuguuucucc uguguuu 27

<210> SEQ ID NO 408
<211> LENGTH: 27
<212> TYPE: RNA
<213> ORGANISM: Artificial Sequence
<220> FEATURE:
<223> OTHER INFORMATION: RNAi molecule

<400> SEQUENCE: 408
auccacgaga uuuuucuuau cugcauu 27

<210> SEQ ID NO 409
<211> LENGTH: 27
<212> TYPE: RNA
<213> ORGANISM: Artificial Sequence
<220> FEATURE:
<223> OTHER INFORMATION: RNAi molecule

<400> SEQUENCE: 409
aacuucuaca aaaggaucca cgagauu 27

<210> SEQ ID NO 410
<211> LENGTH: 27
<212> TYPE: RNA
<213> ORGANISM: Artificial Sequence
<220> FEATURE:
<223> OTHER INFORMATION: RNAi molecule

<400> SEQUENCE: 410
uucucaacaa ccagcagguc aucauuu 27

<210> SEQ ID NO 411
<211> LENGTH: 27
<212> TYPE: RNA
<213> ORGANISM: Artificial Sequence
<220> FEATURE:
<223> OTHER INFORMATION: RNAi molecule

<400> SEQUENCE: 411
uuucucaaca accagcaggu caucauu 27

<210> SEQ ID NO 412
<211> LENGTH: 27
<212> TYPE: RNA
<213> ORGANISM: Artificial Sequence
<220> FEATURE:
<223> OTHER INFORMATION: RNAi molecule

<400> SEQUENCE: 412
aaacaaaucc aacaucaauc uuaaauu 27

<210> SEQ ID NO 413
<211> LENGTH: 27
<212> TYPE: RNA
<213> ORGANISM: Artificial Sequence
<220> FEATURE:
<223> OTHER INFORMATION: RNAi molecule

<400> SEQUENCE: 413
auuuuagaga gguguagaua uguuguu 27

<210> SEQ ID NO 414
<211> LENGTH: 27
<212> TYPE: RNA
<213> ORGANISM: Artificial Sequence
<220> FEATURE:
<223> OTHER INFORMATION: RNAi molecule

<400> SEQUENCE: 414
acuuucucau gacagcaugg ccagguu 27

<210> SEQ ID NO 415
<211> LENGTH: 27
<212> TYPE: RNA
<213> ORGANISM: Artificial Sequence
<220> FEATURE:
<223> OTHER INFORMATION: RNAi molecule

<400> SEQUENCE: 415
cugaagauug acgaccugau uccacuc 27

<210> SEQ ID NO 416
<211> LENGTH: 27
<212> TYPE: RNA
<213> ORGANISM: Artificial Sequence
<220> FEATURE:
<223> OTHER INFORMATION: RNAi molecule

<400> SEQUENCE: 416
acucuccaca ucaucacugu cauuauc 27

<210> SEQ ID NO 417
<211> LENGTH: 27
<212> TYPE: RNA
<213> ORGANISM: Artificial Sequence
<220> FEATURE:

<223> OTHER INFORMATION: RNAi molecule

<400> SEQUENCE: 417
uaauucaacc aagauccugc cucugua 27

<210> SEQ ID NO 418
<211> LENGTH: 27
<212> TYPE: RNA
<213> ORGANISM: Artificial Sequence
<220> FEATURE:
<223> OTHER INFORMATION: RNAi molecule

<400> SEQUENCE: 418
ucacugucau uaucacgauc ucgucuc 27

<210> SEQ ID NO 419
<211> LENGTH: 27
<212> TYPE: RNA
<213> ORGANISM: Artificial Sequence
<220> FEATURE:
<223> OTHER INFORMATION: RNAi molecule

<400> SEQUENCE: 419
caucacuguc auuaucacga ucucguc 27

<210> SEQ ID NO 420
<211> LENGTH: 27
<212> TYPE: RNA
<213> ORGANISM: Artificial Sequence
<220> FEATURE:
<223> OTHER INFORMATION: RNAi molecule

<400> SEQUENCE: 420
gaagauugac gaccugauuc cacucug 27

<210> SEQ ID NO 421
<211> LENGTH: 27
<212> TYPE: RNA
<213> ORGANISM: Artificial Sequence
<220> FEATURE:
<223> OTHER INFORMATION: RNAi molecule

<400> SEQUENCE: 421
ugaagauuga cgaccugauu ccacucu 27

<210> SEQ ID NO 422
<211> LENGTH: 27
<212> TYPE: RNA
<213> ORGANISM: Artificial Sequence
<220> FEATURE:
<223> OTHER INFORMATION: RNAi molecule

<400> SEQUENCE: 422
ucugaagauu gacgaccuga uuccacu 27

<210> SEQ ID NO 423
<211> LENGTH: 27
<212> TYPE: RNA
<213> ORGANISM: Artificial Sequence
<220> FEATURE:
<223> OTHER INFORMATION: RNAi molecule

<400> SEQUENCE: 423
aaguggcuaa uucaaccaag auccugc 27

<210> SEQ ID NO 424

<211> LENGTH: 27
<212> TYPE: RNA
<213> ORGANISM: Artificial Sequence
<220> FEATURE:
<223> OTHER INFORMATION: RNAi molecule

<400> SEQUENCE: 424
aucacuguca uuaucacgau cucgucu 27

<210> SEQ ID NO 425
<211> LENGTH: 27
<212> TYPE: RNA
<213> ORGANISM: Artificial Sequence
<220> FEATURE:
<223> OTHER INFORMATION: RNAi molecule

<400> SEQUENCE: 425
ucaucacugu cauuaucacg aucucgu 27

<210> SEQ ID NO 426
<211> LENGTH: 27
<212> TYPE: RNA
<213> ORGANISM: Artificial Sequence
<220> FEATURE:
<223> OTHER INFORMATION: RNAi molecule

<400> SEQUENCE: 426
ccacaucauc acugucauua ucacgau 27

<210> SEQ ID NO 427
<211> LENGTH: 27
<212> TYPE: RNA
<213> ORGANISM: Artificial Sequence
<220> FEATURE:
<223> OTHER INFORMATION: RNAi molecule

<400> SEQUENCE: 427
uccacaucau cacugucauu aucacga 27

<210> SEQ ID NO 428
<211> LENGTH: 27
<212> TYPE: RNA
<213> ORGANISM: Artificial Sequence
<220> FEATURE:
<223> OTHER INFORMATION: RNAi molecule

<400> SEQUENCE: 428
ucuccacauc aucacuguca uuaucac 27

<210> SEQ ID NO 429
<211> LENGTH: 27
<212> TYPE: RNA
<213> ORGANISM: Artificial Sequence
<220> FEATURE:
<223> OTHER INFORMATION: RNAi molecule

<400> SEQUENCE: 429
cucuccacau caucacuguc auuauca 27

<210> SEQ ID NO 430
<211> LENGTH: 27
<212> TYPE: RNA
<213> ORGANISM: Artificial Sequence
<220> FEATURE:
<223> OTHER INFORMATION: RNAi molecule

<400> SEQUENCE: 430
cuccacauca ucacugucau uaucacg 27

<210> SEQ ID NO 431
<211> LENGTH: 27
<212> TYPE: RNA
<213> ORGANISM: Artificial Sequence
<220> FEATURE:
<223> OTHER INFORMATION: RNAi molecule

<400> SEQUENCE: 431
aucugaagau ugacgaccug auuccac 27

<210> SEQ ID NO 432
<211> LENGTH: 27
<212> TYPE: RNA
<213> ORGANISM: Artificial Sequence
<220> FEATURE:
<223> OTHER INFORMATION: RNAi molecule

<400> SEQUENCE: 432
cuaauucaac caagauccug ccucugu 27

<210> SEQ ID NO 433
<211> LENGTH: 27
<212> TYPE: RNA
<213> ORGANISM: Artificial Sequence
<220> FEATURE:
<223> OTHER INFORMATION: RNAi molecule

<400> SEQUENCE: 433
gucauuauca cgaucucguc ucucagg 27

<210> SEQ ID NO 434
<211> LENGTH: 27
<212> TYPE: RNA
<213> ORGANISM: Artificial Sequence
<220> FEATURE:
<223> OTHER INFORMATION: RNAi molecule

<400> SEQUENCE: 434
aagauugacg accugauucc acucugg 27

<210> SEQ ID NO 435
<211> LENGTH: 27
<212> TYPE: RNA
<213> ORGANISM: Artificial Sequence
<220> FEATURE:
<223> OTHER INFORMATION: RNAi molecule

<400> SEQUENCE: 435
acaucaucac ugucauuauc acgaucu 27

<210> SEQ ID NO 436
<211> LENGTH: 27
<212> TYPE: RNA
<213> ORGANISM: Artificial Sequence
<220> FEATURE:
<223> OTHER INFORMATION: RNAi molecule

<400> SEQUENCE: 436
uacucuccac aucaucacug ucauuau 27

<210> SEQ ID NO 437
<211> LENGTH: 27
<212> TYPE: RNA
<213> ORGANISM: Artificial Sequence
<220> FEATURE:

<223> OTHER INFORMATION: RNAi molecule

<400> SEQUENCE: 437
aauuacucuc cacaucauca cugucau 27

<210> SEQ ID NO 438
<211> LENGTH: 27
<212> TYPE: RNA
<213> ORGANISM: Artificial Sequence
<220> FEATURE:
<223> OTHER INFORMATION: RNAi molecule

<400> SEQUENCE: 438
aucaucacug ucauuaucac gaucucg 27

<210> SEQ ID NO 439
<211> LENGTH: 27
<212> TYPE: RNA
<213> ORGANISM: Artificial Sequence
<220> FEATURE:
<223> OTHER INFORMATION: RNAi molecule

<400> SEQUENCE: 439
ucauuaucac gaucucgucu cucagga 27

<210> SEQ ID NO 440
<211> LENGTH: 27
<212> TYPE: RNA
<213> ORGANISM: Artificial Sequence
<220> FEATURE:
<223> OTHER INFORMATION: RNAi molecule

<400> SEQUENCE: 440
ugucauuauc acgaucucgu cucucag 27

<210> SEQ ID NO 441
<211> LENGTH: 27
<212> TYPE: RNA
<213> ORGANISM: Artificial Sequence
<220> FEATURE:
<223> OTHER INFORMATION: RNAi molecule

<400> SEQUENCE: 441
cugucauuau cacgaucucg ucucuca 27

<210> SEQ ID NO 442
<211> LENGTH: 27
<212> TYPE: RNA
<213> ORGANISM: Artificial Sequence
<220> FEATURE:
<223> OTHER INFORMATION: RNAi molecule

<400> SEQUENCE: 442
cacugucauu aucacgaucu cgucucu 27

<210> SEQ ID NO 443
<211> LENGTH: 27
<212> TYPE: RNA
<213> ORGANISM: Artificial Sequence
<220> FEATURE:
<223> OTHER INFORMATION: RNAi molecule

<400> SEQUENCE: 443
aauucaacca agauccugcc ucuguag 27

<210> SEQ ID NO 444

<211> LENGTH: 27
<212> TYPE: RNA
<213> ORGANISM: Artificial Sequence
<220> FEATURE:
<223> OTHER INFORMATION: RNAi molecule

<400> SEQUENCE: 444
uagagaggug uagauauguu guuccaa 27

<210> SEQ ID NO 445
<211> LENGTH: 27
<212> TYPE: RNA
<213> ORGANISM: Artificial Sequence
<220> FEATURE:
<223> OTHER INFORMATION: RNAi molecule

<400> SEQUENCE: 445
uuagagaggu guagauaugu uguucca 27

<210> SEQ ID NO 446
<211> LENGTH: 27
<212> TYPE: RNA
<213> ORGANISM: Artificial Sequence
<220> FEATURE:
<223> OTHER INFORMATION: RNAi molecule

<400> SEQUENCE: 446
cacuugccaa gagaucguug uaacauu 27

<210> SEQ ID NO 447
<211> LENGTH: 27
<212> TYPE: RNA
<213> ORGANISM: Artificial Sequence
<220> FEATURE:
<223> OTHER INFORMATION: RNAi molecule

<400> SEQUENCE: 447
cugaucauac acgagccacu gcugauu 27

<210> SEQ ID NO 448
<211> LENGTH: 27
<212> TYPE: RNA
<213> ORGANISM: Artificial Sequence
<220> FEATURE:
<223> OTHER INFORMATION: RNAi molecule

<400> SEQUENCE: 448
uugaagauaa ccuucugauu caggcuu 27

<210> SEQ ID NO 449
<211> LENGTH: 27
<212> TYPE: RNA
<213> ORGANISM: Artificial Sequence
<220> FEATURE:
<223> OTHER INFORMATION: RNAi molecule

<400> SEQUENCE: 449
uuacaagcaa uugaugcugc acauguu 27

<210> SEQ ID NO 450
<211> LENGTH: 27
<212> TYPE: RNA
<213> ORGANISM: Artificial Sequence
<220> FEATURE:
<223> OTHER INFORMATION: RNAi molecule

<400> SEQUENCE: 450
ggagcuccuu aagaauuaca agcaauu 27

<210> SEQ ID NO 451
<211> LENGTH: 27
<212> TYPE: RNA
<213> ORGANISM: Artificial Sequence
<220> FEATURE:
<223> OTHER INFORMATION: RNAi molecule

<400> SEQUENCE: 451
cggaucucuu cuucucuucu ucaaguu 27

<210> SEQ ID NO 452
<211> LENGTH: 27
<212> TYPE: RNA
<213> ORGANISM: Artificial Sequence
<220> FEATURE:
<223> OTHER INFORMATION: RNAi molecule

<400> SEQUENCE: 452
cuucucucgu ugucucuucc agcuguu 27

<210> SEQ ID NO 453
<211> LENGTH: 27
<212> TYPE: RNA
<213> ORGANISM: Artificial Sequence
<220> FEATURE:
<223> OTHER INFORMATION: RNAi molecule

<400> SEQUENCE: 453
ucugcuucuc uucuugaaga uaaccuu 27

<210> SEQ ID NO 454
<211> LENGTH: 27
<212> TYPE: RNA
<213> ORGANISM: Artificial Sequence
<220> FEATURE:
<223> OTHER INFORMATION: RNAi molecule

<400> SEQUENCE: 454
gaucauacac gagccacugc ugauuuu 27

<210> SEQ ID NO 455
<211> LENGTH: 27
<212> TYPE: RNA
<213> ORGANISM: Artificial Sequence
<220> FEATURE:
<223> OTHER INFORMATION: RNAi molecule

<400> SEQUENCE: 455
uucgugaggu ugcagcagac aacuguu 27

<210> SEQ ID NO 456
<211> LENGTH: 27
<212> TYPE: RNA
<213> ORGANISM: Artificial Sequence
<220> FEATURE:
<223> OTHER INFORMATION: RNAi molecule

<400> SEQUENCE: 456
gaugcugcac auguugacgg ucgaguu 27

<210> SEQ ID NO 457
<211> LENGTH: 27
<212> TYPE: RNA
<213> ORGANISM: Artificial Sequence
<220> FEATURE:

<223> OTHER INFORMATION: RNAi molecule

<400> SEQUENCE: 457
acuugccaag agaucguugu aacauuu 27

<210> SEQ ID NO 458
<211> LENGTH: 27
<212> TYPE: RNA
<213> ORGANISM: Artificial Sequence
<220> FEATURE:
<223> OTHER INFORMATION: RNAi molecule

<400> SEQUENCE: 458
agauaagagc ucuucggauc ucuucuu 27

<210> SEQ ID NO 459
<211> LENGTH: 27
<212> TYPE: RNA
<213> ORGANISM: Artificial Sequence
<220> FEATURE:
<223> OTHER INFORMATION: RNAi molecule

<400> SEQUENCE: 459
cuaaaguaca ugccugcauc uguuguu 27

<210> SEQ ID NO 460
<211> LENGTH: 27
<212> TYPE: RNA
<213> ORGANISM: Artificial Sequence
<220> FEATURE:
<223> OTHER INFORMATION: RNAi molecule

<400> SEQUENCE: 460
agucuaaagu acaugccugc aucuguu 27

<210> SEQ ID NO 461
<211> LENGTH: 27
<212> TYPE: RNA
<213> ORGANISM: Artificial Sequence
<220> FEATURE:
<223> OTHER INFORMATION: RNAi molecule

<400> SEQUENCE: 461
ugaucauaca cgagccacug cugauuu 27

<210> SEQ ID NO 462
<211> LENGTH: 27
<212> TYPE: RNA
<213> ORGANISM: Artificial Sequence
<220> FEATURE:
<223> OTHER INFORMATION: RNAi molecule

<400> SEQUENCE: 462
cugagauaag agcucuucgg aucucuu 27

<210> SEQ ID NO 463
<211> LENGTH: 27
<212> TYPE: RNA
<213> ORGANISM: Artificial Sequence
<220> FEATURE:
<223> OTHER INFORMATION: RNAi molecule

<400> SEQUENCE: 463
gugagguugc agcagacaac uguuguu 27

<210> SEQ ID NO 464

<211> LENGTH: 27
<212> TYPE: RNA
<213> ORGANISM: Artificial Sequence
<220> FEATURE:
<223> OTHER INFORMATION: RNAi molecule

<400> SEQUENCE: 464
uuauuuauug augaguugaa gcaguuu 27

<210> SEQ ID NO 465
<211> LENGTH: 27
<212> TYPE: RNA
<213> ORGANISM: Artificial Sequence
<220> FEATURE:
<223> OTHER INFORMATION: RNAi molecule

<400> SEQUENCE: 465
auuauuuauu gaugaguuga agcaguu 27

<210> SEQ ID NO 466
<211> LENGTH: 27
<212> TYPE: RNA
<213> ORGANISM: Artificial Sequence
<220> FEATURE:
<223> OTHER INFORMATION: RNAi molecule

<400> SEQUENCE: 466
ucucuucuug aagauaaccu ucugauu 27

<210> SEQ ID NO 467
<211> LENGTH: 27
<212> TYPE: RNA
<213> ORGANISM: Artificial Sequence
<220> FEATURE:
<223> OTHER INFORMATION: RNAi molecule

<400> SEQUENCE: 467
ucaaccucaa gaucuuuuuu ugcacuu 27

<210> SEQ ID NO 468
<211> LENGTH: 27
<212> TYPE: RNA
<213> ORGANISM: Artificial Sequence
<220> FEATURE:
<223> OTHER INFORMATION: RNAi molecule

<400> SEQUENCE: 468
ugucguucaa ccucaagauc uuuuuuu 27

<210> SEQ ID NO 469
<211> LENGTH: 27
<212> TYPE: RNA
<213> ORGANISM: Artificial Sequence
<220> FEATURE:
<223> OTHER INFORMATION: RNAi molecule

<400> SEQUENCE: 469
uugucguuca accucaagau cuuuuuu 27

<210> SEQ ID NO 470
<211> LENGTH: 27
<212> TYPE: RNA
<213> ORGANISM: Artificial Sequence
<220> FEATURE:
<223> OTHER INFORMATION: RNAi molecule

<400> SEQUENCE: 470
uuugucguuc aaccucaaga ucuuuuu 27

<210> SEQ ID NO 471
<211> LENGTH: 27
<212> TYPE: RNA
<213> ORGANISM: Artificial Sequence
<220> FEATURE:
<223> OTHER INFORMATION: RNAi molecule

<400> SEQUENCE: 471
aguacaugcc ugcaucuguu guuccaa 27

<210> SEQ ID NO 472
<211> LENGTH: 27
<212> TYPE: RNA
<213> ORGANISM: Artificial Sequence
<220> FEATURE:
<223> OTHER INFORMATION: RNAi molecule

<400> SEQUENCE: 472
ucggagcucc uuaagaauua caagcaa 27

<210> SEQ ID NO 473
<211> LENGTH: 27
<212> TYPE: RNA
<213> ORGANISM: Artificial Sequence
<220> FEATURE:
<223> OTHER INFORMATION: RNAi molecule

<400> SEQUENCE: 473
gcacuugcca agagaucguu guaacau 27

<210> SEQ ID NO 474
<211> LENGTH: 27
<212> TYPE: RNA
<213> ORGANISM: Artificial Sequence
<220> FEATURE:
<223> OTHER INFORMATION: RNAi molecule

<400> SEQUENCE: 474
ugcacuugcc aagagaucgu uguaaca 27

<210> SEQ ID NO 475
<211> LENGTH: 27
<212> TYPE: RNA
<213> ORGANISM: Artificial Sequence
<220> FEATURE:
<223> OTHER INFORMATION: RNAi molecule

<400> SEQUENCE: 475
uugcacuugc caagagaucg uuguaac 27

<210> SEQ ID NO 476
<211> LENGTH: 27
<212> TYPE: RNA
<213> ORGANISM: Artificial Sequence
<220> FEATURE:
<223> OTHER INFORMATION: RNAi molecule

<400> SEQUENCE: 476
aaguacaugc cugcaucugu uguucca 27

<210> SEQ ID NO 477
<211> LENGTH: 27
<212> TYPE: RNA
<213> ORGANISM: Artificial Sequence
<220> FEATURE:

<223> OTHER INFORMATION: RNAi molecule

<400> SEQUENCE: 477
aagugacuaa uggcucugug auggcaa 27

<210> SEQ ID NO 478
<211> LENGTH: 27
<212> TYPE: RNA
<213> ORGANISM: Artificial Sequence
<220> FEATURE:
<223> OTHER INFORMATION: RNAi molecule

<400> SEQUENCE: 478
guacaugccu gcaucuguug uuccaac 27

<210> SEQ ID NO 479
<211> LENGTH: 27
<212> TYPE: RNA
<213> ORGANISM: Artificial Sequence
<220> FEATURE:
<223> OTHER INFORMATION: RNAi molecule

<400> SEQUENCE: 479
gcugaucaua cacgagccac ugcugau 27

<210> SEQ ID NO 480
<211> LENGTH: 27
<212> TYPE: RNA
<213> ORGANISM: Artificial Sequence
<220> FEATURE:
<223> OTHER INFORMATION: RNAi molecule

<400> SEQUENCE: 480
ugcugaucau acacgagcca cugcuga 27

<210> SEQ ID NO 481
<211> LENGTH: 27
<212> TYPE: RNA
<213> ORGANISM: Artificial Sequence
<220> FEATURE:
<223> OTHER INFORMATION: RNAi molecule

<400> SEQUENCE: 481
uccuuaagaa uuacaagcaa uugaugc 27

<210> SEQ ID NO 482
<211> LENGTH: 27
<212> TYPE: RNA
<213> ORGANISM: Artificial Sequence
<220> FEATURE:
<223> OTHER INFORMATION: RNAi molecule

<400> SEQUENCE: 482
gcuccuuaag aauuacaagc aauugau 27

<210> SEQ ID NO 483
<211> LENGTH: 27
<212> TYPE: RNA
<213> ORGANISM: Artificial Sequence
<220> FEATURE:
<223> OTHER INFORMATION: RNAi molecule

<400> SEQUENCE: 483
agcuccuuaa gaauuacaag caauuga 27

<210> SEQ ID NO 484

<211> LENGTH: 27
<212> TYPE: RNA
<213> ORGANISM: Artificial Sequence
<220> FEATURE:
<223> OTHER INFORMATION: RNAi molecule

<400> SEQUENCE: 484
cuugaagaua accuucugau ucaggcu 27

<210> SEQ ID NO 485
<211> LENGTH: 27
<212> TYPE: RNA
<213> ORGANISM: Artificial Sequence
<220> FEATURE:
<223> OTHER INFORMATION: RNAi molecule

<400> SEQUENCE: 485
ucggaucucu ucuucucuuc uucaagu 27

<210> SEQ ID NO 486
<211> LENGTH: 27
<212> TYPE: RNA
<213> ORGANISM: Artificial Sequence
<220> FEATURE:
<223> OTHER INFORMATION: RNAi molecule

<400> SEQUENCE: 486
uucggaucuc uucuucucuu cuucaag 27

<210> SEQ ID NO 487
<211> LENGTH: 27
<212> TYPE: RNA
<213> ORGANISM: Artificial Sequence
<220> FEATURE:
<223> OTHER INFORMATION: RNAi molecule

<400> SEQUENCE: 487
cuucggaucu cuucuucucu ucuucaa 27

<210> SEQ ID NO 488
<211> LENGTH: 27
<212> TYPE: RNA
<213> ORGANISM: Artificial Sequence
<220> FEATURE:
<223> OTHER INFORMATION: RNAi molecule

<400> SEQUENCE: 488
acaagcaauu gaugcugcac auguuga 27

<210> SEQ ID NO 489
<211> LENGTH: 27
<212> TYPE: RNA
<213> ORGANISM: Artificial Sequence
<220> FEATURE:
<223> OTHER INFORMATION: RNAi molecule

<400> SEQUENCE: 489
uucggagcuc cuuaagaauu acaagca 27

<210> SEQ ID NO 490
<211> LENGTH: 27
<212> TYPE: RNA
<213> ORGANISM: Artificial Sequence
<220> FEATURE:
<223> OTHER INFORMATION: RNAi molecule

<400> SEQUENCE: 490
aagcaaugcg guaguacuau aucuggc 27

<210> SEQ ID NO 491
<211> LENGTH: 27
<212> TYPE: RNA
<213> ORGANISM: Artificial Sequence
<220> FEATURE:
<223> OTHER INFORMATION: RNAi molecule

<400> SEQUENCE: 491
caagcaaugc gguaguacua uaucugg 27

<210> SEQ ID NO 492
<211> LENGTH: 27
<212> TYPE: RNA
<213> ORGANISM: Artificial Sequence
<220> FEATURE:
<223> OTHER INFORMATION: RNAi molecule

<400> SEQUENCE: 492
aagcaauuga ugcugcacau guugacg 27

<210> SEQ ID NO 493
<211> LENGTH: 27
<212> TYPE: RNA
<213> ORGANISM: Artificial Sequence
<220> FEATURE:
<223> OTHER INFORMATION: RNAi molecule

<400> SEQUENCE: 493
caagcaauug augcugcaca uguugac 27

<210> SEQ ID NO 494
<211> LENGTH: 27
<212> TYPE: RNA
<213> ORGANISM: Artificial Sequence
<220> FEATURE:
<223> OTHER INFORMATION: RNAi molecule

<400> SEQUENCE: 494
ucucguuguc ucuuccagcu guucaag 27

<210> SEQ ID NO 495
<211> LENGTH: 27
<212> TYPE: RNA
<213> ORGANISM: Artificial Sequence
<220> FEATURE:
<223> OTHER INFORMATION: RNAi molecule

<400> SEQUENCE: 495
cucucguugu cucuuccagc uguucaa 27

<210> SEQ ID NO 496
<211> LENGTH: 27
<212> TYPE: RNA
<213> ORGANISM: Artificial Sequence
<220> FEATURE:
<223> OTHER INFORMATION: RNAi molecule

<400> SEQUENCE: 496
ucuaagaacc uggaucuccu gacuguu 27

<210> SEQ ID NO 497
<211> LENGTH: 27
<212> TYPE: RNA
<213> ORGANISM: Artificial Sequence
<220> FEATURE:

<223> OTHER INFORMATION: RNAi molecule

<400> SEQUENCE: 497
cuccgcaagc uguauauaga gccaauu 27

<210> SEQ ID NO 498
<211> LENGTH: 27
<212> TYPE: RNA
<213> ORGANISM: Artificial Sequence
<220> FEATURE:
<223> OTHER INFORMATION: RNAi molecule

<400> SEQUENCE: 498
cucuccauca gucaccacaa uggccuu 27

<210> SEQ ID NO 499
<211> LENGTH: 27
<212> TYPE: RNA
<213> ORGANISM: Artificial Sequence
<220> FEATURE:
<223> OTHER INFORMATION: RNAi molecule

<400> SEQUENCE: 499
ucaucauauu cagaaccucu uacucuu 27

<210> SEQ ID NO 500
<211> LENGTH: 27
<212> TYPE: RNA
<213> ORGANISM: Artificial Sequence
<220> FEATURE:
<223> OTHER INFORMATION: RNAi molecule

<400> SEQUENCE: 500
aucaucauug aaugugcaau acugguu 27

<210> SEQ ID NO 501
<211> LENGTH: 27
<212> TYPE: RNA
<213> ORGANISM: Artificial Sequence
<220> FEATURE:
<223> OTHER INFORMATION: RNAi molecule

<400> SEQUENCE: 501
cuugaugaca ucuucuggcc augcauu 27

<210> SEQ ID NO 502
<211> LENGTH: 27
<212> TYPE: RNA
<213> ORGANISM: Artificial Sequence
<220> FEATURE:
<223> OTHER INFORMATION: RNAi molecule

<400> SEQUENCE: 502
ccacauccag aaugacaggc agacauu 27

<210> SEQ ID NO 503
<211> LENGTH: 27
<212> TYPE: RNA
<213> ORGANISM: Artificial Sequence
<220> FEATURE:
<223> OTHER INFORMATION: RNAi molecule

<400> SEQUENCE: 503
ucaccacaau ggccuugaug acaucuu 27

<210> SEQ ID NO 504

<211> LENGTH: 27
<212> TYPE: RNA
<213> ORGANISM: Artificial Sequence
<220> FEATURE:
<223> OTHER INFORMATION: RNAi molecule

<400> SEQUENCE: 504
caugaauguu caauugcugu cucucuu 27

<210> SEQ ID NO 505
<211> LENGTH: 27
<212> TYPE: RNA
<213> ORGANISM: Artificial Sequence
<220> FEATURE:
<223> OTHER INFORMATION: RNAi molecule

<400> SEQUENCE: 505
aaugacaggc agacauucuu gaggauu 27

<210> SEQ ID NO 506
<211> LENGTH: 27
<212> TYPE: RNA
<213> ORGANISM: Artificial Sequence
<220> FEATURE:
<223> OTHER INFORMATION: RNAi molecule

<400> SEQUENCE: 506
guucaggaga cgaaaugcau ucacauu 27

<210> SEQ ID NO 507
<211> LENGTH: 27
<212> TYPE: RNA
<213> ORGANISM: Artificial Sequence
<220> FEATURE:
<223> OTHER INFORMATION: RNAi molecule

<400> SEQUENCE: 507
gccguagucc aauguagagu ggaucuu 27

<210> SEQ ID NO 508
<211> LENGTH: 27
<212> TYPE: RNA
<213> ORGANISM: Artificial Sequence
<220> FEATURE:
<223> OTHER INFORMATION: RNAi molecule

<400> SEQUENCE: 508
agaccugcaa cugcaacaga ugcuguu 27

<210> SEQ ID NO 509
<211> LENGTH: 27
<212> TYPE: RNA
<213> ORGANISM: Artificial Sequence
<220> FEATURE:
<223> OTHER INFORMATION: RNAi molecule

<400> SEQUENCE: 509
guggcaacaa uccaugaaug uucaauu 27

<210> SEQ ID NO 510
<211> LENGTH: 27
<212> TYPE: RNA
<213> ORGANISM: Artificial Sequence
<220> FEATURE:
<223> OTHER INFORMATION: RNAi molecule

<400> SEQUENCE: 510
uccgcaagcu guauauagag ccaauuu 27

<210> SEQ ID NO 511
<211> LENGTH: 27
<212> TYPE: RNA
<213> ORGANISM: Artificial Sequence
<220> FEATURE:
<223> OTHER INFORMATION: RNAi molecule

<400> SEQUENCE: 511
ggaagguggc aacaauccau gaauguu 27

<210> SEQ ID NO 512
<211> LENGTH: 27
<212> TYPE: RNA
<213> ORGANISM: Artificial Sequence
<220> FEATURE:
<223> OTHER INFORMATION: RNAi molecule

<400> SEQUENCE: 512
aaaaaaucau cauauucaga accucuu 27

<210> SEQ ID NO 513
<211> LENGTH: 27
<212> TYPE: RNA
<213> ORGANISM: Artificial Sequence
<220> FEATURE:
<223> OTHER INFORMATION: RNAi molecule

<400> SEQUENCE: 513
ugaauucguc caaaaaauca ucauauu 27

<210> SEQ ID NO 514
<211> LENGTH: 27
<212> TYPE: RNA
<213> ORGANISM: Artificial Sequence
<220> FEATURE:
<223> OTHER INFORMATION: RNAi molecule

<400> SEQUENCE: 514
ucuuuaagua acuccucauu uucgguu 27

<210> SEQ ID NO 515
<211> LENGTH: 27
<212> TYPE: RNA
<213> ORGANISM: Artificial Sequence
<220> FEATURE:
<223> OTHER INFORMATION: RNAi molecule

<400> SEQUENCE: 515
guggaucuuu aaguaacucc ucauuuu 27

<210> SEQ ID NO 516
<211> LENGTH: 27
<212> TYPE: RNA
<213> ORGANISM: Artificial Sequence
<220> FEATURE:
<223> OTHER INFORMATION: RNAi molecule

<400> SEQUENCE: 516
aguggaucuu uaaguaacuc cucauuu 27

<210> SEQ ID NO 517
<211> LENGTH: 27
<212> TYPE: RNA
<213> ORGANISM: Artificial Sequence
<220> FEATURE:

<223> OTHER INFORMATION: RNAi molecule

<400> SEQUENCE: 517
ucaucauuga augugcaaua cugguuu 27

<210> SEQ ID NO 518
<211> LENGTH: 27
<212> TYPE: RNA
<213> ORGANISM: Artificial Sequence
<220> FEATURE:
<223> OTHER INFORMATION: RNAi molecule

<400> SEQUENCE: 518
cugaauaagg caauucaugc cauacuu 27

<210> SEQ ID NO 519
<211> LENGTH: 27
<212> TYPE: RNA
<213> ORGANISM: Artificial Sequence
<220> FEATURE:
<223> OTHER INFORMATION: RNAi molecule

<400> SEQUENCE: 519
gagaagauac cugucaaagu cagaguu 27

<210> SEQ ID NO 520
<211> LENGTH: 27
<212> TYPE: RNA
<213> ORGANISM: Artificial Sequence
<220> FEATURE:
<223> OTHER INFORMATION: RNAi molecule

<400> SEQUENCE: 520
cauccagaau gacaggcaga cauucuu 27

<210> SEQ ID NO 521
<211> LENGTH: 27
<212> TYPE: RNA
<213> ORGANISM: Artificial Sequence
<220> FEATURE:
<223> OTHER INFORMATION: RNAi molecule

<400> SEQUENCE: 521
aagaaccugg aucuccugac uguugaa 27

<210> SEQ ID NO 522
<211> LENGTH: 27
<212> TYPE: RNA
<213> ORGANISM: Artificial Sequence
<220> FEATURE:
<223> OTHER INFORMATION: RNAi molecule

<400> SEQUENCE: 522
uaagaaccug gaucuccuga cuguuga 27

<210> SEQ ID NO 523
<211> LENGTH: 27
<212> TYPE: RNA
<213> ORGANISM: Artificial Sequence
<220> FEATURE:
<223> OTHER INFORMATION: RNAi molecule

<400> SEQUENCE: 523
cucuaagaac cuggaucucc ugacugu 27

<210> SEQ ID NO 524

<211> LENGTH: 27
<212> TYPE: RNA
<213> ORGANISM: Artificial Sequence
<220> FEATURE:
<223> OTHER INFORMATION: RNAi molecule

<400> SEQUENCE: 524
agauccauua agagaagaua ccuguca 27

<210> SEQ ID NO 525
<211> LENGTH: 27
<212> TYPE: RNA
<213> ORGANISM: Artificial Sequence
<220> FEATURE:
<223> OTHER INFORMATION: RNAi molecule

<400> SEQUENCE: 525
ucaaugucag augucagcac ucuauaa 27

<210> SEQ ID NO 526
<211> LENGTH: 27
<212> TYPE: RNA
<213> ORGANISM: Artificial Sequence
<220> FEATURE:
<223> OTHER INFORMATION: RNAi molecule

<400> SEQUENCE: 526
uuacuacucu aagaaccugg aucuccu 27

<210> SEQ ID NO 527
<211> LENGTH: 27
<212> TYPE: RNA
<213> ORGANISM: Artificial Sequence
<220> FEATURE:
<223> OTHER INFORMATION: RNAi molecule

<400> SEQUENCE: 527
ucucaauguc agaugucagc acucuau 27

<210> SEQ ID NO 528
<211> LENGTH: 27
<212> TYPE: RNA
<213> ORGANISM: Artificial Sequence
<220> FEATURE:
<223> OTHER INFORMATION: RNAi molecule

<400> SEQUENCE: 528
augcauugag aacugaagca auaugcc 27

<210> SEQ ID NO 529
<211> LENGTH: 27
<212> TYPE: RNA
<213> ORGANISM: Artificial Sequence
<220> FEATURE:
<223> OTHER INFORMATION: RNAi molecule

<400> SEQUENCE: 529
uauucagaac cucuuacucu ucucugc 27

<210> SEQ ID NO 530
<211> LENGTH: 27
<212> TYPE: RNA
<213> ORGANISM: Artificial Sequence
<220> FEATURE:
<223> OTHER INFORMATION: RNAi molecule

<400> SEQUENCE: 530
uacucuaaga accuggaucu ccugacu 27

<210> SEQ ID NO 531
<211> LENGTH: 27
<212> TYPE: RNA
<213> ORGANISM: Artificial Sequence
<220> FEATURE:
<223> OTHER INFORMATION: RNAi molecule

<400> SEQUENCE: 531
aauacgcucu ccaucaguca ccacaau 27

<210> SEQ ID NO 532
<211> LENGTH: 27
<212> TYPE: RNA
<213> ORGANISM: Artificial Sequence
<220> FEATURE:
<223> OTHER INFORMATION: RNAi molecule

<400> SEQUENCE: 532
auucagaacc ucuuacucuu cucugcc 27

<210> SEQ ID NO 533
<211> LENGTH: 27
<212> TYPE: RNA
<213> ORGANISM: Artificial Sequence
<220> FEATURE:
<223> OTHER INFORMATION: RNAi molecule

<400> SEQUENCE: 533
cuacucuaag aaccuggauc uccugac 27

<210> SEQ ID NO 534
<211> LENGTH: 27
<212> TYPE: RNA
<213> ORGANISM: Artificial Sequence
<220> FEATURE:
<223> OTHER INFORMATION: RNAi molecule

<400> SEQUENCE: 534
ucuggccaug cauugagaac ugaagca 27

<210> SEQ ID NO 535
<211> LENGTH: 27
<212> TYPE: RNA
<213> ORGANISM: Artificial Sequence
<220> FEATURE:
<223> OTHER INFORMATION: RNAi molecule

<400> SEQUENCE: 535
gaauacgcuc uccaucaguc accacaa 27

<210> SEQ ID NO 536
<211> LENGTH: 27
<212> TYPE: RNA
<213> ORGANISM: Artificial Sequence
<220> FEATURE:
<223> OTHER INFORMATION: RNAi molecule

<400> SEQUENCE: 536
ccuccgcaag cuguauauag agccaau 27

<210> SEQ ID NO 537
<211> LENGTH: 27
<212> TYPE: RNA
<213> ORGANISM: Artificial Sequence
<220> FEATURE:

<223> OTHER INFORMATION: RNAi molecule

<400> SEQUENCE: 537
acucuucucu gccguagucc aauguag 27

<210> SEQ ID NO 538
<211> LENGTH: 27
<212> TYPE: RNA
<213> ORGANISM: Artificial Sequence
<220> FEATURE:
<223> OTHER INFORMATION: RNAi molecule

<400> SEQUENCE: 538
aucauauuca gaaccucuua cucuucu 27

<210> SEQ ID NO 539
<211> LENGTH: 27
<212> TYPE: RNA
<213> ORGANISM: Artificial Sequence
<220> FEATURE:
<223> OTHER INFORMATION: RNAi molecule

<400> SEQUENCE: 539
uaucaucauu gaaugugcaa uacuggu 27

<210> SEQ ID NO 540
<211> LENGTH: 27
<212> TYPE: RNA
<213> ORGANISM: Artificial Sequence
<220> FEATURE:
<223> OTHER INFORMATION: RNAi molecule

<400> SEQUENCE: 540
auaucaucau ugaaugugca auacugg 27

<210> SEQ ID NO 541
<211> LENGTH: 27
<212> TYPE: RNA
<213> ORGANISM: Artificial Sequence
<220> FEATURE:
<223> OTHER INFORMATION: RNAi molecule

<400> SEQUENCE: 541
uccuugaaua ucaucauuga augugca 27

<210> SEQ ID NO 542
<211> LENGTH: 27
<212> TYPE: RNA
<213> ORGANISM: Artificial Sequence
<220> FEATURE:
<223> OTHER INFORMATION: RNAi molecule

<400> SEQUENCE: 542
uuccuugaau aucaucauug aaugugc 27

<210> SEQ ID NO 543
<211> LENGTH: 27
<212> TYPE: RNA
<213> ORGANISM: Artificial Sequence
<220> FEATURE:
<223> OTHER INFORMATION: RNAi molecule

<400> SEQUENCE: 543
gauccauuaa gagaagauac cugucaa 27

<210> SEQ ID NO 544

<211> LENGTH: 27
<212> TYPE: RNA
<213> ORGANISM: Artificial Sequence
<220> FEATURE:
<223> OTHER INFORMATION: RNAi molecule

<400> SEQUENCE: 544
aauguucaau ugcugucucu cuuccag 27

<210> SEQ ID NO 545
<211> LENGTH: 27
<212> TYPE: RNA
<213> ORGANISM: Artificial Sequence
<220> FEATURE:
<223> OTHER INFORMATION: RNAi molecule

<400> SEQUENCE: 545
gaauguucaa uugcugucuc ucuucca 27

<210> SEQ ID NO 546
<211> LENGTH: 27
<212> TYPE: RNA
<213> ORGANISM: Artificial Sequence
<220> FEATURE:
<223> OTHER INFORMATION: RNAi molecule

<400> SEQUENCE: 546
agagaacucc acggugaacu cugacuu 27

<210> SEQ ID NO 547
<211> LENGTH: 27
<212> TYPE: RNA
<213> ORGANISM: Artificial Sequence
<220> FEATURE:
<223> OTHER INFORMATION: RNAi molecule

<400> SEQUENCE: 547
gacaucugug augaugaugg ccaaguu 27

<210> SEQ ID NO 548
<211> LENGTH: 27
<212> TYPE: RNA
<213> ORGANISM: Artificial Sequence
<220> FEATURE:
<223> OTHER INFORMATION: RNAi molecule

<400> SEQUENCE: 548
guagauguug gugcuguaag gcagguu 27

<210> SEQ ID NO 549
<211> LENGTH: 27
<212> TYPE: RNA
<213> ORGANISM: Artificial Sequence
<220> FEATURE:
<223> OTHER INFORMATION: RNAi molecule

<400> SEQUENCE: 549
ccuggucuug ucuugaucug uggcguu 27

<210> SEQ ID NO 550
<211> LENGTH: 27
<212> TYPE: RNA
<213> ORGANISM: Artificial Sequence
<220> FEATURE:
<223> OTHER INFORMATION: RNAi molecule

<400> SEQUENCE: 550
cagcagguau guaucaaaga agugguu 27

<210> SEQ ID NO 551
<211> LENGTH: 27
<212> TYPE: RNA
<213> ORGANISM: Artificial Sequence
<220> FEATURE:
<223> OTHER INFORMATION: RNAi molecule

<400> SEQUENCE: 551
agaaugcucg uagauguugg ugcugua 27

<210> SEQ ID NO 552
<211> LENGTH: 27
<212> TYPE: RNA
<213> ORGANISM: Artificial Sequence
<220> FEATURE:
<223> OTHER INFORMATION: RNAi molecule

<400> SEQUENCE: 552
aacuccacgg ugaacucuga cuugguc 27

<210> SEQ ID NO 553
<211> LENGTH: 27
<212> TYPE: RNA
<213> ORGANISM: Artificial Sequence
<220> FEATURE:
<223> OTHER INFORMATION: RNAi molecule

<400> SEQUENCE: 553
gagaacucca cggugaacuc ugacuug 27

<210> SEQ ID NO 554
<211> LENGTH: 27
<212> TYPE: RNA
<213> ORGANISM: Artificial Sequence
<220> FEATURE:
<223> OTHER INFORMATION: RNAi molecule

<400> SEQUENCE: 554
uugucuugau cuguggcguu gaccgug 27

<210> SEQ ID NO 555
<211> LENGTH: 27
<212> TYPE: RNA
<213> ORGANISM: Artificial Sequence
<220> FEATURE:
<223> OTHER INFORMATION: RNAi molecule

<400> SEQUENCE: 555
ggaggagaau gcucguagau guuggug 27

<210> SEQ ID NO 556
<211> LENGTH: 27
<212> TYPE: RNA
<213> ORGANISM: Artificial Sequence
<220> FEATURE:
<223> OTHER INFORMATION: RNAi molecule

<400> SEQUENCE: 556
cuggucuugu cuugaucugu ggcguug 27

<210> SEQ ID NO 557
<211> LENGTH: 27
<212> TYPE: RNA
<213> ORGANISM: Artificial Sequence
<220> FEATURE:

<223> OTHER INFORMATION: RNAi molecule

<400> SEQUENCE: 557
ggagaaugcu cguagauguu ggugcug 27

<210> SEQ ID NO 558
<211> LENGTH: 27
<212> TYPE: RNA
<213> ORGANISM: Artificial Sequence
<220> FEATURE:
<223> OTHER INFORMATION: RNAi molecule

<400> SEQUENCE: 558
uccauguccu ggacaucugu gaugaug 27

<210> SEQ ID NO 559
<211> LENGTH: 27
<212> TYPE: RNA
<213> ORGANISM: Artificial Sequence
<220> FEATURE:
<223> OTHER INFORMATION: RNAi molecule

<400> SEQUENCE: 559
auucaagguc agcacuccgc ugaugua 27

<210> SEQ ID NO 560
<211> LENGTH: 27
<212> TYPE: RNA
<213> ORGANISM: Artificial Sequence
<220> FEATURE:
<223> OTHER INFORMATION: RNAi molecule

<400> SEQUENCE: 560
guccucgcug aucagcaggu auguauc 27

<210> SEQ ID NO 561
<211> LENGTH: 27
<212> TYPE: RNA
<213> ORGANISM: Artificial Sequence
<220> FEATURE:
<223> OTHER INFORMATION: RNAi molecule

<400> SEQUENCE: 561
guguccucgc ugaucagcag guaugua 27

<210> SEQ ID NO 562
<211> LENGTH: 27
<212> TYPE: RNA
<213> ORGANISM: Artificial Sequence
<220> FEATURE:
<223> OTHER INFORMATION: RNAi molecule

<400> SEQUENCE: 562
uucacaguca ggaugaagcc auggcug 27

<210> SEQ ID NO 563
<211> LENGTH: 27
<212> TYPE: RNA
<213> ORGANISM: Artificial Sequence
<220> FEATURE:
<223> OTHER INFORMATION: RNAi molecule

<400> SEQUENCE: 563
acaucuguga ugaugauggc caaguug 27

<210> SEQ ID NO 564

<211> LENGTH: 27
<212> TYPE: RNA
<213> ORGANISM: Artificial Sequence
<220> FEATURE:
<223> OTHER INFORMATION: RNAi molecule

<400> SEQUENCE: 564
auguccugga caucugugau gaugaug 27

<210> SEQ ID NO 565
<211> LENGTH: 27
<212> TYPE: RNA
<213> ORGANISM: Artificial Sequence
<220> FEATURE:
<223> OTHER INFORMATION: RNAi molecule

<400> SEQUENCE: 565
gugcuguaag gcagguugau gaagaug 27

<210> SEQ ID NO 566
<211> LENGTH: 27
<212> TYPE: RNA
<213> ORGANISM: Artificial Sequence
<220> FEATURE:
<223> OTHER INFORMATION: RNAi molecule

<400> SEQUENCE: 566
auguuggugc uguaaggcag guugaug 27

<210> SEQ ID NO 567
<211> LENGTH: 27
<212> TYPE: RNA
<213> ORGANISM: Artificial Sequence
<220> FEATURE:
<223> OTHER INFORMATION: RNAi molecule

<400> SEQUENCE: 567
uagauguugg ugcuguaagg cagguug 27

<210> SEQ ID NO 568
<211> LENGTH: 27
<212> TYPE: RNA
<213> ORGANISM: Artificial Sequence
<220> FEATURE:
<223> OTHER INFORMATION: RNAi molecule

<400> SEQUENCE: 568
ugacagagaa cuccacggug aacucug 27

<210> SEQ ID NO 569
<211> LENGTH: 27
<212> TYPE: RNA
<213> ORGANISM: Artificial Sequence
<220> FEATURE:
<223> OTHER INFORMATION: RNAi molecule

<400> SEQUENCE: 569
accuggaugu ucaccuuccg ugugauc 27

<210> SEQ ID NO 570
<211> LENGTH: 27
<212> TYPE: RNA
<213> ORGANISM: Artificial Sequence
<220> FEATURE:
<223> OTHER INFORMATION: RNAi molecule

<400> SEQUENCE: 570
cacagucagg augaagccau ggcugua 27

<210> SEQ ID NO 571
<211> LENGTH: 27
<212> TYPE: RNA
<213> ORGANISM: Artificial Sequence
<220> FEATURE:
<223> OTHER INFORMATION: RNAi molecule

<400> SEQUENCE: 571
agaacuccac ggugaacucu gacuugg 27

<210> SEQ ID NO 572
<211> LENGTH: 27
<212> TYPE: RNA
<213> ORGANISM: Artificial Sequence
<220> FEATURE:
<223> OTHER INFORMATION: RNAi molecule

<400> SEQUENCE: 572
aaugcucgua gauguuggug cuguaag 27

<210> SEQ ID NO 573
<211> LENGTH: 27
<212> TYPE: RNA
<213> ORGANISM: Artificial Sequence
<220> FEATURE:
<223> OTHER INFORMATION: RNAi molecule

<400> SEQUENCE: 573
gaaugcucgu agauguuggu gcuguaa 27

<210> SEQ ID NO 574
<211> LENGTH: 27
<212> TYPE: RNA
<213> ORGANISM: Artificial Sequence
<220> FEATURE:
<223> OTHER INFORMATION: RNAi molecule

<400> SEQUENCE: 574
augcucguag auguuggugc uguaagg 27

<210> SEQ ID NO 575
<211> LENGTH: 27
<212> TYPE: RNA
<213> ORGANISM: Artificial Sequence
<220> FEATURE:
<223> OTHER INFORMATION: RNAi molecule

<400> SEQUENCE: 575
gaacuccacg gugaacucug acuuggu 27

<210> SEQ ID NO 576
<211> LENGTH: 27
<212> TYPE: RNA
<213> ORGANISM: Artificial Sequence
<220> FEATURE:
<223> OTHER INFORMATION: RNAi molecule

<400> SEQUENCE: 576
ugucuugauc uguggcguug accguga 27

<210> SEQ ID NO 577
<211> LENGTH: 27
<212> TYPE: RNA
<213> ORGANISM: Artificial Sequence
<220> FEATURE:

<223> OTHER INFORMATION: RNAi molecule

<400> SEQUENCE: 577
cuugucuuga ucuguggcgu ugaccgu 27

<210> SEQ ID NO 578
<211> LENGTH: 27
<212> TYPE: RNA
<213> ORGANISM: Artificial Sequence
<220> FEATURE:
<223> OTHER INFORMATION: RNAi molecule

<400> SEQUENCE: 578
ucuugucuug aucuguggcg uugaccg 27

<210> SEQ ID NO 579
<211> LENGTH: 27
<212> TYPE: RNA
<213> ORGANISM: Artificial Sequence
<220> FEATURE:
<223> OTHER INFORMATION: RNAi molecule

<400> SEQUENCE: 579
gaggagaaug cucguagaug uuggugc 27

<210> SEQ ID NO 580
<211> LENGTH: 27
<212> TYPE: RNA
<213> ORGANISM: Artificial Sequence
<220> FEATURE:
<223> OTHER INFORMATION: RNAi molecule

<400> SEQUENCE: 580
cggaggagaa ugcucguaga uguuggu 27

<210> SEQ ID NO 581
<211> LENGTH: 27
<212> TYPE: RNA
<213> ORGANISM: Artificial Sequence
<220> FEATURE:
<223> OTHER INFORMATION: RNAi molecule

<400> SEQUENCE: 581
gagaaugcuc guagauguug gugcugu 27

<210> SEQ ID NO 582
<211> LENGTH: 27
<212> TYPE: RNA
<213> ORGANISM: Artificial Sequence
<220> FEATURE:
<223> OTHER INFORMATION: RNAi molecule

<400> SEQUENCE: 582
aggagaaugc ucguagaugu uggugcu 27

<210> SEQ ID NO 583
<211> LENGTH: 27
<212> TYPE: RNA
<213> ORGANISM: Artificial Sequence
<220> FEATURE:
<223> OTHER INFORMATION: RNAi molecule

<400> SEQUENCE: 583
ggucuugucu ugaucugugg cguugac 27

<210> SEQ ID NO 584

<211> LENGTH: 27
<212> TYPE: RNA
<213> ORGANISM: Artificial Sequence
<220> FEATURE:
<223> OTHER INFORMATION: RNAi molecule

<400> SEQUENCE: 584
ugcucguaga uguuggugcu guaaggc 27

<210> SEQ ID NO 585
<211> LENGTH: 27
<212> TYPE: RNA
<213> ORGANISM: Artificial Sequence
<220> FEATURE:
<223> OTHER INFORMATION: RNAi molecule

<400> SEQUENCE: 585
cauguccugg acaucuguga ugaugau 27

<210> SEQ ID NO 586
<211> LENGTH: 27
<212> TYPE: RNA
<213> ORGANISM: Artificial Sequence
<220> FEATURE:
<223> OTHER INFORMATION: RNAi molecule

<400> SEQUENCE: 586
ccucgcugau cagcagguau guaucaa 27

<210> SEQ ID NO 587
<211> LENGTH: 27
<212> TYPE: RNA
<213> ORGANISM: Artificial Sequence
<220> FEATURE:
<223> OTHER INFORMATION: RNAi molecule

<400> SEQUENCE: 587
uccucgcuga ucagcaggua uguauca 27

<210> SEQ ID NO 588
<211> LENGTH: 27
<212> TYPE: RNA
<213> ORGANISM: Artificial Sequence
<220> FEATURE:
<223> OTHER INFORMATION: RNAi molecule

<400> SEQUENCE: 588
uguccucgcu gaucagcagg uauguau 27

<210> SEQ ID NO 589
<211> LENGTH: 27
<212> TYPE: RNA
<213> ORGANISM: Artificial Sequence
<220> FEATURE:
<223> OTHER INFORMATION: RNAi molecule

<400> SEQUENCE: 589
aacucugacu uggucucucu guccagu 27

<210> SEQ ID NO 590
<211> LENGTH: 27
<212> TYPE: RNA
<213> ORGANISM: Artificial Sequence
<220> FEATURE:
<223> OTHER INFORMATION: RNAi molecule

<400> SEQUENCE: 590

```
uggucuuguc uugaucugug gcguuga                                              27

<210> SEQ ID NO 591
<211> LENGTH: 27
<212> TYPE: RNA
<213> ORGANISM: Artificial Sequence
<220> FEATURE:
<223> OTHER INFORMATION: RNAi molecule

<400> SEQUENCE: 591

cuggacaucu gugaugauga uggccaa                                              27

<210> SEQ ID NO 592
<211> LENGTH: 27
<212> TYPE: RNA
<213> ORGANISM: Artificial Sequence
<220> FEATURE:
<223> OTHER INFORMATION: RNAi molecule

<400> SEQUENCE: 592

ccauguccug gacaucugug augauga                                              27

<210> SEQ ID NO 593
<211> LENGTH: 27
<212> TYPE: RNA
<213> ORGANISM: Artificial Sequence
<220> FEATURE:
<223> OTHER INFORMATION: RNAi molecule

<400> SEQUENCE: 593

guccaugucc uggacaucug ugaugau                                              27

<210> SEQ ID NO 594
<211> LENGTH: 27
<212> TYPE: RNA
<213> ORGANISM: Artificial Sequence
<220> FEATURE:
<223> OTHER INFORMATION: RNAi molecule

<400> SEQUENCE: 594

gaacucugac uuggucucuc uguccag                                              27

<210> SEQ ID NO 595
<211> LENGTH: 27
<212> TYPE: RNA
<213> ORGANISM: Artificial Sequence
<220> FEATURE:
<223> OTHER INFORMATION: RNAi molecule

<400> SEQUENCE: 595

acuccacggu gaacucugac uuggucu                                              27

<210> SEQ ID NO 596
<211> LENGTH: 27
<212> TYPE: RNA
<213> ORGANISM: Artificial Sequence
<220> FEATURE:
<223> OTHER INFORMATION: RNAi molecule

<400> SEQUENCE: 596

uguguuagaa cuccucuugc cuauguu                                              27

<210> SEQ ID NO 597
<211> LENGTH: 27
<212> TYPE: RNA
<213> ORGANISM: Artificial Sequence
<220> FEATURE:
```

<223> OTHER INFORMATION: RNAi molecule

<400> SEQUENCE: 597
uguacgaaau guguuagaac uccucuu 27

<210> SEQ ID NO 598
<211> LENGTH: 27
<212> TYPE: RNA
<213> ORGANISM: Artificial Sequence
<220> FEATURE:
<223> OTHER INFORMATION: RNAi molecule

<400> SEQUENCE: 598
caugguuccu gccaagcacc auuccuu 27

<210> SEQ ID NO 599
<211> LENGTH: 27
<212> TYPE: RNA
<213> ORGANISM: Artificial Sequence
<220> FEATURE:
<223> OTHER INFORMATION: RNAi molecule

<400> SEQUENCE: 599
ucacacauaa uugugcugag uggaguu 27

<210> SEQ ID NO 600
<211> LENGTH: 27
<212> TYPE: RNA
<213> ORGANISM: Artificial Sequence
<220> FEATURE:
<223> OTHER INFORMATION: RNAi molecule

<400> SEQUENCE: 600
gaaccaaagu auaaaaggau ucuacuu 27

<210> SEQ ID NO 601
<211> LENGTH: 27
<212> TYPE: RNA
<213> ORGANISM: Artificial Sequence
<220> FEATURE:
<223> OTHER INFORMATION: RNAi molecule

<400> SEQUENCE: 601
uacaauuuuu cagcuucaca cauaauu 27

<210> SEQ ID NO 602
<211> LENGTH: 27
<212> TYPE: RNA
<213> ORGANISM: Artificial Sequence
<220> FEATURE:
<223> OTHER INFORMATION: RNAi molecule

<400> SEQUENCE: 602
aaaaaggaac caaaguauaa aaggauu 27

<210> SEQ ID NO 603
<211> LENGTH: 27
<212> TYPE: RNA
<213> ORGANISM: Artificial Sequence
<220> FEATURE:
<223> OTHER INFORMATION: RNAi molecule

<400> SEQUENCE: 603
guguuagaac uccucuugcc uauguua 27

<210> SEQ ID NO 604

<211> LENGTH: 27
<212> TYPE: RNA
<213> ORGANISM: Artificial Sequence
<220> FEATURE:
<223> OTHER INFORMATION: RNAi molecule

<400> SEQUENCE: 604
aauguguuag aacuccucuu gccuaug 27

<210> SEQ ID NO 605
<211> LENGTH: 27
<212> TYPE: RNA
<213> ORGANISM: Artificial Sequence
<220> FEATURE:
<223> OTHER INFORMATION: RNAi molecule

<400> SEQUENCE: 605
gaaauguguu agaacuccuc uugccua 27

<210> SEQ ID NO 606
<211> LENGTH: 27
<212> TYPE: RNA
<213> ORGANISM: Artificial Sequence
<220> FEATURE:
<223> OTHER INFORMATION: RNAi molecule

<400> SEQUENCE: 606
acugguucug cagcucugga auggaug 27

<210> SEQ ID NO 607
<211> LENGTH: 27
<212> TYPE: RNA
<213> ORGANISM: Artificial Sequence
<220> FEATURE:
<223> OTHER INFORMATION: RNAi molecule

<400> SEQUENCE: 607
guacgaaaug uguuagaacu ccucuug 27

<210> SEQ ID NO 608
<211> LENGTH: 27
<212> TYPE: RNA
<213> ORGANISM: Artificial Sequence
<220> FEATURE:
<223> OTHER INFORMATION: RNAi molecule

<400> SEQUENCE: 608
augguuccug ccaagcacca uuccuuc 27

<210> SEQ ID NO 609
<211> LENGTH: 27
<212> TYPE: RNA
<213> ORGANISM: Artificial Sequence
<220> FEATURE:
<223> OTHER INFORMATION: RNAi molecule

<400> SEQUENCE: 609
ccaaaguaua aaaggauucu acuucua 27

<210> SEQ ID NO 610
<211> LENGTH: 27
<212> TYPE: RNA
<213> ORGANISM: Artificial Sequence
<220> FEATURE:
<223> OTHER INFORMATION: RNAi molecule

<400> SEQUENCE: 610
aaccaaagua uaaaaggauu cuacuuc 27

<210> SEQ ID NO 611
<211> LENGTH: 27
<212> TYPE: RNA
<213> ORGANISM: Artificial Sequence
<220> FEATURE:
<223> OTHER INFORMATION: RNAi molecule

<400> SEQUENCE: 611
agaacuccuc uugccuaugu uaaaaug 27

<210> SEQ ID NO 612
<211> LENGTH: 27
<212> TYPE: RNA
<213> ORGANISM: Artificial Sequence
<220> FEATURE:
<223> OTHER INFORMATION: RNAi molecule

<400> SEQUENCE: 612
cagcuucaca cauaauugug cugagug 27

<210> SEQ ID NO 613
<211> LENGTH: 27
<212> TYPE: RNA
<213> ORGANISM: Artificial Sequence
<220> FEATURE:
<223> OTHER INFORMATION: RNAi molecule

<400> SEQUENCE: 613
ugguucugca gcucuggaau ggaugug 27

<210> SEQ ID NO 614
<211> LENGTH: 27
<212> TYPE: RNA
<213> ORGANISM: Artificial Sequence
<220> FEATURE:
<223> OTHER INFORMATION: RNAi molecule

<400> SEQUENCE: 614
cucuacaauu uuucagcuuc acacaua 27

<210> SEQ ID NO 615
<211> LENGTH: 27
<212> TYPE: RNA
<213> ORGANISM: Artificial Sequence
<220> FEATURE:
<223> OTHER INFORMATION: RNAi molecule

<400> SEQUENCE: 615
ccucuugccu auguuaaaau gugaaug 27

<210> SEQ ID NO 616
<211> LENGTH: 27
<212> TYPE: RNA
<213> ORGANISM: Artificial Sequence
<220> FEATURE:
<223> OTHER INFORMATION: RNAi molecule

<400> SEQUENCE: 616
aacuccucuu gccuauguua aaaugug 27

<210> SEQ ID NO 617
<211> LENGTH: 27
<212> TYPE: RNA
<213> ORGANISM: Artificial Sequence
<220> FEATURE:

<223> OTHER INFORMATION: RNAi molecule

<400> SEQUENCE: 617
cacagaaucu ugcagaggcc uccagug 27

<210> SEQ ID NO 618
<211> LENGTH: 27
<212> TYPE: RNA
<213> ORGANISM: Artificial Sequence
<220> FEATURE:
<223> OTHER INFORMATION: RNAi molecule

<400> SEQUENCE: 618
aauuuuucag cuucacacau aauugug 27

<210> SEQ ID NO 619
<211> LENGTH: 27
<212> TYPE: RNA
<213> ORGANISM: Artificial Sequence
<220> FEATURE:
<223> OTHER INFORMATION: RNAi molecule

<400> SEQUENCE: 619
acaauuuuuc agcuucacac auaauug 27

<210> SEQ ID NO 620
<211> LENGTH: 27
<212> TYPE: RNA
<213> ORGANISM: Artificial Sequence
<220> FEATURE:
<223> OTHER INFORMATION: RNAi molecule

<400> SEQUENCE: 620
aaaaggaacc aaaguauaaa aggauuc 27

<210> SEQ ID NO 621
<211> LENGTH: 27
<212> TYPE: RNA
<213> ORGANISM: Artificial Sequence
<220> FEATURE:
<223> OTHER INFORMATION: RNAi molecule

<400> SEQUENCE: 621
auguguuaga acuccucuug ccuaugu 27

<210> SEQ ID NO 622
<211> LENGTH: 27
<212> TYPE: RNA
<213> ORGANISM: Artificial Sequence
<220> FEATURE:
<223> OTHER INFORMATION: RNAi molecule

<400> SEQUENCE: 622
ccugaaucag uuagagcucc acgaagg 27

<210> SEQ ID NO 623
<211> LENGTH: 27
<212> TYPE: RNA
<213> ORGANISM: Artificial Sequence
<220> FEATURE:
<223> OTHER INFORMATION: RNAi molecule

<400> SEQUENCE: 623
uguuagaacu ccucuugccu auguuaa 27

<210> SEQ ID NO 624

<211> LENGTH: 27
<212> TYPE: RNA
<213> ORGANISM: Artificial Sequence
<220> FEATURE:
<223> OTHER INFORMATION: RNAi molecule

<400> SEQUENCE: 624
uacgaaaugu guuagaacuc cucuugc 27

<210> SEQ ID NO 625
<211> LENGTH: 27
<212> TYPE: RNA
<213> ORGANISM: Artificial Sequence
<220> FEATURE:
<223> OTHER INFORMATION: RNAi molecule

<400> SEQUENCE: 625
cgaaaugugu uagaacuccu cuugccu 27

<210> SEQ ID NO 626
<211> LENGTH: 27
<212> TYPE: RNA
<213> ORGANISM: Artificial Sequence
<220> FEATURE:
<223> OTHER INFORMATION: RNAi molecule

<400> SEQUENCE: 626
acgaaaugug uuagaacucc ucuugcc 27

<210> SEQ ID NO 627
<211> LENGTH: 27
<212> TYPE: RNA
<213> ORGANISM: Artificial Sequence
<220> FEATURE:
<223> OTHER INFORMATION: RNAi molecule

<400> SEQUENCE: 627
gacugguucu gcagcucugg aauggau 27

<210> SEQ ID NO 628
<211> LENGTH: 27
<212> TYPE: RNA
<213> ORGANISM: Artificial Sequence
<220> FEATURE:
<223> OTHER INFORMATION: RNAi molecule

<400> SEQUENCE: 628
uuguacgaaa uguguuagaa cuccucu 27

<210> SEQ ID NO 629
<211> LENGTH: 27
<212> TYPE: RNA
<213> ORGANISM: Artificial Sequence
<220> FEATURE:
<223> OTHER INFORMATION: RNAi molecule

<400> SEQUENCE: 629
aauugugcug aguggaguuu ugacaac 27

<210> SEQ ID NO 630
<211> LENGTH: 27
<212> TYPE: RNA
<213> ORGANISM: Artificial Sequence
<220> FEATURE:
<223> OTHER INFORMATION: RNAi molecule

<400> SEQUENCE: 630
ucagcuucac acauaauugu gcugagu 27

<210> SEQ ID NO 631
<211> LENGTH: 27
<212> TYPE: RNA
<213> ORGANISM: Artificial Sequence
<220> FEATURE:
<223> OTHER INFORMATION: RNAi molecule

<400> SEQUENCE: 631
uucagcuuca cacauaauug ugcugag 27

<210> SEQ ID NO 632
<211> LENGTH: 27
<212> TYPE: RNA
<213> ORGANISM: Artificial Sequence
<220> FEATURE:
<223> OTHER INFORMATION: RNAi molecule

<400> SEQUENCE: 632
auugugcuga guggaguuuu gacaacc 27

<210> SEQ ID NO 633
<211> LENGTH: 27
<212> TYPE: RNA
<213> ORGANISM: Artificial Sequence
<220> FEATURE:
<223> OTHER INFORMATION: RNAi molecule

<400> SEQUENCE: 633
ccuagucaug gcuaguucau ccugugg 27

<210> SEQ ID NO 634
<211> LENGTH: 27
<212> TYPE: RNA
<213> ORGANISM: Artificial Sequence
<220> FEATURE:
<223> OTHER INFORMATION: RNAi molecule

<400> SEQUENCE: 634
cugguucugc agcucuggaa uggaugu 27

<210> SEQ ID NO 635
<211> LENGTH: 27
<212> TYPE: RNA
<213> ORGANISM: Artificial Sequence
<220> FEATURE:
<223> OTHER INFORMATION: RNAi molecule

<400> SEQUENCE: 635
aaaguauaaa aggauucuac uucuacc 27

<210> SEQ ID NO 636
<211> LENGTH: 27
<212> TYPE: RNA
<213> ORGANISM: Artificial Sequence
<220> FEATURE:
<223> OTHER INFORMATION: RNAi molecule

<400> SEQUENCE: 636
caaaguauaa aaggauucua cuucuac 27

<210> SEQ ID NO 637
<211> LENGTH: 27
<212> TYPE: RNA
<213> ORGANISM: Artificial Sequence
<220> FEATURE:

<223> OTHER INFORMATION: RNAi molecule

<400> SEQUENCE: 637
accaaaguau aaaaggauuc uacuucu 27

<210> SEQ ID NO 638
<211> LENGTH: 27
<212> TYPE: RNA
<213> ORGANISM: Artificial Sequence
<220> FEATURE:
<223> OTHER INFORMATION: RNAi molecule

<400> SEQUENCE: 638
uagaacuccu cuugccuaug uuaaaau 27

<210> SEQ ID NO 639
<211> LENGTH: 27
<212> TYPE: RNA
<213> ORGANISM: Artificial Sequence
<220> FEATURE:
<223> OTHER INFORMATION: RNAi molecule

<400> SEQUENCE: 639
uuagaacucc ucuugccuau guuaaaa 27

<210> SEQ ID NO 640
<211> LENGTH: 27
<212> TYPE: RNA
<213> ORGANISM: Artificial Sequence
<220> FEATURE:
<223> OTHER INFORMATION: RNAi molecule

<400> SEQUENCE: 640
acuccucuug ccuauguuaa aauguga 27

<210> SEQ ID NO 641
<211> LENGTH: 27
<212> TYPE: RNA
<213> ORGANISM: Artificial Sequence
<220> FEATURE:
<223> OTHER INFORMATION: RNAi molecule

<400> SEQUENCE: 641
gaacuccucu ugccuauguu aaaaugu 27

<210> SEQ ID NO 642
<211> LENGTH: 27
<212> TYPE: RNA
<213> ORGANISM: Artificial Sequence
<220> FEATURE:
<223> OTHER INFORMATION: RNAi molecule

<400> SEQUENCE: 642
guuagaacuc cucuugccua uguuaaa 27

<210> SEQ ID NO 643
<211> LENGTH: 27
<212> TYPE: RNA
<213> ORGANISM: Artificial Sequence
<220> FEATURE:
<223> OTHER INFORMATION: RNAi molecule

<400> SEQUENCE: 643
aaauguguua gaacuccucu ugccuau 27

<210> SEQ ID NO 644

-continued

<211> LENGTH: 27
<212> TYPE: RNA
<213> ORGANISM: Artificial Sequence
<220> FEATURE:
<223> OTHER INFORMATION: RNAi molecule

<400> SEQUENCE: 644
uaauugugcu gaguggaguu uugacaa 27

<210> SEQ ID NO 645
<211> LENGTH: 27
<212> TYPE: RNA
<213> ORGANISM: Artificial Sequence
<220> FEATURE:
<223> OTHER INFORMATION: RNAi molecule

<400> SEQUENCE: 645
auaauugugc ugaguggagu uuugaca 27

<210> SEQ ID NO 646
<211> LENGTH: 27
<212> TYPE: RNA
<213> ORGANISM: Artificial Sequence
<220> FEATURE:
<223> OTHER INFORMATION: RNAi molecule

<400> SEQUENCE: 646
uuguuggcca ucaugugacu ucgaauu 27

<210> SEQ ID NO 647
<211> LENGTH: 27
<212> TYPE: RNA
<213> ORGANISM: Artificial Sequence
<220> FEATURE:
<223> OTHER INFORMATION: RNAi molecule

<400> SEQUENCE: 647
ucauugcgga uguuaugcuc aauuauu 27

<210> SEQ ID NO 648
<211> LENGTH: 27
<212> TYPE: RNA
<213> ORGANISM: Artificial Sequence
<220> FEATURE:
<223> OTHER INFORMATION: RNAi molecule

<400> SEQUENCE: 648
uagaacucgc uuguagaugg cugaauu 27

<210> SEQ ID NO 649
<211> LENGTH: 27
<212> TYPE: RNA
<213> ORGANISM: Artificial Sequence
<220> FEATURE:
<223> OTHER INFORMATION: RNAi molecule

<400> SEQUENCE: 649
cauuccggaa caucagcuuc augucuu 27

<210> SEQ ID NO 650
<211> LENGTH: 27
<212> TYPE: RNA
<213> ORGANISM: Artificial Sequence
<220> FEATURE:
<223> OTHER INFORMATION: RNAi molecule

<400> SEQUENCE: 650
uaacuucucc aggauaugug caucauu 27

<210> SEQ ID NO 651
<211> LENGTH: 27
<212> TYPE: RNA
<213> ORGANISM: Artificial Sequence
<220> FEATURE:
<223> OTHER INFORMATION: RNAi molecule

<400> SEQUENCE: 651
aguccucaac cauagaguca auaucuu 27

<210> SEQ ID NO 652
<211> LENGTH: 27
<212> TYPE: RNA
<213> ORGANISM: Artificial Sequence
<220> FEATURE:
<223> OTHER INFORMATION: RNAi molecule

<400> SEQUENCE: 652
aacaucagcu ucaugucuuc uaucauu 27

<210> SEQ ID NO 653
<211> LENGTH: 27
<212> TYPE: RNA
<213> ORGANISM: Artificial Sequence
<220> FEATURE:
<223> OTHER INFORMATION: RNAi molecule

<400> SEQUENCE: 653
cauagaguca auaucuuggu acuuguu 27

<210> SEQ ID NO 654
<211> LENGTH: 27
<212> TYPE: RNA
<213> ORGANISM: Artificial Sequence
<220> FEATURE:
<223> OTHER INFORMATION: RNAi molecule

<400> SEQUENCE: 654
uucaagucca uuggcuccaa gaugauu 27

<210> SEQ ID NO 655
<211> LENGTH: 27
<212> TYPE: RNA
<213> ORGANISM: Artificial Sequence
<220> FEATURE:
<223> OTHER INFORMATION: RNAi molecule

<400> SEQUENCE: 655
uggcucucga gcuucaagaa caacauu 27

<210> SEQ ID NO 656
<211> LENGTH: 27
<212> TYPE: RNA
<213> ORGANISM: Artificial Sequence
<220> FEATURE:
<223> OTHER INFORMATION: RNAi molecule

<400> SEQUENCE: 656
cgauaucguc ucuccuggca agcucuu 27

<210> SEQ ID NO 657
<211> LENGTH: 27
<212> TYPE: RNA
<213> ORGANISM: Artificial Sequence
<220> FEATURE:

<223> OTHER INFORMATION: RNAi molecule

<400> SEQUENCE: 657
gcuucaagaa caacauugaa uaagauu 27

<210> SEQ ID NO 658
<211> LENGTH: 27
<212> TYPE: RNA
<213> ORGANISM: Artificial Sequence
<220> FEATURE:
<223> OTHER INFORMATION: RNAi molecule

<400> SEQUENCE: 658
guuggccauc augugacuuc gaauuuu 27

<210> SEQ ID NO 659
<211> LENGTH: 27
<212> TYPE: RNA
<213> ORGANISM: Artificial Sequence
<220> FEATURE:
<223> OTHER INFORMATION: RNAi molecule

<400> SEQUENCE: 659
uguuggccau caugugacuu cgaauuu 27

<210> SEQ ID NO 660
<211> LENGTH: 27
<212> TYPE: RNA
<213> ORGANISM: Artificial Sequence
<220> FEATURE:
<223> OTHER INFORMATION: RNAi molecule

<400> SEQUENCE: 660
agaaaugcca cucuuccuac ucagcuu 27

<210> SEQ ID NO 661
<211> LENGTH: 27
<212> TYPE: RNA
<213> ORGANISM: Artificial Sequence
<220> FEATURE:
<223> OTHER INFORMATION: RNAi molecule

<400> SEQUENCE: 661
ugguacuugu uggccaucau gugacuu 27

<210> SEQ ID NO 662
<211> LENGTH: 27
<212> TYPE: RNA
<213> ORGANISM: Artificial Sequence
<220> FEATURE:
<223> OTHER INFORMATION: RNAi molecule

<400> SEQUENCE: 662
aauaagauuu ucauucgcug cuuucuu 27

<210> SEQ ID NO 663
<211> LENGTH: 27
<212> TYPE: RNA
<213> ORGANISM: Artificial Sequence
<220> FEATURE:
<223> OTHER INFORMATION: RNAi molecule

<400> SEQUENCE: 663
uacagcuuca uagaccucau uuaguuu 27

<210> SEQ ID NO 664

<211> LENGTH: 27
<212> TYPE: RNA
<213> ORGANISM: Artificial Sequence
<220> FEATURE:
<223> OTHER INFORMATION: RNAi molecule

<400> SEQUENCE: 664
uucuuuacag cuucauagac cucauuu 27

<210> SEQ ID NO 665
<211> LENGTH: 27
<212> TYPE: RNA
<213> ORGANISM: Artificial Sequence
<220> FEATURE:
<223> OTHER INFORMATION: RNAi molecule

<400> SEQUENCE: 665
uugucauugc ggauguuaug cucaauu 27

<210> SEQ ID NO 666
<211> LENGTH: 27
<212> TYPE: RNA
<213> ORGANISM: Artificial Sequence
<220> FEATURE:
<223> OTHER INFORMATION: RNAi molecule

<400> SEQUENCE: 666
uagaccucau uuaguuucug cugcauu 27

<210> SEQ ID NO 667
<211> LENGTH: 27
<212> TYPE: RNA
<213> ORGANISM: Artificial Sequence
<220> FEATURE:
<223> OTHER INFORMATION: RNAi molecule

<400> SEQUENCE: 667
guucuuuaca gcuucauaga ccucauu 27

<210> SEQ ID NO 668
<211> LENGTH: 27
<212> TYPE: RNA
<213> ORGANISM: Artificial Sequence
<220> FEATURE:
<223> OTHER INFORMATION: RNAi molecule

<400> SEQUENCE: 668
uggccaucau gugacuucga auuuuuu 27

<210> SEQ ID NO 669
<211> LENGTH: 27
<212> TYPE: RNA
<213> ORGANISM: Artificial Sequence
<220> FEATURE:
<223> OTHER INFORMATION: RNAi molecule

<400> SEQUENCE: 669
uuggccauca ugugacuucg aauuuuu 27

<210> SEQ ID NO 670
<211> LENGTH: 27
<212> TYPE: RNA
<213> ORGANISM: Artificial Sequence
<220> FEATURE:
<223> OTHER INFORMATION: RNAi molecule

<400> SEQUENCE: 670
gcucuuucuu cuuugccugc auaacuu 27

<210> SEQ ID NO 671
<211> LENGTH: 27
<212> TYPE: RNA
<213> ORGANISM: Artificial Sequence
<220> FEATURE:
<223> OTHER INFORMATION: RNAi molecule

<400> SEQUENCE: 671
uugaguaacu ucuccaggau augugca 27

<210> SEQ ID NO 672
<211> LENGTH: 27
<212> TYPE: RNA
<213> ORGANISM: Artificial Sequence
<220> FEATURE:
<223> OTHER INFORMATION: RNAi molecule

<400> SEQUENCE: 672
cuugaguaac uucuccagga uaugugc 27

<210> SEQ ID NO 673
<211> LENGTH: 27
<212> TYPE: RNA
<213> ORGANISM: Artificial Sequence
<220> FEATURE:
<223> OTHER INFORMATION: RNAi molecule

<400> SEQUENCE: 673
cuuguuggcc aucaugugac uucgaau 27

<210> SEQ ID NO 674
<211> LENGTH: 27
<212> TYPE: RNA
<213> ORGANISM: Artificial Sequence
<220> FEATURE:
<223> OTHER INFORMATION: RNAi molecule

<400> SEQUENCE: 674
acuuguuggc caucauguga cuucgaa 27

<210> SEQ ID NO 675
<211> LENGTH: 27
<212> TYPE: RNA
<213> ORGANISM: Artificial Sequence
<220> FEATURE:
<223> OTHER INFORMATION: RNAi molecule

<400> SEQUENCE: 675
uacuuguugg ccaucaugug acuucga 27

<210> SEQ ID NO 676
<211> LENGTH: 27
<212> TYPE: RNA
<213> ORGANISM: Artificial Sequence
<220> FEATURE:
<223> OTHER INFORMATION: RNAi molecule

<400> SEQUENCE: 676
agaucaugcu gucuccgucc ucgauau 27

<210> SEQ ID NO 677
<211> LENGTH: 27
<212> TYPE: RNA
<213> ORGANISM: Artificial Sequence
<220> FEATURE:

<223> OTHER INFORMATION: RNAi molecule

<400> SEQUENCE: 677
gcauuccgga acaucagcuu caugucu 27

<210> SEQ ID NO 678
<211> LENGTH: 27
<212> TYPE: RNA
<213> ORGANISM: Artificial Sequence
<220> FEATURE:
<223> OTHER INFORMATION: RNAi molecule

<400> SEQUENCE: 678
uggcauuccg gaacaucagc uucaugu 27

<210> SEQ ID NO 679
<211> LENGTH: 27
<212> TYPE: RNA
<213> ORGANISM: Artificial Sequence
<220> FEATURE:
<223> OTHER INFORMATION: RNAi molecule

<400> SEQUENCE: 679
aaugccacuc uuccuacuca gcuugag 27

<210> SEQ ID NO 680
<211> LENGTH: 27
<212> TYPE: RNA
<213> ORGANISM: Artificial Sequence
<220> FEATURE:
<223> OTHER INFORMATION: RNAi molecule

<400> SEQUENCE: 680
augcugucuc cguccucgau aucgucu 27

<210> SEQ ID NO 681
<211> LENGTH: 27
<212> TYPE: RNA
<213> ORGANISM: Artificial Sequence
<220> FEATURE:
<223> OTHER INFORMATION: RNAi molecule

<400> SEQUENCE: 681
ucaugcuguc uccguccucg auaucgu 27

<210> SEQ ID NO 682
<211> LENGTH: 27
<212> TYPE: RNA
<213> ORGANISM: Artificial Sequence
<220> FEATURE:
<223> OTHER INFORMATION: RNAi molecule

<400> SEQUENCE: 682
aucaugcugu cuccguccuc gauaucg 27

<210> SEQ ID NO 683
<211> LENGTH: 27
<212> TYPE: RNA
<213> ORGANISM: Artificial Sequence
<220> FEATURE:
<223> OTHER INFORMATION: RNAi molecule

<400> SEQUENCE: 683
ggagaagcca ugucaucauc aucaggc 27

<210> SEQ ID NO 684

<211> LENGTH: 27
<212> TYPE: RNA
<213> ORGANISM: Artificial Sequence
<220> FEATURE:
<223> OTHER INFORMATION: RNAi molecule

<400> SEQUENCE: 684
gaacaucagc uucaugucuu cuaucau 27

<210> SEQ ID NO 685
<211> LENGTH: 27
<212> TYPE: RNA
<213> ORGANISM: Artificial Sequence
<220> FEATURE:
<223> OTHER INFORMATION: RNAi molecule

<400> SEQUENCE: 685
uuagaacucg cuuguagaug gcugaau 27

<210> SEQ ID NO 686
<211> LENGTH: 27
<212> TYPE: RNA
<213> ORGANISM: Artificial Sequence
<220> FEATURE:
<223> OTHER INFORMATION: RNAi molecule

<400> SEQUENCE: 686
ggaacaucag cuucaugucu ucuauca 27

<210> SEQ ID NO 687
<211> LENGTH: 27
<212> TYPE: RNA
<213> ORGANISM: Artificial Sequence
<220> FEATURE:
<223> OTHER INFORMATION: RNAi molecule

<400> SEQUENCE: 687
guaacuucuc caggauaugu gcaucau 27

<210> SEQ ID NO 688
<211> LENGTH: 27
<212> TYPE: RNA
<213> ORGANISM: Artificial Sequence
<220> FEATURE:
<223> OTHER INFORMATION: RNAi molecule

<400> SEQUENCE: 688
aguaacuucu ccaggauaug ugcauca 27

<210> SEQ ID NO 689
<211> LENGTH: 27
<212> TYPE: RNA
<213> ORGANISM: Artificial Sequence
<220> FEATURE:
<223> OTHER INFORMATION: RNAi molecule

<400> SEQUENCE: 689
ugaguaacuu cuccaggaua ugugcau 27

<210> SEQ ID NO 690
<211> LENGTH: 27
<212> TYPE: RNA
<213> ORGANISM: Artificial Sequence
<220> FEATURE:
<223> OTHER INFORMATION: RNAi molecule

<400> SEQUENCE: 690
auaguaguca ggcaacucag aucuaga 27

<210> SEQ ID NO 691
<211> LENGTH: 27
<212> TYPE: RNA
<213> ORGANISM: Artificial Sequence
<220> FEATURE:
<223> OTHER INFORMATION: RNAi molecule

<400> SEQUENCE: 691
ccggaacauc agcuucaugu cuucuau 27

<210> SEQ ID NO 692
<211> LENGTH: 27
<212> TYPE: RNA
<213> ORGANISM: Artificial Sequence
<220> FEATURE:
<223> OTHER INFORMATION: RNAi molecule

<400> SEQUENCE: 692
uuccggaaca ucagcuucau gucuucu 27

<210> SEQ ID NO 693
<211> LENGTH: 27
<212> TYPE: RNA
<213> ORGANISM: Artificial Sequence
<220> FEATURE:
<223> OTHER INFORMATION: RNAi molecule

<400> SEQUENCE: 693
uaguagucag gcaacucaga ucuagag 27

<210> SEQ ID NO 694
<211> LENGTH: 27
<212> TYPE: RNA
<213> ORGANISM: Artificial Sequence
<220> FEATURE:
<223> OTHER INFORMATION: RNAi molecule

<400> SEQUENCE: 694
gauaguaguc aggcaacuca gaucuag 27

<210> SEQ ID NO 695
<211> LENGTH: 27
<212> TYPE: RNA
<213> ORGANISM: Artificial Sequence
<220> FEATURE:
<223> OTHER INFORMATION: RNAi molecule

<400> SEQUENCE: 695
guacuuguug gccaucaugu gacuucg 27

<210> SEQ ID NO 696
<211> LENGTH: 27
<212> TYPE: RNA
<213> ORGANISM: Artificial Sequence
<220> FEATURE:
<223> OTHER INFORMATION: RNAi molecule

<400> SEQUENCE: 696
ugaccagcau caucagauca augaucu 27

<210> SEQ ID NO 697
<211> LENGTH: 27
<212> TYPE: RNA
<213> ORGANISM: Artificial Sequence
<220> FEATURE:

<223> OTHER INFORMATION: RNAi molecule

<400> SEQUENCE: 697
cauggacuuc accuucuuca ccaccuu 27

<210> SEQ ID NO 698
<211> LENGTH: 27
<212> TYPE: RNA
<213> ORGANISM: Artificial Sequence
<220> FEATURE:
<223> OTHER INFORMATION: RNAi molecule

<400> SEQUENCE: 698
gaacaucugc auggacuuca ccuucuu 27

<210> SEQ ID NO 699
<211> LENGTH: 27
<212> TYPE: RNA
<213> ORGANISM: Artificial Sequence
<220> FEATURE:
<223> OTHER INFORMATION: RNAi molecule

<400> SEQUENCE: 699
acuguaaugu ggaacuuggc cuugguu 27

<210> SEQ ID NO 700
<211> LENGTH: 27
<212> TYPE: RNA
<213> ORGANISM: Artificial Sequence
<220> FEATURE:
<223> OTHER INFORMATION: RNAi molecule

<400> SEQUENCE: 700
aaucggugca ccucggaacu ugguguu 27

<210> SEQ ID NO 701
<211> LENGTH: 27
<212> TYPE: RNA
<213> ORGANISM: Artificial Sequence
<220> FEATURE:
<223> OTHER INFORMATION: RNAi molecule

<400> SEQUENCE: 701
uauuuuguuc agcaccacga ccagcuu 27

<210> SEQ ID NO 702
<211> LENGTH: 27
<212> TYPE: RNA
<213> ORGANISM: Artificial Sequence
<220> FEATURE:
<223> OTHER INFORMATION: RNAi molecule

<400> SEQUENCE: 702
uaucaauugc ugccugucuc uuuccuu 27

<210> SEQ ID NO 703
<211> LENGTH: 27
<212> TYPE: RNA
<213> ORGANISM: Artificial Sequence
<220> FEATURE:
<223> OTHER INFORMATION: RNAi molecule

<400> SEQUENCE: 703
guggaacauc ugcauggacu ucaccuu 27

<210> SEQ ID NO 704

<211> LENGTH: 27
<212> TYPE: RNA
<213> ORGANISM: Artificial Sequence
<220> FEATURE:
<223> OTHER INFORMATION: RNAi molecule

<400> SEQUENCE: 704
aggcaaucug gccgaucaca aggcauu 27

<210> SEQ ID NO 705
<211> LENGTH: 27
<212> TYPE: RNA
<213> ORGANISM: Artificial Sequence
<220> FEATURE:
<223> OTHER INFORMATION: RNAi molecule

<400> SEQUENCE: 705
uccuucaggu aagaggucua uuuuguu 27

<210> SEQ ID NO 706
<211> LENGTH: 27
<212> TYPE: RNA
<213> ORGANISM: Artificial Sequence
<220> FEATURE:
<223> OTHER INFORMATION: RNAi molecule

<400> SEQUENCE: 706
cuuuccuuca gguaagaggu cuauuuu 27

<210> SEQ ID NO 707
<211> LENGTH: 27
<212> TYPE: RNA
<213> ORGANISM: Artificial Sequence
<220> FEATURE:
<223> OTHER INFORMATION: RNAi molecule

<400> SEQUENCE: 707
cauuuuauca auugcugccu gucucuu 27

<210> SEQ ID NO 708
<211> LENGTH: 27
<212> TYPE: RNA
<213> ORGANISM: Artificial Sequence
<220> FEATURE:
<223> OTHER INFORMATION: RNAi molecule

<400> SEQUENCE: 708
ggucuucugc auuuucuugg ucauuuu 27

<210> SEQ ID NO 709
<211> LENGTH: 27
<212> TYPE: RNA
<213> ORGANISM: Artificial Sequence
<220> FEATURE:
<223> OTHER INFORMATION: RNAi molecule

<400> SEQUENCE: 709
guccaguaua ggcuccuggu caaaguu 27

<210> SEQ ID NO 710
<211> LENGTH: 27
<212> TYPE: RNA
<213> ORGANISM: Artificial Sequence
<220> FEATURE:
<223> OTHER INFORMATION: RNAi molecule

<400> SEQUENCE: 710
auuuuaucaa uugcugccug ucucuuu 27

<210> SEQ ID NO 711
<211> LENGTH: 27
<212> TYPE: RNA
<213> ORGANISM: Artificial Sequence
<220> FEATURE:
<223> OTHER INFORMATION: RNAi molecule

<400> SEQUENCE: 711
cucuuuccuu cagguaagag gucuauu 27

<210> SEQ ID NO 712
<211> LENGTH: 27
<212> TYPE: RNA
<213> ORGANISM: Artificial Sequence
<220> FEATURE:
<223> OTHER INFORMATION: RNAi molecule

<400> SEQUENCE: 712
cuguaaugug gaacuuggcc uugguuu 27

<210> SEQ ID NO 713
<211> LENGTH: 27
<212> TYPE: RNA
<213> ORGANISM: Artificial Sequence
<220> FEATURE:
<223> OTHER INFORMATION: RNAi molecule

<400> SEQUENCE: 713
auggacuuca ccuucuucac caccuug 27

<210> SEQ ID NO 714
<211> LENGTH: 27
<212> TYPE: RNA
<213> ORGANISM: Artificial Sequence
<220> FEATURE:
<223> OTHER INFORMATION: RNAi molecule

<400> SEQUENCE: 714
gguauaaucg gugcaccucg gaacuug 27

<210> SEQ ID NO 715
<211> LENGTH: 27
<212> TYPE: RNA
<213> ORGANISM: Artificial Sequence
<220> FEATURE:
<223> OTHER INFORMATION: RNAi molecule

<400> SEQUENCE: 715
uuaucuggag caggacugaa gaacauc 27

<210> SEQ ID NO 716
<211> LENGTH: 27
<212> TYPE: RNA
<213> ORGANISM: Artificial Sequence
<220> FEATURE:
<223> OTHER INFORMATION: RNAi molecule

<400> SEQUENCE: 716
uggaacaucu gcauggacuu caccuuc 27

<210> SEQ ID NO 717
<211> LENGTH: 27
<212> TYPE: RNA
<213> ORGANISM: Artificial Sequence
<220> FEATURE:

<223> OTHER INFORMATION: RNAi molecule

<400> SEQUENCE: 717
aacaucugca uggacuucac cuucuuc 27

<210> SEQ ID NO 718
<211> LENGTH: 27
<212> TYPE: RNA
<213> ORGANISM: Artificial Sequence
<220> FEATURE:
<223> OTHER INFORMATION: RNAi molecule

<400> SEQUENCE: 718
uuggucacau cgaugaccag caucauc 27

<210> SEQ ID NO 719
<211> LENGTH: 27
<212> TYPE: RNA
<213> ORGANISM: Artificial Sequence
<220> FEATURE:
<223> OTHER INFORMATION: RNAi molecule

<400> SEQUENCE: 719
uuuguucagc accacgacca gcuucug 27

<210> SEQ ID NO 720
<211> LENGTH: 27
<212> TYPE: RNA
<213> ORGANISM: Artificial Sequence
<220> FEATURE:
<223> OTHER INFORMATION: RNAi molecule

<400> SEQUENCE: 720
auaaucggug caccucggaa cuuggug 27

<210> SEQ ID NO 721
<211> LENGTH: 27
<212> TYPE: RNA
<213> ORGANISM: Artificial Sequence
<220> FEATURE:
<223> OTHER INFORMATION: RNAi molecule

<400> SEQUENCE: 721
aucgugcaga aguaggcauu ccuuccu 27

<210> SEQ ID NO 722
<211> LENGTH: 27
<212> TYPE: RNA
<213> ORGANISM: Artificial Sequence
<220> FEATURE:
<223> OTHER INFORMATION: RNAi molecule

<400> SEQUENCE: 722
cugaaguccg aaguaauccu ccucauu 27

<210> SEQ ID NO 723
<211> LENGTH: 27
<212> TYPE: RNA
<213> ORGANISM: Artificial Sequence
<220> FEATURE:
<223> OTHER INFORMATION: RNAi molecule

<400> SEQUENCE: 723
ugcaucaaug aucaacugaa uuacauu 27

<210> SEQ ID NO 724

<211> LENGTH: 27
<212> TYPE: RNA
<213> ORGANISM: Artificial Sequence
<220> FEATURE:
<223> OTHER INFORMATION: RNAi molecule

<400> SEQUENCE: 724
uuggaucuga guaauauccu cuggcuu 27

<210> SEQ ID NO 725
<211> LENGTH: 27
<212> TYPE: RNA
<213> ORGANISM: Artificial Sequence
<220> FEATURE:
<223> OTHER INFORMATION: RNAi molecule

<400> SEQUENCE: 725
gaaggauaau cauaauaaug gcucauu 27

<210> SEQ ID NO 726
<211> LENGTH: 27
<212> TYPE: RNA
<213> ORGANISM: Artificial Sequence
<220> FEATURE:
<223> OTHER INFORMATION: RNAi molecule

<400> SEQUENCE: 726
gaucaacuga auuacauugc uagaauu 27

<210> SEQ ID NO 727
<211> LENGTH: 27
<212> TYPE: RNA
<213> ORGANISM: Artificial Sequence
<220> FEATURE:
<223> OTHER INFORMATION: RNAi molecule

<400> SEQUENCE: 727
ugcagauaau guuccuacug cugacuu 27

<210> SEQ ID NO 728
<211> LENGTH: 27
<212> TYPE: RNA
<213> ORGANISM: Artificial Sequence
<220> FEATURE:
<223> OTHER INFORMATION: RNAi molecule

<400> SEQUENCE: 728
ugugcuaaug uaaggcauca cagucuu 27

<210> SEQ ID NO 729
<211> LENGTH: 27
<212> TYPE: RNA
<213> ORGANISM: Artificial Sequence
<220> FEATURE:
<223> OTHER INFORMATION: RNAi molecule

<400> SEQUENCE: 729
gcuccuugua aacaggcuga aauucuu 27

<210> SEQ ID NO 730
<211> LENGTH: 27
<212> TYPE: RNA
<213> ORGANISM: Artificial Sequence
<220> FEATURE:
<223> OTHER INFORMATION: RNAi molecule

<400> SEQUENCE: 730
ucaucacauc gugcagaagu aggcauu                                             27

<210> SEQ ID NO 731
<211> LENGTH: 27
<212> TYPE: RNA
<213> ORGANISM: Artificial Sequence
<220> FEATURE:
<223> OTHER INFORMATION: RNAi molecule

<400> SEQUENCE: 731
cugaguaaua uccucuggcu ugagcuu                                             27

<210> SEQ ID NO 732
<211> LENGTH: 27
<212> TYPE: RNA
<213> ORGANISM: Artificial Sequence
<220> FEATURE:
<223> OTHER INFORMATION: RNAi molecule

<400> SEQUENCE: 732
auaauggcuc auuguguaca uauuauu                                             27

<210> SEQ ID NO 733
<211> LENGTH: 27
<212> TYPE: RNA
<213> ORGANISM: Artificial Sequence
<220> FEATURE:
<223> OTHER INFORMATION: RNAi molecule

<400> SEQUENCE: 733
ucauucauca gaucuguucc aagacuu                                             27

<210> SEQ ID NO 734
<211> LENGTH: 27
<212> TYPE: RNA
<213> ORGANISM: Artificial Sequence
<220> FEATURE:
<223> OTHER INFORMATION: RNAi molecule

<400> SEQUENCE: 734
guccgaagua auccuccuca uuucauu                                             27

<210> SEQ ID NO 735
<211> LENGTH: 27
<212> TYPE: RNA
<213> ORGANISM: Artificial Sequence
<220> FEATURE:
<223> OTHER INFORMATION: RNAi molecule

<400> SEQUENCE: 735 ugaagccga aguaauccuc cucauuu                                              27

<210> SEQ ID NO 736
<211> LENGTH: 27
<212> TYPE: RNA
<213> ORGANISM: Artificial Sequence
<220> FEATURE:
<223> OTHER INFORMATION: RNAi molecule

<400> SEQUENCE: 736
cuggcuugag cuucucugcu guuccuu                                             27

<210> SEQ ID NO 737
<211> LENGTH: 27
<212> TYPE: RNA
<213> ORGANISM: Artificial Sequence
<220> FEATURE:

<223> OTHER INFORMATION: RNAi molecule

<400> SEQUENCE: 737
uccucuggcu ugagcuucuc ugcuguu 27

<210> SEQ ID NO 738
<211> LENGTH: 27
<212> TYPE: RNA
<213> ORGANISM: Artificial Sequence
<220> FEATURE:
<223> OTHER INFORMATION: RNAi molecule

<400> SEQUENCE: 738
cauuccuucc uguaaaaaug uugaauu 27

<210> SEQ ID NO 739
<211> LENGTH: 27
<212> TYPE: RNA
<213> ORGANISM: Artificial Sequence
<220> FEATURE:
<223> OTHER INFORMATION: RNAi molecule

<400> SEQUENCE: 739
caacaaguuc auuaaauacu ucuccuu 27

<210> SEQ ID NO 740
<211> LENGTH: 27
<212> TYPE: RNA
<213> ORGANISM: Artificial Sequence
<220> FEATURE:
<223> OTHER INFORMATION: RNAi molecule

<400> SEQUENCE: 740
uuaaucgcaa aaccaacugc ugugguu 27

<210> SEQ ID NO 741
<211> LENGTH: 27
<212> TYPE: RNA
<213> ORGANISM: Artificial Sequence
<220> FEATURE:
<223> OTHER INFORMATION: RNAi molecule

<400> SEQUENCE: 741
cacaucgugc agaaguaggc auuccuu 27

<210> SEQ ID NO 742
<211> LENGTH: 27
<212> TYPE: RNA
<213> ORGANISM: Artificial Sequence
<220> FEATURE:
<223> OTHER INFORMATION: RNAi molecule

<400> SEQUENCE: 742
cuugcaugau ggcaucgaaa ccaccuu 27

<210> SEQ ID NO 743
<211> LENGTH: 27
<212> TYPE: RNA
<213> ORGANISM: Artificial Sequence
<220> FEATURE:
<223> OTHER INFORMATION: RNAi molecule

<400> SEQUENCE: 743
auaauaaugg cucauugugu acauauu 27

<210> SEQ ID NO 744

<211> LENGTH: 27
<212> TYPE: RNA
<213> ORGANISM: Artificial Sequence
<220> FEATURE:
<223> OTHER INFORMATION: RNAi molecule

<400> SEQUENCE: 744
ccuuuauuag uaagacugag cacauuu 27

<210> SEQ ID NO 745
<211> LENGTH: 27
<212> TYPE: RNA
<213> ORGANISM: Artificial Sequence
<220> FEATURE:
<223> OTHER INFORMATION: RNAi molecule

<400> SEQUENCE: 745
uccuuuauua guaagacuga gcacauu 27

<210> SEQ ID NO 746
<211> LENGTH: 27
<212> TYPE: RNA
<213> ORGANISM: Artificial Sequence
<220> FEATURE:
<223> OTHER INFORMATION: RNAi molecule

<400> SEQUENCE: 746
cauccugcuc augucacuca auucauu 27

<210> SEQ ID NO 747
<211> LENGTH: 27
<212> TYPE: RNA
<213> ORGANISM: Artificial Sequence
<220> FEATURE:
<223> OTHER INFORMATION: RNAi molecule

<400> SEQUENCE: 747
cucaauuaag ugguccuucu cauccuu 27

<210> SEQ ID NO 748
<211> LENGTH: 27
<212> TYPE: RNA
<213> ORGANISM: Artificial Sequence
<220> FEATURE:
<223> OTHER INFORMATION: RNAi molecule

<400> SEQUENCE: 748
aauuaagugg uccuucucau ccuuguu 27

<210> SEQ ID NO 749
<211> LENGTH: 27
<212> TYPE: RNA
<213> ORGANISM: Artificial Sequence
<220> FEATURE:
<223> OTHER INFORMATION: RNAi molecule

<400> SEQUENCE: 749
guauagucgc ucaauuaagu gguccuu 27

<210> SEQ ID NO 750
<211> LENGTH: 27
<212> TYPE: RNA
<213> ORGANISM: Artificial Sequence
<220> FEATURE:
<223> OTHER INFORMATION: RNAi molecule

<400> SEQUENCE: 750
cugaucucuc uguauagucg cucaauu 27

<210> SEQ ID NO 751
<211> LENGTH: 27
<212> TYPE: RNA
<213> ORGANISM: Artificial Sequence
<220> FEATURE:
<223> OTHER INFORMATION: RNAi molecule

<400> SEQUENCE: 751
gguacuccau cuugguucuu agcaguu 27

<210> SEQ ID NO 752
<211> LENGTH: 27
<212> TYPE: RNA
<213> ORGANISM: Artificial Sequence
<220> FEATURE:
<223> OTHER INFORMATION: RNAi molecule

<400> SEQUENCE: 752
guccuucuca uccuuguuca caccauu 27

<210> SEQ ID NO 753
<211> LENGTH: 27
<212> TYPE: RNA
<213> ORGANISM: Artificial Sequence
<220> FEATURE:
<223> OTHER INFORMATION: RNAi molecule

<400> SEQUENCE: 753
aaugagccgc uugaaguacu gcagguu 27

<210> SEQ ID NO 754
<211> LENGTH: 27
<212> TYPE: RNA
<213> ORGANISM: Artificial Sequence
<220> FEATURE:
<223> OTHER INFORMATION: RNAi molecule

<400> SEQUENCE: 754
aacuggaaaa aguuguucac gucacuu 27

<210> SEQ ID NO 755
<211> LENGTH: 27
<212> TYPE: RNA
<213> ORGANISM: Artificial Sequence
<220> FEATURE:
<223> OTHER INFORMATION: RNAi molecule

<400> SEQUENCE: 755
guacuccauc uugguucuua gcaguuu 27

<210> SEQ ID NO 756
<211> LENGTH: 27
<212> TYPE: RNA
<213> ORGANISM: Artificial Sequence
<220> FEATURE:
<223> OTHER INFORMATION: RNAi molecule

<400> SEQUENCE: 756
ggaguugaau acuguuugga agagguu 27

<210> SEQ ID NO 757
<211> LENGTH: 27
<212> TYPE: RNA
<213> ORGANISM: Artificial Sequence
<220> FEATURE:

<223> OTHER INFORMATION: RNAi molecule

<400> SEQUENCE: 757 uuggguguggu acuccaucuu gguucuu 27

<210> SEQ ID NO 758
<211> LENGTH: 27
<212> TYPE: RNA
<213> ORGANISM: Artificial Sequence
<220> FEATURE:
<223> OTHER INFORMATION: RNAi molecule

<400> SEQUENCE: 758
uccagguagu caaacaucuc cacuguu 27

<210> SEQ ID NO 759
<211> LENGTH: 27
<212> TYPE: RNA
<213> ORGANISM: Artificial Sequence
<220> FEATURE:
<223> OTHER INFORMATION: RNAi molecule

<400> SEQUENCE: 759
gguugcugga gcgguagaac agaucuu 27

<210> SEQ ID NO 760
<211> LENGTH: 27
<212> TYPE: RNA
<213> ORGANISM: Artificial Sequence
<220> FEATURE:
<223> OTHER INFORMATION: RNAi molecule

<400> SEQUENCE: 760
ggcauccaug uccaugaggu cauccuu 27

<210> SEQ ID NO 761
<211> LENGTH: 27
<212> TYPE: RNA
<213> ORGANISM: Artificial Sequence
<220> FEATURE:
<223> OTHER INFORMATION: RNAi molecule

<400> SEQUENCE: 761
ugaauacugu uuggaagagg uugaguu 27

<210> SEQ ID NO 762
<211> LENGTH: 27
<212> TYPE: RNA
<213> ORGANISM: Artificial Sequence
<220> FEATURE:
<223> OTHER INFORMATION: RNAi molecule

<400> SEQUENCE: 762
acugccaaag augucaucaa acuuguu 27

<210> SEQ ID NO 763
<211> LENGTH: 27
<212> TYPE: RNA
<213> ORGANISM: Artificial Sequence
<220> FEATURE:
<223> OTHER INFORMATION: RNAi molecule

<400> SEQUENCE: 763
ugaacugcca aagaugucau caaacuu 27

<210> SEQ ID NO 764

<211> LENGTH: 27
<212> TYPE: RNA
<213> ORGANISM: Artificial Sequence
<220> FEATURE:
<223> OTHER INFORMATION: RNAi molecule

<400> SEQUENCE: 764
auccuuguuc acaccauuuu gacuguu 27

<210> SEQ ID NO 765
<211> LENGTH: 27
<212> TYPE: RNA
<213> ORGANISM: Artificial Sequence
<220> FEATURE:
<223> OTHER INFORMATION: RNAi molecule

<400> SEQUENCE: 765
gagcgguaga acagaucuuu caacuuu 27

<210> SEQ ID NO 766
<211> LENGTH: 27
<212> TYPE: RNA
<213> ORGANISM: Artificial Sequence
<220> FEATURE:
<223> OTHER INFORMATION: RNAi molecule

<400> SEQUENCE: 766
ccuucucauc cuuguucaca ccauuuu 27

<210> SEQ ID NO 767
<211> LENGTH: 27
<212> TYPE: RNA
<213> ORGANISM: Artificial Sequence
<220> FEATURE:
<223> OTHER INFORMATION: RNAi molecule

<400> SEQUENCE: 767
uccuucucau ccuuguucac accauuu 27

<210> SEQ ID NO 768
<211> LENGTH: 27
<212> TYPE: RNA
<213> ORGANISM: Artificial Sequence
<220> FEATURE:
<223> OTHER INFORMATION: RNAi molecule

<400> SEQUENCE: 768
agucuucaug uuuucuagcu gugccuu 27

<210> SEQ ID NO 769
<211> LENGTH: 27
<212> TYPE: RNA
<213> ORGANISM: Artificial Sequence
<220> FEATURE:
<223> OTHER INFORMATION: RNAi molecule

<400> SEQUENCE: 769
ggagcgguag aacagaucuu ucaacuu 27

<210> SEQ ID NO 770
<211> LENGTH: 27
<212> TYPE: RNA
<213> ORGANISM: Artificial Sequence
<220> FEATURE:
<223> OTHER INFORMATION: RNAi molecule

<400> SEQUENCE: 770
guaucucaga gaguccuuca ggacguu 27

<210> SEQ ID NO 771
<211> LENGTH: 27
<212> TYPE: RNA
<213> ORGANISM: Artificial Sequence
<220> FEATURE:
<223> OTHER INFORMATION: RNAi molecule

<400> SEQUENCE: 771
acauccugcu caugucacuc aauucau 27

<210> SEQ ID NO 772
<211> LENGTH: 27
<212> TYPE: RNA
<213> ORGANISM: Artificial Sequence
<220> FEATURE:
<223> OTHER INFORMATION: RNAi molecule

<400> SEQUENCE: 772
caauuaagug guccuucuca uccuugu 27

<210> SEQ ID NO 773
<211> LENGTH: 27
<212> TYPE: RNA
<213> ORGANISM: Artificial Sequence
<220> FEATURE:
<223> OTHER INFORMATION: RNAi molecule

<400> SEQUENCE: 773
ucucuguaua gucgcucaau uaagugg 27

<210> SEQ ID NO 774
<211> LENGTH: 27
<212> TYPE: RNA
<213> ORGANISM: Artificial Sequence
<220> FEATURE:
<223> OTHER INFORMATION: RNAi molecule

<400> SEQUENCE: 774
aagugguccu ucucauccuu guucaca 27

<210> SEQ ID NO 775
<211> LENGTH: 27
<212> TYPE: RNA
<213> ORGANISM: Artificial Sequence
<220> FEATURE:
<223> OTHER INFORMATION: RNAi molecule

<400> SEQUENCE: 775
gcucaauuaa gugguccuuc ucauccu 27

<210> SEQ ID NO 776
<211> LENGTH: 27
<212> TYPE: RNA
<213> ORGANISM: Artificial Sequence
<220> FEATURE:
<223> OTHER INFORMATION: RNAi molecule

<400> SEQUENCE: 776
gguugaguuc acacuccagg uagucaa 27

<210> SEQ ID NO 777
<211> LENGTH: 27
<212> TYPE: RNA
<213> ORGANISM: Artificial Sequence
<220> FEATURE:

<223> OTHER INFORMATION: RNAi molecule

<400> SEQUENCE: 777
agguugaguu cacacuccag guaguca 27

<210> SEQ ID NO 778
<211> LENGTH: 27
<212> TYPE: RNA
<213> ORGANISM: Artificial Sequence
<220> FEATURE:
<223> OTHER INFORMATION: RNAi molecule

<400> SEQUENCE: 778
cauguccaug aggucauccu ucucuag 27

<210> SEQ ID NO 779
<211> LENGTH: 27
<212> TYPE: RNA
<213> ORGANISM: Artificial Sequence
<220> FEATURE:
<223> OTHER INFORMATION: RNAi molecule

<400> SEQUENCE: 779
uuaagugguc cuucucaucc uuguuca 27

<210> SEQ ID NO 780
<211> LENGTH: 27
<212> TYPE: RNA
<213> ORGANISM: Artificial Sequence
<220> FEATURE:
<223> OTHER INFORMATION: RNAi molecule

<400> SEQUENCE: 780
auagucgcuc aauuaagugg uccuucu 27

<210> SEQ ID NO 781
<211> LENGTH: 27
<212> TYPE: RNA
<213> ORGANISM: Artificial Sequence
<220> FEATURE:
<223> OTHER INFORMATION: RNAi molecule

<400> SEQUENCE: 781
uguauagucg cucaauuaag ugguccu 27

<210> SEQ ID NO 782
<211> LENGTH: 27
<212> TYPE: RNA
<213> ORGANISM: Artificial Sequence
<220> FEATURE:
<223> OTHER INFORMATION: RNAi molecule

<400> SEQUENCE: 782
acugaucucu cuguauaguc gcucaau 27

<210> SEQ ID NO 783
<211> LENGTH: 27
<212> TYPE: RNA
<213> ORGANISM: Artificial Sequence
<220> FEATURE:
<223> OTHER INFORMATION: RNAi molecule

<400> SEQUENCE: 783
cacauccugc ucaugucacu caauuca 27

<210> SEQ ID NO 784

```
<211> LENGTH: 27
<212> TYPE: RNA
<213> ORGANISM: Artificial Sequence
<220> FEATURE:
<223> OTHER INFORMATION: RNAi molecule

<400> SEQUENCE: 784

ugguacucca ucuugguucu uagcagu                                          27

<210> SEQ ID NO 785
<211> LENGTH: 27
<212> TYPE: RNA
<213> ORGANISM: Artificial Sequence
<220> FEATURE:
<223> OTHER INFORMATION: RNAi molecule

<400> SEQUENCE: 785

uaaguggucc uucucauccu uguucac                                          27

<210> SEQ ID NO 786
<211> LENGTH: 27
<212> TYPE: RNA
<213> ORGANISM: Artificial Sequence
<220> FEATURE:
<223> OTHER INFORMATION: RNAi molecule

<400> SEQUENCE: 786

agucgcucaa uuaagugguc cuucuca                                          27

<210> SEQ ID NO 787
<211> LENGTH: 27
<212> TYPE: RNA
<213> ORGANISM: Artificial Sequence
<220> FEATURE:
<223> OTHER INFORMATION: RNAi molecule

<400> SEQUENCE: 787

uucuagcugu gccuucaauc cacugau                                          27

<210> SEQ ID NO 788
<211> LENGTH: 27
<212> TYPE: RNA
<213> ORGANISM: Artificial Sequence
<220> FEATURE:
<223> OTHER INFORMATION: RNAi molecule

<400> SEQUENCE: 788

ucugaaugag ccgcuugaag uacugca                                          27

<210> SEQ ID NO 789
<211> LENGTH: 27
<212> TYPE: RNA
<213> ORGANISM: Artificial Sequence
<220> FEATURE:
<223> OTHER INFORMATION: RNAi molecule

<400> SEQUENCE: 789

ggaucugaau gagccgcuug aaguacu                                          27

<210> SEQ ID NO 790
<211> LENGTH: 27
<212> TYPE: RNA
<213> ORGANISM: Artificial Sequence
<220> FEATURE:
<223> OTHER INFORMATION: RNAi molecule

<400> SEQUENCE: 790
```

gguccuucuc auccuuguuc acaccau 27

<210> SEQ ID NO 791
<211> LENGTH: 27
<212> TYPE: RNA
<213> ORGANISM: Artificial Sequence
<220> FEATURE:
<223> OTHER INFORMATION: RNAi molecule

<400> SEQUENCE: 791
ugguccuucu cauccuuguu cacacca 27

<210> SEQ ID NO 792
<211> LENGTH: 27
<212> TYPE: RNA
<213> ORGANISM: Artificial Sequence
<220> FEATURE:
<223> OTHER INFORMATION: RNAi molecule

<400> SEQUENCE: 792
agugguccuu cucauccuug uucacac 27

<210> SEQ ID NO 793
<211> LENGTH: 27
<212> TYPE: RNA
<213> ORGANISM: Artificial Sequence
<220> FEATURE:
<223> OTHER INFORMATION: RNAi molecule

<400> SEQUENCE: 793
cgcucaauua agugguccuu cucaucc 27

<210> SEQ ID NO 794
<211> LENGTH: 27
<212> TYPE: RNA
<213> ORGANISM: Artificial Sequence
<220> FEATURE:
<223> OTHER INFORMATION: RNAi molecule

<400> SEQUENCE: 794
ggaacacaug gcagaacuuc cagcaga 27

<210> SEQ ID NO 795
<211> LENGTH: 27
<212> TYPE: RNA
<213> ORGANISM: Artificial Sequence
<220> FEATURE:
<223> OTHER INFORMATION: RNAi molecule

<400> SEQUENCE: 795
ugaaugagcc gcuugaagua cugcagg 27

<210> SEQ ID NO 796
<211> LENGTH: 27
<212> TYPE: RNA
<213> ORGANISM: Artificial Sequence
<220> FEATURE:
<223> OTHER INFORMATION: RNAi molecule

<400> SEQUENCE: 796
cagcauagcg uccaacuugg ugucauu 27

<210> SEQ ID NO 797
<211> LENGTH: 27
<212> TYPE: RNA
<213> ORGANISM: Artificial Sequence
<220> FEATURE:

<223> OTHER INFORMATION: RNAi molecule

<400> SEQUENCE: 797
auucuucucc uucuccgugc cgcaguu 27

<210> SEQ ID NO 798
<211> LENGTH: 27
<212> TYPE: RNA
<213> ORGANISM: Artificial Sequence
<220> FEATURE:
<223> OTHER INFORMATION: RNAi molecule

<400> SEQUENCE: 798
acaugguguu gaaguccagg auggcuu 27

<210> SEQ ID NO 799
<211> LENGTH: 27
<212> TYPE: RNA
<213> ORGANISM: Artificial Sequence
<220> FEATURE:
<223> OTHER INFORMATION: RNAi molecule

<400> SEQUENCE: 799
gcucuccaug aucucagaca ugguguu 27

<210> SEQ ID NO 800
<211> LENGTH: 27
<212> TYPE: RNA
<213> ORGANISM: Artificial Sequence
<220> FEATURE:
<223> OTHER INFORMATION: RNAi molecule

<400> SEQUENCE: 800
guucagcucc uccuuaacga ggucguu 27

<210> SEQ ID NO 801
<211> LENGTH: 27
<212> TYPE: RNA
<213> ORGANISM: Artificial Sequence
<220> FEATURE:
<223> OTHER INFORMATION: RNAi molecule

<400> SEQUENCE: 801
ucaaucacau cuucuaaggu gacgauu 27

<210> SEQ ID NO 802
<211> LENGTH: 27
<212> TYPE: RNA
<213> ORGANISM: Artificial Sequence
<220> FEATURE:
<223> OTHER INFORMATION: RNAi molecule

<400> SEQUENCE: 802
gaaaaacuug gugaggaaga ugguguu 27

<210> SEQ ID NO 803
<211> LENGTH: 27
<212> TYPE: RNA
<213> ORGANISM: Artificial Sequence
<220> FEATURE:
<223> OTHER INFORMATION: RNAi molecule

<400> SEQUENCE: 803
aaauucuucc agcauagcgu ccaacuu 27

<210> SEQ ID NO 804

<211> LENGTH: 27
<212> TYPE: RNA
<213> ORGANISM: Artificial Sequence
<220> FEATURE:
<223> OTHER INFORMATION: RNAi molecule

<400> SEQUENCE: 804
auuugaugau uucuucaauc acaucuu 27

<210> SEQ ID NO 805
<211> LENGTH: 27
<212> TYPE: RNA
<213> ORGANISM: Artificial Sequence
<220> FEATURE:
<223> OTHER INFORMATION: RNAi molecule

<400> SEQUENCE: 805
gaugcgcuug gcguaauucu ucuccuu 27

<210> SEQ ID NO 806
<211> LENGTH: 27
<212> TYPE: RNA
<213> ORGANISM: Artificial Sequence
<220> FEATURE:
<223> OTHER INFORMATION: RNAi molecule

<400> SEQUENCE: 806
cacgauagcc aggugagauu uaccuuu 27

<210> SEQ ID NO 807
<211> LENGTH: 27
<212> TYPE: RNA
<213> ORGANISM: Artificial Sequence
<220> FEATURE:
<223> OTHER INFORMATION: RNAi molecule

<400> SEQUENCE: 807
gcacgauagc caggugagau uuaccuu 27

<210> SEQ ID NO 808
<211> LENGTH: 27
<212> TYPE: RNA
<213> ORGANISM: Artificial Sequence
<220> FEATURE:
<223> OTHER INFORMATION: RNAi molecule

<400> SEQUENCE: 808
gucgagcagg auggugagcg ugguguu 27

<210> SEQ ID NO 809
<211> LENGTH: 27
<212> TYPE: RNA
<213> ORGANISM: Artificial Sequence
<220> FEATURE:
<223> OTHER INFORMATION: RNAi molecule

<400> SEQUENCE: 809
uuggcguaau ucuucuccuu cuccgug 27

<210> SEQ ID NO 810
<211> LENGTH: 27
<212> TYPE: RNA
<213> ORGANISM: Artificial Sequence
<220> FEATURE:
<223> OTHER INFORMATION: RNAi molecule

<400> SEQUENCE: 810
aucucuccga agaugacgau accgaug                                          27

<210> SEQ ID NO 811
<211> LENGTH: 27
<212> TYPE: RNA
<213> ORGANISM: Artificial Sequence
<220> FEATURE:
<223> OTHER INFORMATION: RNAi molecule

<400> SEQUENCE: 811
ggcacgaucu cuccgaagau gacgaua                                          27

<210> SEQ ID NO 812
<211> LENGTH: 27
<212> TYPE: RNA
<213> ORGANISM: Artificial Sequence
<220> FEATURE:
<223> OTHER INFORMATION: RNAi molecule

<400> SEQUENCE: 812
aauucuucca gcauagcguc caacuug                                          27

<210> SEQ ID NO 813
<211> LENGTH: 27
<212> TYPE: RNA
<213> ORGANISM: Artificial Sequence
<220> FEATURE:
<223> OTHER INFORMATION: RNAi molecule

<400> SEQUENCE: 813
agcauagcgu ccaacuuggu gucauug                                          27

<210> SEQ ID NO 814
<211> LENGTH: 27
<212> TYPE: RNA
<213> ORGANISM: Artificial Sequence
<220> FEATURE:
<223> OTHER INFORMATION: RNAi molecule

<400> SEQUENCE: 814
uagccgcucu ccaugaucuc agacaug                                          27

<210> SEQ ID NO 815
<211> LENGTH: 27
<212> TYPE: RNA
<213> ORGANISM: Artificial Sequence
<220> FEATURE:
<223> OTHER INFORMATION: RNAi molecule

<400> SEQUENCE: 815
uuccagcaua gcguccaacu ugguguc                                          27

<210> SEQ ID NO 816
<211> LENGTH: 27
<212> TYPE: RNA
<213> ORGANISM: Artificial Sequence
<220> FEATURE:
<223> OTHER INFORMATION: RNAi molecule

<400> SEQUENCE: 816
ucuuccagca uagcguccaa cuuggug                                          27

<210> SEQ ID NO 817
<211> LENGTH: 27
<212> TYPE: RNA
<213> ORGANISM: Artificial Sequence
<220> FEATURE:

<223> OTHER INFORMATION: RNAi molecule

<400> SEQUENCE: 817
ucuccgaaga ugacgauacc gauggug 27

<210> SEQ ID NO 818
<211> LENGTH: 27
<212> TYPE: RNA
<213> ORGANISM: Artificial Sequence
<220> FEATURE:
<223> OTHER INFORMATION: RNAi molecule

<400> SEQUENCE: 818
gauguucagc uccuccuuaa cgagguc 27

<210> SEQ ID NO 819
<211> LENGTH: 27
<212> TYPE: RNA
<213> ORGANISM: Artificial Sequence
<220> FEATURE:
<223> OTHER INFORMATION: RNAi molecule

<400> SEQUENCE: 819
caugaucuca gacauggugu ugaaguc 27

<210> SEQ ID NO 820
<211> LENGTH: 27
<212> TYPE: RNA
<213> ORGANISM: Artificial Sequence
<220> FEATURE:
<223> OTHER INFORMATION: RNAi molecule

<400> SEQUENCE: 820
ccuuggauga uguucagcuc cuccuua 27

<210> SEQ ID NO 821
<211> LENGTH: 27
<212> TYPE: RNA
<213> ORGANISM: Artificial Sequence
<220> FEATURE:
<223> OTHER INFORMATION: RNAi molecule

<400> SEQUENCE: 821
cucuccgaag augacgauac cgauggu 27

<210> SEQ ID NO 822
<211> LENGTH: 27
<212> TYPE: RNA
<213> ORGANISM: Artificial Sequence
<220> FEATURE:
<223> OTHER INFORMATION: RNAi molecule

<400> SEQUENCE: 822
guagccgcuc uccaugaucu cagacau 27

<210> SEQ ID NO 823
<211> LENGTH: 27
<212> TYPE: RNA
<213> ORGANISM: Artificial Sequence
<220> FEATURE:
<223> OTHER INFORMATION: RNAi molecule

<400> SEQUENCE: 823
uguagccgcu cuccaugauc ucagaca 27

<210> SEQ ID NO 824

<211> LENGTH: 27
<212> TYPE: RNA
<213> ORGANISM: Artificial Sequence
<220> FEATURE:
<223> OTHER INFORMATION: RNAi molecule

<400> SEQUENCE: 824
gaucucuccg aagaugacga uaccgau 27

<210> SEQ ID NO 825
<211> LENGTH: 27
<212> TYPE: RNA
<213> ORGANISM: Artificial Sequence
<220> FEATURE:
<223> OTHER INFORMATION: RNAi molecule

<400> SEQUENCE: 825
gaugauguuc agcuccuccu uaacgag 27

<210> SEQ ID NO 826
<211> LENGTH: 27
<212> TYPE: RNA
<213> ORGANISM: Artificial Sequence
<220> FEATURE:
<223> OTHER INFORMATION: RNAi molecule

<400> SEQUENCE: 826
uggcguaauu cuucuccuuc uccgugc 27

<210> SEQ ID NO 827
<211> LENGTH: 27
<212> TYPE: RNA
<213> ORGANISM: Artificial Sequence
<220> FEATURE:
<223> OTHER INFORMATION: RNAi molecule

<400> SEQUENCE: 827
ucucuccgaa gaugacgaua ccgaugg 27

<210> SEQ ID NO 828
<211> LENGTH: 27
<212> TYPE: RNA
<213> ORGANISM: Artificial Sequence
<220> FEATURE:
<223> OTHER INFORMATION: RNAi molecule

<400> SEQUENCE: 828
cgaucucucc gaagaugacg auaccga 27

<210> SEQ ID NO 829
<211> LENGTH: 27
<212> TYPE: RNA
<213> ORGANISM: Artificial Sequence
<220> FEATURE:
<223> OTHER INFORMATION: RNAi molecule

<400> SEQUENCE: 829
acgaucucuc cgaagaugac gauaccg 27

<210> SEQ ID NO 830
<211> LENGTH: 27
<212> TYPE: RNA
<213> ORGANISM: Artificial Sequence
<220> FEATURE:
<223> OTHER INFORMATION: RNAi molecule

<400> SEQUENCE: 830
cacgaucucu ccgaagauga cgauacc 27

<210> SEQ ID NO 831
<211> LENGTH: 27
<212> TYPE: RNA
<213> ORGANISM: Artificial Sequence
<220> FEATURE:
<223> OTHER INFORMATION: RNAi molecule

<400> SEQUENCE: 831
gcacgaucuc uccgaagaug acgauac 27

<210> SEQ ID NO 832
<211> LENGTH: 27
<212> TYPE: RNA
<213> ORGANISM: Artificial Sequence
<220> FEATURE:
<223> OTHER INFORMATION: RNAi molecule

<400> SEQUENCE: 832
aacuugguga ggaagauggu guuggcc 27

<210> SEQ ID NO 833
<211> LENGTH: 27
<212> TYPE: RNA
<213> ORGANISM: Artificial Sequence
<220> FEATURE:
<223> OTHER INFORMATION: RNAi molecule

<400> SEQUENCE: 833
cauagcgucc aacuuggugu cauugaa 27

<210> SEQ ID NO 834
<211> LENGTH: 27
<212> TYPE: RNA
<213> ORGANISM: Artificial Sequence
<220> FEATURE:
<223> OTHER INFORMATION: RNAi molecule

<400> SEQUENCE: 834
cuuggcguaa uucuucuccu ucuccgu 27

<210> SEQ ID NO 835
<211> LENGTH: 27
<212> TYPE: RNA
<213> ORGANISM: Artificial Sequence
<220> FEATURE:
<223> OTHER INFORMATION: RNAi molecule

<400> SEQUENCE: 835
ucucagacau gguguugaag uccagga 27

<210> SEQ ID NO 836
<211> LENGTH: 27
<212> TYPE: RNA
<213> ORGANISM: Artificial Sequence
<220> FEATURE:
<223> OTHER INFORMATION: RNAi molecule

<400> SEQUENCE: 836
aucucagaca ugguguugaa guccagg 27

<210> SEQ ID NO 837
<211> LENGTH: 27
<212> TYPE: RNA
<213> ORGANISM: Artificial Sequence
<220> FEATURE:

<223> OTHER INFORMATION: RNAi molecule

<400> SEQUENCE: 837
gcauagcguc caacuuggug ucauuga 27

<210> SEQ ID NO 838
<211> LENGTH: 27
<212> TYPE: RNA
<213> ORGANISM: Artificial Sequence
<220> FEATURE:
<223> OTHER INFORMATION: RNAi molecule

<400> SEQUENCE: 838
uucuuccagc auagcgucca acuuggu 27

<210> SEQ ID NO 839
<211> LENGTH: 27
<212> TYPE: RNA
<213> ORGANISM: Artificial Sequence
<220> FEATURE:
<223> OTHER INFORMATION: RNAi molecule

<400> SEQUENCE: 839
auucuuccag cauagcgucc aacuugg 27

<210> SEQ ID NO 840
<211> LENGTH: 27
<212> TYPE: RNA
<213> ORGANISM: Artificial Sequence
<220> FEATURE:
<223> OTHER INFORMATION: RNAi molecule

<400> SEQUENCE: 840
aauucuucuc cuucuccgug ccgcagu 27

<210> SEQ ID NO 841
<211> LENGTH: 27
<212> TYPE: RNA
<213> ORGANISM: Artificial Sequence
<220> FEATURE:
<223> OTHER INFORMATION: RNAi molecule

<400> SEQUENCE: 841
uaauucuucu ccuucuccgu gccgcag 27

<210> SEQ ID NO 842
<211> LENGTH: 27
<212> TYPE: RNA
<213> ORGANISM: Artificial Sequence
<220> FEATURE:
<223> OTHER INFORMATION: RNAi molecule

<400> SEQUENCE: 842
guaauucuuc uccuucuccg ugccgca 27

<210> SEQ ID NO 843
<211> LENGTH: 27
<212> TYPE: RNA
<213> ORGANISM: Artificial Sequence
<220> FEATURE:
<223> OTHER INFORMATION: RNAi molecule

<400> SEQUENCE: 843
gcuuggcgua auucuucucc uucuccg 27

<210> SEQ ID NO 844

-continued

```
<211> LENGTH: 27
<212> TYPE: RNA
<213> ORGANISM: Artificial Sequence
<220> FEATURE:
<223> OTHER INFORMATION: RNAi molecule

<400> SEQUENCE: 844

ccagcauagc guccaacuug gugucau                                          27


<210> SEQ ID NO 845
<211> LENGTH: 27
<212> TYPE: RNA
<213> ORGANISM: Artificial Sequence
<220> FEATURE:
<223> OTHER INFORMATION: RNAi molecule

<400> SEQUENCE: 845

uccagcauag cguccaacuu gguguca                                          27
```